(12) United States Patent
Breitenstein et al.

(10) Patent No.: US 8,178,559 B2
(45) Date of Patent: May 15, 2012

(54) ORGANIC COMPOUNDS

(75) Inventors: Werner Breitenstein, Basel (CH); Takeru Ehara, Cambridge, MA (US); Claus Ehrhardt, Basel (CH); Philipp Grosche, Basel (CH); Yuko Hitomi, Tsukuba (JP); Yuki Iwaki, Cambridge, MA (US); Takanori Kanazawa, Tokyo (JP); Kazuhide Konishi, Tsukuba (JP); Juergen Klaus Maibaum, Basel (CH); Keiichi Masuya, Basel (CH); Atsuko Iwasaki, Tsukuba (JP); Nils Ostermann, Basel (CH); Masaki Suzuki, Tsukuba (JP); Atsushi Toyao, Tsukuba (JP); Fumiaki Yokokawa, Chromos (SG)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/176,930

(22) Filed: Jul. 6, 2011

(65) Prior Publication Data

US 2011/0263560 A1   Oct. 27, 2011

Related U.S. Application Data

(63) Continuation of application No. 11/719,762, filed as application No. PCT/EP2005/014102 on Dec. 28, 2005.

(30) Foreign Application Priority Data

Dec. 30, 2004 (GB) .................................. 0428526.8

(51) Int. Cl.
*A61K 31/451* (2006.01)
*C07D 211/60* (2006.01)
(52) U.S. Cl. ........................................ 514/330; 546/225
(58) Field of Classification Search ............ 514/210.21, 514/315, 318, 323, 230.5, 224.2; 546/184, 546/194, 201; 544/105, 52
See application file for complete search history.

(56) References Cited

U.S. PATENT DOCUMENTS

| | | | |
|---|---|---|---|
| 5,721,251 | A | 2/1998 | Chen et al. |
| 6,150,526 | A | 11/2000 | Binggeli et al. |
| 6,197,959 | B1 | 3/2001 | Breu et al. |
| 2002/0087002 | A1 | 7/2002 | Breu et al. |
| 2004/0204455 | A1 | 10/2004 | Cody et al. |

FOREIGN PATENT DOCUMENTS

| | | |
|---|---|---|
| WO | 9513069 A | 5/1995 |
| WO | 97/09311 A1 | 3/1997 |
| WO | 0020390 A | 4/2000 |
| WO | 0063173 A1 | 10/2000 |
| WO | 00/64887 A1 | 11/2000 |
| WO | 0064873 A | 11/2000 |
| WO | 02076440 A2 | 10/2002 |
| WO | 02088101 A | 11/2002 |
| WO | 03093267 A1 | 11/2003 |
| WO | 2004058727 A | 7/2004 |
| WO | 2004089903 A | 10/2004 |
| WO | 2004089915 A1 | 10/2004 |
| WO | 2004096116 A2 | 11/2004 |
| WO | 2004096366 A1 | 11/2004 |
| WO | 2004096769 A1 | 11/2004 |
| WO | 2004096799 A1 | 11/2004 |
| WO | 2004096803 A1 | 11/2004 |
| WO | 2004096804 | 11/2004 |
| WO | 2005/051911 A1 | 6/2005 |
| WO | 2005061457 A1 | 7/2005 |
| WO | 2006/005741 A2 | 1/2006 |
| WO | 2006/066896 A2 | 6/2006 |
| WO | 2006069788 A1 | 7/2006 |

OTHER PUBLICATIONS

Database Caplus (online) Chemical abstracts Service, Columbus, OH, XP002372913, Database Accession No. 2002:849607 [abstract], 2002.

Database Caplus (online) Chemical Abstracts Service Columbus, OH, XP002372914 Database accession No. 1995:951172 [abstract], 1995.

Dissertation von Edgar Specker, D-Munster, De Novo Design und Synthese neuer Leitstrukturen als Ueergangszustandsmime tika sur selektiven inhibition der HIV-1 Protease und Cathepsi D: nur p-substituierte verbindungen [English translation], 2004.

Maibaum, et al., "Renin inhibitors as novel treatment for cardiovascular diseases", Expert Opinion on Therapeutic Patents. vol. 13, No. 5, 2003, pp. 589-603.

(Continued)

*Primary Examiner* — Kamal Saeed
*Assistant Examiner* — Kristin Bianchi
(74) *Attorney, Agent, or Firm* — Sophie Binet Cross

(57) ABSTRACT

3,4-substituted piperidine compounds, these compounds for use in the diagnostic and therapeutic treatment of a warm-blooded animal, especially for the treatment of a disease (=disorder) that depends on activity of renin; the use of a compound of that class for the preparation of a pharmaceutical formulation for the treatment of a disease that depends on activity of renin; the use of a compound of that class in the treatment of a disease that depends on activity of renin; pharmaceutical formulations comprising a 3,4-substituted piperidine compound, and/or a method of treatment comprising administering a 3,4substituted piperidine compound, a method for the manufacture of a 3,4-substituted piperidine compound, and novel intermediates and partial steps for their synthesis are disclosed. The 3,4-disubstituted piperidine compounds have the formula (I), wherein the symbols have the meanings defined in the specification.

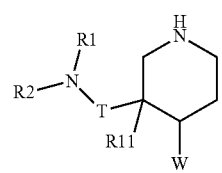

(I)

9 Claims, No Drawings

OTHER PUBLICATIONS

Marki, "Piperidine Renin Inhibitors: From Leads to Drug Candidates", IL FARMACO, vol. 56, No. 1-2, 2001, pp. 21-27.

Ujjainwalla, Feroze et al. "Design and Synthesis of Melanocortin Subtype-4 Receptor Agonists: Evolution of the Pyridazinone Archetype" biorg. Med. Chem. Lett. vol. 13, 2003, pp. 4431-4435.

ORGANIC COMPOUNDS

This application is a U.S. Continuation of U.S. application Ser. No 11/719,762 filed May 11, 2009, which is a U.S. National Phase filing of International Ser. No. PCT/EP2005/014102 filed Dec. 28, 2005, and claims priority to GB Application Ser. No. 0428526.8 filed Dec. 30, 2004 the contents of which are incorporated herein by reference in their entirety.

The invention relates to 3,4-substituted piperidine compounds, these compounds for use in the diagnostic and therapeutic treatment of a warm-blooded animal, especially for the treatment of a disease (=disorder) that depends on activity of renin; the use of a compound of that class for the preparation of a pharmaceutical formulation for the treatment of a disease that depends on activity of renin; the use of a compound of that class in the treatment of a disease that depends on activity of renin; pharmaceutical formulations comprising a 3,4-substituted piperidine compound, and/or a method of treatment comprising administering a 3,4-substituted piperidine compound, a method for the manufacture of a 3,4-substituted piperidine compound, and novel intermediates and partial steps for their synthesis.

The present invention relates to a compound of the formula I

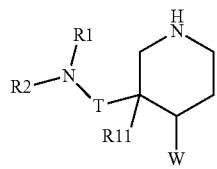
(I)

wherein $R^1$ is hydrogen, unsubstituted or substituted alkyl, unsubstituted or substituted alkenyl, unsubstituted or substituted alkynyl, unsubstituted or substituted aryl, unsubstituted or substituted heterocyclyl or unsubstituted or substituted cycloalkyl;

$R^2$ is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;

W is a moiety selected from those of the formulae IA, IB and IC,

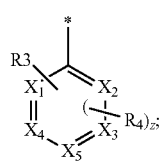
(IA)

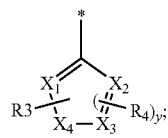
(IB)

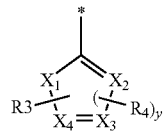
(IC)

wherein the asterisk (*) denotes the position where the moiety W is bound to the 4-carbon in the piperidine ring in formula I, and wherein $X_1, X_2, X_3, X_4$ and $X_5$ are independently selected from carbon and nitrogen, where $X_4$ in formula IB and $X_1$ in formula IC may have one of these meanings or further be selected from S and O, where carbon and nitrogen ring atoms can carry the required number of hydrogen or substituents $R_3$ or (if present within the limitations given below) $R_4$ to complete the number of bonds emerging from a ring carbon to four, from a ring nitrogen to three; with the proviso that in formula IA at least 2, preferably at least 3 of $X_1$ to $X_5$ are carbon and in formulae IB and IC at least one of $X_1$ to $X_4$ is carbon, preferably two of $X_1$ to $X_4$ are carbon;

y is 0, 1, 2 or 3;

z is 0, 1, 2, 3 or 4

(the obligatory moiety) R3 which can only be bound to any one of $X_1$, $X_2$, $X_3$ and $X_4$ (instead of a hydrogen and replacing it) is hydrogen or preferably unsubstituted or substituted $C_1$-$C_7$-alkyl, unsubstituted or substituted $C_2$-$C_7$-alkenyl, unsubstituted or substituted $C_2$-$C_7$-alkynyl, unsubstituted or substituted aryl, unsubstituted or substituted heterocyclyl, unsubstituted or substituted cycloalkyl, halo, hydroxy, etherified or esterified hydroxy, unsubstituted or substituted mercapto, unsubstituted or substituted sulfinyl (—S(=O)—), unsubstituted or substituted sulfonyl (—S(=O)$_2$—), amino, mono- or di-substituted amino, carboxy, esterified or amidated carboxy, unsubstituted or substituted sulfamoyl, nitro or cyano, with the proviso that if R3 is hydrogen y and z are 0 (zero);

$R_4$ (which is preferably bound to a ring atom other than that to which $R_3$ is bound) is—if y or z is 2 or more, independently-selected from a group of substituents consisting of unsubstituted or substituted $C_1$-$C_7$-alkyl, unsubstituted or substituted $C_2$-$C_7$-alkenyl, unsubstituted or substituted $C_2$-$C_7$-alkynyl, halo, hydroxy, etherified or esterified hydroxy, unsubstituted or substituted mercapto, unsubstituted or substituted sulfonyl (—S(=O)—), unsubstituted or substituted sulfonyl (—S(=O)$_2$—), amino, mono- or di-substituted amino, carboxy, esterified or amidated carboxy, unsubstituted or substituted sulfamoyl, nitro and cyano;

T is methylene (—CH$_2$—) or carbonyl (—C(=O)—); and

R11 is hydrogen, hydroxy, halo, $C_1$-$C_7$-alkyl, halo-$C_1$-$C_7$-alkyl, cycloalkyl, halo-substituted cycloalkyl, $C_1$-$C_7$-alkoxy, halo-$C_1$-$C_7$-alkoxy or cyano, or a (preferably pharmaceutically acceptable) salt thereof.

Preferred is a compound of the formula I

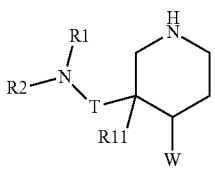

wherein
R¹ is unsubstituted or substituted cycloalkyl;
R² is unsubstituted or substituted alkyl, unsubstituted or substituted aryl, or unsubstituted or substituted heterocyclyl,
W is a moiety selected from those of the formulae IA and IC,

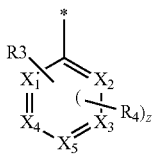

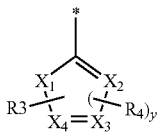

wherein the asterisk (*) denotes the position where the moiety W is bound to the 4-carbon in the piperidine ring in formula I, and wherein
$X_1, X_2, X_3, X_4$ and $X_5$ are independently selected from carbon and nitrogen, preferably carbon, where $X_1$ in formula IC may have one of these meanings or further be selected from S and O, where carbon and nitrogen ring atoms can carry the required number of hydrogen or substituents $R_3$ or—if present within the limitations given below—$R_4$ to complete the number of bonds emerging from a ring carbon to four, from a ring nitrogen to three; with the proviso that in formula IA at least 2, preferably at least 3 of $X_1$ to $X_5$ are carbon and in formulae IB and IC at least one of $X_1$ to $X_4$ is carbon, preferably two of $X_1$ to $X_4$ are carbon;
y is 0 or 1;
z is 0 or 1,
R3 which can only be bound to any one of $X_1, X_2, X_3$ and $X_4$ is hydrogen or preferably unsubstituted or substituted $C_1$-$C_7$-alkyl, unsubstituted or substituted $C_2$-$C_7$-alkynyl, unsubstituted or substituted aryl, unsubstituted or substituted heterocyclyl, unsubstituted or substituted cycloalkyl, hydroxy, etherified hydroxy, or cyano,
with the proviso that if R3 is hydrogen y and z are 0;
R4 is—if y or z is 2 or more, independently—selected from a group of substituents consisting of hydroxy, or etherified hydroxy;
T is methylene (—CH₂—) or carbonyl (—C(=O)—);
and
R11 is hydrogen,
or a salt thereof.

The compounds of the present invention exhibit inhibitory activity on the natural enzyme renin. Thus, compounds of formula I may be employed for the treatment (this term also including prophylaxis) of one or more disorders or diseases selected from, inter alia, hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders.

Listed below are definitions of various terms used to describe the compounds of the present invention as well as their use and synthesis, starting materials and intermediates and the like. These definitions, either by replacing one, more than one or all general expressions or symbols used in the present disclosure and thus yielding preferred embodiments of the invention, preferably apply to the terms as they are used throughout the specification unless they are otherwise limited in specific instances either individually or as part of a larger group.

The term "lower" or "$C_1$-$C_7$-" defines a moiety with up to and including maximally 7, especially up to and including maximally 4, carbon atoms, said moiety being branched (one or more times) or straight-chained and bound via a terminal or a non-terminal carbon. Lower or $C_1$-$C_7$-alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl, tert-butyl.

Halo or halogen is preferably fluoro, chloro, bromo or iodo, most preferably fluoro, chloro or bromo, if not indicated otherwise.

Unsubstituted or substituted alkyl is preferably $C_1$-$C_{20}$-alkyl, more preferably $C_1$-$C_7$-alkyl, that is straight-chained or branched (one or, if desired and possible, more times), which is unsubstituted or substituted by one or more, e.g. up to three moieties selected from unsubstituted or substituted aryl as described below, especially phenyl or naphthyl each of which is unsubstituted or substituted as described below for unsubstituted or substituted aryl, unsubstituted or substituted heterocycyclyl as described below, especially pyrrolyl, furanyl, thienyl, pyrimidinyl, pyrazolyl, triazolyl, tetrazolyl, oxetidinyl, 3-($C_1$-$C_7$-alkyl)-oxetidinyl, pyridyl, pyrimidinyl, morpholino, piperidinyl, piperazinyl, tetrahydrofuran-onyl, tetrahydro-pyranyl, indolyl, indazolyl, 1H-indazanyl, benzofuranyl, benzothiophenyl, quinolinyl, isoquinolinyl, 1,2,3,4-tetrahydro-1,4-benzoxazinyl, 2H-1,4-benzoxazin-3(4H)-onyl, 2H,3H-1,4-benzodioxinyl or benzo[1,2,5]oxadiazolyl, each of which is unsubstituted or substituted as described below for unsubstituted or substituted heterocyclyl, unsubstituted or substituted cycloalkyl as described below, especially cyclopropyl, cyclobutyl, cyclopentyl or cyclohexyl, each of which is unsubstituted or substituted as described below for unsubstituted or substituted cycloalkyl, halo, hydroxy, $C_1$-$C_7$-alkoxy, halo-$C_1$-$C_7$-alkoxy, such as trifluoromethoxy, hydroxy-$C_1$-$C_7$-alkoxy, $C_1$-$C_7$-alkoxy-$C_1$-$C_7$-alkoxy, phenyl- or naphthyloxy, phenyl- or naphthyl-$C_1$-$C_7$-alkyloxy, $C_1$-$C_7$-alkanoyloxy, benzoyl- or naphthoyloxy, $C_1$-$C_7$-alkylthio, halo-$C_1$-$C_7$-alkthio, such as trifluoromethylthio, $C_1$-$C_7$-alkoxy-$C_1$-$C_7$-alkylthio, phenyl- or naphthylthio, phenyl- or naphthyl-$C_1$-$C_7$-alkylthio, $C_1$-$C_7$-alkanoylthio, benzoyl- or naphthoylthio, nitro, amino, mono- or di-($C_1$-$C_7$-alkyl and/or $C_1$-$C_7$-alkoxy-$C_1$-$C_7$-alkyl)-amino, mono- or di-(naphthyl- or phenyl-$C_1$-$C_7$-alkyl)-amino, $C_1$-$C_7$-alkanoylamino, benzoyl- or naphthoylamino, $C_1$-$C_7$-alkylsulfonylamino, phenyl- or naphthylsulfonylamino wherein phenyl or naphthyl is unsubstituted or substituted by one or more, especially one to three, $C_1$-$C_7$-alkyl moieties, phenyl- or naphthyl-$C_1$-$C_7$-alkylsulfonylamino, carboxyl, $C_1$-$C_7$-alkyl-carbonyl, $C_1$-$C_7$-alkoxy-carbonyl, phenyl- or naphthyloxycarbonyl, phenyl- or naphthyl-$C_1$-$C_7$-alkoxycarbonyl, carbamoyl, N-mono- or N,N-di-($C_1$-$C_7$-alkyl)aminocarbonyl, N-mono- or N,N-di-(naphthyl- or phenyl-$C_1$-$C_7$-alkyl)-aminocarbonyl, cyano, $C_1$-$C_7$-alkylene, $C_1$-$C_7$-alkenylene or -alkynylene, $C_1$-$C_7$-alkylenedioxy, sulfonyl (—S—OH), sulfonyl (—S(=O)—OH), $C_1$-$C_7$-alkylsulfinyl ($C_1$-$C_7$-alkyl- S(=O)—), phenyl- or naphthylsulfinyl wherein phenyl or naphthyl is unsubstituted or substituted by one or more, especially one to three, $C_1$-$C_7$-alkyl moieties, phenyl- or naphthyl-$C_1$-$C_7$-alkylsulfinyl, sulfonyl (—S(O)$_2$OH), $C_1$-$C_7$-alkylsulfonyl ($C_1$-$C_7$-alkyl-SO$_2$—), phenyl- or naphthylsulfonyl wherein phenyl or naphthyl is unsubstituted or substituted by one or more, especially one to three, $C_1$-$C_7$-alkoxy-$C_1$-$C_7$-alkyl or $C_1$-$C_7$-alkyl moieties, phenyl- or naphthyl-$C_1$-$C_7$-alkylsulfonyl, sulfamoyl and N-mono or N,N-di-($C_1$-$C_7$-alkyl, phenyl-, naphthyl, phenyl-$C_1$-$C_7$-alkyl or naphthyl-$C_1$-$C_7$-alkyl)-aminosulfonyl.

Unsubstituted or substituted alkenyl preferably has 2 to 20 carbon atoms and includes one or more double bonds, and is more preferably $C_2$-$C_7$-alkenyl that is unsubstituted or substituted as described above for unsubstituted or substituted alkyl. Examples are vinyl or allyl.

Unsubstituted or substituted alkynyl preferably has 2 to 20 carbon atoms and includes one or more triple bonds, and is more preferably $C_2$-$C_7$-alkynyl that is unsubstituted or substituted as described above for unsubstituted or substituted alkyl. An example is prop-2-ynyl.

Unsubstituted or substituted aryl preferably is a mono- or polycyclic, especially monocyclic, bicyclic or tricyclic aryl moiety with 6 to 22 carbon atoms, especially phenyl, naphthyl, indenyl, fluorenyl, acenapthylenyl, phenylenyl or phenanthryl, and is unsubstituted or substituted by one or more, especially one to three, moieties, preferably independently selected from the group consisting of a substituent of the formula —($C_0$-$C_7$-alkylene)-(X)$_r$—($C_1$-$C_7$-alkylene)-(Y)$_s$—($C_0$-$C_7$-alkylene)-H where $C_0$-alkylene means that a bond is present instead of bound alkylene, r and s, each independently of the other, are 0 or 1 and each of X and Y, if present and independently of the others, is —O—, —NV—, —S—, —C(=O)—, —C(=S), —O—CO—, —CO—O—, —NV—CO—, —CO—NV—; —NV—SO$_2$—, —SO$_2$—NV; —NV—CO—NV—, —NV—CO—O—, —O—CO—NV—, —NV—SO$_2$—NV— wherein V is hydrogen or unsubstituted or substituted alkyl as defined below, especially selected from $C_1$-$C_7$-alkyl, phenyl, naphthyl, phenyl- or naphthyl-$C_1$-$C_7$-alkyl and halo-$C_1$-$C_7$-alkyl; e.g. $C_1$-$C_7$-alkyl, such as methyl, ethyl, n-propyl, isopropyl, n-butyl, isobutyl, sec-butyl or tert-butyl, hydroxy-$C_1$-$C_7$-alkyl, $C_1$-$C_7$-alkoxy-$C_1$-$C_7$-alkyl, such as 3-methoxypropyl or 2-methoxyethyl, $C_1$-$C_7$-alkoxy-$C_1$-$C_7$-alkoxy-$C_1$-$C_7$-alkyl, $C_1$-$C_7$-alkanoyloxy-$C_1$-$C_7$-alkyl, $C_1$-$C_7$-alkyloxycarbonyl-$C_1$-$C_7$-alkyl, amino-$C_1$-$C_7$-alkyl, such as aminomethyl, (N—) mono- or (N,N—) di-($C_1$-$C_7$-alkyl)-amino-$C_1$-$C_7$-alkyl, $C_1$-$C_7$-alkoxy-$C_1$-$C_7$-alkylamino-$C_1$-$C_7$-alkyl, mono-(naphthyl- or phenyl)-amino-$C_1$-$C_7$-alkyl, mono-(naphthyl- or phenyl-$C_1$-$C_7$-alkyl)-amino-$C_1$-$C_7$-alkyl, $C_1$-$C_7$-alkanoylamino-$C_1$-$C_7$-alkyl, $C_1$-$C_7$-alkyl-O—CO—NH—$C_1$-$C_7$-alkyl, $C_1$-$C_7$-alkylsulfonylamino-$C_1$-$C_7$-alkyl, $C_1$-$C_7$-alkyl-NH—CO—NH—$C_1$-$C_7$-alkyl, $C_1$-$C_7$-alkyl-NH—SO$_2$—NH—$C_1$-$C_7$-alkyl, $C_1$-$C_7$-alkoxy, hydroxy-$C_1$-$C_7$-alkoxy, $C_1$-$C_7$-alkoxy-$C_1$-$C_7$-alkoxy, carboxy-$C_1$-$C_7$-alkyloxy, $C_1$-$C_7$-alkyloxycarbonyl-$C_1$-$C_7$-alkoxy, mono- or di-($C_1$-$C_7$-alkyl)-aminocarbonyl-$C_1$-$C_7$-alkyloxy, $C_1$-$C_7$-alkanoyloxy, mono- or di-($C_1$-$C_7$-alkyl)-amino, mono-di-(naphthyl- or phenyl-$C_1$-$C_7$-alkyl)-amino, N-mono-$C_1$-$C_7$-alkoxy-$C_1$-$C_7$-alkylamino, $C_1$-$C_7$-alkanoylamino, $C_1$-$C_7$-alkylsulfonylamino, $C_1$-$C_7$-alkylcarbonyl, halo-$C_1$-$C_7$-alkylcarbonyl, hydroxy-$C_1$-$C_7$-alkylcarbonyl, $C_1$-$C_7$-alkoxy-$C_1$-$C_7$-alkylcarbonyl, amino-$C_1$-$C_7$-alkylcarbonyl, (N—) mono- or (N,N—) di-($C_1$-$C_7$-alkyl)-amino-$C_1$-$C_7$-alkylcarbonyl, $C_1$-$C_7$-alkanoylamino-$C_1$-$C_7$-alkylcarbonyl, $C_1$-$C_7$-alkoxy-carbonyl, hydroxy-$C_1$-$C_7$-alkoxycarbonyl, $C_1$-$C_7$-alkoxy-$C_1$-$C_7$-alkoxycarbonyl, amino-$C_1$-$C_7$-alkoxycarbonyl, (N—) mono-($C_1$-$C_7$-alkyl)-amino-$C_1$-$C_7$-alkoxycarbonyl, $C_1$-$C_7$-alkanoylamino-$C_1$-$C_7$-alkoxycarbonyl, N-mono- or N,N-di-($C_1$-$C_7$-alkyl)-aminocarbonyl, N—$C_1$-$C_7$-alkoxy-$C_1$-$C_7$-alkylcarbamoyl or N-mono- or N,N-di-($C_1$-$C_7$-alkyl)-aminosulfonyl;

from $C_2$-$C_7$-alkenyl, $C_2$-$C_7$-alkinyl, phenyl, naphtyl, heterocyclyl, especially as defined below for heterocyclyl, preferably selected from pyrrolyl, furanyl, thienyl, pyrimidinyl, pyrazolyl, pyrazolidinonyl, N—($C_1$-$C_7$-alkyl, phenyl, naphthyl, phenyl-$C_1$-$C_7$-alkyl or naphthyl-$C_1$-$C_7$-alkyl)-pyrazolidinonyl, triazolyl, tetrazolyl, oxetidinyl, 3-$C_1$-$C_7$-alkyl-oxetidinyl, pyridyl, pyrimidinyl, morpholino, piperidinyl, piperazinyl, tetrahydrofuran-onyl, indolyl, indazolyl, 1H-indazolyl, benzofuranyl, benzothiophenyl, quinolinyl, isoquinolinyl, 1,2,3,4-tetrahydro-1,4-benzoxazinyl, 2H-1,4-benzoxazin-3(4H)-onyl, benzo[1,2,5]oxadiazolyl or 9H-xanthenyl, phenyl- or naphthyl- or heterocyclyl-$C_1$-$C_7$-alkyl or —$C_1$-$C_7$-alkyloxy wherein heterocyclyl is as defined below, preferably selected from pyrrolyl, furanyl, thienyl, pyrimidinyl, pyrazolyl, pyrazolidinonyl, N—($C_1$-$C_7$-alkyl, phenyl, naphthyl, phenyl-$C_1$-$C_7$-alkyl or naphthyl-$C_1$-$C_7$-alkyl)-pyrazolidinonyl, triazolyl, tetrazolyl, oxetidinyl, pyridyl, pyrimidinyl, morpholino, piperidinyl, piperazinyl, tetrahydrofuran-onyl, indolyl, indazolyl, 1H-indazanyl, benzofuranyl, benzothiophenyl, quinolinyl, isoquinolinyl, 1,2,3,4-tetrahydro-1,4-benzoxazinyl, 2H-1,4-benzoxazin-3(4H)-onyl-, benzo[1,2,5]oxadiazolyl or 9H-xanthenyl; such as benzyl or naphthylmethyl, halo-$C_1$-$C_7$-alkyl, such as trifluoromethyl, phenyloxy- or naphthyloxy-$C_1$-$C_7$-alkyl, phenyl-$C_1$-$C_7$-alkoxy- or naphthyl-$C_1$-$C_7$-alkoxy-$C_1$-$C_7$-alkyl, di-(naphthyl- or phenyl)-amino-$C_1$-$C_7$-alkyl, di-(naphthyl- or phenyl-$C_1$-$C_7$-alkyl)-amino-$C_1$-$C_7$-alkyl, benzoyl- or naphthoylamino-$C_1$-$C_7$-alkyl, phenyl- or naphthylsulfonylamino-$C_1$-$C_7$-alkyl wherein phenyl or naphthyl is unsubstituted or substituted by one or more, especially one to three, $C_1$-$C_7$-alkyl moieties, phenyl- or naphthyl-$C_1$-$C_7$-alkylsulfonylamino-$C_1$-$C_7$-alkyl, carboxy-$C_1$-$C_7$-alkyl, halo, especially fluoro or chloro, hydroxy, phenyl-$C_1$-$C_7$-alkoxy wherein phenyl is unsubstituted or substituted by $C_1$-$C_7$-alkoxy and/or halo, halo-$C_1$-$C_7$-alkoxy, such as trifluoromethoxy, phenyl- or naphthyloxy, phenyl- or naphthyl-$C_1$-$C_7$-alkyloxy, phenyl- or naphthyl-oxy-$C_1$-$C_7$-alkyloxy, benzoyl- or naphthoyloxy, halo-$C_1$-$C_7$-alkylthio, such as trifluoromethylthio, phenyl- or naphthylthio, phenyl- or naphthyl-$C_1$-$C_7$-alkylthio, benzoyl- or naphthoylthio, nitro, amino, di-(naphthyl- or phenyl-$C_1$-$C_7$-alkyl)-amino, benzoyl- or naphthoylamino, phenyl- or naphthylsulfonylamino wherein phenyl or naphthyl is unsubstituted or substituted by one or more, especially one to three, $C_1$-$C_7$-alkoxy-$C_1$-$C_7$-alkyl or $C_1$-$C_7$-alkyl moieties, phenyl- or naphthyl-$C_1$-$C_7$-alkylsulfonylamino, carboxyl, (N,N—) di-($C_1$-$C_7$-alkyl)amino-$C_1$-$C_7$-alkoxycarbonyl, halo-$C_1$-$C_7$-alkoxycarbonyl, phenyl- or naphthyloxycarbonyl, phenyl- or naphthyl-$C_1$-$C_7$-alkoxycarbonyl, (N,N—) di-($C_1$-$C_7$-alkyl)-amino-$C_1$-$C_7$-alkoxycarbonyl, carbamoyl, N-mono or N,N-di-(naphthyl-, phenyl-, $C_1$-$C_7$-alkyloxyphenyl and/or $C_1$-$C_7$-alkyloxynapthtyl-)aminocarbonyl, N-mono- or N,N-di-(naphthyl- or phenyl-$C_1$-$C_7$-alkyl)-aminocarbonyl, cyano, $C_1$-$C_7$-alkylene which is unsubstituted or substituted by up to four $C_1$-$C_7$-alkyl substituents and bound to two adjacent ring atoms of the aryl moiety, $C_2$-$C_7$-alkenylene or -alkenylene which are bound to two adjacent ring atoms of the aryl moiety, sulfenyl, sulfinyl, $C_1$-$C_7$-alkylsulfinyl, phenyl- or naphthylsulfinyl wherein phenyl or naphthyl is unsubstituted or substituted by one or more, especially one to three, $C_1$-$C_7$-alkoxy-$C_1$-$C_7$-alkyl or $C_1$-$C_7$-alkyl moieties, phenyl- or naphthyl-$C_1$-$C_7$-alkylsulfinyl, sulfonyl, $C_1$-$C_7$-alkylsulfonyl, halo-$C_1$-$C_7$-alkylsulfonyl, hydroxy-$C_1$-$C_7$-alkylsulfonyl, $C_1$-$C_7$-alkoxy-$C_1$-$C_7$-alkylsulfonyl, amino-$C_1$-$C_7$-alkylsulfonyl, (N,N—) di-($C_1$-$C_7$-alkyl)-amino-$C_1$-$C_7$-alkylsulfonyl, $C_1$-$C_7$-alkanoylamino-$C_1$-$C_7$-alkylsulfonyl, phenyl- or naphthylsulfonyl wherein phenyl or naphthyl is unsubstituted or substituted by one or more, especially one to three, $C_1$-$C_7$-alkoxy-$C_1$-$C_7$-alkyl or $C_1$-$C_7$-alkyl moieties, phenyl- or naphthyl-$C_1$-$C_7$-alkylsulfonyl, sulfamoyl and N-mono or N,N-di-($C_1$-$C_7$-alkyl, phenyl-, naphthyl, phenyl-$C_1$-$C_7$-alkyl and/or naphthyl-$C_1$-$C_7$-alkyl)-aminosulfonyl.

Unsubstituted or substituted heterocyclyl is preferably a mono- or polycyclic, preferably a mono- or bicyclic-, unsaturated, partially saturated or saturated ring system with preferably 3 to 22 (more preferably 3 to 14) ring atoms and with one or more, preferably one to four, heteroatoms independently selected from nitrogen (=N—, —NH— or substituted —NH—), oxygen, sulfur (—S—, S(=O)— or S—(=O)$_2$—) which is unsubstituted or substituted by one or more, e.g. up to three, substitutents preferably independently selected from the substitutents mentioned above for aryl. Preferably, heterocyclyl (which is unsubstituted or substituted as just mentioned) is selected from the following moieties (the asterisk marks the point of binding to the rest of the molecule of formula I):

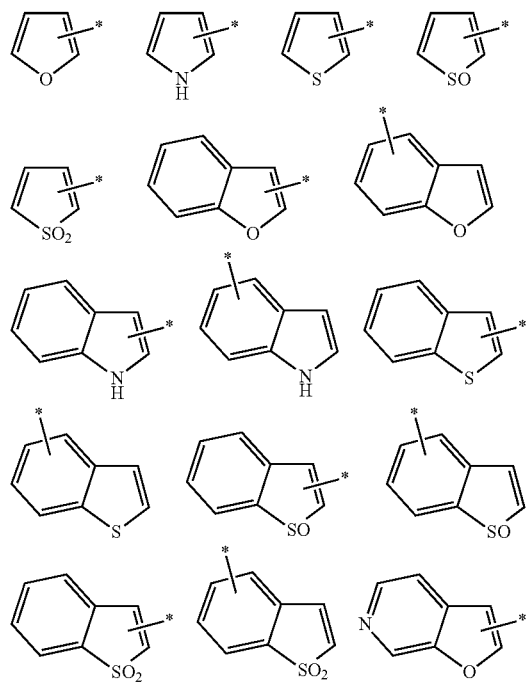

-continued

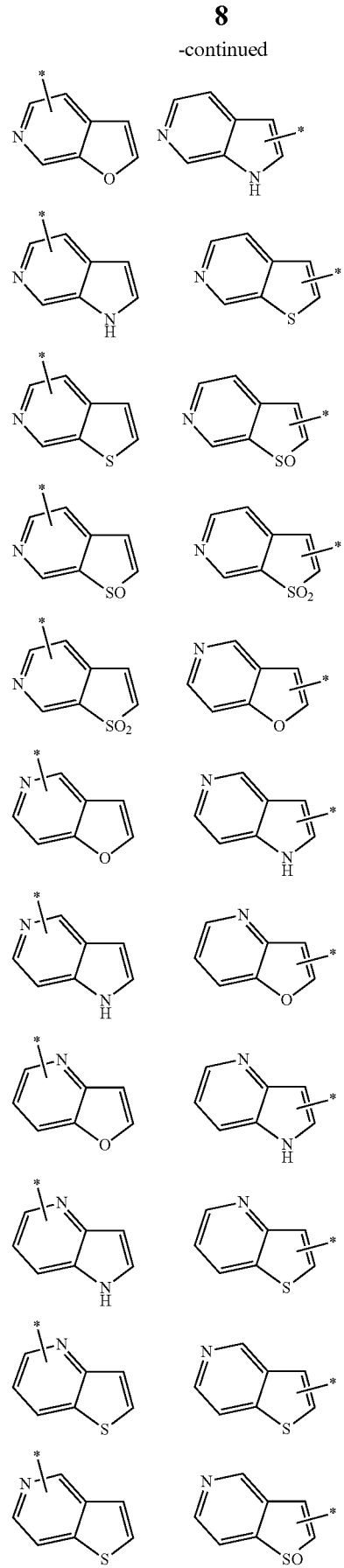

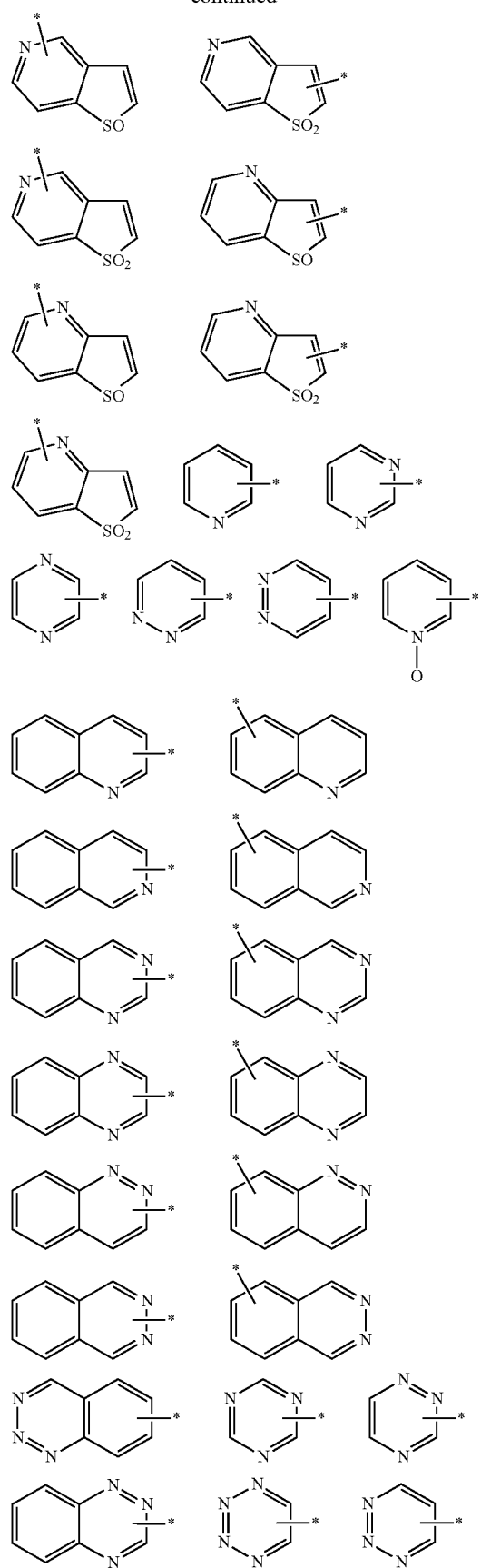
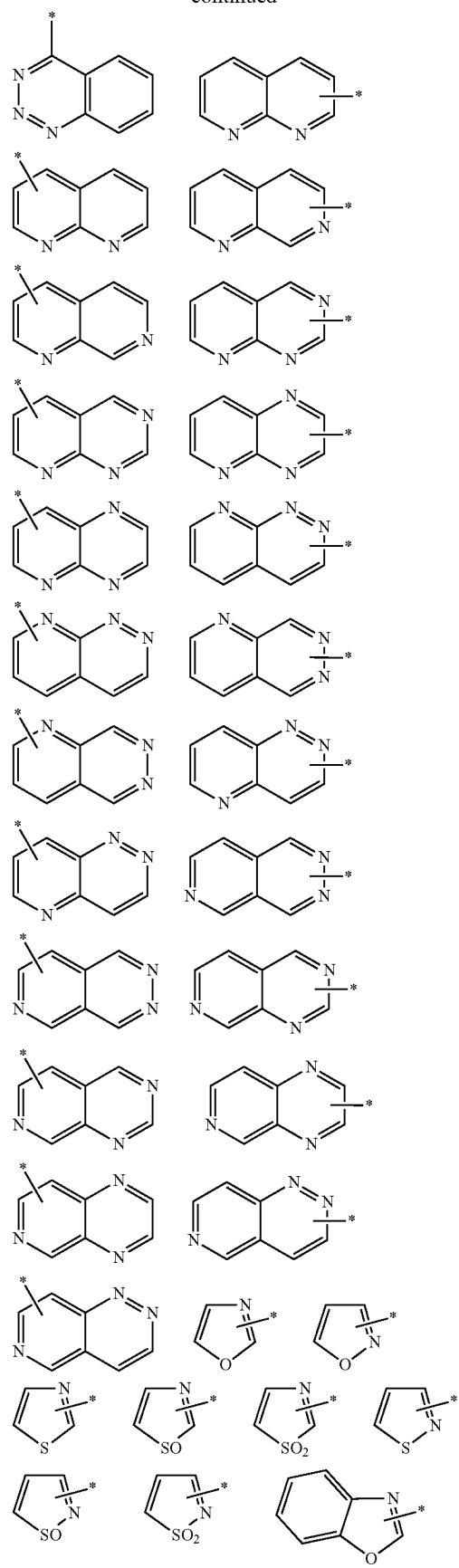

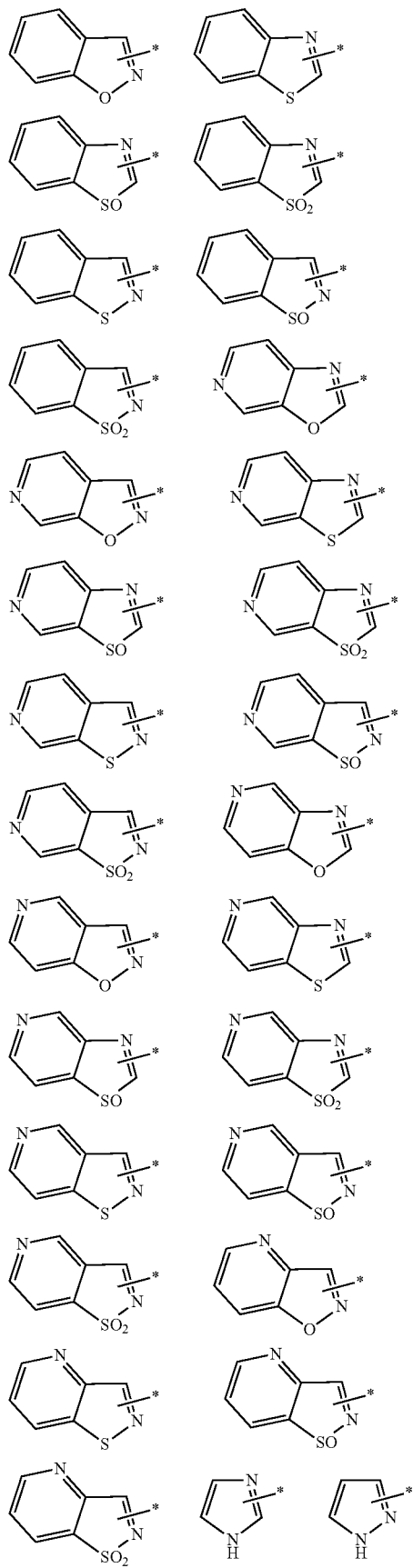
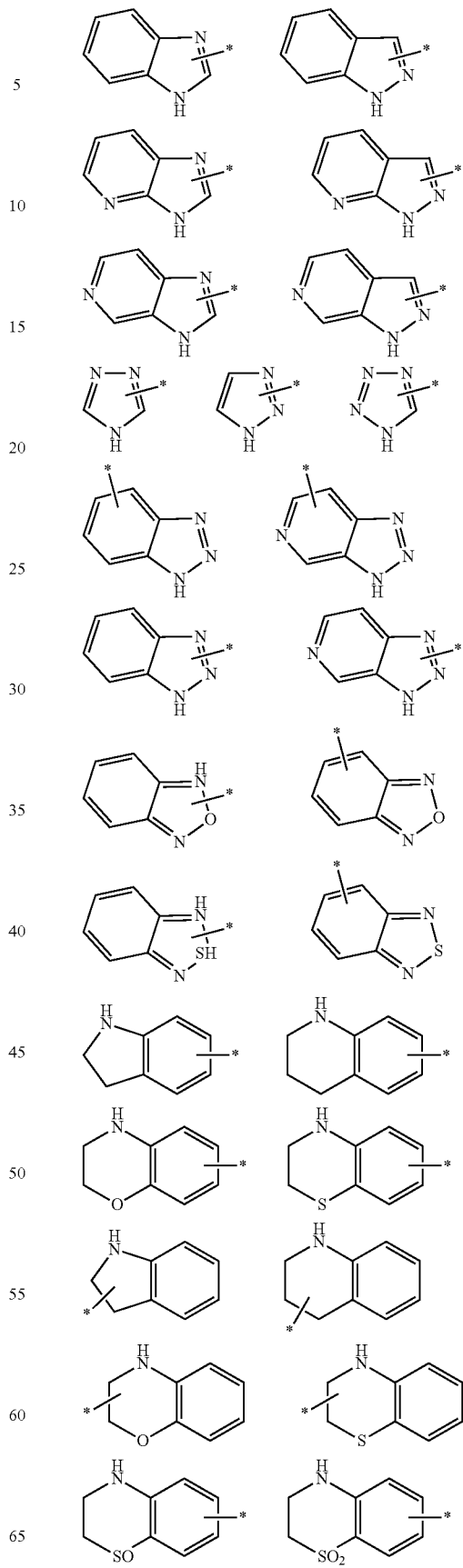

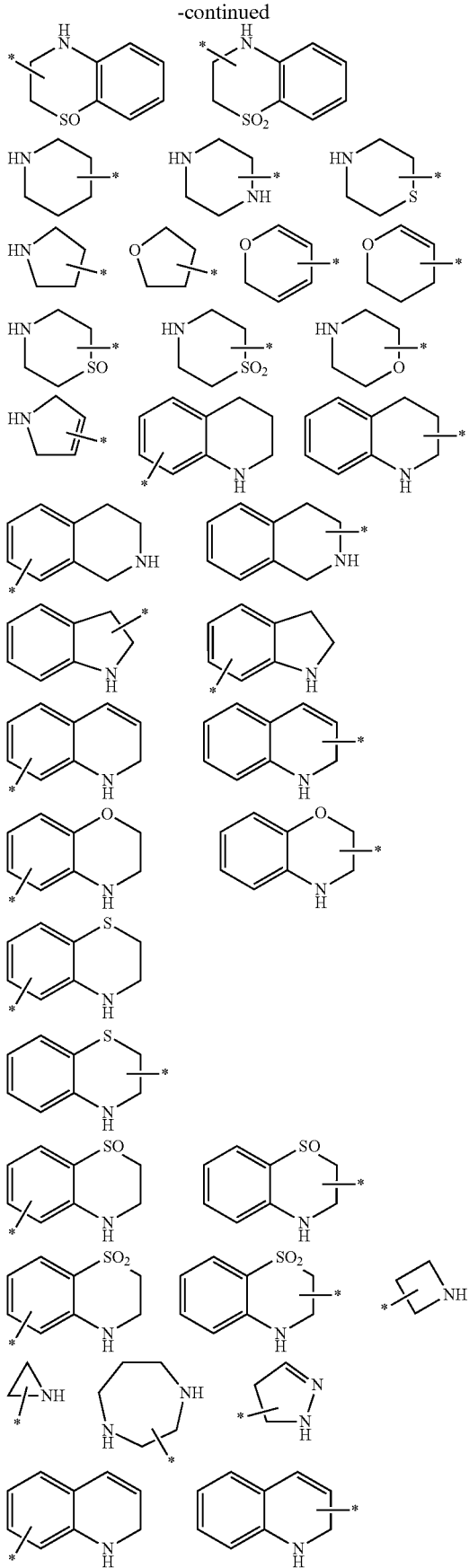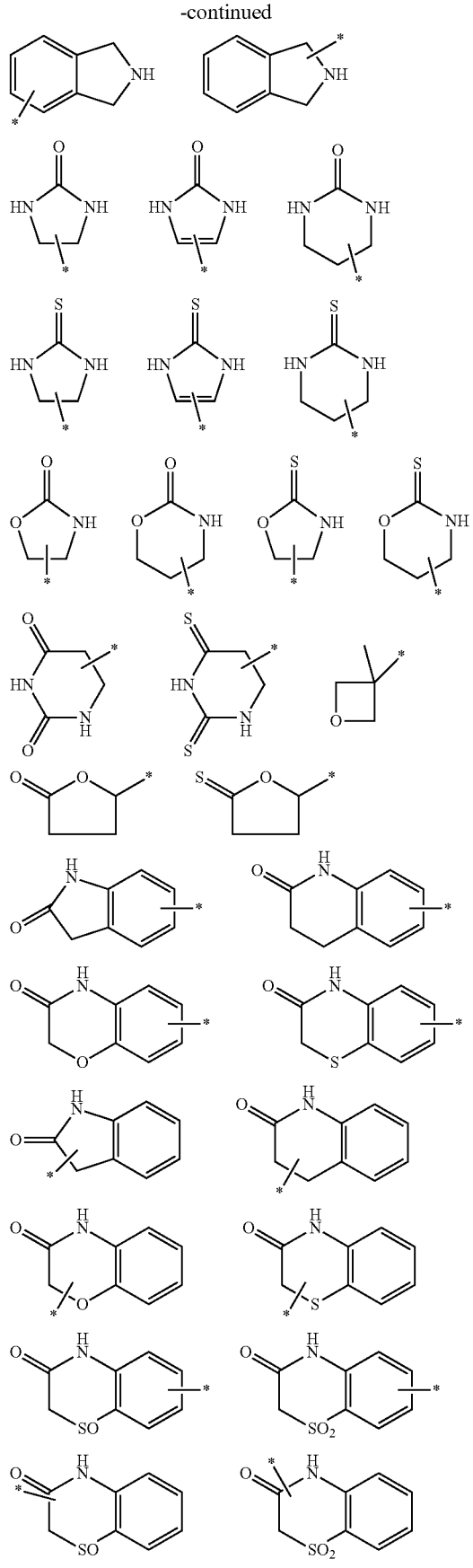

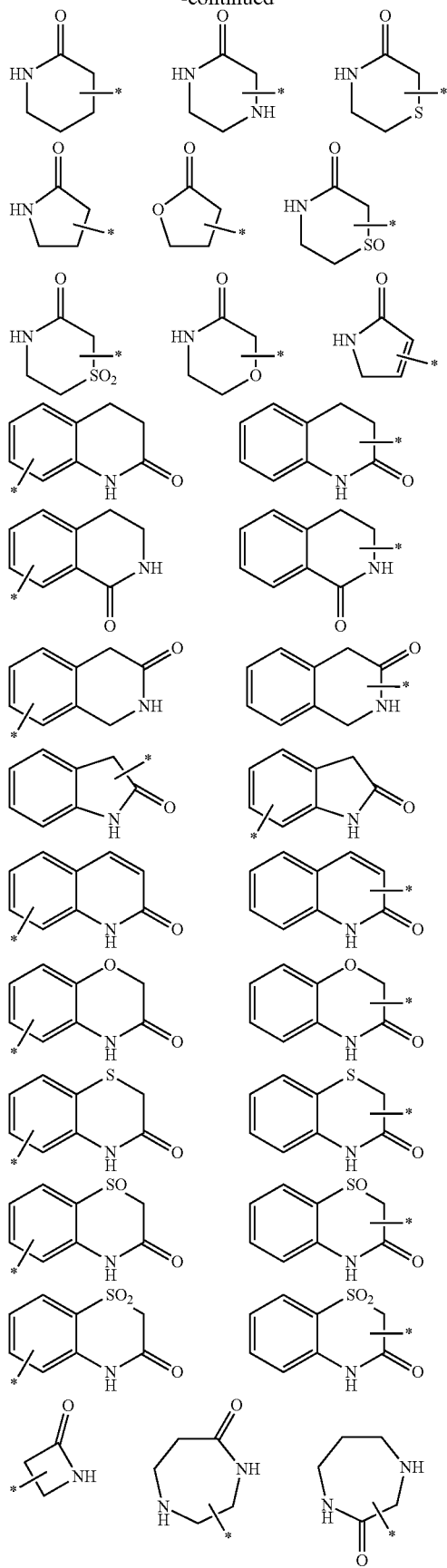
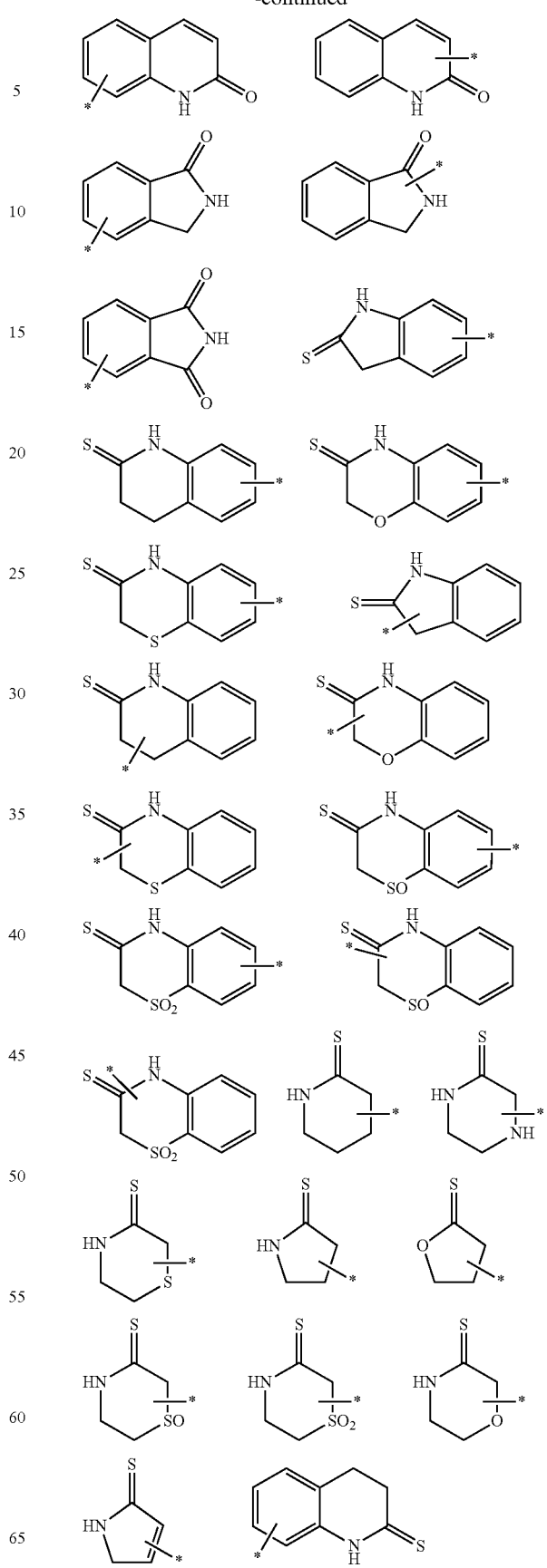

where in each case where an NH is present the bond with the asterisk connecting the respective heterocyclyl moiety to the rest of the molecule the H may be replaced with said bond and/or the H may be replaced by a substituent, preferably as defined above. Especially preferred as heterocyclyl is pyrrolyl, furanyl, thienyl, pyrimidinyl, pyrazolyl, pyrazolidinonyl (=oxo-pyrazolidinyl), triazolyl, tetrazolyl, oxetidinyl, pyridyl, pyrimidinyl, morpholino, piperidinyl, piperazinyl, tetrahydrofuran-onyl (=oxo-tetrahydrofuranyl), tetrahydropyranyl, indolyl, indazolyl, 1H-indazanyl, benzofuranyl, benzothiophenyl, quinolinyl, isoquinolinyl, 1,2,3,4-tetrahydro-1,4-benzoxazinyl, 2H-1,4-benzoxazin-3(4H)-onyl, 2H,3H-1,4-benzodioxinyl, benzo[1,2,5]oxadiazolyl or thiophenyl, each of which is unsubstituted or substituted by one or more, e.g. up to three, substituents as mentioned above for substituted aryl, preferably independently selected from the group consisting of $C_1$-$C_7$-alkyl, hydroxy-$C_1$-$C_7$-alkyl, $C_1$-$C_7$-alkoxy-$C_1$-$C_7$-alkyl, $C_1$-$C_7$-alkoxy-$C_1$-$C_7$-alkoxy-$C_1$-$C_7$-alkyl, $C_1$-$C_7$-alkanoyloxy-$C_1$-$C_7$-alkyl, amino-$C_1$-$C_7$-alkyl, $C_1$-$C_7$-alkoxy-$C_1$-$C_7$-alkylamino-$C_1$-$C_7$-alkyl, $C_1$-$C_7$-alkanoylamino-$C_1$-$C_7$-alkyl, carboxy-$C_1$-$C_7$-alkyl, $C_1$-$C_7$-alkyloxycarbonyl-$C_1$-$C_7$-alkyl, $C_1$-$C_7$-alkylsulfonylamino-$C_1$-$C_7$-alkyl, halo, hydroxy, $C_1$-$C_7$-alkoxy, $C_1$-$C_7$-alkoxy-$C_1$-$C_7$-alkoxy, amino-$C_1$-$C_7$-alkoxy, N—$C_1$-$C_7$-alkanoylamino-$C_1$-$C_7$-alkoxy, carbamoyl-$C_1$-$C_7$-alkoxy, N—$C_1$-$C_7$-alkylcarbamoyl-$C_1$-$C_7$-alkoxy, N-mono- or N,N-di-($C_1$-$C_7$-alkyl, phenyl, naphthyl, phenyl-$C_1$-$C_7$-alkyl and/or naphthyl-$C_1$-$C_7$-alkyl)-amino, $C_1$-$C_7$-alkanoyl, $C_1$-$C_7$-alkoxy-$C_1$-$C_7$-alkanoyl, carboxy, $C_1$-$C_7$-alkyloxycarbonyl-$C_1$-$C_7$-alkoxy, $C_1$-$C_7$-alkoxy-$C_1$-$C_7$-alkylcarbonyl, carbamoyl and N—$C_1$-$C_7$-alkoxy-$C_1$-$C_7$-alkylcarbamoyl. In the case of heterocycles including an NH ring member, the substitutents, as far as bound via a carbon or oxygen atom, can preferably be bound at the nitrogen instead of an H.

Unsubstituted or substituted cycloalkyl is preferably mono- or polycyclic, more preferably monocyclic, $C_3$-$C_{10}$-cycloalkyl which may include one or more double (e.g. in cycloalkenyl) and/or triple bonds (e.g. in cycloalkynyl), and is unsubstituted or substituted by one or more, e.g. one to three substitutents preferably independently selected from those mentioned above as substituents for aryl. Preferred is cyclopropyl, cyclobutyl, cyclopentyl, cyclohexyl or cycloheptyl.

Acyl is preferably unsubstituted or substituted aryl-carbonyl or -sulfonyl, unsubstituted or substituted heterocyclylcarbonyl or -sulfonyl, unsubstituted or substituted cycloalkylcarbonyl or -sulfonyl, formyl or unsubstituted or substituted alkylcarbonyl or -sulfonyl, wherein unsubstituted or substituted aryl, unsubstituted or substituted heterocyclyl, unsubstituted or substituted cycloalkyl and unsubstituted or substituted alkyl are preferably as described above. Preferred is $C_1$-$C_7$-alkanoyl. $R_2$ preferably has one of the meanings given herein other than acyl.

Etherified or esterified hydroxy is especially hydroxy that is esterified with acyl as defined above, especially in lower alkanoyloxy; or preferably etherified with alkyl, alkenyl, alkynyl, aryl, heterocyclyl or cycloalkyl each of which is unsubstituted or substituted and is preferably as described above for the corresponding unsubstituted or substituted moieties. Especially preferred is unsubstituted or especially substituted $C_1$-$C_7$-alkyloxy, especially with a substituent selected from $C_1$-$C_7$-alkoxy; phenyl, tetrazolyl, tetrahydrofuran-onyl, oxetidinyl, 3-($C_1$-$C_7$-alkyl)-oxetidinyl, pyridyl or 2H,3H-1,4-benzodioxinyl, each of which is unsubstituted or substituted by one or more, preferably up to three, e.g. 1 or two substituents independently selected from $C_1$-$C_7$-alkyl, hydroxy, $C_1$-$C_7$-alkoxy, phenyloxy wherein phenyl is unsubstituted or substituted by $C_1$-$C_7$-alkoxy and/or halo, phenyl-$C_1$-$C_7$-alkoxy wherein phenyl is unsubstituted or substituted by $C_1$-$C_7$-alkoxy and/or halo, halo, amino, N-mono- or N,N-di($C_1$-$C_7$-alkyl, phenyl, naphthyl, phenyl-$C_1$-$C_7$-alkyl or naphthyl-$C_1$-$C_7$-alkyl)amino, $C_1$-$C_7$-alkanoylamino, carboxy, N-mono- or N,N-di($C_1$-$C_7$-alkyl, phenyl, naphthyl, phenyl-$C_1$-$C_7$-alkyl or naphthyl-$C_1$-$C_7$-alkyl)-aminocarbonyl, morpholino, morpholino-$C_1$-$C_7$-alkoxy, pyridyl-$C_1$-$C_7$-alkoxy, pyrazolyl, 4-$C_1$-$C_7$-alkylpiperidin-1-yl and cyano;

unsubstituted or substituted aryloxy with unsubstituted or substituted aryl as described above, especially phenyloxy with phenyl that is unsubstituted or substituted as just described; or unsubstituted or substituted heterocyclyloxy with unsubstituted or substituted heterocyclyl as described above, preferably tetrahydropyranyloxy.

Substituted mercapto can be mercapto that is thioesterified with acyl as defined above, especially with lower alkanoyloxy; or preferably thioetherified with alkyl, alkenyl, alkynyl, aryl, heterocyclyl or cycloalkyl each of which is unsubstituted or substituted and is preferably as described above for the corresponding unsubstituted or substituted moieties. Especially preferred is unsubstituted or especially substituted $C_1$-$C_7$-alkylthio or unsubstituted or substituted arylthio with unsubstituted or substituted $C_1$-$C_7$-alkyl or aryl as just described for the corresponding moieties under etherified hydroxy.

Substituted sulfinyl or sulfonyl can be substituted with alkyl, alkenyl, alkynyl, aryl, heterocyclyl or cycloalkyl each of which is unsubstituted or substituted and is preferably as described above for the corresponding unsubstituted or substituted moieties. Especially preferred is unsubstituted or especially substituted $C_1$-$C_7$-alkylsulfinyl ($C_1$-$C_7$-alkyl-SO—) or -sulfonyl ($C_1$-$C_7$-alkyl-$SO_2$—) or unsubstituted or substituted arylsulfinyl or -sulfonyl with unsubstituted or substituted $C_1$-$C_7$-alkyl or aryl as just described for the corresponding moieties under etherified hydroxy.

In mono- or di-substituted amino, amino is preferably substituted by one or more substituents selected from one acyl, especially $C_1$-$C_7$-alkanoyl, phenylcarbonyl (=benzoyl), $C_1$-$C_7$-alkylsulfonyl or phenylsulfonyl wherein phenyl is unsubstituted or substituted by one to 3 $C_1$-$C_7$-alkyl groups, and one or two moieties selected from alkyl, alkenyl, alkynyl, aryl, heterocyclyl and cycloalkyl each of which is unsubstituted or substituted and is preferably as described above for the corresponding unsubstituted or substituted moieties. Preferred is $C_1$-$C_7$-alkanoylamino, mono- or di-(phenyl, naphthyl, $C_1$-$C_7$-alkoxy-phenyl, $C_1$-$C_7$-alkoxynaphthyl, naphthyl-$C_1$-$C_7$-alkyl or phenyl-$C_1$-$C_7$-alkyl)-carbonylamino (e.g. 4-methoxybenzoylamino), mono- or di-($C_1$-$C_7$-alkyl and/or $C_1$-$C_7$-alkoxy-$C_1$-$C_7$-alkyl)-amino or mono- or di-(phenyl, naphthyl, $C_1$-$C_7$-alkoxy-phenyl, $C_1$-$C_7$-alkoxynaphthyl, phenyl-$C_1$-$C_7$-alkyl, naphthyl-$C_1$-$C_7$-alkyl, $C_1$-$C_7$-alkoxy-naphthyl-$C_1$-$C_7$-alkyl or $C_1$-$C_7$-alkoxy-phenyl-$C_1$-$C_7$-alkyl)-amino.

Esterified carboxy is preferably alkyloxycarbonyl, aryloxycarbonyl, heterocyclyloxycarbonyl or cycloalkyloxycarbonyl, wherein alkyl, aryl, heterocyclyl and cycloalkyl are unsubstituted or substituted and the corresponding moieties and their substituents are preferably as described above. Preferred is $C_1$-$C_7$-alkoxycarbonyl, phenyl-$C_1$-$C_7$-alkoxycarbonyl, naphthyl-$C_1$-$C_7$-alkoxycarbonyl, phenoxycarbonyl or naphthoxycarbonyl.

In amidated carboxy, the amino part bound to the carbonyl in the amido function ($D_2$N—C(=O)—) wherein each D is independently of the other hydrogen or an amino substituent) is unsubstituted or substituted as described for substituted amino, but preferably without acyl as amino substituent. Preferred is mono- or di-($C_1$-$C_7$-alkyl and/or $C_1$-$C_7$-alkoxy-$C_1$-$C_7$-alkyl)-aminocarbonyl or mono- or di-($C_1$-$C_7$-alkyloxyphenyl, $C_1$-$C_7$-alkyloxynaphthyl, naphthyl-$C_1$-$C_7$-alkyl or phenyl-$C_1$-$C_7$-alkyl)-aminocarbonyl.

In substituted sulfamoyl, the amino part bound to the sulfonyl in the sulfamoyl function ($D_2$N—S(=O)$_2$—) wherein each D is independently of the other hydrogen or an amino substituent) is unsubstituted or substituted as described for substituted amino, but preferably without acyl as amino substituent. Preferred is mono- or di-($C_1$-$C_7$-alkyl and/or $C_1$-$C_7$-alkoxy-$C_1$-$C_7$-alkyl)-aminosulfonyl or mono- or di-($C_1$-$C_7$-alkyloxyphenyl, $C_1$-$C_7$-alkyloxynaphthyl, naphthyl-$C_1$-$C_7$-alkyl or phenyl-$C_1$-$C_7$-alkyl)-aminosulfonyl.

Unsubstituted or substituted $C_1$-$C_7$-alkyl, unsubstituted or substituted $C_2$-$C_7$-alkenyl and unsubstituted or substituted $C_2$-$C_7$-alkynyl and their substituents are defined as above under the corresponding (un)substituted alkyl, (un)substituted alkinyl and (un)substituted alkynyl moieties but with the given number of carbon atoms in the alkyl, alkenyl or alkynyl moieties.

Preferred Definitions for R1

As R1, hydrogen, $C_1$-$C_7$-alkyl, di-(phenyl)-$C_1$-$C_7$-alkyl or $C_3$-$C_8$-cyclopropyl is especially preferred. R1 is more preferably $C_3$-$C_8$-cycloalkyl, still more preferably $C_3$-, $C_4$-, $C_5$- or $C_6$-cycloalkyl, most preferably cyclopropyl.

Preferred Definitions for R2

As R2, these or preferably any other mentioned moieties mentioned herein as falling under the definition of R2 are preferred.

In a first embodiment R2 is preferably unsubstituted or substituted alkyl.

Preferred examples for alkyl are branched or straight chain $C_1$-$C_7$-alkyl which may be substituted or unsubstituted. Preferred examples include methyl, ethyl, isopropyl, n-propyl, n-butyl, sec-butyl or tert-butyl, more preferably methyl, ethyl or isopropyl, most preferably methyl. The alkyl moiety is preferably substituted. When the alkyl moiety is substituted, it is preferably mono-, di- or tri-substituted, more preferably mono-substituted. Suitable substituents for the alkyl moiety are as defined herein, preferably O—$C_1$-$C_4$-alkyl, halo, hydroxy, unsubstituted or substituted, preferably substituted, phenyl, unsubstituted or substituted, preferably substituted, naphthyl, unsubstituted or substituted, preferably substituted, phenyl- or naphthyloxy, unsubstituted or substituted, preferably substituted, phenyl- or naphthyl-$C_1$-$C_7$-alkyloxy, unsubstituted or substituted, preferably substituted, heterocyclcl, unsubstituted or substituted, preferably unsubstituted, cycloalkyl, nitro, amino, amino-$C_1$-$C_7$-alkyl, N-mono- or N,N-di-substituted aminocarbonyl, carboxyl, and cyano, more preferably unsubstituted or substituted, preferably substituted, phenyl, unsubstituted or substituted, preferably substituted, naphthyl, unsubstituted or substituted, preferably substituted, phenyl- or naphthyloxy, or unsubstituted or substituted, preferably substituted, heterocyclycl. The heterocyclyl moietyl is in this connection preferably mono- or bicyclic. Preferred are aromatic ring systems, or in particular if a bicyclic moiety is contemplated, partially saturated ring systems, in particular whereby one of the rings is aromatic and the other is saturated or partially saturated, most preferred are aromatic. The heterocyclyl moiety has preferably 1, 2 or 3, more preferably 1 or 2, most preferably 1, heteroatoms selected from O, N or S, more preferably S or N. Particularly preferred examples include 6-membered rings preferably containing a nitrogen atom, in particular pyridyl; or bicyclic ring systems preferably containing a N or S atom, in particular indolyl, 1H-indazolyl, quinolyl, isoquinolyl, 1,2,3,4-tetrahydro-1,4-benzoxazinyl, 2H-1,4-benzoxazin-3(4H)-onyl, 9-xanthenyl, or 1-benzothiophenyl, where each moiety mentioned above as being substituted, in particular phenyl, naphthyl, pyridyl, indolyl, 1H-indazolyl, quinolyl, isoquinolyl, 1,2,3,4-tetrahydro-1,4-benzoxazinyl, 2H-1,4-benzoxazin-3 (4H)-onyl or 1-benzothiophenyl is unsubstituted or substituted by one or more, e.g. up to three, substituents independently selected from the group consisting of $C_1$-$C_7$-alkyl, hydroxy-$C_1$-$C_7$-alkyl, $C_1$-$C_7$-alkoxy-$C_1$-$C_7$-alkyl, $C_1$-$C_7$-alkoxy-$C_1$-$C_7$-alkoxy-$C_1$-$C_7$-alkyl, $C_1$-$C_7$-alkanoyloxy-$C_1$-$C_7$-alkyl, amino-$C_1$-$C_7$-alkyl, $C_1$-$C_7$-alkoxy-$C_1$-$C_7$-alkylamino-$C_1$-$C_7$-alkyl, $C_1$-$C_7$-alkanoylamino-$C_1$-$C_7$-alkyl, $C_1$-$C_7$-alkylsulfonylamino-$C_1$-$C_7$-alkyl, carboxy-$C_1$-$C_7$-alkyl, $C_1$-$C_7$-alkoxycarbonyl-$C_1$-$C_7$-alkyl, halo, hydroxy, $C_1$-$C_7$-alkoxy, $C_1$-$C_7$-alkoxy-$C_1$-$C_7$-alkoxy, carboxy-$C_1$-$C_7$-alkoxy, amino-$C_1$-$C_7$-alkoxy, N—$C_1$-$C_7$-alkanoylamino-$C_1$-$C_7$-alkoxy, carbamoyl-$C_1$-$C_7$-alkyl, carbamoyl-$C_1$-$C_7$-alkoxy, N—$C_1$-$C_7$-alkylcarbamoyl-$C_1$-$C_7$-alkoxy, $C_1$-$C_7$-alkanoyl, $C_1$-$C_7$-alkyloxy-$C_1$-$C_7$-alkanoyl, $C_1$-$C_7$-alkoxy-$C_1$-$C_7$-alkanoyl, carboxyl, carbamoyl and N—$C_1$-$C_7$-alkoxy-$C_1$-$C_7$-alkylcarbamoyl, more preferably $C_1$-$C_7$-alkyl, hydroxy-$C_1$-$C_7$-alkyl, $C_1$-$C_7$-alkoxy-$C_1$-$C_7$-alkyl, halo, $C_1$-$C_7$-alkoxy, $C_1$-$C_7$-alkoxy-$C_1$-$C_7$-alkoxy, carboxy-$C_1$-$C_7$-alkoxy, and, carbamoyl-$C_1$-$C_7$-alkyl, in particular methyl, hydroxy-propyl, hydroxyl-butyl, methoxy-propyl, Cl, F, methoxy, methoxy-propyloxy, carboxy-ethyloxy and, carbamoyl-propyl. The heterocyclyl moiety is preferably substituted on the N, if present.

In a second embodiment R2 is preferably unsubstituted or substituted aryl.

Preferred examples of aryl include phenyl or naphthyl, more preferably phenyl. When the aryl moiety is substituted, it is preferably mono- or di-substituted. Most preferably aryl is di-substituted. Suitable substituents are as defined herein, preferably $C_1$-$C_7$-alkyl, alkyl, halo-$C_1$-$C_7$-alkyl, —O-halo-$C_1$-$C_7$-alkyl, halo, hydroxy, nitro, amino, amino-$C_1$-$C_7$-alkyl, carboxyl, cyano, hydroxy-$C_1$-$C_7$-alkyl, $C_1$-$C_7$-alkoxy-$C_1$-$C_7$-alkoxy-$C_1$-$C_7$-alkoxy-$C_1$-$C_7$-alkoxy , $C_1$-$C_7$-alkanoyloxy-$C_1$-$C_7$-alkyl, $C_1$-$C_7$-alkoxy-$C_1$-$C_7$-alkylamino-$C_1$-$C_7$-alkanoylamino-$C_1$-$C_7$-alkyl, $C_1$-$C_7$-alkanoylamino, N—$C_1$-$C_7$-alkoxy-$C_1$-$C_7$-alkyl-amino, N—$C_1$-$C_7$-alkanoyl-N—$C_1$-$C_7$-alkoxy-$C_1$-$C_7$-alkyl-amino, $C_1$-$C_7$-alkylsulfonylamino-$C_1$-$C_7$-alkyl, carboxy-$C_1$-$C_7$-alkyl, $C_1$-$C_7$-alkoxycarbonyl-$C_1$-$C_7$-alkyl, $C_1$-$C_7$-alkoxy-$C_1$-$C_7$-alkoxy, amino-$C_1$-$C_7$-alkoxy, N—$C_1$-$C_7$-alkanoylamino-$C_1$-$C_7$-alkoxy, carbamoyl-$C_1$-$C_7$-alkyl, N—$C_1$-$C_7$-alkylcarbamoyl-$C_1$-$C_7$-alkyl, N—$C_1$-$C_7$-haloalkylcarbamoyl-$C_1$-$C_7$-alkyl, carbamoyl-$C_1$-$C_7$-alkoxy, N—$C_1$-$C_7$-alkylcarbamoyl-$C_1$-$C_7$-alkoxy, $C_1$-$C_7$-alkanoyl, $C_1$-$C_7$-alkyloxy-$C_1$-$C_7$-alkanoyl, $C_1$-$C_7$-alkoxy-$C_1$-$C_7$-alkanoyl, carbamoyl and N—$C_1$-$C_7$-alkoxy-$C_1$-$C_7$-alkylcarbamoyl, more preferably $C_1$-$C_7$-alkyl, halo-$C_1$-$C_7$-alkyl, halo, cyano, hydroxy-$C_1$-$C_7$-alkyl, $C_1$-$C_7$-alkoxy-$C_1$-$C_7$-alkoxy, $C_1$-$C_7$-alkanoylamino-$C_1$-$C_7$-alkyl, $C_1$-$C_7$-alkanoylamino, N—$C_1$-$C_7$-alkoxy-$C_1$-$C_7$-alkyl-amino, N—$C_1$-$C_7$-alkanoyl-N—$C_1$-$C_7$-alkoxy-$C_1$-$C_7$-alkyl-amino, in particular, methyl, O-methyl, Cl, Br, CN, methoxypropyloxy, N(methoxypropyl)-amino, N(acetyl)-amino, and N(methoxypropyl)(acetyl)-amino.

In a third embodiment R2 is preferably unsubstituted or substituted heterocyclyl.

The heterocyclyl moietyl preferably mono- or bicyclic, more preferably bicyclic. Preferred are aromatic ring systems, or partially saturated ring systems, in particular whereby one of the rings is aromatic and the other is saturated or partially saturated, most preferred are partially saturated. The heterocyclyl moiety has preferably 1, 2 or 3, more preferably 1 or 2, most preferably 2, heteroatoms selected from O, N or S, more preferably O or N. The ring system contains preferably an oxo moiety. Particularly preferred examples include bicyclic 10-membered rings preferably containing a nitrogen atom, in particular, quinolyl, isoquinolyl, 1,2,3,4-tetrahydro-1,4-benzoxazinyl, 2H-1,4-benzoxazin-3(4H)-only, 3,4-dihydro-1H-quinolin-2-onyl, or 4H-benzo[1,4]thiazin-3-onyl; or bicyclic 9-membered ring systems preferably containing a N atom, in particular indolyl, 1H-indazolyl, benzothiophenyl, imidazo[1,2-a]pyridyl or 3H-benzooxazol-2-onyl, where each heterocyclyl is unsubstituted or substituted by one or more, e.g. up to three, substituents independently selected from the group consisting of $C_1$-$C_7$-alkyl, hydroxy-$C_1$-$C_7$-alkyl, $C_1$-$C_7$-alkoxy-$C_1$-$C_7$-alkyl, $C_1$-$C_7$-alkoxy-$C_1$-$C_7$-alkoxy-$C_1$-$C_7$-alkyl, $C_1$-$C_7$-alkanoyloxy-$C_1$-$C_7$-alkyl, amino-$C_1$-$C_7$-alkyl, $C_1$-$C_7$-alkoxy-$C_1$-$C_7$-alkylamino-$C_1$-$C_7$-alkyl, $C_1$-$C_7$-alkanoylamino-$C_1$-$C_7$-alkyl, $C_1$-$C_7$-alkylsulfonylamino-$C_1$-$C_7$-alkyl, carboxy-$C_1$-$C_7$-alkyl, $C_1$-$C_7$-alkoxycarbonyl-$C_1$-$C_7$-alkyl, halo, hydroxy, $C_1$-$C_7$-alkoxy, $C_1$-$C_7$-alkoxy-$C_1$-$C_7$-alkoxy, carboxy-$C_1$-$C_7$-alkoxy, amino-$C_1$-$C_7$-alkoxy, N—$C_1$-$C_7$-alkanoylamino-$C_1$-$C_7$-alkoxy, carbamoyl-$C_1$-$C_7$-alkyl, carbamoyl-$C_1$-$C_7$-alkoxy, N—$C_1$-$C_7$-alkylcarbamoyl-$C_1$-$C_7$-alkoxy, $C_1$-$C_7$-alkanoyl, $C_1$-$C_7$-alkyloxy-$C_1$-$C_7$-alkanoyl, $C_1$-$C_7$-alkoxy-$C_1$-$C_7$-alkanoyl, carboxyl, carbamoyl and N—$C_1$-$C_7$-alkoxy-$C_1$-$C_7$-alkylcarbamoyl, more preferably $C_1$-$C_7$-alkyl, halo, hydroxy-$C_1$-$C_7$-alkyl, $C_1$-$C_7$-alkoxy-$C_1$-$C_7$-alkyl, $C_1$-$C_7$-alkanoylamino-$C_1$-$C_7$-alkyl, alkoxy-$C_1$-$C_7$-alkoxy, carbamoyl-$C_1$-$C_7$-alkyl, N—$C_1$-$C_7$-alkylcarbamoyl-$C_1$-$C_7$-alkyl, haloalkylcarbamoyl-$C_1$-$C_7$-alkyl, in particular methyl, pentyl, methoxy-propyl, methoxy-butyl, ethoxy-ethyl, hydroxy-butyl, methoxypropyloxy, F, $CH_3$—C(O)—NH—$CH_2CH_2$, $NH_2$—CO—$CH_2CH_2CH_2$, $N(CH_2CH_3)$—CO—$CH_2$, $N(CH_2CF_3)$—CO—$CH_2$. The heterocyclyl moiety is preferably substituted on the N if present.

Thus preferably R2 is phenyl-$C_1$-$C_7$-alkyl, di-(phenyl)-$C_1$-$C_7$-alkyl, naphthyl-$C_1$-$C_7$-alkyl, phenyl, naphthyl, quinolyl-1,2,3,4-tetrahydro-1,4-benzoxazinyl-$C_1$-$C_7$-alkyl, 2H-1,4-benzoxazin-3(4H)-onyl-$C_1$-$C_7$-alkyl, 9-xanthenyl-$C_1$-$C_7$-alkyl, 1-benzothiophenyl-$C_1$-$C_7$-alkyl, pyridyl, indolyl, 1H-indazolyl, quinolyl, isoquinolyl, 1,2,3,4-tetrahydro-1,4-benzoxazinyl, 2H-1,4-benzoxazin-3(4H)-onyl, 9-xanthenyl or 1-benzothiophenyl, 3,4-Dihydro-1H-quinolin-2-onyl, 4H-Benzo[1,4]thiazin-3-onyl, 3H-benzooxazol-2-onyl, where each phenyl, naphthyl, pyridyl, indolyl, 1H-indazolyl, quinolyl, isoquinolyl, 1,2,3,4-tetrahydro-1,4-benzoxazinyl, 2H-1,4-benzoxazin-3(4H)-onyl or 1-benzothiophenyl is unsubstituted or substituted by one or more, e.g. up to three, substituents independently selected from the group consisting of $C_1$-$C_7$-alkyl, hydroxy-$C_1$-$C_7$-alkyl, $C_1$-$C_7$-alkoxy-$C_1$-$C_7$-alkyl, $C_1$-$C_7$-alkoxy-$C_1$-$C_7$-alkoxy-$C_1$-$C_7$-alkyl, $C_1$-$C_7$-alkanoyloxy-$C_1$-$C_7$-alkyl, $C_1$-$C_7$-alkoxy-$C_1$-$C_7$-alkylamino-$C_1$-$C_7$-alkyl, $C_1$-$C_7$-alkanoylamino-$C_1$-$C_7$-alkyl, $C_1$-$C_7$-alkylsulfonylamino-$C_1$-$C_7$-alkyl, carboxy-$C_1$-$C_7$-alkyl, $C_1$-$C_7$-alkoxycarbonyl-$C_1$-$C_7$-alkyl, halo, hydroxy, $C_1$-$C_7$-alkoxy, $C_1$-$C_7$-alkoxy-$C_1$-$C_7$-alkoxy, amino-$C_1$-$C_7$-alkoxy, N—$C_1$-$C_7$-alkanoylamino-$C_1$-$C_7$-alkoxy, carbamoyl-$C_1$-$C_7$-alkoxy, N—$C_1$-$C_7$-alkylcarbamoyl-$C_1$-$C_7$-alkoxy, $C_1$-$C_7$-alkanoyl, $C_1$-$C_7$-alkyloxy-$C_1$-$C_7$-alkanoyl, $C_1$-$C_7$-alkoxy-$C_1$-$C_7$-alkanoyl, carboxyl, carbamoyl and N—$C_1$-$C_7$-alkoxy-$C_1$-$C_7$-alkylcarbamoyl; more preferably R2 is phenyl-$C_1$-$C_7$-alkyl, di-(phenyl)-$C_1$-$C_7$-alkyl, phenyl, indolyl-$C_1$-$C_7$-alkyl, 1H-9-xanthenyl-$C_1$-$C_7$-alkyl, 1,2,3,4-tetrahydro-1,4-benzoxazinyl or 2H-1,4-benzoxazin-3(4H)-onyl, where each phenyl, indolyl, 1H-indazolyl, 1,2,3,4-tetrahydro-1,4-benzoxazinyl, 2H-1,4-benzoxazin-3(4H)-only or 9-xanthenyl is unsubstituted or substituted by up to three substituents independently selected from the group consisting of $C_1$-$C_7$-alkyl, $C_1$-$C_7$-alkoxy-$C_1$-$C_7$-alkyl, $C_1$-$C_7$-alkoxy-$C_1$-$C_7$-alkoxy- $C_1$-$C_7$-alkyl, $C_1$-$C_7$-alkanoylamino-$C_1$-$C_7$-alkyl, $C_1$-$C_7$-alkylsulfonylamino-$C_1$-$C_7$-alkyl, carboxy-$C_1$-$C_7$-alkyl, $C_1$-$C_7$-alkoxycarbonyl-$C_1$-$C_7$-alkyl, halo, $C_1$-$C_7$-alkoxy, $C_1$-$C_7$-alkoxy-$C_1$-$C_7$-alkoxy and $C_1$-$C_7$-alkyloxy-$C_1$-$C_7$-alkanoyl.
Particularly preferred examples for R2 are
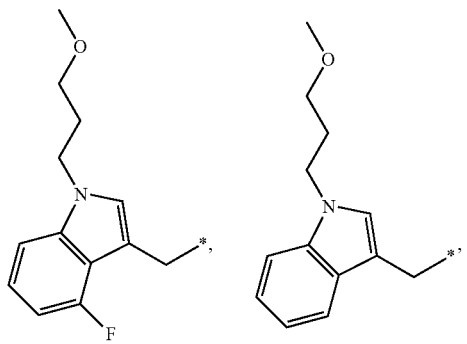
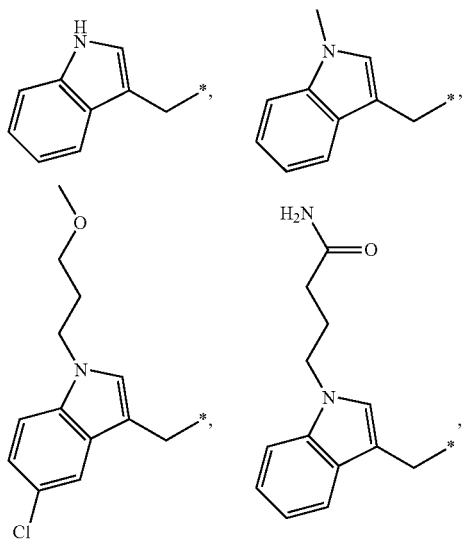
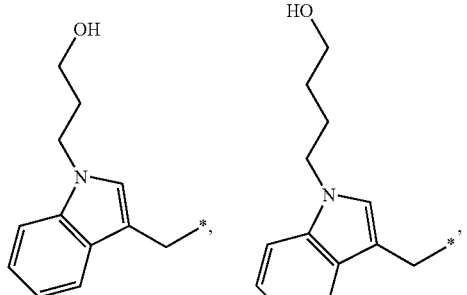
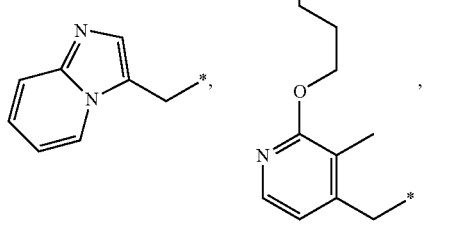
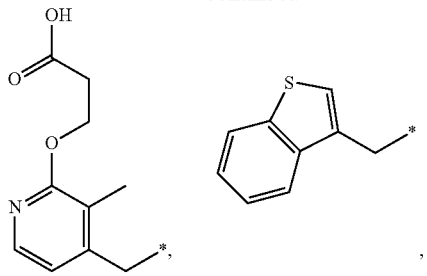
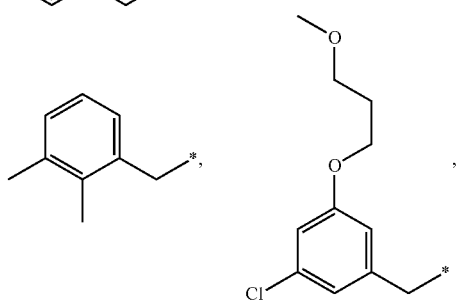
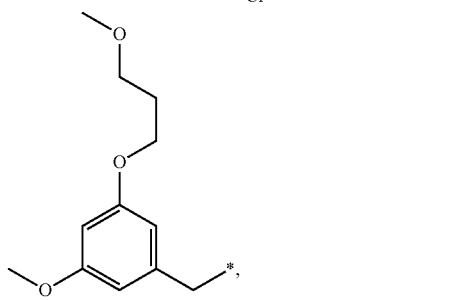
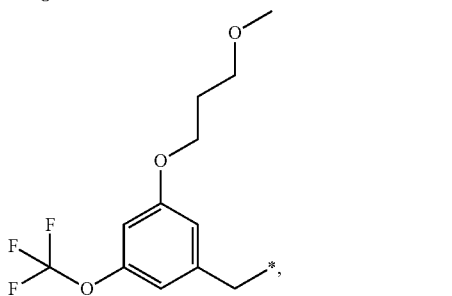
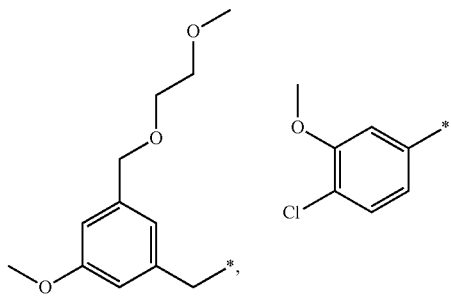
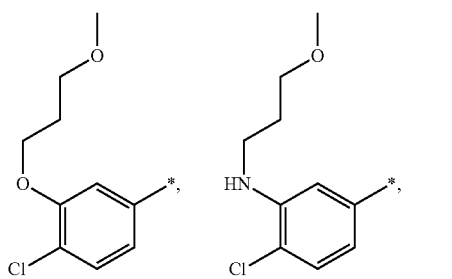

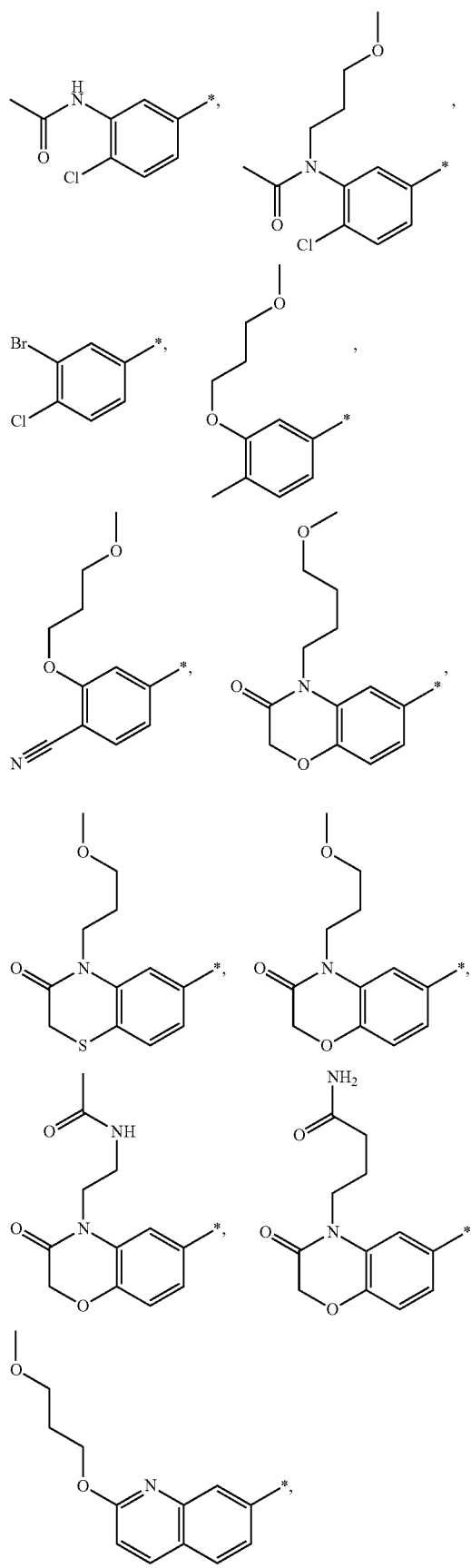
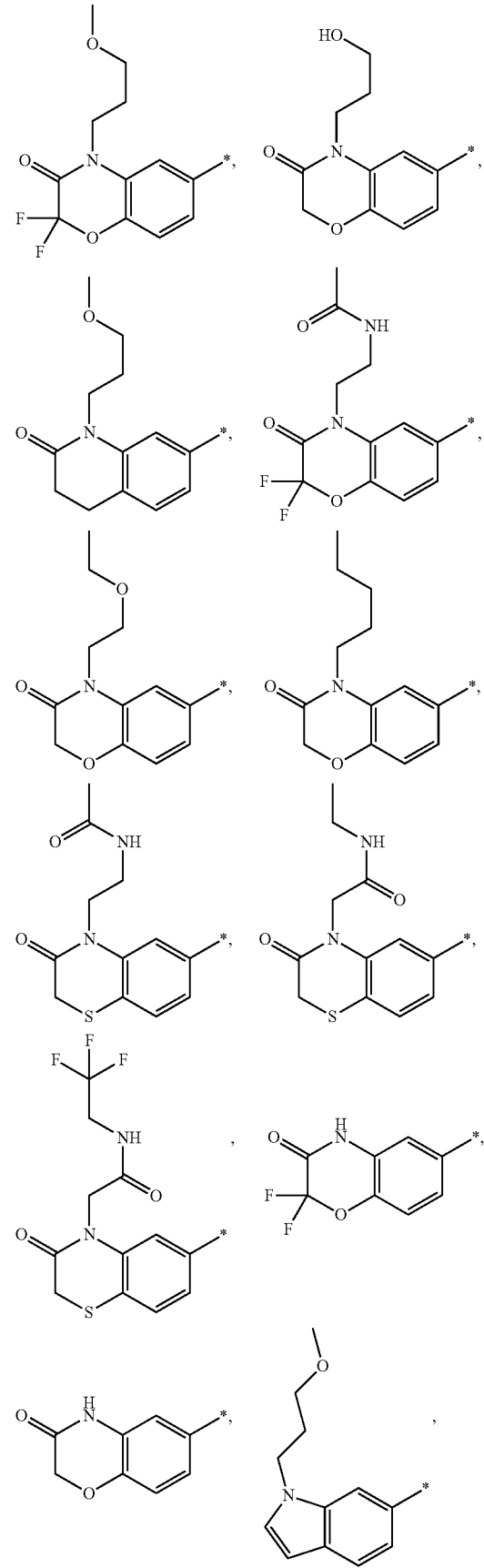

-continued

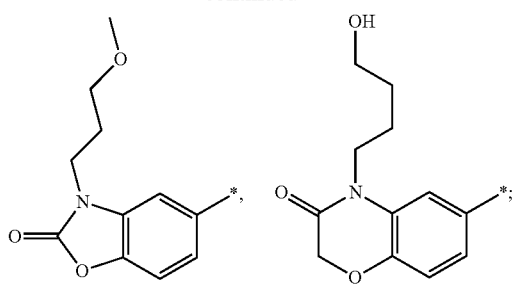

most preferred are

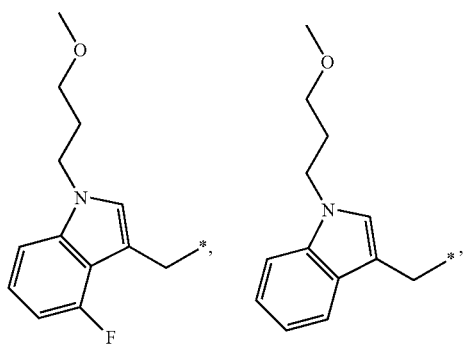

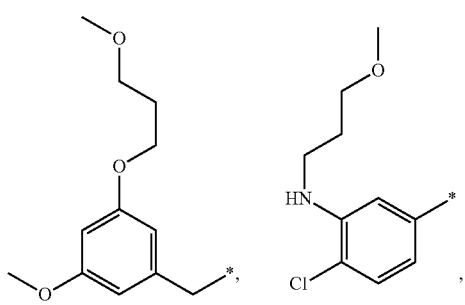

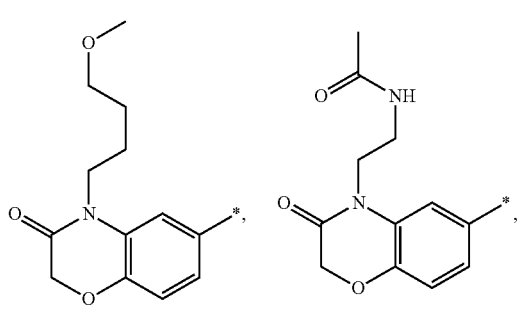

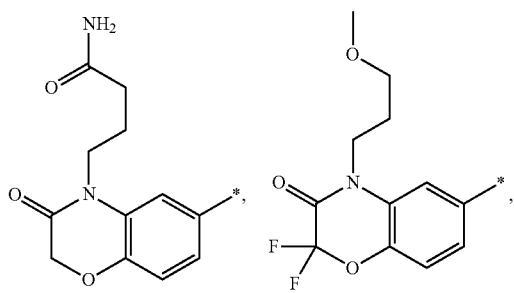

-continued

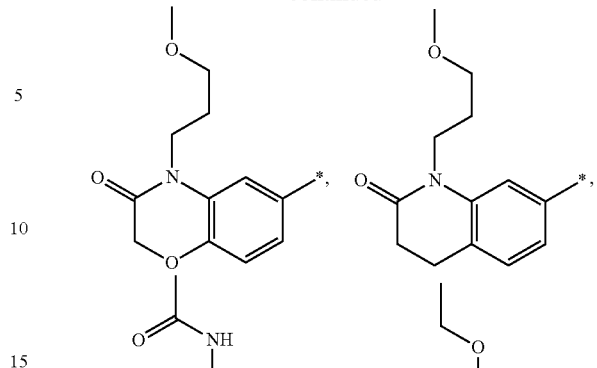

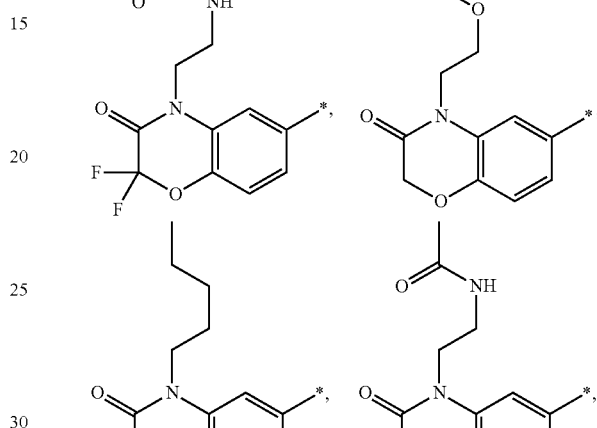

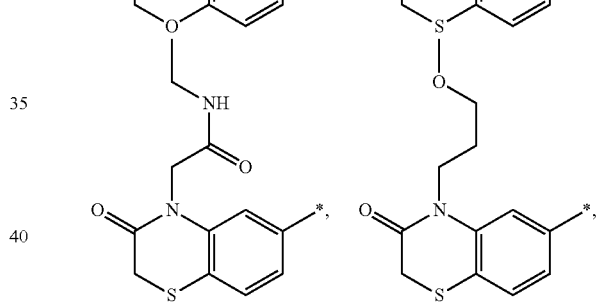

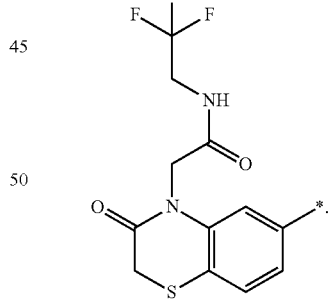

Preferred Definitions for W

In a moiety W of the formula IA, preferably one of $X_1$ and $X_2$ is nitrogen or CH, while the other and $X_3$, $X_4$ and $X_5$ are CH.

In a moiety W of the formula IB, preferably $X_4$ is $CH_2$, NH, S or O and one of $X_1$, $X_2$ and (preferably if $X_4$ is $CH_2$ or N) $X_3$, more preferably $X_2$, is N, while the others are each CH, with the proviso that at least one ring nitrogen (N or in the case or $X_4$NH) is present. R3 is then preferably bound to $X_3$ instead of a hydrogen.

In a moiety W if the formula IC, preferably $X_1$ is $CH_2$, NH, S or O and one of $X_2$, $X_3$ and $X_4$ is N, while the others are CH, with the proviso that at least one ring nitrogen (N or in the case or $X_1$NH) is present. R3 is then preferably bound to $X_2$ or more preferably to $X_3$ or to $X_4$ instead of a hydrogen.

The skilled person will understand that a substituent R3 (and, where present, R4) can only be present at the position of and instead of a hydrogen bound to a ring member $X_1$ to $X_4$ selected from CH, $CH_2$ or NH so that only four-bonded carbon or three-bonded nitrogen (which, in the case of salt formation, may however be protonated to become four-bonded and then positively charged).

In a first embodiment W is preferably a moiety of the formula IA,

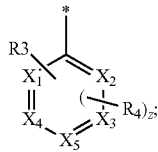

(IA)

wherein the asterisk (*) denotes the position where the moiety W is bound to the 4-carbon in the piperidine ring in formula I, and wherein one of $X_1$ and $X_2$ is nitrogen or CH, while the other and $X_3$, $X_4$ and $X_5$ are CH; with the proviso that R3 is bound to $X_1$ or $X_2$ or preferably to $X_3$ or $X_4$. Preferably all of $X_1$, $X_2$, $X_3$, $X_4$ and $X_5$ are CH.

In a second embodiment W is preferably a moiety of the formula IC,

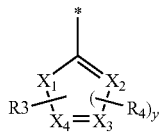

(IC)

wherein the asterisk (*) denotes the position where the moiety W is bound to the 4-carbon in the piperidine ring in formula I, and wherein $X_1$ is $CH_2$, NH, S or O and one of $X_2$, $X_3$ and $X_4$ is N, while the others are CH, with the proviso that at least one ring nitrogen (N or in the case or $X_1$NH) is present, preferably $X_1$ is O, $X_2$ is CH or N, more preferably N, $X_3$ is CH and $X_4$ is CH or N, more preferably CH, with the proviso that not more than one of $X_2$ and $X_4$ is N; and with the proviso that R3 is bound to $X_2$ or preferably to $X_3$ or $X_4$.

When W is a moiety of formula (IC), R3 is preferably aryl as defined herein, more preferably unsubstituted or substituted phenyl as described below for R3, most preferably unsubstituted phenyl.

Most preferably, W is a moiety of formula (IA) such as phenyl.

Preferred Definitions for y and z y is 0, 1, 2 or 3, preferably 0 or 1, most preferably 0, and z is 0, 1, 2, 3 or 4, preferably 0 or 1.

Preferred Definitions for $R_3$

As $R_3$, phenyl, pyridyl, hydroxyphenyl, halophenyl, mono- or di-($C_1$-$C_7$-alkyloxy)-phenyl, mono- or di-($C_1$-$C_7$-alkyloxy)-pyridyl, phenyl substituted by halo and $C_1$-$C_7$-alkyloxy, pyridyl substituted by halo and $C_1$-$C_7$-alkyloxy, N-mono- or N,N-di-($C_1$-$C_7$-alkyl)-aminopyridyl, halophenyl-$C_1$-$C_7$-alkyloxy, mono- or di-($C_1$-$C_7$-alkyloxy)-phenyl-$C_1$-$C_7$-alkyloxy, mono- or di-($C_1$-$C_7$-alkyloxy)-pyridyl-$C_1$-$C_7$-alkyloxy, phenyl-$C_1$-$C_7$-alkyloxy with phenyl substituted by halo and $C_1$-$C_7$-alkyloxy, pyridyl-$C_1$-$C_7$-alkyloxy with pyridyl substituted by halo and $C_1$-$C_7$-alkyloxy, N-mono- or N,N-di-($C_1$-$C_7$-alkyl)-aminopyridyl-$C_1$-$C_7$-alkyloxy, $C_1$-$C_7$-alkyloxy-$C_1$-$C_7$-alkyloxy, phenyl-$C_1$-$C_7$-alkyloxy, tetrahydropyranyloxy, 2H,3;-1,4-benzodioxinyl-$C_1$-$C_7$-alkyloxy, N—($C_1$-$C_7$-alkyloxyphenyl)-aminocarbonyl or $C_1$-$C_7$-alkyloxybenzoyl-amino are especially preferred. Other preferred substituents are carboxyphenyl, $C_1$-$C_7$-alkylaminocarbonylphenyl, carboxy-$C_1$-$C_7$-alkyloxyphenyl, $C_1$-$C_7$-alkylaminocarbonyl-$C_1$-$C_7$-alkyloxyphenyl, tetrazol-5-yl, 2-oxo-3-phenyl-tetrahydropyrazolidin-1-yl, oxetidin-3-yl-$C_1$-$C_7$-alkyloxy, 3-$C_1$-$C_7$-alkyl-oxetidin-3-yl-$C_1$-$C_7$-alkyloxy, 2-oxo-tetrahydrofuran-4-yl-$C_1$-$C_7$-alkyloxy or $C_1$-$C_7$-alkyloxyphenylaminocarbonyl. Most preferably, these moieties are bound to $X_3$ or to $X_4$. More generally, $R_3$ is hydrogen or more preferably a moiety different from hydrogen given at the definitions for $R_3$ herein.

In a first embodiment, $R_3$ is preferably substituted or unsubstituted aryl.

Preferred examples of aryl include phenyl or naphthyl, more preferably phenyl. In one embodiment, R3 is preferably unsubstituted phenyl. In another embodiment, R3 is substituted phenyl. When the aryl moiety is substituted, it is preferably mono-di- or tri-substituted, more preferably mono- or di-substituted. Most preferably aryl is mono-substituted. Suitable substituents are as defined herein, preferably $C_1$-$C_7$-alkyl, hydroxy, $C_1$-$C_7$-alkoxy, halo-$C_1$-$C_7$-alkyl, carboxy-$C_1$-$C_7$-alkyl, carboxy-$C_1$-$C_7$-alkenyl, halo-$C_1$-$C_7$-alkyloxy, phenyl-$C_1$-$C_7$-alkoxy wherein phenyl is unsubstituted or substituted by $C_1$-$C_7$-alkoxy and/or halo, carboxy-$C_1$-$C_7$-alkyloxy, $C_1$-$C_7$-alkyloxy-carbonyl-$C_1$-$C_7$-alkyloxy, hydroxy-$C_1$-$C_7$-alkyloxy, amino-$C_1$-$C_7$-alkyloxy, carboxy-hydroxy-$C_1$-$C_7$-alkyloxy, aminocarbonyl-$C_1$-$C_7$-alkyloxy, N-mono- or N,N-di-($C_1$-$C_7$-alkyl)-aminocarbonyl-$C_1$-$C_7$-alkyloxy, N-mono- or N,N-di-(hydroxyl-$C_1$-$C_7$-alkyl)-aminocarbonyl-$C_1$-$C_7$-alkyloxy, alkylsulfonylamino-$C_1$-$C_7$-alkyloxy, alkylsulfonylaminocarbonyl-$C_1$-$C_7$-alkyloxy, halo, amino, N-mono- or N,N-di-($C_1$-$C_7$-alkyl)amino, $C_1$-$C_7$-alkanoylamino, amino-$C_1$-$C_7$-alkanoylamino, N-mono- or N,N-di-($C_1$-$C_7$-alkyl)-aminocarbonyl-amino, alkylsulfonylamino, carboxy-$C_1$-$C_7$-alkylamino, $C_1$-$C_7$-alkanoyloxy, amino-$C_1$-$C_7$-alkyloxy, N-mono- or N,N-di-($C_1$-$C_7$-alkyl)amino-$C_1$-$C_7$-alkyloxy, $C_1$-$C_7$-alkanoyl, carboxyl, heterocyclyl, such as monocyclic heterocyclyl, preferably containing at least one nitrogen atom, preferably 5 or 6-membered monocyclic heterocyclyl, in particular pyrazolyl, 2-oxo-3-phenyl-tetrahydropyrazolidin-1-yl or tetrazolyl; N-mono- or N,N-di-($C_1$-$C_7$-alkylamino)-carbonyl, carboxy-$C_1$-$C_7$-alkyl-aminocarbonyl, alkylsulfonyl-$C_1$-$C_7$-alkanoyl, N-mono- or N,N-di-($C_1$-$C_7$-alkyloxy-$C_1$-$C_7$-alkyl)-amino-$C_1$-$C_7$-alkyl cyano; heterocyclyl-$C_1$-$C_7$-alkyloxy, where the heterocyclyl moiety is preferably monocyclic heterocyclyl, preferably containing at least one nitrogen atom, preferably 5 or 6-membered monocyclic heterocyclyl, preferably saturated or aromatic heterocyclyl, in particular piperidyl-$C_1$-$C_7$-alkoxy, pyrrolidinyl-$C_1$-$C_7$-alkoxy, piperazinyl-$C_1$-$C_7$-alkoxy, morpholino-$C_1$-$C_7$-alkoxy, thiomorpholino-$C_1$-$C_7$-alkoxy, pyridyl-$C_1$-$C_7$-alkoxy, oxetidin-3-yl-$C_1$-$C_7$-alkyloxy, 3-$C_1$-$C_7$-alkyl-oxetidin-3-yl-$C_1$-$C_7$-alkyloxy or 2-oxo-tetrahydrofuran-4-yl-$C_1$-$C_7$-alkyloxy or tetrazolyl-$C_1$-$C_7$-alkyloxy, whereby the heterocyclyl is unsubstituted or substituted by $C_1$-$C_7$-alkyl, hydroxyl, carboxyl, amino and/or N-mono- or N,N-di-($C_1$-$C_7$-alkyl)amino; heterocyclyl-$C_1$-$C_7$-alkyl, where the heterocyclyl moiety is preferably monocyclic heterocyclyl, preferably containing at least one nitrogen atom, preferably 5 or 6-membered monocyclic heterocyclyl, preferably saturated heterocyclyl, in particular morpholino-$C_1$-$C_7$-alkyl or piperazinyl-$C_1$-$C_7$-alkyl, whereby the heterocyclyl is unsubstituted or substituted by $C_1$-$C_7$-alkyl, hydroxyl, carboxyl, amino and/or N-mono- or N,N-di-($C_1$-$C_7$-alkyl)amino; heterocyclyl-carbonyl, where the heterocyclyl moiety is preferably monocyclic heterocyclyl, preferably containing at least one nitrogen atom, preferably 4, 5 or 6-membered monocyclic heterocyclyl, preferably saturated heterocyclyl, in particular azetidinyl-carbonyl, whereby the heterocyclyl is unsubstituted or substituted by $C_1$-$C_7$-alkyl, hydroxyl, carboxyl, amino and/or N-mono- or N,N-di-($C_1$-$C_7$-alkyl)amino; heterocyclyl-carbonyl-$C_1$-$C_7$-alkyloxy, where the heterocyclyl moiety is preferably monocyclic heterocyclyl, preferably containing at least one nitrogen atom, preferably 4, 5 or 6-membered monocyclic heterocyclyl, preferably saturated heterocyclyl, in particular azetidinyl-carbonyl-$C_1$-$C_7$-alkyloxy or piperidinyl-carbonyl-$C_1$-$C_7$-alkyloxy, whereby the heterocyclyl is unsubstituted or substituted by $C_1$-$C_7$-alkyl, hydroxyl, carboxyl, amino and/or N-mono- or N,N-di-($C_1$-$C_7$-alkyl)amino; and heterocyclyl-carbonyl-$C_1$-$C_7$-alkyl, where the heterocyclyl moiety is preferably monocyclic heterocyclyl, preferably containing at least one nitrogen atom, preferably 5 or 6-membered monocyclic heterocyclyl, preferably saturated heterocyclyl, in particular piperazinyl-carbonyl-$C_1$-$C_7$-alkyl, whereby the heterocyclyl is unsubstituted or substituted by $C_1$-$C_7$-alkyl, hydroxyl, carboxyl, amino and/or N-mono- or N,N-di-($C_1$-$C_7$-alkyl)amino;

More preferably the substituent is selected from $C_1$-$C_7$-alkyl, hydroxy, $C_1$-$C_7$-alkoxy, halo-$C_1$-$C_7$-alkyl, carboxy-$C_1$-$C_7$-alkyl, carboxy-$C_1$-$C_7$-alkenyl, halo-$C_1$-$C_7$-alkyloxy, carboxy-$C_1$-$C_7$-alkyloxy, $C_1$-$C_7$-alkyloxy-carbonyl-$C_1$-$C_7$-alkyloxy, hydroxy-$C_1$-$C_7$-alkyloxy, amino-$C_1$-$C_7$-alkyloxy, carboxy-hydroxy-$C_1$-$C_7$-alkyloxy, aminocarbonyl-$C_1$-$C_7$-alkyloxy, N-mono- or N,N-di-($C_1$-$C_7$-alkyl)-aminocarbonyl-$C_1$-$C_7$-alkyloxy, N-mono- or N,N-di-(hydroxyl-$C_1$-$C_7$-alkyl)-aminocarbonyl-$C_1$-$C_7$-alkyloxy, alkylsulfonylamino-$C_1$-$C_7$-alkyloxy, alkylsulfonylaminocarbonyl-$C_1$-$C_7$-alkyloxy, halo, $C_1$-$C_7$-alkanoylamino, amino-$C_1$-$C_7$-alkanoylamino, N-mono- or N,N-di-($C_1$-$C_7$-alkyl)aminocarbonyl-amino, alkylsulfonylamino, carboxy-$C_1$-$C_7$-alkylamino, $C_1$-$C_7$-alkanoyloxy, amino-$C_1$-$C_7$-alkyloxy, N-mono- or N,N-di-($C_1$-$C_7$-alkyl)amino-$C_1$-$C_7$-alkyloxy, $C_1$-$C_7$-alkanoyl, carboxyl, heterocyclyl, such as tetrazolyl; N-mono- or N,N-di-($C_1$-$C_7$-alkylamino)-carbonyl, carboxy-$C_1$-$C_7$-alkyl-aminocarbonyl, alkylsulfonyl-$C_1$-$C_7$-alkanoyl, N-mono- or N,N-di-($C_1$-$C_7$-alkyloxy-$C_1$-$C_7$-alkyl)-amino-$C_1$-$C_7$-alkyl cyano; heterocyclyl-$C_1$-$C_7$-alkyloxy, in particular piperidyl-$C_1$-$C_7$-alkoxy, pyrrolidinyl-$C_1$-$C_7$-alkoxy, piperazinyl-$C_1$-$C_7$-alkoxy, pyridyl-$C_1$-$C_7$-alkoxy, heterocyclyl-$C_1$-$C_7$-alkyl, in particular morpholino-$C_1$-$C_7$-alkyl or piperazinyl-$C_1$-$C_7$-alkyl, heterocyclyl-carbonyl, in particular azetidinyl-carbonyl, heterocyclyl-carbonyl-$C_1$-$C_7$-alkyloxy, in particular azetidinyl-carbonyl-$C_1$-$C_7$-alkyloxy or piperidinyl-carbonyl-$C_1$-$C_7$-alkyloxy, and heterocyclyl-carbonyl-$C_1$-$C_7$-alkyl, in particular piperazinyl-carbonyl-$C_1$-$C_7$-alkyl, whereby the heterocyclyl moiety is in each case unsubstituted or substituted by $C_1$-$C_7$-alkyl, hydroxyl, carboxyl, amino and/or N-mono- or N,N-di-($C_1$-$C_7$-alkyl)amino.

Yet more preferred substituents are halo such as F, hydroxyl, cyano, $C_1$-$C_7$-alkyloxy such as methoxy, heterocyclyl-$C_1$-$C_7$-alkyloxy, in particular piperidyl-$C_1$-$C_7$-alkoxy such as piperidyl-ethoxy, $C_1$-$C_7$-alkanoylamino such as acetylamino, $C_1$-$C_7$-alkanoyloxy such as acetyloxy, hydroxy-$C_1$-$C_7$-alkyloxy such as hydroxy-ethoxy, $C_1$-$C_7$-alkanoyl such as acetyl, N,N-di-($C_1$-$C_7$-alkyl)-amino-$C_1$-$C_7$-alkyloxy such as N-di-(methyl)-amino-propyloxy, heterocyclyl such as tetrazolyl, carboxy-$C_1$-$C_7$-alkyloxy such as carboxymethoxy, heterocyclyl-$C_1$-$C_7$-alkoxy in particular piperazinyl-$C_1$-$C_7$-alkoxy such as piperazinyl-ethoxy, heterocyclyl-carbonyl-$C_1$-$C_7$-alkyloxy, in particular azetidinyl-carbonyl-$C_1$-$C_7$-alkyloxy or piperidinyl-carbonyl-$C_1$-$C_7$-alkyloxy such as azetidinyl-carbonyl-methoxy and piperidinyl-carbonyl-methoxy.

In a second embodiment, R3 is preferably substituted or unsubstituted heterocyclyl.

The heterocyclyl moiety is preferably mono- or bicyclic, more preferably bicyclic. Preferred are aromatic ring systems, saturated or partially saturated ring systems, in particular whereby one of the rings is aromatic and the other is saturated or partially saturated, most preferred are partially saturated. The heterocyclyl moiety has preferably 1, 2 or 3, more preferably 1 or 2, most preferably 1, heteroatom selected from O, N or S, more preferably O or N. The ring system contains preferably an oxo moiety. Particularly preferred examples include monocyclic 4, 5 or 6-membered rings preferably containing a nitrogen atom, in particular, pyridyl, thiophenyl, pyrazolyl, pyridazinyl, piperidyl, azetidinyl, tetrazolyl, triazolyl, 1,2,3,6-tetrahydropyridyl, and pyrrolyl; or bicyclic 9-membered ring systems preferably containing a N atom, in particular indolyl, benzoisoxazolyl, 1H-indazolyl, 2,3-dihydro-isoindol-1-onyl, 2,3-dihydro-indol-1-onyl, 1,3-dihydro-benzimidazol-2-onyl, dihydrobenzofuranyl, 2-oxo-3-phenyl-tetrahydropyrazolidin-1-yl, benzo[1,3]dioxolyl or is 2,3-dihydrobenzo[1,4]dioxine. Each heterocyclyl is unsubstituted or substituted by one or more, e.g. up to three, preferably 1, substituents independently selected from the group consisting of $C_1$-$C_7$-alkyl, hydroxy-$C_1$-$C_7$-alkyl, $C_1$-$C_7$-alkanoyloxy-$C_1$-$C_7$-alkyl, $C_1$-$C_7$-alkoxy, $C_1$-$C_7$-alkanoylamino-$C_1$-$C_7$-alkyl, carboxy-$C_1$-$C_7$-alkyl, $C_1$-$C_7$-alkoxycarbonyl-$C_1$-$C_7$-alkyl, halo, hydroxy, $C_1$-$C_7$-alkoxy-$C_1$-$C_7$-alkoxy, carboxy-$C_1$-$C_7$-alkoxy, amino-$C_1$-$C_7$-alkoxy, N—$C_1$-$C_7$-alkanoylamino-$C_1$-$C_7$-alkoxy, carbamoyl-$C_1$-$C_7$-alkyl, carbamoyl-$C_1$-$C_7$-alkoxy, $C_1$-$C_7$-alkanoyl, $C_1$-$C_7$-alkyloxy-$C_1$-$C_7$-alkanoyl, $C_1$-$C_7$-alkoxy-$C_1$-$C_7$-alkanoyl, carboxyl, carbamoyl, N-mono- or N,N-di-($C_1$-$C_7$-alkyl)amino and amino, more preferably of $C_1$-$C_7$-alkyl, amino-$C_1$-$C_7$-alkyl, $C_1$-$C_7$-alkoxy, carboxy-$C_1$-$C_7$-alkyl, carboxy-$C_1$-$C_7$-alkoxy, carboxyl, N-mono- or N,N-di-($C_1$-$C_7$-alkyl)amino and amino, in particular methyl, amino, dimethylamino, carboxy, carboxymethyl, aminomethyl, methoxy, and carboxymethoxy.

When R3 is heterocyclyl, R2 is preferably also heterocyclyl as explained above, in particular

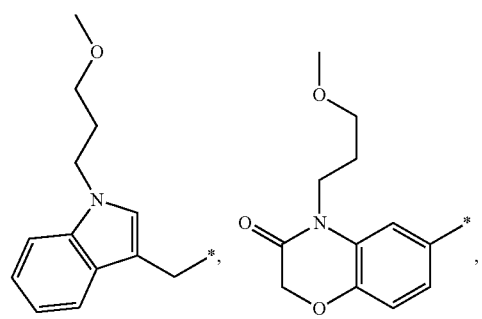

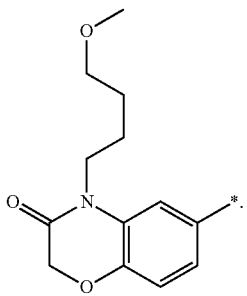

In a third embodiment R3 is preferably hydrogen.

In this embodiment R4 is preferably absent. In this embodiment R2 is preferably heterocyclyl as explained above, in particular

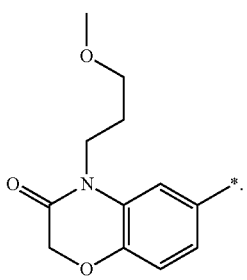

In a fourth embodiment R3 is preferably hydroxyl.

In this embodiment R4 is preferably absent. In this embodiment R2 is preferably heterocyclyl as explained above, in particular

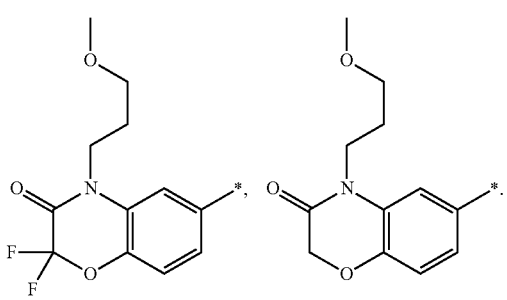

In a fifth embodiment R3 is preferably cyano.

In this embodiment R4 is preferably absent. In this embodiment R2 is preferaby heterocyclyl as explained above, in particular

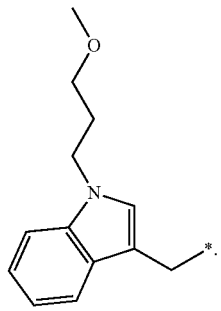

In a sixth embodiment R3 is preferably unsubstituted or substituted alkyl.

Preferred examples for alkyl are branched or straight chain $C_1$-$C_7$-alkyl which may be substituted or unsubstituted. Preferred examples include methyl, ethyl, isopropyl, n-propyl, n-butyl, sec-butyl or tert-butyl, more preferably methyl, ethyl or isopropyl, most preferably ethyl. In one embodiment the alkyl moiety is preferably unsubstituted. In another embodiment the alkyl moiety is preferably substituted as defined herein, e.g. by aryloxy such as phenyloxy. Aryloxy may be substituted by one to three, preferably two substituents as defined herein, e.g. $C_1$-$C_7$-alkyloxy such as methoxy.

In this embodiment R4 is preferably absent. In this embodiment R2 is preferably heterocyclyl as explained above, in particular

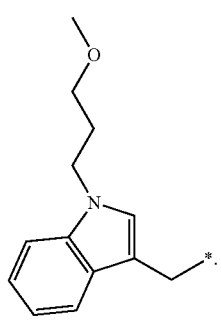

In a seventh embodiment R3 is preferably unsubstituted or substituted cycloalkyl.

Preferred examples for cycloalkyl are $C_3$-$C_8$-alkyl which may be substituted or unsubstituted. Preferred examples include cyclopropyl, cyclypentyl and cyclohexyl, more preferably cyclopropyl. The alkyl moiety is preferably unsubstituted.

In this embodiment R4 is preferably absent. In this embodiment R2 is preferably heterocyclyl as explained above, in particular

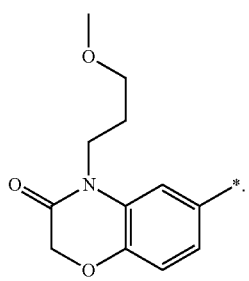

In an eighth embodiment R3 is preferably etherified hydroxyl.

Etherified hydroxyl is as defined herein, preferably the H of the OH group has been replaced by a substituted or unsubstituted alkyl. Preferred examples for alkyl are branched or straight chain $C_1$-$C_7$-alkyl which may be substituted or unsubstituted. Preferred examples include methyl, ethyl, iso-propyl, n-propyl, n-butyl, sec-butyl or tert-butyl, more preferably methyl, ethyl or isopropyl, most preferably methyl. In one embodiment the alkyl moiety is preferably substituted such as mono-substituted. Examples of suitable substituents are as defined herein, preferably $C_1$-$C_7$-alkyloxy such as methoxy; aryl, such as phenyl, which may be substituted by one to three, preferably two substituents as defined herein, e.g. $C_1$-$C_7$-alkyloxy such as methoxy; and heterocyclyl such as mono- or bicyclic, more preferably monocyclic, preferably aromatic or saturated ring systems, having preferably 1, 2 or 3, more preferably 1, heteroatom selected from O, N or S, more preferably O or N, in particular 5- or 6-membered rings such as pyridyl or tetrahydrofuranyl, which may be substituted by one to three, preferably one substituent as defined herein, e.g. amino, -mono- or N,N-di-($C_1$-$C_7$-alkyl)amino.

In this embodiment R4 is preferably absent or is hydroxyl. In this embodiment R2 is
preferably heterocyclyl as explained above, in particular

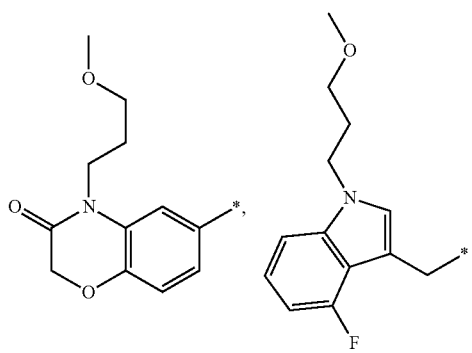

In a ninth embodiment R3 is preferably unsubstituted or substituted alkynyl.

Preferred examples for alkynyl are branched or straight chain $C_1$-$C_7$-alkynyl which may be substituted or unsubstituted. Preferred examples include ethyl, n-propyl, n-butyl or n-pentyl moieties containing a triple bond, more preferably ethyl, n-butyl or n-pentyl moieties, most preferably ethyne. In one embodiment the alkynyl moiety is preferably substituted as defined herein, e.g. by amino, N-mono- or N,N-di-($C_1$-$C_7$-alkyl)amino, carboxyl, heterocyclyl such as mono- or bicyclic, more preferably monocyclic, preferably aromatic or saturated ring systems, having preferably 1, 2 or 3, more preferably 1, heteroatom selected from O, N or S, more preferably O or N, in particular 5- or 6-membered rings such as pyridyl, which may be substituted by one to three, preferably one substituent as defined herein, e.g. amino, N-mono- or N,N-di-($C_1$-$C_7$-alkyl)amino; or aryl, such as phenyl, which may be unsubstituted or substituted by one to three, preferably one substituents as defined herein, e.g. carboxy or alkoxycarbonyl such as methoxycarbonyl.

In this embodiment R4 is preferably absent. In this embodiment R2 is preferably heterocyclyl as explained above, in particular

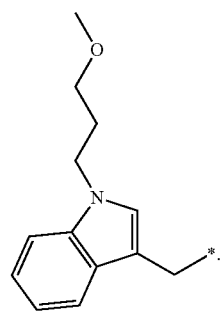

Particularly preferred examples for W—R3 are

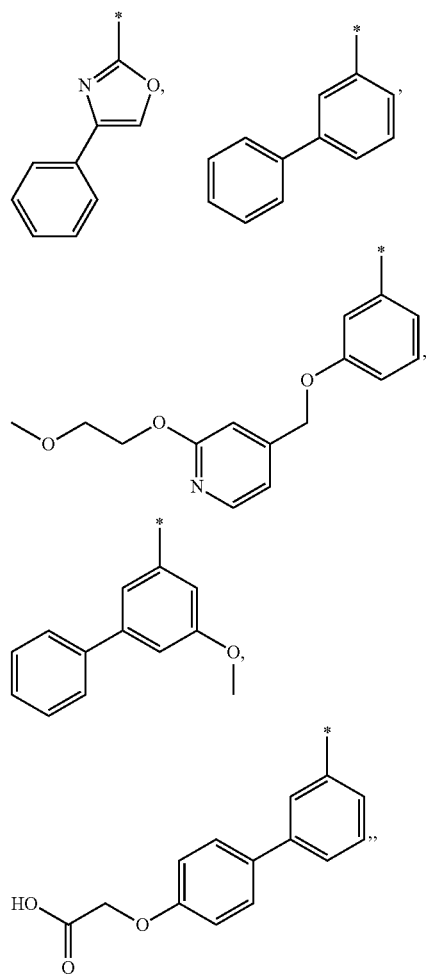

-continued
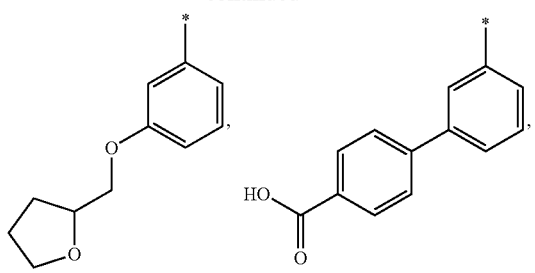
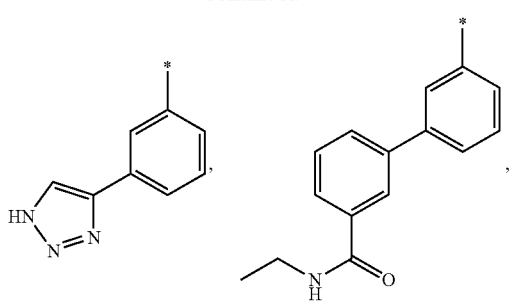
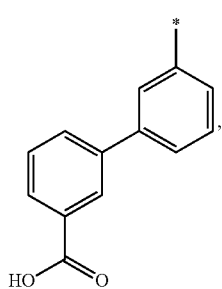
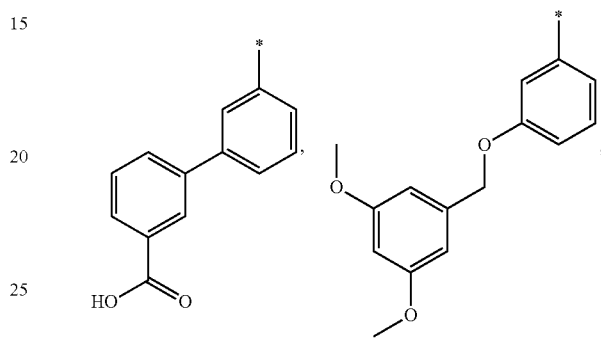
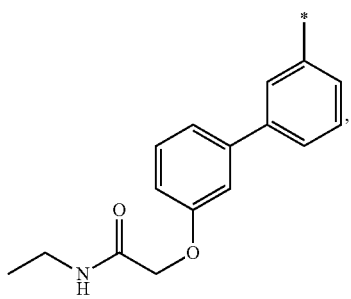
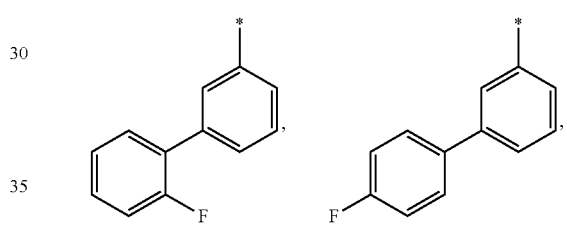
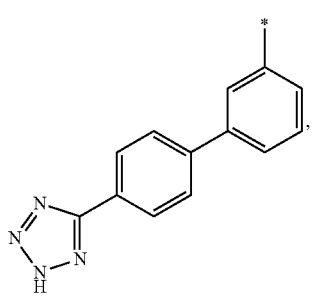
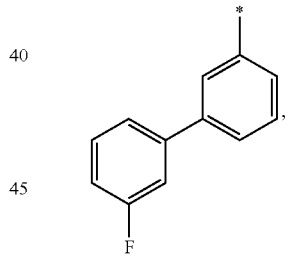
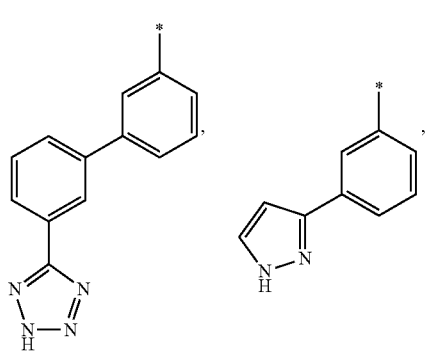
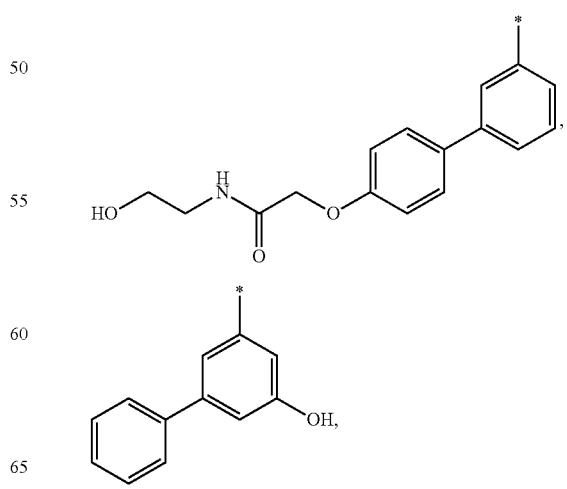

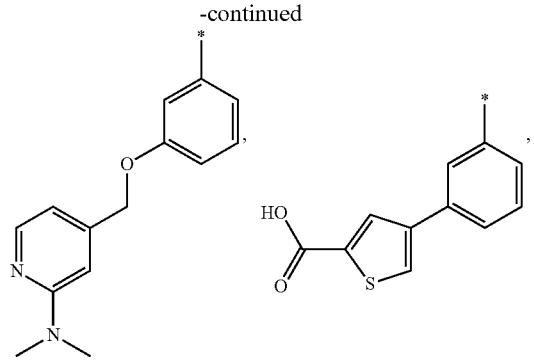
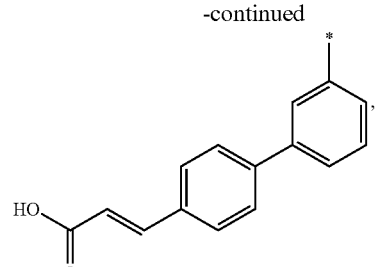
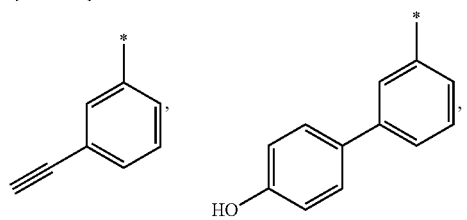
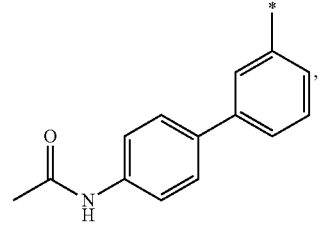
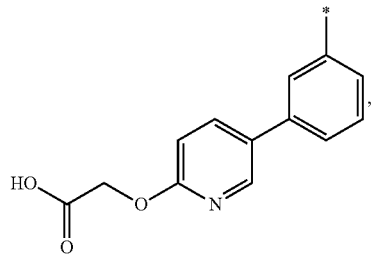
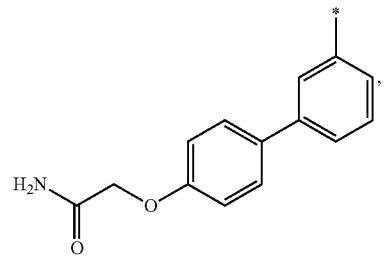
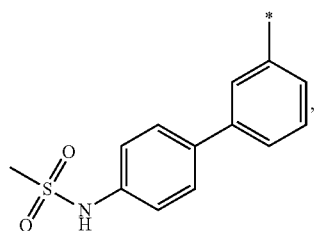
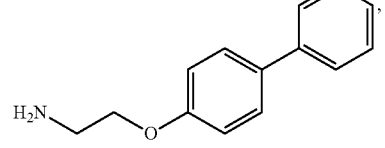
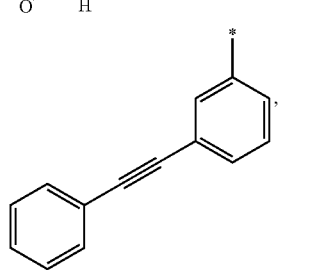
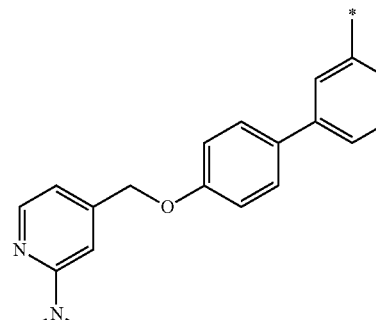
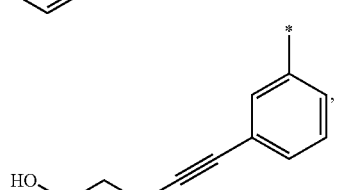
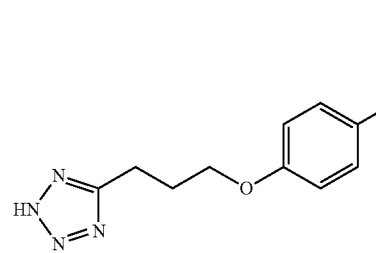
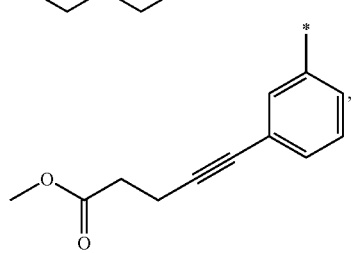

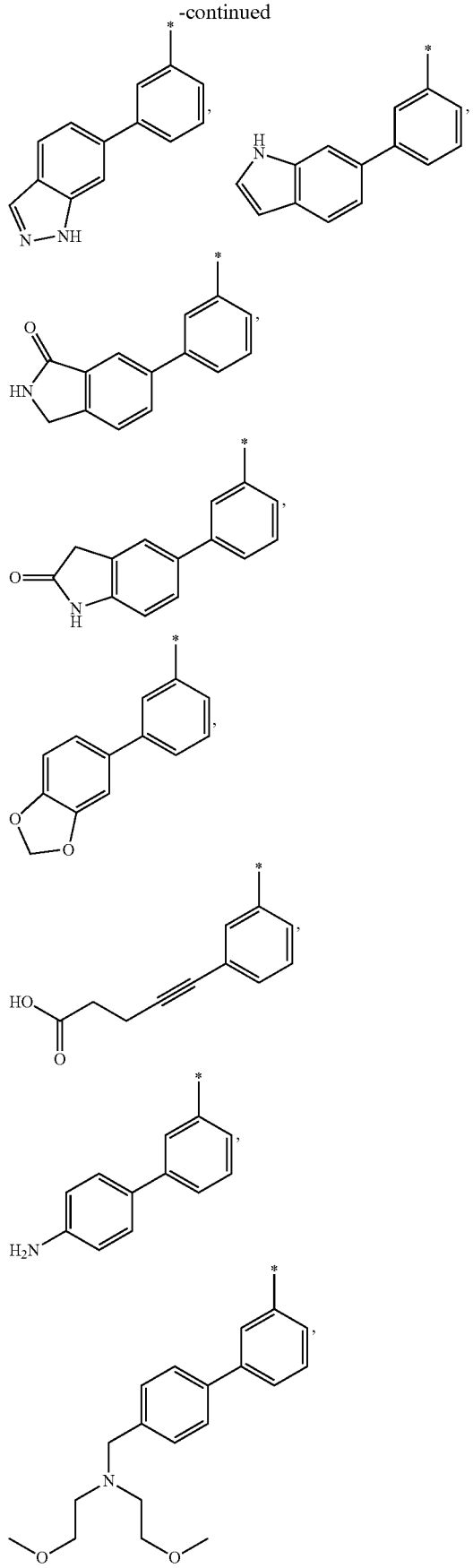
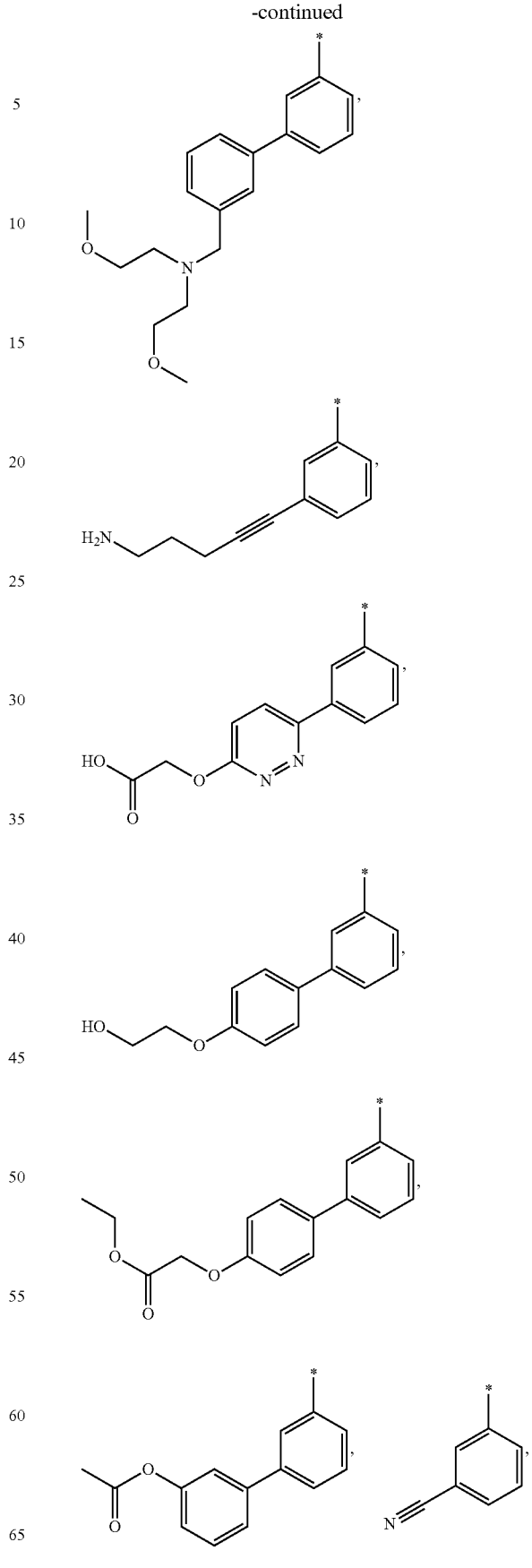

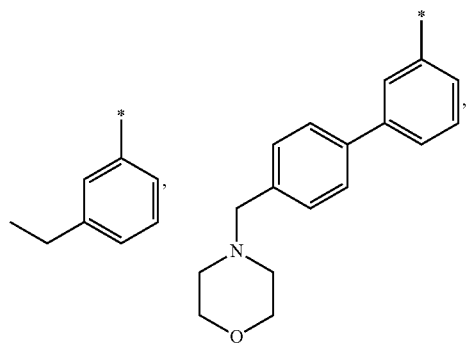
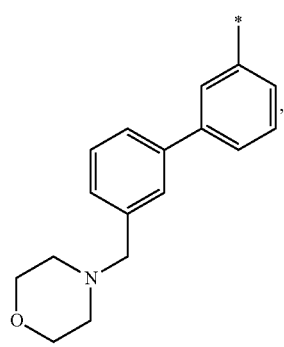
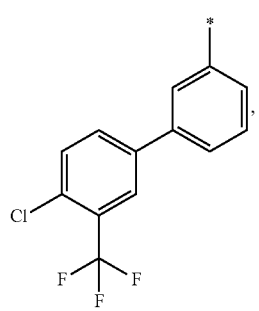
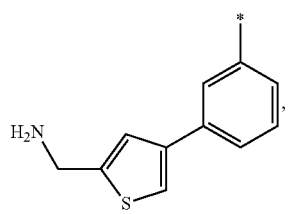
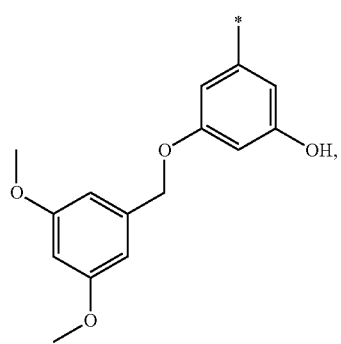
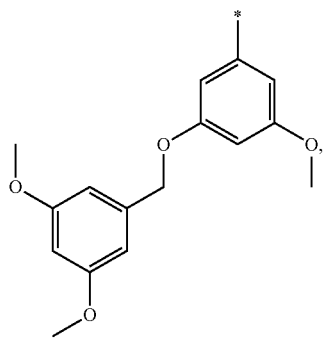
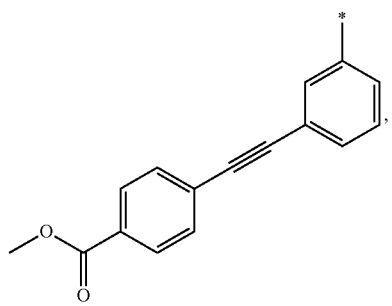
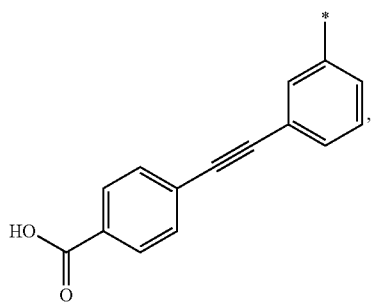
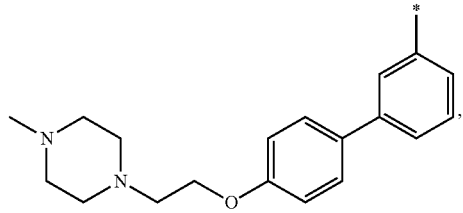
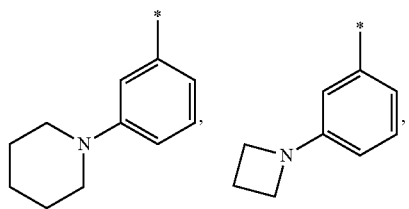

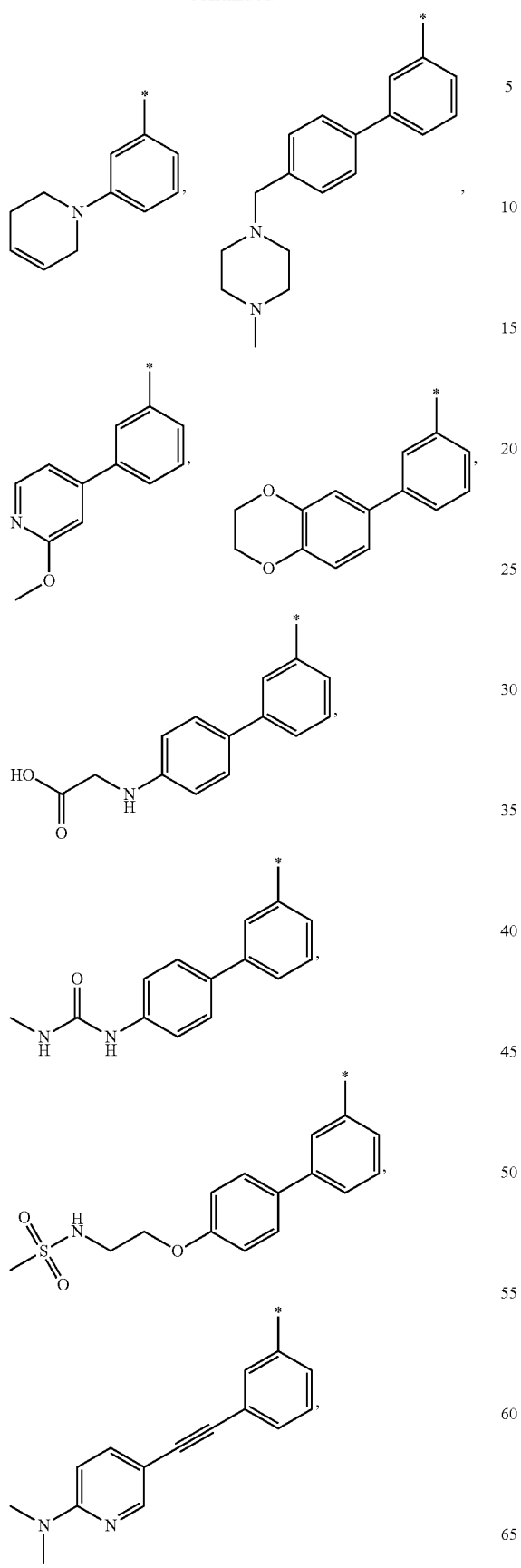
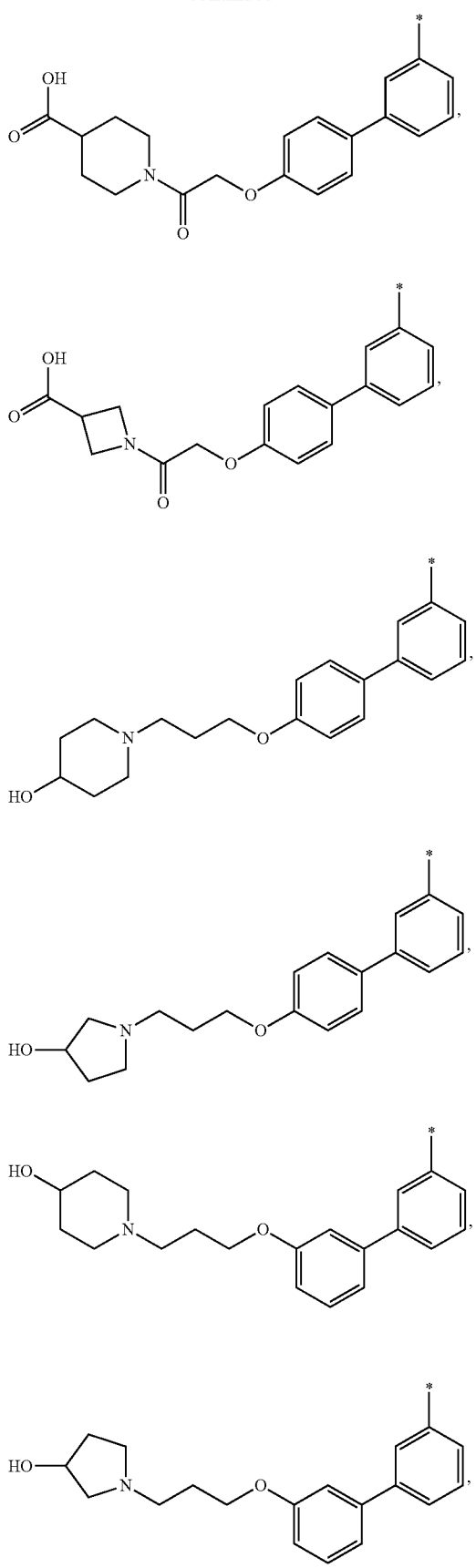

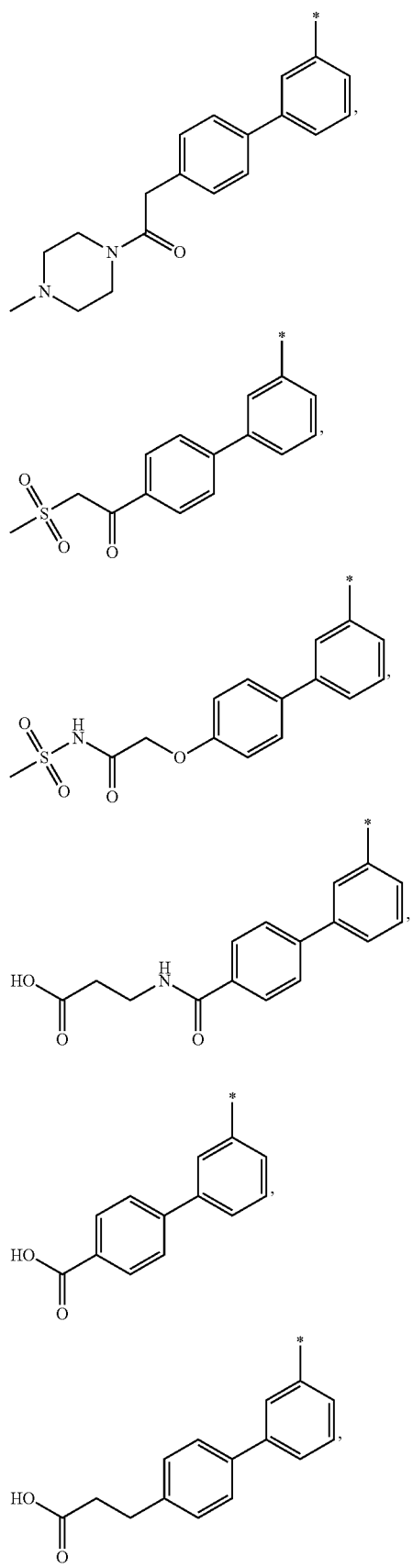
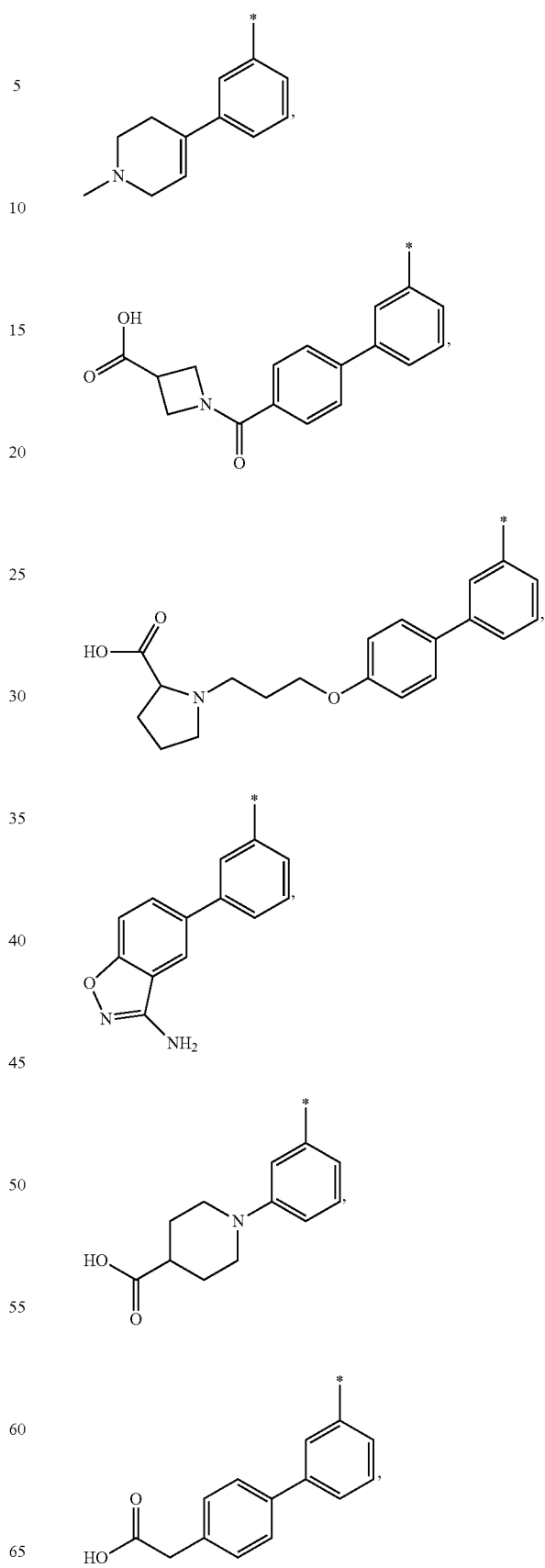

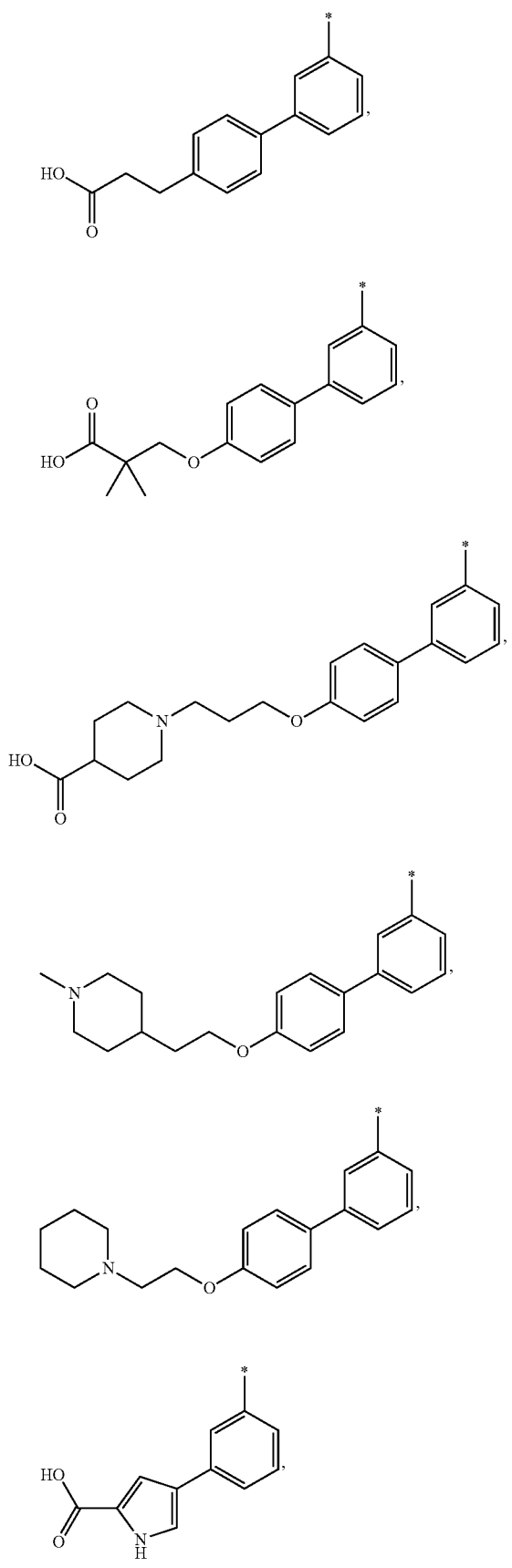

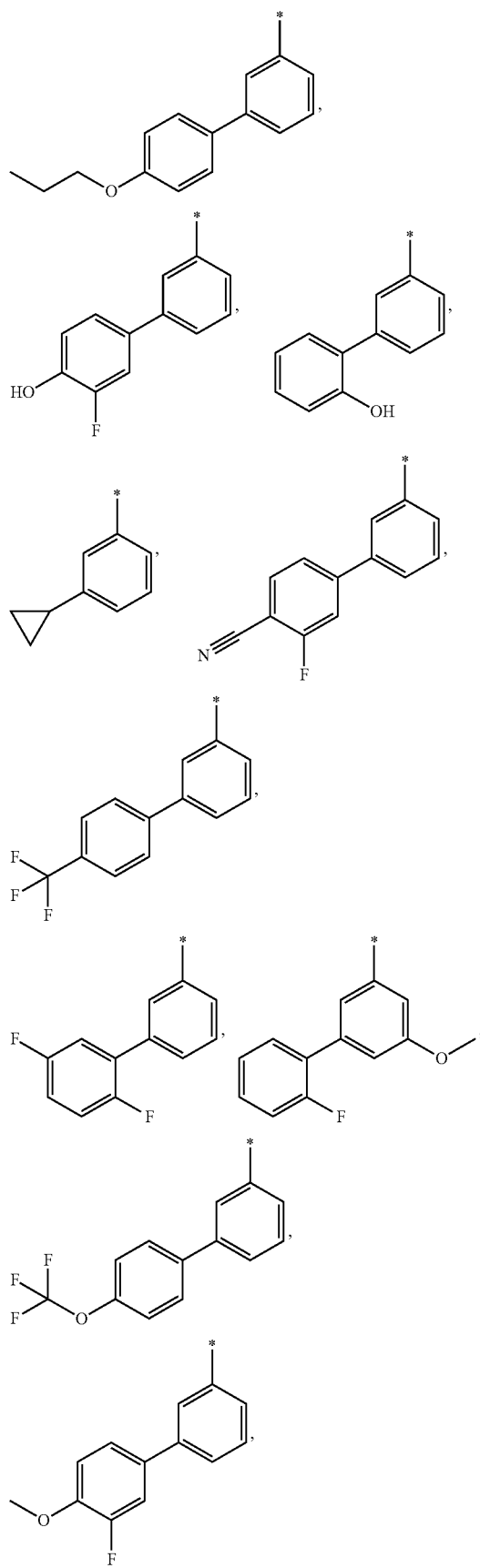
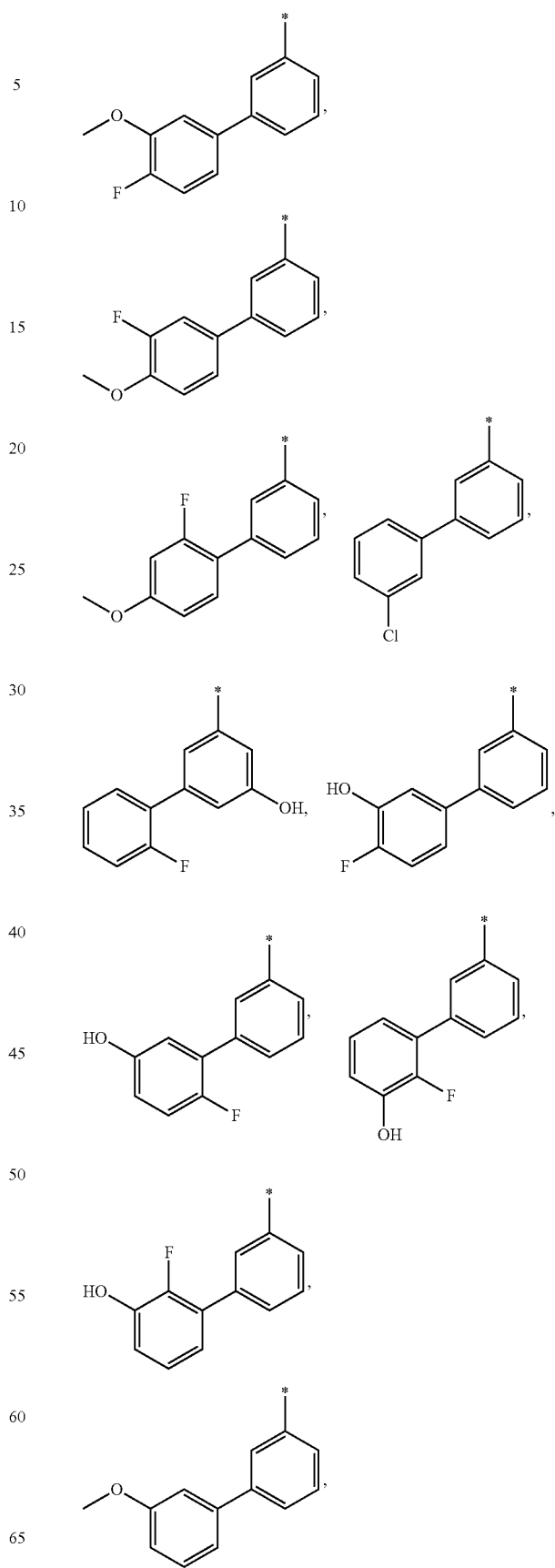

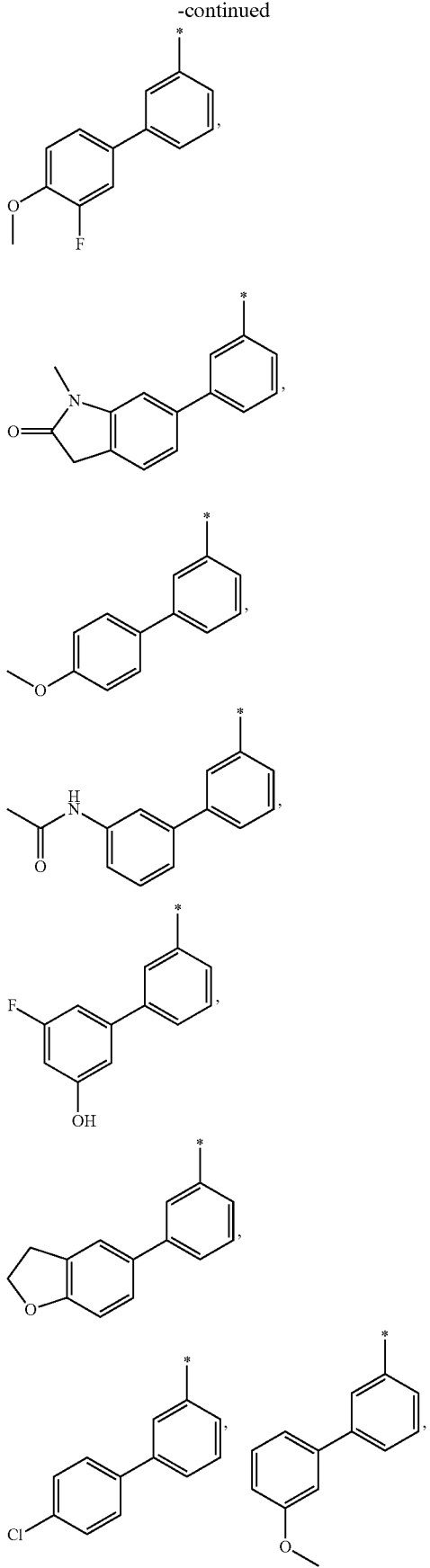
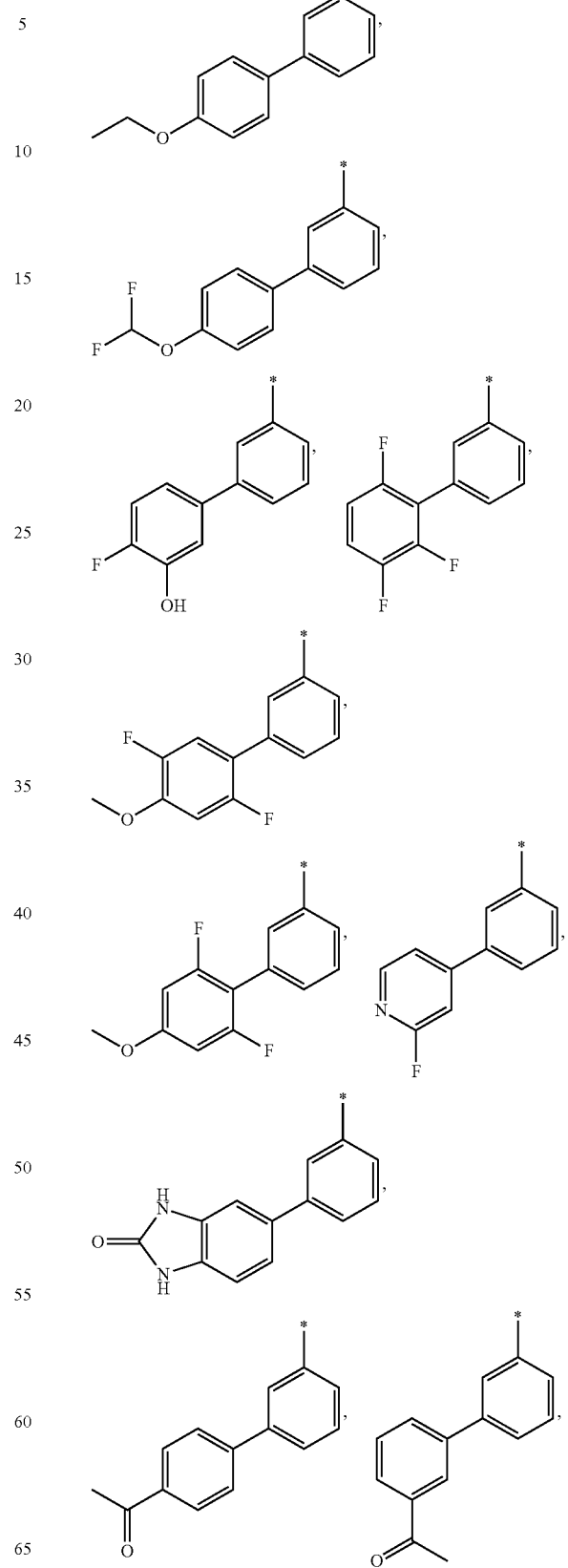

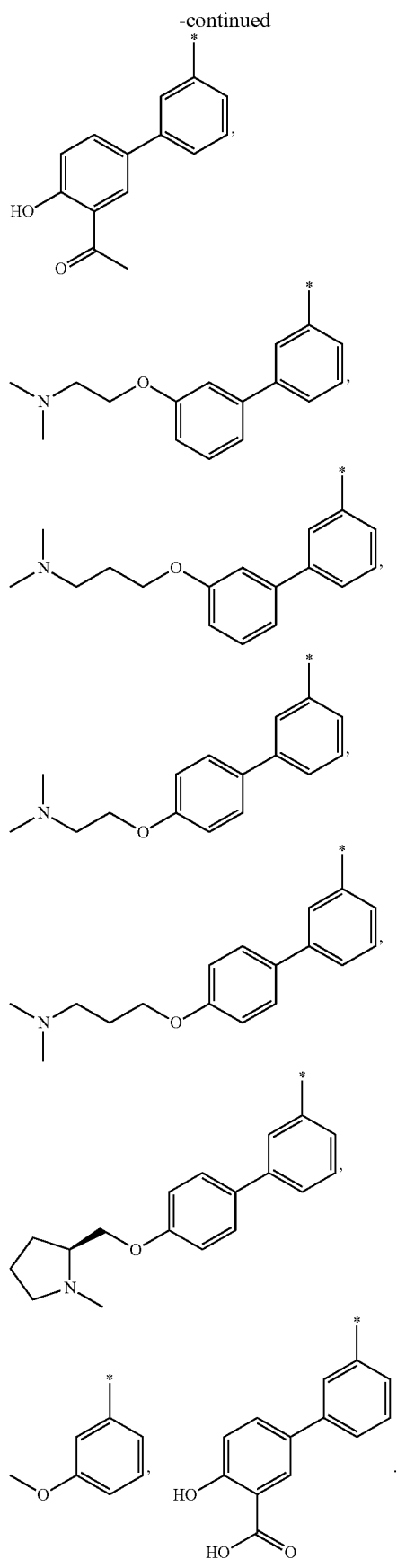
More preferred are
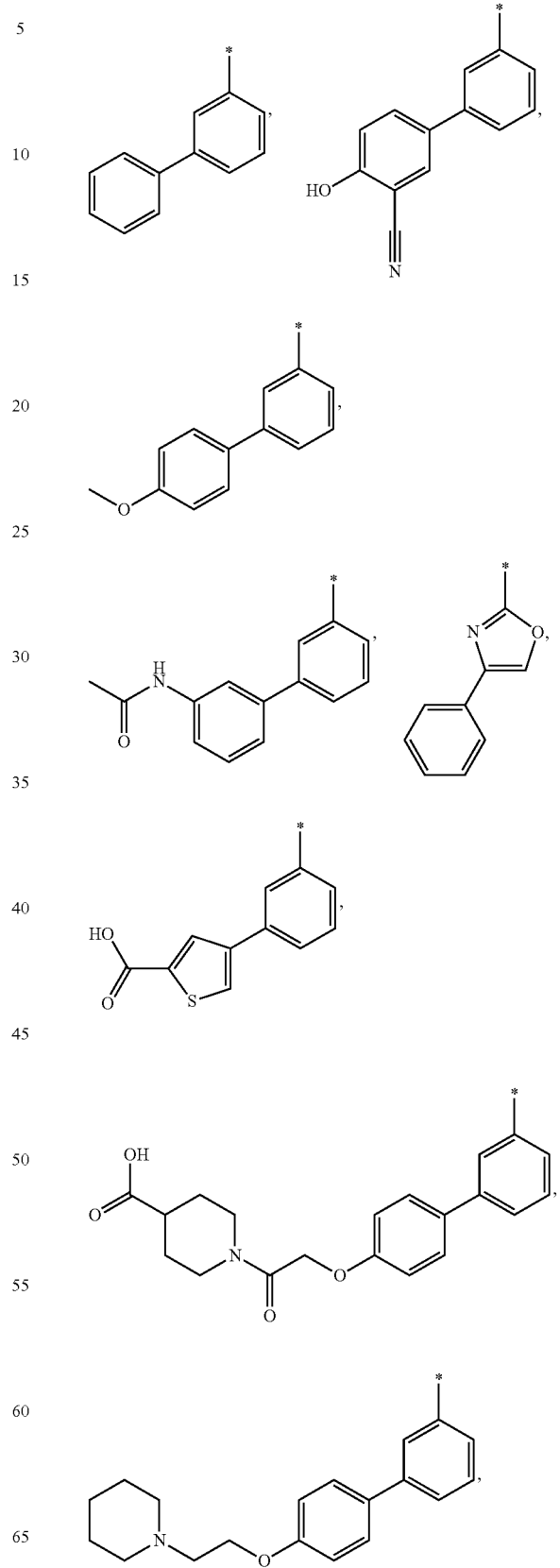

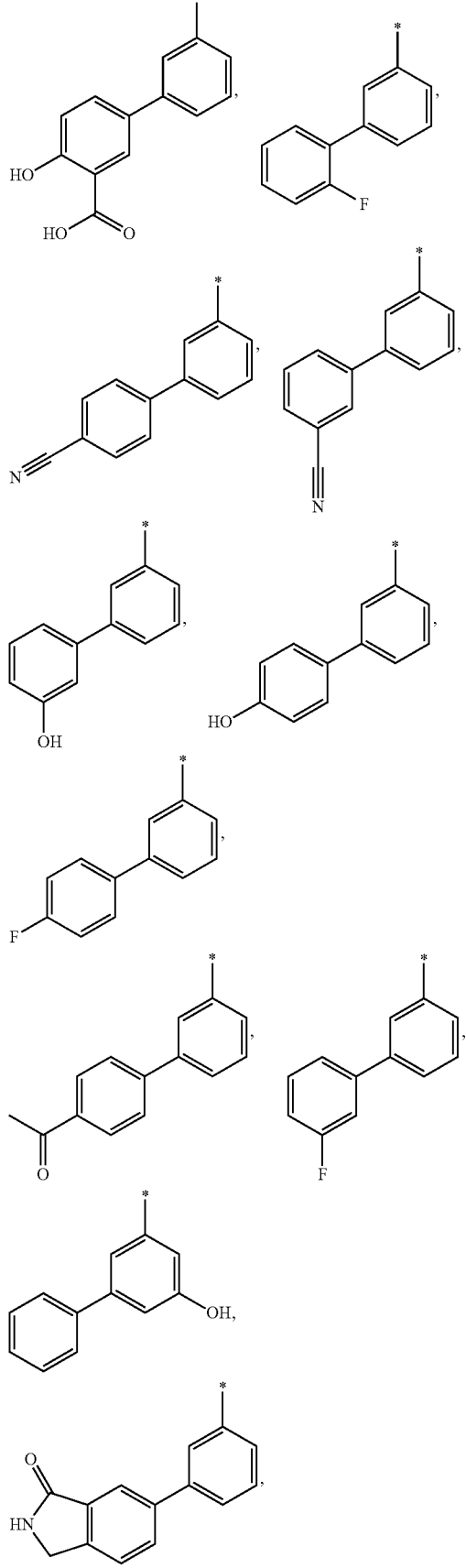
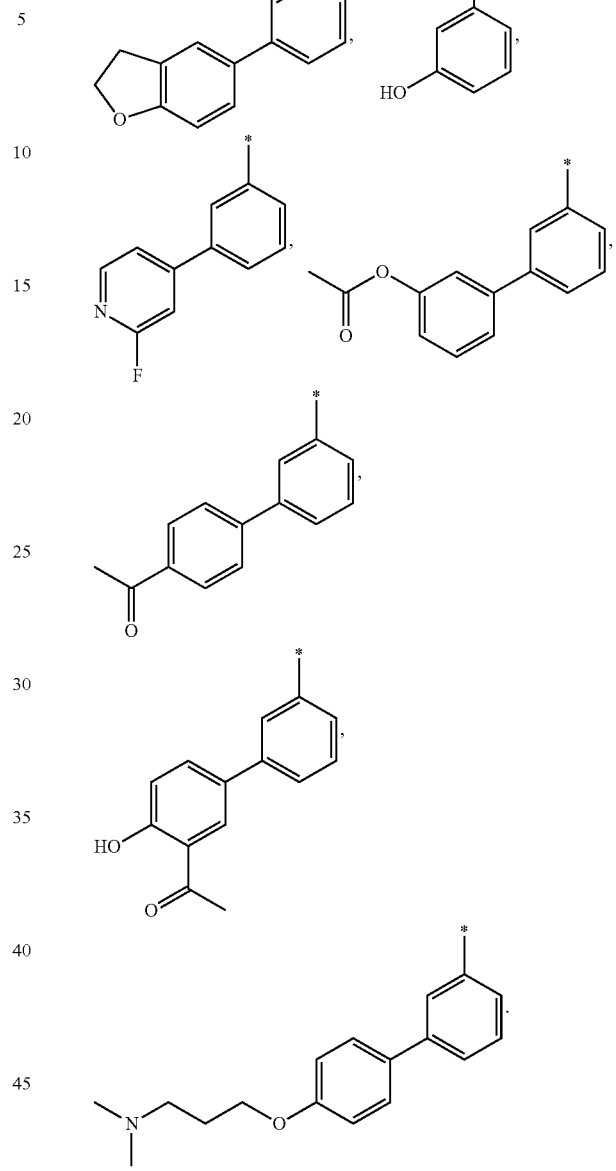

Preferred Definitions for $R_4$

As $R_4$, hydroxy, halo or $C_1$-$C_7$-alkoxy are especially preferred or $R_4$ is absent. Most preferably R4 is absent.

Preferred Definitions for T

T is preferably either methylene (—$CH_2$—) or carbonyl (—C(=O)—), more preferably carbonyl.

Preferred Definitions for R11

R11 is hydrogen, hydroxy, halo, $C_1$-$C_7$-alkyl, cycloalkyl, halo-substituted cycloalkyl, $C_1$-$C_7$-alkoxy, halo-$C_1$-$C_7$-alkyl or cyano, but preferably hydrogen.

The respective definitions of preferred embodiments of the invention for each substituent as mentioned above can be combined with any definition of preferred embodiments of the invention for any one or more other substituent as defined above without any limitation.

In all definitions above the person having skill in the art will, without undue experimentation or considerations, be able to recognize which are relevant (e.g. those that are sufficiently stable for the manufacture of pharmaceuticals, e.g. having a half-life of more than 30 seconds) and thus are preferably encompassed by the present claims and that only chemically feasible bonds and substitutions (e.g. in the case of double or triple bonds, hydrogen carrying amino or hydroxy groups and the like) are encompassed, as well as tautomeric forms where present.

Salts are especially the pharmaceutically acceptable salts of compounds of formula I. They can be formed where salt forming groups, such as basic or acidic groups, are present that can exist in dissociated form at least partially, e.g. in a pH range from 4 to 10 in aqueous solutions, or can be isolated especially in solid form.

Such salts are formed, for example, as acid addition salts, preferably with organic or inorganic acids, from compounds of formula I with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-di-methylpiperazine.

When a basic group and an acid group are present in the same molecule, a compound of formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable comprised in pharmaceutical preparations), and these are therefore preferred.

In view of the close relationship between the compounds in free form and in the form of their salts, including those salts that can be used as intermediates, for example in the purification or identification of the compounds or salts thereof, any reference to "compounds" and "intermediates" hereinbefore and hereinafter, especially to the compound(s) of the formula I, is to be understood as referring also to one or more salts thereof or a mixture of a free compound and one or more salts thereof, each of which is intended to include also any solvate, metabolic precursor such as ester or amide of the compound of formula I, or salt of any one or more of these, as appropriate and expedient and if not explicitly mentioned otherwise. Different crystal forms may be obtainable and then are also included.

Where the plural form is used for compounds, salts, pharmaceutical preparations, diseases, disorders and the like, this is intended to mean one (preferred) or more single compound(s), salt(s), pharmaceutical preparation(s), disease(s), disorder(s) or the like, where the singular or the indefinite article ("a", "an") is used, this is intended to include the plural or preferably the singular.

The compounds of the present invention possess two or more asymmetric centers depending on the choice of the substituents. The preferred absolute configuration at the C-3 and C-4 asymmetric centers in the central piperidine moiety is as indicated specifically within the present disclosure. However, any possible isolated or pure diastereoisomers, enantiomers and geometric isomers, and mixtures thereof, e.g., racemates, are encompassed by the present invention. A very preferred embodiment of the invention relates to the 3,4-trans-compounds of the present invention (wherein W- and R1R2N-T- are in trans position to each other).

As described herein above, the present invention provides 3,4-disubstituted piperidine derivatives of formula I, these compounds for use in the (prophylactic and/or therapeutic) treatment of a disease (=condition, disorder) in a warm-blooded animal, especially a human, preferably of a disease dependent on (especially inappropriate) renin activity, a pharmaceutical composition comprising a compound of the formula I, methods for preparing said compound or pharmaceutical preparation, and methods of treating conditions dependent on (especially inappropriate) renin activity by administration of a therapeutically effective amount of a compound of the formula I, or a pharmaceutical composition thereof.

"Inappropriate" renin activity preferably relates to a state of a warm-blooded animal, especially a human, where renin shows a renin activity that is too high in the given situation (e.g. due to one or more of misregulation, overexpression e.g. due to gene amplification or chromosome rearrangement or infection by microorganisms such as virus that express an aberrant gene, abnormal activity e.g. leading to an erroneous substrate specificity or a hyperactive renin e.g. produced in normal amounts, too low activity of renin activity product removing pathways, high substrate concentration, other circumstances that make the activity of renin relatively too high, such as other mechanisms leading to blood pressure increase, and/or the like) and/or leads to or supports a renin dependent disease or disorder as mentioned above and below, e.g. by renin activity the reduction of which has beneficial effects in the given disease. Such inappropriate renin activity may, for example, comprise a higher than normal activity, or further an activity in the normal or even below the normal range which, however, due to preceding, parallel and or subsequent processes, e.g. signaling, regulatory effect on other processes, higher substrate or product concentration and the like, leads to direct or indirect support or maintenance of a disease or disorder, and/or an activity that supports the outbreak and/or presence of a disease or disorder in any other way. The inappropriate activity of renin may or may not be dependent on parallel other mechanisms supporting the disorder or disease, and/or the prophylactic or therapeutic effect may or may include other mechanisms in addition to inhibition of renin. Therefore "dependent" has to be read as "dependent inter alia", (especially in cases where a disease or disorder is really exclusively dependent only on renin) preferably as "dependent mainly", more preferably as "dependent essentially only". "Inappropriate" does not necessarily mean that renin is the cause of a disease or disorder but that modulation, especially inhibition, of renin activity may be of beneficial effect in a disease or disorder even if it is due to other causes.

Where a disease or disorder dependent on inappropriate activity of a renin is mentioned (such in the definition of "use" in the following paragraph and also especially where a compound of the formula I is mentioned for use in the diagnostic or therapeutic treatment which is preferably the treatment of a disease or disorder dependent on inappropriate renin activity, this refers preferably to any one or more diseases or disorders that depend on inappropriate activity of natural renin and/or one or more altered or mutated forms thereof.

Where subsequently or above the term "use" is mentioned (as verb or noun) (relating to the use of a compound of the formula I or of a pharmaceutically acceptable salt thereof, or a method of use thereof), this (if not indicated differently or to be read differently in the context) includes any one or more of the following embodiments of the invention, respectively (if not stated otherwise): the use in the treatment of a disease or disorder that depends on (especially inappropriate) activity of renin, the use for the manufacture of pharmaceutical compositions for use in the treatment of a disease or disorder that depends on (especially inappropriate) activity of renin; a method of use of one or more compounds of the formula I in the treatment of a disease or disorder that depends on (especially inappropriate) activity of renin; a pharmaceutical preparation comprising one or more compounds of the formula I for the treatment of a disease or disorder that depends on (especially inappropriate) activity of renin; and one or more compounds of the formula I for use in the treatment of a disease or disorder in a warm-blooded animal, especially a human, preferably a disease that depends on (especially inappropriate) activity of renin; as appropriate and expedient, if not stated otherwise.

The terms "treat", "treatment" or "therapy" refer to the prophylactic (e.g. delaying or preventing the onset of a disease or disorder) or preferably therapeutic (including but not limited to preventive, delay of onset and/or progression, palliative, curing, symptom-alleviating, symptom-reducing, patient condition ameliorating, renin-modulating and/or renin-inhibiting) treatment of said disease(s) or disorder(s), especially of the one or more disease or disorder mentioned above or below.

PREFERRED EMBODIMENTS ACCORDING TO THE INVENTION

The groups of preferred embodiments of the invention mentioned below are not to be regarded as exclusive, rather, e.g., in order to replace general expressions or symbols with more specific definitions, parts of those groups of compounds can be interchanged or exchanged using the definitions given above, or omitted, as appropriate.

A highly preferred embodiment of the invention relates to a compound of the formula I with the following configuration

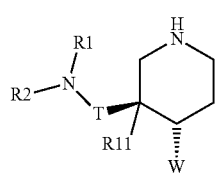

(A)

wherein R1, R2, R11, T and W are as defined for a compound of the formula I hereinabove or hereinbelow, or a pharmaceutically acceptable salt thereof.

Preferred is also a compound of the formula I with the following configuration

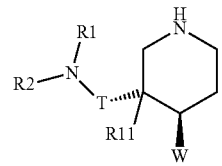

(B)

wherein R1, R2, R11, T and W are as defined for a compound of the formula I, or a pharmaceutically acceptable salt thereof.

A different group of preferred compounds relates to any one of a compound of the formula I with the following configuration

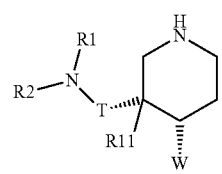

(C)

or of the formula I with the following configuration

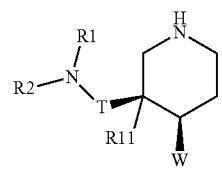

(D)

wherein R1, R2, R11, T and W are as defined for a compound of the formula I, or a pharmaceutically acceptable salt thereof, respectively.

Preferred is a compound of the formula I (especially in configuration A, given above) wherein
R1 is hydrogen or preferably $C_1$-$C_7$-alkyl, di-(phenyl)-$C_1$-$C_7$-alkyl, $C_3$-$C_B$-cycloalkyl or halo-$C_1$-$C_7$-alkyl;
R2 is phenyl-$C_1$-$C_7$-alkyl, di-(phenyl)-$C_1$-$C_7$-alkyl, naphthyl-$C_1$-$C_7$-alkyl, phenyl, naphthyl, pyridyl-$C_1$-$C_7$-alkyl, indolyl-$C_1$-$C_7$-alkyl, 1H-indazolyl-$C_1$-$C_7$-alkyl, quinolyl-$C_1$-$C_7$-alkyl, isoquinolyl-$C_1$-$C_7$-alkyl, 1,2,3,4-tetrahydro-1,4-benzoxazinyl-$C_1$-$C_7$-alkyl, 2H-1,4-benzoxazin-3(4H)-onyl-$C_1$-$C_7$-alkyl, 9-xanthenyl-$C_1$-$C_7$-alkyl, 1-benzothiophenyl-$C_1$-$C_7$-alkyl, pyridyl, indolyl, 1H-indazolyl, quinolyl, isoquinolyl, 1,2,3,4-tetrahydro-1,4-benzoxazinyl, 2H-1,4-benzoxazin-3(4H)-onyl, 9-xanthenyl or 1-benzothiophenyl, where each phenyl, naphthyl, pyridyl, indolyl, 1H-indazolyl, quinolyl, isoquinolyl, 1,2,3,4-tetrahydro-1,4-benzoxazinyl, 2H-1,4-benzoxazin-3(4H)-only or 1-benzothiophenyl is unsubstituted or substituted by one or more, e.g. up to three, substituents independently selected from the group consisting of $C_1$-$C_7$-alkyl, hydroxy-$C_1$-$C_7$-alkyl, $C_1$-$C_7$-alkoxy-$C_1$-$C_7$-alkyl, $C_1$-$C_7$-alkoxy-$C_1$-$C_7$-alkoxy-$C_1$-$C_7$-alkyl, $C_1$-$C_7$-alkanoyloxy-$C_1$-$C_7$-alkyl, amino-$C_1$-$C_7$-alkyl, $C_1$-$C_7$-alkoxy-$C_1$-$C_7$-alkylamino-$C_1$-$C_7$-alkyl, $C_1$-$C_7$-alkanoylamino-$C_1$-$C_7$-alkyl, $C_1$-$C_7$-alkylsulfonylamino-$C_1$-$C_7$-alkyl, carboxy-$C_1$-$C_7$-alkyl, $C_1$-$C_7$-alkoxycarbonyl-$C_1$-$C_7$-alkyl, halo, hydroxy, $C_1$-$C_7$-alkoxy, $C_1$-$C_7$-alkoxy-$C_1$-$C_7$-alkoxy, amino-$C_1$-$C_7$-alkoxy, N—$C_1$-$C_7$-alkanoylamino-$C_1$-$C_7$-alkoxy, carbamoyl-$C_1$-$C_7$-alkoxy, N—$C_1$-$C_7$-alkylcarbamoyl-$C_1$-$C_7$-alkoxy, $C_1$-$C_7$-alkanoyl, $C_1$-$C_7$-alkyloxy-$C_1$-$C_7$-alkanoyl, $C_1$-$C_7$-alkoxy-$C_1$-$C_7$-alkanoyl, carboxyl, carbamoyl and N—$C_1$-$C_7$-alkoxy-$C_1$-$C_7$-alkylcarbamoyl;

W is either a moiety of the formula IA,

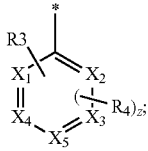

wherein the asterisk (*) denotes the position where the moiety W is bound to the 4-carbon in the piperidine ring in formula I, and wherein one of $X_1$ and $X_2$ is nitrogen or CH, while the other and $X_3$, $X_4$ and $X_5$ are CH; preferably with the proviso that R3 is bound to X, or $X_2$ or preferably to $X_3$ or $X_4$; or a moiety of the formula IB,

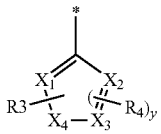

wherein the asterisk (*) denotes the position where the moiety W is bound to the 4-carbon in the piperidine ring in formula I, and wherein $X_4$ is $CH_2$, NH, S or O and one of $X_1$, $X_2$ and (preferably if $X_4$ is $CH_2$ or N) $X_3$, more preferably $X_2$, is N, while the others are each CH, with the proviso that at least one ring nitrogen (N or in the case or $X_4$NH) is present and that R3 is then preferably bound to $X_3$; preferably, $X_1$ is CH or N, $X_2$ is CH or N, $X_3$ is CH or N and $X_4$ is NH, O or S, with the proviso that not more than one of $X_1$, $X_2$ and $X_3$ is N; and preferably with the proviso that R3 is bound to $X_1$ or $X_2$ or preferably to $X_3$ or $X_4$;

or a moiety of the formula IC,

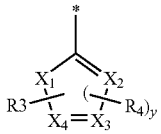

wherein the asterisk (*) denotes the position where the moiety W is bound to the 4-carbon in the piperidine ring in formula I, and wherein $X_1$ is $CH_2$, NH, S or O and one of $X_2$, $X_3$ and $X_4$ is N, while the others are CH, with the proviso that at least one ring nitrogen (N or in the case or $X_1$NH) is present; preferably, $X_1$ is S or O, $X_2$ is CH or N, $X_3$ is CH or N, and $X_4$ is CH or N, with the proviso that not more than one of $X_2$, $X_3$ and $X_4$ is N; and preferably with the proviso that R3 is bound to $X_2$ or preferably to $X_3$ or $X_4$, where in each case where R3 is bond to a moiety of the formula IA, IB or IC, instead of a hydrogen atom at a ring member NH, $CH_2$ or CH mentioned so far where R3 is bound a moiety R3 is present;

y is 0 or 1, preferably 0, and z is 0, 1 or 2, preferably 0 or 1;

R3 is hydrogen or preferably $C_1$-$C_7$-alkyloxy-$C_1$-$C_7$-alkyloxy, phenyloxy-$C_1$-$C_7$-alkyl, phenyl, pyridyl, phenyl-$C_1$-$C_7$-alkoxy, phenyloxy, phenyloxy-$C_1$-$C_7$-alkoxy, pyridyl-$C_1$-$C_7$-alkoxy, tetrahydropyranyloxy, 2H,3H-1,4-benzodioxinyl-$C_1$-$C_7$-alkoxy, phenylaminocarbonyl or phenylcarbonylamino, wherein each phenyl or pyridyl is unsubstituted or substituted by one or more, preferably up to three, e.g. 1 or two substituents independently selected from $C_1$-$C_7$-alkyl, hydroxy, $C_1$-$C_7$-alkoxy, phenyl-$C_1$-$C_7$-alkoxy wherein phenyl is unsubstituted or substituted by $C_1$-$C_7$-alkoxy and/or halo, carboxy-$C_1$-$C_7$-alkyloxy, N-mono- or N,N-di-($C_1$-$C_7$-alkyl)-aminocarbonyl-$C_1$-$C_7$-alkyloxy, halo, amino, N-mono- or N,N-di-($C_1$-$C_7$-alkyl) amino, $C_1$-$C_7$-alkanoylamino, morpholino-$C_1$-$C_7$-alkoxy, thiomorpholino-$C_1$-$C_7$-alkoxy, pyridyl-$C_1$-$C_7$-alkoxy, pyrazolyl, 4-$C_1$-$C_7$-alkylpiperidin-1-yl, tetrazolyl, carboxyl, N-mono- or N,N-di-($C_1$-$C_7$-alkylamino)-carbonyl and cyano; or is 2-oxo-3-phenyl-tetrahydropyrazolidin-1-yl, oxetidin-3-yl-$C_1$-$C_7$-alkyloxy, 3-$C_1$-$C_7$-alkyl-oxetidin-3-yl-$C_1$-$C_7$-alkyloxy or 2-oxo-tetrahydrofuran-4-yl-$C_1$-$C_7$-alkyloxy; with the proviso that if R3 is hydrogen y and z are 0 (zero);

R4 if present (which is the case if y or z is other than zero) is hydroxy, halo or $C_1$-$C_7$-alkoxy;

T is methylene or carbonyl, and

R11 is hydrogen, or a pharmaceutically acceptable salt thereof; or the use thereof.

Especially preferred is a compound of the formula I wherein R1, R2, T, W, R11, $X_1$-$X_5$, y and z are as defined in the preceding paragraph and R3 is hydrogen, or a pharmaceutically acceptable salt thereof; or the use thereof, with the proviso that y and z are zero.

More preferably, the invention relates to a compound of the formula I (especially in the configurations A given above), wherein R1 is hydrogen or preferably $C_1$-$C_4$-alkyl or $C_3$-$C_8$-cycloalkyl;

R2 is phenyl-$C_1$-$C_7$-alkyl, di-(phenyl)-$C_1$-$C_7$-alkyl, phenyl, indolyl-$C_1$-$C_7$-alkyl, 1H-indazolyl-$C_1$-$C_7$-alkyl, 9-xanthenyl-$C_1$-$C_7$-alkyl, 1,2,3,4-tetrahydro-1,4-benzoxazinyl or 2H-1,4-benzoxazin-3(4H)-onyl, where each phenyl, indolyl, 1H-indazolyl, 1,2,3,4-tetrahydro-1,4-benzoxazinyl, 2H-1,4-benzoxazin-3(4H)-only or 9-xanthenyl is unsubstituted or substituted by up to three substituents independently selected from the group consisting of $C_1$-$C_7$-alkyl, $C_1$-$C_7$-alkoxy-$C_1$-$C_7$-alkyl, $C_1$-$C_7$-alkoxy-$C_1$-$C_7$-alkoxy-$C_1$-$C_7$-alkyl, $C_1$-$C_7$-alkanoylamino-$C_1$-$C_7$-alkyl, alkylsulfonylamino-$C_1$-$C_7$-alkyl, carboxy-$C_1$-$C_7$-alkyl, $C_1$-$C_7$-alkoxycarbonyl-$C_1$-$C_7$-alkyl, halo, $C_1$-$C_7$-alkoxy, $C_1$-$C_7$-alkoxy-$C_1$-$C_7$-alkoxy and $C_1$-$C_7$-alkyloxy-$C_1$-$C_7$-alkanoyl;

W is either a moiety of the formula IA,

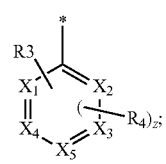

wherein the asterisk (*) denotes the position where the moiety W is bound to the 4-carbon in the piperidine ring in formula I, and wherein one of $X_1$ and $X_2$ is nitrogen or CH, while the other and $X_3$, $X_4$ and $X_5$ are CH; with the proviso that R3 is bound to $X_1$ or $X_2$ or preferably to $X_3$ or $X_4$; or a moiety of the formula IC,

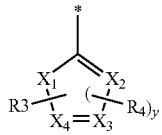
(IC)

wherein the asterisk (*) denotes the position where the moiety W is bound to the 4-carbon in the piperidine ring in formula I, and wherein $X_1$ is O, $X_2$ is CH or N, $X_3$ is CH and $X_4$ is CH or N, with the proviso that not more than one of $X_2$ and $X_4$ is N; and with the proviso that R3 is bound to $X_2$ or preferably to $X_3$ or $X_4$;

where in each case where R3 is bond to a moiety of the formula IA or IC, instead of a hydrogen atom at a ring member NH or CH mentioned so far where R3 is bound a moiety R3 is present;

y is 0 or 1, preferably 0, and z is 0, 1 or 2, preferably 0 or 1;

R3 is hydrogen or preferably $C_1$-$C_7$-alkyloxy-$C_1$-$C_7$-alkyloxy, phenyl, pyridyl, phenyl-$C_1$-$C_7$-alkoxy, phenyloxy, phenyloxy-$C_1$-$C_7$-alkoxy, pyridyl-$C_1$-$C_7$-alkoxy, tetrahydropyranyloxy, 2H,3H-1,4-benzodioxinyl-$C_1$-$C_7$-alkoxy, phenylaminocarbonyl or phenylcarbonylamino, wherein each phenyl or pyridyl is unsubstituted or substituted by up to three, e.g. 1 or two, substituents independently selected from hydroxy, $C_1$-$C_7$-alkoxy, halo, amino and N-mono- or N,N-di-($C_1$-$C_7$-alkyl)amino, with the proviso that if R3 is hydrogen then y and z are 0 (zero);

R4 if present (y or z other than 0) is hydroxy, halo or $C_1$-$C_7$-alkoxy;

T is carbonyl or preferably methylene, and

R11 is hydrogen, or a pharmaceutically acceptable salt thereof; or the use thereof.

Particular embodiments of the invention, especially of compounds of the formula I and/or salts thereof, are provided in the Examples—the invention thus, in a very preferred embodiment, relates to a compound of the formula I, or a salt thereof, selected from the compounds given in the Examples, as well as the use thereof.

Process of Manufacture

A compound of formula I, or a salt thereof, is prepared analogously to methods that, for other compounds, are in principle known in the art, so that for the novel compounds of the formula I the process is novel at least as analogy process, especially as described or in analogy to methods described herein in the illustrative Examples, or modifications thereof, preferably in general by (a) for the synthesis of a compound of the formula I wherein T is carbonyl and the other moieties are as defined for a compound of the formula I, reacting a carbonic acid compound of the formula II

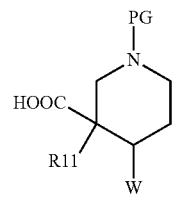
(II)

wherein W and R11 are as defined for a compound of the formula I and PG is a protecting group, or an active derivative thereof, with an amine of the formula III,

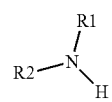
(III)

wherein R1 and R2 are as defined for a compound of the formula I, and removing protecting groups to give the corresponding compound of the formula I, or (b) for the preparation of a compound of the formula I wherein $R_3$ is unsubstituted or substituted aryl, unsubstituted or substituted heterocyclyl, etherified or esterified hydroxy, unsubstituted or substituted mercapto or unsubstituted or substituted amino, and W is a moiety of the formula IA given above, by reacting a compound of the formula IV,

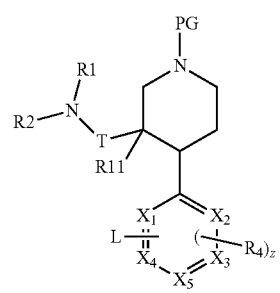
(IV)

wherein R1, R2, T, R11, $X_1$, $X_2$, $X_3$, $X_4$, z and $R_4$ are as defined for a compound of the formula I, PG is a protecting group and L is a leaving group or hydroxy, with a compound of the formula V,

R3-Q  (V)

wherein R3 is as just defined and Q is —B(OH)$_2$ or a leaving group, and removing protecting groups to give the corresponding compound of the formula I, or (c) for the preparation of a compound of the formula I wherein T is —CH$_2$—, reacting an aldehyde compound of the formula VI,

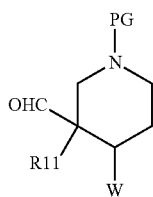

(VI)

wherein R11 and W are as defined for a compound of the formula I and PG is a protecting group, under the conditions of reductive amination with an amine of the formula III as given above wherein R1 is as defined for a compound of the formula I and R2 is hydrogen, to give the corresponding protected compound of the formula I, if desired introducing R2 as defined above for a compound of the formula I other than hydrogen by reacting with a compound of the formula VII,

R2*-D  (VII)

wherein R2* is defined as R2 in a compound of the formula I other than hydrogen and D is a leaving group, and removing protecting groups to give the corresponding compound of the formula I, and, if desired, subsequent to any one or more of the processes mentioned above converting an obtainable compound of the formula I or a protected form thereof into a different compound of the formula I, converting a salt of an obtainable compound of formula I into the free compound or a different salt, converting an obtainable free compound of formula I into a salt thereof, and/or separating an obtainable mixture of isomers of a compound of formula I into individual isomers;

where in any of the starting materials (especially of the formulae II to VII), in addition to specific protecting groups mentioned, further protecting groups may be present, and any protecting groups are removed at an appropriate stage in order to obtain the corresponding compound of the formula I, or a salt thereof.

Preferred Reaction Conditions

The preferred reaction conditions for the reactions mentioned above, as well as for the transformations and conversions, are as follows (or analogous to methods used in the Examples or as described there):

The reaction under (a) between an acid of the formula II, or a reactive derivative thereof, and an amino compound of the formula III preferably takes place under customary condensation conditions, where among the possible reactive derivatives of an acid of the formula II reactive esters (such as the hydroxybenzotriazole (HOBT), pentafluorophenyl, 4-nitrophenyl or N-hydroxysuccinimide ester), acid halogenides (such as the acid chloride or bromide) or reactive anhydrides (such as mixed anhydrides with lower alkanoic acids or symmetric anhydrides) are preferred. Reactive carbonic acid derivatives can also be formed in situ. The reaction is carried out by dissolving the compounds of formulae II and III in a suitable solvent, for example a halogenated hydrocarbon, such as methylene chloride, N,N-dimethylformamide, N,N-dimethylacetamide, N-methyl-2-pyrrolidone, methylene chloride, or a mixture of two or more such solvents, and by the addition of a suitable base, for example triethylamine, diisopropylethylamine (DIEA) or N-methylmorpholine and, if the reactive derivative of the acid of the formula II is formed in situ, a suitable coupling agent that forms a preferred reactive derivative of the carbonic acid of formula III in situ, for example dicyclohexylcarbodiimide/1-hydroxybenzotriazole (DCC/HOBT); bis(2-oxo-3-oxazolidinyl)phosphinic chloride (BOPCl); O-(1,2-dihydro-2-oxo-1-pyridyl)-N,N,N',N'-tetramethyluronium tetrafluoroborate (TPTU); O-(benzotriazol-1-yl)-N,N,N',N'-tetramethyluronium tetrafluoroborate (TBTU); (benzotriazol-1-yloxy)-tripyrrolidinophosphonium-hexafluorophosphate (PyBOP), 1-(3-dimethylaminopropyl)-3-ethylcarbodiimide hydrochloride/hydroxybenzotriazole or/1-hydroxy-7-azabenzotriazole (EDC/HOBT or EDC/HOAt) or HOAt alone, or with (1-chloro-2-methyl-propenyl)-dimethylamine. For review of some other possible coupling agents, see e.g. Klauser; Bodansky, *Synthesis* 1972, 453-463. The reaction mixture is preferably stirred at a temperature of between approximately −20 and 50° C., especially between 0° C. and 30° C., e.g. at room temperature. The reaction is preferably carried out under an inert gas, e.g. nitrogen or argon.

The subsequent removal of a protecting group, e.g. PG, such as tert-butoxycarbonyl, benzyl or 2-(trimethylsilyl)-ethoxycarbonyl, takes place under standard conditions, see also the literature mentioned below under General Process Conditions. For example, tert-butoxycarbonyl is removed in the presence of an acid, e.g. a hydrohalic acid, such as HCl, in an appropriate solvent, e.g. an ether, such as dioxane, or an alcohol, e.g. isopropanol, at customary temperatures, e.g. at room temperature, the removal of benzyl can be achieved e.g. by reaction with ethylchloroformate in an appropriate solvent, e.g. toluene, at elevated temperatures, e.g. from 80 to 110° C., and subsequent removal of the resulting ethoxycarbonyl group by hydrolysis in the presence of a base, e.g. an alkali metal hydroxide, such as potassium hydroxide, in an appropriate solvent, e.g. in an alcohol, such as ethanol, at elevated temperatures, e.g. from 80 to 120° C., or by removal by means of trimethylsilyl trifluoroacetate in a tertiary nitrogen base, such as 2,6-lutidine, in the presence of an appropriate solvent, such as a halogenated hydrocarbon, e.g. methylene chloride, and the removal of 2-(trimethylsilyl)-ethoxycarbonyl can be achieved, for example, by reaction with a tetra-lower alkylammonium fluoride, such as tetraethylammoniumfluoride, in an appropriate solvent or solvent mixture, e.g. a halogenated hydrocarbon, such as methylene chloride, and/or a nitrile, such as acetonitrile, preferably at elevated temperatures, e.g. under reflux conditions.

Where the reaction under (b) takes place with a compound of the formula IV wherein L is a leaving group and with a compound of the formula V wherein Q is —B(OH)$_2$, L is preferably halo, such as bromo or iodo, or trifluoromethylsulfonyloxy, and the reaction preferably takes place in an appropriate solvent, such as dioxane in the presence or absence of water, a basic buffering substance, e.g. potassium phosphate or potassium carbonate, and catalyst, e.g. Pd(PPh$_3$)$_4$, at preferably elevated temperatures, e.g. between 60° C. and the reflux temperature of the mixture. Where the reaction under (b) takes place with a compound of the formula IV wherein L is hydroxy and with a compound of the formula V wherein Q is a leaving group, the leaving group is preferably halo, e.g. bromo or iodo, and the coupling reaction preferably takes place in the presence of a base, such as potassium carbonate, in an appropriate solvent, e.g. N,N-dimethylformamide, at preferably elevated temperatures, e.g. from 30 to 80° C. Removal of protecting groups can take place as described above under (a) and below in the general process conditions.

The reductive amination in reaction (c) preferably takes place under customary conditions for reductive amination, e.g. in the presence of an appropriate hydrogenation agent, such as hydrogen in the presence of a catalyst or a complex hydride, e.g. sodium triacetoxyborohydride or sodium cyanoborhydride, in an appropriate solvent, such as a halogenated hydrocarbon, e.g. methylene chloride or 1,2,-dichloroethane, and optionally a carbonic acid, e.g. acetic acid, at preferred temperatures between −10° C. and 50° C., e.g. from 0° C. to room temperature.

Where desired, $R_2$ other than hydrogen can subsequently be introduced by reaction with a compound of the formula VII wherein preferably D is—the reaction preferably takes place under customary substitution conditions, e.g. in the case where an aryl moiety $R^2$ is to be coupled and Z is halo, e.g. iodo, in the presence of copper (e.g. Venus copper), sodium iodide and a base, such as potassium carbonate, in the presence or preferably absence of an appropriate solvent, e.g. at elevated temperatures in the range from, for example, 150 to 250° C., or (especially if Z in formula VIII is bromo) in the presence of a strong base, such as an alkali metal alcoholate, e.g. sodium tert-butylate, in the presence of an appropriate catalyst, such as $[Pd(\mu\text{-}Br)(t\text{-}Bu_3P)]_2$, and of an appropriate solvent, e.g. an aromatic solvent, such as toluene, at preferred temperatures between room temperature and the reflux temperature of the mixture, or (e.g. where the moiety $R^2$ is unsubstituted or substituted alkyl) in the presence of a base, such as an alkali metal carbonate, such as potassium carbonate, if useful in the presence of an alkali metal halogenide, e.g. sodium iodide, in an appropriate solvent, such as dimethyl formamide, at preferably elevated temperatures, e.g. between 50° C. and the reflux temperature of the mixture, or in presence of $NaN(TMS)_2$ in an appropriate solvent such as tetrahydrofurane at preferred temperatures from −20 to 30° C., e.g. at about 0° C., or, where $R^1$ is to be bound via a carbonyl or sulfonyl group, under condensation conditions e.g. as described above for reaction (a). The removal of protecting groups, both with or without preceding reaction with a compound of the formula VII, takes place e.g. as described above under the preferred conditions for reaction (a).

These and other appropriate reaction conditions can be found in the examples.

Optional Reactions and Conversions

Compounds of the formula I, or protected forms thereof directly obtained according to any one of the preceding procedures or after introducing protecting groups anew, which are included subsequently as starting materials for conversions as well even if not mentioned specifically, can be converted into different compounds of the formula I according to known procedures, where required after removal of protecting groups.

Where R2 is hydrogen in a compound of the formula I, this can be converted into the corresponding compound wherein R2 has a meaning other than hydrogen given for compounds of the formula I by reaction with a compound of the formula VII as described above, e.g. under reaction conditions as given above in the corresponding reaction under (c).

In a compound of the formula I wherein T is carbonyl, this carbonyl can be reduced to a corresponding methylene by treatment with an appropriate complex hydride of the required specificity, especially borane dimethylsulfide complex, in an appropriate solvent, such as an ether, e.g. tetrahydrofurane, at preferred temperatures between room temperature and the reflux temperature of the reaction mixture or at 140-150° C.; the subsequent removal of protecting group can be achieved as above for reaction (a) and below under "General Process Conditions", yielding a corresponding compound of the formula I.

Other conversion can be made in analogy to or as described for conversions given in the Examples.

Salts of compounds of formula I having at least one salt-forming group may be prepared in a manner known per se. For example, salts of compounds of formula I having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of formula I are obtained in customary manner, e.g. by treating the compounds with an acid or a suitable anion exchange reagent. Internal salts of compounds of formula I containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

A salt of a compound of the formula I can be converted in customary manner into the free compound; metal and ammonium salts can be converted, for example, by treatment with suitable acids, and acid addition salts, for example, by treatment with a suitable basic agent. In both cases, suitable ion exchangers may be used.

Stereoisomeric mixtures, e.g. mixtures of diastereomers, can be separated into their corresponding isomers in a manner known per se by means of appropriate separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

Intermediates and final products can be worked up and/or purified according to standard methods, e.g. using chromatographic methods, distribution methods, (re-) crystallization, and the like.

Starting Materials

Starting Materials, including intermediates, for compounds of the formula I, such as the compounds of the formulae II, III, IV, V, VI and VII, can be prepared, for example, according to methods that are known in the art, according to methods described in the examples or methods analogous to those described in the examples, and/or they are known or commercially available.

In the subsequent description of starting materials and intermediates and their synthesis, R1, R2, R3, R4, y, z, T, W, $X_1$-$X_5$, and PG have the meanings given above or in the Examples for the respective starting materials or intermediates, if not indicated otherwise directly or by the context. Protecting groups, if not specifically mentioned, can be introduced and removed at appropriate steps in order to prevent functional groups, the reaction of which is not desired in the corresponding reaction step or steps, employing protecting groups, methods for their introduction and their removal are as described above or below, e.g. in the references mentioned under "General Process Conditions". The person skilled in the art will readily be able to decide whether and which protecting groups are useful or required.

A compound of the formula II wherein R11 is hydrogen can, for example, be prepared by reducing a tetrahydropyridine compound of the formula VIII,

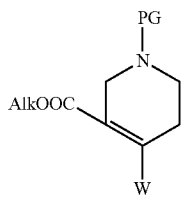
(VIII)

wherein Alk is the moiety of an alcohol, e.g. of methyl or ethyl, to the corresponding compound of the formula II wherein R11 is hydrogen. The reduction can take place under customary conditions, for example (i) with hydrogen in the presence of a noble metal catalyst, e.g. in dispersion such as Pd on charcoal or with a homogenous catalyst such as Pd(OAc)$_2$, in an appropriate solvent, for example an alcohol, such as ethanol, or N-methylpyrrolidone, or mixtures of two or more thereof, at preferred temperatures in the range from 0 to 50° C., e.g. at room temperature; (ii) in the presence of a complex hydride, especially sodium borohydride, and e.g. NiCl$_2$ in an appropriate solvent, such as an alcohol, e.g. at temperatures from −30 to 30° C.; or (iii) in the presence of a reducing metal, such as Mg, in an appropriate solvent, e.g. an alcohol, such as methanol, at preferred temperatures from −20 to 40° C., resulting in a compound of the formula IX,

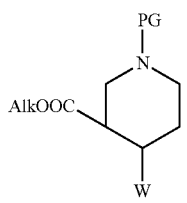
(IX)

which can then, if desired under epimerization, preferably be hydrolyzed to the corresponding compound of the formula II wherein the carboxy group and W are present in the configuration of the R1R2N-T- and the W in formula A given above, be converted to the corresponding compound of the formula II, e.g. (i) in the presence of an alcoholate of the formula MeOAlk, where Me is preferably an alkali metal, e.g. Na, and Alk is as defined under formula VIII, in the presence of an appropriate solvent, e.g. the corresponding alcohol AlcOH, e.g. methanol or ethanol, to achieve epimerization, followed by hydrolysis with water, e.g. at elevated temperatures from 30 to 80° C. or under reflux, or (ii) by addition of a metal hydroxide, e.g. potassium hydroxide, in the presence of water at elevated temperatures, e.g. from 50° C. to the reflux temperature of the mixture.

A tetrahydropyridine compound of the formula VIII can, for example, be prepared by reacting a compound of the formula X,

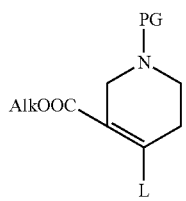
(X)

wherein L is as described above for a compound of the formula IV and the other moieties have the meanings described for a compound of the formula VIII, with a compound of the formula XI,

W-Q (XI)

wherein W is as described for a compound of the formula I and Q is —B(OH)$_2$ or a leaving group as defined for a compound of the formula V, under reaction conditions analogous to those described under reaction (b) above. Where W is a ring of the formula IC wherein X$_1$ is oxygen, X$_2$ is N, and each of X$_3$ and X$_4$ is CH and R3 is bound instead of the hydrogen at X$_4$ can be prepared by reaction of 4-R3-substituted phenyloxazole with a compound of the formula X given by first reacting the 4-R3-substituted phenyloxazole in the presence of a strong base, such as butyllithium, followed by treatment with zinc chloride, both in an appropriate solvent, such as tetrahydrofurane, at low temperatures e.g. from −90 to −50° C., followed by the addition of the compound of the formula XII and a catalyst, especially Pd(PPh$_3$)$_4$ in the same solvent and at appropriate temperatures, e.g. from −30 to 30° C., thus obtaining the corresponding compound of the formula VIII. The latter then can be reduced and epimerized by reaction first with magnesium in an appropriate solvent such as methanol and at appropriate temperatures e.g. from −30 to 30° C., then reaction with sodium alocoholate in the corresponding alcohol, such as methanol, at appropriate temperatures, e.g. from 40 to 80° C., and then with (trimethylsilyl)diazomethane in an appropriate solvent or solvent mixture, e.g. toluene and/or methanol, e.g. at temperatures from 0 to 50° C.

A compound of the formula VIII wherein W is a moiety of the formula IC wherein X$_1$ is O, X$_2$ is CH, X$_3$ is CH and X$_4$ is N and R3 is bound instead of the H at position X$_3$ can be prepared from a compound of the formula X given above by reaction with trimethylsilyl-acetylene (Me$_3$-Si—C≡CH) in the presence e.g. of CuI and a tertiary nitrogen base, such as triethylamine, and a catalyst, e.g. Pd(PPh$_3$)$_4$, in an appropriate solvent, such as dimethylformamide, and at appropriate temperatures, e.g. from 30 to 70° C., to give the corresponding compound of the formula XA,

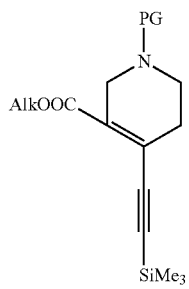
(XA)

which is then reacted under desilylation, e.g. with cesium fluoride in an appropriate solvent, such as methanol and/or water, at an appropriate temperature, e.g. from 0 to 50° C., followed by reaction of the free acetylene compound (where in formula XA instead of the SiMe$_3$ group a hydrogen is present) with an carboximidoylhalogenide of the formula VA, R3-C(=NH—OH)-Hal  (VA)

wherein Hal is halogen, especially chloro, in the presence of a nitrogen base, e.g. triethylamine, in an appropriate solvent, e.g. methylene chloride, and at appropriate temperatures, e.g. from 0 to 50° C.; thus obtaining the corresponding compound of the formula VIII with the ring IC as described.

In a compound of the formula VIII wherein W carries a nitro substituent at a position of R3, the nitro and the double bond in the tetrahydropyridine ring can be reduced to give an amino group and a piperidine ring, respectively, and then the amino can be converted into substituted amino e.g. by reaction with a complementary acid chloride under customary conditions, e.g. in the presence of a nitrogen base, such as triethylamine, in an appropriate solvent, e.g. methylene chloride, and at customary temperatures, e.g. from 0 to 50° C., thus yielding a corresponding compound of the formula IX.

Aldehydes of the formula VI can, for example, be obtained from the acids of the formula II by reduction, e.g. by first reducing the carboxy function in the presence of an appropriate complex hydride, e.g. borane dimethylsulfide, in an appropriate solvent, e.g. tetrahydrofurane, at preferred temperatures between −20 and 40° C., to the corresponding hydroxymethylene group which is then oxidized to the aldehyde group, for example in the presence of Dess Martin periodinane e.g. in methylene chloride and/or water or of 2,2,6,6,-tetramethyl-1-piperidinyloxy free radical e.g. in toluene and/or ethyl acetate in the presence of potassium bromide, water and potassium hydrogencarbonate, at preferred temperatures in the range from 0 to 50° C.

A compound of the formula IV can, for example, be prepared analogously to a compound of the formula I but using starting materials (e.g. corresponding to those of the formula II or VI) wherein instead of W the moiety

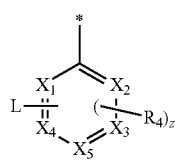

(ID)

is present wherein the symbols have the meanings given under a compound of the formula IV, L is bound to a ring carbon and the asterisk denotes the point of binding to the rest of the molecule. The processes can then be analogous to those described under (a) or (c) used for the synthesis of compounds of the formula I, the starting materials can be analogous to those mentioned there as starting materials, e.g. analogues of the compounds of the formula VIII or IX wherein instead of the moiety W one of the formula IC is present can be used. The reaction conditions can be as described for the other starting materials given hereinbefore.

Starting materials of the formula IV wherein L is hydroxy and the other symbols have the meanings given under formula IV can, for example, be prepared from the precursors wherein instead of hydroxy L a protected hydroxy is present by removal of the protecting group, e.g. in case of methoxymethyl by reaction with an acid, such as TFA, in an appropriate solvent, e.g. dichloromethane, for example at temperatures between 0 and 50° C. These precursors can be prepared in analogy to an analogue of a compound of the formula VIII and II or I wherein instead of the group W the moiety of the formula IC with protected hydroxy instead of L is present, e.g. from analogues of compounds of the formula IX wherein instead of W the moiety of the formula IC with protected hydroxy instead of L is present, in each case under conditions analogous to those for the corresponding compounds as given above.

Compounds of the formula III, wherein R2 is bound via methylene (as part of R2), can, for example, be prepared by reacting a compound of the formula XII, R2a-CHO  (XII)

(obtainable e.g. from the corresponding acids or their esters by reduction to a hydroxymethyl group and then oxidation to the —CHO group, e.g. under comparable conditions as described for the synthesis of aldehydes of the formula VI above) wherein $R^2a$ is a moiety that together with —CH$_2$— by which it is bound in formula III forms a corresponding moiety R2 in a compound of the formula I, under conditions of reductive amination, e.g. analogous to those described for reaction (c) above, with an amine of the formula XIII,

R1-NH$_2$  (XIII)

wherein R1 is as defined for a compound of the formula I.

Alternatively, compounds of the formula III as described under reaction (b) above can be prepared by reaction of a compound of the formula XIV,

R2-LG  (XIV)

wherein R2 is as defined for compounds of the formula I and LG is a leaving group, e.g. halo, under customary substitution reaction conditions with a compound of the formula XIII as described above. Compounds of the formula XIV can be obtained from precursors wherein instead of LG hydroxy is present by introducing LG, e.g. by halogenation with halosuccinimides.

Compounds of the formula V or X$_1$ wherein Q is —B(OH)$_2$ can, for example, be obtained from the corresponding precursors wherein instead of Q halo, e.g. bromo or chloro Analogues of the starting materials of the formula VIII wherein instead of W the moiety of the formula IC is present can be prepared by reacting a compound of the formula X as described above with an analogue of a compound of the formula XI given above wherein instead of W the group of the formula IC is present, under conditions as given above, is present, for example by reaction with an alkyl alkali metal, such as butyllithium, in an appropriate solvent, e.g. tetrahydrofurane and/or hydrocarbons, such as hexane, at low temperatures, e.g. from −100 to −50° C.

Other starting materials, their synthesis or analogous methods for their synthesis are known in the art, commercially available, and/or they can be found in or derived from the Examples.

General Process Conditions

The following applies in general to all processes mentioned hereinbefore and hereinafter, while reaction conditions specifically mentioned above or below are preferred:

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible wherever reactions without specific mentioning of protection and/or deprotection are described in this specification.

Within the scope of this disclosure only a readily removable group that is not a constituent of the particular desired end product of formula I is designated a "protecting group", unless the context indicates otherwise. The protection of functional groups by such protecting groups, the protectting groups themselves, and the reactions appropriate for their introduction and removal are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, *Peptides, Proteins*), Verlag Chemie, Weinheim, Deerfield Beach, and Basel 1982, and in Jochen Lehmann, "Chemie der Kohlenhydrate: Monosaccharide and Derivate" (*Chemistry of Carbohydrates: Monosaccharides and Derivatives*), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the H$^+$ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in compounds of formula I described as being preferred. Special preference is given to reaction conditions that are identical or analogous to those mentioned in the Examples.

Pharmaceutical Use, Pharmaceutical Preparations and Methods

As described above, the compounds of the present invention are inhibitors of renin activity and, thus, may be employed for the treatment of hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, Alzheimer's disease, dementia, anxiety states and cognitive disorders, and the like.

The present invention further provides pharmaceutical compositions comprising a therapeutically effective amount of a pharmacologically active compound of the instant invention, alone or in combination with one or more pharmaceutically acceptable carriers.

The pharmaceutical compositions according to the present invention are those suitable for enteral, such as oral or rectal, transdermal and parenteral administration to mammals, including man, to inhibit renin activity, and for the treatment of conditions associated with (especially inappropriate) renin activity. Such conditions include hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders and the like.

Thus, the pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbants, colorants, flavors and sweeteners.

Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and pre-determined rate over a prolonged period of time, and means to secure the device to the skin.

Accordingly, the present invention provides pharmaceutical compositions as described above for the treatment of conditions mediated by renin activity, preferably, hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, Alzheimer's disease, dementia, anxiety states and cognitive disorders, as well as methods of their use.

The pharmaceutical compositions may contain a therapeutically effective amount of a compound of the formula I as defined herein, either alone or in a combination with another therapeutic agent, e.g., each at an effective therapeutic dose as reported in the art. Such therapeutic agents include:
a) antidiabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; peroxisome proliferator-activated receptor (PPAR) ligands; protein tyrosine phosphatase-1B (PTP-1B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose cotransporter inhibitors such as T-1095; glycogen phosphorylase A inhibitors such as BAY R3401; biguanides such as met-formin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as LAF237;
b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;
c) anti-obesity agents such as orlistat; and
d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perindopril, quinapril, ramipril and trandolapril; inhibitors of the Na-K-ATPase membrane pump such as digoxin; neutralendopeptidase (NEP) inhibittors; ACE/NEP inhibitors such as omapatrilat, sampatrilat and fasidotril; angiotensin II antagonists such as candesartan, eprosartan, irbesartan, losartan, telmisartan and valsartan, in particular valsartan; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

Other specific anti-diabetic compounds are described by Patel Mona in *Expert Opin Investig Drugs*, 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions comprising a therapeutically effective amount of a compound of the invention alone or in combination with a therapeutically effective amount of another therapeutic agent, preferably selected from anti-diabetics, hypolipidemic agents, anti-obesity agents or anti-hypertensive agents, most preferably from antidiabetics, anti-hypertensive agents or hypolipidemic agents as described above.

The present invention further relates to pharmaceutical compositions as described above for use as a medicament.

The present invention further relates to use of pharmaceutical compositions or combinations as described above for the preparation of a medicament for the treatment of conditions mediated by (especially inappropriate) renin activity, preferably, hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angio-plasty, raised intra-ocular pressure, glaucoma, abnormal vascular growth and/or hyperaldosteronism, and/or further cognitive impairment, Alzheimer's disease, dementia, anxiety states and cognitive disorders, and the like.

Thus, the present invention also relates to a compound of formula I for use as a medicament, to the use of a compound of formula I for the preparation of a pharmaceutical composition for the prevention and/or treatment of conditions mediated by (especially inappropriate) renin activity, and to a pharmaceutical composition for use in conditions mediated by (especially inappropriate) renin activity comprising a compound of formula I, or a pharmaceutically acceptable salt thereof, in association with a pharmaceutically acceptable diluent or carrier material therefore.

The present invention further provides a method for the prevention and/or treatment of conditions mediated by (especially inappropriate) renin activity, which comprises administering a therapeutically effective amount of a compound of the present invention to a warm-blooded animal, especially a human, in need of such treatment.

A unit dosage for a mammal of about 50-70 kg may contain between about 1 mg and 1000 mg, advantageously between about 5-600 mg of the active ingredient. The therapeutically effective dosage of active compound is dependent on the species of warm-blooded animal (especially mammal, more especially human), the body weight, age and individual condition, on the form of administration, and on the compound involved.

In accordance with the foregoing the present invention also provides a therapeutic combination, e.g., a kit, kit of parts, e.g., for use in any method as defined herein, comprising a compound of formula I, or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents or anti-hypertensive agents. The kit may comprise instructions for its administration.

Similarly, the present invention provides a kit of parts comprising: (i) a pharmaceutical composition comprising a compound of the formula I according to the invention; and (ii) a pharmaceutical composition comprising a compound selected from an anti-diabetic, a hypolipidemic agent, an anti-obesity agent, an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound of formula I, or a pharmaceutically acceptable salt thereof, and at least a second drug substance, said second drug substance preferably being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to a modulation of (especially inappropriate) renin activity.

Preferably, the condition associated with (especially inappropriate) renin activity is selected from hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, Alzheimer's disease, dementia, anxiety states and cognitive disorders.

Finally, the present invention provides a method or use which comprises administering a compound of formula I in combination with a therapeutically effective amount of an anti-diabetic agent, a hypolipidemic agent, an anti-obesity agent or an anti-hypertensive agent.

Ultimately, the present invention provides a method or use which comprises administering a compound of formula I in the form of a pharmaceutical composition as described herein.

The above-cited properties are demonstrable in vitro and in vivo tests using advantageously mammals, e.g., mice, rats, rabbits, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The concentration level in vitro may range between about $10^{-3}$ molar and $10^{-10}$ molar concentrations. A therapeutically effective amount in vivo may range depending on the route of administration, between about 0.001 and 500 mg/kg, preferably between about 0.1 and 100 mg/kg.

As described above, the compounds of the present invention have enzyme-inhibiting properties. In particular, they inhibit the action of the natural enzyme renin. Renin passes from the kidneys into the blood where it effects the cleavage of angiotensinogen, releasing the decapeptide angiotensin I which is then cleaved in the lungs, the kidneys and other organs to form the octapeptide angiotensin II. The octapeptide increases blood pressure both directly by arterial vasoconstriction and indirectly by liberating from the adrenal glands the sodium-ion-retaining hormone aldosterone, accompanied by an increase in extracellular fluid volume which increase can be attributed to the action of angiotensin II. Inhibitors of the enzymatic activity of renin lead to a reduction in the formation of angiotensin I, and consequently a smaller amount of angiotensin II is produced. The reduced concentration of that active peptide hormone is a direct cause of the hypotensive effect of renin inhibitors.

The action of renin inhibitors may be demonstrated inter alia experimentally by means of in vitro tests, the reduction in the formation of angiotensin I being measured in various systems (human plasma, purified human renin together with synthetic or natural renin substrate).

Inter alia the following in vitro tests may be used:

Recombinant human renin (expressed in Chinese Hamster Ovary cells and purified using standard methods) at 7.5 nM concentration is incubated with test compound at various concentrations for 1 h at RT in 0.1 M Tris-HCl buffer, pH 7.4, containing 0.05 M NaCl, 0.5 mM EDTA and 0.05% CHAPS. Synthetic peptide substrate Arg-Glu(EDANS)-Ile-His-Pro-Phe-His-Leu-Val-Ile_His_Thr-Lys(DABCYL)-Arg9 is added to a final concentration of 2 µM and increase in fluorescence is recorded at an excitation wave-length of 350 nm and at an emission wave-length of 500 nm in a microplate spectro-fluorimeter. IC50 values are calculated from percentage of inhibition of renin activity as a function of test compound concentration (Fluorescence Resonance Energy Transfer, FRET, assay). Compounds of the formula I, in this assay, preferably can show $IC_{50}$ values in the range from 1 nM to 5 µM.

Alternatively, recombinant human renin (expressed in Chinese Hamster Ovary cells and purified using standard methods) at 0.5 nM concentration is incubated with test compound at various concentrations for 2 h at 37° C. in 0.1 M Tris-HCl buffer, pH 7.4, containing 0.05 M NaCl, 0.5 mM EDTA and 0.05% CHAPS. Synthetic peptide substrate Arg-Glu (EDANS)-Ile-His-Pro-Phe-His-Leu-Val-Ile_His_Thr-Lys (DABCYL)-Arg9 is added to a final concentration of 4 µM and increase in fluorescence is recorded at an excitation wave-length of 340 nm and at an emission wave-length of 485 nm in a microplate spectro-fluorimeter. IC50 values are calculated from percentage of inhibition of renin activity as a function of test compound concentration (Fluorescence Resonance Energy Transfer, FRET, assay). Compounds of the formula I, in this assay, preferably can show $IC_{50}$ values in the range from 1 nM to 5 µM.

In another assay, human plasma spiked with recombinant human renin (expressed in Chinese Hamster Ovary cells and purified using standard methods) at 0.8 nM concentration is incubated with test compound at various concentrations for 2 h at 37° C. in 0.1 M Tris/HCl pH 7.4 containing 0.05 M NaCl, 0.5 mM EDTA and 0.025% (w/v) CHAPS. Synthetic peptide substrate Ac-Ile-His-Pro-Phe-His-Leu-Val-Ile-His-Asn-Lys-

[DY-505-X5] is added to a final concentration of 2.5 µM. The enzyme reaction is stopped by adding an excess of a blocking inhibitor. The product of the reaction is separated by capillary electrophoresis and quantified by spectrophotometric measurement at 505 nM wave-length. IC50 values are calculated from percentage of inhibition of renin activity as a function of test compound concentration. Compounds of the formula I, in this assay, preferably can show $IC_{50}$ values in the range from 1 nM to 5 µM.

In another assay, recombinant human renin (expressed in Chinese Hamster Ovary cells and purified using standard methods) at 0.8 nM concentration is incubated with test compound at various concentrations for 2 h at 37° C. in 0.1 M Tris/HCl pH 7.4 containing 0.05 M NaCl, 0.5 mM EDTA and 0.025% (w/v) CHAPS. Synthetic peptide substrate Ac-Ile-His-Pro-Phe-His-Leu-Val-Ile-His-Asn-Lys-[DY-505-X5] is added to a final concentration of 2.5 µM. The enzyme reaction is stopped by adding an excess of a blocking inhibitor. The product of the reaction is separated by capillary electrophoresis and quantified by spectrophotometric measurement at 505 nM wave-length. IC50 values are calculated from percentage of inhibition of renin activity as a function of test compound concentration. Compounds of the formula I, in this assay, preferably show $IC_{50}$ values in the range from 1 nM to 5 µM.

In animals deficient in salt, renin inhibitors bring about a reduction in blood pressure. Human renin may differ from the renin of other species. In order to test inhibitors of human renin, primates, e.g., marmosets (*Callithrix jacchus*) may be used, because human renin and primate renin are substantially homologous in the enzymatically active region. Inter alia the following in vivo tests may be used:

Compounds can be tested in vivo in primates as described in the literature (see for example by Schnell C R et al. Measurement of blood pressure and heart rate by telemetry in conscious, unrestrained marmosets. Am J Physiol 264 (Heart Circ Physiol 33). 1993: 1509-1516; or Schnell C R et al. Measurement of blood pressure, heart rate, body temperature, ECG and activity by telemetry in conscious, unrestrained marmosets. Proceedings of the fifth FELASA symposium: Welfare and Science. Eds BRIGHTON. 1993.

The following examples serve to illustrate the invention without limiting the scope thereof:
Abbreviations
  Ac acetyl
  aq. aqueous
  Boc tert-butoxycarbonyl
  Brine saturated sodium chloride solution
  Celite trademark of Celite Corp. for filtering aid based on kieselguhr
  conc. concentrated
  DCM dichloromethane
  DEAD diethyl azodicarboxylate
  DIBAL diisobutylaluminum hydride
  dppf 1,1'-Bis(diphenylphosphino)ferrocene
  DIEA N,N-diisopropylethylamine
  DMF N,N-dimethylformamide
  DMSO dimethylsulfoxide
  DMT-MM 4-(4,6-dimethoxy-1,3,5-triazin-2-yl)-4-methylmorpholinium chloride
  EDC 1-(3-Dimethylaminopropyl)-3-ethylcarbodiimide hydrochloride
  ES-MS electrospray mass spectrometry
  Et ethyl
  EtOAc ethyl acetate
  h hour(s)
  HMPA hexamethylphosphoramide
  HOAt 1-hydroxy-7-azabenzotriazole
  HPLC high-pressure liquid chromatography
  HyFlo diatomaceous earth based filtering aid
  IPr isopropyl
  LAH lithium aluminium hydride
  LDA lithium diisopropylamide
  mCPBA 3-chloroperbenzoic acid
  Me methyl
  min minute(s)
  mL milliliter(s)
  MOMCl methoxymethyl chloride
  MS Mass Spectrometry
  MsCl Methylsulfonylchlorid
  nBuLi n-butyllithium
  n-Hex n-hexyl
  NaOMe sodium methoxylate
  NMP 1-methyl-2-pyrrolidinone
  NMR nuclear magnetic resonance
  Ph phenyl
  RT room temperature
  TBTU O-(benzotriazol-1-yl)-N,N,N',N'-tetramethylammonium tetrafluoroborate
  TFA trifluoroacetic acid
  $Tf_2O$ trifluoromethanesulfonic anhydride
  THF tetrahydrofurane
  TMS trimethylsilyl
  TMSOTf trifluoromethanesulfonic acid trimethylsilyl ester
  WSCD=EDC
  $A^rRet$ HPLC retention time in min determined by HPLC condition-A
  $B^rRet$ HPLC retention time in min determined by HPLC condition-B
Synthesis Flash chromatography is performed by using silica gel (Merck; 40-63 µm). For thin layer chromatography, pre-coated silica gel (Merck 60 F254; Merck KgaA, Darmstadt, Germany)) plates are used. $^1$NMR measurements are performed on a Varian Gemin±400 or a Bruker DRX 500 or a Bruker DXR 400 spectrometer using tetramethylsilane as internal standard. Chemical shifts (δ) are expressed in ppm downfield from tetramethylsilane. Electrospray mass spectra are obtained with a Fisons Instruments VG Platform II. Commercially available solvents and chemicals are used for syntheses.

HPLC Condition-A
Column: CombiScreen ODS-AM, 50×4.6 mm.
Flow rate: 2.0 ml/min
Mobile phase: A) TFA/water (0.1/100, v/v), B) TFA/acetonitrile (0.1/100, v/v)
Gradient: linear gradient from 5% B to 100% B in 5 min then 100% B in 2 min
Detection: UV at 254 nm
HPLC Condition-B
Column: Prontosil 120-3-C18-H 3.0 µm, 53×4.0 mm.

Flow rate: 1.5 ml/min
Mobile phase: A) TFA/water (0.1/100, v/v), B) TFA/acetonitrile (0.1/100, v/v)
Gradient: linear gradient from 5% B to 100% B in 10 min
Detection: UV at 214 nm
HPLC Condition-C
Column: ACQUITY UPLC™ BEH $C_{18}$ 1.7 µm, 50×2.1 mm.
Flow rate: 0.5 ml/min
Mobile phase: A) TFA/water (0.1/100, v/v), B) TFA/acetonitrile (0.1/100, v/v)
Gradient: linear gradient from 5% B to 100% B in 2 min then 100% B in 1 min
Detection: UV at 254 nm
HPLC Condition-D Column: ACQUITY UPLC™ BEH $C_{18}$ 1.7 µm, 50×2.1 mm.
Flow rate: 0.5 ml/min
Mobile phase: A) TFA/water (0.1/100, v/v), B) TFA/acetonitrile (0.1/100, v/v)
Gradient: linear gradient from 5% B to 100% B in 5.5 min then 100% B in 1.5 min
Detection: UV at 254 nm The HPLC conditions A, B, C, and D can be identified by the subscript prefixes of the $T_{Ret}$ values given in the examples. For instance, B int $B^rRet=\ldots$ Min means condition-B in the case of HPLC.

In the following reaction schemes, moieties such as Rz preferably have the meanings corresponding to the Examples.

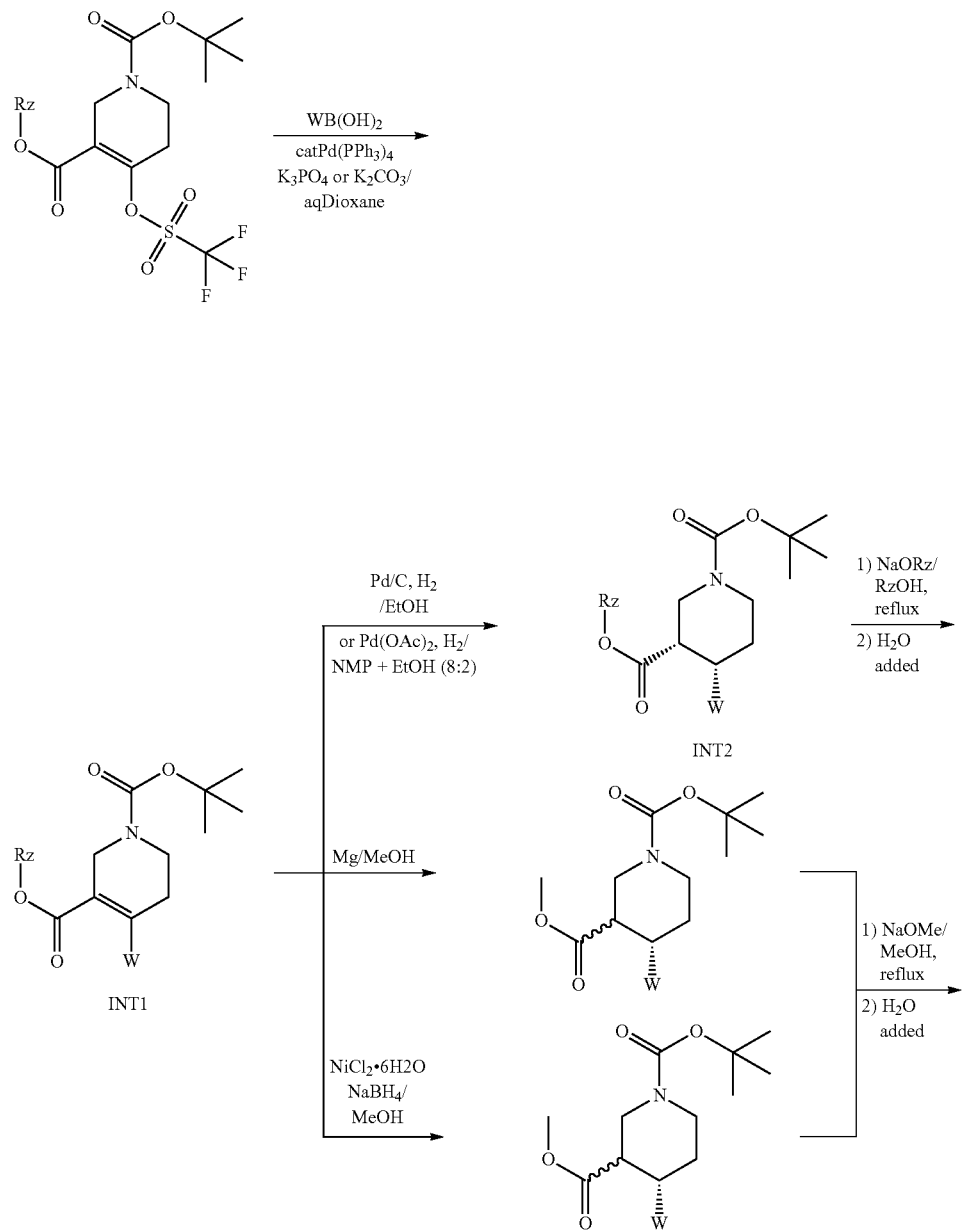

-continued
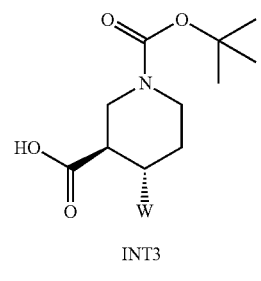
INT3
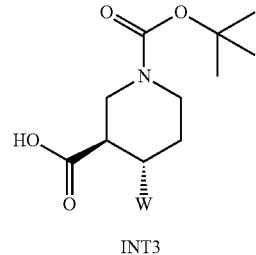
INT3
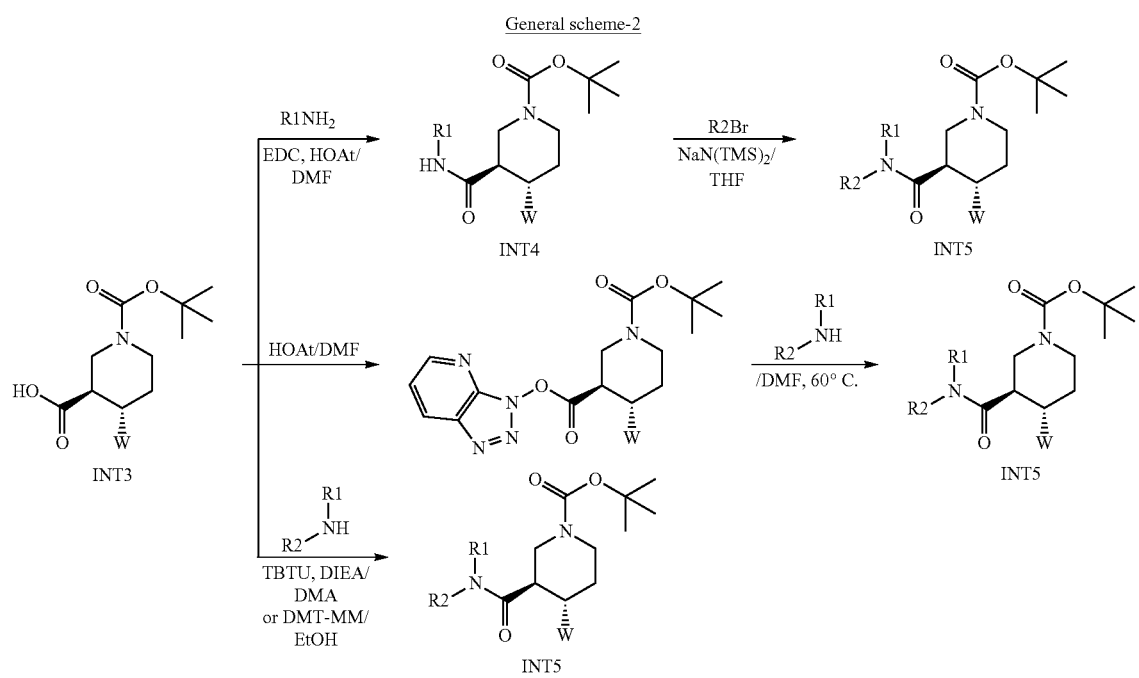
General scheme-2

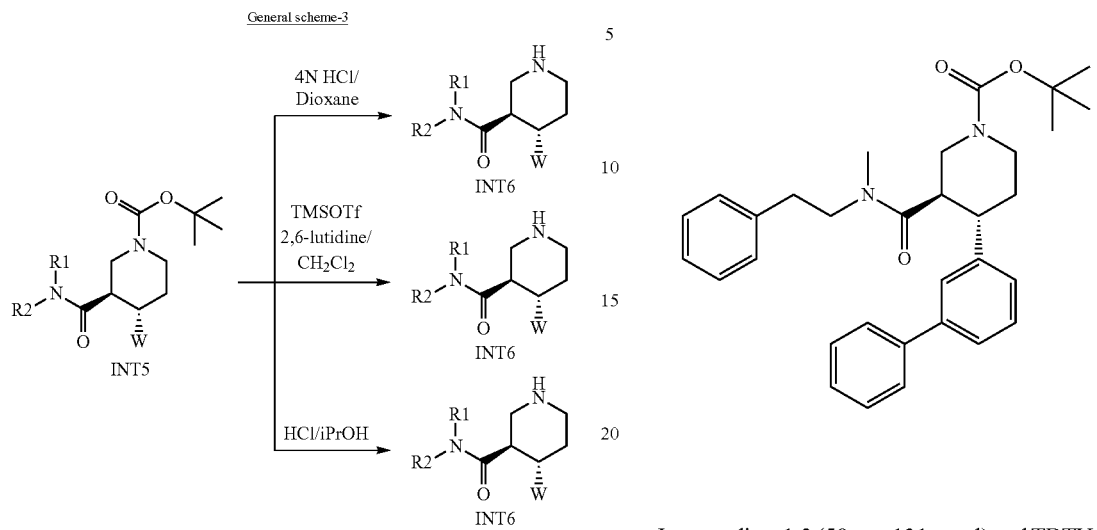

Intermediates INT1, INT2, INT3, INT4, INT5 are obtained as a racemic mixture, or optical resolution of INT3 using an appropriate chiral amine (such as cinchonidine, cinchonine, quinine or quinidine) affords corresponding enantiomeric pure INT3. And the final product INT6 can be separated into the pure enantiomers by common techniques like chiral chromatography.

EXAMPLE 1

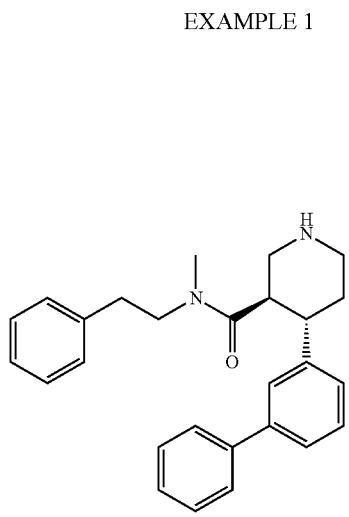

A mixture of Intermediate 1.1 (54 mg, 0.108 mmol) and 5-6M 2-propanol solution of HCl (2 mL) is stirred at RT for 2 h. The reaction mixture is concentrated under reduced pressure and the residue is lyophilized from dioxane to give a white solid; ES-MS: M=399; HPLC: $_Bt_{Ret}$=5.21 min.

Intermediate 1.1

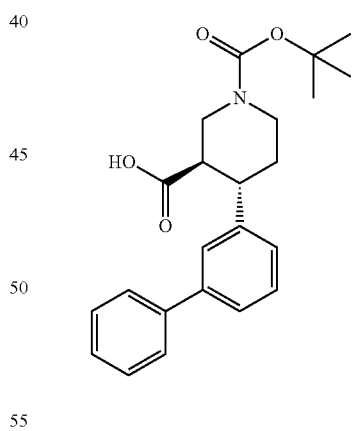

Intermediate 1.2 (50 mg, 131 μmol) and TBTU (51 mg, 159 μmol) are dissolved in DMA (1 mL), DIEA (54 μL, 316 μmol) is added and the mixture is shaken for 30 min at room temperature. N-methylphenethylamine (25 μL, 169 μmol) is added and shaking is continued for 50 min. EtOAc is added and the organic layer is washed with aqueous 5% NaHCO$_3$, aqueous 0.5 M HCl and brine, dried over Na$_2$SO$_4$ and evaporated in vacuo. Flash chromatography of the residue (SiO$_2$, hexane/ethyl acetate) affords Intermediate 1.1 as an oil; ES-MS: M+H=499; HPLC: $_Bt_{Ret}$=7.69 min.

Intermediate 1.2

A solution of Intermediate 1.3 (540 mg, 1.32 mmol) and ~20% NaOEt in EtOH (2.5 mL, 6.47 mmol) in THF/EtOH (1:1, 50 mL) is stirred at 60° C. for 3.5 h. H$_2$O (0.470 mL) is added and stirring at 60° C. is continued for 15 h. The solvent is removed in vacuo and the residue is suspended in EtOAc. The organic layer is washed with 0.5 M HCl and brine, dried over Na$_2$SO$_4$ and the solvent is removed in vacuo to give Intermediate 1.2 as a light brown oil; ES-MS: M+H=382; HPLC: $_Bt_{Ret}$=6.49 min.

Intermediate 1.3

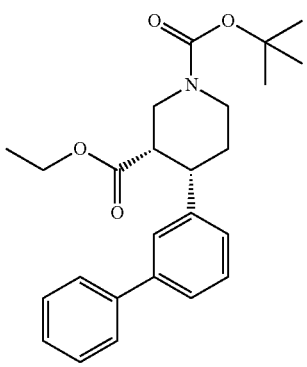

A mixture of Intermediate 1.4 (900 mg, 2.21 mmol) and Pd(OAc)$_2$ (75 mg, 0.334 mmol) in NMP/EtOH (4:1, 50 mL) is shaken under a H$_2$-atmosphere (1 bar). More Pd(OAc)$_2$ (150 mg, 0.668 mmol) is added portionwise during the reaction. After 161 h, the reaction mixture is filtered through HyFlo and the solvent is removed in vacuo. Flash chromatography of the residue (SiO$_2$, hexane/ethyl acetate) affords Intermediate 1.3 as a yellow oil; ES-MS: M+H=410; HPLC: $_B t_{Ret}$=7.65 min.

Intermediate 1.4

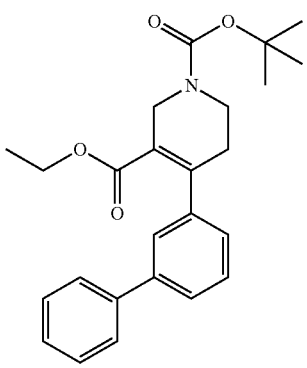

A mixture of 4-trifluoromethanesulfonyloxy-5,6-dihydro-2H-pyridine-1,3-dicarboxylic acid 1-tert-butyl ester 3-methyl ester (2.12 g, 4.46 mmol) (see e.g. WO 2004/002957 or US 2003/216441), 3-biphenylboronic acid (0.9 g, 4.54 mmol), K$_2$CO$_3$ (1.11 g, 8.03 mmol) and Pd(PPh$_3$)$_4$ (258 mg, 0.223 mmol) in dioxane (30 mL) is stirred under N$_2$ at 80° C. for 15 h. After adding H$_2$O, the reaction mixture is extracted with EtOAc. The combined organic phases are washed with H$_2$O, brine and dried (Na$_2$SO$_4$). Concentration under reduced pressure and silica gel flash chromatography give Intermediate 1.4 as yellow oil; ES-MS: M+H=408; HPLC: $_B t_{Ret}$=7.77 min.

EXAMPLE 2

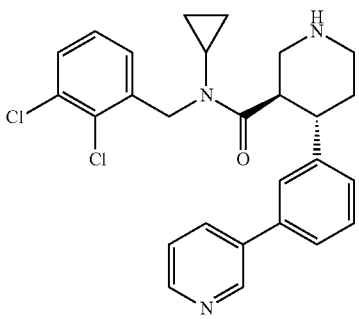

Example 2 is synthesized by deprotection of Intermediate 2.1 (64 mg, 0.11 mmol) analogously to the preparation of Example 1. White solid; ES-MS: M+H=480; HPLC: $_A t_{Ret}$=2.54 min.

Intermediate 2.1

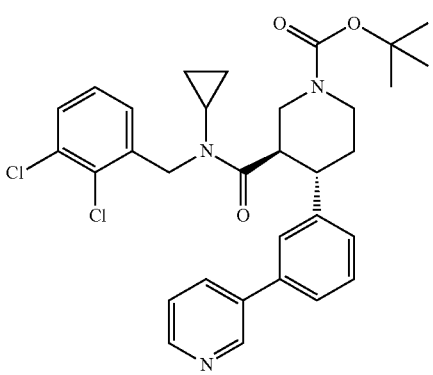

A mixture of Intermediate 2.2 (404 mg, 0.69 mmol), 3-pyridylboronic acid (85 mg, 0.69 mmol), K$_3$PO$_4$ (221 mg, 1.04 mmol) and Pd(PPh$_3$)$_4$ (80 mg, 0.07 mmol), H$_2$O (0.2 mL) in dioxane (7 mL) is refluxed under N$_2$ for 3 h. After adding H$_2$O, the reaction mixture is extracted with EtOAc. The combined organic phases are washed with H$_2$O, brine and dried (MgSO$_4$). Concentration under reduced pressure and silica gel flash chromatography give Intermediate 2.1 as white amorphous material; ES-MS: M+H=580; $_A t_{Ret}$=3.82 min.

Intermediate 2.2

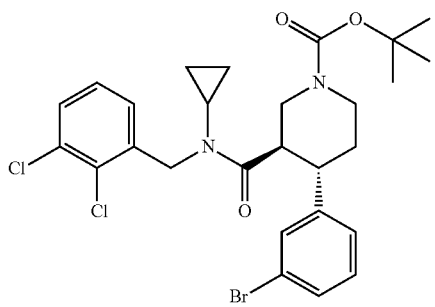

To a mixture of Intermediate 2.3 (454 mg, 1.07 mmol) and 1-bromomethyl-2,3-dichlorobenzene (585 mg, 2.44 mmol) in THF (4 mL), 1 M THF solution of NaN(TMS)$_2$ (2.20 mL, 2.20 mmol) is added under N$_2$ at 0° C. After stirring at RT for 5 h and adding H$_2$O, the reaction mixture is extracted with EtOAc. The combined organic phases are washed with H$_2$O, brine and dried (MgSO$_4$). Concentration under reduced pressure and silica gel flash chromatography give Intermediate 2.2 as white amorphous material; ES-MS: M+H=583; HPLC: $_At_{Ret}$=5.77 min.

Intermediate 2.3

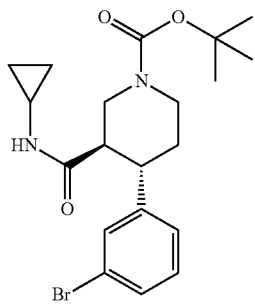

A mixture of Intermediate 2.4 (845 mg, 2.20 mmol), cyclopropylamine (0.38 mL, 5.48 mmol), EDC (632 mg, 3.30 mmol) and HOAt (299 mg, 2.20 mmol) in DMF (11 mL) is stirred under N$_2$ at RT for 5 h. After adding H$_2$O, the reaction mixture is extracted with EtOAc. The combined organic phases are washed with H$_2$O, brine and dried (MgSO$_4$). Concentration under reduced pressure and silica gel flash chromatography give Intermediate 2.3 as white amorphous material; ES-MS: M+H=423; HPLC: $_At_{Ret}$=3.98 min.

Intermediate 2.4

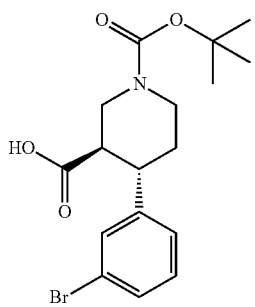

To a solution of Intermediate 2.5 (1.33 g, 3.35 mmol) and NiCl$_2$.6H$_2$O (954 mg, 4.01 mmol) in MeOH (18 mL), NaBH$_4$ (506 mg, 13.4 mmol) is added at −10° C. under N$_2$. After stirring for 2 h, H$_2$O is added and the reaction mixture is extracted with Et$_2$O. The combined organic phases are washed with brine, and dried (MgSO$_4$). Concentration under reduced pressure. A solution of the resulting residue (1.32 g, 3.31 mmol) and NaOMe (0.77 mL, 25 wt % MeOH solution, 3.31 mmol) in MeOH (18 mL) is refluxed under N$_2$ for 3 h. After cooling down to RT, H$_2$O is added and the reaction mixture is extracted with EtOAc. The combined organic phases are washed with brine and dried (MgSO$_4$). Concentration under reduced pressure yields an oil which is then dissolved in dioxane (4 mL) and 8N KOH (2 mL), and refluxed under N$_2$ for 14 h. After cooling down to RT, the reaction mixture is adjusted to weakly acidic pH by slowly adding 1N KHSO$_4$, and mixture is extracted with EtOAc. The combined organic phases are washed with H$_2$O, brine and dried (MgSO$_4$). Concentration under reduced pressure gives Intermediate 2.4 as white amorphous material; ES-MS: M+H=384; HPLC: $_At_{Ret}$=4.05 min.

Intermediate 2.5

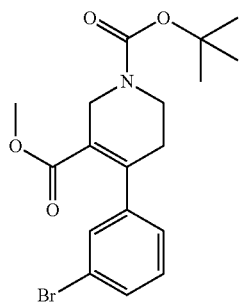

A mixture of 4-trifluoromethanesulfonyloxy-5,6-dihydro-2H-pyridine-1,3-dicarboxylic acid 1-tert-butyl ester 3-methyl ester (20.5 g, 52.7 mmol) (see e.g. WO 2004/002957 or US 2003/216441), 3-bromophenylboronic acid (12.7 g, 63.2 mmol), K$_3$PO$_4$ (13.4 g, 63.2 mmol) and Pd(PPh$_3$)$_4$ (3.0 g, 2.60 mmol) in dioxane (270 mL) is stirred under N$_2$ at 50° C. for 4 h. After adding H$_2$O, the reaction mixture is extracted with EtOAc. The combined organic phases are washed with H$_2$O, brine and dried (MgSO$_4$). Concentration under reduced pressure and silica gel flash chromatography give Intermediate 2.5 as white amorphous material; ES-MS: M=396; HPLC: $_At_{Ret}$=4.82 min.

EXAMPLE 3

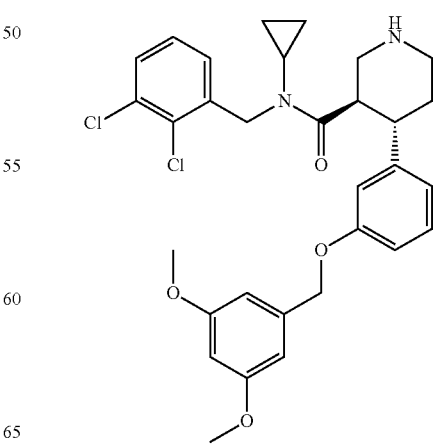

Example 3 is synthesized by deprotection of Intermediate 3.1 (212 mg, 0.32 mmol) analogously to the preparation of Example 1. White solid; ES-MS: M+H=569; HPLC: $_A t_{Ret}$=3.73 min.

Intermediate 3.1

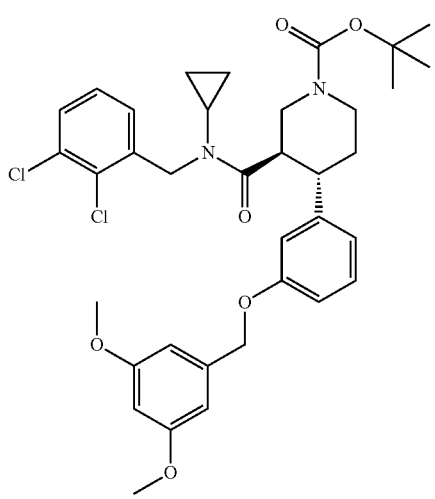

A mixture of Intermediate 3.2 (175 mg, 0.34 mmol), 1-bromomethyl-3,5-dimethoxybenzene (93 mg, 0.40 mmol) and K$_2$CO$_3$ (112 mg, 0.81 mmol) in DMF (2 mL) is stirred under N$_2$ at 60° C. for 3 h. After adding H$_2$O, the reaction mixture is extracted with Et$_2$O. The combined organic phases are washed with H$_2$O, brine and dried (MgSO$_4$). Concentration under reduced pressure and silica gel flash chromatography give Intermediate 3.1 as white solid; ES-MS: M+H=669; HPLC: $_A t_{Ret}$=5.79 min.

Intermediate 3.2

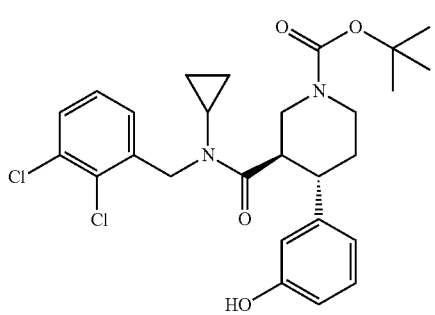

A mixture of Intermediate 3.3 (634 mg, 1.13 mmol) and TFA (2 mL) in DCM (4 mL) is stirred under N$_2$ at RT. After stirring for 2 h, the reaction mixture are concentrated under reduced pressure to give crude product. Then a mixture of crude product, Et$_3$N (0.47 mL, 3.39 mmol) and (Boc)$_2$O (295 mg, 1.35 mmol) in DCM (4 mL) is stirred under N$_2$ at RT for 1 h. After adding aqueous KHSO$_4$, the reaction mixture is extracted with EtOAc. The combined organic phases are washed with H$_2$O, brine and dried (MgSO$_4$). Concentration under reduced pressure and silica gel flash chromatography give Intermediate 3.2 as white amorphous material; ES-MS: M+H=519; HPLC: $_A t_{Ret}$=4.74 min.

Intermediate 3.3

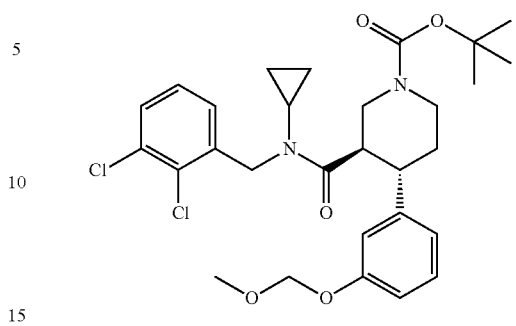

Intermediate 3.3 is synthesized by condensation of Intermediate 3.4 (2.17 g, 5.36 mmol) analogously to the preparation of Intermediate 2.2. White amorphous material; ES-MS: M+H=563; HPLC: $_A t_{Ret}$=5.40 min.

Intermediate 3.4

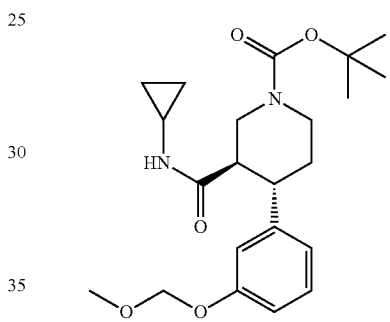

Intermediate 3.4 is synthesized by condensation of Intermediate 3.5 (2.20 g, 5.97 mmol) analogously to the preparation of Intermediate 2.3. White amorphous material; ES-MS: M+H=405; HPLC: $_A t_{Ret}$=3.62 min.

Intermediate 3.5

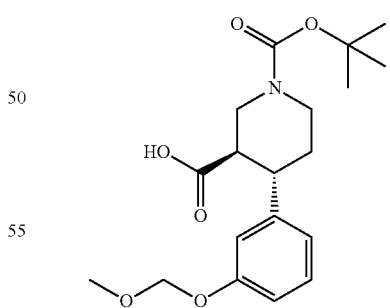

Intermediate 3.5 is synthesized by 1,4-reduction, epimerization and hydrolysis of Intermediate 3.6 (2.56 g, 6.78 mmol) analogously to the preparation of Intermediate 2.4. White amorphous material; ES-MS: M+H=366; HPLC: $_A t_{Ret}$=3.73 min.

Intermediate 3.6

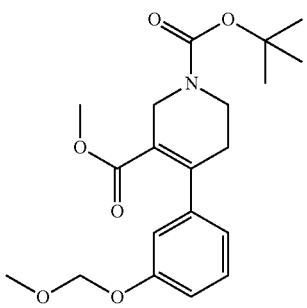

Intermediate 3.6 is synthesized by condensation of 4-trifluoromethanesulfonyloxy-5,6-dihydro-2H-pyridine-1,3-dicarboxylic acid 1-tert-butyl ester 3-methyl ester (5.35 g, 13.7 mmol) and 3-Methoxymethoxyphenylboronic acid (3.75 g, 20.6 mmol) analogously to the preparation of Intermediate 2.5. Colorless oil; ES-MS: M+H=378; HPLC: $_At_{Ret}$=4.37 min.

EXAMPLE 4

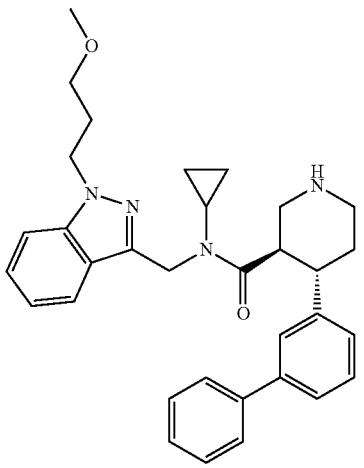

Example 4 is synthesized by deprotection of Intermediate 4.1 (110 mg, 0.29 mmol) analogously to the preparation of Example 1. White solid; ES-MS: M+H=523; HPLC: $_At_{Ret}$=3.32 min.

Intermediate 4.1

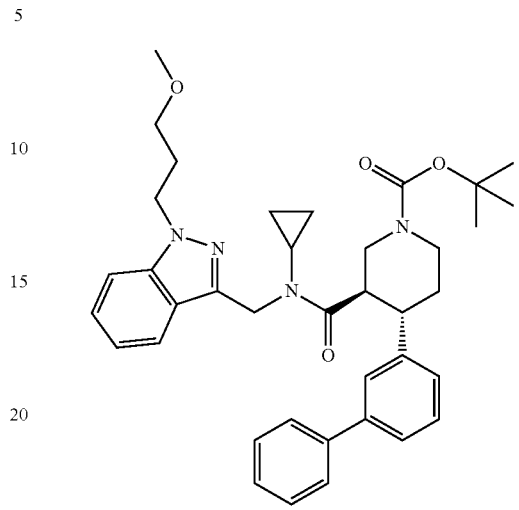

Intermediate 4.2 (110 mg, 0.29 mmol), EDC (83 mg, 0.44 mmol) and HOAt (47 mg, 0.35 mmol) are dissolved in DMF (1 mL) under $N_2$. After stirring at RT for 1 h, Intermediate 4.5 (90 mg, 0.35 mmol) is added and stirred at 50° C. for 14 h. After adding $H_2O$, the reaction mixture is extracted with EtOAc. The combined organic phases are washed with $H_2O$, brine and dried ($MgSO_4$). Concentration under reduced pressure gives Intermediate 4.1 as white amorphous material; ES-MS: M+H=623; HPLC: $_At_{Ret}$=5.37 min.

Intermediate 4.2

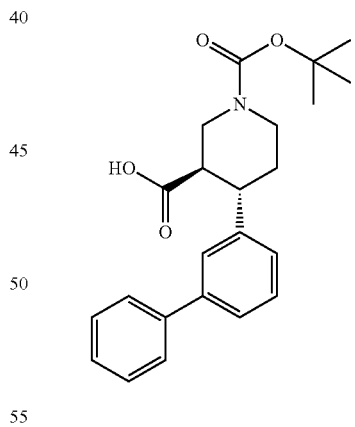

To a solution of Intermediate 4.3 (1.06 g, 2.68 mmol) in dioxane (4 mL), 8N KOH (2 mL) is added. After refluxing for 14 h, the reaction mixture is cooled down to RT, adjusted to weakly acidic pH by slowly adding 1N $KHSO_4$ and extracted with EtOAc. The combined organic phases are washed with brine and dried ($MgSO_4$). Concentration under reduced pressure and purified by silica gel flash chromatography give Intermediate 4.2 as white amorphous material; ES-MS: M+H=382; HPLC: $_At_{Ret}$=4.40 min.

Intermediate 4.3

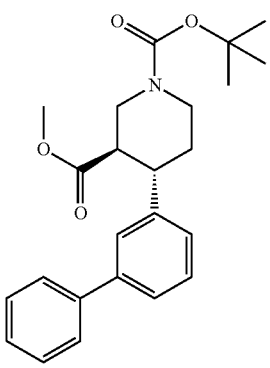

To a solution of Intermediate 4.4 (209.0 mg, 0.53 mmol) in MeOH (5.3 mL), Mg (103.3 mg, 4.24 mmol) is added at 0° C. under $N_2$. After stirring at RT for 2 h, the reaction mixture is filtered through Celite pad and diluted with EtOAc. The reaction mixture is washed with saturated aqueous $NH_4Cl$ and brine, and dried ($MgSO_4$). Concentration under reduced pressure follows. The residue and NaOMe (0.25 mL, 25 wt % MeOH solution, 1.16 mmol) are dissolved in MeOH. After adding $H_2O$, the reaction mixture is extracted with EtOAc. The combined organic phases are washed with brine and dried ($MgSO_4$). Concentration under reduced pressure gives Intermediate 4.3 as white amorphous material; ES-MS: M+H=396; HPLC: $_At_{Ret}$=5.07 min.

Intermediate 4.4

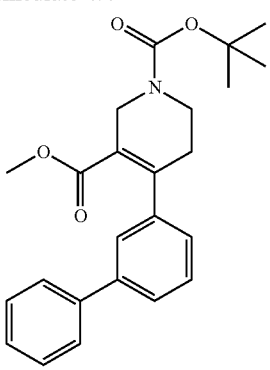

Intermediate 4.4 is synthesized by condensation of 4-trifluoromethanesulfonyloxy-5,6-dihydro-2H-pyridine-1,3-dicarboxylic acid 1-tert-butyl ester 3-methyl ester (14.0 g, 36.0 mmol) and 3-Biphenylboronic acid (11.9 g, 43.0 mmol) analogously to the preparation of Intermediate 2.5. Colorless oil; ES-MS: M+H=394; HPLC: $_At_{Ret}$=5.12 min.

Intermediate 4.5

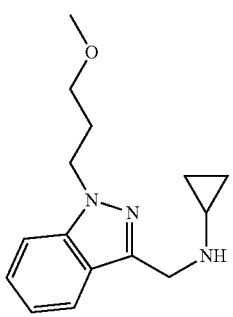

A mixture of Intermediate 4.6 (500 mg, 2.3 mmol), cyclopropylamine (157 mg, 2.75 mmol) and $NaBH(OAc)_3$ (731 mg, 3.45 mmol) in DCM (10 mL) and MeOH (5 mL) is stirred under $N_2$ at 0° C. After stirring at RT for 9 hour, the reaction mixture is quenched with saturated aqueous $NaHCO_3$ and extracted with DCM. The combined organic phases are washed with $H_2O$, brine and dried ($Na_2SO_4$). Concentration under reduced pressure and silica gel flash chromatography give Intermediate 4.5 as brown oil; ES-MS: M+H=260; HPLC: $_At_{Ret}$=2.38 min.

Intermediate 4.6

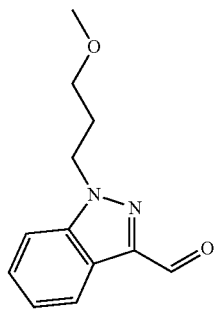

A mixture of Intermediate 4.7 (700 mg, 3.18 mmol) and $MnO_2$ (7 g, excess) in toluene (30 mL) is stirred under $N_2$ at RT for 12 h. After filtration removing $MnO_2$, the filtrate is concentrated under reduced pressure and silica gel flash chromatography to give Intermediate 4.6 as colorless oil; ES-MS: M+H=219; HPLC: $_At_{Ret}$=3.52 min Intermediate 4.7

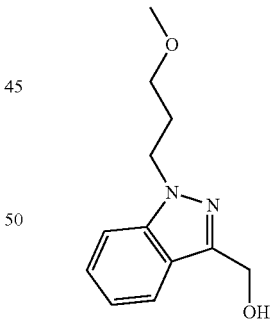

To a solution of LAH (190 mg, 5.0 mmol) in THF (10 mL) is added a solution of Intermediate 4.8 (1.05 g, 3.4 mmol) in THF (5 mL) under $N_2$ at 0° C., then the mixture is stirred at 0° C. for 2 h. After stirring additional 2 h at RT, the mixture is cooled down to 0° C. and diluted with THF, and $Na_2SO_4$ $10H_2O$ is added. The THF phase is concentrated under reduced pressure after filtration through Celite pad to give Intermediate 4.7 as colorless oil; ES-MS: M+H=221; HPLC: $_At_{Ret}$=2.73 min.

Intermediate 4.8

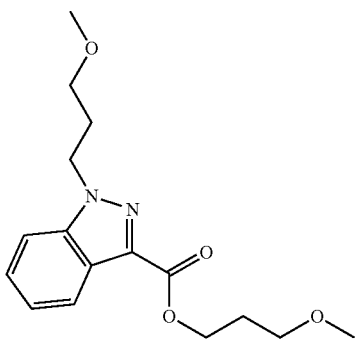

To a mixture of indazole-3-carboxylic acid (2 g, 13.7 mmol), toluene-4-sulfonic acid 3-methoxy-propyl ester (5 g, 20.6 mmol) in DMF (15 mL), NaH (1.12 g, 28 mmol) is added under $N_2$ at 0° C. After stirring at 50° C. for 12 h, $H_2O$ is added to the reaction mixture as well as concentrated HCl aq., and the mixture is extracted with EtOAc. The combined organic phases are washed with $H_2O$, brine and dried ($Na_2SO_4$). Concentration under reduced pressure and silica gel flash chromatography give Intermediate 4.8 as colorless oil; ES-MS: M+H=307; HPLC: $_A t_{Ret}$=3.65 min The following Examples enlisted on Table 1 are synthesized analogously to the preparation of Example 1-4. As far as not being commercially available, the synthesis of intermediates for the preparation of compounds of Examples 5-74 is described below the Table 1.

TABLE 1

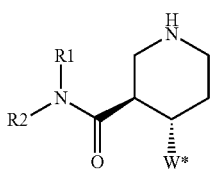

| Example | R1 | R2 | W* | Analytical data |
|---|---|---|---|---|
| 5 | cyclopropyl-CH< | 2-chlorobenzyl | 3-biphenyl | MS: [M + 1]⁺ = 447; HPLC: $_B t_{Ret}$ = 5.60 min |
| 6 | cyclopropyl-CH< | 1-(2-chlorophenyl)ethyl | 3-biphenyl | MS: [M + 1]⁺ = 461.5 HPLC $_B t_{Ret}$ = 5.63 min and 5.78 min. |
| 7 | cyclopropyl-CH< | 2,3-dichlorobenzyl | 3-biphenyl | MS: [M + 1]⁺ = 481.4 HPLC $_B t_{Ret}$ = 5.95 min. |

TABLE 1-continued

| Example | R1 | R2 | W* | Analytical data |
|---|---|---|---|---|
| 8 | cyclopropyl | 2,3-dimethylbenzyl | biphenyl-3-yl | MS: [M + 1]$^+$ = 439.6<br>HPLC$_B$t$_{Ret}$ = 5.68 min. |
| 9 | cyclopropyl | 3-methoxy-2-methylbenzyl | biphenyl-3-yl | MS: [M + 1]$^+$ = 455.5<br>HPLC$_B$t$_{Ret}$ = 5.40 mn. |
| 10 | cyclobutylmethyl | 2-chlorobenzyl | biphenyl-3-yl | MS: [M + 1]$^+$ = 461.5<br>HPLC$_B$t$_{Ret}$ = 5.89 min. |
| 11 | H | 2,2-diphenylethyl | biphenyl-3-yl | MS: [M + 1]$^+$ = 461.6<br>HPLC$_B$t$_{Ret}$ = 5.61min. |
| 12 | H | 3-methyl-2-phenylbutyl | biphenyl-3-yl | MS: [M + 1]$^+$ = 427.6<br>HPLC$_B$t$_{Ret}$ = 5.66 min. |

TABLE 1-continued

| Example | R1 | R2 | W* | Analytical data |
|---|---|---|---|---|
| 13 | cyclopropyl | 2,3-dimethylbenzyl | 3,5-dimethoxybenzyl-oxy-phenyl (3-(3,5-dimethoxybenzyloxy)phenyl) | MS: [M + 1]⁺ = 529<br>HPLC $_A$t$_{Ret}$ = 3.67 min. |
| 14 | cyclopropyl | 3-(3-methoxypropoxy)-5-methoxybenzyl | 3-(3,5-dimethoxybenzyloxy)phenyl | MS: [M + 1]⁺ = 619<br>HPLC $_A$t$_{Ret}$ = 3.55 min. |
| 15 | cyclopropyl | 2,3-dimethylbenzyl | 3-(pyridin-3-yl)phenyl | MS: [M + 1]⁺ = 440<br>HPLC $_A$t$_{Ret}$ = 2.48 min. |
| 16 | cyclopropyl | 2,3-dimethylbenzyl | 3-(pyridin-4-yl)phenyl | MS: [M + 1]⁺ = 440<br>HPLC $_A$t$_{Ret}$ = 2.75 min. |
| 17 | cyclopropyl | 2,3-dimethylbenzyl | 3'-hydroxybiphenyl-3-yl | MS: [M + 1]⁺ = 445<br>HPLC $_A$t$_{Ret}$ = 3.35 min. |

TABLE 1-continued
| Example | R1 | R2 | W* | Analytical data |
|---|---|---|---|---|
| 18 | 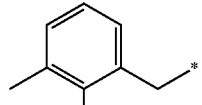 | 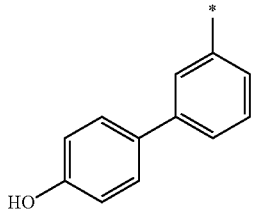 |  | MS: [M + 1]⁺ = 455<br>HPLC $_A$t$_{Ret}$ = 3.26 min. |
| 19 | 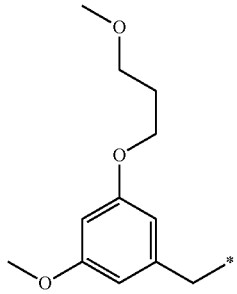 | 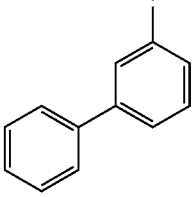 |  | MS: [M + 1]⁺ = 529<br>HPLC $_A$t$_{Ret}$ = 3.60 min. |
| 20 | 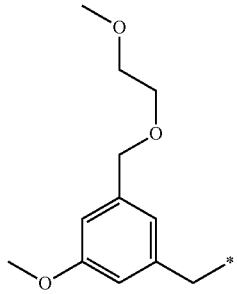 | 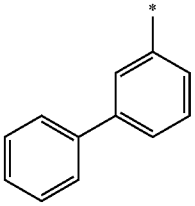 |  | MS: [M + 1]⁺ = 529<br>HPLC $_A$t$_{Ret}$ = 3.55 min. |
| 21 | 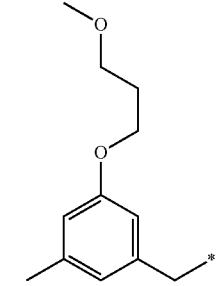 | 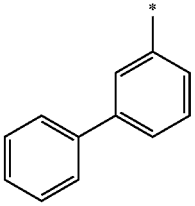 | | MS: [M + 1]⁺ = 513<br>HPLC $_A$t$_{Ret}$ = 3.75 min. |

TABLE 1-continued
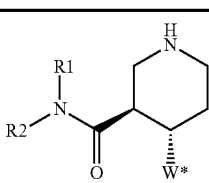
| Example | R1 | R2 | W* | Analytical data |
|---|---|---|---|---|
| 22 |  | 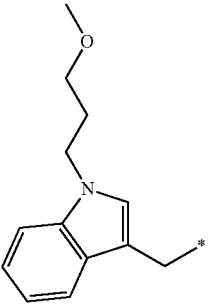 | 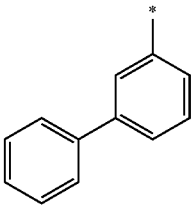 | MS: [M + 1]$^+$ = 522<br>HPLC $_A$t$_{Ret}$ = 3.73 min. |
| 23 |  | 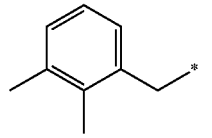 | 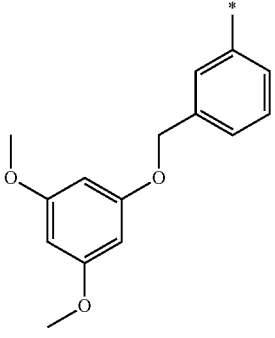 | MS: [M + 1]$^+$ = 529<br>HPLC $_A$t$_{Ret}$ = 3.62 min. |
| 24 |  | 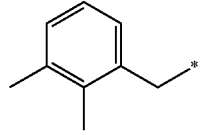 | 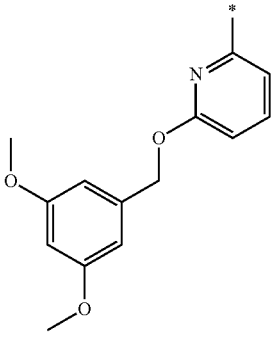 | MS: [M + 1]$^+$ = 530<br>HPLC $_A$t$_{Ret}$ = 3.84 min. |
| 25 |  | 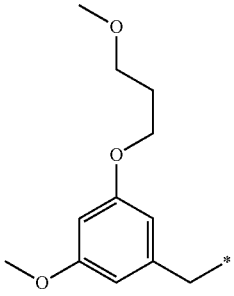 | 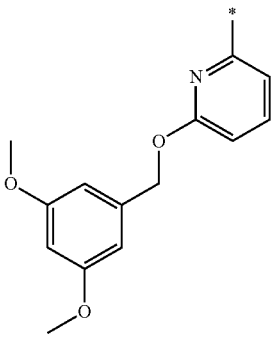 | MS: [M + 1]$^+$ = 620<br>HPLC $_A$t$_{Ret}$ = 3.40 min. |

TABLE 1-continued

| Example | R1 | R2 | W* | Analytical data |
|---|---|---|---|---|
| 26 | cyclopropyl | 2,3-dimethylbenzyl | 3-[(2,6-dimethoxypyridin-4-yl)methoxy]phenyl | MS: [M + 1]⁺ = 530<br>HPLC $_A t_{Ret}$ = 3.63 min. |
| 27 | cyclopropyl | 2,3-dimethylbenzyl | 3-[(2,6-diethoxypyridin-4-yl)methoxy]phenyl | MS: [M + 1]⁺ = 558<br>HPLC $_A t_{Ret}$ = 4.03 min. |
| 28 | cyclopropyl | 2,3-dimethylbenzyl | 3-[(2-chloro-6-methoxypyridin-4-yl)methoxy]phenyl | MS: [M]⁺ = 534<br>HPLC $_A t_{Ret}$ = 3.73 min. |
| 29 | cyclopropyl | 2,3-dimethylbenzyl | 3-methoxy-5-phenylphenyl | MS: [M + 1]⁺ = 469<br>HPLC $_A t_{Ret}$ = 3.67 min. |

TABLE 1-continued

| Example | R1 | R2 | W* | Analytical data |
|---|---|---|---|---|
| 30 | H | 2,3-dichlorobenzyl | biphenyl-3-yl | MS: [M]⁺ = 439 HPLC_A t_Ret = 3.37 min. |
| 31 | cyclopropyl | 2,3-dimethylbenzyl | 3-[(6-methoxypyridin-3-yl)methoxy]phenyl | MS: [M + 1]⁺ = 500 HPLC_A t_Ret = 3.22 min. |
| 32 | cyclopropyl | 2,3-dimethylbenzyl | 3-[(2-methoxypyridin-4-yl)methoxy]phenyl | MS: [M + 1]⁺ = 500 HPLC_A t_Ret = 3.07 min. |
| 33 | cyclopropyl | [1-(3-methoxypropanoyl)-1H-indol-3-yl]methyl | biphenyl-3-yl | MS: [M + 1]⁺ = 536 HPLC_A t_Ret = 3.43 min. |

TABLE 1-continued
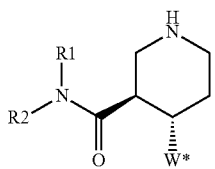
| Example | R1 | R2 | W* | Analytical data |
|---|---|---|---|---|
| 34 |  | 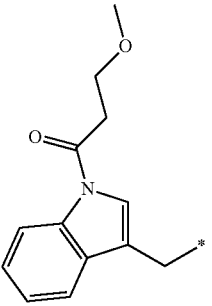 | 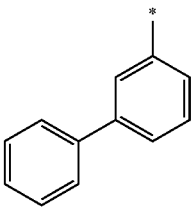 | MS: [M + 1]⁺ = 550<br>HPLC $_A$t$_{Ret}$ = 3.60 min. |
| 35 |  | 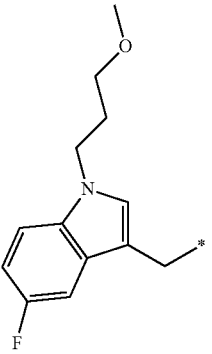 | 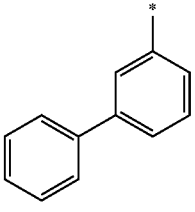 | MS: [M + 1]⁺ = 540<br>HPLC $_A$t$_{Ret}$ = 3.62 min. |
| 36 |  | 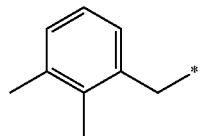 | 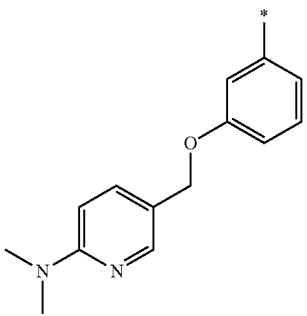 | MS: [M + 1]⁺ = 513<br>HPLC $_A$t$_{Ret}$ = 2.57 min. |
| 37 | H | 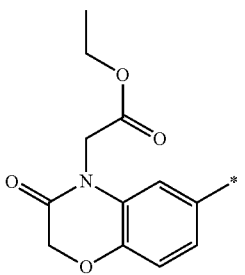 | 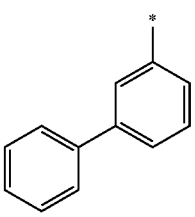 | MS: [M + 1]⁺ = 514<br>HPLC $_A$t$_{Ret}$ = 3.07 min. |

TABLE 1-continued

| Example | R1 | R2 | W* | Analytical data |
|---|---|---|---|---|
| 38 | H | 4-(3-methoxypropyl)-3-oxo-3,4-dihydro-2H-benzo[1,4]oxazin-6-yl | 3-biphenyl | MS: [M + 1]$^+$ = 500<br>HPLC $_A$t$_{Ret}$ = 2.98 min. |
| 39 | ethyl | 4-(3-methoxypropyl)-3-oxo-3,4-dihydro-2H-benzo[1,4]oxazin-6-yl | 3-biphenyl | MS: [M + 1]$^+$ = 528<br>HPLC $_A$t$_{Ret}$ = 3.27 min. |
| 40 | cyclopropyl | [1-(ethoxycarbonylmethyl)-1H-indol-3-yl]methyl | 3-biphenyl | MS: [M + 1]$^+$ = 536<br>HPLC $_A$t$_{Ret}$ = 3.54 min. |
| 41 | cyclopropyl | 2,3-dimethylbenzyl | 3-phenylisoxazol-5-yl | MS: [M + 1]$^+$ = 430<br>HPLC $_A$t$_{Ret}$ = 3.24 min. |

TABLE 1-continued
| Example | R1 | R2 | W* | Analytical data |
|---|---|---|---|---|
| 42 | 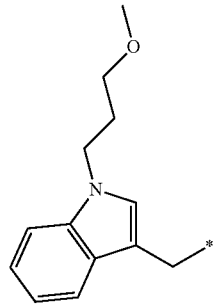 | 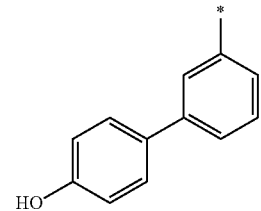 |  | MS: [M + 1]⁺ = 538<br>HPLC $_A t_{Ret}$ = 3.17 min. |
| 43 | 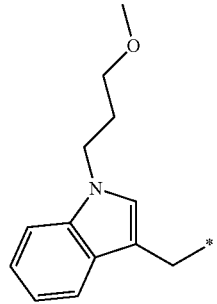 | 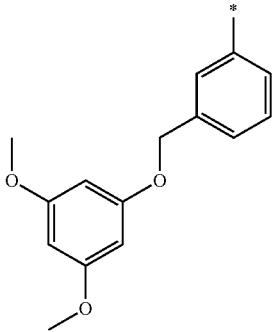 |  | MS: [M + 1]⁺ = 612<br>HPLC $_A t_{Ret}$ = 3.68 min. |
| 44 | 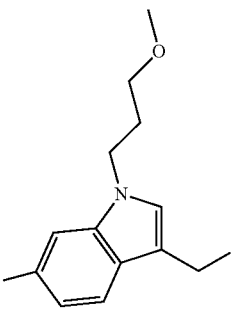 | 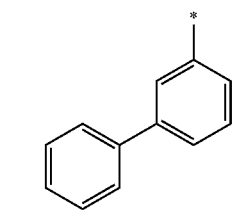 |  | MS: [M + 1]⁺ = 540<br>HPLC $_A t_{Ret}$ = 3.62 min. |
| 45 | 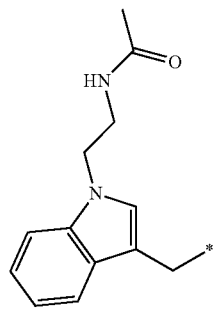 | 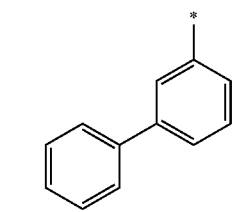 | | MS: [M + 1]⁺ 535<br>HPLC $_A t_{Ret}$ = 3.07 min. |

TABLE 1-continued
| Example | R1 | R2 | W* | Analytical data |
|---|---|---|---|---|
| 46 | 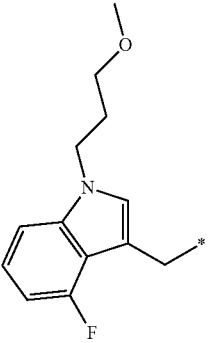 | 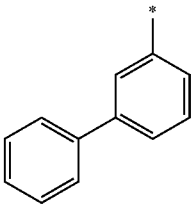 |  | MS: [M + 1]⁺ = 540<br>HPLC $_A$t$_{Ret}$ = 3.68 min. |
| 47 | 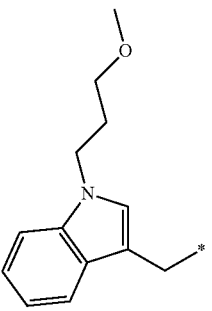 | 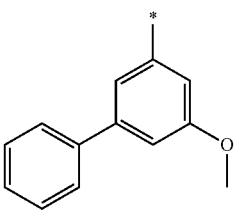 |  | MS: [M + 1]⁺ = 552<br>HPLC $_A$t$_{Ret}$ = 3.57 min. |
| 48 | 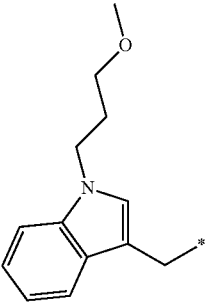 | 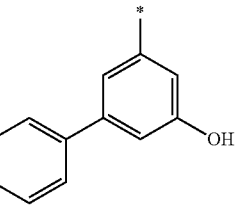 |  | MS: [M + 1]⁺ = 538<br>HPLC $_A$t$_{Ret}$ = 3.25 min. |
| 49 | | 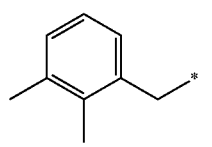 | 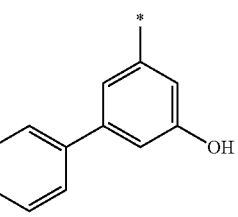 | MS: [M + 1]⁺ = 455<br>HPLC $_A$t$_{Ret}$ = 3.25 min. |

TABLE 1-continued

| Example | R1 | R2 | W* | Analytical data |
|---|---|---|---|---|
| 50 | cyclopropyl | 2-(2-(3-methoxypropoxy)phenyl)ethyl | biphenyl-3-yl | MS: [M + 1]⁺ = 513<br>HPLC_A t_Ret = 3.68 min. |
| 51 | cyclopropyl | 2,3-dimethylbenzyl | 3-((2-(dimethylamino)pyridin-4-yl)methoxy)phenyl | MS: [M + 1]⁺ = 513<br>HPLC_A t_Ret = 2.60 min. |
| 52 | cyclopropyl | 1-(3-methoxypropyl)-1H-indol-3-ylmethyl | 3-((3,5-dimethoxybenzyl)oxy)phenyl | MS: [M + 1]⁺ = 612<br>HPLC_A t_Ret = 3.65 min. |
| 53 | cyclopropyl | 1-(3-methoxypropyl)-1H-indol-3-ylmethyl | phenyl | MS: [M + 1]⁺ = 446<br>HPLC_A t_Ret = 3.15 min. |

TABLE 1-continued
| Example | R1 | R2 | W* | Analytical data |
|---|---|---|---|---|
| 54 | 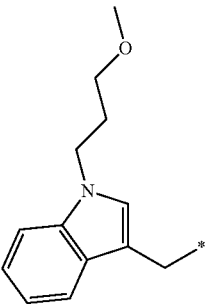 | 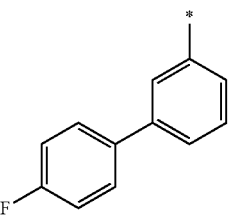 |  | MS: [M + 1]⁺ = 540<br>HPLC $_A$t$_{Ret}$ = 3.67 min. |
| 55 | 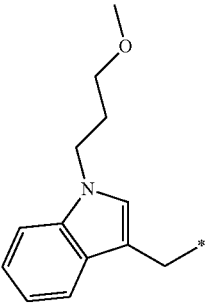 | 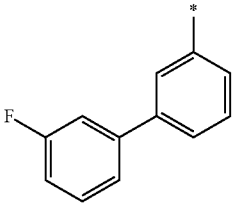 |  | MS: [M + 1]⁺ = 540<br>HPLC $_A$t$_{Ret}$ = 3.63 min. |
| 56 | 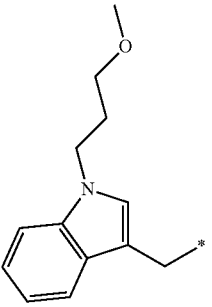 | 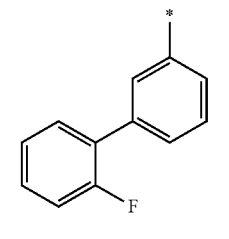 |  | MS: [M + 1]⁺ = 540<br>HPLC $_A$t$_{Ret}$ = 3.62 min. |
| 57 | 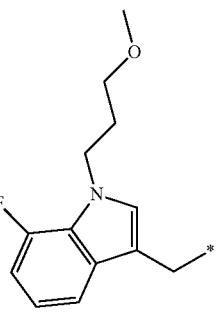 | 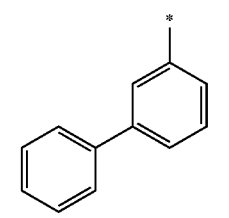 | | MS: [M + 1]⁺ = 540<br>HPLC $_A$t$_{Ret}$ = 3.73 min. |

TABLE 1-continued
| Example | R1 | R2 | W* | Analytical data |
|---|---|---|---|---|
| 58 | 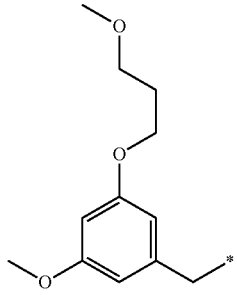 | 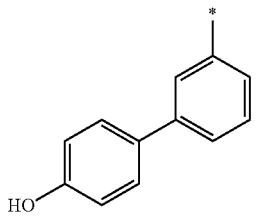 |  | MS: [M + 1]⁺ = 545<br>HPLC $_A$t$_{Ret}$ = 3.09 min. |
| 59 | 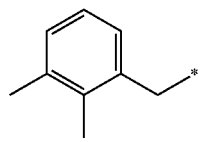 | 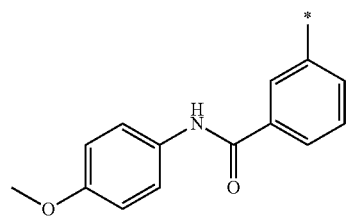 |  | MS: [M + 1]⁺ = 512<br>HPLC $_A$t$_{Ret}$ = 3.24 min. |
| 60 | 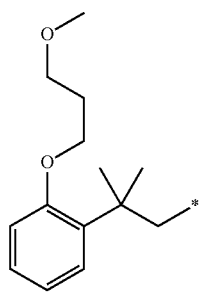 | 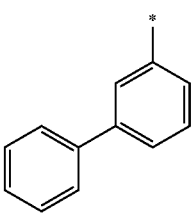 |  | MS: [M + 1]⁺ = 541<br>HPLC $_A$t$_{Ret}$ = 3.93 min. |
| 61 | 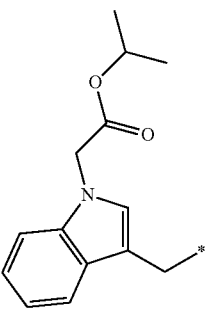 | 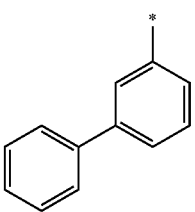 | | MS: [M + 1]⁺ = 550<br>HPLC $_A$t$_{Ret}$ = 3.73 min. |

TABLE 1-continued

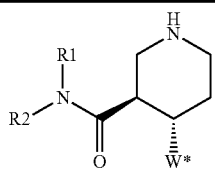

| Example | R1 | R2 | W* | Analytical data |
|---|---|---|---|---|
| 62 | cyclopropyl | 2,3-dimethylbenzyl | 3-(tetrahydropyran-4-yloxy)phenyl | MS: [M + 1]⁺ = 463<br>HPLC $_A$t$_{Ret}$ = 3.18 min. |
| 63 | cyclopropyl | 2,3-dimethylbenzyl | 3-(2-methoxyethoxy)phenyl | MS: [M + 1]⁺ = 437<br>HPLC $_A$t$_{Ret}$ = 3.12 min. |
| 64 | cyclopropyl | 2,3-dimethylbenzyl | 3-(4-methoxybenzamido)phenyl | MS: [M + 1]⁺ = 512<br>HPLC $_A$t$_{Ret}$ = 3.40 min. |
| 65 | cyclopropyl | (5-fluoro-1H-indol-3-yl)methyl | biphenyl-3-yl | MS: [M + 1]⁺ = 468<br>HPLC $_A$t$_{Ret}$ = 3.37 min. |
| 66 | cyclopropyl | [5-fluoro-1-(3-methoxypropanoyl)-1H-indol-3-yl]methyl | biphenyl-3-yl | MS: [M + 1]⁺ = 554<br>HPLC $_A$t$_{Ret}$ = 3.65 min. |

TABLE 1-continued

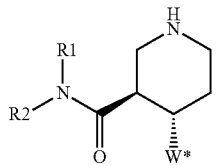

| Example | R1 | R2 | W* | Analytical data |
|---|---|---|---|---|
| 67 | cyclopropyl | 2,3-dimethylbenzyl | 3-(2-phenoxyethoxy)phenyl | MS: [M + 1]$^+$ = 499<br>HPLC $_A$t$_{Ret}$ = 3.79 min. |
| 68 | cyclopropyl | 2,3-dimethylbenzyl | 3-((2,3-dihydrobenzo[b][1,4]dioxin-2-yl)methoxy)phenyl | MS: [M + 1]$^+$ = 527<br>HPLC $_A$t$_{Ret}$ = 3.85 min. |
| 69 | cyclopropyl | 1-(3-methoxypropyl)-4-fluoro-1H-indol-3-ylmethyl | 5-phenyloxazol-2-yl | MS: [M + 1]$^+$ = 531<br>HPLC $_A$t$_{Ret}$ = 3.50 min. |
| 70 | ethyl | 4-(3-methoxypropyl)-3,4-dihydro-2H-benzo[b][1,4]oxazin-6-yl | biphenyl-3-yl | MS: [M + 1]$^+$ = 514<br>HPLC $_A$t$_{Ret}$ = 3.70 min. |

TABLE 1-continued
| Example | R1 | R2 | W* | Analytical data |
|---|---|---|---|---|
| 71 | 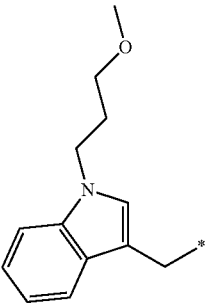 | 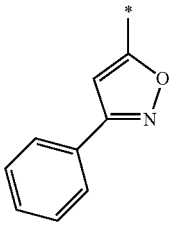 |  | MS: [M + 1]⁺ = 513<br>HPLC $_A$t$_{Ret}$ = 3.54 min. |
| 72 | 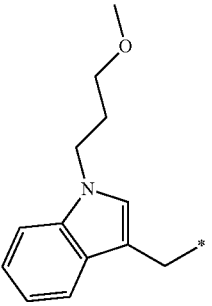 | 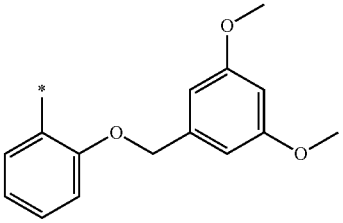 |  | MS: [M + 1]⁺ = 612<br>HPLC $_A$t$_{Ret}$ = 3.65 min. |
| 73 | 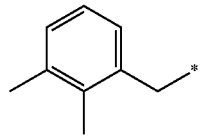 | 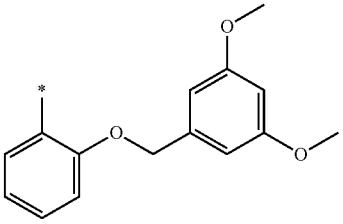 |  | MS: [M + 1]⁺ = 529<br>HPLC $_A$t$_{Ret}$ = 3.77 min. |
| 74 | 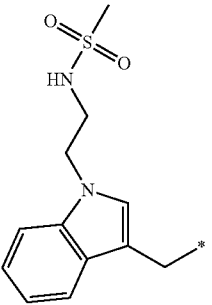 | 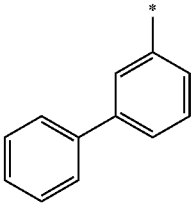 |  | MS: [M + 1]⁺ = 571<br>HPLC $_A$t$_{Ret}$ = 3.38 min. |
| 75 | 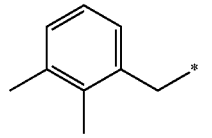 | 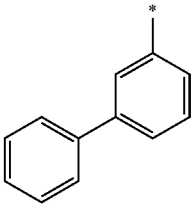 |  | MS: [M + 1]⁺ = 439;<br>HPLC: $_A$t$_{Ret}$ = 3.70 min. |

US 8,178,559 B2
133                                                      134
TABLE 1-continued
| Example | R1 | R2 | W* | Analytical data |
|---|---|---|---|---|
| 76 | 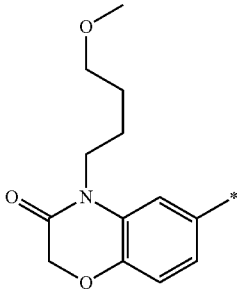 | 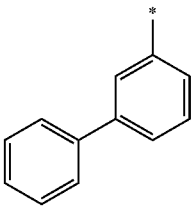 |  | MS: [M + 1]$^+$ = 542<br>HPLC $_A$t$_{Ret}$ = 3.38 min |
| 77 | 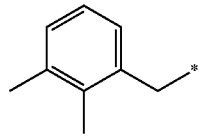 | 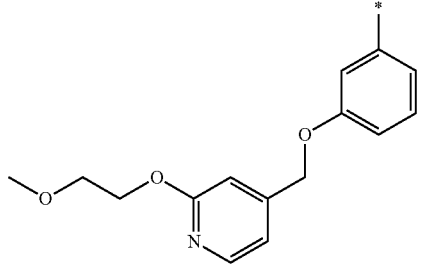 |  | MS: [M + 1]$^+$ = 544<br>HPLC $_A$t$_{Ret}$ = 3.13 min. |
| 78 | 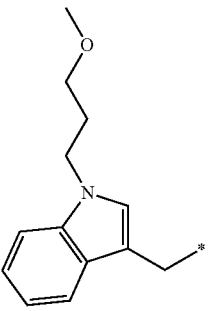 | 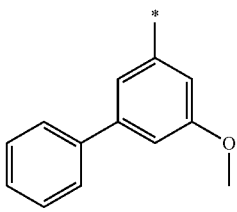 |  | MS: [M + 1]$^+$ = 552<br>HPLC $_A$t$_{Ret}$ = 3.56 min. |
| 79 | 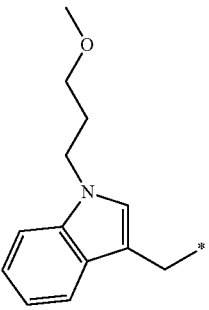 | 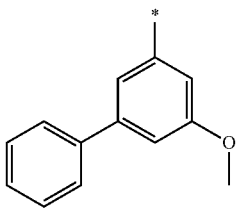 | (same as above) | MS: [M + 1]$^+$ = 552<br>HPLC $_A$t$_{Ret}$ = 3.60 min. |

TABLE 1-continued

| Example | R1 | R2 | W* | Analytical data |
|---|---|---|---|---|
| 80 | cyclopropyl | 1-(3-methoxypropyl)-1H-indol-3-ylmethyl | 2-((4'-biphenyl-4-yloxy)acetic acid)-3-yl | MS: [M + 1]⁺ = 596  HPLC $_A$t$_{Ret}$ = 3.14 min. |
| 81 | cyclopropyl | 1-(3-methoxypropyl)-1H-indol-3-ylmethyl | 4'-cyanobiphenyl-3-yl | MS: [M + 1]⁺ = 547  HPLC $_A$t$_{Ret}$ = 3.48 min. |
| 82 | ethyl | 4-(3-methoxypropyl)-3-oxo-3,4-dihydro-2H-benzo[1,4]oxazin-6-yl | biphenyl-3-yl | MS: [M + 1]⁺ = 528;  HPLC $_A$t$_{Ret}$ = 3.18 min. |
| 83 | ethyl | 1-(3-methoxypropyl)-1H-indol-6-yl | biphenyl-3-yl | MS: [M + 1]⁺ = 496  HPLC $_A$t$_{Ret}$ = 3.67 m |

TABLE 1-continued
| Example | R1 | R2 | W* | Analytical data |
|---|---|---|---|---|
| 84 | 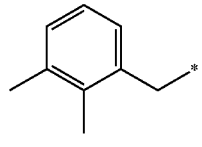 | 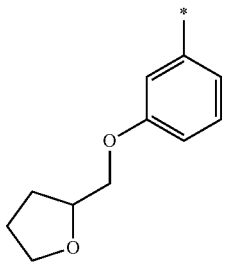 |  | MS: [M + 1]$^+$ = 463<br>HPLC $_A$t$_{Ret}$ = 3.35 min. |
| 85 | 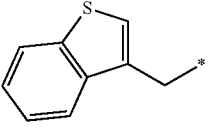 | 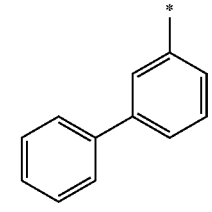 |  | MS: [M + 1]$^+$ = 467<br>HPLC: $_A$t$_{Ret}$ = 5.68 min |
| 86 | 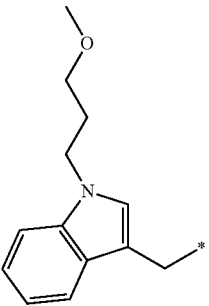 | 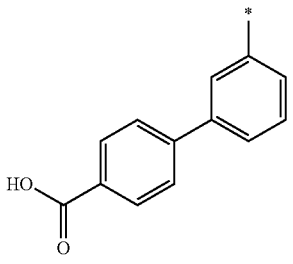 |  | MS: [M + 1]$^+$ = 566<br>HPLC $_A$t$_{Ret}$ = 3.17 min. |
| 87 | 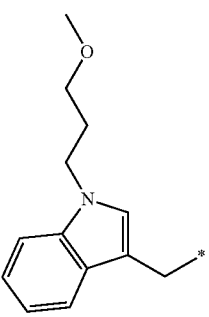 | 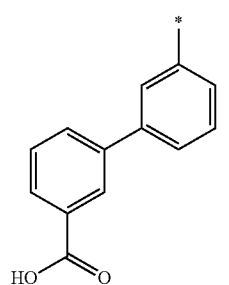 | | MS: [M + 1]$^+$ = 566<br>HPLC $_A$t$_{Ret}$ = 3.29 min. |

TABLE 1-continued
| Example | R1 | R2 | W* | Analytical data |
|---|---|---|---|---|
| 88 | 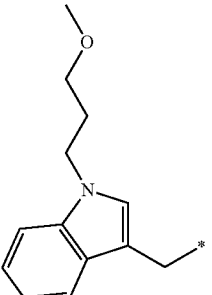 | 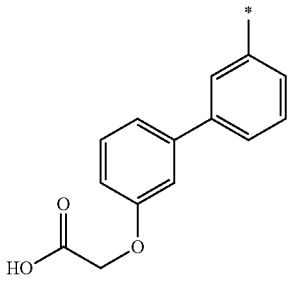 |  | MS: [M + 1]⁺ = 596<br>HPLC $_A$t$_{Ret}$ = 3.32 min. |
| 89 | 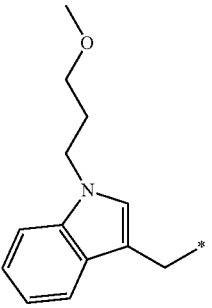 | 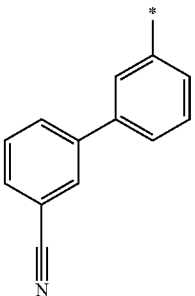 |  | MS: [M + 1]⁺ = 547<br>HPLC $_A$t$_{Ret}$ = 3.54 min. |
| 90 | 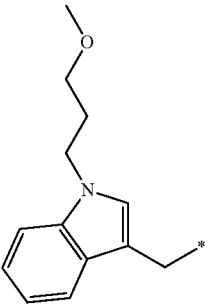 | 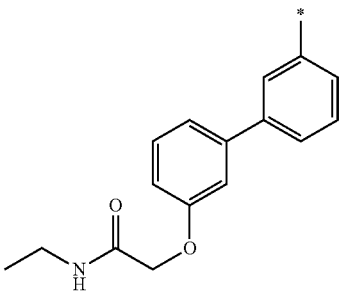 |  | MS: [M + 1]⁺ = 623<br>HPLC $_A$t$_{Ret}$ = 3.38 min. |
| 91 | 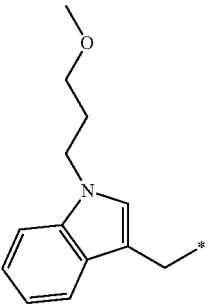 | 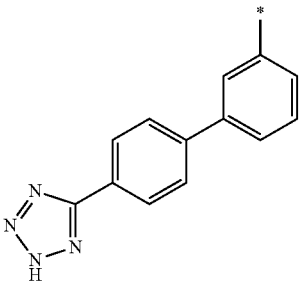 | | MS: [M + 1]⁺ = 590<br>HPLC $_A$t$_{Ret}$ = 3.22 min. |

TABLE 1-continued
| Example | R1 | R2 | W* | Analytical data |
|---|---|---|---|---|
| 92 | 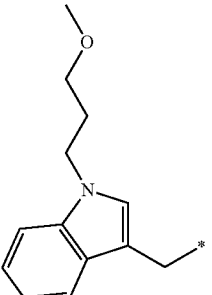 | 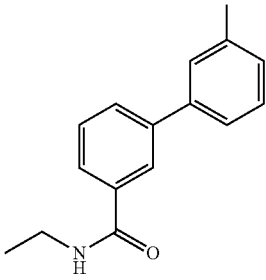 |  | MS: [M + 1]+ = 593<br>HPLC $A^{t}{}_{Ret}$ = 3.32 min. |
| 93 | 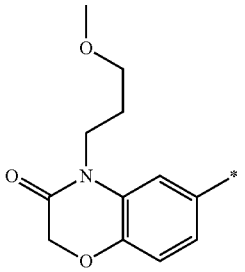 | 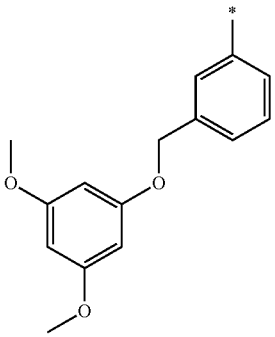 |  | MS: [M + 1]+ = 618<br>HPLC $A^{t}{}_{Ret}$ = 3.52 min. |
| 94 | 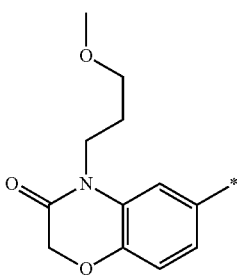 | 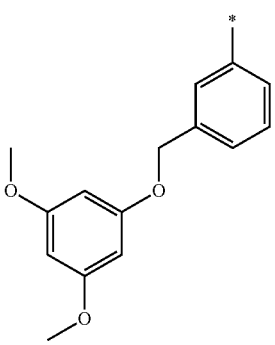 |  | MS: [M + 1]+ = 618<br>HPLC $A^{t}{}_{Ret}$ = 3.57 min. |
| 95 | | 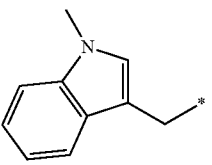 | 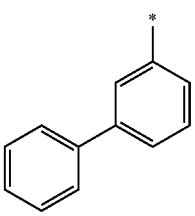 | MS: [M + 1]+ = 464<br>HPLC $A^{t}{}_{Ret}$ = 3.70 min. |

US 8,178,559 B2
TABLE 1-continued
| Example | R1 | R2 | W* | Analytical data |
|---|---|---|---|---|
| 96 |  | 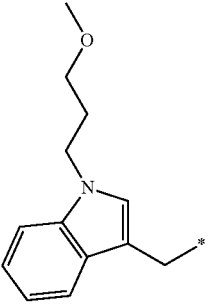 | 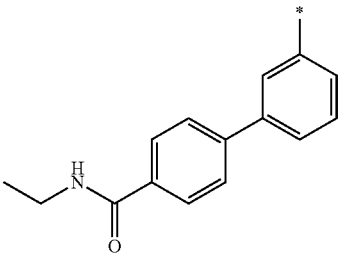 | MS: [M + 1]+ = 593<br>HPLC $_A t_{Ret}$ = 3.29 min. |
| 97 |  | 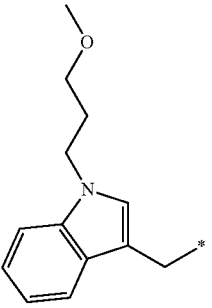 | 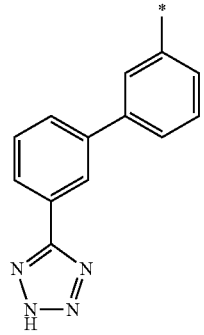 | MS: M+ = 590<br>HPLC $_A t_{Ret}$ = 3.34 min. |
| 98 |  | 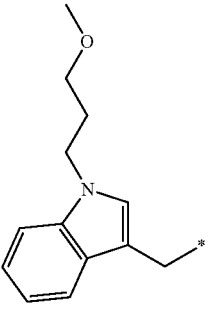 | 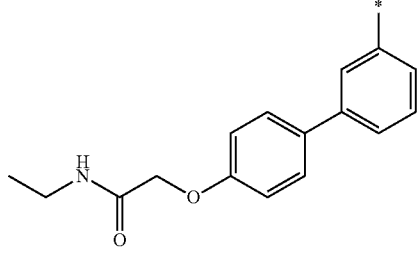 | MS: [M + 1]+ = 623<br>HPLC $_A t_{Ret}$ = 3.42 min. |
| 99 |  | 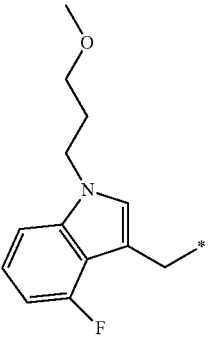 | 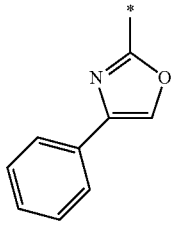 | MS: [M + 1]+ = 531;<br>HPLC: $_A t_{Ret}$ = 3.40 min |

TABLE 1-continued
| Example | R1 | R2 | W* | Analytical data |
|---|---|---|---|---|
| 99 |  |  | 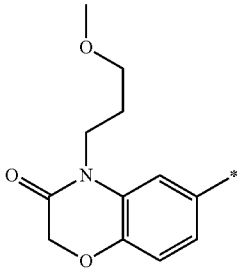 | MS: [M + 1]⁺ = 519<br>HPLC $A^t_{Ret}$ = 3.18 min. |
| 100 | 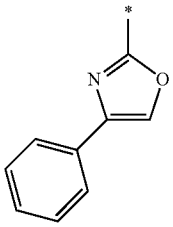 |  | 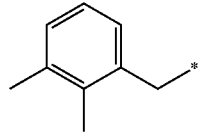 | MS: [M + 1]⁺ = 499<br>HPLC $A^t_{Ret}$ = 2.77 min. |
| 101 | 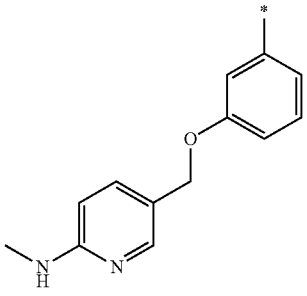 |  |  | MS: [M + 1]⁺ =<br>HPLC $A^t_{Ret}$ = min. |
| 102 | 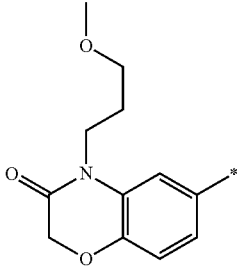 | 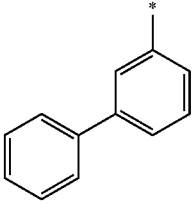 |  | MS: [M + 1]⁺ = 614<br>HPLC $A^t_{Ret}$ = 2.98 min. |

TABLE 1-continued

| Example | R1 | R2 | W* | Analytical data |
|---|---|---|---|---|
| 103 | cyclopropyl | 3-(3-methoxypropyl)-5-chloro-1H-indol-3-ylmethyl | biphenyl-3-yl | MS: [M + 1]⁺ = 556<br>HPLC_A tRet = 3.72 min. |
| 104 | cyclopropyl | 1-(3-methoxypropyl)-1H-indol-3-ylmethyl | 4'-[2-(4-methylpiperazin-1-yl)ethoxy]biphenyl-3-yl | MS: [M + 1]⁺ = 664<br>HPLC_A tRet = 2.48 min. |
| 105 | cyclopropyl | 1-(3-methoxypropyl)-1H-indol-3-ylmethyl | 4'-{[(2-hydroxyethyl)carbamoyl]methoxy}biphenyl-3-yl | MS: [M + 1]⁺ = 639<br>HPLC_A tRet = 2.84 min. |
| 106 | ethyl | 4-(3-methoxypropyl)-3-oxo-3,4-dihydro-2H-benzo[1,4]oxazin-6-yl | 3'-hydroxybiphenyl-5-yl | MS: [M + 1]⁺ = 544<br>HPLC_A tRet = 2.85 min. |

TABLE 1-continued
| Example | R1 | R2 | W* | Analytical data |
|---|---|---|---|---|
| 107 |  | 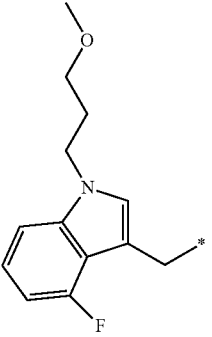 | 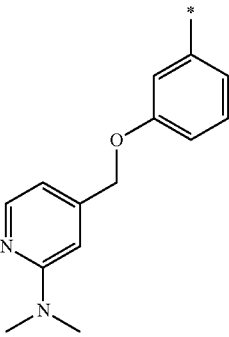 | MS: [M + 1]+ = 614<br>HPLC $_A$t$_{Ret}$ = 2.62 min. |
| 108 |  | 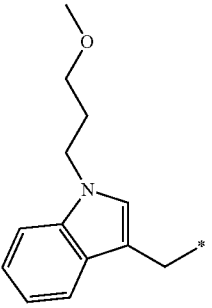 | 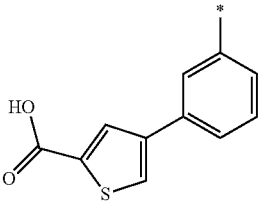 | MS: [M + 1]+ = 572<br>HPLC $_A$t$_{Ret}$ = 2.98 min. |
| 109 |  | 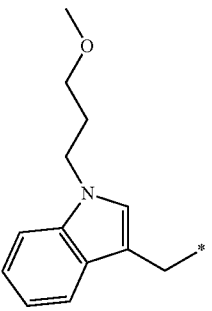 | 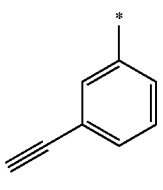 | MS: [M + 1]+ = 470<br>HPLC $_A$t$_{Ret}$ = 3.15 min. |
| 110 |  | 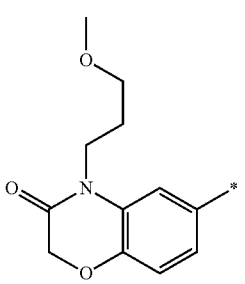 | 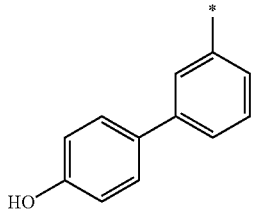 | MS: [M + 1]+ = 544<br>HPLC $_A$t$_{Ret}$ = 2.73 min. |

TABLE 1-continued
| Example | R1 | R2 | W* | Analytical data |
|---|---|---|---|---|
| 111 | 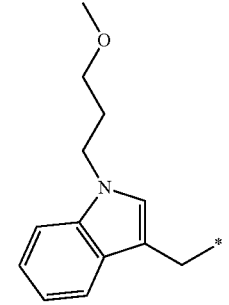 | 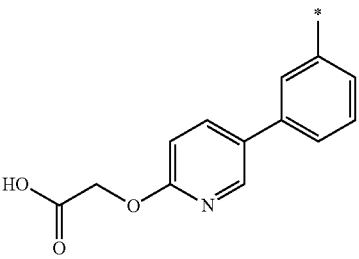 |  | MS: [M + 1]⁺ = 597<br>HPLC $_A$t$_{Ret}$ = 2.97 min. |
| 112 | 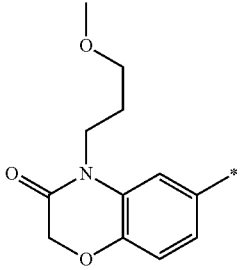 | 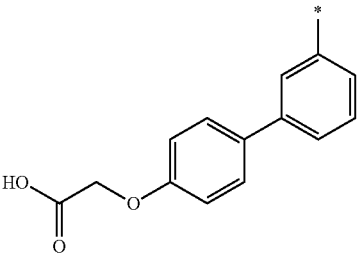 |  | MS: [M + 1]⁺ = 602<br>HPLC $_A$t$_{Ret}$ = 2.77 min. |
| 113 | 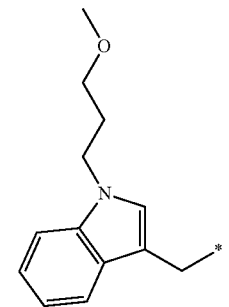 | 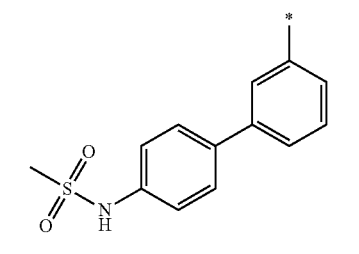 |  | MS: [M + 1]⁺ = 615<br>HPLC $_A$t$_{Ret}$ = 3.06 min. |
| 114 | 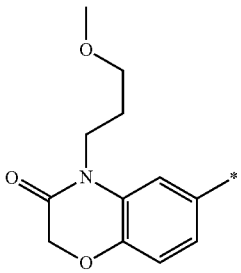 | 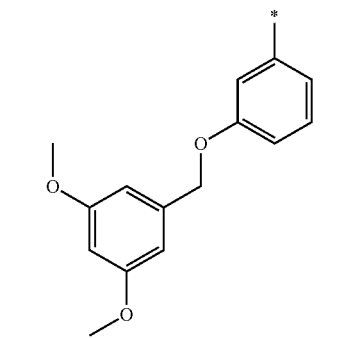 |  | MS: [M + 1]⁺ = 630<br>HPLC $_A$t$_{Ret}$ = 3.20 min. |

TABLE 1-continued
| Example | R1 | R2 | W* | Analytical data |
|---|---|---|---|---|
| 115 | 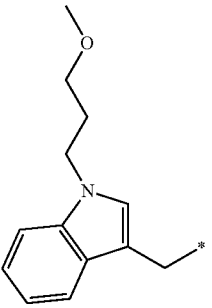 | 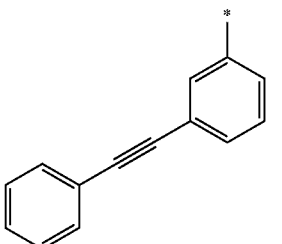 |  | MS: [M + 1]⁺ = 546<br>HPLC $_A$t$_{Ret}$ = 3.68 min. |
| 116 | 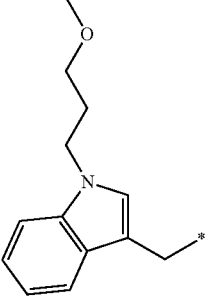 |  |  | MS: [M + 1]⁺ = 528<br>HPLC $_A$t$_{Ret}$ = 2.95 min. |
| 117 | 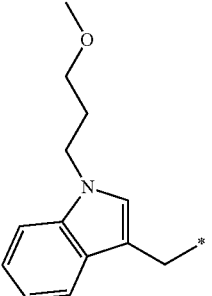 | 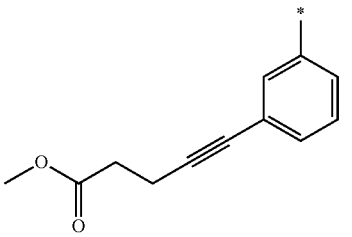 |  | MS: [M + 1]⁺ = 556<br>HPLC $_A$t$_{Ret}$ = 3.29 min. |
| 118 | | 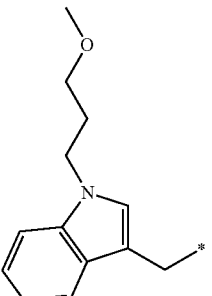 | 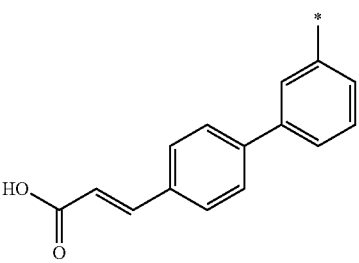 | MS: [M + 1]⁺ = 592<br>HPLC $_A$t$_{Ret}$ = 3.11 min. |

TABLE 1-continued

| Example | R1 | R2 | W* | Analytical data |
|---|---|---|---|---|
| 119 | cyclopropyl | 3-methoxypropyl-indol-1-yl (attached via indol-3-yl CH2*) | 4'-acetamido-biphenyl-3-yl* | MS: [M + 1]$^+$ = 579<br>HPLC $_A$t$_{Ret}$ = 2.99 min. |
| 120 | cyclopropyl | 3-methoxypropyl-(3-oxo-2H-benzo[b][1,4]thiazin-4-yl), attached at 6-position* | biphenyl-3-yl* | MS: [M + 1]$^+$ = 556<br>HPLC $_A$t$_{Ret}$ = 3.22 min. |
| 121 | cyclopropyl | 3-methoxypropyl-indol-1-yl (attached via indol-3-yl CH2*) | 3-(1H-pyrazol-3-yl)phenyl* | MS: [M + 1]$^+$ = 512<br>HPLC $_A$t$_{Ret}$ = 2.85 min. |
| 122 | cyclopropyl | 3-methoxypropyl-(4-fluoro-indol-1-yl) (attached via indol-3-yl CH2*) | 5-hydroxy-biphenyl-3-yl* | MS: [M + 1]$^+$ = 556<br>HPLC $_A$t$_{Ret}$ = 3.29 min. |

US 8,178,559 B2

TABLE 1-continued

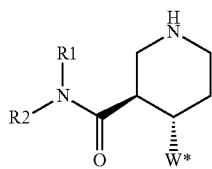

| Example | R1 | R2 | W* | Analytical data |
|---|---|---|---|---|
| 123 | cyclopropyl | 1-(3-methoxypropyl)-1H-indol-3-ylmethyl | 2-(4-(biphenyl-3-yl)phenoxy)acetamide | MS: [M + 1]+ = 595<br>HPLC AtRet = 2.90 min. |
| 124 | cyclopropyl | 1-(3-methoxypropyl)-1H-indol-3-ylmethyl | 2-(4-(biphenyl-3-yl)phenoxy)ethylamine | MS: [M + 1]+ = 581<br>HPLC AtRet = 2.59 min. |
| 125 | cyclopropyl | 1-(3-methoxypropyl)-1H-indol-3-ylmethyl | 4-((4-(biphenyl-3-yl)phenoxy)methyl)-N,N-dimethylpyridin-2-amine | MS: [M + 1]+ = 672<br>HPLC AtRet = 2.87 min. |
| 126 | cyclopropyl | 1-(3-methoxypropyl)-1H-indol-3-ylmethyl | 5-(3-(4-(biphenyl-3-yl)phenoxy)propyl)-1H-tetrazole | MS: [M + 1]+ = 648<br>HPLC AtRet = 3.10 min. |

TABLE 1-continued
| Example | R1 | R2 | W* | Analytical data |
|---|---|---|---|---|
| 127 | 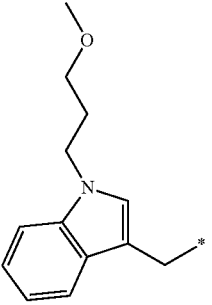 | 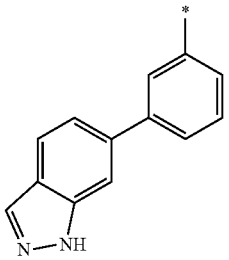 |  | MS: [M + 1]+ = 562<br>HPLC $_A$t$_{Ret}$ = 3.09 min. |
| 128 | 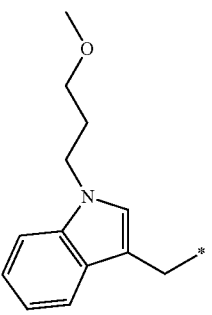 | 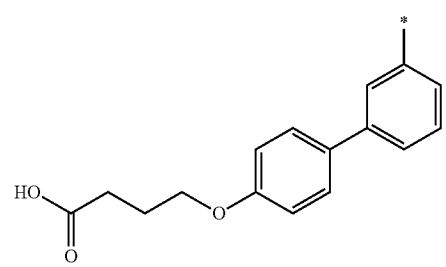 |  | MS: [M + 1]+ = 624<br>HPLC $_A$t$_{Ret}$ = 3.22 min. |
| 129 | 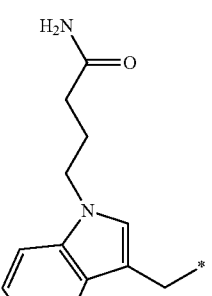 | 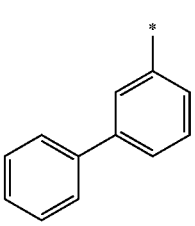 |  | MS: [M + 1]+ = 535<br>HPLC $_A$t$_{Ret}$ = 3.02 min. |
| 130 | | 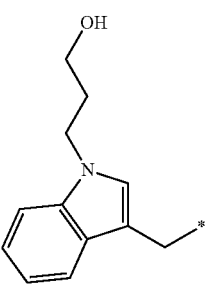 | 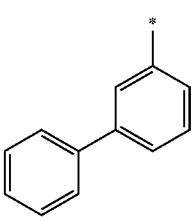 | MS: [M + 1]+ = 508<br>HPLC $_A$t$_{Ret}$ = 3.13 min. |

TABLE 1-continued
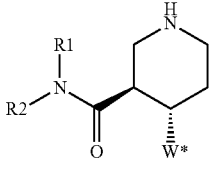
| Example | R1 | R2 | W* | Analytical data |
|---|---|---|---|---|
| 131 |  | 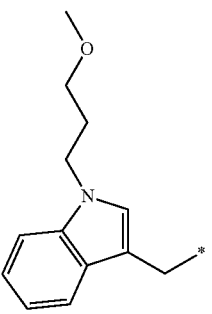 | 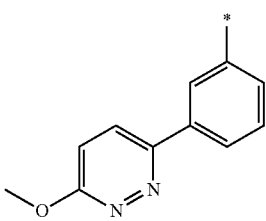 | MS: [M + 1]⁺ = 554<br>HPLC $_A$t$_{Ret}$ = 3.00 min. |
| 132 |  | 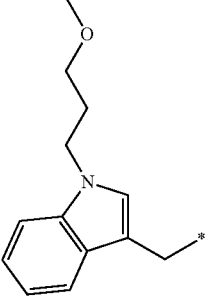 | 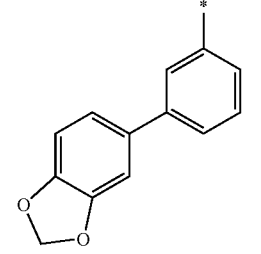 | MS: [M + 1]⁺ = 566<br>HPLC $_A$t$_{Ret}$ = 3.41 min. |
| 133 |  | 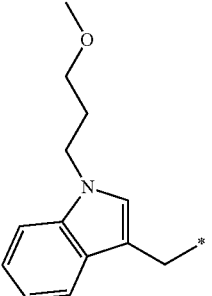 | 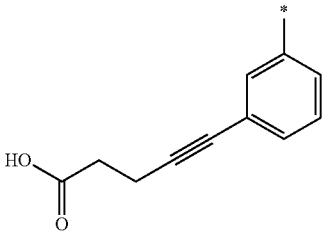 | MS: [M + 1]⁺ = 542<br>HPLC $_A$t$_{Ret}$ = 2.97 min. |
| 134 |  | 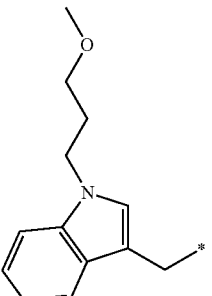 | 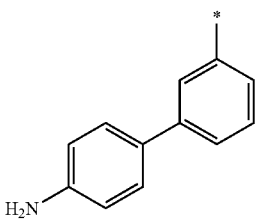 | MS: [M + 1]⁺ = 537<br>HPLC $_A$t$_{Ret}$ = 2.57 min. |

TABLE 1-continued
| Example | R1 | R2 | W* | Analytical data |
|---|---|---|---|---|
| 135 | 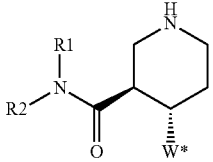 |  |  | MS: [M + 1]$^+$ = 522<br>HPLC $_A$t$_{Ret}$ = 3.20 min. |
| 136 | 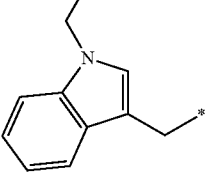 | 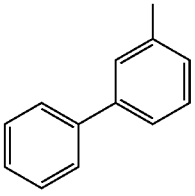 |  | MS: [M + 1]$^+$ = 519<br>HPLC $_A$t$_{Ret}$ = 3.18 min. |
| 137 |  | 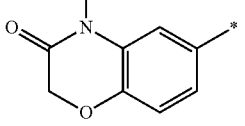 | 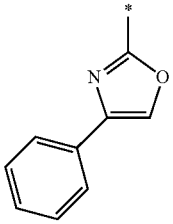 | MS: [M + 1]$^+$ = 667<br>HPLC $_A$t$_{Ret}$ = 2.78 min. |
| 138 |  |  | 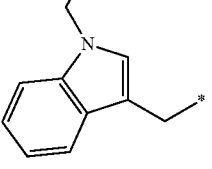 | MS: [M + 1]$^+$ = 527<br>HPLC $_A$t$_{Ret}$ = 2.60 min. |

TABLE 1-continued
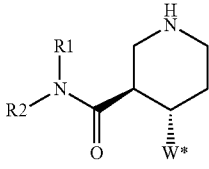
| Example | R1 | R2 | W* | Analytical data |
|---|---|---|---|---|
| 139 |  | 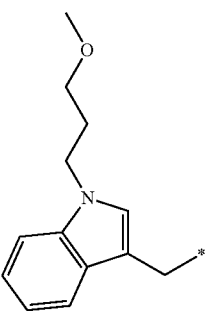 | 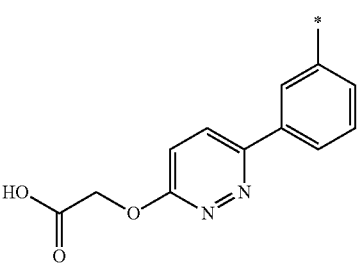 | MS: [M + 1]⁺ = 598<br>HPLC $_A$t$_{Ret}$ = 2.88 min. |
| 140 |  | 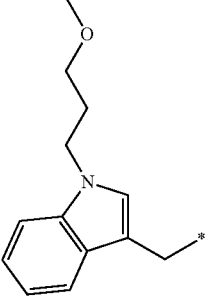 | 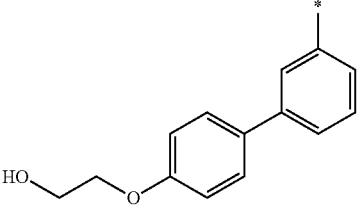 | MS: [M + 1]⁺ = 582<br>HPLC $_A$t$_{Ret}$ = 3.05 min. |
| 141 |  | 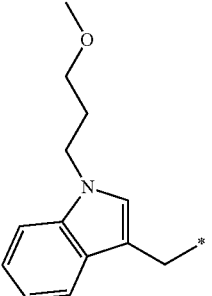 | 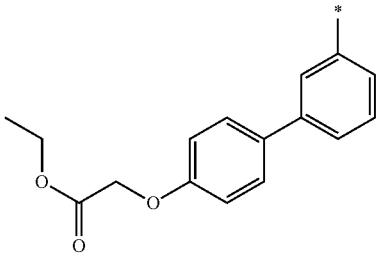 | MS: [M + 1]⁺ = 624<br>HPLC $_A$t$_{Ret}$ = 3.55 min. |
| 142 |  | 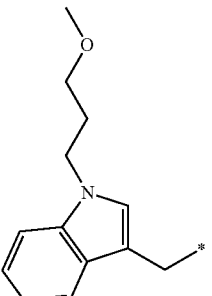 | 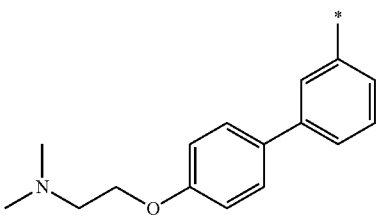 | MS: [M + 1]⁺ = 609<br>HPLC $_A$t$_{Ret}$ = 2.67 min. |

TABLE 1-continued
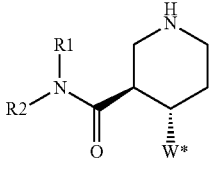
| Example | R1 | R2 | W* | Analytical data |
|---|---|---|---|---|
| 143 |  | 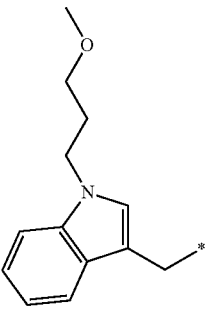 | 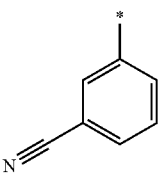 | MS: [M + 1]⁺ = 471<br>HPLC $_A$t$_{Ret}$ = 3.07 min. |
| 144 |  | 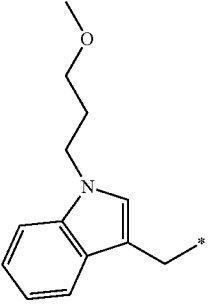 | 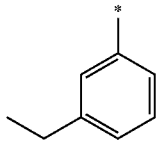 | MS: [M + 1]⁺ = 474<br>HPLC $_A$t$_{Ret}$ = 3.42 min. |
| 145 |  | 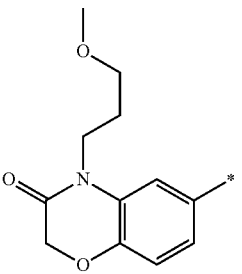 | 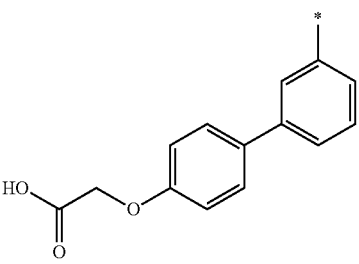 | MS: [M + 1]⁺ = 614<br>HPLC $_A$t$_{Ret}$ = 2.81 min. |
| 146 |  | 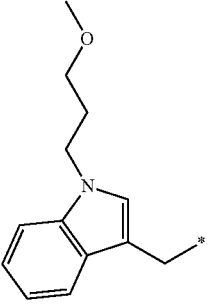 | 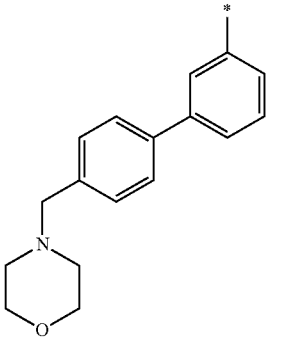 | MS: [M + 1]⁺ = 621<br>HPLC $_A$t$_{Ret}$ = 2.69 min. |

TABLE 1-continued
| Example | R1 | R2 | W* | Analytical data |
|---|---|---|---|---|
| 147 | 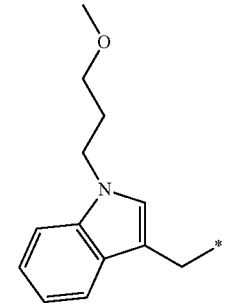 | 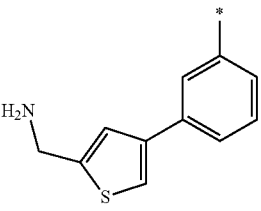 |  | MS: [M + 1]⁺ = 657<br>HPLC $_A$t$_{Ret}$ = 3.63 min. |
| 148 | 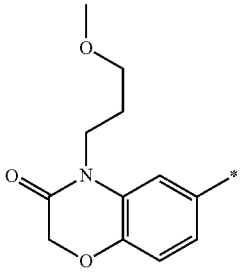 | 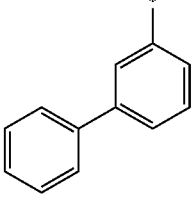 |  | MS: [M + 1]⁺ = 540<br>HPLC $_A$t$_{Ret}$ = 3.15 min. |
| 149 | 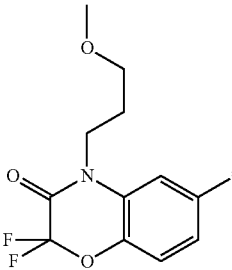 | 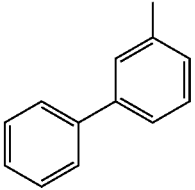 |  | MS: [M + 1]⁺ = 576<br>HPLC $_A$t$_{Ret}$ = 3.52 min. |
| 150 | 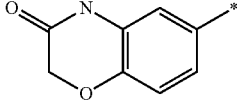 | 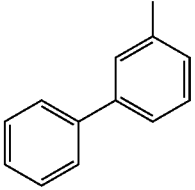 |  | MS: [M + 1]⁺ = 468<br>HPLC $_A$t$_{Ret}$ = 2.93 min. |
| 151 | 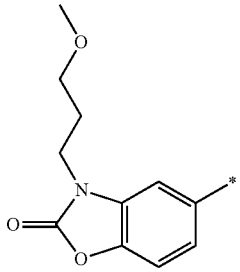 | 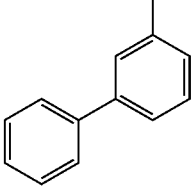 | | MS: [M + 1]⁺ = 526<br>HPLC $_A$t$_{Ret}$ = 3.15 min. |

TABLE 1-continued
| Example | R1 | R2 | W* | Analytical data |
|---|---|---|---|---|
| 152 |  | 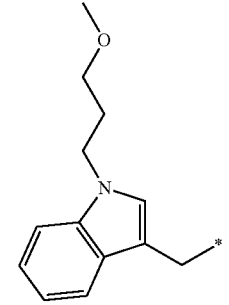 | 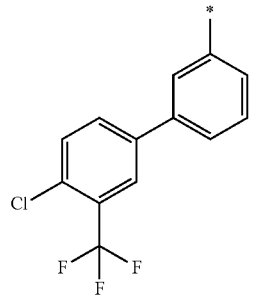 | MS: [M]+ = 624 HPLC A tRet = 3.94 min. |
| 153 |  | 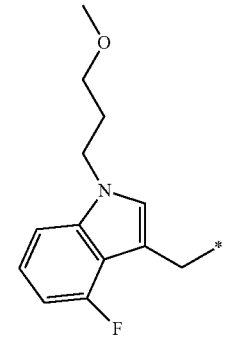 | 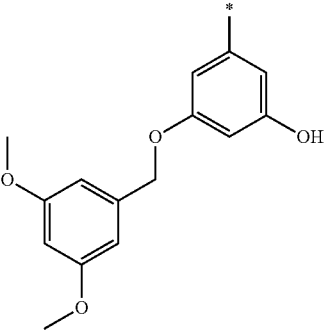 | MS: [M + 1]+ = 646 HPLC A tRet = 3.35 min. |
| 154 |  | 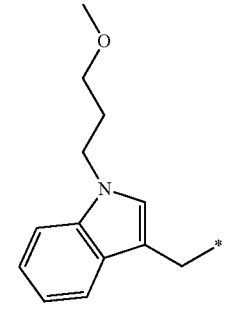 | 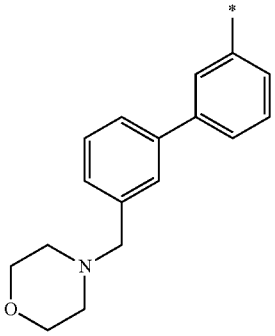 | MS: [M + 1]+ = 621 HPLC A tRet = 2.62 min. |
| 155 |  | 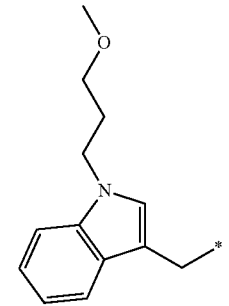 | 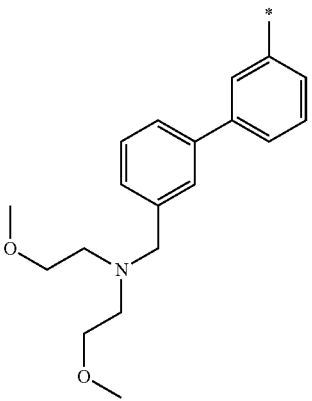 | MS: [M + 1]+ = 667 HPLC A tRet = 2.74 min. |

TABLE 1-continued

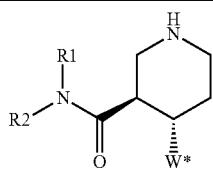

| Example | R1 | R2 | W* | Analytical data |
|---|---|---|---|---|
| 156 | cyclopropyl | 1-(3-methoxypropyl)-1H-indol-3-ylmethyl | methyl 4-[(3-*-phenyl)ethynyl]benzoate | MS: [M + 1]+ = 604<br>HPLC $A^t{}_{Ret}$ = 3.67 min. |
| 157 | cyclopropyl | 4-(3-methoxypropyl)-3-oxo-3,4-dihydro-2H-benzo[1,4]oxazin-6-yl | 3-[(3,5-dimethoxybenzyl)oxy]-5-hydroxyphenyl | MS: [M + 1]+ = 646<br>HPLC $A^t{}_{Ret}$ = 2.93 min. |
| 158 | cyclopropyl | 4-(3-methoxypropyl)-3-oxo-3,4-dihydro-2H-benzo[1,4]oxazin-6-yl | 3-[(3,5-dimethoxybenzyl)oxy]phenyl | MS: [M + 1]+ = 630<br>HPLC $A^t{}_{Ret}$ = 3.20 min. |
| 159 | cyclopropyl | 4-(3-methoxypropyl)-3-oxo-3,4-dihydro-2H-benzo[1,4]oxazin-6-yl | 3-[(3,5-dimethoxybenzyl)oxy]-5-methoxyphenyl | MS: [M + 1]+ = 660<br>HPLC $A^t{}_{Ret}$ = 3.23 min. |

TABLE 1-continued
| Example | R1 | R2 | W* | Analytical data |
|---|---|---|---|---|
| 160 | cyclopropyl |  | 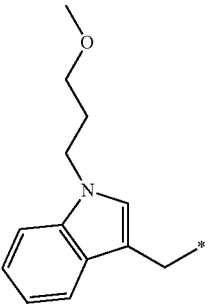 | MS: [M + 1]+ = 590<br>HPLC $A_{tRet}$ = 3.15 min. |
| 161 | cyclopropyl |  | 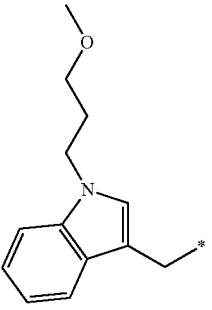 | MS: [M + 1]+ =<br>HPLC $A_{tRet}$ = min. |
| 162 | cyclopropyl |  | 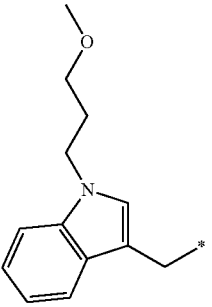 | MS: [M + 1]+ = 529<br>HPLC $A_{tRet}$ = 2.47 min. |
| 163 | cyclopropyl |  | 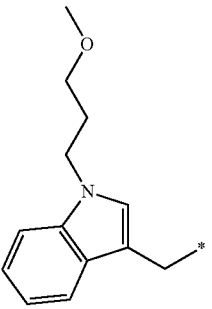 | MS: [M + 1]+ = 501<br>HPLC $A_{tRet}$ = 2.57 min. |

TABLE 1-continued
| Example | R1 | R2 | W* | Analytical data |
|---|---|---|---|---|
| 164 | cyclopropyl | 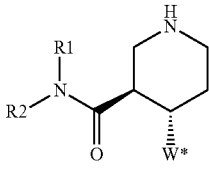 |  | MS: [M + 1]⁺ = 634<br>HPLC $A^t{}_{Ret}$ = 2.43 min. |
| 165 | cyclopropyl | 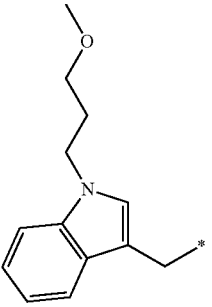 | 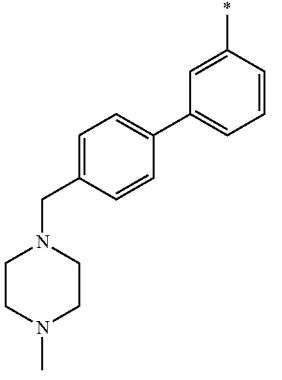 | MS: [M + 1]⁺ = 594<br>HPLC $A^t{}_{Ret}$ = 2.54 min. |
| 166 | cyclopropyl |  | 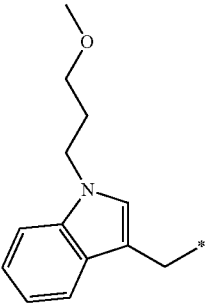 | MS: [M + 1]⁺ = 608<br>HPLC $A^t{}_{Ret}$ = 3.05 min. |
| 167 | cyclopropyl | 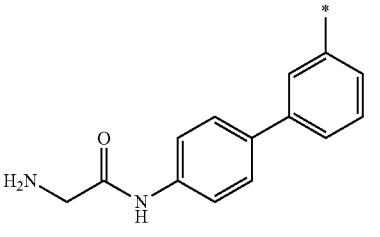 |  | MS: [M + 1]⁺ = 461<br>HPLC $A^t{}_{Ret}$ = 3.48 min. |

TABLE 1-continued
| Example | R1 | R2 | W* | Analytical data |
|---|---|---|---|---|
| 168 | 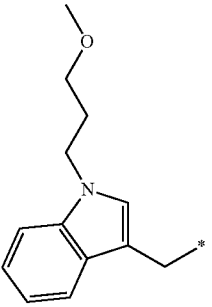 | 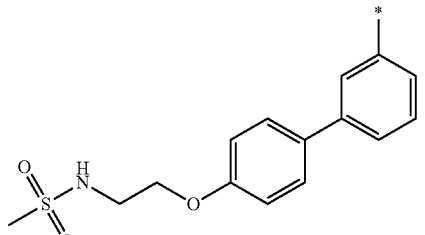 |  | MS: [M + 1]⁺ = 659<br>HPLC $_A$t$_{Ret}$ = 3.12 min. |
| 169 | 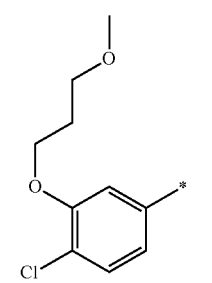 | 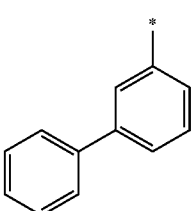 |  | MS: [M + 1]⁺ = 519<br>HPLC $_A$t$_{Ret}$ = 3.62 min. |
| 170 | 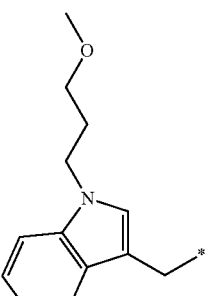 | 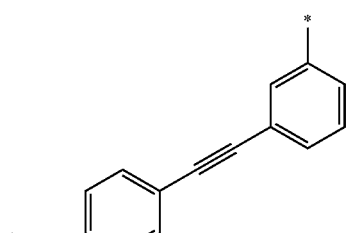 |  | MS: [M + 1]⁺ = 590<br>HPLC $_A$t$_{Ret}$ = 2.68 min. |
| 171 | | 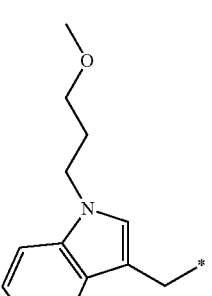 | 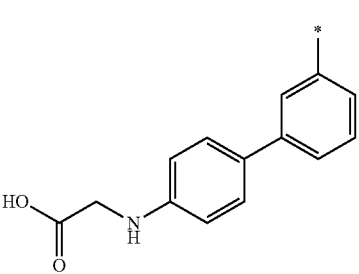 | MS: [M + 1]⁺ = 596<br>HPLC $_A$t$_{Ret}$ = 2.97 min. |

TABLE 1-continued

| Example | R1 | R2 | W* | Analytical data |
|---|---|---|---|---|
| 172 | cyclopropyl | 2-chloro-5-[(3-methoxypropyl)amino]phenyl | biphenyl-3-yl | MS: [M + 1]$^+$ = 518<br>HPLC $_A$t$_{Ret}$ = 5.59 min. |
| 172 | cyclopropyl | 4-(4-methoxybutyl)-3-oxo-3,4-dihydro-2H-benzo[1,4]oxazin-6-yl | biphenyl-3-yl | MS: [M + 1]$^+$ = 554<br>HPLC $_A$t$_{Ret}$ = 3.18 min. |
| 173 | cyclopropyl | 1-(3-methoxypropyl)-1H-indol-3-ylmethyl | 1-{2-[4-(biphenyl-3-yl)phenoxy]acetyl}piperidine-4-carboxylic acid | MS: [M + 1]$^+$ = 707<br>HPLC $_A$t$_{Ret}$ = 2.98 min. |
| 174 | cyclopropyl | 1-(3-methoxypropyl)-1H-indol-3-ylmethyl | 1-{2-[4-(biphenyl-3-yl)phenoxy]acetyl}azetidine-3-carboxylic acid | MS: [M + 1]$^+$ = 679<br>HPLC $_A$t$_{Ret}$ = 2.88 min. |

TABLE 1-continued
| Example | R1 | R2 | W* | Analytical data |
|---|---|---|---|---|
| 175 |  | 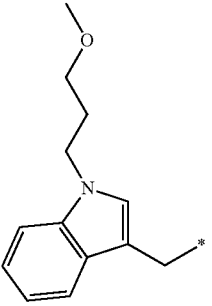 | 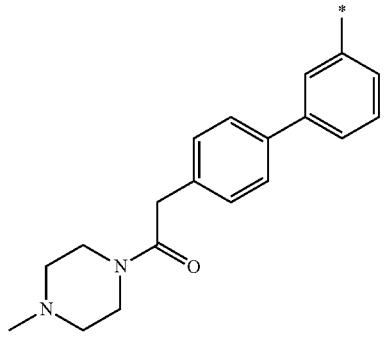 | MS: [M + 1]⁺ = 662<br>HPLC $_A t_{Ret}$ = 2.62 min. |
| 176 |  | 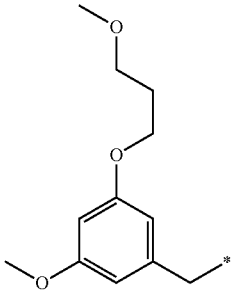 | 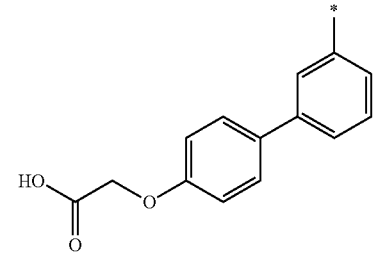 | MS: [M + 1]⁺ = 603<br>HPLC $_A t_{Ret}$ = 2.92 min. |
| 177 |  | 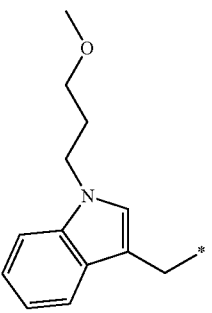 | 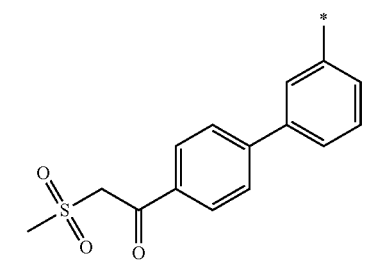 | MS: [M + 1]⁺ = <br>HPLC $_A t_{Ret}$ = m. |
| 178 |  | 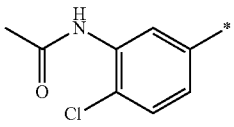 | 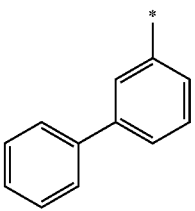 | MS: [M + 1]⁺ = 488<br>HPLC $_A t_{Ret}$ = 3.10 min. |

US 8,178,559 B2
TABLE 1-continued
| Example | R1 | R2 | W* | Analytical data |
|---|---|---|---|---|
| 179 |  | 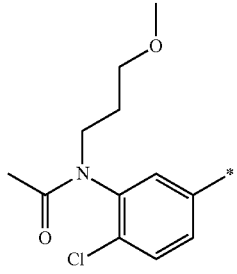 | 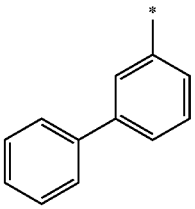 | MS: [M + 1]⁺ = 560<br>HPLC $_A$t$_{Ret}$ = 3.22 min. |
| 180 |  | 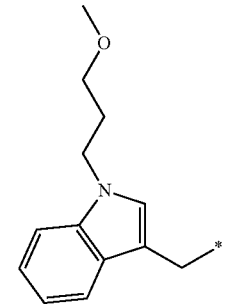 | 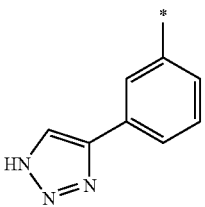 | MS: [M + 1]⁺ = 513<br>HPLC $_A$t$_{Ret}$ = 2.72 min. |
| 181 |  | 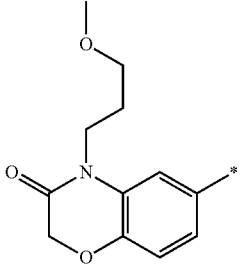 | 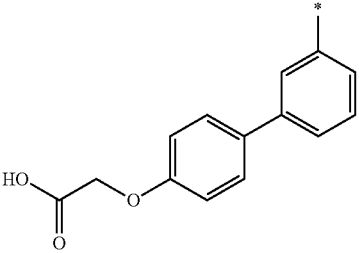 | MS: [M + 1]⁺ = 614<br>HPLC $_A$t$_{Ret}$ = 2.74 min. |
| 182 |  | 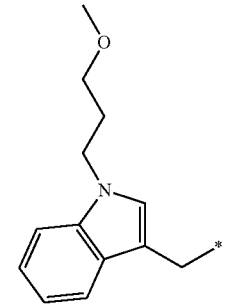 | 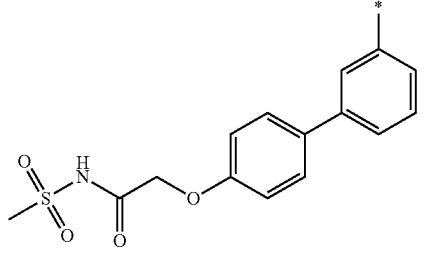 | MS: [M + 1]⁺ = 673<br>HPLC $_A$t$_{Ret}$ = 3.09 min. |

TABLE 1-continued
| Example | R1 | R2 | W* | Analytical data |
|---|---|---|---|---|
| 183 | 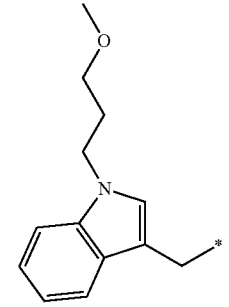 | 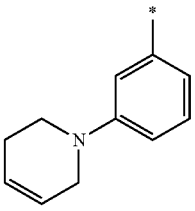 |  | MS: [M + 1]$^+$ = 527<br>HPLC $_A$t$_{Ret}$ = 2.63 min. |
| 184 | 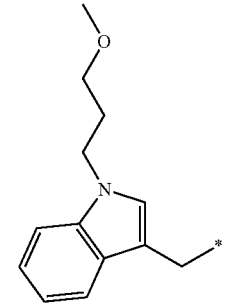 | 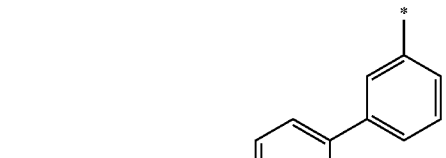 |  | MS: [M + 1]$^+$ = 637<br>HPLC $_A$t$_{Ret}$ = 2.98 min. |
| 185 | 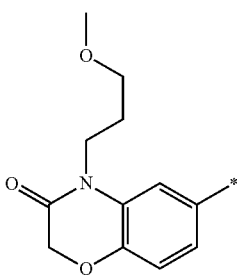 | 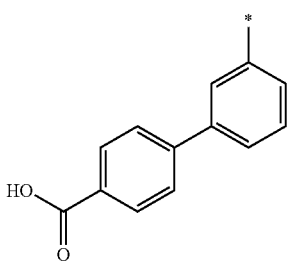 |  | MS: [M + 1]$^+$ = 584<br>HPLC $_A$t$_{Ret}$ = 2.92 min. |
| 186 | 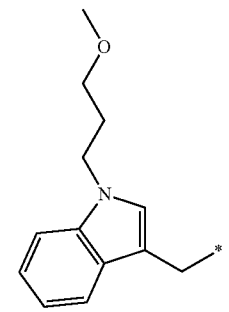 | 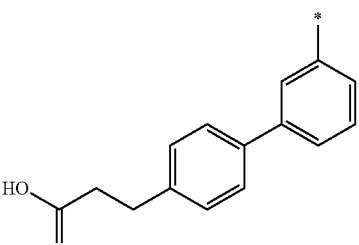 |  | MS: [M + 1]$^+$ = 594<br>HPLC $_A$t$_{Ret}$ = 3.34 min. |

TABLE 1-continued

| Example | R1 | R2 | W* | Analytical data |
|---|---|---|---|---|
| 187 | cyclopropyl | 1-(3-methoxypropyl)-1H-indol-3-ylmethyl | 1-methyl-4-(3-yl-phenyl)-1,2,3,6-tetrahydropyridine | MS: [M + 1]⁺ = 541<br>HPLC $A_{tRet}$ = 2.23 min. |
| 188 | cyclopropyl | 1-(3-methoxypropyl)-1H-indol-3-ylmethyl | 1-(2-(4'-yl-biphenyl-4-yloxy)ethyl)pyrrolidine-2-carboxylic acid | MS: [M + 1]⁺ = 679<br>HPLC $A_{tRet}$ = 2.65 min. |
| 189 | cyclopropyl | 1-(3-methoxypropyl)-1H-indol-3-ylmethyl | 2-(1-(3-yl-phenyl)piperidin-4-yl)acetic acid | MS: [M + 1]⁺ = 587<br>HPLC $A_{tRet}$ = 2.40 min. |
| 190 | cyclopropyl | 4-(6-yl-3-oxo-2H-benzo[b][1,4]oxazin-4(3H)-yl)butanamide | biphenyl-3-yl | MS: [M + 1]⁺ = 553<br>HPLC $A_{tRet}$ = 2.88 mi |

TABLE 1-continued
| Example | R1 | R2 | W* | Analytical data |
|---|---|---|---|---|
| 191 |  | 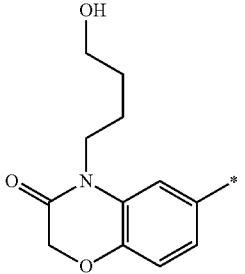 | 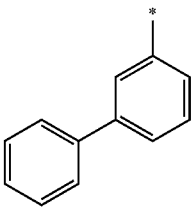 | MS: [M + 1]⁺ = 540<br>HPLC $_A$t$_{Ret}$ = 2.93 min. |
| 192 |  | 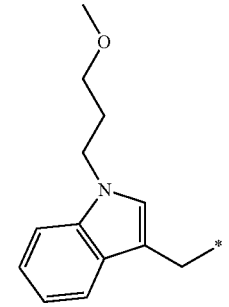 | 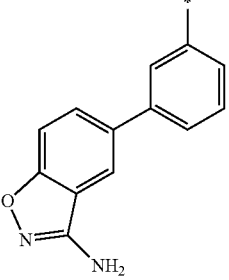 | MS: [M + 1]⁺ = 578<br>HPLC $_A$t$_{Ret}$ = 3.02 min. |
| 193 |  | 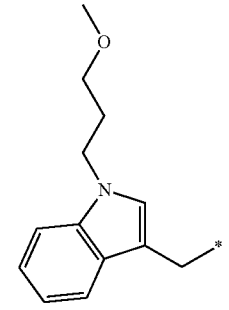 | 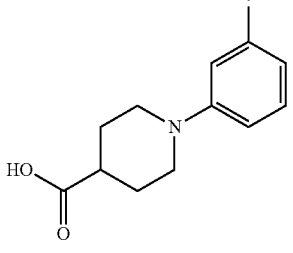 | MS: [M + 1]⁺ = 573<br>HPLC $_A$t$_{Ret}$ = 2.42 min. |
| 194 |  | 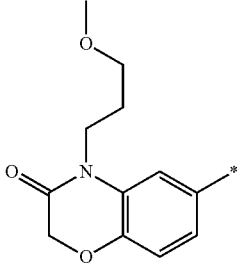 | 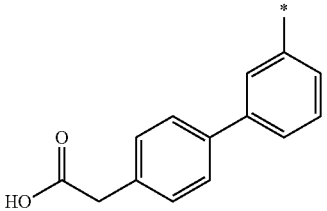 | MS: [M + 1]⁺ = 598<br>HPLC $_A$t$_{Ret}$ = 2.77 min. |

TABLE 1-continued
| Example | R1 | R2 | W* | Analytical data |
|---|---|---|---|---|
| 195 |  | 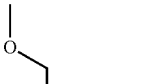 | 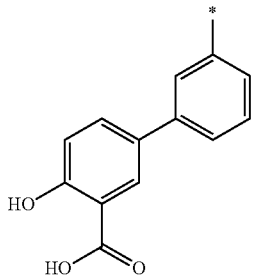 | MS: [M + 1]$^+$ = 600<br>HPLC $_A$t$_{Ret}$ = 2.84 min. |
| 196 |  | 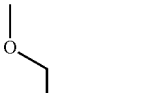 | 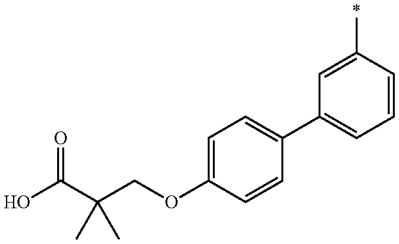 | MS: [M + 1]$^+$ = 656<br>HPLC $_A$t$_{Ret}$ = 3.09 min. |
| 197 |  |  | 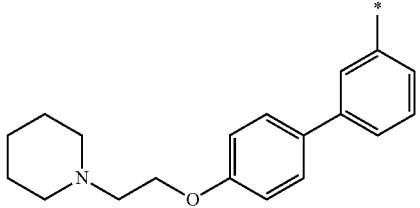 | MS: [M + 1]$^+$ = 649<br>HPLC $_A$t$_{Ret}$ = 2.79 min. |
| 198 |  |  | 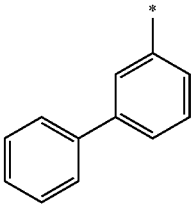 | MS: [M + 1]$^+$ = 576<br>HPLC $_A$t$_{Ret}$ = 3.47 min. |

TABLE 1-continued
| Example | R1 | R2 | W* | Analytical data |
|---|---|---|---|---|
| 199 | 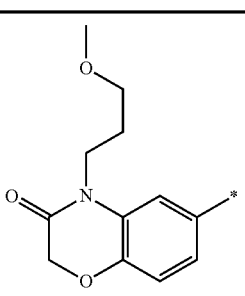 | 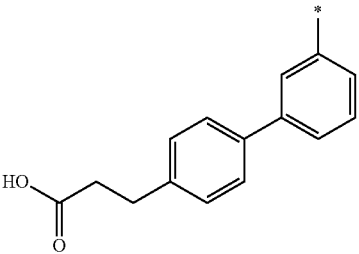 |  | MS: [M + 1]+ = 612<br>HPLC $A^t{}_{Ret}$ = 2.82 min. |
| 200 | 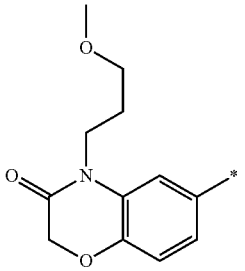 | 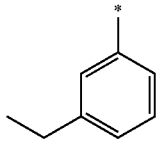 |  | MS: [M + 1]+ = 492<br>HPLC $A^t{}_{Ret}$ = 2.93 min. |
| 201 | 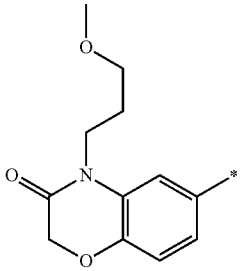 | 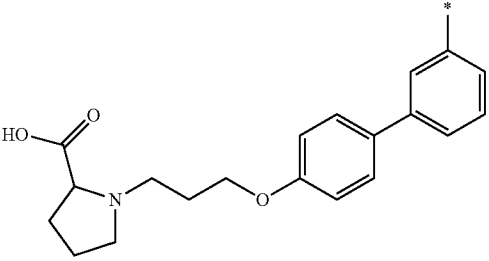 |  | MS: [M + 1]+ = 711<br>HPLC $A^t{}_{Ret}$ = 2.45 min. |
| 202 | 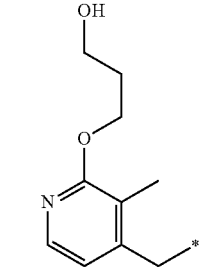 | 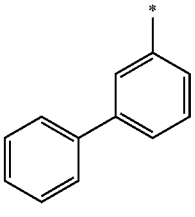 |  | MS: [M + 1]+ = 500<br>HPLC $A^t{}_{Ret}$ = 2.62 min. |
| 203 | 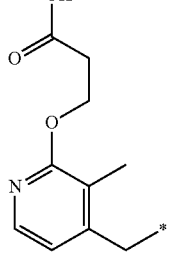 | 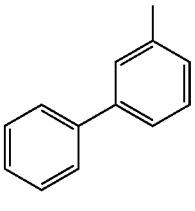 | | MS: [M + 1]+ = 514<br>HPLC $A^t{}_{Ret}$ = 2.77 min. |

TABLE 1-continued
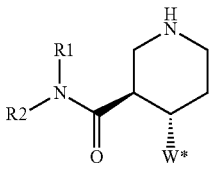
| Example | R1 | R2 | W* | Analytical data |
|---|---|---|---|---|
| 204 |  | 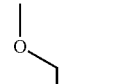 | 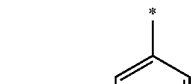 | MS: [M + 1]⁺ = 545<br>HPLC $_A$t$_{Ret}$ = 2.29 min. |
| 205 |  | 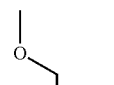 | 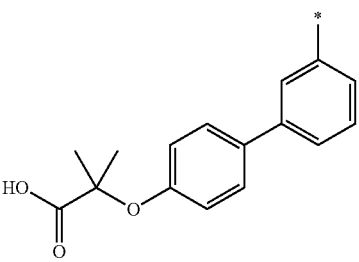 | MS: [M + 1]⁺ = 642<br>HPLC $_A$t$_{Ret}$ = 2.92 min. |
| 206 |  | 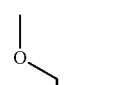 | 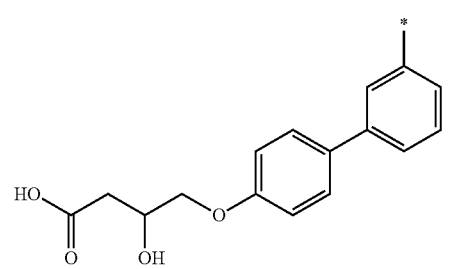 | MS: [M + 1]⁺ = 658<br>HPLC $_A$t$_{Ret}$ = 2.60 min. |
| 207 |  | 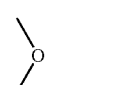 | 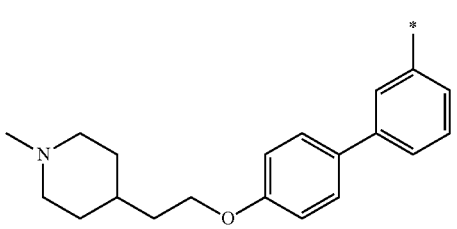 | MS: [M + 1]⁺ = 663<br>HPLC $_A$t$_{Ret}$ = 2.80 min. |

TABLE 1-continued
| Example | R1 | R2 | W* | Analytical data |
|---|---|---|---|---|
| 208 | 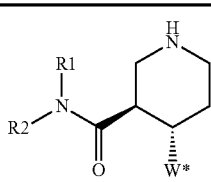 |  | 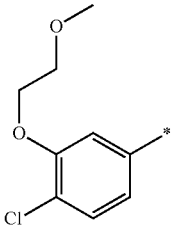 | MS: [M + 1]⁺ = 505<br>HPLC $_A$t$_{Ret}$ = 3.45 min. |
| 209 | 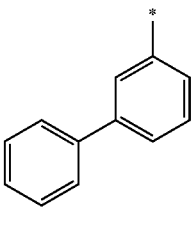 |  | 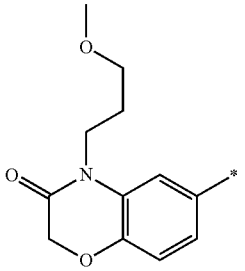 | MS: [M + 1]⁺ = 584<br>HPLC $_A$t$_{Ret}$ = 2.75 min. |
| 210 | 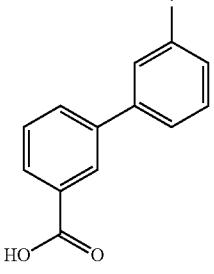 |  | 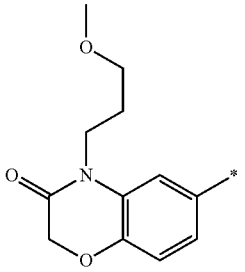 | MS: [M + 1]⁺ = 558<br>HPLC $_A$t$_{Ret}$ = 3.13 min. |
| 211 | 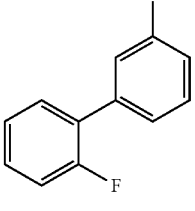 |  | 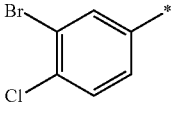 | MS: [M + 1]⁺ = 510<br>HPLC $_A$t$_{Ret}$ = 3.65 min. |
| 212 | 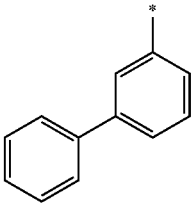 |  | 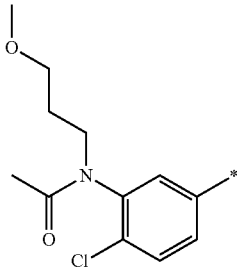 | MS: [M + 1]⁺ = 532<br>HPLC $_A$t$_{Ret}$ = 3.35 min. |

TABLE 1-continued
| Example | R1 | R2 | W* | Analytical data |
|---|---|---|---|---|
| 213 |  | 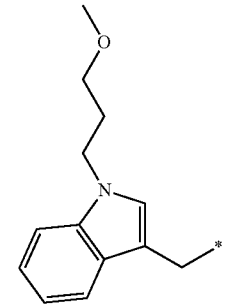 | 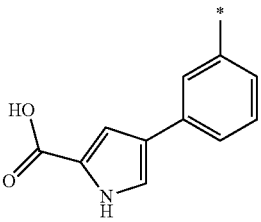 | MS: [M + 1]⁺ = 555<br>HPLC $A^t{}_{Ret}$ = 2.87 in. |
| 214 |  | 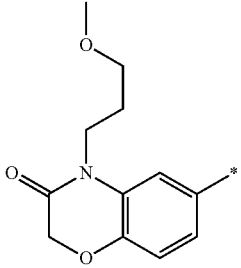 | 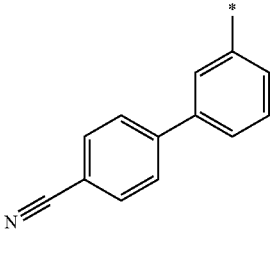 | MS: [M + 1]⁺ = 565<br>HPLC $A^t{}_{Ret}$ = 3.09 min. |
| 215 |  | 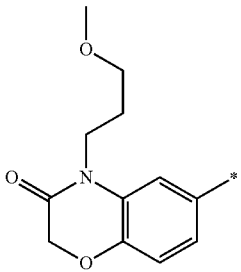 | 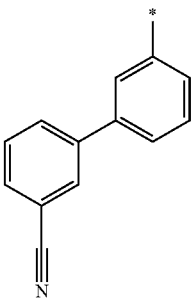 | MS: [M + 1]⁺ = 565<br>HPLC $A^t{}_{Ret}$ = 3.09 min. |
| 216 |  | 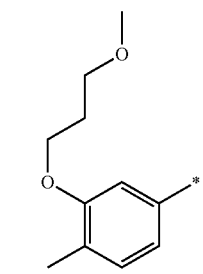 | 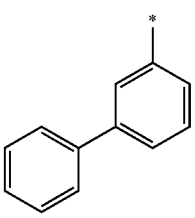 | MS: [M + 1]⁺ = 499<br>HPLC $A^t{}_{Ret}$ = 3.84 mi |

TABLE 1-continued
| Example | R1 | R2 | W* | Analytical data |
|---|---|---|---|---|
| 217 |  |  | 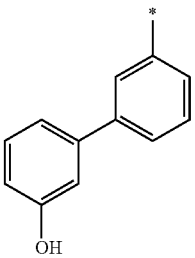 | MS: [M + 1]⁺ = 556<br>HPLC $_A$t$_{Ret}$ = 2.95 min. |
| 218 |  |  | 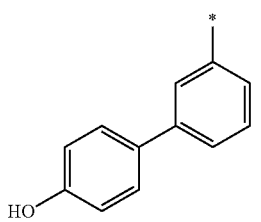 | MS: [M + 1]⁺ = 556<br>HPLC $_A$t$_{Ret}$ = 2.92 min. |
| 219 |  | 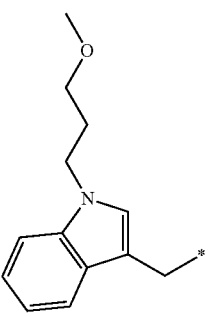 | 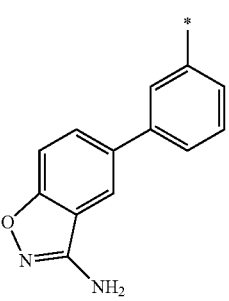 | MS: [M + 1]⁺ = 578<br>HPLC $_A$t$_{Ret}$ = 3.02 min. |
| 220 |  | 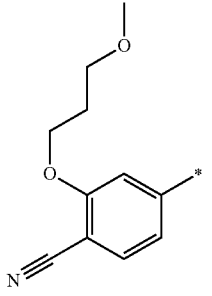 | 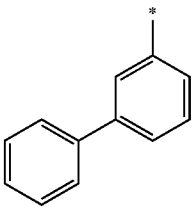 | MS: [M + 1]⁺ = 510<br>HPLC $_A$t$_{Ret}$ = 3.25 min. |

TABLE 1-continued
| Example | R1 | R2 | W* | Analytical data |
|---|---|---|---|---|
| 221 | 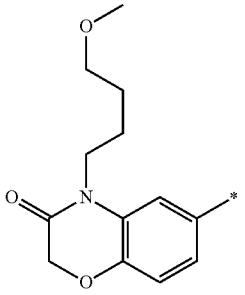 | 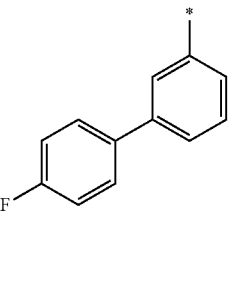 |  | MS: [M + 1]⁺ = 558; HPLC: $_A$t$_{Ret}$ = 3.12 min. |
| 222 | 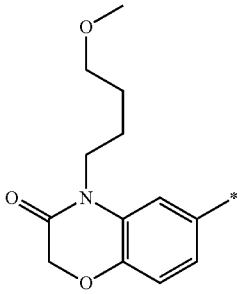 | 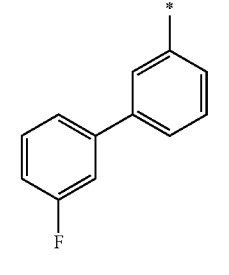 |  | MS: [M + 1]⁺ = 558 HPLC $_A$t$_{Ret}$ = 3.10 min |
| 223 | 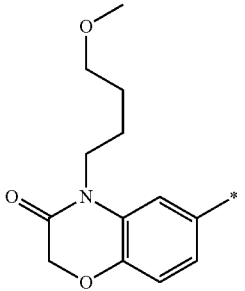 | 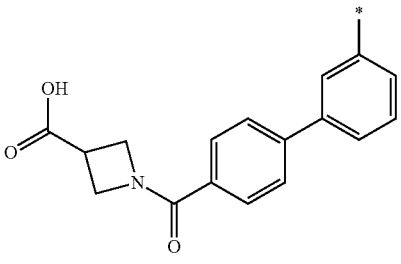 |  | MS: [M + 1]⁺ = 667 HPLC $_A$t$_{Ret}$ = 2.55 min. |
| 224 | | 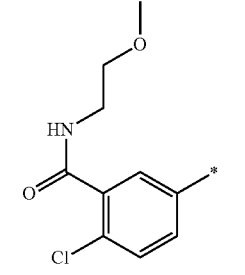 | 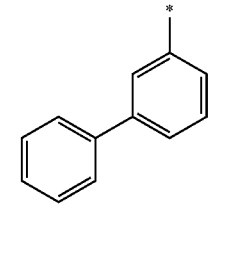 | MS: [M + 1]⁺ = 532 HPLC $_A$t$_{Ret}$ = 3.00 min. |

TABLE 1-continued
| Example | R1 | R2 | W* | Analytical data |
|---|---|---|---|---|
| 225 | 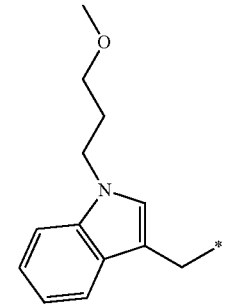 | 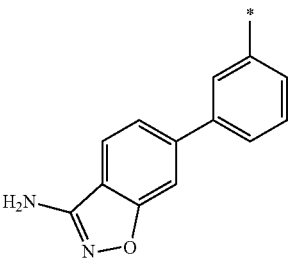 |  | MS: [M + 1]$^+$ = 578<br>HPLC $_A$t$_{Ret}$ = 2.97 min. |
| 226 | 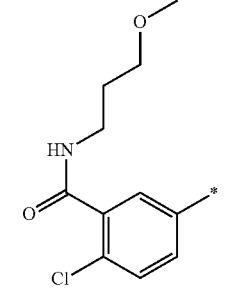 | 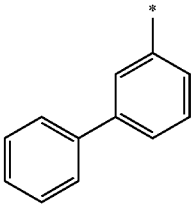 |  | MS: [M + 1]$^+$ = 546<br>HPLC $_A$t$_{Ret}$ = 2.84 min. |
| 227 | 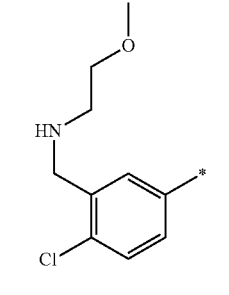 | 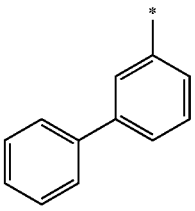 |  | MS: [M + 1]$^+$ = 518<br>HPLC $_A$t$_{Ret}$ = 3.32 min. |
| 228 | 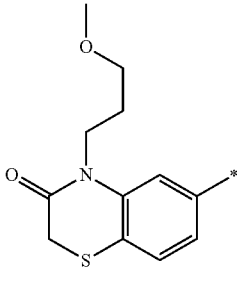 | 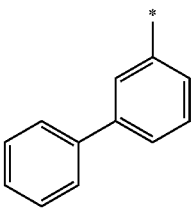 | | MS: [M + 1]$^+$ = 556<br>HPLC $_A$t$_{Ret}$ = 2.98 min. |

TABLE 1-continued
| Example | R1 | R2 | W* | Analytical data |
|---|---|---|---|---|
| 229 | 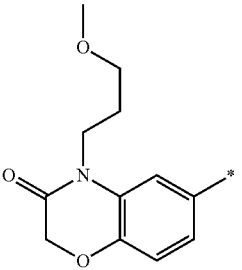 | 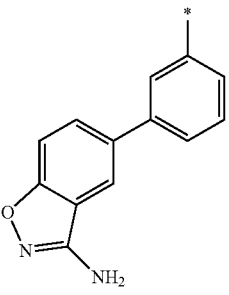 |  | MS: [M + 1]$^+$ = 596<br>HPLC $_A$t$_{Ret}$ = 2.47 min. |
| 230 | 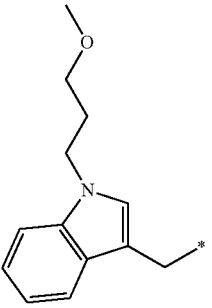 | 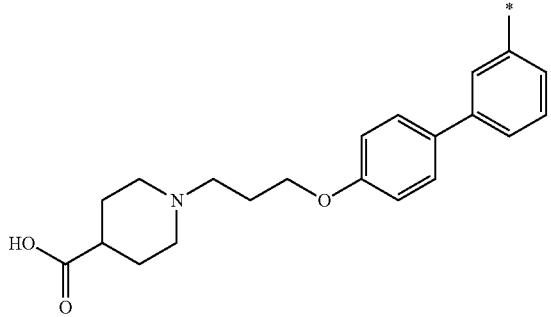 |  | MS: [M + 1]$^+$ = 707<br>HPLC $_A$t$_{Ret}$ = 2.42 min. |
| 231 | 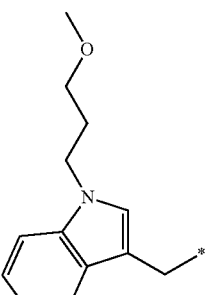 | 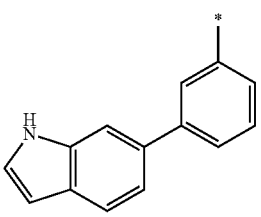 |  | MS: [M + 1]$^+$ = 561<br>HPLC $_A$t$_{Ret}$ = 3.20 min. |
| 232 | 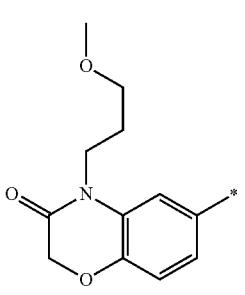 | 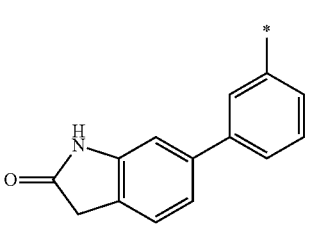 | | MS: [M + 1]$^+$ =; 595<br>HPLC: $_A$t$_{Ret}$ = 2.37 min |

TABLE 1-continued
| Example | R1 | R2 | W* | Analytical data |
|---|---|---|---|---|
| 233 | 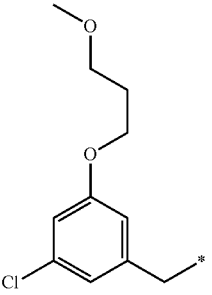 | 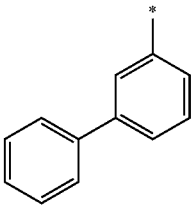 |  | MS: [M + 1]$^+$ = 533<br>HPLC $_A$t$_{Ret}$ = 3.38 min. |
| 234 | 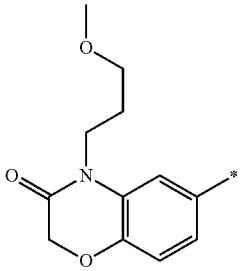 | 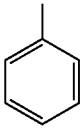 |  | MS: [M + 1]$^+$ = 464<br>HPLC $_A$t$_{Ret}$ = 2.42 min. |
| 235 | 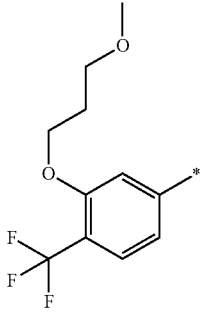 | 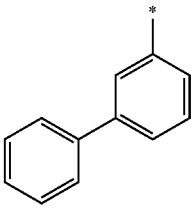 |  | MS: [M + 1]$^+$ = 553<br>HPLC $_A$t$_{Ret}$ = 3.48 min. |
| 236 | | 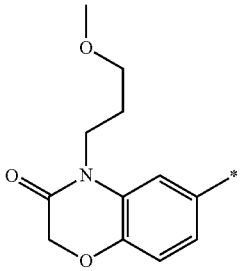 | 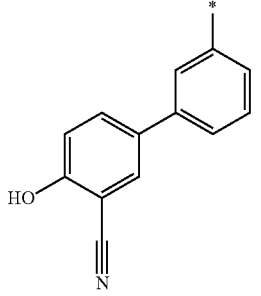 | MS: [M + 1]$^+$ = 581<br>HPLC $_A$t$_{Ret}$ = 2.50 min. |

TABLE 1-continued

| Example | R1 | R2 | W* | Analytical data |
|---|---|---|---|---|
| 237 | cyclopropyl | 4-(3-methoxypropyl)-3-oxo-3,4-dihydro-2H-benzo[b][1,4]oxazin-6-yl | 4'-methoxybiphenyl-3-yl | MS: [M + 1]⁺ = 570<br>HPLC_A t_Ret = 2.87 min. |
| 238 | cyclopropyl | 4-(3-methoxypropyl)-3-oxo-3,4-dihydro-2H-benzo[b][1,4]oxazin-6-yl | 3-fluoro-4-hydroxybiphenyl-3'-yl | MS: [M + 1]⁺ = 574<br>HPLC_A t_Ret = 2.54 min. |
| 239 | cyclopropyl | 4-(3-methoxypropyl)-3-oxo-3,4-dihydro-2H-benzo[b][1,4]oxazin-6-yl | 6-(1H-indol-6-yl)phenyl | MS: [M + 1]⁺ = 579<br>HPLC_A t_Ret = 2.88 min. |
| 240 | cyclopropyl | 4-(3-methoxypropyl)-3-oxo-3,4-dihydro-2H-benzo[b][1,4]oxazin-6-yl | 4-cyano-3-hydroxybiphenyl-3'-yl | MS: [M + 1]⁺ = 581<br>HPLC_A t_Ret = 2.59 min. |
| 241 | cyclopropyl | (1H-indol-3-yl)methyl | biphenyl-3-yl | MS: [M + 1]⁺ = 450<br>HPLC_A t_Ret = 2.98 min. |

TABLE 1-continued
| Example | R1 | R2 | W* | Analytical data |
|---|---|---|---|---|
| 242 |  | 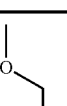 | 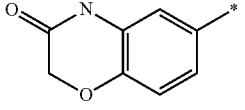 | MS: [M + 1]⁺ = 556 HPLC $_A$t$_{Ret}$ = 2.62 min. |
| 243 | 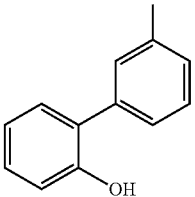 |  | 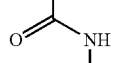 | MS: [M + 1]⁺ = 553 HPLC $_A$t$_{Ret}$ = 2.68 min. |
| 244 | 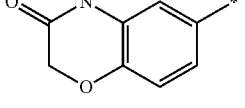 | 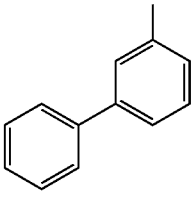 |  | MS: [M+]⁺ = 569 HPLC $_A$t$_{Ret}$ = 2.30 min. |
| 245 | 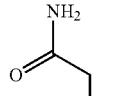 | 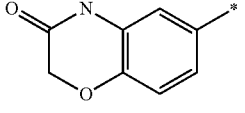 | 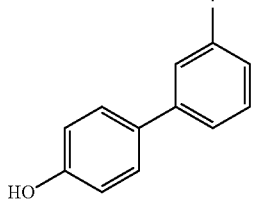 | MS: [M + 1]⁺ = 536 HPLC $_A$t$_{Ret}$ = 3.23 min. |
| 246 |  | 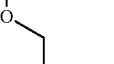 | 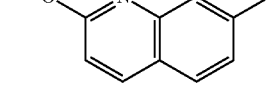 | MS: [M]⁺ = 504 HPLC $_A$t$_{Ret}$ = 2.73 min. |

TABLE 1-continued

| Example | R1 | R2 | W* | Analytical data |
|---|---|---|---|---|
| 247 | cyclopropyl | 3-methoxypropoxy-2-(trifluoromethyl)benzyl | biphenyl-3-yl | MS: [M + 1]$^+$ = 567<br>HPLC $_A$t$_{Ret}$ = 3.50 min. |
| 248 | cyclopropyl | 4-(3-methoxypropyl)-3-oxo-3,4-dihydro-2H-benzo[b][1,4]oxazin-6-yl | 3'-cyano-2'-fluorobiphenyl-3-yl | MS: [M + 1]$^+$ = 583<br>HPLC $_A$t$_{Ret}$ = 2.82 min. |
| 249 | cyclopropyl | 4-(3-methoxypropyl)-3-oxo-3,4-dihydro-2H-benzo[b][1,4]oxazin-6-yl | 4'-(trifluoromethyl)biphenyl-3-yl | MS: [M + 1]$^+$ = 608<br>HPLC $_A$t$_{Ret}$ = 3.17 min. |
| 250 | cyclopropyl | 2,2-difluoro-4-(3-methoxypropyl)-3-oxo-3,4-dihydro-2H-benzo[b][1,4]oxazin-6-yl | 4'-hydroxybiphenyl-3-yl | MS: [M + 1]$^+$ = 592<br>HPLC $_A$t$_{Ret}$ = 2.80 min. |

TABLE 1-continued
| Example | R1 | R2 | W* | Analytical data |
|---|---|---|---|---|
| 251 | 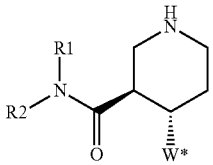 |  | 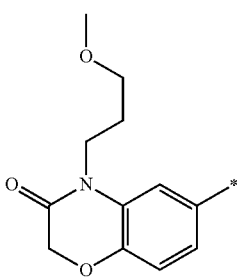 | MS: [M + 1]⁺ = 576<br>HPLC $_A$t$_{Ret}$ = 2.95 min. |
| 252 | 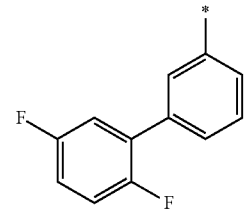 |  | 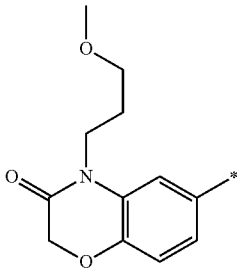 | MS: [M + 1]⁺ = 556<br>HPLC $_A$t$_{Ret}$ = 2.59 min. |
| 253 | 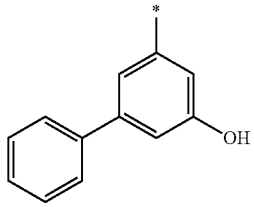 |  | 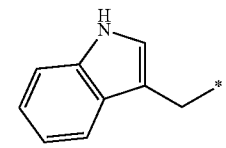 | MS: [M + 1]⁺ = 577<br>HPLC $_A$t$_{Ret}$ = 2.35 min. |
| 254 | 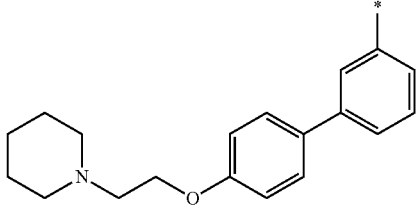 |  | 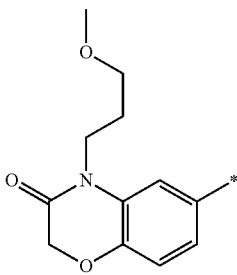 | MS: [M + 1]⁺ = 667<br>HPLC $_A$t$_{Ret}$ = 2.29 min. |
| 255 | 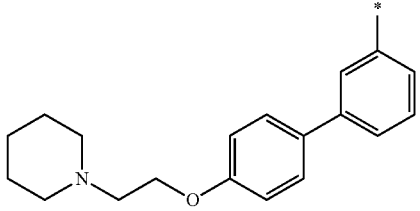 |  | 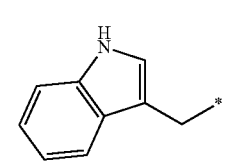 | MS: [M + 1]⁺ = 621<br>HPLC $_A$t$_{Ret}$ = 2.30 min. |

TABLE 1-continued
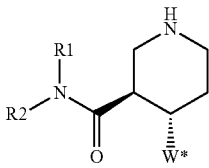
| Example | R1 | R2 | W* | Analytical data |
|---|---|---|---|---|
| 256 |  | 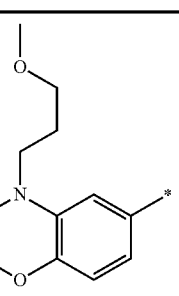 | 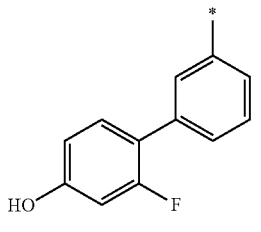 | MS: [M + 1]⁺ = 574<br>HPLC $_A$t$_{Ret}$ = 2.60 min. |
| 257 |  | 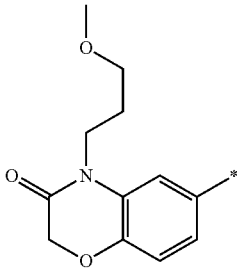 | 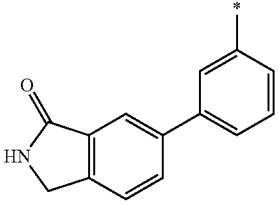 | MS: [M + 1]⁺ = 595<br>HPLC $_A$t$_{Ret}$ = 2.35 min. |
| 258 |  | 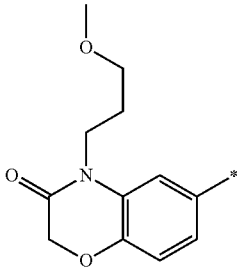 | 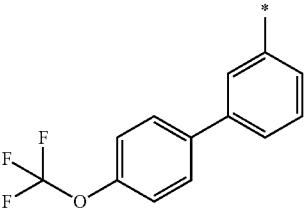 | MS: [M + 1]⁺ = 624<br>HPLC $_A$t$_{Ret}$ = 3.29 min. |
| 259 |  | 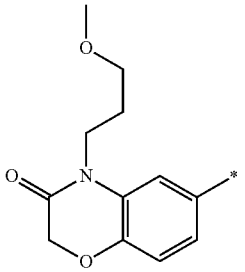 | 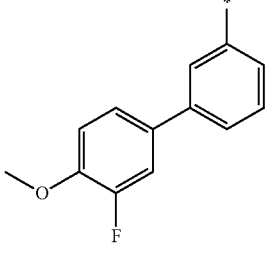 | MS: [M + 1]⁺ = 588<br>HPLC $_A$t$_{Ret}$ = 2.88 min. |
| 260 |  | 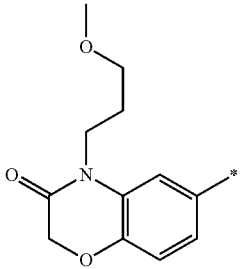 | 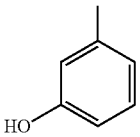 | MS: [M + 1]⁺ = 480<br>HPLC $_A$t$_{Ret}$ = 2.17 min. |

US 8,178,559 B2
223 224
TABLE 1-continued
| Example | R1 | R2 | W* | Analytical data |
|---|---|---|---|---|
| 261 | 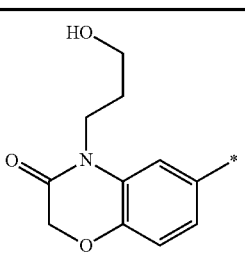 | 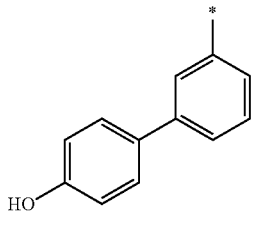 |  | MS: [M + 1]⁺ = 556<br>HPLC $_A$t$_{Ret}$ = 2.32 min. |
| 262 | 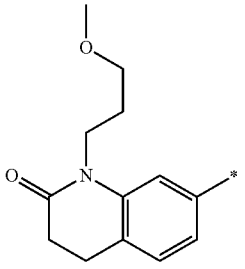 | 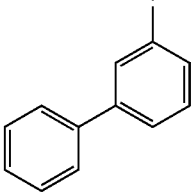 |  | MS: [M + 1]⁺ = 538<br>HPLC $_A$t$_{Ret}$ = 2.88 min. |
| 263 | 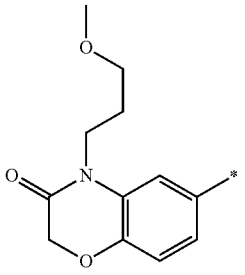 | 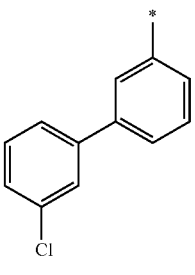 |  | MS: [M + 1]⁺ = 574<br>HPLC $_A$t$_{Ret}$ = 3.12 min. |
| 264 | 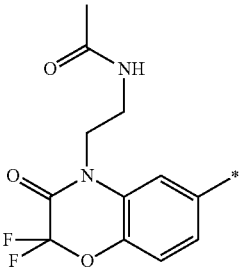 | 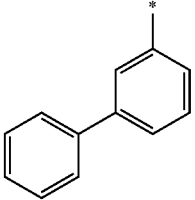 |  | MS: [M + 1]⁺ = 589<br>HPLC $_A$t$_{Ret}$ = 3.02 min. |
| 265 | 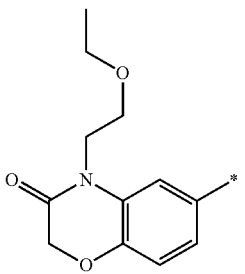 | 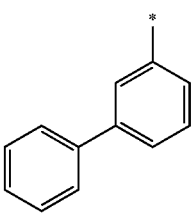 |  | MS: [M + 1]⁺ = 540<br>HPLC $_A$t$_{Ret}$ = 2.97 min. |

TABLE 1-continued
| Example | R1 | R2 | W* | Analytical data |
|---|---|---|---|---|
| 266 |  | 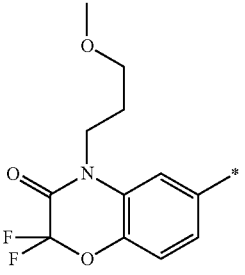 | 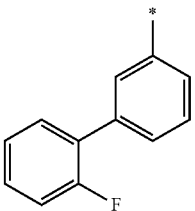 | MS: [M + 1]⁺ = 594<br>HPLC $_A$t$_{Ret}$ = 3.29 min. |
| 267 |  | 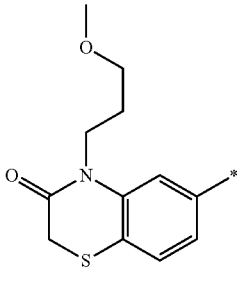 | 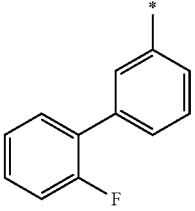 | MS: [M + 1]⁺ = 574<br>HPLC $_A$t$_{Ret}$ = 3.02 min. |
| 268 |  | 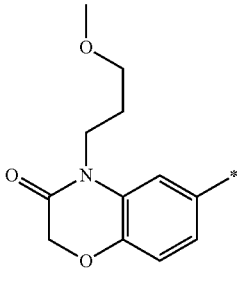 | 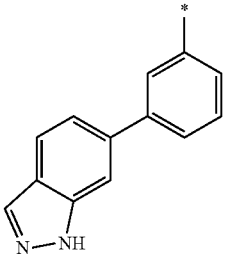 | MS: [M + 1]⁺ = 580<br>HPLC $_A$t$_{Ret}$ = 2.54 min. |
| 269 |  | 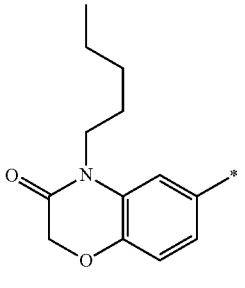 | 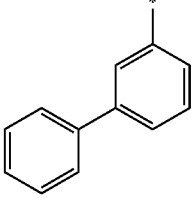 | MS: [M + 1]⁺ = 538.04<br>HPLC $_c$t$_{Ret}$ = 1.89 min. |
| 270 |  | 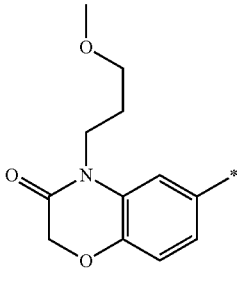 | 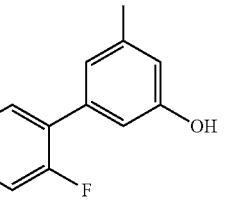 | MS: [M + 1]⁺ = 574<br>HPLC $_A$t$_{Ret}$ = 2.65 min. |

TABLE 1-continued
| Example | R1 | R2 | W* | Analytical data |
|---|---|---|---|---|
| 271 | 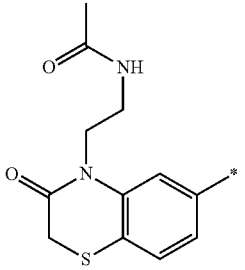 | 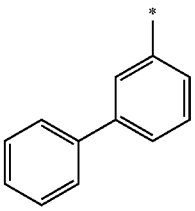 |  | MS: [M + 1]⁺ = 569<br>HPLC $_A$t$_{Ret}$ = 2.82 min. |
| 272 | 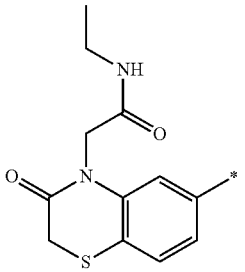 | 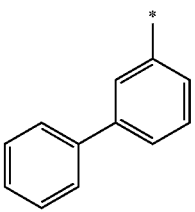 |  | MS: [M + 1]⁺ = 569<br>HPLC $_A$t$_{Ret}$ = 2.88 min. |
| 273 | 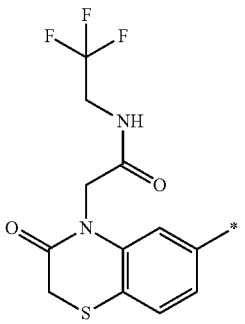 | 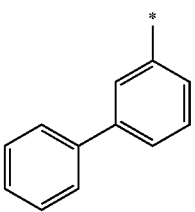 |  | MS: [M + 1]⁺ = 623<br>HPLC $_A$t$_{Ret}$ = 3.04 min. |
| 274 | 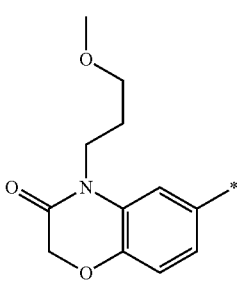 | 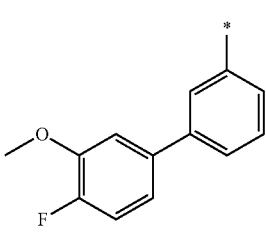 |  | MS: [M + 1]⁺ = 588<br>HPLC $_A$t$_{Ret}$ = 2.92 |

TABLE 1-continued

| Example | R1 | R2 | W* | Analytical data |
|---|---|---|---|---|
| 275 | cyclopropyl | 4-(3-methoxypropyl)-3-oxo-3,4-dihydro-2H-benzo[1,4]oxazin-6-yl | 4-fluoro-3-hydroxy-biphenyl-3'-yl | MS: [M + 1]⁺ = 574 HPLC $_A$t$_{Ret}$ = 2.65 min. |
| 276 | cyclopropyl | 4-(3-methoxypropyl)-3-oxo-3,4-dihydro-2H-benzo[1,4]oxazin-6-yl | 2'-fluoro-5'-hydroxy-biphenyl-3-yl | MS: [M + 1]⁺ = 574 HPLC $_A$t$_{Ret}$ = 2.63 min. |
| 277 | cyclopropyl | 4-(3-methoxypropyl)-3-oxo-3,4-dihydro-2H-benzo[1,4]oxazin-6-yl | 2-fluoro-3-hydroxy-biphenyl-3'-yl | MS: [M + 1]⁺ = 574 HPLC $_A$t$_{Ret}$ = 2.60 min. |
| 278 | cyclopropyl | 4-(3-methoxypropyl)-3-oxo-3,4-dihydro-2H-benzo[1,4]oxazin-6-yl | 3'-methoxy-biphenyl-3-yl | MS: [M + 1]⁺ = 570 HPLC $_A$t$_{Ret}$ = 2.92 min. |
| 279 | cyclopropyl | 4-(3-methoxypropyl)-3-oxo-3,4-dihydro-2H-benzo[1,4]oxazin-6-yl | 5-(2-oxo-2,3-dihydro-1H-indol-5-yl)phenyl | MS: [M + 1]⁺ = 595 HPLC $_A$t$_{Ret}$ = 2.35 min. |

TABLE 1-continued
| Example | R1 | R2 | W* | Analytical data |
|---|---|---|---|---|
| 280 |  | 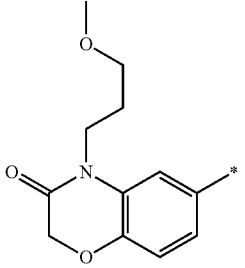 | 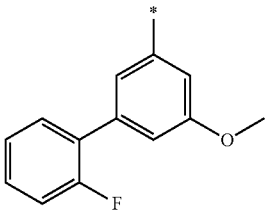 | MS: [M + 1]⁺ = 588<br>HPLC $_A$t$_{Ret}$ = 2.95 min. |
| 281 |  | 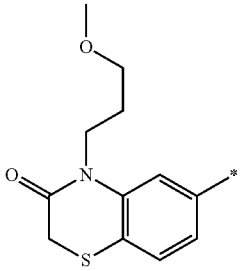 | 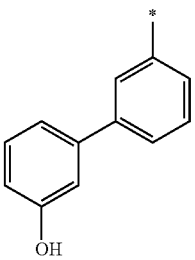 | MS: [M + 1]⁺ = 572<br>HPLC $_A$t$_{Ret}$ = 2.63 min. |
| 282 |  | 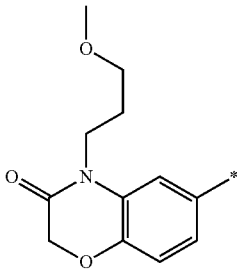 | 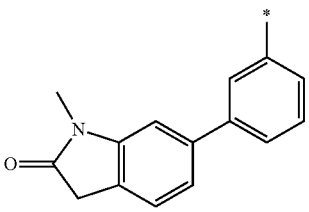 | MS: [M + 1]⁺ = 609<br>HPLC $_A$t$_{Ret}$ = 2.54 min. |
| 283 |  | 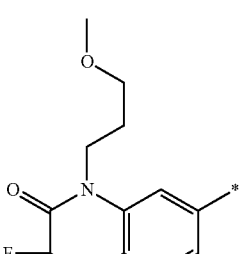 | 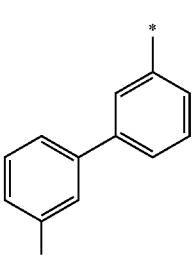 | MS: [M + 1]⁺ = 592<br>HPLC $_A$t$_{Ret}$ = 2.90 min. |

TABLE 1-continued

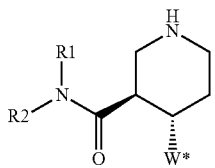

| Example | R1 | R2 | W* | Analytical data |
|---|---|---|---|---|
| 284 | cyclopropyl | 4-(3-methoxypropyl)-2,2-difluoro-3-oxo-benzo[1,4]oxazin-6-yl | 4'-methoxybiphenyl-3-yl | MS: [M + 1]⁺ = 606 HPLC $_A$t$_{Ret}$ = 3.20 min. |
| 285 | cyclopropyl | 4-(3-methoxypropyl)-3-oxo-benzo[1,4]oxazin-6-yl | 3'-acetamidobiphenyl-3-yl | MS: [M + 1]⁺ = 597 HPLC $_A$t$_{Ret}$ = 2.48 min. |
| 286 | cyclopropyl | 3-(3-methoxypropoxy)-5-methyl-6-fluorobenzyl | biphenyl-3-yl | MS: [M + 1]⁺ = 531 HPLC $_A$t$_{Ret}$ = 3.34 min. |
| 287 | cyclopropyl | 4-(3-methoxypropyl)-3-oxo-benzo[1,4]oxazin-6-yl | 5-fluoro-3'-hydroxybiphenyl-3-yl | MS: [M + 1]⁺ = 574 HPLC $_C$t$_{Ret}$ = 1.59 min. |

TABLE 1-continued
| Example | R1 | R2 | W* | Analytical data |
|---|---|---|---|---|
| 288 |  | 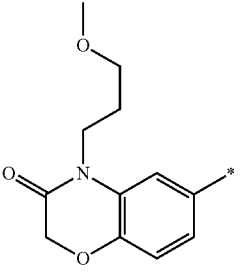 | 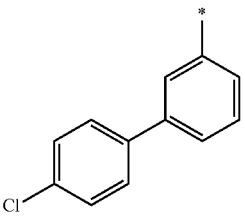 | MS: [M + 1]⁺ = 574<br>HPLC $_A$t$_{Ret}$ = 3.13 min. |
| 289 |  | 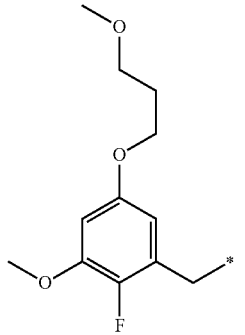 | 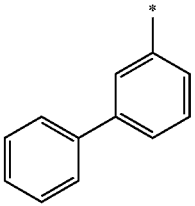 | MS: [M + 1]⁺ = 547<br>HPLC $_A$t$_{Ret}$ = 3.18 min. |
| 290 |  | 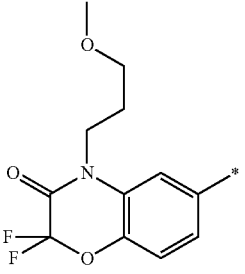 | 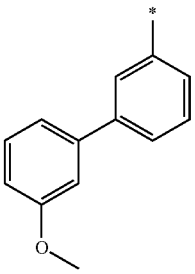 | MS: [M + 1]⁺ = 606<br>HPLC $_A$t$_{Ret}$ = 3.27 min. |
| 291 |  | 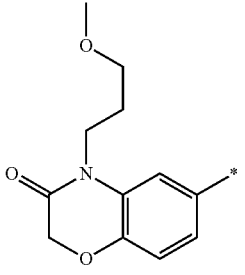 | 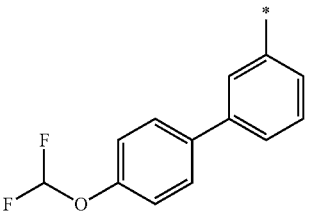 | MS: [M + 1]⁺ = 606<br>HPLC $_A$t$_{Ret}$ = 3.02 min. |

TABLE 1-continued
| Example | R1 | R2 | W* | Analytical data |
|---|---|---|---|---|
| 292 | 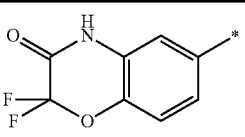 | 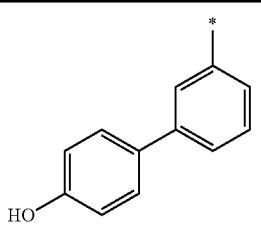 |  | MS: [M + 1]$^+$ = 520<br>HPLC $_{A}{}^{t}{}_{Ret}$ = 2.59 min. |
| 293 | 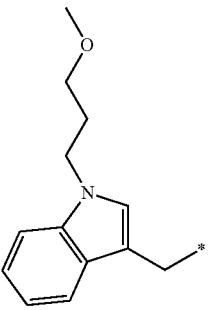 | 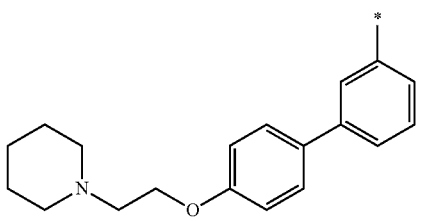 |  | MS: [M + 1]$^+$ = 649<br>HPLC $_{A}{}^{t}{}_{Ret}$ = 2.59 min. |
| 294 | 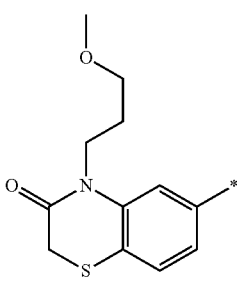 | 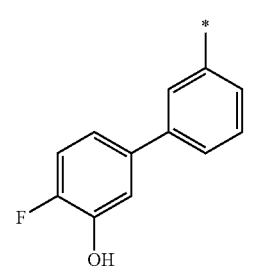 |  | MS: [M + 1]$^+$ = 590<br>HPLC $_{A}{}^{t}{}_{Ret}$ = 2.70 min. |
| 295 | 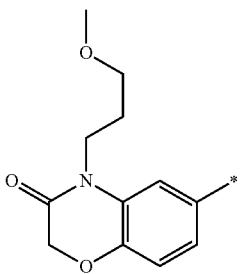 | 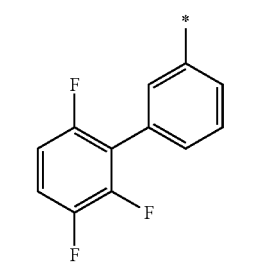 |  | MS: [M + 1]$^+$ = 594<br>HPLC $_{A}{}^{t}{}_{Ret}$ = 2.98 min. |
| 296 | 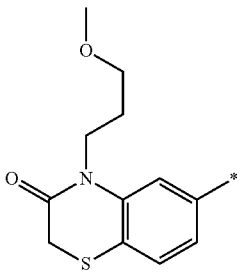 | 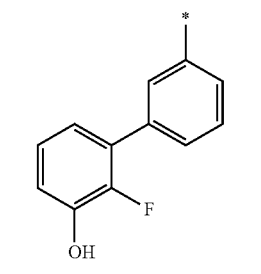 | | MS: [M + 1]$^+$ = 590<br>HPLC $_{A}{}^{t}{}_{Ret}$ = 2.65 min. |

TABLE 1-continued
| Example | R1 | R2 | W* | Analytical data |
|---|---|---|---|---|
| 297 | 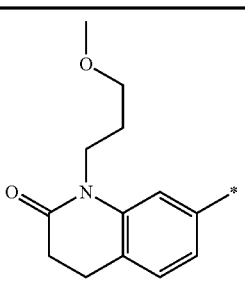 | 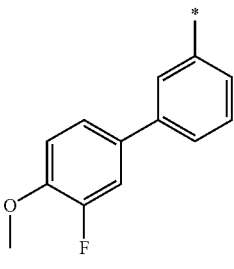 |  | MS: [M + 1]⁺ = 586<br>HPLC $_A$t$_{Ret}$ = 2.84 min. |
| 298 | 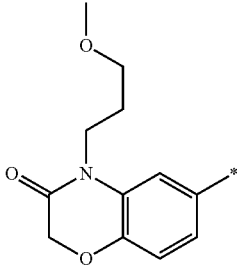 | 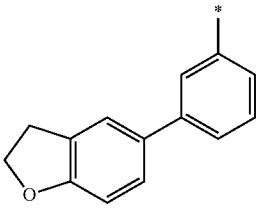 |  | MS: [M + 1]⁺ = 582<br>HPLC $_A$t$_{Ret}$ = 2.87 min. |
| 299 | 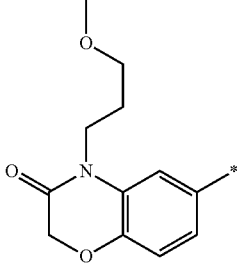 | 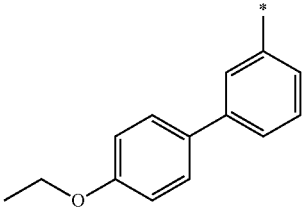 |  | MS: [M + 1]⁺ = 584<br>HPLC $_A$t$_{Ret}$ = 3.05 min. |
| 300 | 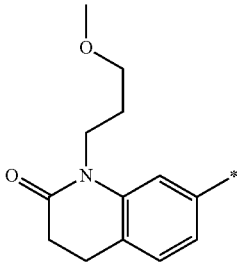 | 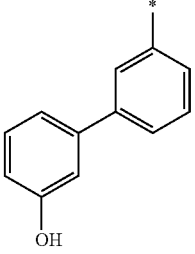 |  | MS: [M + 1]⁺ = 554<br>HPLC $_A$t$_{Ret}$ = 2.52 min. |
| 301 | 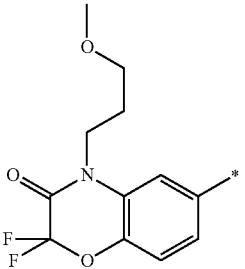 | 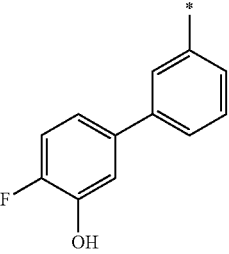 |  | MS: [M + 1]⁺ = 410<br>HPLC $_A$t$_{Ret}$ = 2.93 min. |

TABLE 1-continued
| Example | R1 | R2 | W* | Analytical data |
|---|---|---|---|---|
| 302 |  | 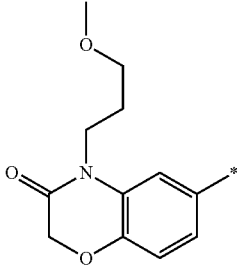 | 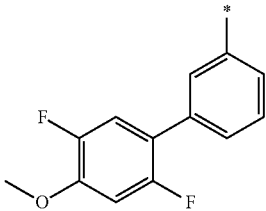 | MS: [M + 1]+ = 606<br>HPLC $_A$t$_{Ret}$ = 2.98 min. |
| 303 |  | 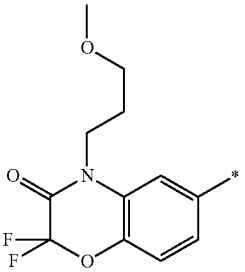 | 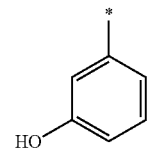 | MS: [M + 1]+ = 515<br>HPLC $_A$t$_{Ret}$ = 1.64 min. |
| 304 |  | 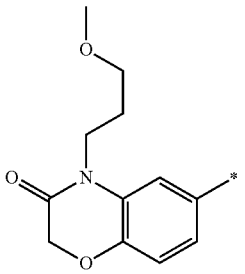 | 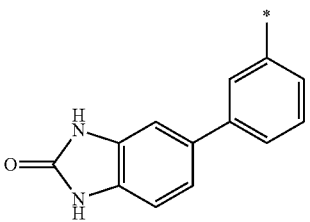 | MS: [M + 1]+ = 596<br>HPLC $_A$t$_{Ret}$ = 2.23 min. |
| 305 |  | 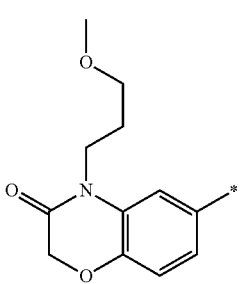 | 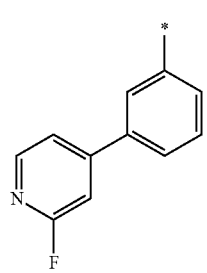 | MS: [M + 1]+ = 558<br>HPLC $_A$t$_{Ret}$ = 1.55 min. |

TABLE 1-continued
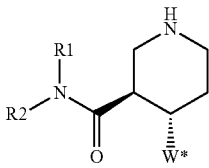
| Example | R1 | R2 | W* | Analytical data |
|---|---|---|---|---|
| 306 |  | 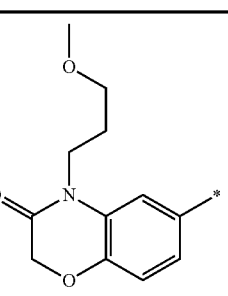 | 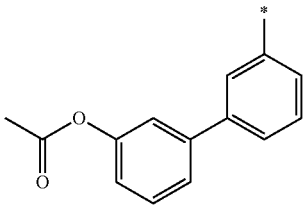 | MS: [M + 1]⁺ = 598<br>HPLC $_A$t$_{Ret}$ = 2.84 min. |
| 307 |  | 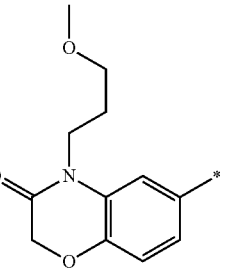 | 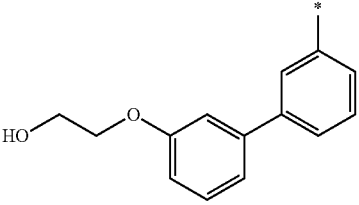 | MS: [M + 1]⁺ = 600<br>HPLC $_A$t$_{Ret}$ = 2.55 min. |
| 308 |  | 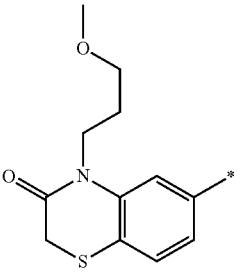 | 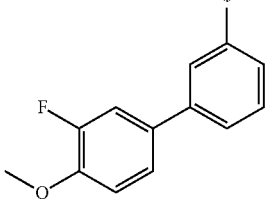 | MS: [M + 1]⁺ = 604<br>HPLC $_A$t$_{Ret}$ = 2.98 min. |
| 309 |  | 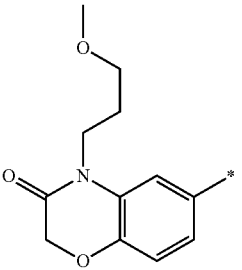 | 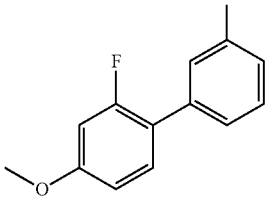 | MS: [M + 1]⁺ = 588<br>HPLC $_A$t$_{Ret}$ = 2.97 min. |
| 310 |  | 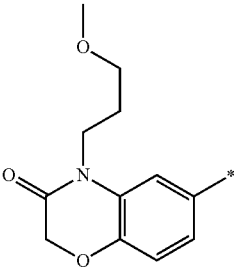 | 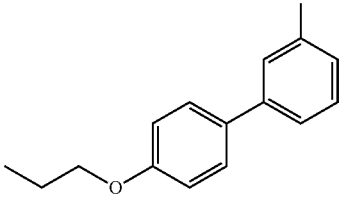 | MS: [M + 1]⁺ = 598<br>HPLC $_A$t$_{Ret}$ = 3.30 min. |

TABLE 1-continued
| Example | R1 | R2 | W* | Analytical data |
|---|---|---|---|---|
| 311 | 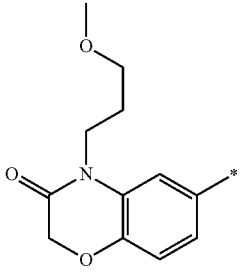 | 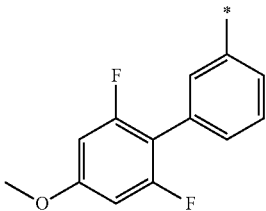 |  | MS: [M + 1]⁺ = 605<br>HPLC $_c$t$_{Ret}$ = 1.72 min. |
| 312 | 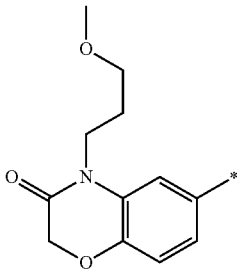 | 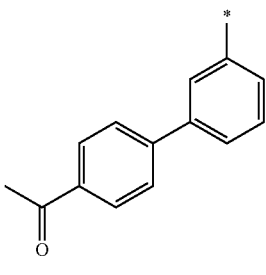 |  | MS: [M + 1]⁺ = 582<br>HPLC $_c$t$_{Ret}$ = 1.61 min. |
| 313 | 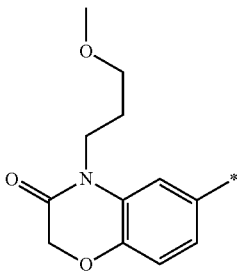 | 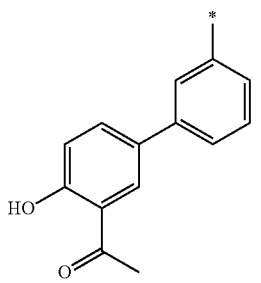 |  | MS: [M + 1]⁺ = 597<br>HPLC $_c$t$_{Ret}$ = 1.66 min |
| 314 | 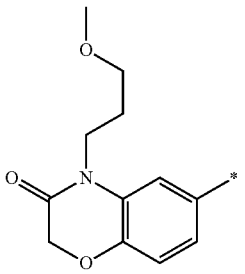 | | 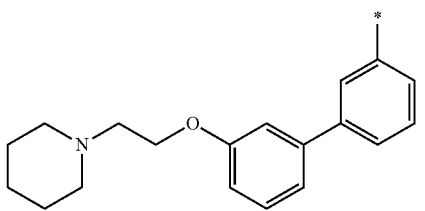 | MS: [M + 1]⁺ = 667<br>HPLC $_A$t$_{Ret}$ = 2.34 min. |

TABLE 1-continued
| Example | R1 | R2 | W* | Analytical data |
|---|---|---|---|---|
| 315 | 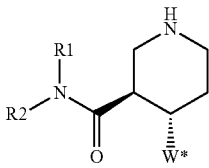 |  | 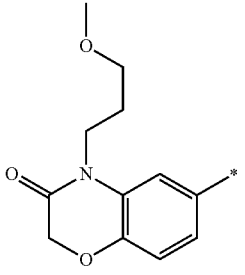 | MS: [M + 1]+ = 627<br>HPLC $_A$$t_{Ret}$ = 2.20 min. |
| 316 | 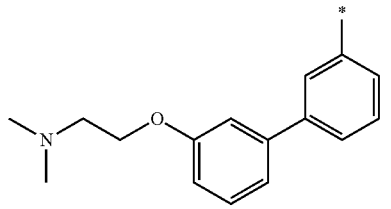 |  | 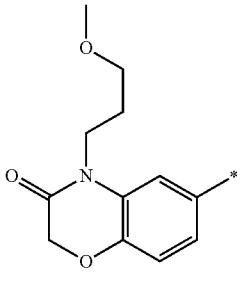 | MS: [M + 1]+ = 641<br>HPLC $_A$$t_{Ret}$ = 2.30 min. |
| 317 | 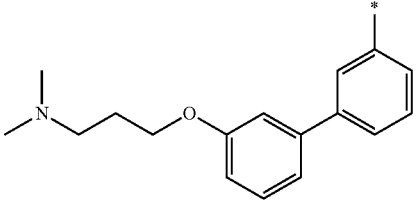 |  | 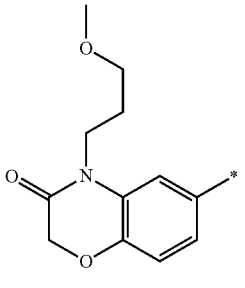 | MS: [M + 1]+ = 627<br>HPLC $_A$$t_{Ret}$ = 2.15 min. |
| 318 | 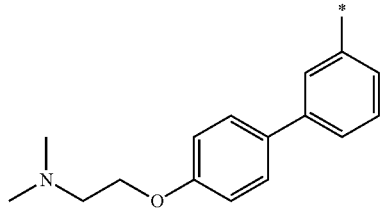 |  | 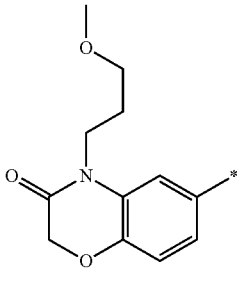 | MS: [M + 1]+ = 641<br>HPLC $_A$$t_{Ret}$ = 2.22 min. |
| 319 | 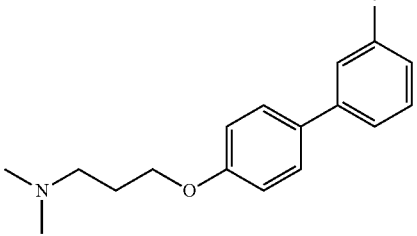 |  | 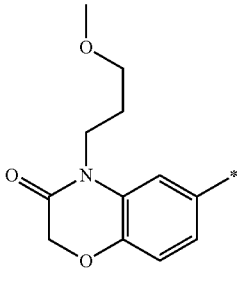 | MS: [M + 1]+ = 653<br>HPLC $_A$$t_{Ret}$ = 2.22 min. |

TABLE 1-continued
| Example | R1 | R2 | W* | Analytical data |
|---|---|---|---|---|
| 320 |  | 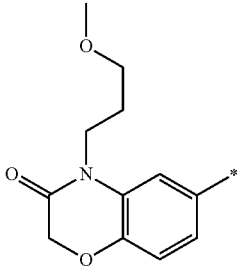 | 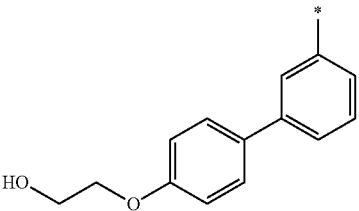 | MS: [M + 1]+ = 600 HPLC_A t_Ret = 2.47 min. |
| 321 |  | 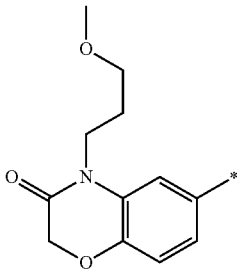 | 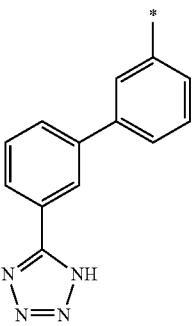 | MS: [M + 1]+ = 607 HPLC_A t_Ret = 1.53 min. |
| 322 |  | 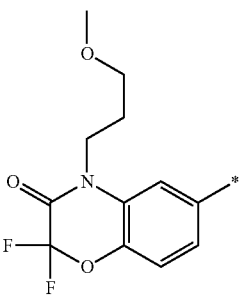 | 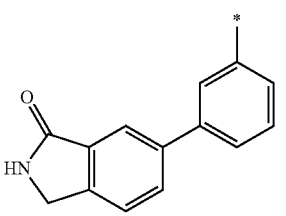 | MS: [M + 1]+ = 631 HPLC_A t_Ret = 2.76 min. |
| 323 |  | 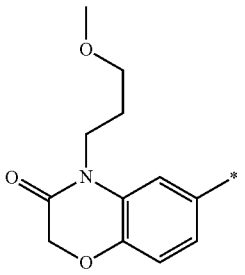 | 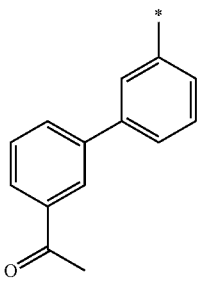 | MS: [M + 1]+ = 581 HPLC_C t_Ret = 1.61 min. |

TABLE 1-continued
| Example | R1 | R2 | W* | Analytical data |
|---|---|---|---|---|
| 324 |  | 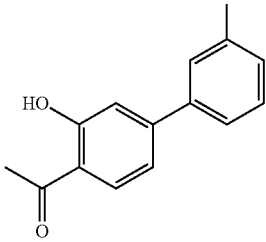 |  | MS: [M + 1]⁺ = 598<br>HPLC $_A$t$_{Ret}$ = 2.80 min. |
| 325 | 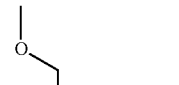 | 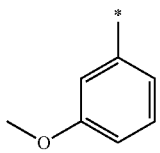 |  | MS: [M + 1]⁺ = 530<br>HPLC $_A$t$_{Ret}$ = 2.78 min. |
| 326 | 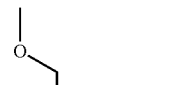 | 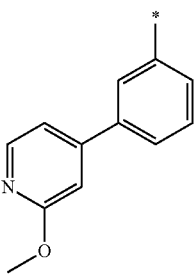 |  | MS: [M + 1]⁺ = 570<br>HPLC $_c$t$_{Ret}$ = 1.50 n. |
| 327 | | 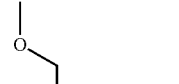 | 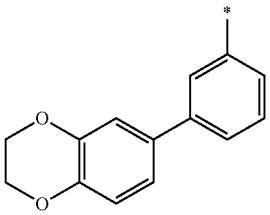 | MS: [M + 1]⁺ = 598<br>HPLC $_A$t$_{Ret}$ = 2.87 min. |

TABLE 1-continued
| Example | R1 | R2 | W* | Analytical data |
|---|---|---|---|---|
| 328 |  | 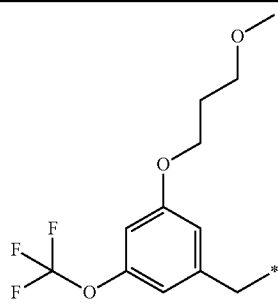 | 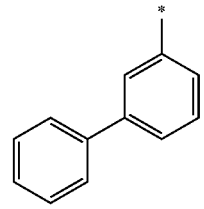 | MS: [M + 1]+ = 583<br>HPLC $_C$t$_{Ret}$ = 1.96 min. |
| 329 |  | 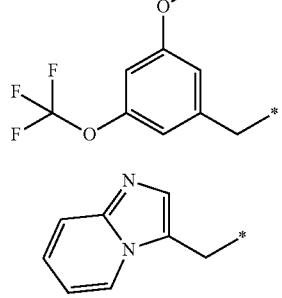 | 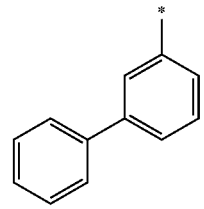 | MS: [M + 1]+ = 451<br>HPLC $_A$t$_{Ret}$ = 2.02 min. |
| 330 |  | 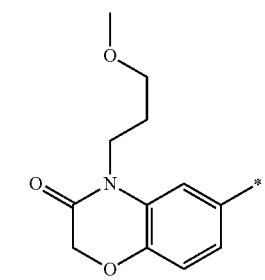 | 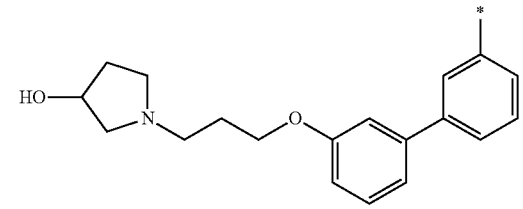 | MS: [M + 1]+ = 683<br>HPLC $_A$t$_{Ret}$ = 2.30 min. |
| 331 |  | 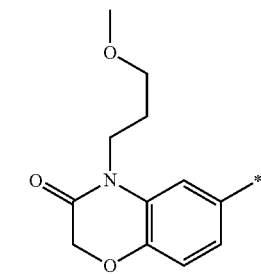 | 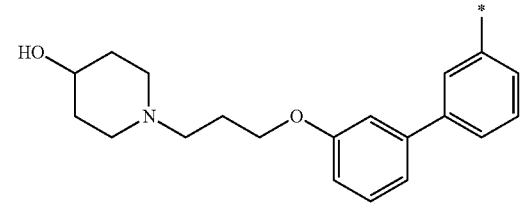 | MS: [M + 1]+ = 697<br>HPLC $_A$t$_{Ret}$ = 2.29 min. |
| 332 |  | 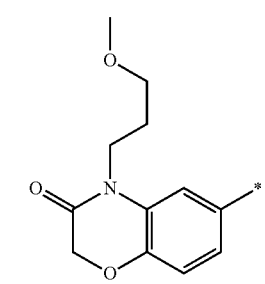 | 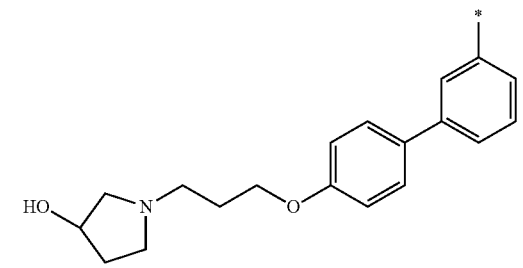 | MS: [M + 1]+ = 683<br>HPLC $_A$t$_{Ret}$ = 2.20 min. |

TABLE 1-continued
| Example | R1 | R2 | W* | Analytical data |
|---|---|---|---|---|
| 333 | cyclopropyl |  | 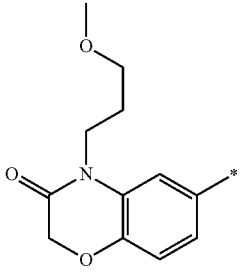 | MS: [M + 1]⁺ = 697<br>HPLC $_A$t$_{Ret}$ = 2.20 min. |
| 334 | cyclopropyl | 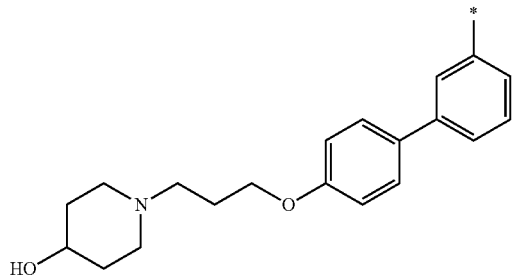 |  | MS: [M + 1]⁺ = 545<br>HPLC $_A$t$_{Ret}$ = 2.60 min. |
| 335 | cyclopropyl | 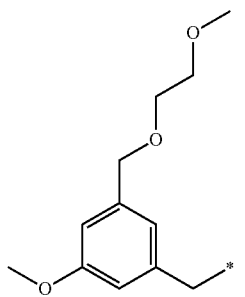 | 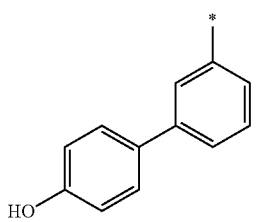 | MS: [M + 1]⁺ = 636<br>HPLC $_A$t$_{Ret}$ = 2.93 min. |
| 336 | cyclopropyl |  | 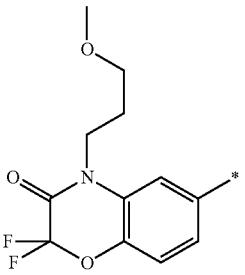 | MS: [M + 1]⁺ = 554<br>HPLC $_A$t$_{Ret}$ = 3.18 min. |

Intermediate 5.1

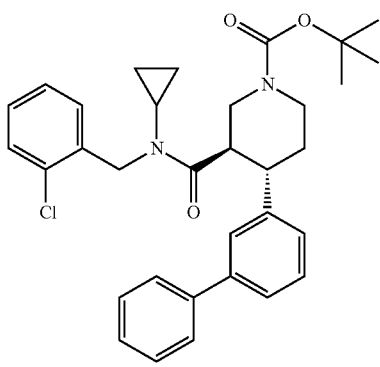

Intermediate 5.1 is synthesized by condensation of Intermediate 1.2 (50.4 mg, 0.132 mmol) and (2-chloro-benzyl)-cyclopropyl-amine (31.3 mg, 0.172 mmol) analogously to the preparation of Intermediate 1.1. Colorless oil; HPLC: $_Bt_{Ret}$=8.28 min Intermediate 6.1

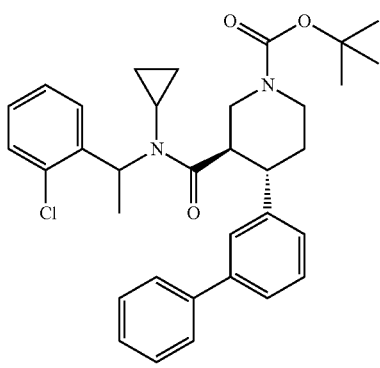

Intermediate 6.1 is synthesized by condensation of Intermediate 1.2 (51.7 mg, 0.136 mmol) and Intermediate 6.2 (52.8 mg, 0.27 mmol) analogously to the preparation of Intermediate 1.1. Colourless resin; HPLC: $_Bt_{Ret}$=8.26 min and 8.42 min (diastereomers); MS (LC/MS): [M+H]$^+$.=559.5/561.5

Intermediate 6.2

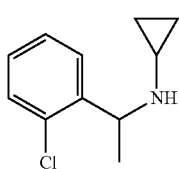

Intermediate 6.2 is synthesized by the reaction of 2-chloroacetophenone (5.00 g, 32.3 mmol) and cyclopropylamine (2.22 g, 38.8 mmol) in methanol (25 mL) and acetic acid (0.5 mL) at room temperature overnight, followed by portionwise addition of sodium borohydride (1.46 g, 38.8 mmol) at 0° C. and subsequent stirring of the mixture at room temperature for 3 hrs. Usual aqueous work-up and flash-purification on silica gel (5:1 hexane/ethyl acetate as eluent) gives the title compound. Colorless liquid. MS (LC/MS): [M]$^+$.=196.0/198.0

Intermediate 7.1

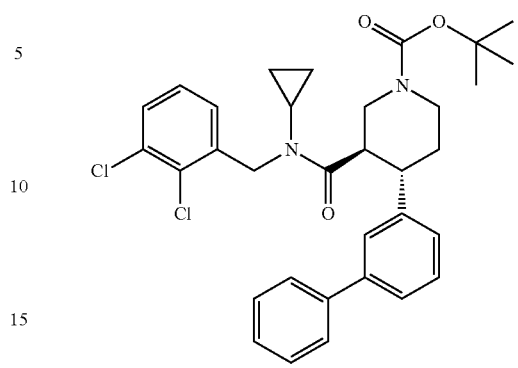

Intermediate 7.1 is synthesized by condensation of Intermediate 1.2 (53.2 mg, 0.139 mmol) and cyclopropyl-(2,3-dichlorobenzyl)-amine (37.2 mg, 0.172 mmol) analogously to the preparation of Intermediate 1.1. Colourless resin; HPLC: $_Bt_{Ret}$=8.60 min Intermediate 8.1

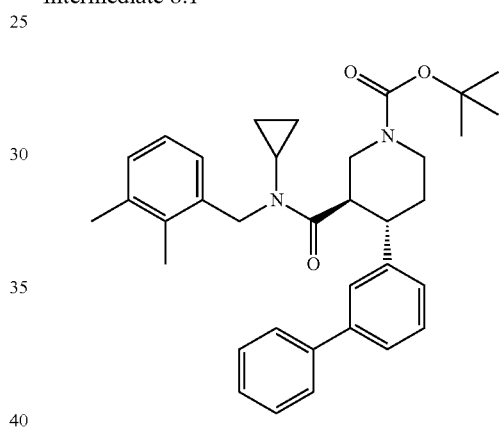

Intermediate 8.1 is synthesized by condensation of Intermediate 1.2 (51.0 mg, 0.134 mmol) and cyclopropyl-(2,3-dimethylbenzyl)-amine (30 mg, 0.171 mmol) analogously to the preparation of Intermediate 1.1. Colourless resin; (LC/MS): [M+H]$^+$=539.6; HPLC: $_Bt_{Ret}$=8.19 min Intermediate 9.1

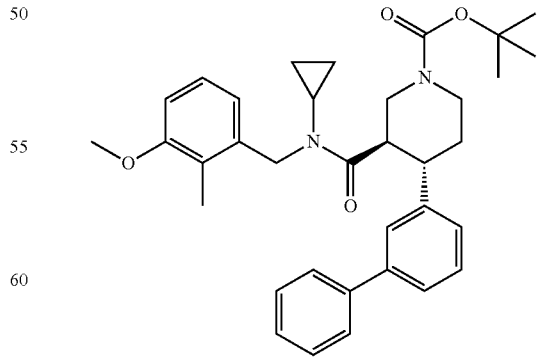

Intermediate 9.1 is synthesized by condensation of Intermediate 1.2 (50.8 mg, 0.133 mmol) and Intermediate 9.2 (33.3 mg, 0.174 mmol) analogously to the preparation of Intermediate 1.1. Colourless resin; MS (LC/MS): [M+H]$^+$= 555.6; HPLC: $_B$t$_{Ret}$=7.84 min Intermediate 9.2

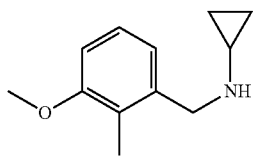

Intermediate 9.2 is prepared by reduction of Intermediate 9.3 (470 mg, 2.29 mmol), dissolved in THF (5.0 mL), with borane-dimethylsulfide complex (6.87 mL (13.7 mmol) of a 2M solution in THF) at reflux temperature overnight. The reaction mixture is concentrated, followed by addition of methanol (10 mL) and concentrated aqueous HCl (10 mL) and heating to reflux for 4 hrs. The reaction mixture is neutralized by addition of aqueous 4M NaOH solution, concentrated and subsequently extracted with methylenechloride. The crude product is purified by flash chromatography on silica gel (95:5 methylenechloride/methanol as eluent). Colorless oil. MS (LC/MS): [M+H]$^+$=192.2.

Intermediate 9.3

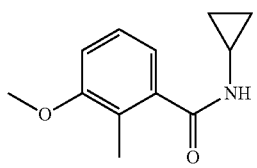

Intermediate 9.3 is prepared by condensation of 3-methoxy-2-methylbenzoic acid (500 mg, 3.01 mmol) and cyclopropylamine (172 mg, 3.01 mmol), dissolved in THF (10.0 mL), in the presence of 1-hydroxybenzotriazole (462 mg, 3.01 mmol) and dicyclohexylcarbodiimide (652 mg, 3.16 mmol) for 1 h at 0° C. and 1 h at room temperature, followed by usual extractive work-up. White solid; MS (LC/MS): [M+H]$^+$.=206.2.

Intermediate 10.1

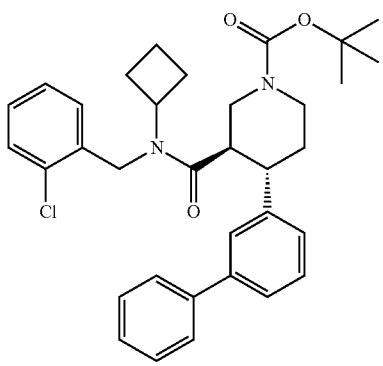

Intermediate 10.1 is synthesized by condensation of Intermediate 1.2 (52.3 mg, 0.137 mmol) and Intermediate 10.2 (33.6 mg, 0.172 mmol) analogously to the preparation of Intermediate 1.1. Colourless resin; MS (LC/MS): [M+H]$^+$= 559.6/561.7; HPLC: $_B$t$_{Ret}$=8.48 min Intermediate 10.2

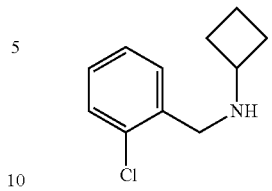

Intermediate 10.2 is prepared by reductive amination of 2-chlorobenzaldehyde (5.00 g, 35.6 mmol), dissolved in methanol (25 mL), in the presence of cyclobutylamine (3.04 g, 42.7 mmol) and sodium borohydride (1.61 g, 42.7 mmol) similarly to the method described for Intermediate 6.2. The crude product is purified by flash chromatography on silica gel (5:1 hexane/ethyl acetate as eluent). Colorless liquid. (LC/MS): [M+H]$^+$=196.1/198.1

Intermediate 11.1

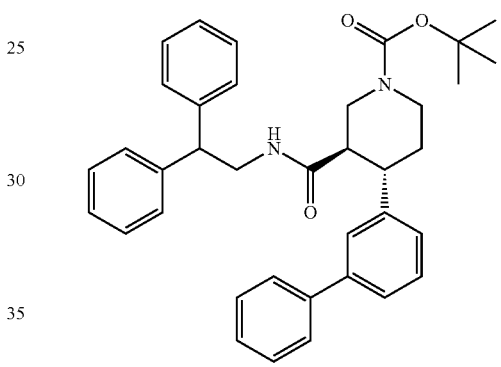

Intermediate 11.1 is synthesized by condensation of Intermediate 1.2 (52.2 mg, 0.137 mmol) and 2,2-diphenyl-ethylamine (32.8 mg, 0.166 mmol) analogously to the preparation of Intermediate 1.1. Colorless resin; MS (LC/MS): [M+H]$^+$= 561.6; HPLC: $_B$t$_{Ret}$=7.70 min Intermediate 12.1

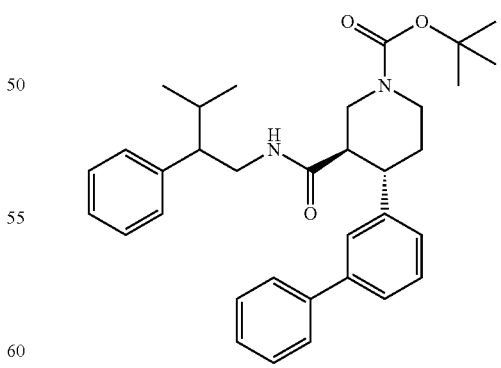

Intermediate 12.1 is synthesized by condensation of Intermediate 1.2 (51.0 mg, 0.134 mmol) and 3-methyl-2-phenylbutylamine (31.9 mg, 0.195 mmol) analogously to the preparation of Intermediate 1.1. Colourless resin; MS (LC/MS): [M+H]$^+$=527.6; HPLC: $_B$t$_{Ret}$=7.84 min Intermediate 13.1

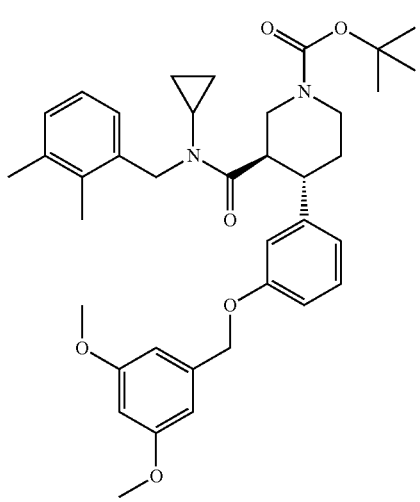

Intermediate 13.1 is synthesized by condensation of Intermediate 13.2 (165 mg, 0.32 mmol) analogously to the preparation of Intermediate 2.2. White amorphous material; ES-MS: M+H=629; HPLC: $_A t_{Ret}$=5.57 min.

Intermediate 13.2

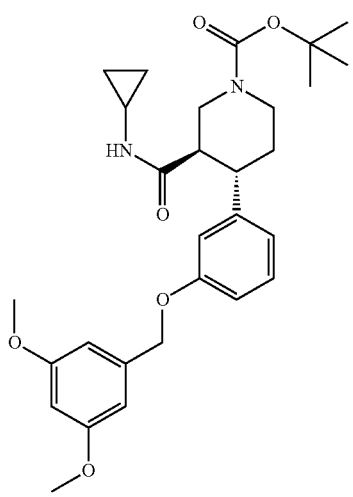

Intermediate 13.2 is synthesized by condensation of Intermediate 13.3 (940 mg, 1.99 mmol) analogously to the preparation of Intermediate 2.3. White amorphous material; ES-MS: M+H=511; HPLC: $_A t_{Ret}$=4.30 min.

Intermediate 13.3

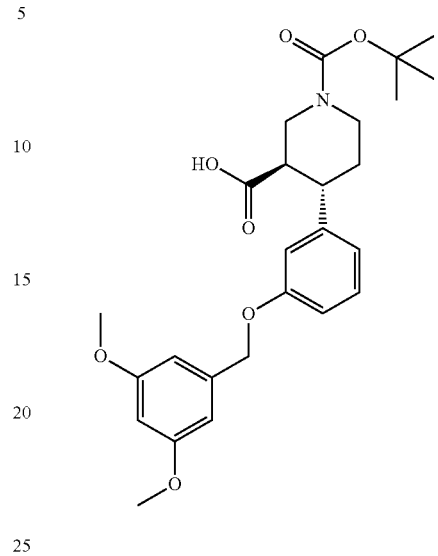

Intermediate 13.3 is synthesized by 1,4-reduction, epimerization and hydrolysis of Intermediate 13.4 (1.54 g, 3.18 mmol) analogously to the preparation of Intermediate 2.4. White amorphous material; ES-MS: M+H=472; HPLC: $_A t_{Ret}$=4.37 min.

Intermediate 13.4

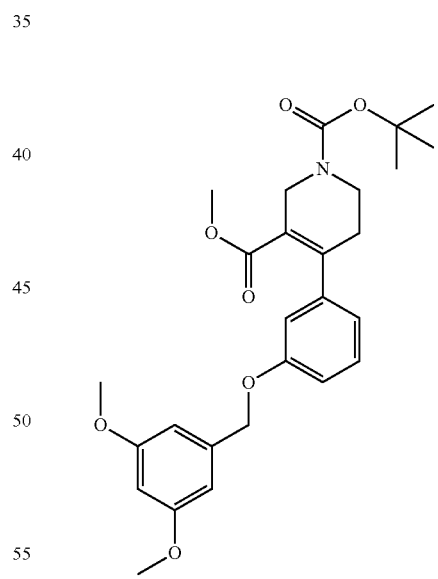

Intermediate 13.4 is synthesized by condensation of 4-trifluoromethanesulfonyloxy-5,6-dihydro-2H-pyridine-1,3-dicarboxylic acid 1-tert-butyl ester 3-methyl ester (5.84 g, 15 mmol) and 3-(3,5-dimethoxybenzyloxy)phenylboronic acid (6.5 g, 22 mmol) analogously to the preparation of Intermediate 2.5. Colorless oil; ES-MS: M-$^t$Bu=428; HPLC: $_A t_{Ret}$=4.95 min.

Intermediate 14.1

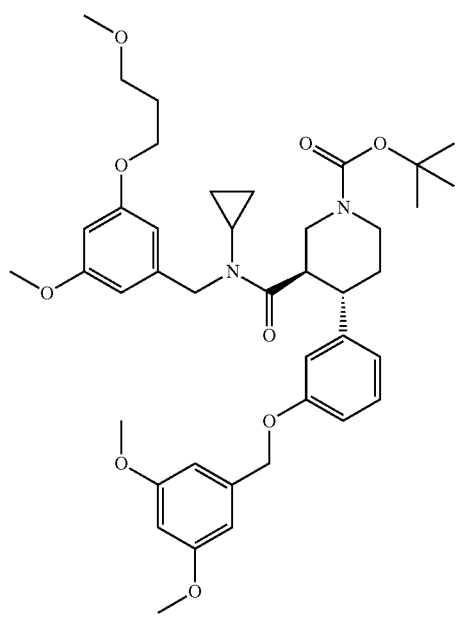

Intermediate 14.1 is synthesized by condensation of Intermediate 13.2 (161 mg, 0.32 mmol) and Intermediate 14.2 (122 mg, 0.42 mmol) analogously to the preparation of Intermediate 2.2. White amorphous material; ES-MS: M+H=719; HPLC: $_At_{Ret}$=5.32 min.

Intermediate 14.2

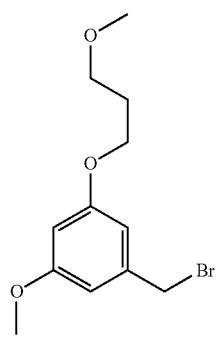

A mixture of Intermediate 14.3 (11.1 g, 49.0 mmol), PPh$_3$ (21.9 g, 83.5 mmol) and NBS (13.2 g, 74.2 mmol) in DCM (170 mL) is stirred under N$_2$ at RT. After stirring 14 h, the reaction mixture is concentrated under reduced pressure and purified by silica gel flash chromatography to give Intermediate 14.2 as colorless oil; ES-MS: M+=291; HPLC: $_At_{Ret}$=4.09 min.

Intermediate 14.3

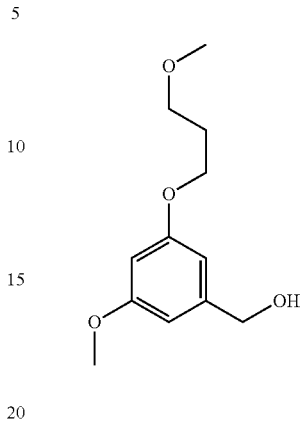

A mixture of Intermediate 14.4 (5 g, 19.7 mmol) and LAH (528 mg, 20 mmol) in THF (110 mL) is stirred under N$_2$ at 0° C. for 3 h. After adding H$_2$O, the reaction mixture is extracted with EtOAc. The combined organic phases are washed with H$_2$O, brine and dried (Na$_2$SO$_4$). Concentration under reduced pressure and silica gel flash chromatography give Intermediate 14.3 as colorless oil; ES-MS: M+H=227; HPLC: $_At_{Ret}$=2.85 min.

Intermediate 14.4

To a mixture of 3-methoxy-5-hydroxybenzoic acid methyl ester (23.2 g, 127 mmol toluene-4-sulfonic acid 3-methoxypropyl ester (40.7 g, 167 mmol) and KI (2.23 g, 13.4 mmol) in DMF (350 mL), K$_2$CO$_3$ (53.1 g, 384 mmol) is added under N$_2$. After stirring at 60° C. for 17 h, the reaction mixture is supplemented with H$_2$O and extracted with Et$_2$O. The combined organic phases are washed with H$_2$O and dried (Na$_2$SO$_4$). Concentration under reduced pressure and silica gel flash chromatography give Intermediate 14.4 as colorless oil; ES-MS: M+H=255, HPLC: $_At_{Ret}$=3.80 min.

Intermediate 15.1

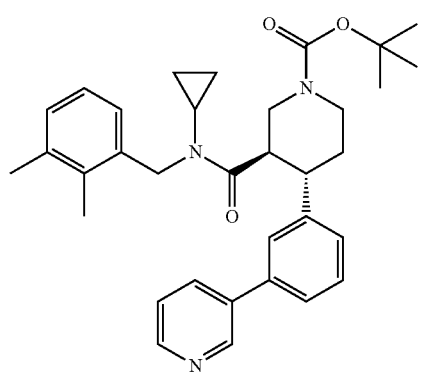

Intermediate 15.1 is synthesized by coupling of Intermediate 15.2 (205.3 mg, 0.38 mmol) analogously to the preparation of Intermediate 2.1. White amorphous material; ES-MS: M+H=540; HPLC: $_A t_{Ret}$=3.70 min.

Intermediate 15.2

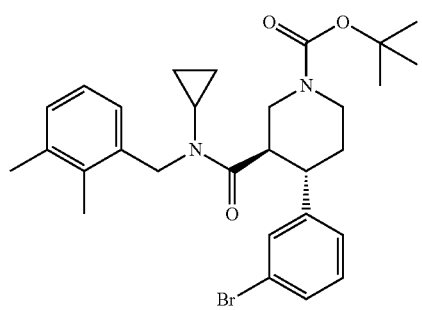

Intermediate 15.2 is synthesized by condensation of Intermediate 2.3 (403.0 mg, 0.95 mmol) analogously to the preparation of Intermediate 2.2. White amorphous material; ES-MS: M+=541; HPLC: $_A t_{Ret}$=5.52 min.

Intermediate 16.1

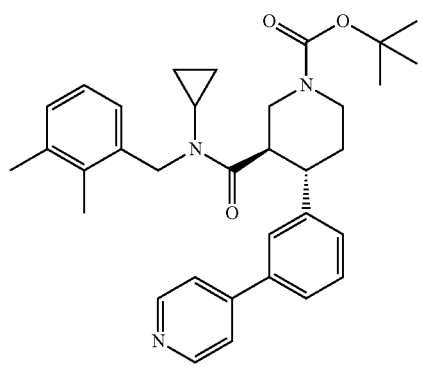

Intermediate 16.1 is synthesized by coupling of Intermediate 15.2 (498.4 mg, 0.92 mmol) analogously to the preparation of Intermediate 2.1. White amorphous material; ES-MS: M+H=540; HPLC: $_A t_{Ret}$=3.67 min.

Intermediate 17.1

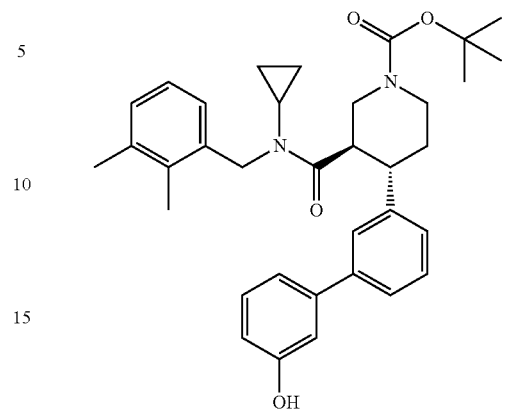

Intermediate 17.1 is synthesized by coupling of Intermediate 15.2 (113.0 mg, 0.21 mmol) analogously to the preparation of 2.1. White amorphous material; ES-MS: M+H=555; HPLC: $_A t_{Ret}$=4.97 min.

Intermediate 18.1

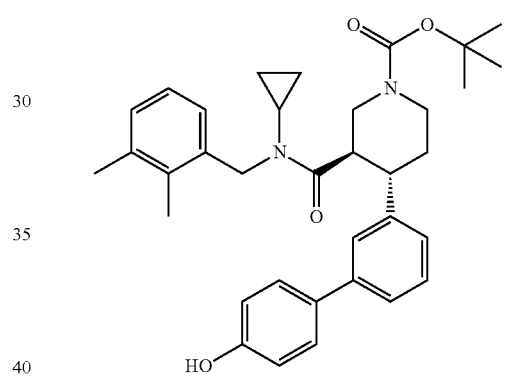

Intermediate 18.1 is synthesized by coupling of Intermediate 15.2 (112.9 mg, 0.21 mmol) analogously to the preparation of Intermediate 2.1. White amorphous material; ES-MS: M+H=555; HPLC: $_A t_{Ret}$=4.90 min.

Intermediate 19.1

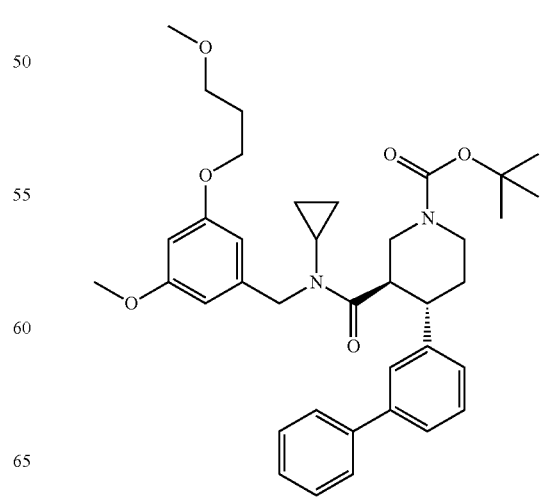

Intermediate 19.1 is synthesized by condensation of Intermediate 19.2 (185 mg, 0.44 mmol) and Intermediate 19.3 (191 mg, 0.66 mmol) analogously to the preparation of Intermediate 2.2. White amorphous material; ES-MS: M+H=629; HPLC: $_A t_{Ret}$=5.30 min.

Intermediat 19.2

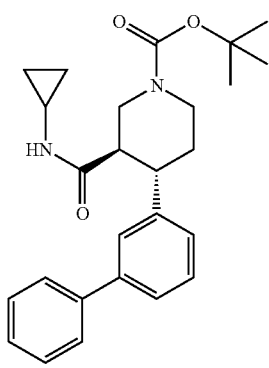

Intermediate 19.2 is synthesized by condensation of Intermediate 1.2 (350 mg, 0.52 mmol) analogously to the preparation of Intermediate 2.2. White amorphous material; ES-MS: M+H=421; HPLC: $_A t_{Ret}$=4.40 min.

Intermediate 20.1

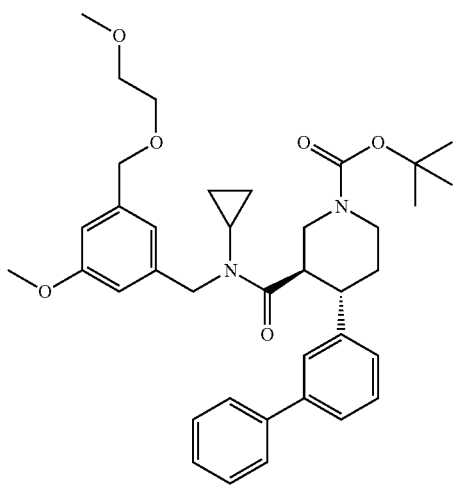

Intermediate 20.1 is synthesized by condensation of Intermediate 19.2 (138.6 mg, 0.33 mmol) and Intermediate 20.2 (114.5 mg, 0.40 mmol) analogously to the preparation of Intermediate 2.2. White amorphous material; ES-MS: M+H=629; HPLC: $_A t_{Ret}$=5.17 min.

Intermediate 20.2

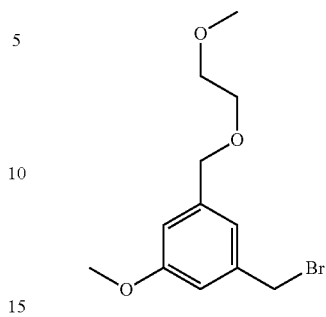

Intermediate 20.2 is synthesized by bromination of Intermediate 20.3 (740 mg, 3.27 mmol) analogously to the preparation of Intermediate 14.2. White powder; ES-MS: M+H=288; HPLC: $_A t_{Ret}$=3.79 min Intermediate 20.3

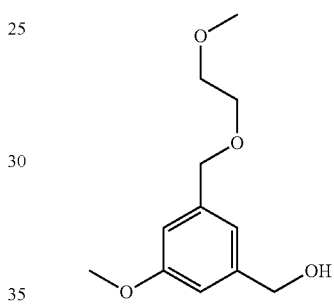

Intermediate 20.3 is synthesized by reduction of Intermediate 20.4 (824 mg, 3.3 mmol) analogously to the preparation of Intermediate 14.3. White powder; HPLC: $_A t_{Ret}$=2.52 min; Rf=0.21 (EtOAc:n-Hex=1:1)

Intermediate 20.4

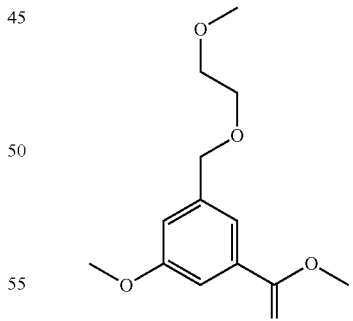

Intermediate 20.4 is synthesized by alkylation of 3-(hydroxymethyl)-5-methoxy-benzoic acid methylester (1.85 g, 9.4 mmol) (see e.g. *Synthetic Communications*, 2001, 31, 1921-1926) analogously to the preparation of Intermediate 14.4. White amorphous material; ES-MS: M+H=255; HPLC: $_A t_{Ret}$=3.44 min Intermediate 21.1

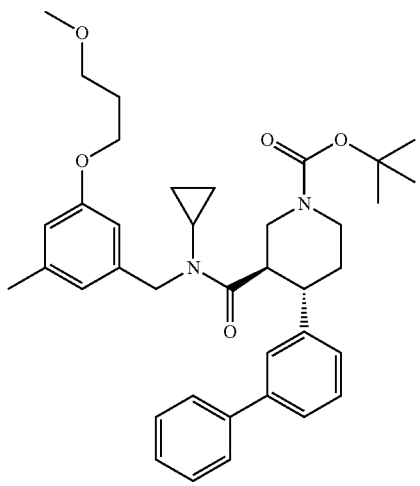

Intermediate 21.1 is synthesized by condensation of Intermediate 19.2 (203.0 mg, 0.48 mmol) and Intermediate 21.2 (158.5 mg, 0.58 mmol) analogously to the preparation of Intermediate 2.2. Colorless amorphous material; ES-MS: M+H=613; HPLC: $_A t_{Ret}$=5.68 min.

Intermediate 21.2

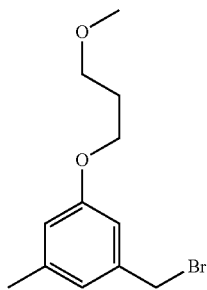

Intermediate 21.2 is synthesized by bromination of Intermediate 21.3 (2.1 g, 10.0 mmol) analogously to the preparation of Intermediate 14.2. Colorless oil; ES-MS: M+H=273; HPLC: $_A t_{Ret}$=4.43 min Intermediate 21.3

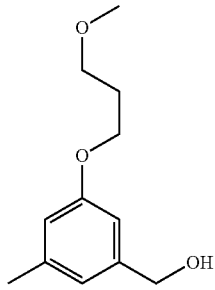

To a mixture of Intermediate 21.4 (5.18 g, 20.4 mmol), trimethylammonium chloride (50 mg) and Et$_3$N (3.4 mL, 24.4 mmol) in DCM (100 mL), p-toluenesulfonyl chloride (4.27 g, 22.4 mmol) is added at 0° C. After stirring for 50 min, the reaction mixture is supplemented with H$_2$O and extracted with EtOAc. The combined organic phases are washed with H$_2$O, brine and dried (Na$_2$SO$_4$). Concentration under reduced pressure gives crude product. Then a solution of this crude product in THF (100 mL) is treated with LAH (2.27 g, 59.8) at 0° C. for 2 h. After adding H$_2$O, the reaction mixture is extracted with EtOAc. The combined organic phases are washed with H$_2$O, brine and dried (Na$_2$SO$_4$). Concentration under reduced pressure and silica gel flash chromatography give Intermediate 21.3 as white amorphous material; ES-MS: M=211; HPLC: $_A t_{Ret}$=3.04 min.

Intermediate 21.4

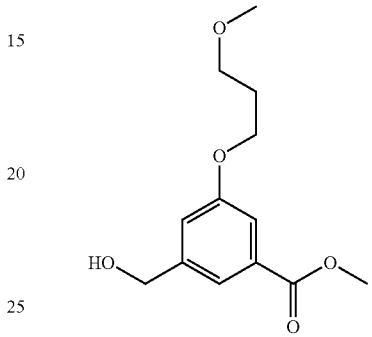

To a mixture of Intermediate 21.5 (5.75 g, 20.4 mmol) and Et$_3$N (3.7 mL, 26.5 mmol) in THF (100 mL), chloroformic acid ethylester (2.5 mL, 26.5 mmol) is added at 0° C. After stirring for 20 min, the reaction mixture is filtered for removing inorganic salt, and the filtrate is concentrated under reduced pressure. A solution of this crude product in MeOH (50 mL) was treated with NaBH$_4$ (excess) at 0° C. for 20 min. After adding H$_2$O, the reaction mixture is extracted with EtOAc. The combined organic phases are washed with H$_2$O, brine and dried (Na$_2$SO$_4$). Concentration under reduced pressure and silica gel flash chromatography give Intermediate 21.4 as white amorphous material; ES-MS: M+Na=283; HPLC: $_A t_{Ret}$=3.92 min.

Intermediate 21.5

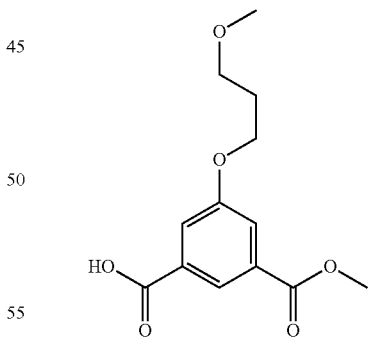

A mixture of Intermediate 21.6 (9.0 g, 31.9 mmol) and KOH (1.61 g, 28.7 mmol) in THF (100 mL) and MeOH (30 mL) is refluxed under N$_2$ for 3.5 h. After cooling down to RT, the reaction mixture is adjusted to weakly acidic pH by slowly adding conc.HCl, and the mixture is extracted with Et$_2$O. The combined organic phases are washed with H$_2$O, brine and dried (Na$_2$SO$_4$). Concentration under reduced pressure and silica gel flash chromatography give Intermediate 21.5 as white amorphous material; ES-MS: M+H=269; HPLC: $_A t_{Ret}$=3.15 min.

Intermediate 21.6

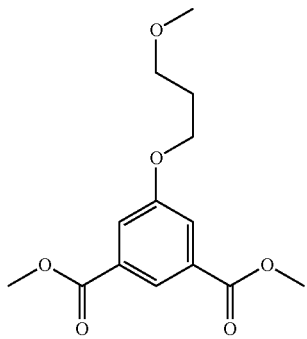

A mixture of 5-hydroxy-isophthalic acid dimethyl ester (7.02 g, 33.4 mmol), toluene-4-sulfonic acid 3-methoxy-propyl ester (8.16 g, 33.4 mmol), KI (6.1 g, 36.7 mmol) and $K_2CO_3$ (5.1 g, 36.7 mmol) in DMF (100 mL) is stirred under $N_2$ at 70° C. for 5 h. After adding $H_2O$, the reaction mixture is extracted with EtOAc. The combined organic phases are washed with $H_2O$, brine and dried ($Na_2SO_4$). Concentration under reduced pressure and silica gel flash chromatography give Intermediate 21.6 as white solid; ES-MS: M+H=283; HPLC: $_At_{Ret}$=3.90 min Intermediate 22.1

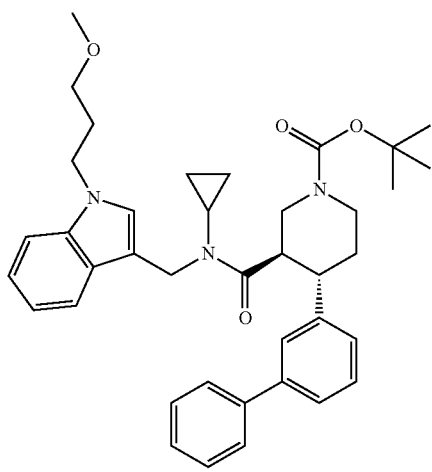

Intermediate 22.1 is synthesized by condensation of Intermediate 1.2 (330 mg, 0.49 mmol) and Intermediate 22.2 (252 mg, 0.98 mmol) analogously to the preparation of Intermediate 1.1. White amorphous material; ES-MS: M+H=622; HPLC: $_At_{Ret}$=5.64 min.

Intermediate 22.2

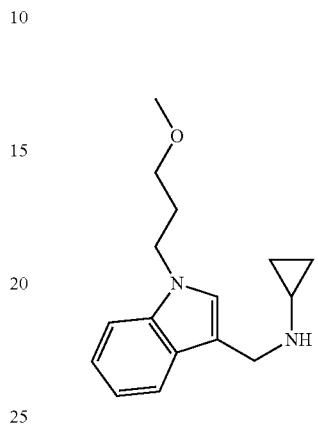

A mixture of Intermediate 22.3 (780 mg, 3.6 mmol), cyclopropylamine (410 mg, 7.2 mmol), AcOH (0.5 mL) and NaBH(OAc)$_3$ (1.1 g, 5.4 mmol) in DCM (3 mL) and MeOH (1 mL) is stirred under $N_2$ at 0° C. After stirring at RT for 1 hour, the reaction mixture is quenched with saturated aqueous $NaHCO_3$ and extracted with DCM. The combined organic phases are washed with $H_2O$, brine and dried ($Na_2SO_4$). Concentration under reduced pressure and silica gel flash chromatography give Intermediate 22.2 as yellow oil; ES-MS: M+H=202; HPLC: $_At_{Ret}$=2.67 min Intermediate 22.3

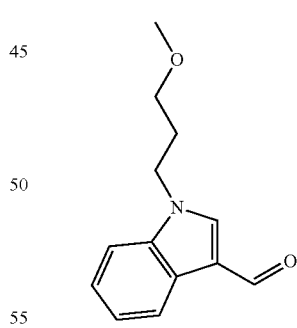

To a mixture of indole-3-carboxaldehyde (1.0 g, 6.9 mmol), toluene-4-sulfonic acid 3-methoxy-propyl ester (2.1 g, 9.0 mmol) and KI (1.1 g, 7.0 mmol) in DMF (15 mL), NaH (320 mg, 7.5 mmol) is added under $N_2$ at 0° C. After stirring at 50° C. for 4 h, the reaction mixture is supplemented with $H_2O$ and extracted with EtOAc. The combined organic phases are washed with $H_2O$, brine and dried ($Na_2SO_4$). Concentration under reduced pressure and silica gel flash chromatography give Intermediate 22.3 as colorless oil; ES-MS: M+H=218, HPLC: $_At_{Ret}$=3.18 min.

Intermediate 23.1

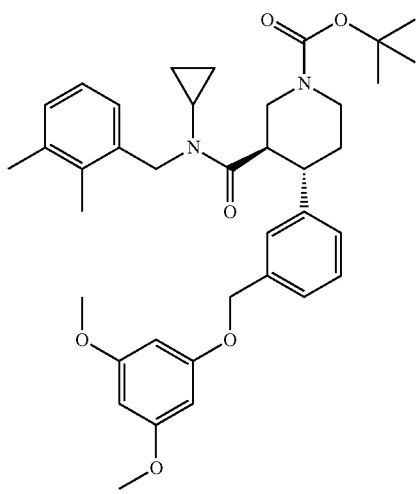

Intermediate 23.1 is synthesized by condensation of Intermediate 23.2 (193 mg, 0.41 mmol) analogously to the preparation of Intermediate 4.1. White amorphous material; ES-MS: M+H=629; HPLC: $_At_{Ret}$=5.57 min.

Intermediate 23.2

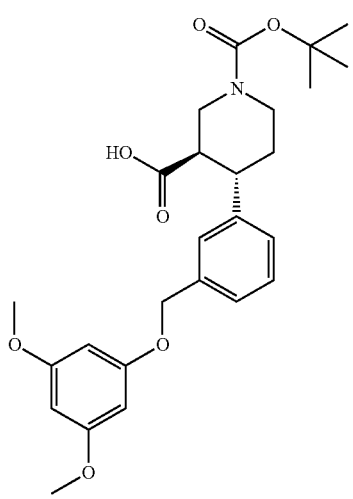

Intermediate 23.2 is synthesized by 1,4-reduction, epimerization and hydrolysis of Intermediate 23.3 (830 mg, 1.71 mmol) analogously to the preparation of Intermediate 4.4/4.3. White amorphous material; ES-MS: M+H=472; HPLC: $_At_{Ret}$=4.47 min.

Intermediate 23.3

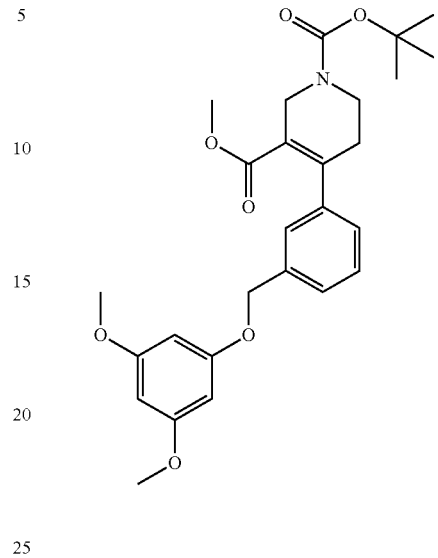

Intermediate 23.3 is synthesized by coupling of 4-trifluoromethanesulfonyloxy-5,6-dihydro-2H-pyridine-1,3-dicarboxylic acid 1-tert-butyl ester 3-methyl ester (3.89 g, 10 mmol) analogously to the preparation of Intermediate 4.4. Colorless oil; Rf=0.30 (AcOEt:n-Hex=1:4); $^1$H NMR (CDCl$_3$) δ 1.52 (s, 9H), 2.53 (brs, 2H), 3.49 (s, 2H), 3.61-3.64 (m, 2H), 3.78 (s, 6H), 4.27 (brs, 2H),), 5.02 (s, 2H), 6.12 (t, 1H), 6.18 (d, 2H), 7.10-7.12 (m, 1H), 7.22 (brs, 1H), 7.37 (d, 2H).

Intermediate 24.1

Intermediate 24.1 is synthesized by condensation of Intermediate 24.2 (203.1 mg, 0.43 mmol) analogously to the preparation of Intermediate 4.1. White amorphous material; ES-MS: M+H=630; HPLC: $_At_{Ret}$=5.50 min.

Intermediate 24.2

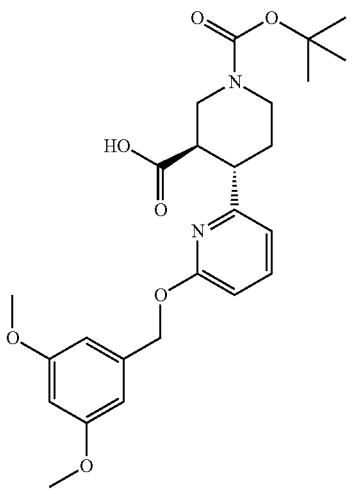

Intermediate 24.2 is synthesized by 1,4-reduction, epimerization and hydrolysis of Intermediate 24.3 (1.40 g, 2.89 mmol) analogously to the preparation of Intermediate 4.4/4.3. White amorphous material; ES-MS: M+H=473; HPLC: $_A t_{Ret}$=4.32 min.

Intermediate 24.3

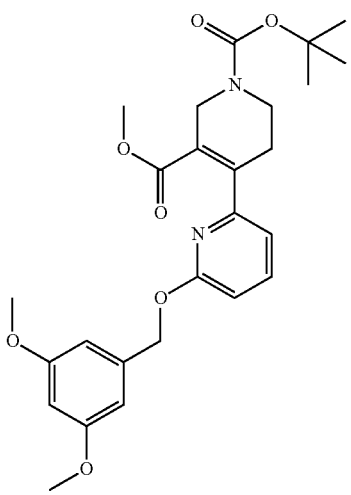

Intermediate 24.3 is synthesized by condensation of 4-trifluoromethanesulfonyloxy-5,6-dihydro-2H-pyridine-1,3-dicarboxylic acid 1-tert-butyl ester 3-methyl ester (238 mg, 0.61 mmol) and Intermediate 24.4 (177 mg, 0.61 mmol) analogously to the preparation of Intermediate 4.4. Colorless oil; ES-MS: M+H=485; HPLC: $_A t_{Ret}$=4.85 min.

Intermediate 24.4

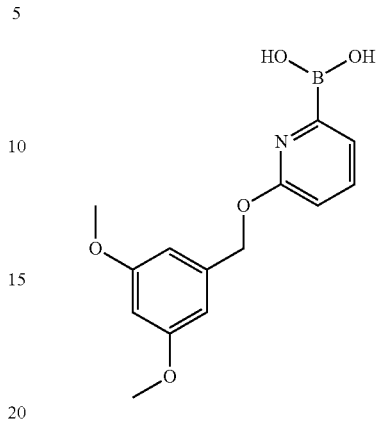

A mixture of Intermediate 24.5 (1.04 g, 3.2 mmol) and 1.6M hexane solution of nBuLi (2.4 mL, 3.85 mmol) in THF (16 mL) is stirred under N$_2$ at −78° C. After stirring at −78° C. for 1 h, (iPrO)$_3$B (0.9 mL, 3.85 mmol) is added, and the reaction mixture is stirred at RT for 3 h. The reaction mixture is adjusted to weakly acidic pH by slowly adding 2N HCl, and the mixture is then extracted with EtOAc. The combined organic phases are washed with H$_2$O, brine and dried (Na$_2$SO$_4$). Concentration under reduced pressure and silica gel flash chromatography give Intermediate 24.4 as white amorphous material; ES-MS: M+H=290; HPLC: $_A t_{Ret}$=2.75 min.

Intermediate 24.5

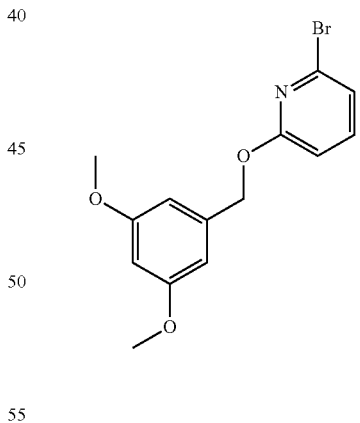

A mixture of 2,6-dibromopyridine (2.06 g, 8.7 mmol), 3,5-dimethoxybenzyl alcohol (1.39 g, 8.26 mmol) and NaH (383 mg, 9.57 mmol) in DMF (35 mL) is stirred under N$_2$ at 0° C. for 2.5 h. After adding H$_2$O, the reaction mixture is extracted with EtOAc. The combined organic phases are washed with H$_2$O, brine and dried (Na$_2$SO$_4$). Concentration under reduced pressure and silica gel flash chromatography give Intermediate 24.5 as white amorphous material; ES-MS: M+H=326; HPLC: $_A t_{Ret}$=4.65 min.

Intermediate 25.1

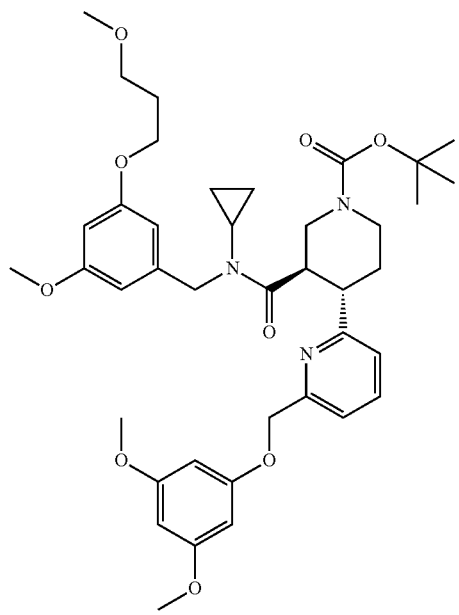

Intermediate 25.1 is synthesized by condensation of Intermediate 25.2 (332.5 mg, 0.65 mmol) analogously to the preparation of Intermediate 2.2. White amorphous material; ES-MS: M+H=721; HPLC: $_At_{Ret}$=5.30 min.

Intermediate 25.2

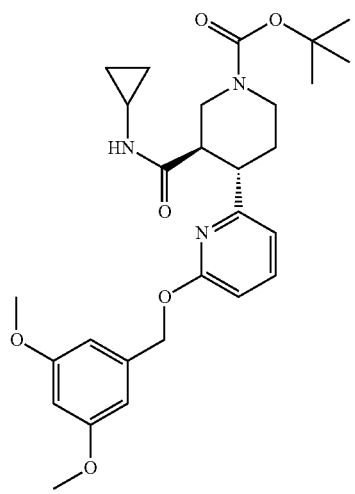

Intermediate 25.2 is synthesized by condensation of Intermediate 24.2 (307.6 mg, 0.65 mmol) analogously to the preparation of Intermediate 2.3. White amorphous material; ES-MS: M+H=512; HPLC: $_At_{Ret}$=4.40 min.

Intermediate 26.1

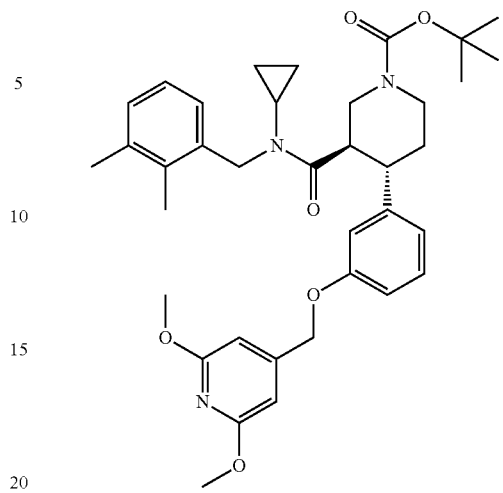

Intermediate 26.1 is synthesized by condensation of Intermediate 26.2 (262 mg, 0.55 mmol) and 2,6-dimethoxy-4-pyridinemethanol (111 mg, 0.66 mmol) (see e.g. *Journal of Heterocyclic Chemistry* 1974, 11, 251-3.) analogously to the preparation of Intermediate 3.1. White amorphous material; ES-MS: M+H=630; HPLC: $_At_{Ret}$=5.62 min.

Intermediate 26.2

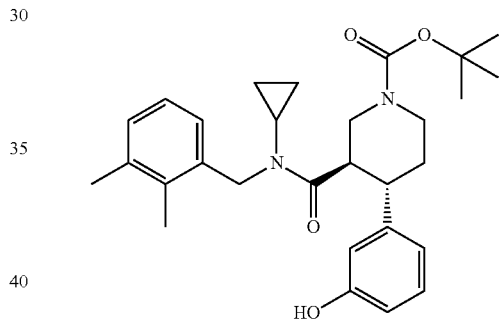

Intermediate 26.2 is synthesized by condensation of Intermediate 26.3 (3.0 g, 9.33 mmol) analogously to the preparation of Intermediate 4.1. White amorphous material; ES-MS: M+H=479; HPLC: $_At_{Ret}$=4.49 min.

Intermediate 26.3

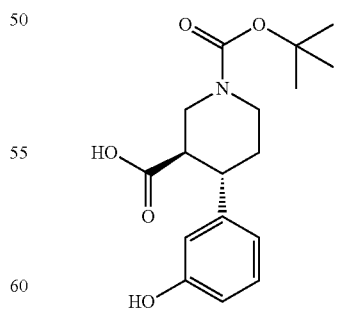

Intermediate 26.3 is synthesized by hydrogenation, epimerization and hydrolysis of Intermediate 26.4 (9.64 g, 28.9 mmol) analogously to the preparation of Intermediate 4.3/4.4. White amorphous material; ES-MS: M+H=322; HPLC: $_At_{Ret}$=3.38 min.

Intermediate 26.4

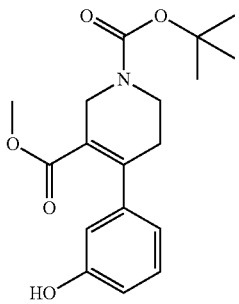

Intermediate 26.4 is synthesized by condensation of 4-trifluoromethanesulfonyloxy-5,6-dihydro-2H-pyridine-1,3-dicarboxylic acid 1-tert-butyl ester 3-methyl ester (14.1 g, 36.3 mmol) and 3-hydroxyphenylboronic acid (6.0 g, 43.5 mmol) analogously to the preparation of Intermediate 2.5. Colorless oil; ES-MS: M+H-$^t$Bu=278; HPLC: $_At_{Ret}$=3.76 min.

Intermediate 27.1

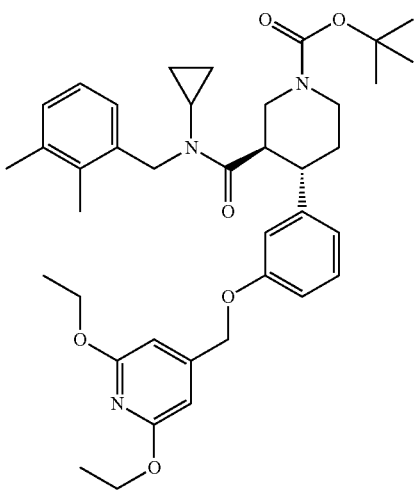

Intermediate 27.1 is synthesized by condensation of Intermediate 26.2 (200 mg, 0.42 mmol) and 2,6-diethoxy-4-pyridinemethanol (130 mg, 0.63 mmol) made analogously to a known method (see e.g. *Journal of Heterocyclic Chemistry* 1974, 11, 251-3.) analogously to the preparation of Intermediate 3.1. White amorphous material; ES-MS: M+H=658; HPLC: $_At_{Ret}$=5.99 min.

Intermediate 28.1

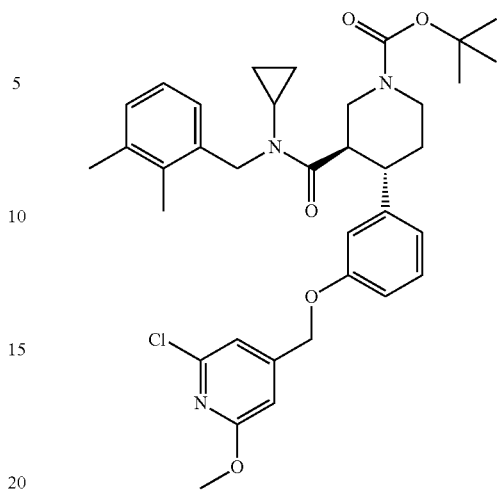

Intermediate 28.1 is synthesized by condensation of Intermediate 26.2 (100 mg, 0.21 mmol) and 2-chloro-6-methoxy-4-pyridinemethanol (54 mg, 0.31 mmol) (see e.g. *Org. Lett.* 2000, 2, 3421-3423.) analogously to the preparation of Intermediate 3.1. White amorphous material; ES-MS: M+=634; HPLC: $_At_{Ret}$=5.70 min.

Intermediate 29.1

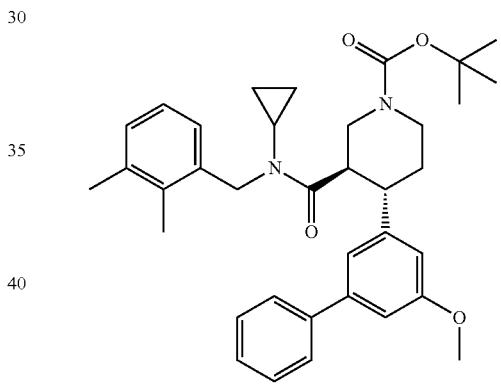

Intermediate 29.1 is synthesized by condensation of Intermediate 29.2 (180 mg, 0.44 mmol) analogously to the preparation of Intermediate 4.1. White amorphous material; ES-MS: M+H=569; HPLC: $_At_{Ret}$=5.57 min.

Intermediate 29.2

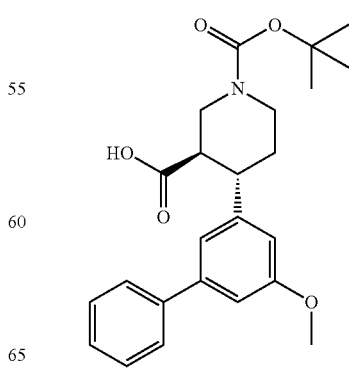

Intermediate 29.2 is synthesized by 1,4-reduction, epimerization and hydrolysis of Intermediate 29.3 (1.15 mg, 2.71 mmol) analogously to the preparation of Intermediate 4.4/4.3. White amorphous material; ES-MS: M+H=412; HPLC: $_A t_{Ret}$=4.50 min.

Intermediate 29.3

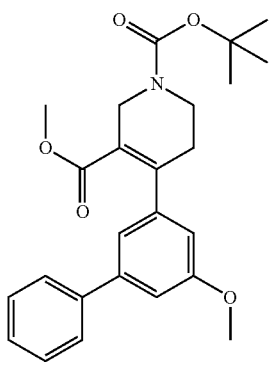

Intermediate 29.3 is synthesized by condensation of 4-trifluoromethanesulfonyloxy-5,6-dihydro-2H-pyidine-1,3-dicarboxylic acid 1-tert-butyl ester 3-methyl ester (1.15 g, 2.89 mmol) and boronate (980 mg, 3.16 mmol) produced from Intermediate 29.4 analogously to the preparation of Intermediate 2.5. Colorless oil; ES-MS: M-87=336; HPLC: $_A t_{Ret}$=4.43 min.

Intermediate 29.4

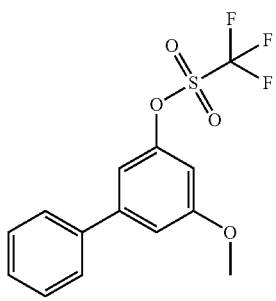

A mixture of 3-methoxy-5-phenyl-phenol (848 mg, 4.23 mmol) (see e.g. *Tetrahedron Lett* 1991, 32, 3441-3444), Tf$_2$O (0.76 mL, 4.65 mmol) and DIEA (0.87 mL, 5.08 mmol) in DCM (20 mL) is stirred at 0° C. for 3.5 h. After adding saturated NaHCO$_3$ solution, the reaction mixture is extracted with DCM The combined organic phases are washed with H$_2$O, brine and dried (MgSO$_4$). Concentration under reduced pressure and silica gel flash chromatography give Intermediate 29.4 as colorless amorphous material; ES-MS: M+H=333; HPLC: $_A t_{Ret}$=5.12 min.

Intermediate 30.1

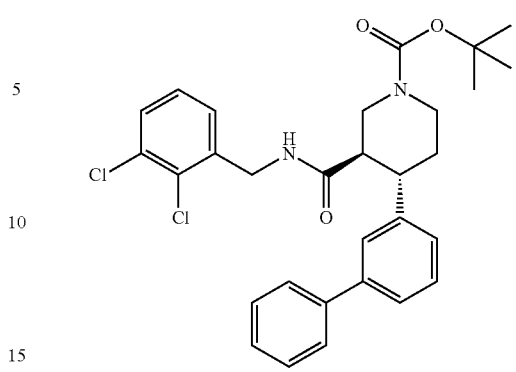

Intermediate 30.1 is synthesized by condensation of Intermediate 1.2 (104 mg, 0.27 mmol) analogously to the preparation of Intermediate 4.1. White amorphous material; ES-MS: M+=539; HPLC: $_A t_{Ret}$=507 min.

Intermediate 31.1

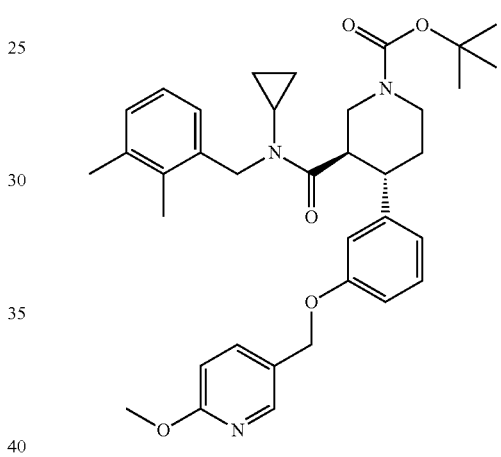

Intermediate 31.1 is synthesized by condensation of Intermediate 26.2 (202 mg, 0.42 mmol) and 2-methoxy-5-pyridinemethanol (88.0 mg, 0.50 mmol) (see e.g. *Tetrahedron.* 1992, 48, 1457-1464.) analogously to the preparation of Intermediate 3.1. White amorphous material; ES-MS: M+H=600; HPLC: $_A t_{Ret}$=4.97 min.

Intermediate 32.1

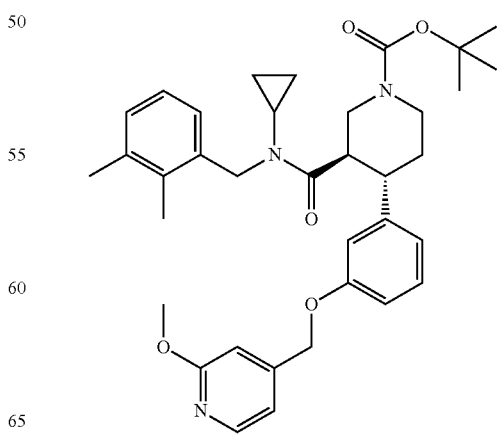

Intermediate 32.1 is synthesized by condensation of Intermediate 26.2 (215 mg, 0.45 mmol) and 2-methoxy-4-pyridinemethanol (94.0 mg, 0.54 mmol) (see e.g. *J. Org. Chem.* 1989, 54, 5580-5585.) analogously to the preparation of Intermediate 3.1. White amorphous material; ES-MS: M+H=600; HPLC: $_At_{Ret}$=4.72 min.

Intermediate 33.1

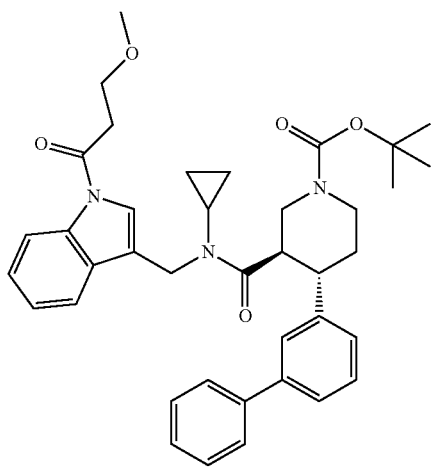

Intermediate 33.1 is synthesized by condensation of Intermediate 1.2 (224 mg, 0.59 mmol) and Intermediate 33.2 (198 mg, 0.77 mmol) analogously to the preparation of Intermediate 4.1. White amorphous material; ES-MS: M+H=636; HPLC: $_At_{Ret}$=5.24 min.

Intermediate 33.2

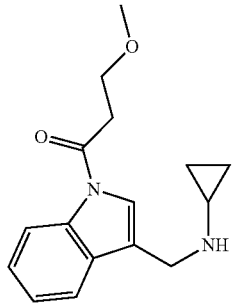

Intermediate 33.2 is synthesized by condensation of Intermediate 33.3 (1.00 g, 4.30 mmol) and cyclopropylamine (370 mg, 6.50 mmol) analogously to the preparation of Intermediate 4.5. Colorless oil; ES-MS: M+H=273; HPLC: $_At_{Ret}$=2.77 min.

Intermediate 33.3

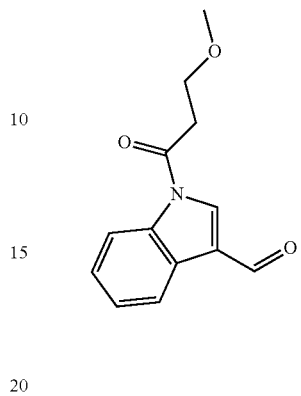

A mixture of Indole-3-carbaldehyde (1.00 g, 7.00 mmol), Et$_3$N (3.10 mL, 20.0 mmol) and 3-Meyhoxypropionyl chloride (1.00 g, 8.00 mmol) in THF (10 mL) and DCM (3 mL) is stirred at 0° C. for 2 h. After adding saturated NaHCO$_3$ solution, the reaction mixture is extracted with EtOAc. The combined organic phases are washed with H$_2$O, brine and dried (MgSO$_4$). Concentration under reduced pressure and silica gel flash chromatography give Intermediate 33.3 as white solid; ES-MS: M+H=232; HPLC: $_At_{Ret}$=3.51 min.

Intermediate 34.1

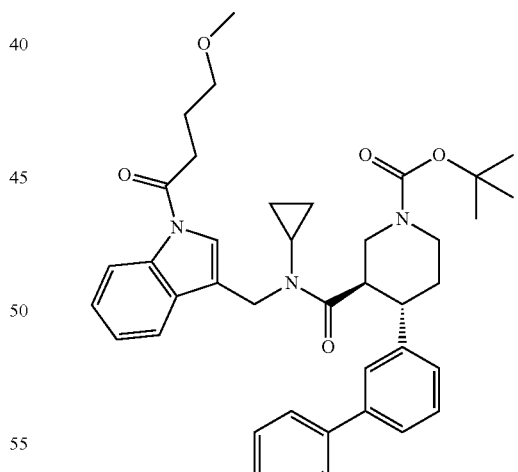

Intermediate 34.1 is synthesized by condensation of Intermediate 1.2 (144 mg, 0.38 mmol) and Intermediate 34.2 (110 mg, 0.38 mmol) analogously to the preparation of Intermediate 4.1. White amorphous material; ES-MS: M+H=650; HPLC: $_At_{Ret}$=5.39 min.

Intermediate 34.2

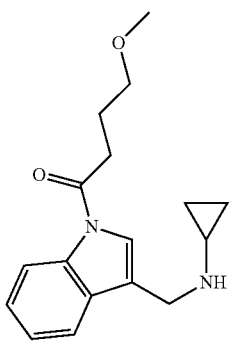

Intermediate 34.2 is synthesized by condensation of Intermediate 34.3 (820 mg, 3.34 mmol) and cyclopropylamine (387 mg, 6.80 mmol) analogously to the preparation of Intermediate 4.5. Colorless oil; ES-MS: M+H=246; HPLC: $_At_{Ret}$=2.42 min.

Intermediate 34.3

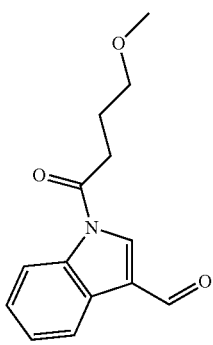

Intermediate 34.3 is synthesized by condensation of indole-3-carbaldehyde (650 mg, 4.5 mmol) and 4-Methoxybutanoyl chloride (929 mg, 6.80 mmol) (see e.g. *Canadian Journal of Chemistry* 1982, 60, 2295-312. or U.S. Pat. No. 4,559,337.) analogously to the preparation of Intermediate 33.3. Colorless oil; Rf=0.30 (EtOAc:n-Hex=1:1), $^1$H NMR (CDCl$_3$), δ: 2.10-2.18 (2H, m), 3.13 (2H, t), 3.36 (3H, s), 3.53 (2H, t), 7.39-7.47 (2H, m), 8.12 (1H, t), 8.28 (1H, d), 8.44 (1H, d), 10.13 (1H, s).

Intermediate 35.1

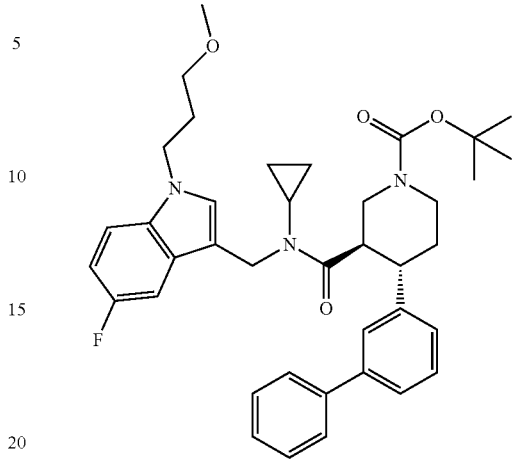

Intermediate 35.1 is synthesized by condensation of Intermediate 1.2 (200 mg, 0.52 mmol) and Intermediate 35.2 (184 mg, 0.67 mmol) analogously to the preparation of Intermediate 4.2. White amorphous material; ES-MS: M+H=640; HPLC: $_At_{Ret}$=5.43 min.

Intermediate 35.2

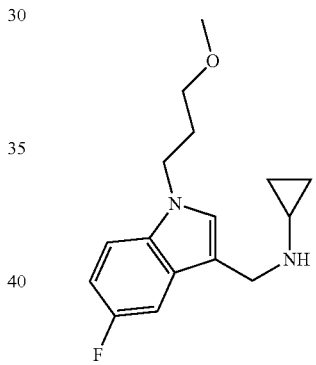

Intermediate 35.2 is synthesized by condensation of Intermediate 35.3 (640 mg, 2.70 mmol) and cyclopropylamine (308 mg, 5.40 mmol) analogously to the preparation of Intermediate 4.5. Colorless oil; ES-MS: M+H=277; HPLC: $_At_{Ret}$=2.57 min.

Intermediate 35.3

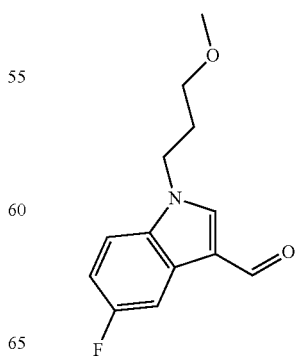

Intermediate 35.3 is synthesized by condensation of 5-fluoro-indole-3-carbaldehyde (500 mg, 3.10 mmol) and toluene-4-sulfonic acid 3-methoxy-propyl ester (973 mg, 3.90 mmol) analogously to the preparation of Intermediate 4.8. Yellow oil; ES-MS: M+H=236; HPLC: $_At_{Ret}$=3.22 min.

Intermediate 36.1

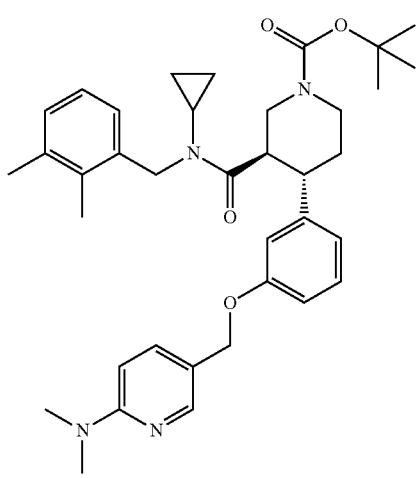

Intermediate 36.1 is synthesized by condensation of Intermediate 26.2 (184 mg, 0.38 mmol) and 2-dimethylamino-5-pyridinemethanol (117 mg, 0.76 mmol) (see e.g. WO2003053912.) analogously to the preparation of Intermediate 3.1. White amorphous material; ES-MS: M+H=613; HPLC: $_At_{Ret}$=3.84 min.

Intermediate 37.1

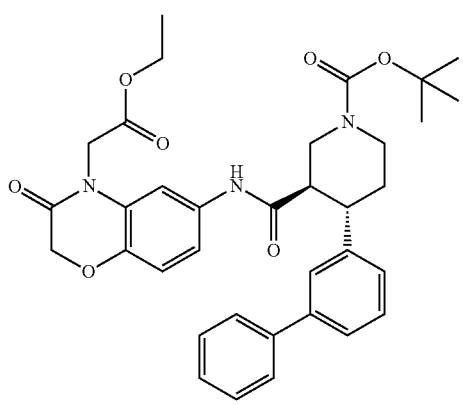

A mixture of Intermediate 1.2 (244 mg, 0.64 mmol), Intermediate 37.2 (240 mg, 0.96 mmol) and DMT-MM (213 mg, 0.77 mmol) in EtOH (5 mL) was stirred under N₂ at 60° C. for 2 h. After adding H₂O, the reaction mixture is extracted with EtOAc. The combined organic phases are washed with H₂O, brine and dried (MgSO₄). Concentration under reduced pressure and silica gel flash chromatography give Intermediate 37.1 as yellow powder; ES-MS: M+H=614; HPLC: $_At_{Ret}$=4.65 min.

Intermediate 37.2

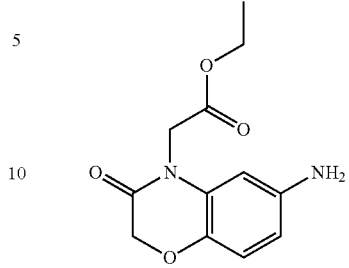

A mixture of Intermediate 37.3 (630 mg, 2.25 mmol) and Tin(II) chloride 2-hydrate (1.53 g, 6.8 mmol) in EtOH (10 mL) was stirred under N₂ at reflux for 3.5 h. After adding 8N KOH solution, the reaction mixture is extracted with EtOAc. The combined organic phases are washed with H₂O, brine and dried (MgSO₄). Concentration under reduced pressure and silica gel flash chromatography give Intermediate 37.2 as yellow oil; ES-MS: M+H=251; HPLC: $_At_{Ret}$=1.82 min.

Intermediate 37.3

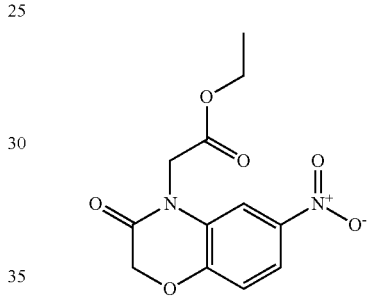

Intermediate 37.3 is synthesized by alkylation of 6-nitro-2H-1,4-benzoxazin-3(4H)-one (388 mg, 2.00 mmol) and Ethyl chloroacetate (234 μL, 2.2 mmol) made analogously to a known method (see e.g. *European Journal of Medicinal Chemistry* 1998, 33, 957-967. or EP 432893). yellow oil; ES-MS: M+H=281; HPLC: $_At_{Ret}$=3.23 min.

Intermediate 38.1

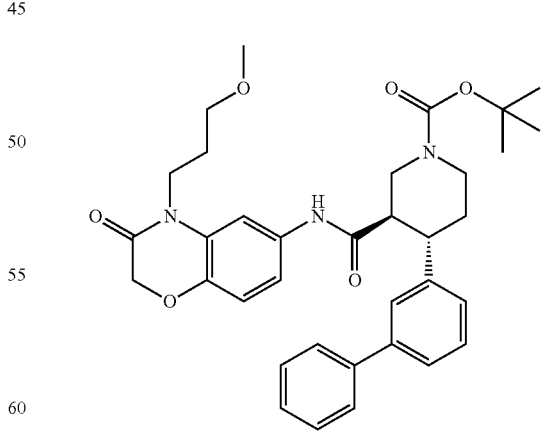

Intermediate 38.1 is synthesized by condensation of Intermediate 1.2 (257 mg, 0.68 mmol) and Intermediate 38.2 (251 mg, 0.95 mmol) analogously to the preparation of Intermediate 37.1. White amorphous material; ES-MS: M+H=600; HPLC: $_At_{Ret}$=4.57 min.

Intermediate 38.2

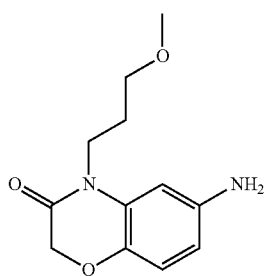

Intermediate 38.2 is synthesized by reduction of Intermediate 38.3 (266 mg, 1.00 mmol) analogously to the preparation of Intermediate 37.2. Brown oil; ES-MS: M+H=237; HPLC: $_A t_{Ret}$=1.78 min.

Intermediate 38.3

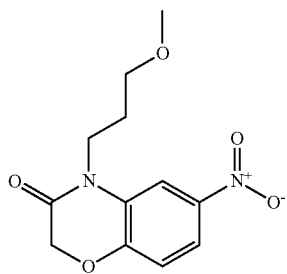

Intermediate 38.3 is synthesized by alkylation of 6-nitro-2H-1,4-benzoxazin-3(4H)-one (582 mg, 3.00 mmol) and toluene-4-sulfonic acid 3-methoxy-propyl ester (1.1 g, 4.50 mmol) analogously to the preparation of Intermediate 4.7. Brown oil; ES-MS: M+H=267; HPLC: $_A t_{Ret}$=3.18 min.

Intermediate 39.1

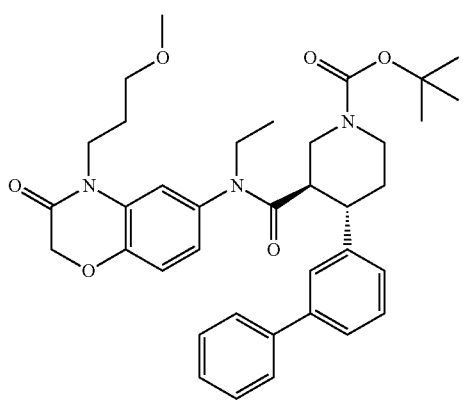

Intermediate 39.1 is synthesized by alkylation of intermediate 38.1 (200 mg, 0.33 mmol) and EU (35.6 µL, 0.45 mmol) analogously to the preparation of Intermediate 4.8. White powder; ES-MS: M+H=628; HPLC: $_A t_{Ret}$=4.90 min.

Intermediate 40.1

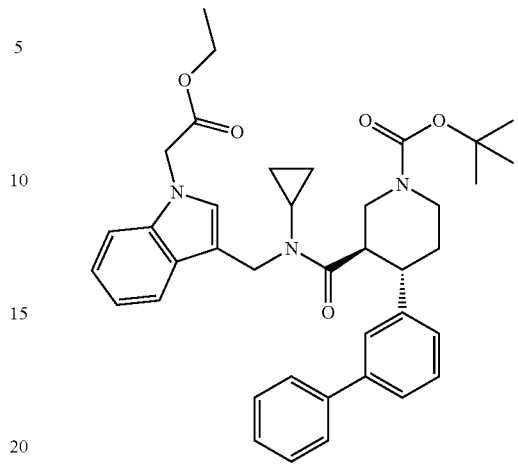

Intermediate 40.1 is synthesized by condensation of Intermediate 1.2 (136 mg, 0.36 mmol) and Intermediate 40.2 (118 mg, 0.43 mmol) analogously to the preparation of Intermediate 4.1. White amorphous material; ES-MS: M+H=636; HPLC: $_A t_{Ret}$=5.25 min.

Intermediate 40.2

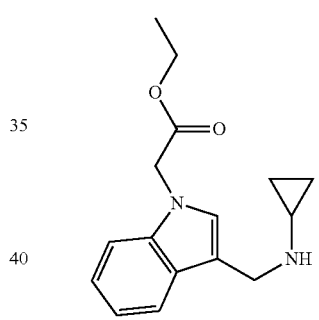

Intermediate 40.2 is synthesized by condensation of Intermediate 40.3 (500 mg, 2.16 mmol) and cyclopropylamine (232 µL, 3.24 mmol) analogously to the preparation of Intermediate 4.5. Colorless oil; ES-MS: M+H=273; HPLC: $_A t_{Ret}$=2.45 min.

Intermediate 40.3

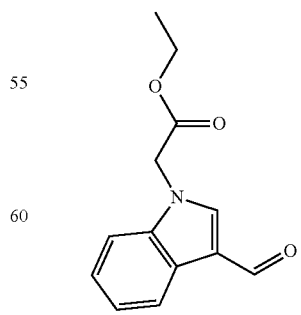

Intermediate 40.3 is synthesized by condensation of Indole-3-carbaldehyde (1.00 g, 6.90 mmol) and Ethyl bromoacetate (920 µL, 8.30 mmol) analogously to the preparation of Intermediate 37.3. Colorless oil; ES-MS: M+H=232; HPLC: $_At_{Ret}$=3.09 min.

Intermediate 41.1

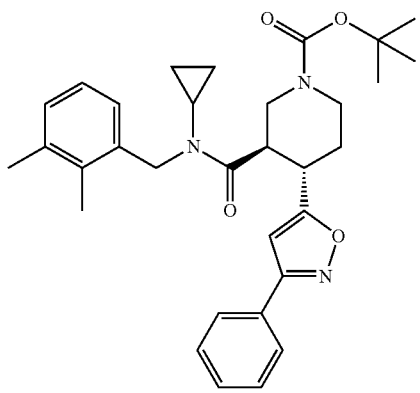

Intermediate 41.1 is synthesized by condensation of Intermediate 41.2 (80 mg, 0.22 mmol) analogously to the preparation of Intermediate 4.1. Colorless oil; Rf=0.54 (EtOAc:n-Hex=2:3), $^1$H NMR (CDCl$_3$), δ: 0.65-0.92 (4H, m), 1.50 (9H, s), 1.93-2.01 (2H, m), 2.06 (3H, s), 2.15 (3H, s), 2.60-2.67 (1H, m), 2.80-3.07 (2H, m), 3.60-3.69 (1H, m), 3.80 (1H, dt), 4.17-4.51 (3H, m), 4.53-4.89 (1H, m), 6.34 (1H, s), 6.47 (1H, d), 6.65 (1H, t), 6.36 (1H, s), 7.42-7.47 (3H, m). 7.74-7.80 (2H, m).

Intermediate 41.2

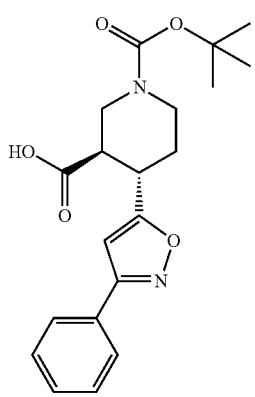

Intermediate 41.2 is synthesized by 1,4-reduction, epimerization and hydrolysis of Intermediate 41.3 (150 mg, 0.39 mmol) analogously to the preparation of Intermediate 4.4/4.3, Colorless amorphous material; Rf=0.13 (EtOAc:n-Hex=2:3), $^1$H NMR (CDCl$_3$), δ: 1.49 (9H, s), 1.74 (1H, dq), 2.08 (1H, dq), 2.87-3.20 (2H, m), 3.48 (1H, dt), 4.09-4.20 (2H, m), 4.25-4.45 (1H, drs), 6.38 (1H, s), 7.39-7.45 (3H, m). 7.72-7.30 (2H, m).

Intermediate 41.3

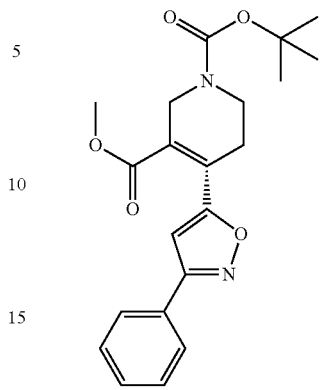

A mixture of Intermediate 41.4 (300 mg, 1.13 mmol), phenylcarboximidoyl chloride (211 mg, 1.36 mmol) and NEt$_3$ (0.24 mL, 1.70 mmol) in dichloromethane (15 mL) are stirred under N$_2$ at RT for 10 hours. After adding H$_2$O, the reaction mixture is extracted with DCM. The combined organic phases are washed with H$_2$O, brine and dried (MgSO$_4$), concentrated under reduced pressure and silica gel flash chromatography to give Intermediate 41.3 as yellow solid; ES-MS: M+H=385; HPLC: $_At_{Ret}$=4.67 minutes.

Intermediate 41.4

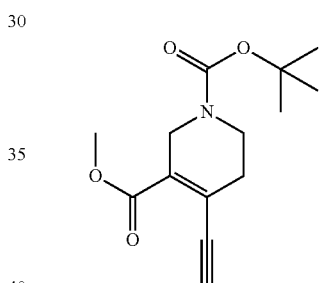

A mixture of Intermediate 41.5 (400 mg, 1.19 mmol) and CsF (432 mg, 2.84 mmol) in MeOH (10 mL) and H$_2$O (2 mL) are stirred under N$_2$ at RT for 10 hours. After evaporating, the residue is added H$_2$O and DCM. The mixture is extracted with DCM. The combined organic phases are washed with H$_2$O, brine and dried (MgSO$_4$), concentrated under reduced pressure and silica gel flash chromatography to give Intermediate 41.4 as white solid; ES-MS: M+H-$^t$Bu=210; HPLC: $_At_{Ret}$=4.00 minutes.

Intermediate 41.5

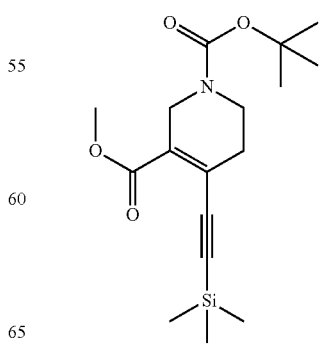

A mixture of 4-trifluoromethanesulfonyloxy-5,6-dihydro-2H-pyridine-1,3-dicarboxylic acid 1-tert-butyl ester 3-methyl ester (600 mg, 1.54 mmol), (Trimethylsilyl)acethylene (0.66 mL, 4.62 mmol), CuI (30.0 mg, 0.15 mmol), NEt$_3$ (1.08 mL, 7.72 mmol) and Pd(PPh$_3$)$_4$ (54.0 mg, 0.08 mmol) in DMF (10 mL) are stirred under N$_2$ at 60° C. for 2.5 hours. After adding H$_2$O, the reaction mixture is extracted with Et$_2$O. The combined organic phases are washed with H$_2$O, brine and dried (MgSO$_4$), concentrated under reduced pressure and silica gel flash chromatography to give Intermediate 41.5 as white amorphous material; Rf=0.65 (EtOAc:n-Hex=1:4), $^1$H NMR (CDCl$_3$), δ: 0.22 (9H, s), 1.03 (9H, s), 1.96-2.01 (2H, m), 3.02 (2H, t), 3.34 (3H, s), 3.78 (2H, brs).

Intermediate 42.1

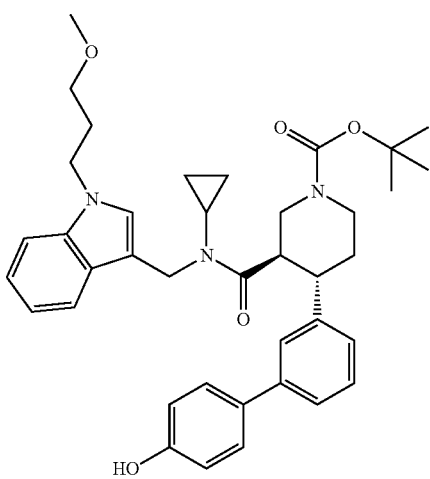

Intermediate 42.1 is synthesized by coupling of Intermediate 42.2 (206 mg, 0.29 mmol) and 4-Hydroxybenzeneboronic acid (60.0 mg, 0.44 mmol) analogously to the preparation of Intermediate 2.1. White amorphous material; ES-MS: M+H=638; HPLC: $_At_{Ret}$=4.67 min.

Intermediate 42.2

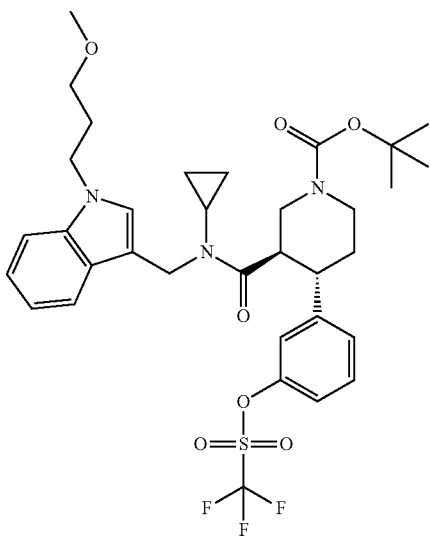

Intermediate 42.2 is synthesized by condensation of Intermediate 42.3 (164 mg, 0.29 mmol) analogously to the preparation of Intermediate 29.4. White amorphous material; ES-MS: M+H=694; HPLC: $_At_{Ret}$=5.34 min.

Intermediate 42.3

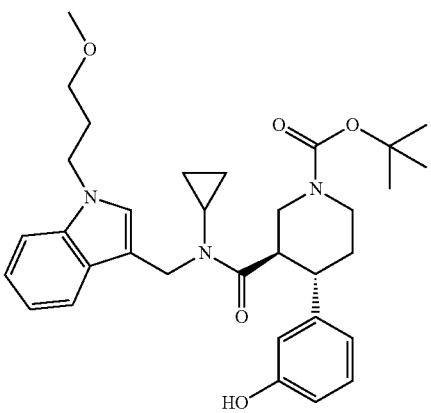

Intermediate 42.3 is synthesized by condensation of Intermediate 26.3 (508 mg, 1.58 mmol) and Intermediate 22.2 (490 mg, 1.90 mmol) analogously to the preparation of Intermediate 4.1. White amorphous material; ES-MS: M+H=562; HPLC: $_At_{Ret}$=4.35 min.

Intermediate 43.1

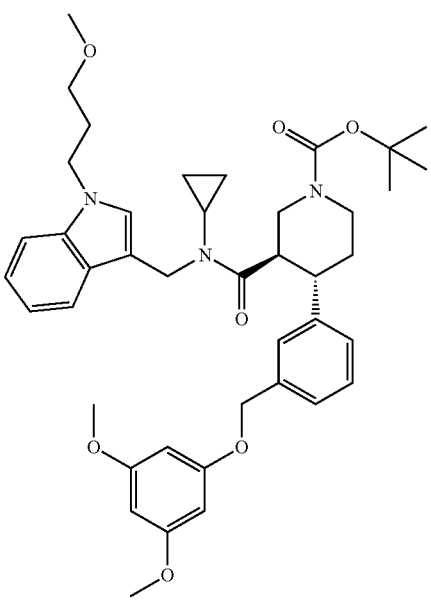

Intermediate 43.1 is synthesized by condensation of Intermediate 23.2 (64.5 mg, 0.14 mmol) and Intermediate 22.2 (42.4 mg, 0.16 mmol) analogously to the preparation of Intermediate 4.1. White amorphous material; ES-MS: M+H=712; HPLC: $_At_{Ret}$=5.34 min.

Intermediate 44.1

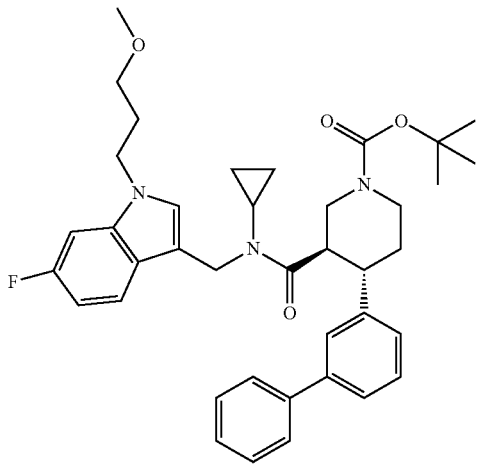

Intermediate 44.1 is synthesized by condensation of Intermediate 1.2 (200 mg, 0.52 mmol) and Intermediate 44.2 (184 mg, 0.67 mmol) analogously to the preparation of Intermediate 1.1. White amorphous material; ES-MS: M+H=640; HPLC: $_A t_{Ret}$=5.47 min.

Intermediate 44.2

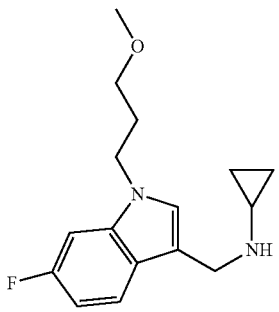

Intermediate 44.2 is synthesized by condensation of Intermediate 44.3 (1.20 g, 5.10 mmol) and cyclopropylamine (581 mg, 10.2 mmol) analogously to the preparation of Intermediate 4.5. Yellow oil; ES-MS: M−H=275; HPLC: $_A t_{Ret}$=2.57 min.

Intermediate 44.3

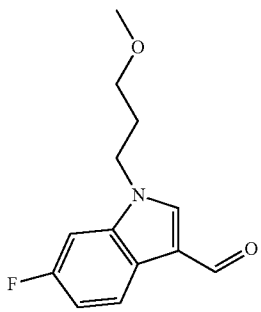

Intermediate 44.3 is synthesized by condensation of 6-fluoro-indole-3-carbaldehyde (1.00 g, 7.40 mmol) and toluene-4-sulfonic acid 3-methoxy-propyl ester (2.30 g, 9.60 mmol) analogously to the preparation of Intermediate 4.8. Yellow oil; ES-MS: M+H=236; HPLC: $_A t_{Ret}$=3.27 min.

Intermediate 45.1

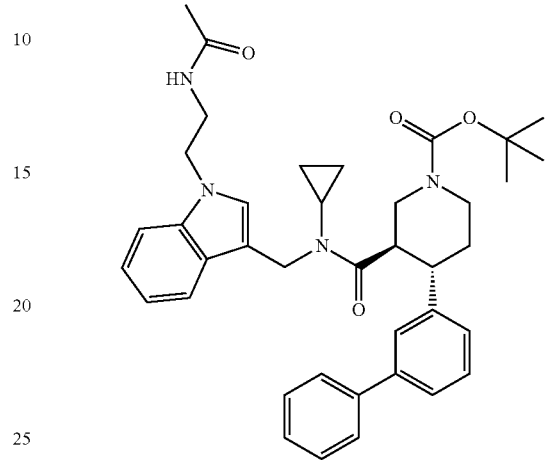

To a solution of Intermediate 45.2 (207 mg, 0.35 mmol) and pyridine (118 mg, 1.5 mmol) in DCM (3 mL) was added Acetic anhydride (102 mg, 1.00 mmol) under $N_2$. After stirring at RT for 2 h, the reaction mixture is quenched by the addition of iced $H_2O$. The resulting mixture is extracted with DCM, and the organic extracts are washed with brine. The organic layer is dried ($MgSO_4$), filtered, and concentrated in vacuo After concentration, the residue is purified by silica gel flash chromatography to give Intermediate 45.1 as colorless oil; ES-MS: M+H=635; HPLC: $_A t_{Ret}$=4.54 min.

Intermediate 45.2

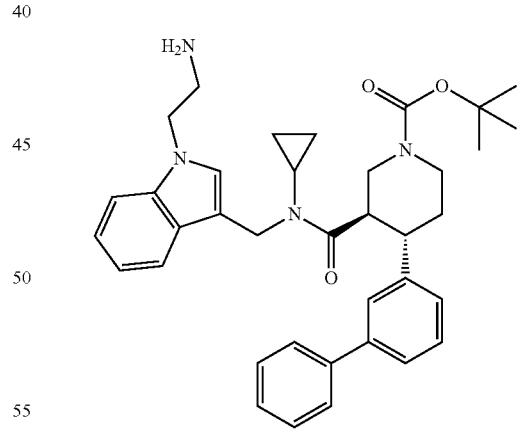

To a solution of Intermediate 45.3 (275 mg, 0.38 mmol) in EtOH (5 mL) was added Hydrazine hydrate (95 mg, 1.90 mmol) under $N_2$. After stirring at 60° C. for 1 h, the reaction mixture is quenched by the addition of iced $H_2O$. The resulting mixture is extracted with EtOAc, and the organic extracts are washed with brine. The organic layer is dried ($MgSO_4$), filtered, and concentrated in vacuo. After concentration, the residue is purified by silica gel flash chromatography to give Intermediate 45.2 as colorless oil; ES-MS: M+H=593; HPLC: $_A t_{Ret}$=3.90 min.

Intermediate 45.3

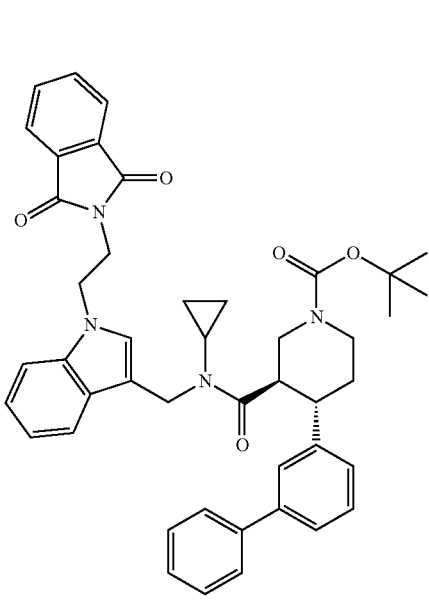

Intermediate 45.3 is synthesized by condensation of Intermediate 1.2 (457 mg, 1.20 mmol) and Intermediate 45.4 (540 mg, 1.50 mmol) analogously to the preparation of Intermediate 4.1. Yellow oil; ES-MS: M+H=723; HPLC: $_A t_{Ret}$=5.37 min.

Intermediate 45.4

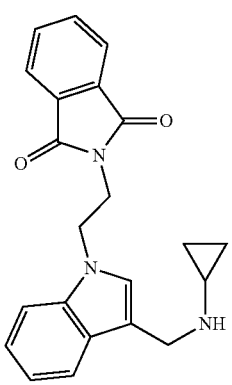

Intermediate 45.4 is synthesized by condensation of Intermediate 45.5 (0.80 g, 2.50 mmol) and cyclopropylamine (716 mg, 12.5 mmol) analogously to the preparation of Intermediate 4.5. Yellow oil; ES-MS: M+H=360; HPLC: $_A t_{Ret}$=2.75 min.

Intermediate 45.5

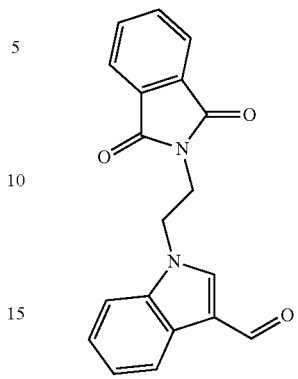

To a solution of Intermediate 45.6 (1.70 g, 6.70 mmol) in DMF (5 mL) was added Potassium phthalimide (1.40 g, 7.40 mmol) under $N_2$ at 0° C. After stirring at 60° C. for 16 h, the reaction mixture is quenched by the addition of iced $H_2O$. The resulting mixture is extracted with EtOAc, and the organic extracts are washed with brine. The organic layer is dried ($MgSO_4$), filtered, and concentrated in vacuo. After concentration, the residue is purified by silica gel flash chromatography to give Intermediate 45.5 as white solid; ES-MS: M+H=319; HPLC: $_A t_{Ret}$=3.32 min.

Intermediate 45.6

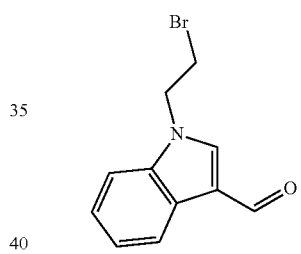

Intermediate 45.6 is synthesized by condensation of Indole-3-carbaldehyde (2.00 g, 13.8 mmol) and 1,2-Dibromoethane (12.9 g, 69.0 mmol) analogously to the preparation of Intermediate 4.8. Red oil; ES-MS: M+=252; HPLC: $_A t_{Ret}$=3.22 min.

Intermediate 46.1

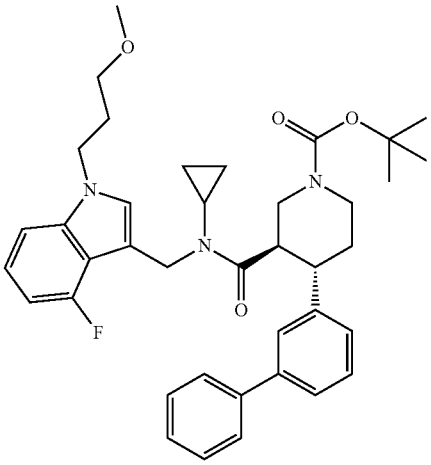

Intermediate 46.1 is synthesized by condensation of Intermediate 1.2 (200 mg, 0.52 mmol) and Intermediate 46.2 (184 mg, 0.67 mmol) analogously to the preparation of Intermediate 4.1. White amorphous material; ES-MS: M+H=640; HPLC: $_A t_{Ret}$=5.57 min.

Intermediate 46.2

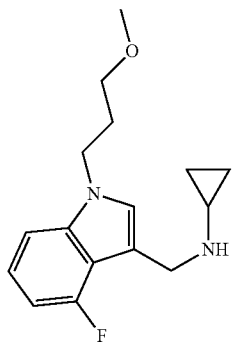

Intermediate 46.2 is synthesized by condensation of Intermediate 46.3 (1.50 g, 6.40 mmol) and cyclopropylamine (730 mg, 12.8 mmol) analogously to the preparation of Intermediate 4.5. Yellow oil; ES-MS: M+H=277; HPLC: $_A t_{Ret}$=2.57 min.

Intermediate 46.3

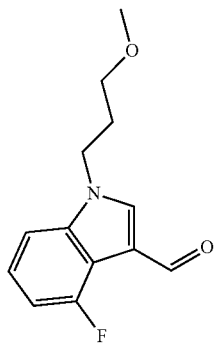

Intermediate 46.3 is synthesized by condensation of Intermediate 46.4 (1.20 g, 7.4 mmol) and toluene-4-sulfonic acid 3-methoxy-propyl ester (2.30 g, 9.60 mmol) analogously to the preparation of Intermediate 4.8. Yellow oil; ES-MS: M+H=236; HPLC: $_A t_{Ret}$=3.17 min.

Intermediate 46.4

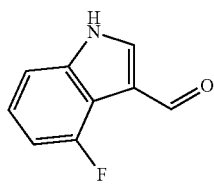

To a solution of 4-fluoro-indole (1.00 g, 7.40 mmol) in DMF (3 mL) was added POCl$_3$ (1.0 mL, 11.0 mmol) under N$_2$ at 0° C. After stirring at room temperature for 30 min, the reaction mixture is quenched by the addition of iced H$_2$O and neutralized by 1N NaOH solution. The resulting mixture is extracted with EtOAc, and the organic extracts are washed with brine. The organic layer is dried (MgSO$_4$), filtered, and concentrated in vacuo. After concentration, the residue is purified by silica gel flash chromatography to give Intermediate 46.4 as colorless oil; ES-MS: M+H=164; HPLC: $_A t_{Ret}$=2.57 min.

Intermediate 47.1

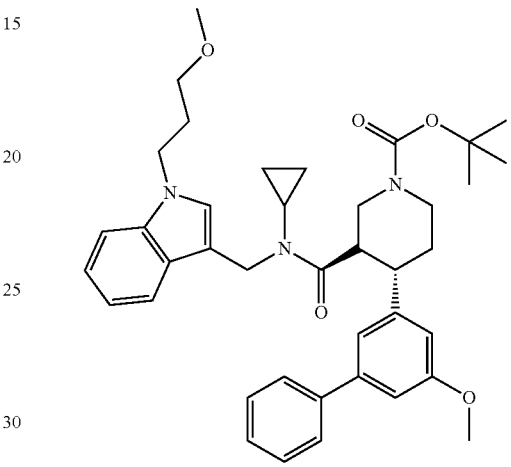

Intermediate 47.1 is synthesized by condensation of Intermediate 29.2 (177 mg, 0.43 mmol) and Intermediate 22.2 (222 mg, 0.86 mmol) analogously to the preparation of Intermediate 4.1. White amorphous material; ES-MS: M+H=652; HPLC: $_A t_{Ret}$=5.37 min.

Intermediate 48.1

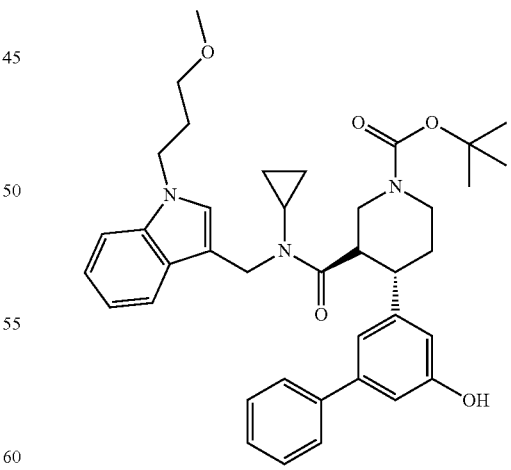

Intermediate 48.1 is synthesized by condensation of Intermediate 48.2 (105 mg, 0.26 mmol) and Intermediate 22.2 (123 mg, 0.47 mmol) analogously to the preparation of Intermediate 4.1. White amorphous material; ES-MS: M+H=638; HPLC: $_A t_{Ret}$=5.02 min.

Intermediate 48.2

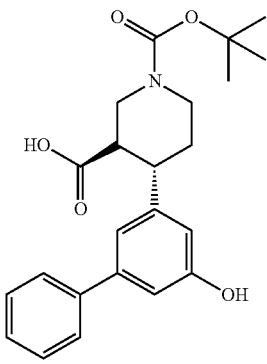

Intermediate 48.2 is synthesized by hydrolysis of Intermediate 48.3 (197 mg, 0.48 mmol) analogously to the preparation of Intermediate 4.2. White amorphous material; ES-MS: M+H-$^t$Bu=342; HPLC: $_A t_{Ret}$=3.80 min.

Intermediate 48.3

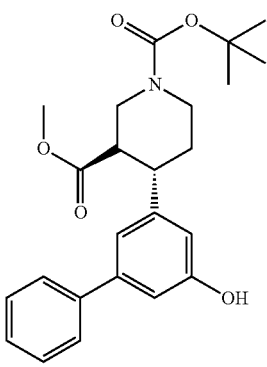

Intermediate 48.3 is synthesized by deprotection and protection of Intermediate 48.4 (203 mg, 0.45 mmol) analogously to the preparation of Intermediate 3.2. White amorphous material; ES-MS: M+H-$^t$Bu=356; HPLC: $_A t_{Ret}$=4.25 min.

Intermediate 48.4

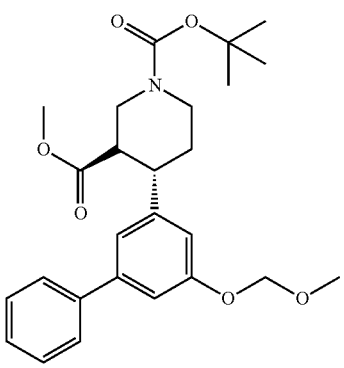

Intermediate 48.4 is synthesized by 1,4-reduction, epimerization and hydrolysis of Intermediate 48.5 (412 mg, 0.90 mmol) analogously to the preparation of Intermediate 4.3. White amorphous material; ES-MS: M+H-$^t$Bu=400; HPLC: $_A t_{Ret}$=5.07 min.

Intermediate 48.5

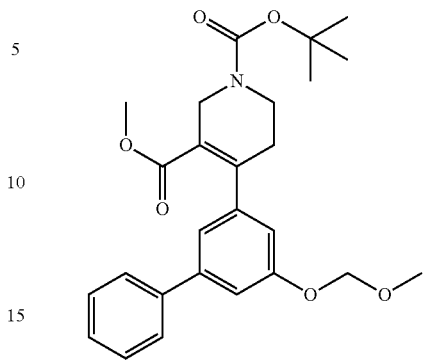

Intermediate 48.5 is synthesized by condensation of 4-trifluoromethanesulfonyloxy-5,6-dihydro-2H-pyridine-1,3-dicarboxylic acid 1-tert-butyl ester 3-methyl ester (1.62 g, 4.2 mmol) and Intermediate 48.6 (1.69 g, 5.0 mmol) analogously to the preparation of Intermediate 2.5. Colorless oil; $^1$H NMR (CDCl$_3$) δ 1.51 (s, 9H), 2.55 (br s, 2H), 3.50 (s, 3H), 3.52 (s, 3H), 3.62 (t, 2H), 4.26 (br s, 2H), 5.21 (s, 2H), 6.82 (m, 1H), 7.02 (m, 1H), 7.19-7.20 (m, 1H), 7.32-7.36 (m, 1H), 7.42 (t, 2H), 7.55-7.57 (m, 2H). Rf=0.16 (EtOAc:n-Hex=1:5).

Intermediate 48.6

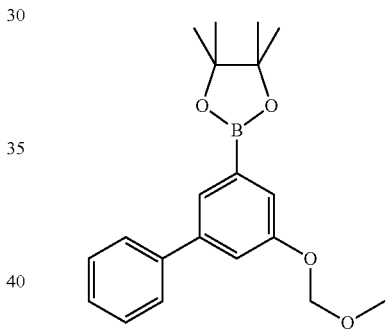

A mixture of 5-phenylresorcinol (3.57 g, 19.1 mmol) (see e.g. Journal of the Chemical Society, Chemical Communications (1978), (3), 118), MOMCl (1.22 mL, 21.1 mmol) and DIEA (3.61 mL, 21.1 mmol) in DCM (100 mL) is stirred at 0° C. for 30 min. After adding saturated NaHCO$_3$ solution, the reaction mixture is extracted with DCM. The combined organic phases are washed with H$_2$O, brine and dried (MgSO$_4$). Concentration under reduced pressure and silica gel flash chromatography give mono-MOM ether as a yellow oil. A mixture of the mono-ether (1.73 g, 7.5 mmol), Tf$_2$O (1.35 mL, 8.25 mmol) and DIEA (1.67 mL, 9.75 mmol) in DCM (30 mL) is stirred at 0° C. for 30 min. After adding saturated NaHCO$_3$ solution, the reaction mixture is extracted with EtOAc The combined organic phases are washed with H$_2$O, brine and dried (MgSO$_4$). Concentration under reduced pressure gives crude mono-triflate as a yellow oil. This crude product is used without purification. A mixture of this crude, bis(pinacolato)diboron (2.87 g, 11.3 mmol), KOAc (2.94 g, 30 mmol) and Pd(PPh$_3$)$_4$ (866 mg, 0.75 mmol) in DMF (30 mL) is stirred under N$_2$ at 110° C. After stirring for 8 h, the reaction mixture is quenched by slowly adding H$_2$O, and the mixture is extracted with EtOAc. The combined organic phases are washed with H$_2$O, brine and dried (Na$_2$SO$_4$). Concentration under reduced pressure and silica gel flash chromatography give Intermediate 48.6 as yellow oil; ES-MS: M+H=341; HPLC: $t_{Ret}$=4.09 min.

Intermediate 49.1

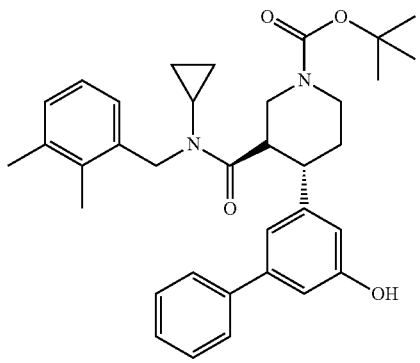

Intermediate 49.1 is synthesized by condensation of Intermediate 48.2 (72.0 mg, 0.18 mmol) analogously to the preparation of Intermediate 4.1. White amorphous material; ES-MS: M+H=555; HPLC: $_At_{Ret}$=4.77 min.

Intermediate 50.1

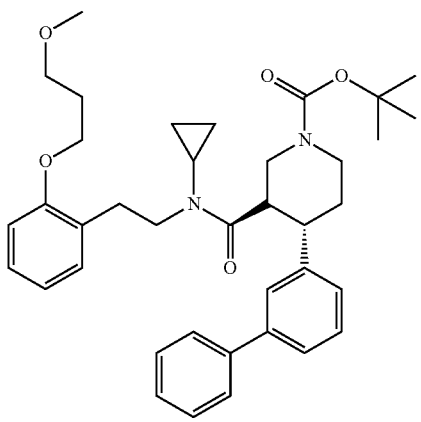

Intermediate 50.1 is synthesized by condensation of Intermediate 1.2 (100 mg, 0.26 mmol) and Intermediate 50.2 (78.0 mg, 0.31 mmol) analogously to the preparation of Intermediate 4.1. White amorphous material; ES-MS: M+H=613; HPLC: $_At_{Ret}$=5.57 min.

Intermediate 50.2

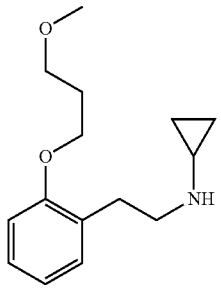

To a solution of Intermediate 50.3 (500 mg, 2.55 mmol) in DCM (10 mL) and EtOAc (5 mL) is added PDC (1.90 g, 5.10 mmol). After stirred at RT for 8 h, the reaction mixture is diluted with EtOAc and filtered though silica gel pad. The resulting mixture is extracted with EtOAc, and the organic extracts are washed with brine. The organic layer is dried (MgSO$_4$), filtered, and concentrated in vacuo After concentration, crude aldehyde is used without purification. Intermediate 50.2 is synthesized by condensation of crude aldehyde analogously to the preparation of Intermediate 4.5. White amorphous material; ES-MS: M+H=250; HPLC: $_At_{Ret}$=2.43 min.

Intermediate 50.3

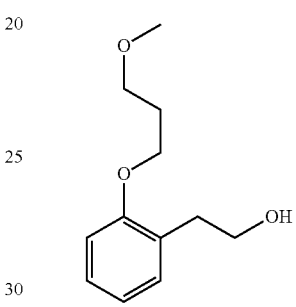

Intermediate 50.3 is synthesized by reduction of Intermediate 50.4 (2.20 g, 7.40 mmol) analogously to the preparation of Intermediate 4.7. Colorless oil; ES-MS: M+H=211; HPLC: $_At_{Ret}$=2.90 min.

Intermediate 50.4

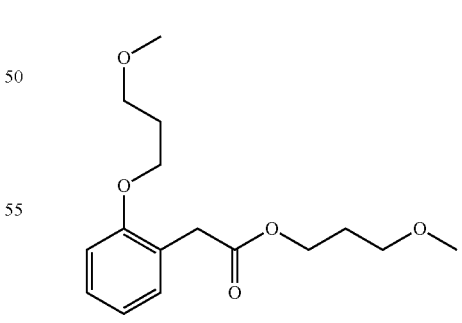

Intermediate 50.4 is synthesized by alkylation of 2-hydroxyphenyl acetic acid (2.00 g, 13.0 mmol) analogously to the preparation of Intermediate 4.8. Colorless oil; ES-MS: M+H=297; HPLC: $_At_{Ret}$=3.63 min.

Intermediate 51.1

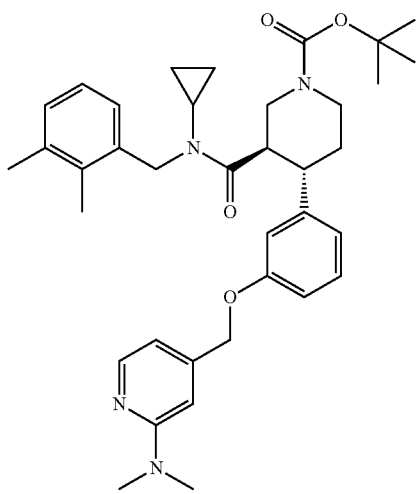

Intermediate 51.1 is synthesized by condensation of Intermediate 26.2 (100 mg, 0.21 mmol) and 2-dimethylamino-4-pyridinemethanol (38 mg, 0.25 mmol) (see e.g. WO9722596.) analogously to the preparation of Intermediate 3.1. White amorphous material; ES-MS: M+H=613; HPLC: $_At_{Ret}$=3.84 min.

Intermediate 52.1

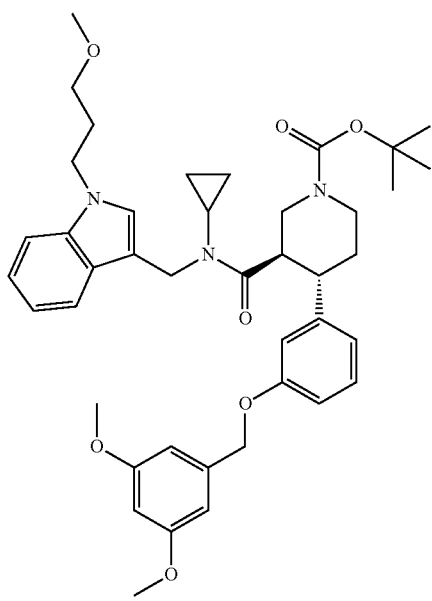

Intermediate 52.1 is synthesized by condensation of Intermediate 13.3 (188 mg, 0.40 mmol) and Intermediate 22.2 (155 mg, 0.60 mmol) analogously to the preparation of Intermediate 4.1. White amorphous material; ES-MS: M+H=712; HPLC: $_At_{Ret}$=5.45 min.

Intermediate 53.1

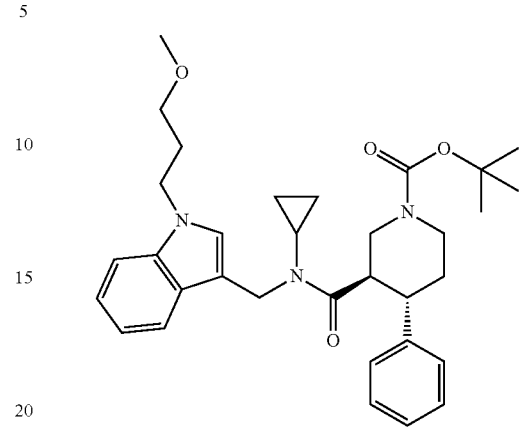

Intermediate 53.1 is synthesized by condensation of 1,3-Piperidinedicarboxylic acid, 4-phenyl-, 1-(1,1-dimethylethyl) ester (267 mg, 0.87 mmol) which is made by known method (see e.g. Bioorganic & Medicinal Chemistry Letters (2003), 13(24), 4431-4435) and Intermediate 22.2 (271 mg, 1.05 mmol) analogously to the preparation of Intermediate 4.1. White amorphous material; ES-MS: M+H=546; HPLC: $_At_{Ret}$=4.99 min.

Intermediate 54.1

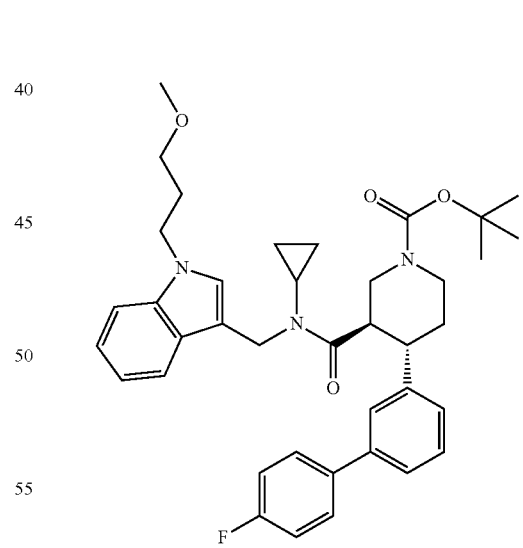

Intermediate 54.1 is synthesized by coupling of Intermediate 42.2 (230 mg, 0.33 mmol) and 4-Fluorobenzeneboronic acid (93 mg, 0.66 mmol) analogously to the preparation of Intermediate 2.1. White amorphous material; ES-MS: M+H=640; HPLC: $_At_{Ret}$=5.45 min.

Intermediate 55.1

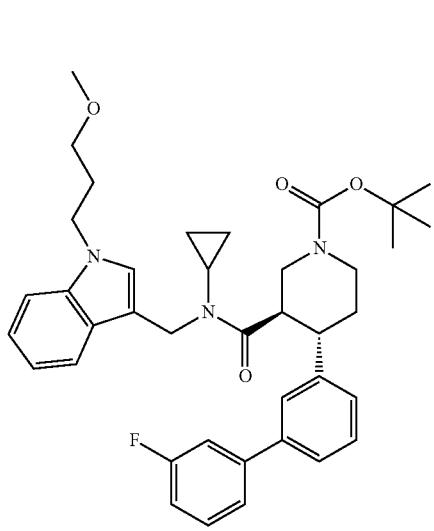

Intermediate 55.1 is synthesized by coupling of Intermediate 42.2 (233 mg, 0.34 mmol) and 3-Fluorobenzeneboronic acid (94 mg, 0.67 mmol) analogously to the preparation of Intermediate 2.1. White amorphous material; ES-MS: M+H=640; HPLC: $_A t_{Ret}$=5.47 min.

Intermediate 56.1

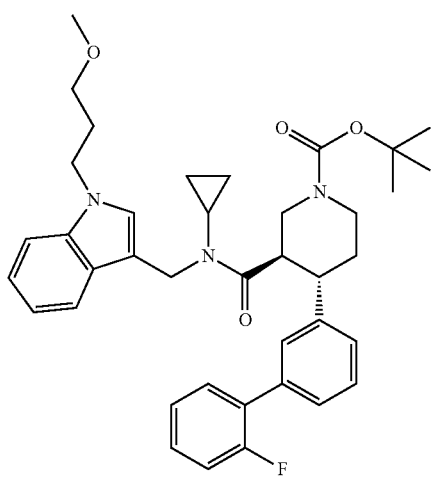

Intermediate 56.1 is synthesized by coupling of Intermediate 42.2 (255 mg, 0.37 mmol) and 2-Fluorobenzeneboronic acid (103 mg, 0.74 mmol) analogously to the preparation of Intermediate 2.1. White amorphous material; ES-MS: M+H=640; HPLC: $_A t_{Ret}$=5.45 min.

Intermediate 57.1

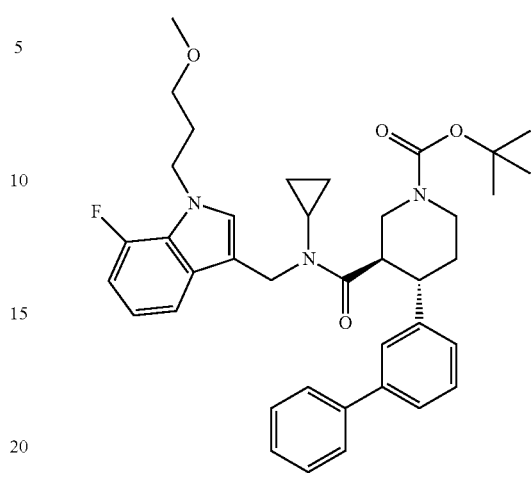

Intermediate 57.1 is synthesized by condensation of Intermediate 1.2 (224 mg, 0.59 mmol) and Intermediate 57.2 (211 mg, 0.78 mmol) analogously to the preparation of Intermediate 4.1. White amorphous material; ES-MS: M+H=640; HPLC: $_A t_{Ret}$=5.60 min.

Intermediate 57.2

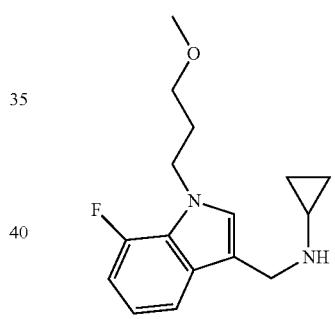

Intermediate 57.2 is synthesized by condensation of Intermediate 57.3 (900 mg, 3.80 mmol) and cyclopropylamine (433 mg, 7.60 mmol) analogously to the preparation of Intermediate 4.5. Yellow oil; ES-MS: M−H=275; HPLC: $_A t_{Ret}$=2.67 min.

Intermediate 57.3

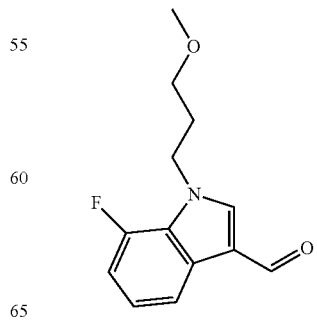

Intermediate 57.3 is synthesized by condensation of Intermediate 57.4 (1.2 g, 7.40 mmol) and toluene-4-sulfonic acid 3-methoxy-propyl ester (2.30 g, 9.60 mmol) analogously to the preparation of Intermediate 4.8. Yellow oil; ES-MS: M+H=236; HPLC: $_At_{Ret}$=3.37 min.

Intermediate 57.4

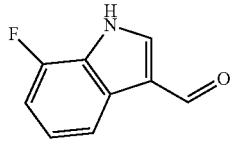

Intermediate 57.4 is synthesized by formylation of 7-Fluoroindole (1.00 g, 7.40 mmol) analogously to the preparation of Intermediate 46.4. Yellow oil; ES-MS: M+H=164; HPLC: $_At_{Ret}$=2.62 min.

Intermediate 58.1

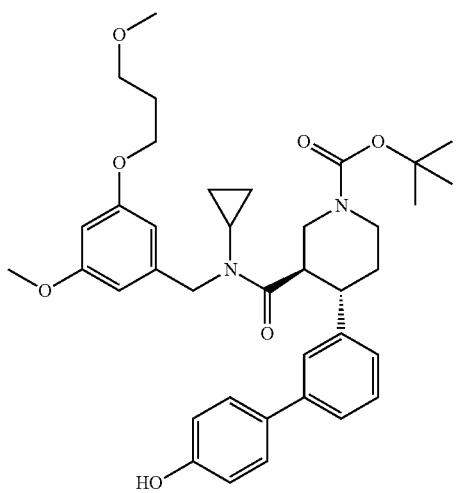

Intermediate 58.1 is synthesized by coupling of Intermediate 58.2 (204 mg, 0.29 mmol) and 4-Hydroxybenzeneboronic acid (60.0 mg, 0.44 mmol) analogously to the preparation of Intermediate 2.1. White amorphous material; ES-MS: M+H=645; HPLC: $_At_{Ret}$=4.53 min.

Intermediate 58.2

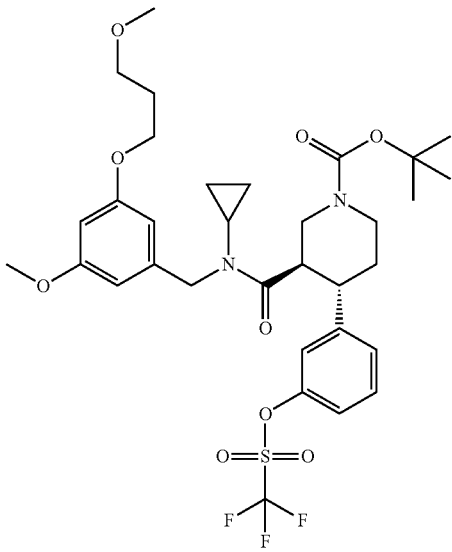

Intermediate 58.2 is synthesized by condensation of Intermediate 58.3 (480 mg, 0.84 mmol) analogously to the preparation of Intermediate 29.4. White amorphous material; ES-MS: M+H=701; HPLC: $_At_{Ret}$=5.15 min.

Intermediate 58.3

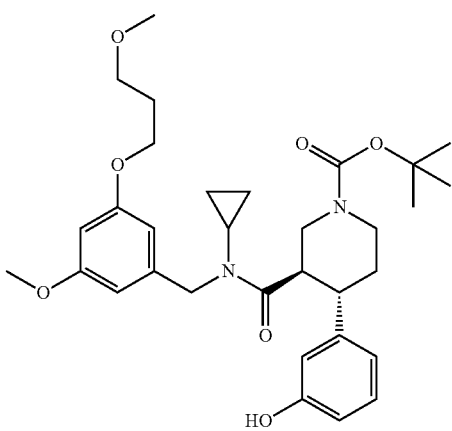

Intermediate 58.3 is synthesized by condensation of Intermediate 26.3 (521 mg, 1.62 mmol) and Intermediate 58.4 (559 mg, 2.11 mmol) analogously to the preparation of Intermediate 4.1. White amorphous material; ES-MS: M+H=569; HPLC: $_At_{Ret}$=4.20 min.

Intermediate 58.4

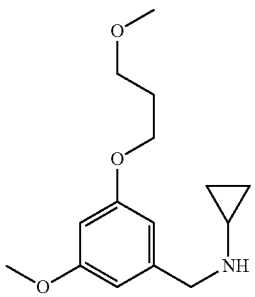

Intermediate 58.4 is synthesized by condensation of Intermediate 58.5 (2.50 g, 11.1 mmol) and cyclopropylamine (855 mg, 15.0 mmol) analogously to the preparation of Intermediate 4.5. Yellow oil; ES-MS: M+H=266; HPLC: $_A t_{Ret}$=2.48 min.

Intermediate 58.5

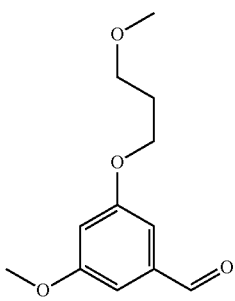

Intermediate 58.5 is synthesized by oxidation of Intermediate 14.3 (4.20 g, 18.6 mmol) analogously to the preparation of Intermediate 4.6. Yellow oil; ES-MS: M+H=225; HPLC: $_A t_{Ret}$=3.59 min.

Intermediate 59.1

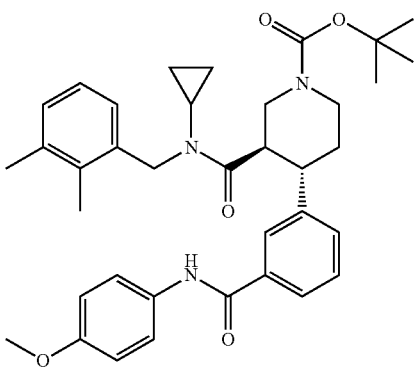

A mixture of compound of Intermediate 59.2 (15 mg, 0.03 mmol), p-anisidine (5 mg, 0.04 mmol), DMT-MM (13 mg, 0.045 mmol) and Et$_3$N (0.006 mL, 0.045 mmol) in THF (2 mL) are stirred under N$_2$ at 70° C. for 1 hours. After added H$_2$O, the reaction mixture is extracted with EtOAc. The combined organic phases are washed with H$_2$O, brine and dried (Na$_2$SO$_4$), concentrated under reduced pressure and silica gel flash chromatography to give Intermediate 59.1 as white amorphous material; ES-MS: M+H=612; HPLC: $t_{Ret}$=4.75 minutes.

Intermediate 59.2

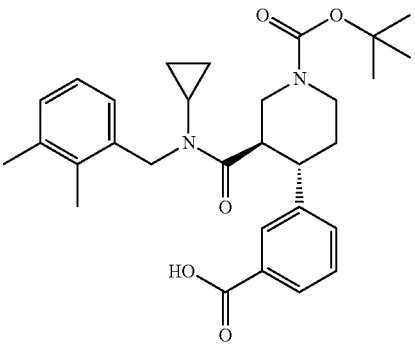

A mixture of Intermediate 59.3 (88 mg, 0.14 mmol), KOAc (57 mg, 0.56 mmol), palladium acetate (3 mg, 0.01 mmol), and dppf (16 mg, 0.03 mmol) in DMSO is stirred under a CO balloon at 65° C. for 3 h. The reaction mixture is diluted with brine, extracted with EtOAc, washed with brine, dried (MgSO$_4$). Concentration under reduced pressure and silica gel flash chromatography give Intermediate 59.2 as white amorphous material; ES-MS: M+H=507; HPLC: $_A t_{Ret}$=4.22 min.

Intermediate 59.3

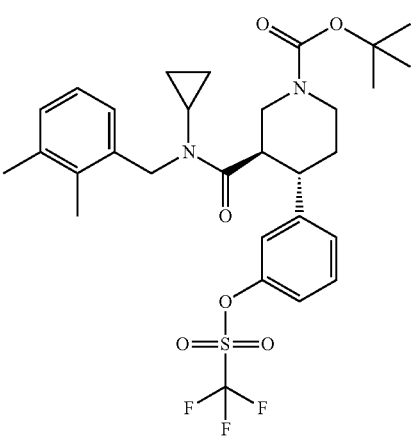

Intermediate 59.3 is synthesized by condensation of Intermediate 26.2 (350 mg, 0.73 mmol) analogously to the preparation of Intermediate 29.4. White amorphous material; ES-MS: M+H=611; HPLC: $_A t_{Ret}$=5.36 min.

Intermediate 60.1

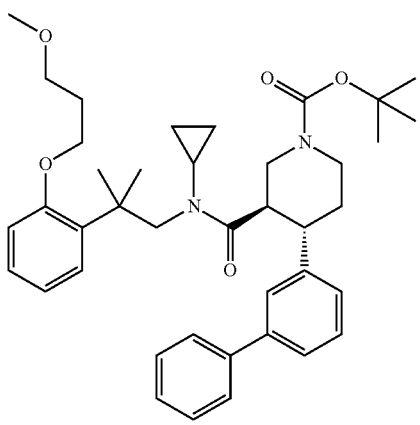

Intermediate 60.1 is synthesized by condensation of Intermediate 1.2 (100 mg, 0.26 mmol) and Intermediate 60.2 (87 mg, 0.32 mmol) analogously to the preparation of Intermediate 4.1. White amorphous material; ES-MS: M+H=641; HPLC: $_At_{Ret}$=5.82 min.

Intermediate 60.2

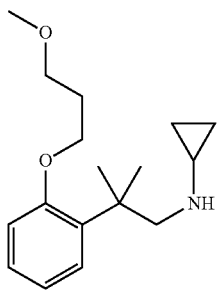

Intermediate 60.2 is synthesized by condensation of Intermediate 60.3 (450 mg, 1.90 mmol) and cyclopropylamine (197 µL, 2.85 mmol) analogously to the preparation of Intermediate 4.5. Yellow oil; ES-MS: M−H=278; HPLC: $_At_{Ret}$=2.72 min.

Intermediate 60.3

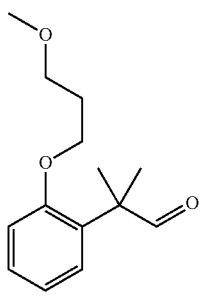

To a solution of Intermediate 60.4 (500 mg, 2.14 mmol) in DCM (20 mL) is added DIBAL (2.93 mL, 0.95 M, 2.79 mmol) under $N_2$ at −78° C. After stirred at −78° C. for 2 h, the reaction mixture is quenched by the addition of aqueous $KHSO_4$. The resulting mixture is extracted with $Et_2O$, and the organic extracts are washed with brine. The organic layer is dried ($MgSO_4$), filtered, and concentrated in vacuo. After concentration, the residue is purified by silica gel flash chromatography to give Intermediate 60.3 as colorless oil; ES-MS: M+H=237; HPLC: $_At_{Ret}$=3.85 min.

Intermeiate 60.4

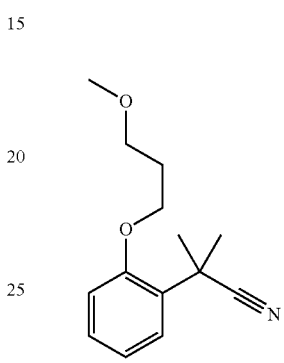

Intermediate 60.4 is synthesized by alkylation of Intermediate 60.5 (1.00 g, 5.43 mmol), Isobutyronitrile (2.2 mL, 25.0 mmol) made analogously to a known method (see e.g. *Journal of the American Chemical Society* 2000, 122, 712-713.). Yellow oil; ES-MS: M+H=234; HPLC: $_At_{Ret}$=3.79 min.

Intermediate 60.5

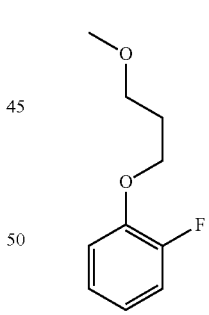

To a mixture of 2-Fluorophenol (2.00 g, 17.8 mmol), toluene-4-sulfonic acid 3-methoxypropyl ester (4.34 g, 17.8 mmol) and KI (1.50 g, 10.0 mmol) in DMF (40 mL) is added NaH (854 mg, 21.3 mmol). After stirred at 90° C. for 3 h, the reaction mixture is quenched by the addition of aqueous $H_2O$. The resulting mixture is extracted with $Et_2O$, and the organic extracts are washed with brine. The organic layer is dried ($MgSO_4$), filtered, and concentrated in vacuo. After concentration, the residue is purified by silica gel flash chromatography to give Intermediate 60.5 as colorless oil; ES-MS: M+H=185; HPLC: $_At_{Ret}$=3.59 min.

Intermediate 61.1

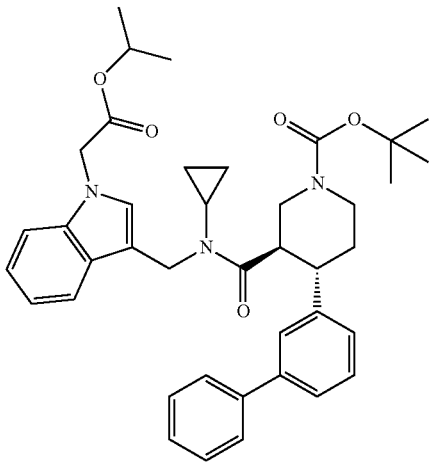

Intermediate 61.1 is synthesized by condensation of Intermediate 1.2 (100 mg, 0.26 mmol) and Intermediate 61.2 (90 mg, 0.31 mmol) analogously to the preparation of Intermediate 4.1. White amorphous material; ES-MS: M+H=650; HPLC: $_At_{Ret}$=5.42 min.

Intermediate 61.2

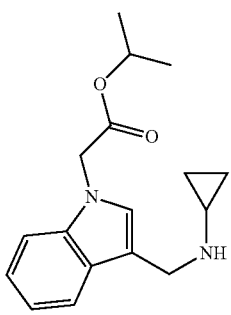

Intermediate 61.2 is synthesized by condensation of Intermediate 61.3 (300 mg, 1.22 mmol) and cyclopropylamine (102 μL, 1.47 mmol) analogously to the preparation of Intermediate 4.5. Yellow oil; ES-MS: M−H=285; HPLC: $_At_{Ret}$=2.72 min.

Intermediate 61.3

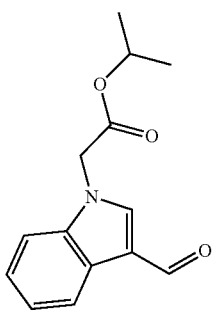

Intermediate 61.3 is synthesized by condensation of Indole-3-carbaldehyde (1.00 g, 6.90 mmol) and iso-propyl bromoacetate (1.00 mL, 8.30 mmol) analogously to the preparation of Intermediate 37.3. Colorless oil; ES-MS: M+H=246; HPLC: $_At_{Ret}$=3.37 min.

Intermediate 62.1

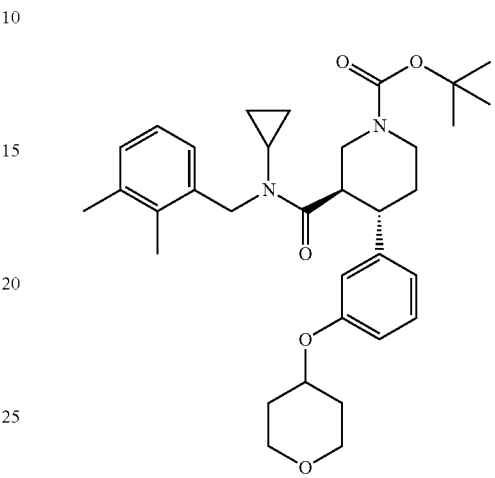

Intermediate 62.1 is synthesized by condensation of Intermediate 26.2 (150 mg, 0.31 mmol) and Tetrahydro-pyran-4-ol (48 mg, 0.47 mmol) analogously to the preparation of Intermediate 3.1. White amorphous material; ES-MS: M+H=563; HPLC: $_At_{Ret}$=4.99 min.

Intermediate 63.1

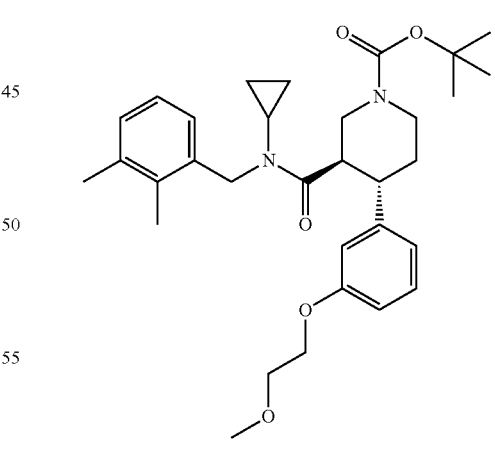

Intermediate 63.1 is synthesized by condensation of Intermediate 26.2 (149 mg, 0.31 mmol) and 2-Methoxyethanol (49 μL, 0.62 mmol) analogously to the preparation of Intermediate 3.1. White amorphous material; ES-MS: M+H=537; HPLC: $_At_{Ret}$=4.87 min.

Intermediate 64.1

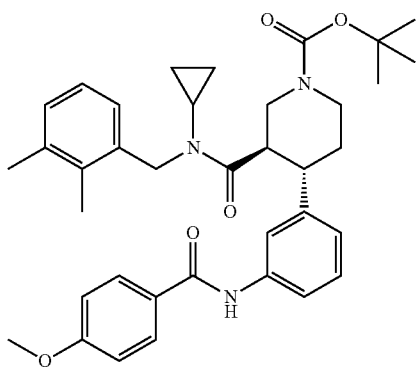

Intermediate 64.1 is synthesized by condensation of Intermediate 64.2 (190 mg, 0.42 mmol) analogously to the preparation of Intermediate 4.1. White amorphous material; ES-MS: M+H=612; HPLC: $_A t_{Ret}$=4.84 min.

Intermediate 64.2

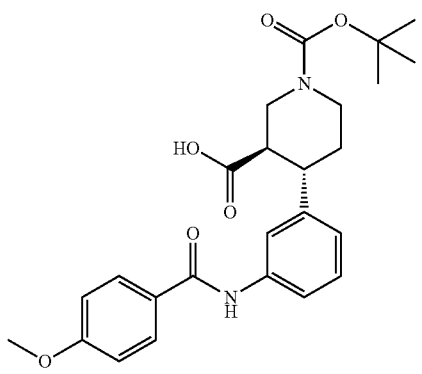

Intermediate 64.2 is synthesized by hydrolysis of Intermediate 64.3 (220 mg, 0.50 mmol) analogously to the preparation of Intermediate 4.2. White amorphous material; ES-MS: M+H=455; HPLC: $_A t_{Ret}$=3.79 min.

Intermediate 64.3

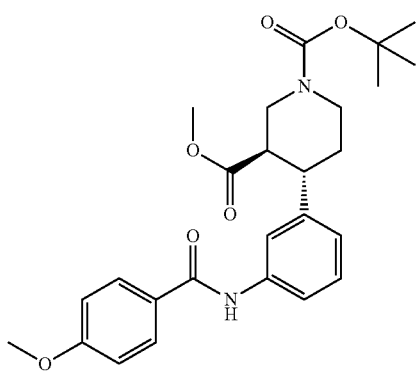

A mixture of Intermediate 64.4 (300 mg, 0.90 mmol), Et₃N (251 μL, 1.76 mmol) and 4-Methoxybenzoyl chloride (230 mg, 1.35 mmol) in DCM (3 mL) was stirred at RT for 1.5 h. After adding saturated NaHCO₃ solution, the reaction mixture is extracted with DCM. The combined organic phases are washed with H₂O, brine and dried (MgSO₄). Concentration under reduced pressure and silica gel flash chromatography give Intermediate 64.3 as white amorphous material; ES-MS: M+H=469; HPLC: $_A t_{Ret}$=4.20 min.

Intermediate 64.4

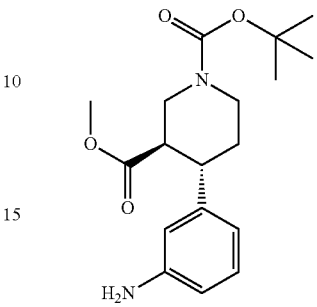

Intermediate 64.4 is synthesized by 1,4-reduction, reduction and epimerization of Intermediate 64.5 (4.45 g, 12.3 mmol) analogously to the preparation of Intermediate 4.3. White amorphous material; ES-MS: M+H=335; HPLC: $_A t_{Ret}$=2.77 min.

Intermediate 64.5

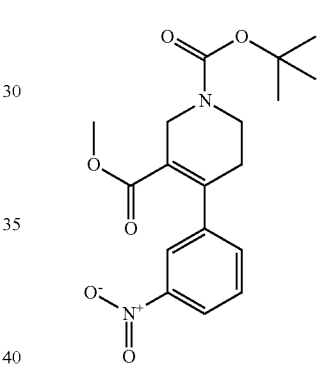

Intermediate 64.5 is synthesized by condensation of 4-trifluoromethanesulfonyloxy-5,6-dihydro-2H-pyridine-1,3-dicarboxylic acid 1-tert-butyl ester 3-methyl ester (5.0 g, 12.8 mmol) and 3-Nitrophenylboronic acid (2.79 g, 16.7 mmol) analogously to the preparation of Intermediate 2.5. Colorless oil; ES-MS: M+H=363; HPLC: $_A t_{Ret}$=4.22 min.

Intermediate 65.1

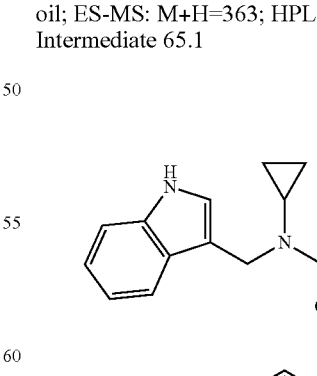

Intermediate 65.1 is synthesized by condensation of Intermediate 1.2 (334 mg, 0.88 mmol) analogously to the preparation of Intermediate 1.1. White amorphous material; ES-MS: M+H=568; HPLC: $_A t_{Ret}$=4.95 min.

Intermediate 66.1

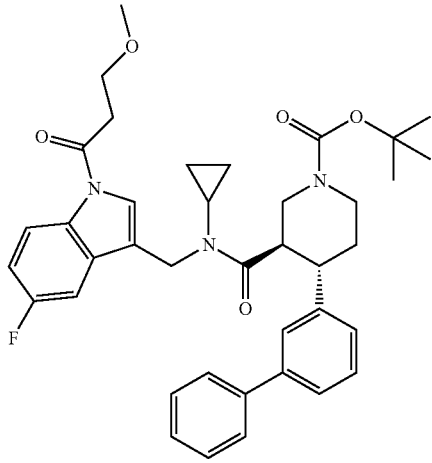

Intermediate 66.1 is synthesized by condensation of Intermediate 1.2 (224 mg, 0.59 mmol) and Intermediate 66.2 (226 mg, 0.78 mmol) analogously to the preparation of Intermediate 4.1. White amorphous material; ES-MS: M+H=654; HPLC: $_A t_{Ret}$=5.34 min.

Intermediate 66.2

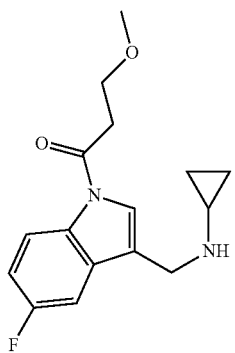

Intermediate 66.2 is synthesized by condensation of Intermediate 66.3 (810 mg, 3.30 mmol) and cyclopropylamine (225 mg, 4.00 mmol) analogously to the preparation of Intermediate 4.5. White solid; ES-MS: M−H=291; HPLC: $_A t_{Ret}$=2.59 min.

Intermediate 66.3

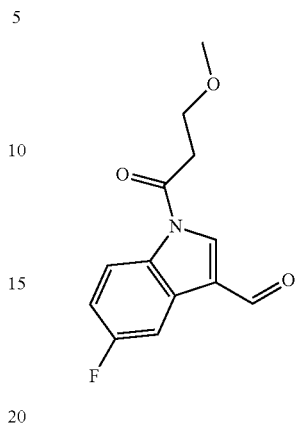

Intermediate 66.3 is synthesized by condensation of 5-Fluoro-indole-3-carbaldehyde (1.00 g, 6.10 mmol) analogously to the preparation of Intermediate 33.3. White solid; ES-MS: M−H=250; HPLC: $_A t_{Ret}$=3.45 min.

Intermediate 67.1

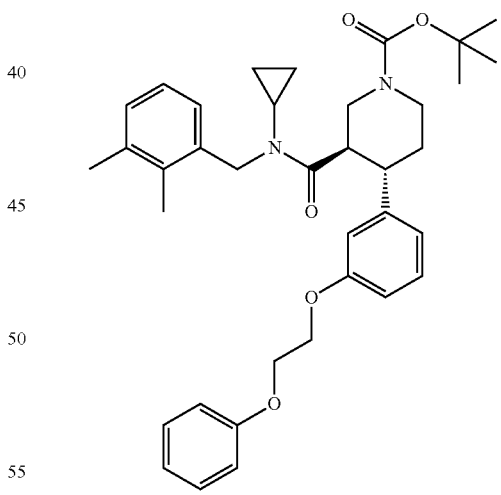

Intermediate 67.1 is synthesized by condensation of Intermediate 26.2 (169 mg, 0.35 mmol) and 2-Phenoxyethanol (88 μL, 0.70 mmol) analogously to the preparation of Intermediate 3.1. White amorphous material; ES-MS: M+H=599; HPLC: $_A t_{Ret}$=5.49 min.

Intermediate 68.1

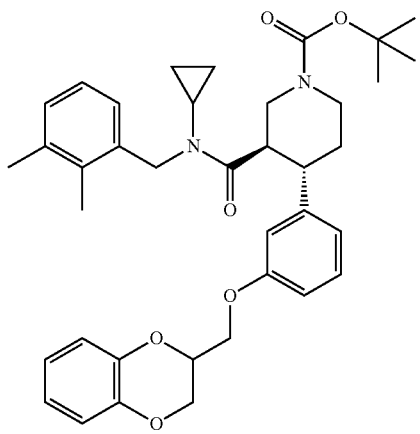

Intermediate 68.1 is synthesized by condensation of Intermediate 26.2 (171 mg, 0.36 mmol) and (2,3-Dihydro-benzo[1,4-]dioxin-2-yl)methanol (119 mg, 0.72 mmol) analogously to the preparation of Intermediate 3.1. White amorphous material; ES-MS: M+H=627; HPLC: $_At_{Ret}$=5.53 min.

Intermediate 69.1

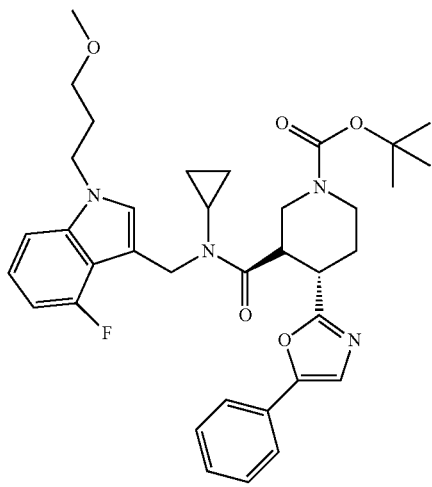

Intermediate 69.1 is synthesized by condensation of Intermediate 69.2 (71 mg, 0.19 mmol) and Intermediate 46.2 (58 mg, 0.21 mmol) analogously to the preparation of Intermediate 1.1. White amorphous material; ES-MS: M+H=631; HPLC: $_At_{Ret}$=5.36 min.

Intermediate 69.2

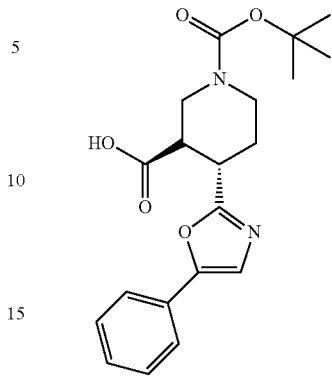

To a solution of Intermediate 69.3 (424 mg, 1.1 mmol) in THF (1 mL) and MeOH (2 mL) is added aqueous NaOH (1.5 mL, 5N, 7.5 mmol). After stirred at 70° C. for 1.5 h, the reaction mixture is quenched by the addition of aqueous KHSO$_4$. The resulting mixture is extracted with Et$_2$O/EtOAc, and the organic extracts are washed with brine. The organic layer is dried (MgSO$_4$), filtered, and concentrated in vacuo. After concentration, the residue is purified by silica gel flash chromatography to give Intermediate 69.2 as colorless oil; ES-MS: M+H=373; HPLC: $_At_{Ret}$=4.01 min.

Intermediate 69.3

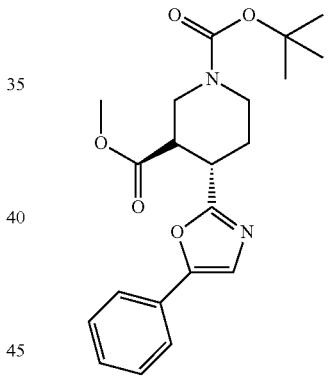

To a solution of Intermediate 69.4 (592 mg, 1.54 mmol) in MeOH (5 mL), Mg (280 mg, 11.5 mmol) is added at 0° C. under N$_2$. After stirring at 0° C. to RT for 12 h, the reaction mixture is quenched by the addition of aqueous KHSO$_4$. The resulting mixture is extracted with EtOAc, and the organic extracts are washed with water and brine. The organic layer is dried (Na$_2$SO$_4$), filtered, and concentrated in vacuo. A solution of the residue in MeOH (2.5 mL) is added to a stirred solution of NaOMe (from 80 mg of Na) in MeOH (1.5 mL). After heated at 70° C. for 4 h, a solution of NaOMe (from 90 mg of Na) in MeOH (1 mL) is added. After 2 h at 70° C., the reaction mixture is quenched by the addition of aqueous KHSO$_4$. The resulting mixture is extracted with Et$_2$O, and the organic extracts are washed with water and brine. The organic layer is dried (MgSO$_4$), filtered, and concentrated in vacuo. The residue is treated with TMSCHN$_2$ (1 mL, 0.6 mol/L in n-hexane, 0.6 mmol) in toluene/MeOH (4:1, 2 mL) at RT for 30 min. After concentration, the residue is purified by silica gel flash chromatography to give Intermediate 69.3 as colorless oil; ES-MS: M+H=387; HPLC: $_At_{Ret}$=4.41 min.

Intermediate 69.4

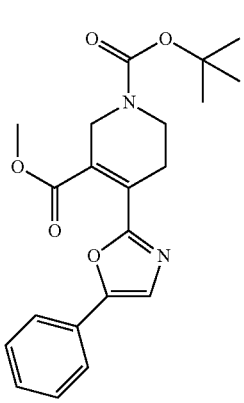

To a stirred solution of 4-phenyloxazole (345 mg, 2.38 mmol) (see *Tetrahedron Lett.* 1972, 2369.) in THF (10 mL) at −78° C. is added n-BuLi (1.63 mL, 1.60 mol/L in n-hexane, 2.61 mmol). After 30 min, ZnCl₂ (7.1 mL, 1.0 mol/L in Et₂O, 7.1 mmol) is added. The reaction mixture is warmed up to 0° C. for 1 h, after which period a solution of 4-trifluoromethanesulfonyloxy-5,6-dihydro-2H-pyridine-1,3-dicarboxylic acid 1-tert-butyl ester 3-methyl ester (925 mg, 2.38 mmol) (see e.g. WO 2004/002957 or US 2003/216441) in THF (2 mL+1 mL rinse) is added via cannula. The palladium catalyst, Pd(PPh₃)₄ (302 mg, 0.26 mmol) is added and the resulting mixture is heated to reflux for 1 h. The final reaction mixture is diluted with EtOAc and washed with water, aqueous KHSO₄, and brine. The organic layer is dried (Na₂SO₄), filtered, and concentrated in vacuo. The residue is purified by silica gel flash chromatography to give Intermediate 69.4 as colorless oil; ES-MS: M+H=385; HPLC: $_A t_{Ret}$=4.54 min.

Intermediate 70.1

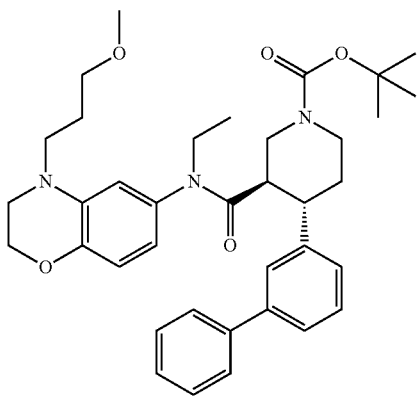

Intermediate 70.1 is synthesized by alkylation of intermediate 70.2 (200 mg, 0.35 mmol) and EtI (41.6 μL, 0.53 mmol) analogously to the preparation of Intermediate 4.8. White powder; ES-MS: M+H=614; HPLC: $_A t_{Ret}$=5.35 min.

Intermediate 70.2

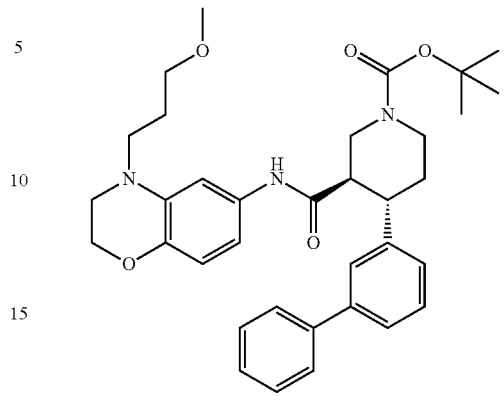

Intermediate 70.2 is synthesized by condensation of Intermediate 1.2 (237 mg, 0.62 mmol) and Intermediate 70.3 (143 mg, 0.62 mmol) analogously to the preparation of Intermediate 37.1. White powder; ES-MS: M+H=586; HPLC: $_A t_{Ret}$=4.78 min.

Intermediate 70.3

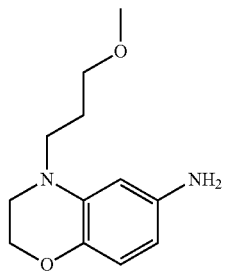

Intermediate 70.3 is synthesized by reduction of Intermediate 70.4 (190 mg, 0.75 mmol) analogously to the preparation of Intermediate 37.2. Brown oil; ES-MS: M+H=223; HPLC: $_A t_{Ret}$=2.05 min.

Intermediate 70.4

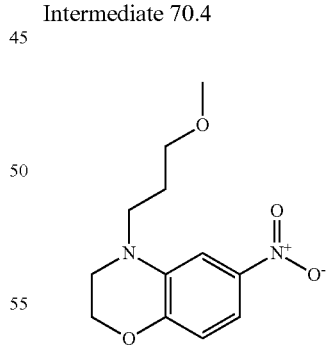

A mixture of Intermediate 38.3 (712 mg, 2.60 mmol) and BH₃ dimethylsulfide complex (493 μL, 5.2 mmol) in THF (10 mL) was stirred at reflux for 2 h. After adding saturated NaHCO₃ solution, the reaction mixture is extracted with EtOAc. The combined organic phases are washed with H₂O, brine and dried (MgSO₄). Concentration under reduced pressure and silica gel flash chromatography give Intermediate 70.4 as orange oil; ES-MS: M+H=253; HPLC: $_A t_{Ret}$=3.79 min.

Intermediate 71.1

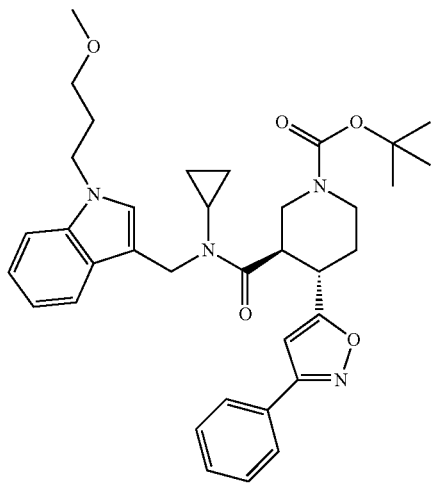

Intermediate 71.1 is synthesized by condensation of Intermediate 41.2 (100 mg, 0.27 mmol) analogously to the preparation of Intermediate 4.1. Colorless oil; Rf=0.36 (EtOAc:n-Hex=1:1), $^1$H NMR (CDCl$_3$), δ: 0.65-0.99 (4H, m), 1.50 (9H, s), 1.45-1.63 (1H, m), 1.69-1.98 (3H, m), 2.01-2.10 (1H, m), 2.40-2.49 (1H, m), 2.78-2.97 (2H, m), 3.03-3.17 (1H, m), 3.25 (3H, s), 3.52-3.69 (2H, m), 3.86-3.97 (2H, m), 4.17-4.41 (3H, m), 4.53-4.99 (1H, m), 6.06 (1H, s), 6.82 (1H, s), 6.98-7.51 (7H, m). 7.59-7.68 (2H, m).

Intermediate 72.1

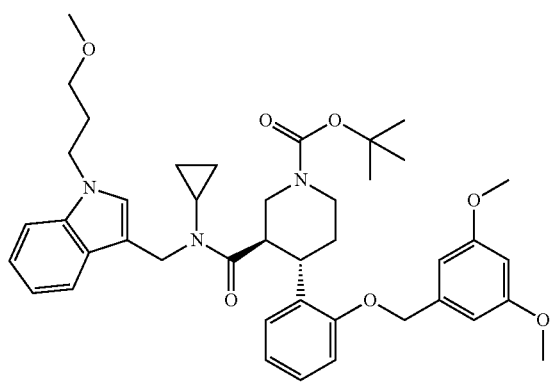

Intermediate 72.1 is synthesized by condensation of Intermediate 72.2 (179 mg, 0.38 mmol) analogously to the preparation of Intermediate 4.1. White amorphous material; ES-MS: M+H=712; HPLC: $_A$t$_{Ret}$=5.43 min.

Intermediate 72.2

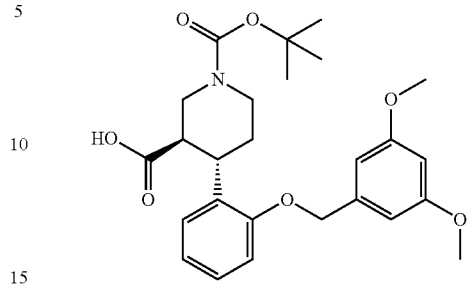

Intermediate 72.2 is synthesized by 1,4-reduction, epimerization and hydrolysis of Intermediate 72.3 (3.80 g, 7.81 mmol) analogously to the preparation of Intermediate 4.3. Colorless oil; ES-MS: M-$^t$Bu=416; HPLC: $_A$t$_{Ret}$=4.32 min.

Intermediate 72.3

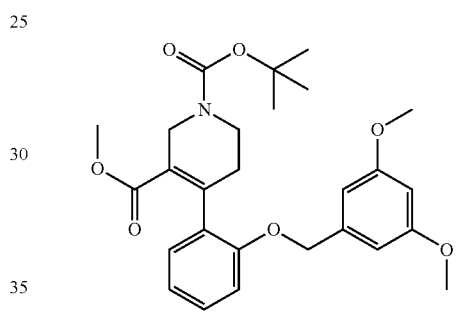

Intermediate 72.3 is synthesized by condensation of 4-trifluoromethanesulfonyloxy-5,6-dihydro-2H-pyridine-1,3-dicarboxylic acid 1-tert-butyl ester 3-methyl ester (5.59 g, 14.3 mmol) and Intermediate 72.4 (4.97 g, 17.2 mmol) analogously to the preparation of Intermediate 2.5. Colorless oil; Rf=0.18 (EtOAc:n-Hex=1:4), $^1$H NMR (CDCl$_3$), δ: 1.49 (9H, s), 2.45-2.55 (2 H, m), 3.46 (3H, s), 3.50-3.62 (2H, m), 3.78 (6H, s), 4.20-4.30 (2H, m), 5.00 (2H, s), 6.37-6.38 (1H, m), 6.50 (2H, bs), 6.89-7.00 (3H, m), 7.20-7.24 (1H, m).

Intermediate 72.4

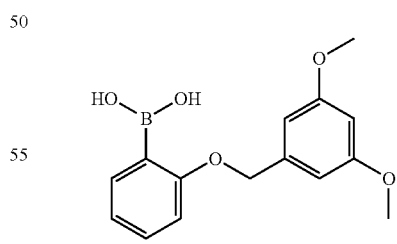

Intermediate 72.4 is synthesized by transformation to boronic acid from 5-[(2-Bromophenoxy)methyl]-1,3-dimethoxybenzene (5.56 g, 17.2 mmol) (see e.g. WO 9806691.) analogously to the preparation of Intermediate 24.4. Orange solid; Rf=0.10 (EtOAc only), $^1$H NMR (CDCl$_3$), δ: 3.79 (6H, s), 5.00 (2H, s), 6.40-6.45 (1H, m), 6.55-6.62 (2H, m), 6.95-7.10 (3H, m), 7.28-7.32 (1H, m).

Intermediate 73.1

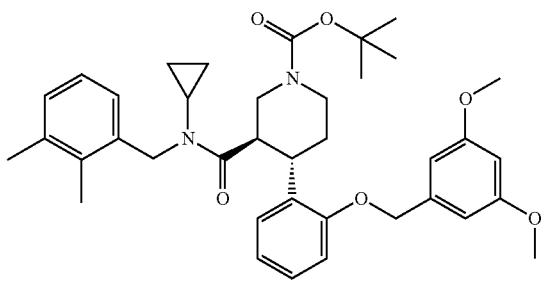

Intermediate 73.1 is synthesized by condensation of Intermediate 72.2 (213 mg, 0.45 mmol) analogously to the preparation of Intermediate 4.1. White amorphous material; ES-MS: M+H=629; HPLC: $_At_{Ret}$=5.52 min.

Intermediate 74.1

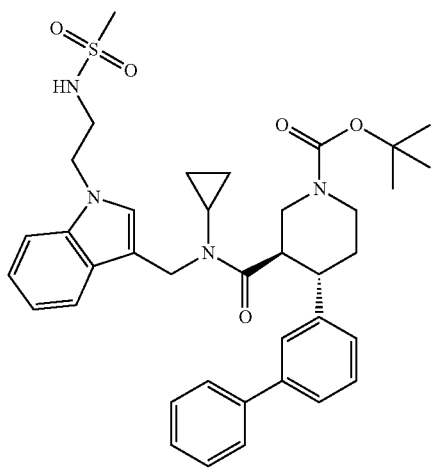

Intermediate 74.1 is synthesized by acylation of Intermediate 45.2 (166 mg, 0.28 mmol) analogously to the preparation of Intermediate 45.1. White amorphous material; ES-MS: M+H=671; HPLC: $_At_{Ret}$=4.92 min.

EXAMPLE 75

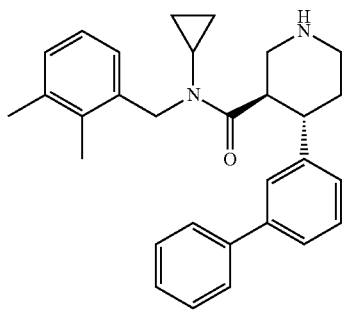

Intermediate 75.1 (144 mg, 0.27 mmol) is treated with 4N HCl in dioxane (2 mL). After stirring for 0.5 h, the resulting mixture is concentrated to give Example 75 as white amorphous; ES-MS: M+H=439; HPLC: $_At_{Ret}$=3.70 minutes. Example 75 show the same inhibitory activity to an active enantiomer of Example 8 which is separated by chiral column technicque in the several assay system as described above.

Intermediate 75.1

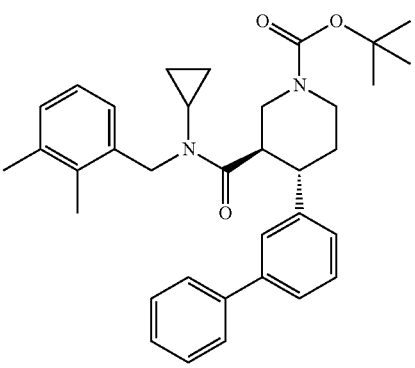

To a solution of Intermediate 75.2 (165 mg, 0.39 mmol) and 2,3-dimethylbenzyl bromide (117 mg, 0.59 mmol) in THF (1.5 mL) is added NaHMDS (1.0 M in THF, 0.59 mL, 0.59 mmol) at 0° C. After stirring at RT for 2 h, H₂O is added. The mixture is extracted with Et₂O, washed with brine and dried over MgSO₄. The organic layer is concentrated and purified by flash silica gel chromatography to give Intermediate 75.1 as colorless oil; ES-MS: M+H=539; HPLC: $_At_{Ret}$=5.72 minutes.

Intermediate 75.2

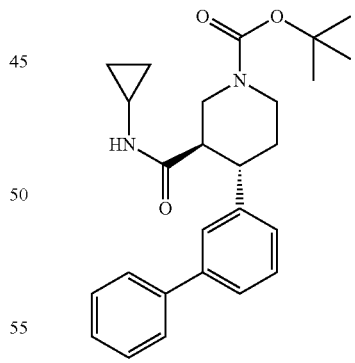

To a solution of Intermediate 75.3 (357 mg, 0.53 mmol) and cyclopropylamine (0.073 mL, 1.05 mmol) in DMF (2 mL) are added EDC (203 mg, 1.05 mmol) and HOAt (93 mg, 0.69 mmol). After stirring at RT for 3 h, the resulting mixture is diluted with Et₂O, washed with H₂O and brine, and dried over MgSO₄. The organic layer is concentrated and purified by flash silica gel chromatography to give Intermediate 75.2 as white amorphous material; ES-MS: M+H=421; HPLC: $_At_{Ret}$=4.32 minutes.

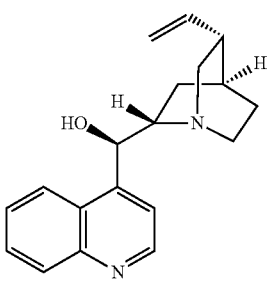

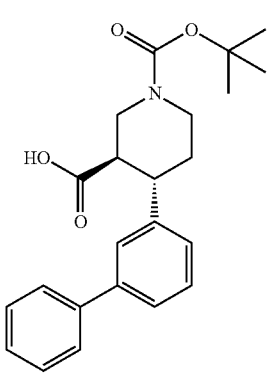

Intermediate 75.3

Intermediate 1.2 (5.54 g, 14.5 mmol) and cinchonidine (4.06 g, 13.8 mmol) are dissolved in MeOH (50 mL). After stirring at 50° C. for 1.5 h, the resulting mixture is concentrated under reduced pressure. The resulting residue is dissolved in Et$_2$O (250 mL) and stirred vigorously at room temperature for 18 h. The resulting white crystals are collected by filtration, washed with Et$_2$O. 3 or 4 recrystallization with same procedure above give diastereomeric pure salt Intermediate 75.3 as white solid (94% ee); ES-MS: M+H=382; HPLC: $_At_{Ret}$=4.28 minutes. Enantiomeric excess is determined by chiral column HPLC, and an absolute configuration is confirmed by X-ray structural analysis.

Intermediate 76.1

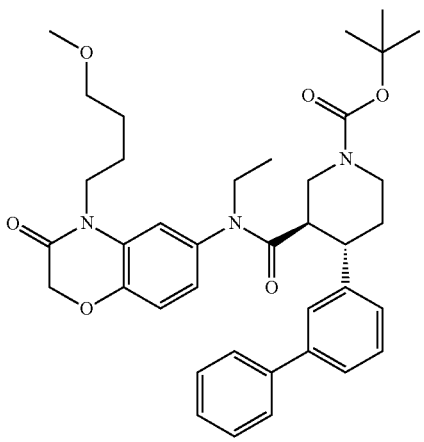

To a solution of Intermediate 76.2 (168 mg, 0.27 mmol) in THF (3 mL) is added 1M solution of NHMDS in THF (410 µL, 0.41 mmol) under N$_2$ at 0° C. After stirring at 0° C. for 0.5 h, EtI (33 µL, 0.41 mmol) is added and stirred at 60° C. for 21 h. H$_2$O is added to the reaction mixture and the mixture is extracted with EtOAc. The combined organic phases are washed with H$_2$O, brine and dried over Na$_2$SO$_4$. Concentration under reduced pressure and silica gel flash chromatography give Intermediate 76.1 as white powder; ES-MS: M+H=642; HPLC: $_At_{Ret}$=5.14 min.

Intermediate 76.2

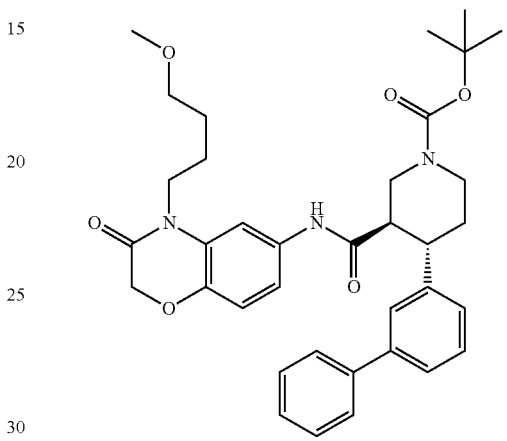

To a solution of Intermediate 76.3 (220 mg, 0.88 mmol) and Intermediate 1.2 (300 mg, 0.80 mmol) in DMF (1 mL), EDCl-HCl (184 mg, 0.96 mmol) and HOAt (131 mg, 0.96 mmol) are added under N$_2$. After stirring at 0° C. and RT for 6 h, the reaction mixture is quenched with H$_2$O and extracted with EtOAc. The combined organic phases are washed with H$_2$O, brine and dried (Na$_2$SO$_4$). Concentration under reduced pressure gives Intermediate 76.2 as white powder; ES-MS: M+H=614; HPLC: $_At_{Ret}$=4.85 min.

Intermediate 76.3

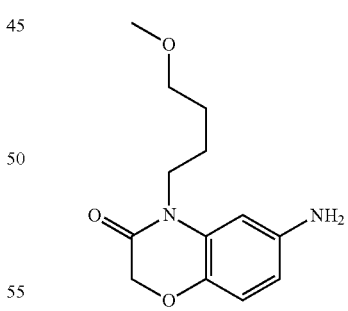

To a solution of Intermediate 76.4 (480 mg, 1.70 mmol) in EtOH (5 mL), Fe (475 mg, 8.5 mmol) and 5N HCl solution (3 mL, 15 mmol) are added at RT under N$_2$. After refluxing for 7 h, the reaction mixture is neutralized by 5N NaOH solution, and filtered through Celite pad. The mixture is extracted with EtOAc. The combined organic phases are washed with brine and dried over Na$_2$SO$_4$. Concentration under reduced pressure and silica gel flash chromatography give Intermediate 76.3 as yellow oil; ES-MS: M+H=251; HPLC: $_At_{Ret}$=2.20 min Intermediate 76.4

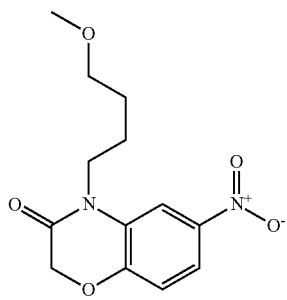

Intermediate 76.4 is synthesized by alkylation of 6-nitro-2H-1,4-benzoxazin-3(4H)-one (582 mg, 3.00 mmol) and toluene-4-sulfonic acid 4-methoxy-propyl ester (1.16 g, 4.50 mmol) analogously to a known method (see e.g. *European Journal of Medicinal Chemistry* 1998, 33, 957-967. or EP 432893). Yellow solid; ES-MS: M+H=281; HPLC: $_A t_{Ret}$=3.47 min.

Intermediate 77.1

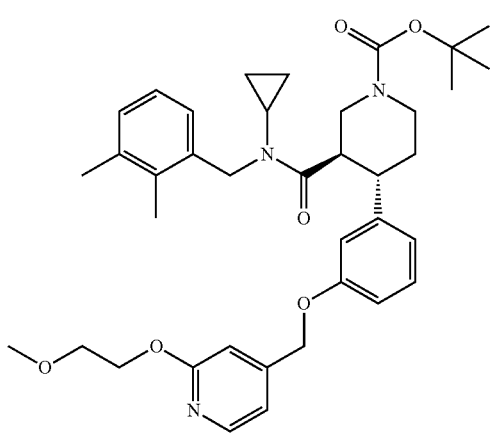

To a solution of Intermediate 26.2 and Intermediate 77.2 in THF are added DEAD and PPh$_3$ at room temperature. After stirring for 3 h, the resulting mixture is concentrated and purified by silicagel column chromatography to give Intermediate 77.1 as white amorphous; ES-MS: M+H=644; HPLC: $_A t_{Ret}$=4.91 min.

Intermediate 77.2

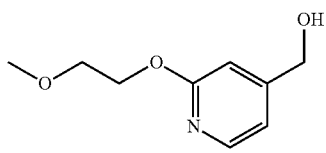

To a solution of 2-(2-Hydroxyethoxy)-4-pyridinecarboxylic acid (1.7 g, 8.62 mmol) in THF (40 mL) are added Et$_3$N (0.99 mL, 10.34 mmol) and Ethyl chloroformate (1.44 mL, 10.34 mmol). After stirring for 0.5 h, the resulting precipitate is filtered off and the filtrate is concentrated. The residue is dissolved in EtOH (20 mL) and then NaBH$_4$ (424 mg, 11.2 mmol) is added at room temperature. After stirring for 2 h, the reaction is quenched with H$_2$O and 1N aqueous HCl. The resulting mixture is diluted and extracted with AcOEt, washed with brine, dried (Na$_2$SO$_4$), and concentrated. Purification by silica gel column chromatograrphy give Intermediate 77.2; M+H=184; HPLC: $_A t_{Ret}$=1.72 min.

Intermediate 78.1

Intermediate 79.1

They (chiral isomers) have same chemical structure as Example 47.

78 would be a eutomer and 79 would be a distomer, according to the result of the enzyme assay. (not confirmed by X-ray)

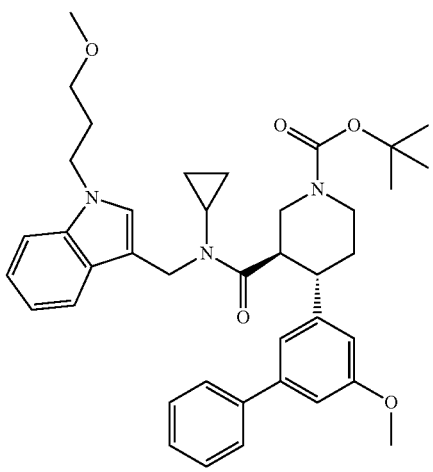

Intermediate 80.1

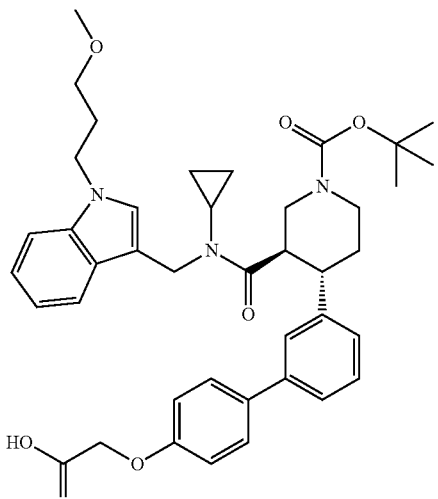

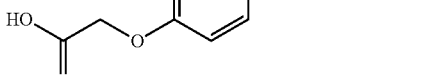

To a solution of Intermediate 80.2 (140 mg, 0.20 mmol) in EtOH (4 mL) is added 6N aqueous NaOH (2 mL) and stirred at 3 h. After cooling to room temperature, the resulting mixture is acidified with 1N KHSO$_4$ solution and extracted with AcOEt. The organic layer is washed with brine, dried over Na$_2$SO$_4$, and concentrated. Silica gel flash chromatography give Intermediate 80.1 as white amorphous; ES-MS: M+H=696; HPLC: $_A t_{Ret}$=4.67 min.

Intermediate 80.2

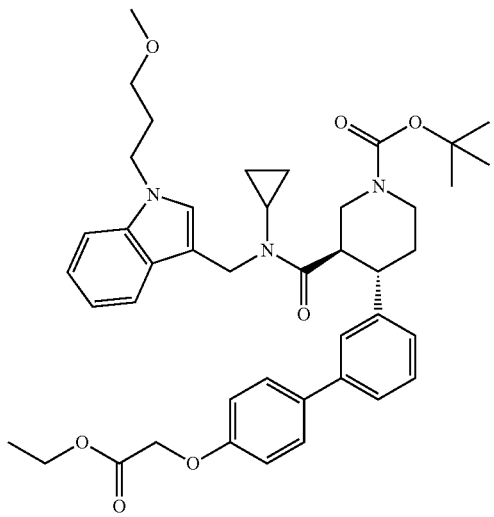

To a solution of Intermediate 42.1 (201 mg, 0.32 mmol) and iodoethyl acetate (0.075 mL, 0.63 mmol) in DMF is added K$_2$CO$_3$ (87 mg, 0.63 mmol) and stirred at 75° C. for 2 h. After cooling to room temperature, the reaction mixture is diluted with AcOEt and washed with H$_2$O and brine. The organic layer is dried over Na$_2$SO$_4$, concentrated and purified by silica gel flash chromatography to give Intermediate 80.2 as white amorphous; ES-MS: M+H=724; HPLC: $_A$t$_{Ret}$=4.85 min.

Itermediate 81.1

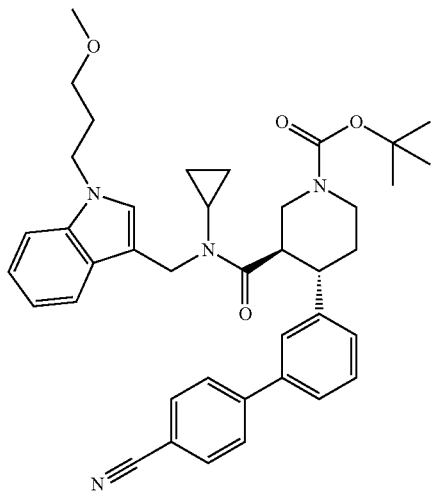

Intermediate 81.1 is synthesized by coupling of Intermediate 42.2 (405 mg, 0.58 mmol) and 4-Cyanophenylboronic acid (129 mg, 0.88 mmol) analogously to the preparation of Intermediate 2.1. White amorphous material; ES-MS: M+H=647; HPLC: $_A$t$_{Ret}$=5.32 min.

Intermediate 82.1

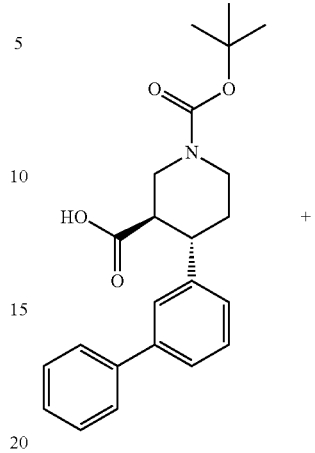

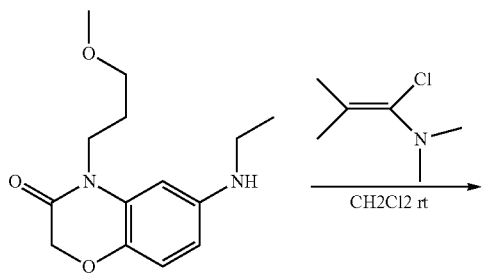

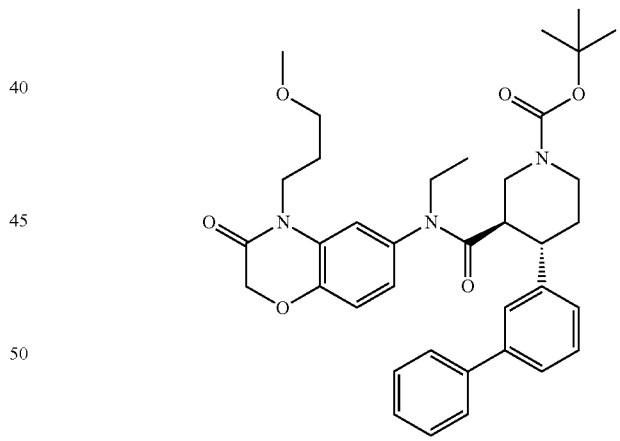

To a solution of Intermediate 75.3 (196 mg, 0.51 mmol) in DCM (3 mL), 1-chloro-N,N-2-trimethylpropaneamine (102 µL, 0.77 mmol) is added under N$_2$ at RT. After stirring at RT for 1 h, the solution is concentrated under reduced pressure to give acid chloride. To a solution of acid chloride in DCM (3 mL) are added Et$_3$N (170 mL, 1.2 mmol) and Intermediate 82.2 (169 mg, 0.56 mmol) under N$_2$ at 0° C. After stirring at RT over night, saturated NaHCO$_3$ solution is added. The mixture is extracted with DCM and dried over Na$_2$SO$_4$. The organic layer is concentrated and purified by flash silica gel chromatography to give Intermediate 82.1; ES-MS: M+H=628; HPLC: $_A$t$_{Ret}$=5.09 min.

Intermediate 82.2

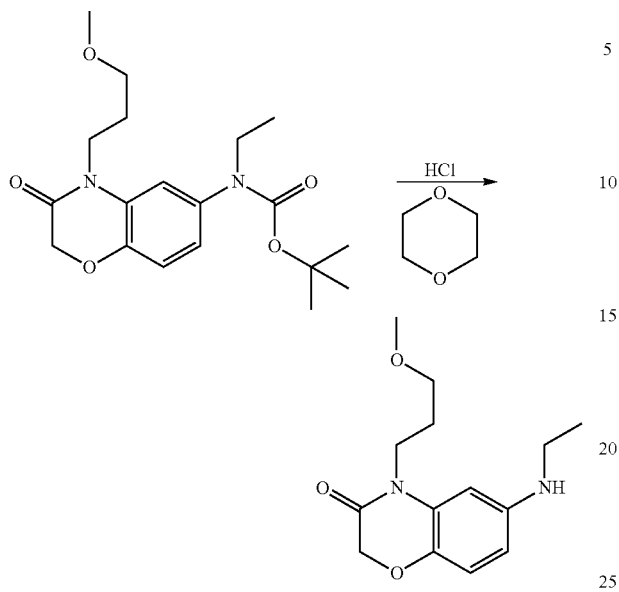

Intermediate 82.3 (1.08 g, 2.96 mmol) is treated with 4N HCl solution in 1,4-dioxane (10 mL) at RT for 2 h. the reaction mixture are concentrated under reduced pressure to give Intermediate 82.2. White powder; ES-MS: M+H=265; HPLC: $_A t_{Ret}$=2.05 min.

Intermediate 82.3

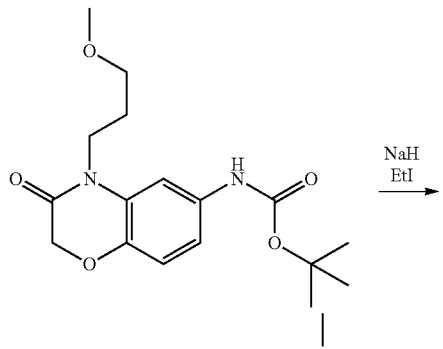

To a solution of Intermediate 82.4 (1.59 g, 4.72 mmol) in THF (20 mL), NaH (208 mg, 5.19 mmol) is added under $N_2$ at 0° C. After stirring at 50° C. for 0.5 h, EtI (411 μL, 5.19 mmol) is added to the mixture and stirred at 50° C. for 12 h. The reaction mixture was quenched with $H_2O$ and extracted with EtOAc. The combined organic phases are washed with $H_2O$ and dried over $Na_2SO_4$. Concentration under reduced pressure and silica gel flash chromatography give Intermediate 82.3 as colorless oil; ES-MS: M+H=309; HPLC: $_A t_{Ret}$=4.03 min Intermediate 82.4

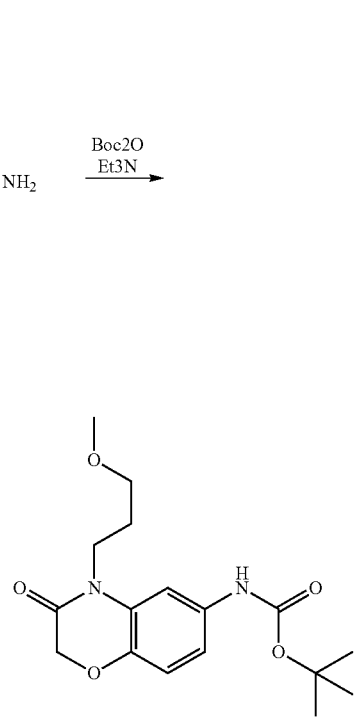

A mixture of Intermediate 38.2 (1.36 g, 5.74 mmol), $Boc_2O$ (2.9 g, 12.6 mmol), and $Et_3N$ (1.92 mL, 7.8 mmol) in THF (20 mL) is stirred under $N_2$ at RT for 2 h. After adding $H_2O$, the reaction mixture is extracted with EtOAc. The combined organic phases are washed with $H_2O$ and dried ($Na_2SO_4$). Concentration under reduced pressure and silica gel flash chromatography give Intermediate 82.4 as colorless amorphous; ES-MS: M+H=337; HPLC: $_A t_{Ret}$=3.67 min.

Intermediate 83.1

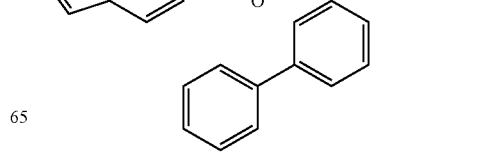

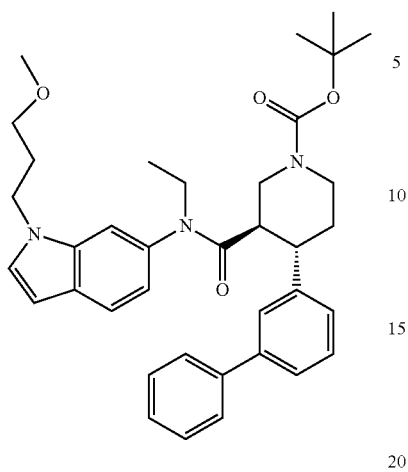
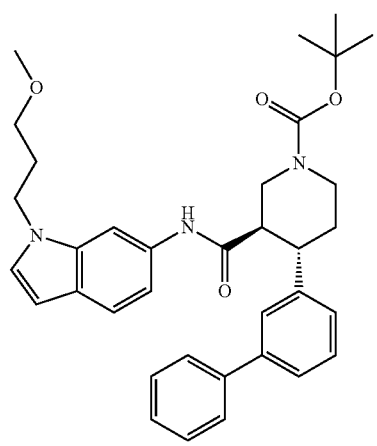

Intermediate 83.1 is synthesized by alkylation of Intermediate 83.2 (303 mg, 0.53 mmol) and EtI (63 µL, 0.8 mmol) analogously to the preparation of Intermediate 82.3. Colorless oil; ES-MS: M+H=596; HPLC: $_A t_{Ret}$=5.60 min.

Intermediate 83.2

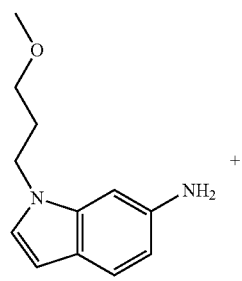

A mixture of Intermediate 83.3 (163 mg, 0.80 mmol), Intermediate 1.2 (254 mg, 0.67 mmol) and DMT-MM (240 mg, 0.87 mmol) in EtOH (5 mL) is stirred under $N_2$ at 60° C. for 5 h. After adding $H_2O$, the reaction mixture is extracted with EtOAc. The combined organic phases are washed with $H_2O$, brine and dried ($Na_2SO_4$). Concentration under reduced pressure and silica gel flash chromatography give Intermediate 83.2 as yellow oil; ES-MS: M+H=568; HPLC: $_A t_{Ret}$=5.09 min.

Intermediate 83.3

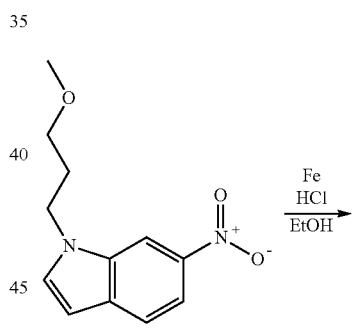

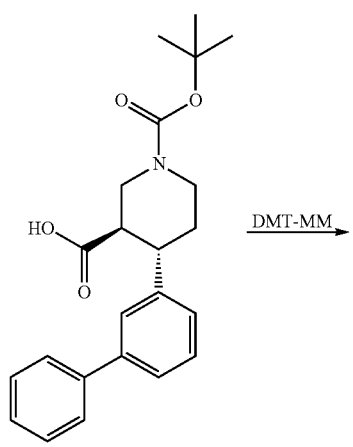

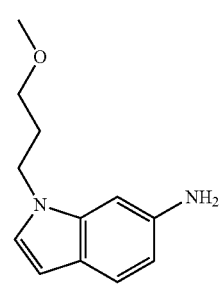

Intermediate 83.3 is synthesized by reduction of Intermediate 83.4 (1.2 g, 5.00 mmol) analogously to the preparation of Intermediate 76.3. Red oil; ES-MS: M+H=205; HPLC: $_A t_{Ret}$=2.23 min Intermediate 83.4

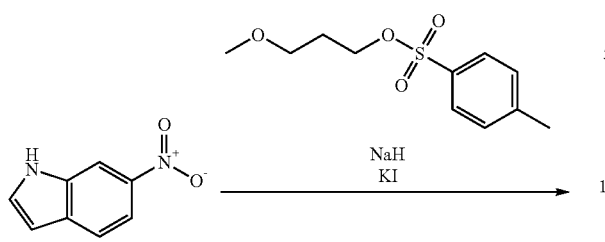

Intermediate 85.1

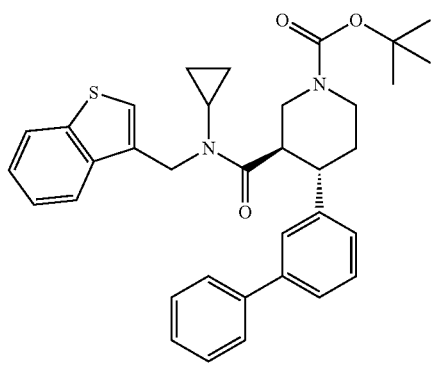

Intermediate 85.1 is synthesized by condensation of Intermediate 1.2 (200 mg, 0.52 mmol) and Intermediate 85.2 (136 mg, 0.67 mmol) analogously to the preparation of Intermediate 4.1. White amorphous material; ES-MS: M+H=567; HPLC: $_A t_{Ret}$=5.70 min.

Intermediate 85.2

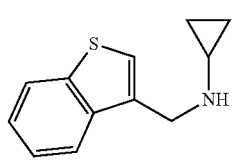

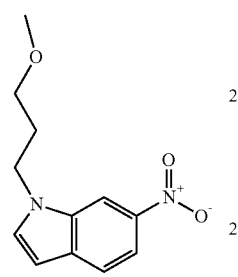

Intermediate 83.3 is synthesized by alkylation of 6-nitroindole (810 mg, 5.00 mmol) and toluene-4-sulfonic acid 3-methoxy-propyl ester (1.34 g, 5.50 mmol) analogously to the known method (see e.g. *European Journal of Medicinal Chemistry* 1998, 33, 957-967. or EP 432893). Yellow oil; ES-MS: M+H=235; HPLC: $_A t_{Ret}$=4.14 min.

Intermediate 84.1

Intermediate 85.2 is synthesized by condensation of benzothiophene-3-carbaldehyde (1.00 g, 6.20 mmol) and cyclopropylamine (530 mg, 9.30 mmol) analogously to the preparation of Intermediate 4.5. Yellow oil; ES-MS: M+H=204; HPLC: $_A t_{Ret}$=2.32 min.

Intermediate 86.1

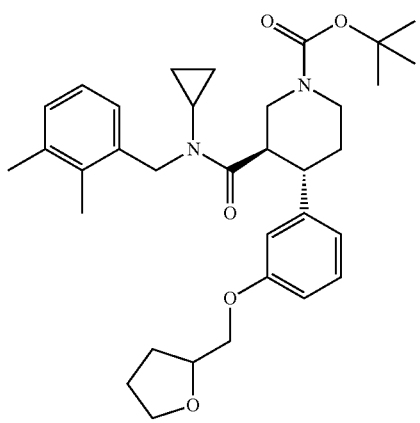

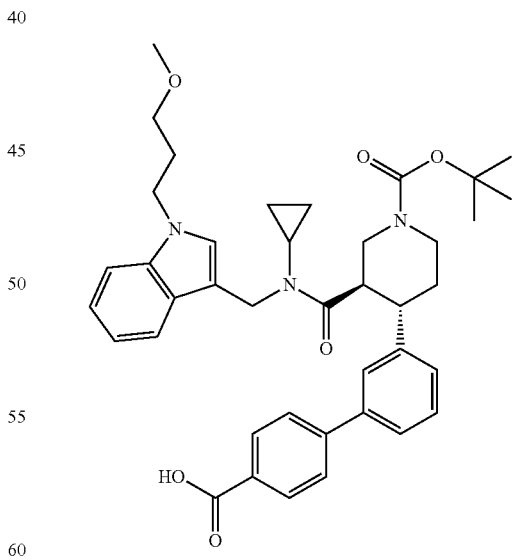

Intermediate 84.1 is synthesized by Mitsunobu reaction of Intermediate 26.2 (150 mg, 0.314 mmol) and (Tetrahydrofuran-2-yl)-methanol (48.1 mg, 0.471 mmol) analogously to the preparation of Intermediate 77.2. White amorphous material; ES-MS: M=563; HPLC: $_A t_{Ret}$=5.20 min.

To a solution of Intermediate 86.2 (241 mg, 0.35 mmol) in EtOH (1.5 mL) and THF (1.5 mL) is added 5N NaOH aqueous solution (1.5 mL). After stirring at 75° C. for 3 h, the reaction mixture is cooled to room temperature and acidified with 1N KHSO₄ solution. The resulting mixture is extracted with AcOEt and washed with brine. The organic layer is dried over Na$_2$SO$_4$ and concentrated to give Intermediate 86.1 as crude product; ES-MS: M+H=666; HPLC: $_At_{Ret}$=4.74 min.

Intermediate 86.2

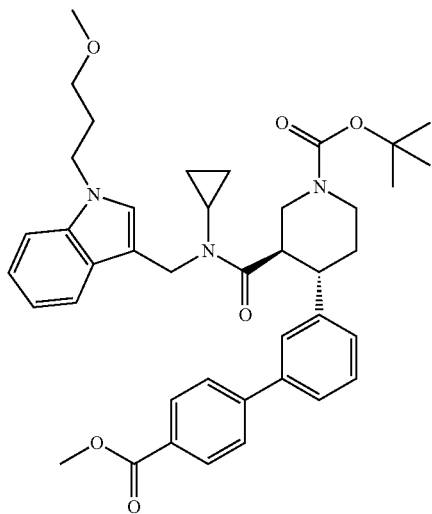

Intermediate 86.2 is synthesized by coupling of Intermediate 42.2 (396 mg, 0.57 mmol) and 4-Methoxycarbonylphenylboronic acid (154 mg, 0.86 mmol) analogously to the preparation of Intermediate 2.1. White amorphous material; ES-MS: M+H=680; HPLC: $_At_{Ret}$=5.50 min.

Intermediate 87.1

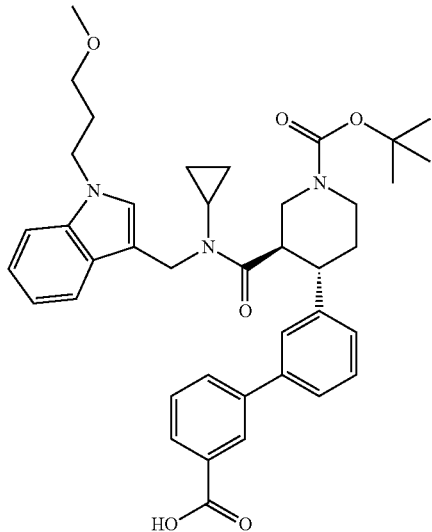

To a solution of Intermediate 87.2 (370 mg, 0.35 mmol) in EtOH (3.0 mL) and THF (1.5 mL) is added 5N NaOH aqueous solution (1.5 mL). After stirring at 80° C. for 3 h, the reaction mixture is cooled to room temperature and acidified with 1N KHSO$_4$ solution. The resulting mixture is extracted with AcOEt and washed with brine. The organic layer is dried over Na$_2$SO$_4$ and concentrated to give Intermediate 87.1 as crude product; ES-MS: M+H=666; HPLC: $_At_{Ret}$=4.77 min.

Intermediate 87.2

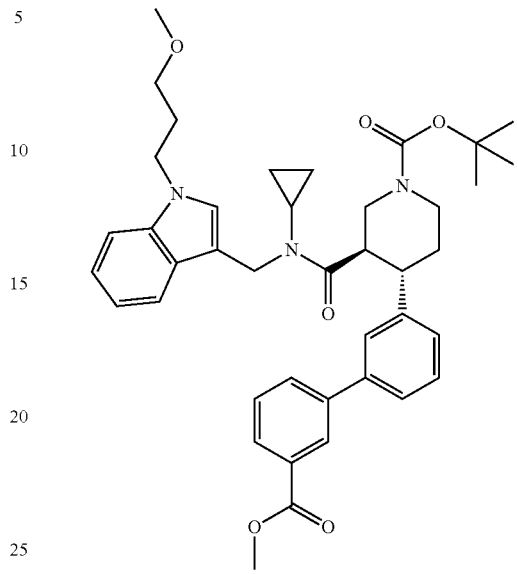

Intermediate 87.2 is synthesized by coupling of Intermediate 42.2 (400 mg, 0.58 mmol) and 3-Methoxycarbonylphenylboronic acid (156 mg, 0.87 mmol) analogously to the preparation of Intermediate 2.1. White amorphous material; ES-MS: M+H=680; HPLC: $_At_{Ret}$=5.52 min.

Intermediate 88.1

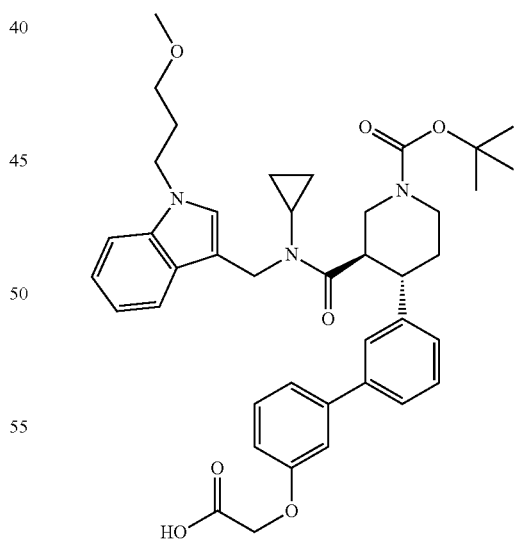

Intermediate 88.1 is synthesized by hydrolysis of Intermediate 88.2 (740 mg, 1.02 mmol) analogously to the preparation of Intermediate 80.1. White amorphous material; ES-MS: M+H=696; HPLC: $_At_{Ret}$=4.72 min.

Intermediate 88.2

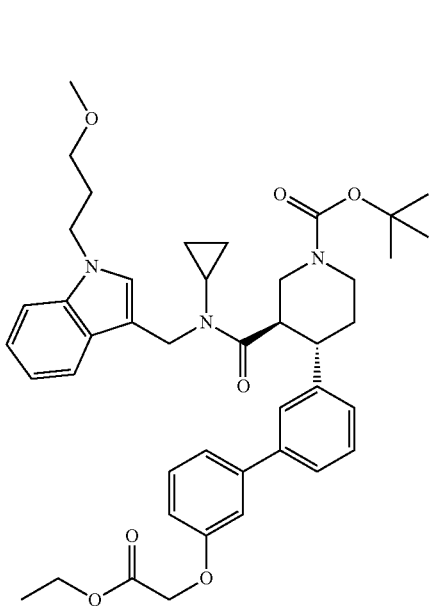

Intermediate 88.2 is synthesized by reaction of Intermediate 88.3 and iodoethyl acetate analogously to the preparation of Intermediate 80.2. White amorphous material; ES-MS: M+H=724; HPLC: $_At_{Ret}$=5.42 min.

Intermediate 88.3

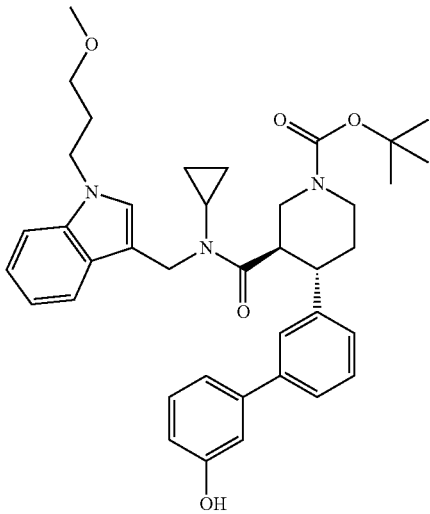

Intermediate 88.3 is synthesized by coupling of Intermediate 42.2 (841 mg, 1.21 mmol) and 3-Hydroxyphenylboronic acid (251 mg, 1.82 mmol) analogously to the preparation of Intermediate 2.1. White amorphous material; ES-MS: M+H=638; HPLC: $_At_{Ret}$=4.90 min.

Intermediate 89.1

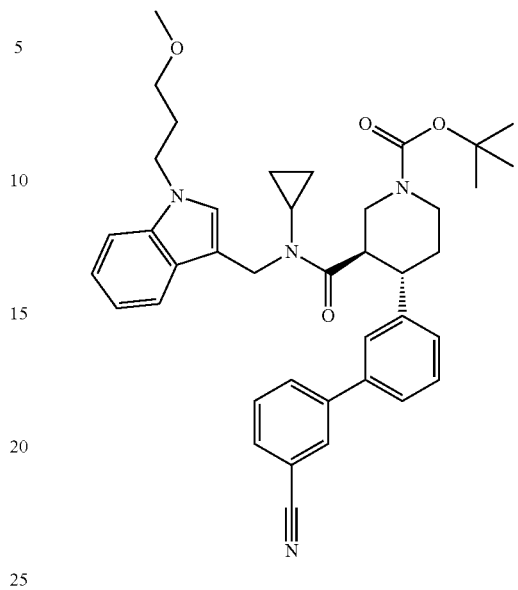

Intermediate 89.1 is synthesized by coupling of Intermediate 42.2 (412 mg, 0.59 mmol) and 3-Cyanophenylboronic acid (131 mg, 0.89 mmol) analogously to the preparation of Intermediate 2.1. White amorphous material; ES-MS: M+H=647; HPLC: $_At_{Ret}$=5.34 min.

Intermediate 90.1

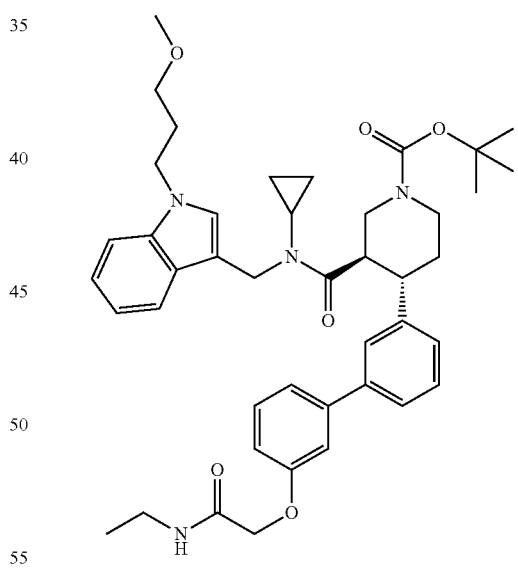

To a solution of Intermediate 88.1 (256 mg, 0.37 mmol) and ethylamine (0.28 mL, 0.55 mmol, 2M in THF) in DMF (2 mL) are added EDCl (85 mg, 0.44 mmol) and HOAt (10 mg, 0.074 mmol). After stirring at room temperature for overnight, the reaction is quenched with $H_2O$. The resulting mixture is extracted with $Et_2O$ and washed with brine. The organic layer is dried ($N_2SO_4$) and concentrated. Silica gel column chromatography give Intermediate 90.1 as white amorphous; ES-MS: M+H=723; HPLC: $_At_{Ret}$=4.95 min.

Intermediate 91.1

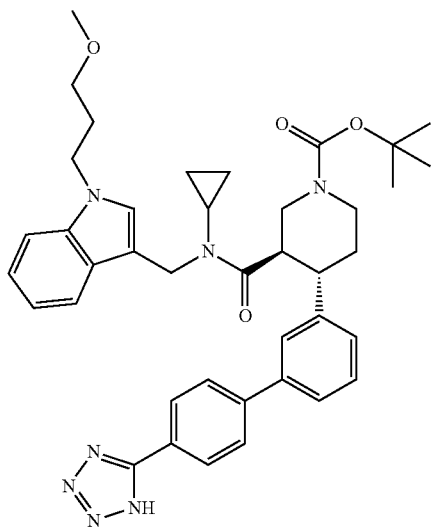

To a solution of Intermediate 81.1 (142 mg, 0.22 mmol) in toluene (1 mL) are added NaN$_3$ (43 mg, 0.66 mmol) and Triethylammonium chloride (90 mg, 0.66 mmol). After stirring at 120° C. for 4 days, the reaction mixture is cooled to room temperature and 1N KHSO$_4$ solution is added. The resulting mixture is extracted with AcOEt, dried (Na$_2$SO$_4$) and concentrated. Purification by silica gel column chromatography give by Intermediate 91.1 as white amorphous; ES-MS: M+H=690; HPLC: $_At_{Ret}$=4.65 min.

Intermediate 92.1

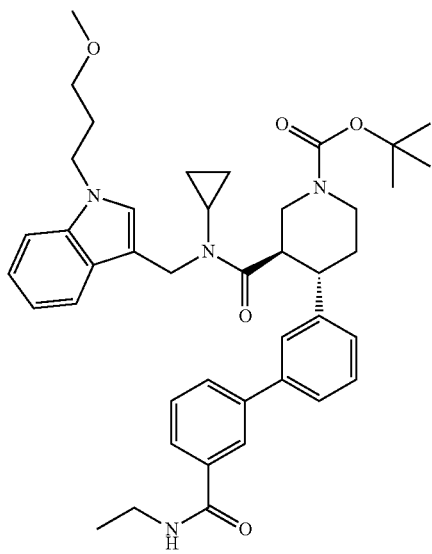

Intermediate 92.1 is synthesized by condensation of Intermediate 87.1 (229 mg, 0.34 mmol) and Ethylamine (0.28 mL, 0.56 mmol, 2M in THF) analogously to the preparation of Intermediate 90.1. White amorphous material; ES-MS: M+H=693; HPLC: $_At_{Ret}$=4.92 min.

Intermediate 93.1

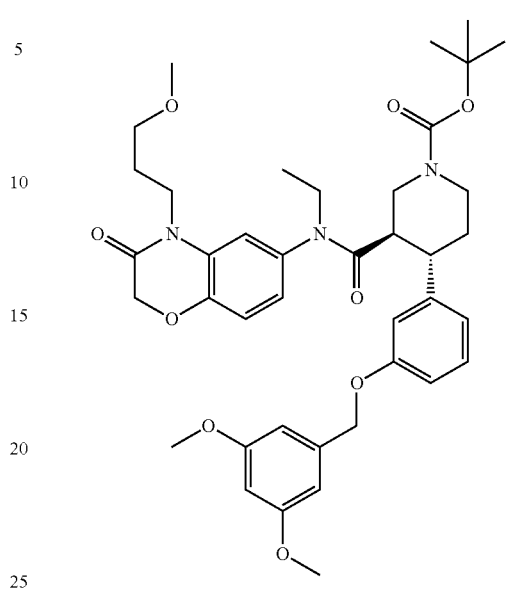

Intermediate 93.1 is synthesized by alkylation of Intermediate 93.2 (109 mg, 0.16 mmol) and EtI (19 μL, 0.24 mmol) analogously to the preparation of Intermediate 76.1. Colorless oil; ES-MS: M+H=718; HPLC: $_At_{Ret}$=5.02 min.

Intermediate 93.2

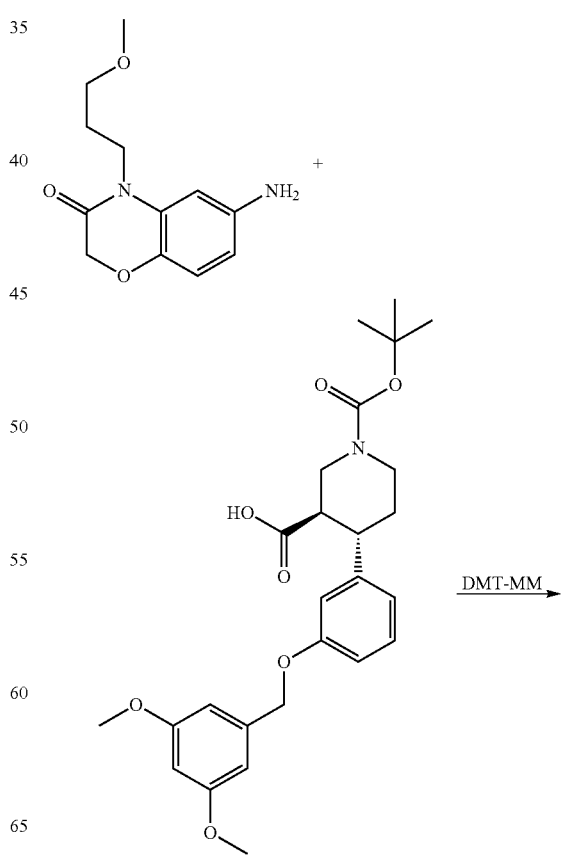

Intermediate 94.2

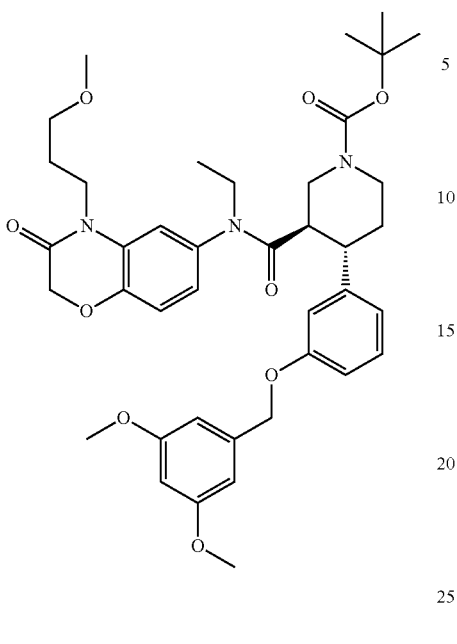

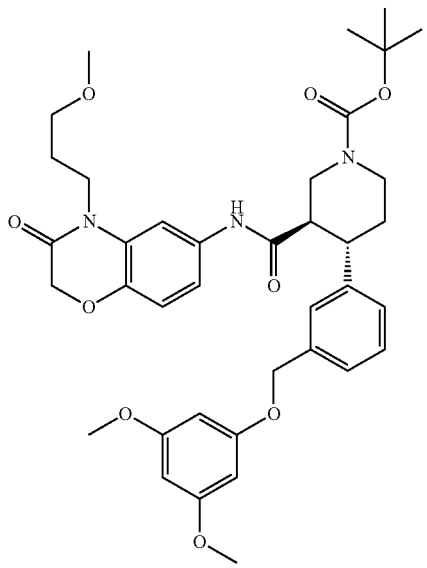

Intermediate 93.2 is synthesized by condensation of Intermediate 38.2 (71 mg, 0.3 mmol) and Intermediate 13.3 (141 mg, 0.3 mmol) analogously to the preparation of Intermediate 83.2. Colorless oil; ES-MS: M+H=690; HPLC: $_A t_{Ret}$=4.75 min.

Intermediate 94.1

Intermediate 94.2 is synthesized by condensation of Intermediate 38.2 (71 mg, 0.3 mmol) and Intermediate 23.2 (141 mg, 0.3 mmol) analogously to the preparation of Intermediate 83.2. Colorless oil; ES-MS: M+H=690; HPLC: $_A t_{Ret}$=4.74 min.

Intermediate 95.1

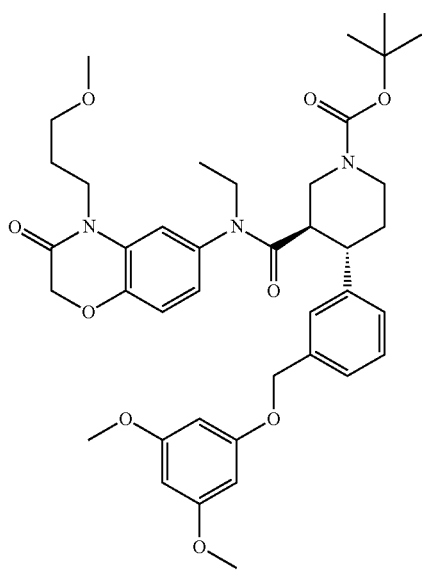

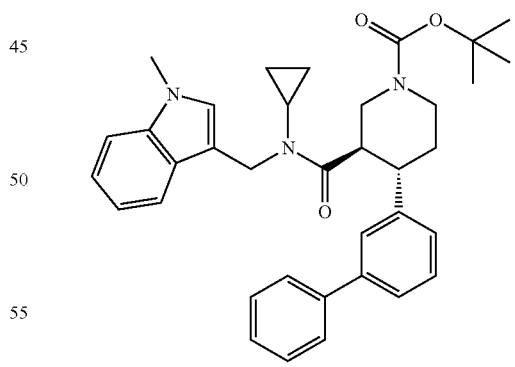

Intermediate 94.1 is synthesized by alkylation of Intermediate 94.2 (114 mg, 0.16 mmol) and EtI (20 pt, 0.25 mmol) analogously to the preparation of Intermediate 76.1. Colorless oil; ES-MS: M+H=718; HPLC: $_A t_{Ret}$=5.03 min.

Intermediate 95.1 is synthesized by condensation of Intermediate 1.2 (200 mg, 0.52 mmol) and cyclopropyl(1-methyl-1H-indol-3-yl-methyl)amine (136 mg, 0.67 mmol) analogously to the preparation of Intermediate 4.1. White amorphous material; ES-MS: M+H=564; HPLC: $_A t_{Ret}$=5.50 min.

Intermediate 96.1

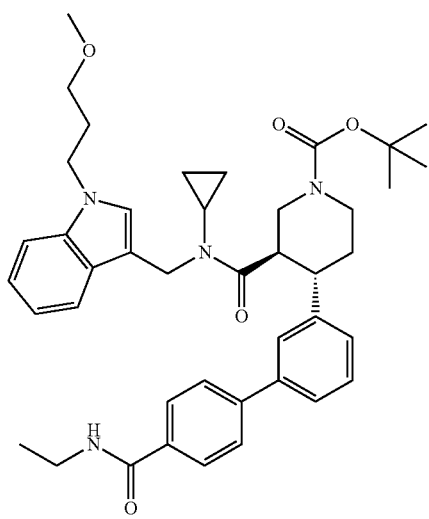

Intermediate 96.1 is synthesized by condensation of Intermediate 86.1 (111 mg, 0.17 mmol) and ethylamine (0.13 mL, 0.26 mmol, 2M in THF) analogously to the preparation of Intermediate 90.1. White amorphous material; ES-MS: M+H=693; HPLC: $_A t_{Ret}$=4.85 min.

Intermediate 97.1

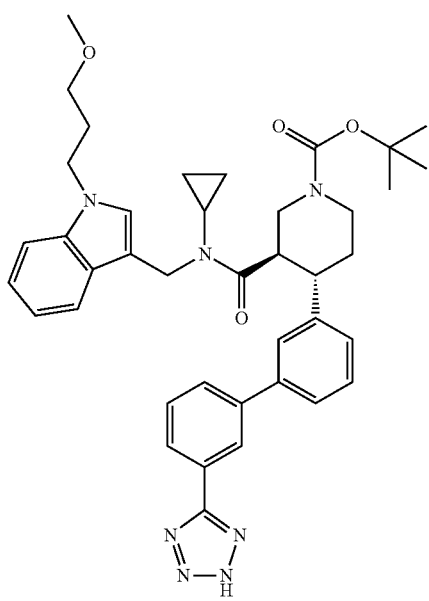

Intermediate 97.1 is synthesized by the reaction of Intermediate 89.1 (200 mg, 0.31 mmol) and NaN$_3$ (60 mg, 0.92 mmol) analogously to the preparation of Intermediate 91.1. White amorphous material; ES-MS: M+H=690; HPLC: $_A t_{Ret}$=4.82 min.

Intermediate 98.1

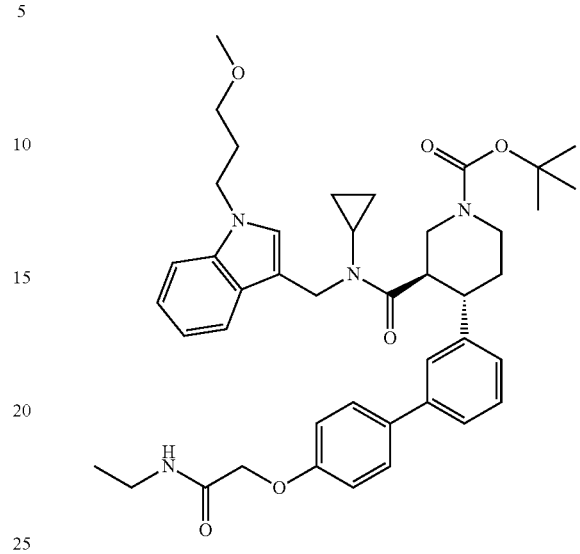

Intermediate 98.1 is synthesized by condensation of Intermediate 80.1 (200 mg, 0.29 mmol) and ethylamine (0.20 mL, 0.4 mmol, 2M in THF) analogously to the preparation of Intermediate 90.1. White amorphous material; ES-MS: M+H=723; HPLC: $_A t_{Ret}$=4.90 min.

Intermediate 99.1

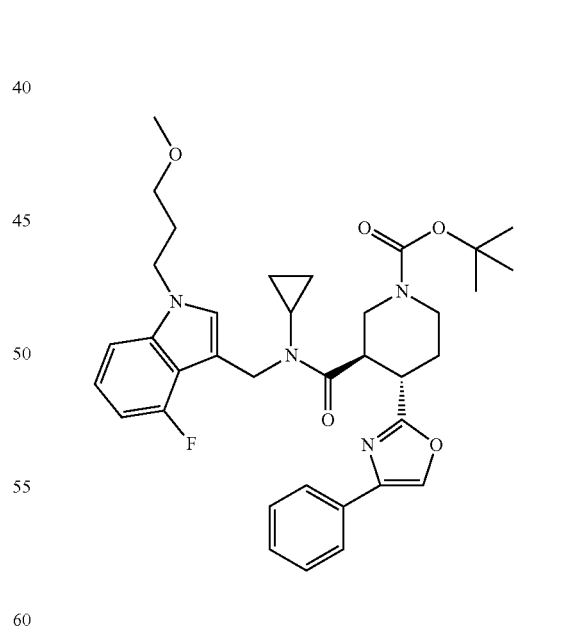

Intermediate 99.1 is synthesized by condensation of Intermediate 99.2 (78 mg, 0.21 mmol) and Intermediate 46.2 (64 mg, 0.23 mmol) analogously to the preparation of Intermediate 4.1. White amorphous material; ES-MS: M+H=631; HPLC: $_A t_{Ret}$=5.52 min.

Intermediate 99.2

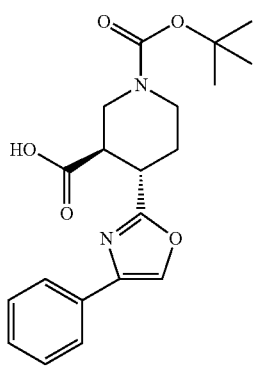

Intermediate 99.2 is synthesized by hydrolysis of Intermediate 99.3 (619 mg, 1.60 mmol) analogously to the preparation of Intermediate 4.2. White amorphous material; ES-MS: M+H=373; HPLC: $_At_{Ret}$=3.90 min.

Intermediate 99.3

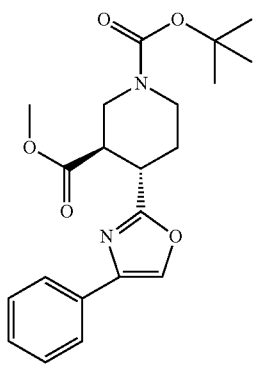

Intermediate 99.3 is synthesized by 1,4-reduction and epimerization of Intermediate 99.4 (835 mg, 2.17 mmol) analogously to the preparation of intermediate 4.3. White amorphous material; ES-MS: M+H=387; HPLC: $_At_{Ret}$=4.53 min.

Intermediate 99.4

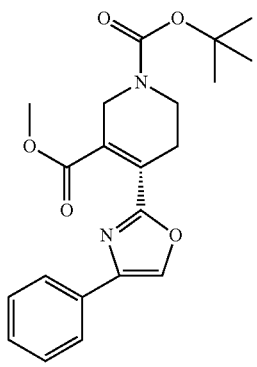

Intermediate 99.4 is synthesized by cross coupling of 5-phenyloxazole (421 mg, 2.90 mmol) (see e.g. *J. Org. Chem.* 1990, 55, 929.) and 4-trifluoromethanesulfonyloxy-5,6-dihydro-2H-pyridine-1,3-dicarboxylic acid 1-tert-butyl ester 3-methyl ester (1.1 g, 2.83 mmol) (see e.g. WO 2004/002957 or US 2003/216441) analogously to the preparation of Intermediate 69.4. colorless oil; ES-MS: M+H=385; HPLC: $_At_{Ret}$=4.67 min.

Intermediate 100.1

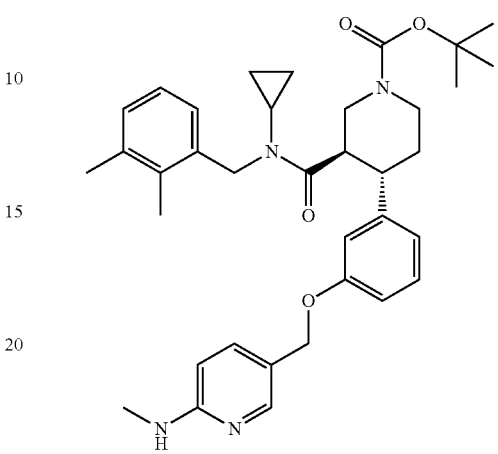

Intermediate 100.1 is synthesized by Mitsunobu reaction of Intermediate 42.1 (220 mg, 0.34 mmol) and Intermediate 100.2 (0.107 mL, 0.68 mmol) analogously to the preparation of Intermediate 77.1. White amorphous material; ES-MS: M=599; HPLC: $_At_{Ret}$=4.00 min.

Intermediate 100.2

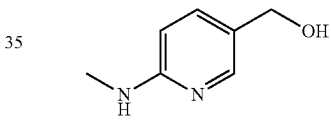

To a solution of 6-(Methylamino)-3-pyridinecarboxylic acid (1.13 g, 7.42 mmol) in THF (10 mL) is added LAH (423 mg, 11.1 mmol) at 0° C. After stirring at 50° C. for 20 h, Na$_2$SO$_4$.10H$_2$O is added at 0° C. The resulting mixture is filtered and the filtrate is concentrated. The residue is purified by silica gel column chromatography to give Intermediate 100.2; ES-MS: M=139; HPLC: $_At_{Ret}$=1.69 min.

Intermediate 101.1

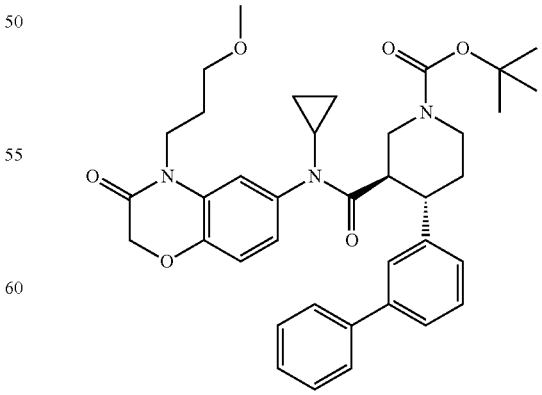

Intermediate 101.1 is synthesized by condensation of Intermediate 1.2 (300 mg, 0.44 mmol) and Intermediate 101.2

(121 mg, 0.44 mmol) analogously to the preparation of Intermediate 99.1. White amorphous material; ES-MS: M+H=640; HPLC: $_A t_{Ref}$=5.02 min.

Intermediate 101.2

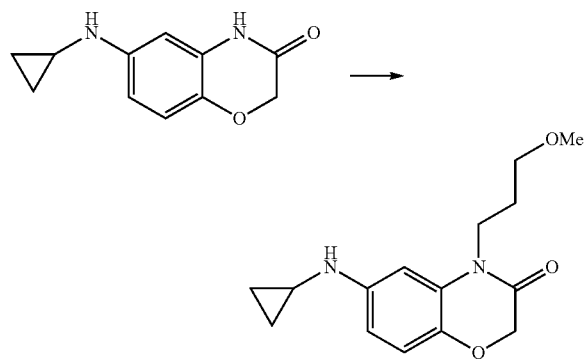

At 0° C., after adding KI (0.50 g, 3.01 mmol), a solution of Intermediate 101.3 (2.79 g, 13.7 mmol) and 1-methoxy-3-(p-toluenesulfonyloxy)propane (4.10 g, 16.8 mmol) in DMF (70 ml) is treated with 60% NaH (0.67 g, 16.8 mmol) over 5 min, stirred for 10 min, heated to 60° C., stirred for 3 h, and treated with H$_2$O (500 ml). After the extraction of the mixture with EtOAc (3×50 ml) and Et$_2$O (3×50 ml), the combined org. layer is washed with H$_2$O (80 ml), dried (Na$_2$SO$_4$), and evaporated. A SiO$_2$ flash chromatography (120 g, CH$_2$Cl$_2$/EtOAc 1:1) gives Intermediate 101.2 (2.81 g, 74%) as orange oil.

Intermediate 101.3

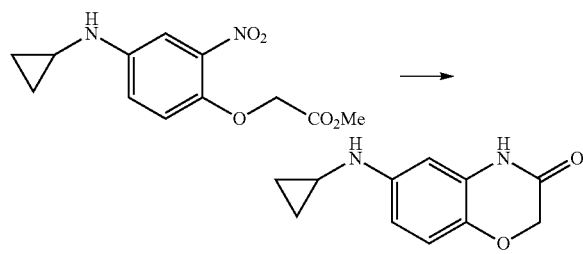

At room temperature, an ethanolic solution (830 ml) of Intermediate 101.4 (41.6 g, 0.16 mol) is treated with 6N HCl (78 ml, 0.47 mol of HCl) and powdered Fe (26.4 g, 0.47 mol), heated to 70° C., stirred for 5 h, filtered via celite pad, and the cake is washed with EtOH for several times. The combined filtrate is cooled, and stood at room temperature for 30 min to generate precipitates. The resulting solid is collected by a filtration followed by washing with EtOH and Et$_2$O in successive to give Intermediate 101.3 (22.2 g, 70%) as yellow solid.

Intermediate 101.4

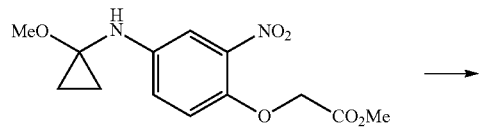

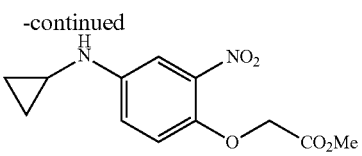

At 0° C., a suspension of NaBH$_4$ (15.1 g, 0.40 mol) in THF (600 ml) is treated dropwise with BF$_3$.Et$_2$O (51 ml, 0.40 mol) over 15 min, and stirred at the same temperature for 30 min. To this mixture is add dropwise a solution of Intermediate 101.5 (78.9 g, 0.27 mol) in THF (600 ml) over 40 min, keeping the internal temperature below 5° C. cooling with an ice-water bath. After stirring for 2 h, the reaction mixture is slowly poured into ice-water (1500 ml), and extracted with EtOAc (3×500 ml). The combined org. layer is washed with brine (350 ml), dried (Na$_2$SO$_4$), and evaporated. A SiO$_2$ flash chromatography (2000 g, hexane/EtOAc 1:1) gives Intermediate 101.4 (41.6 g, 60%) as yellow crystalline.

Intermediate 101.5

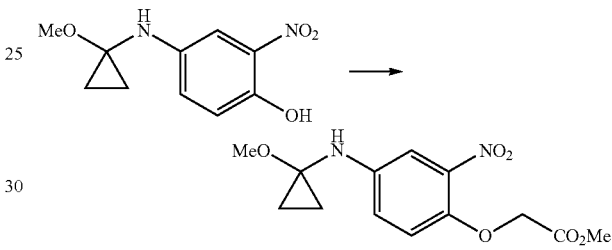

At room temperature, a solution of Intermediate 101.6 (55.8 g, 0.28 mol) in CH$_3$CN (670 ml) is treated with K$_2$CO$_3$ (58.3 g, 0.42 mol) and methyl bromoacetate (35 ml, 0.37 mol), stirred for 19 h, and treated furthermore K$_2$CO$_3$ (30.2 g, 0.22 mol) and methyl bromoacetate (35 ml, 0.37 mol). After additional stirring for 9 h at room temperature, the reaction mixture is filtered, and the filtrate is diluted with EtOAc (1000 ml), and washed with H$_2$O (500 ml). After the aqueous layer is extracted with EtOAc (3×200 ml), the combined org. layer is washed with brine (250 ml), dried (Na$_2$SO$_4$), and evaporated. A SiO$_2$ flash chromatography (2000 g, hexane/EtOAc 1:1) gives Intermediate 101.5 (74.2 g, 100%) as orange oil.

Intermediate 101.6

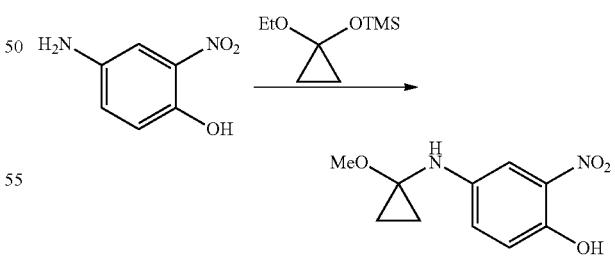

At room temperature, a methanolic solution (320 ml) of 4-amino-2-nitrophenol (39.7 g, 0.26 mol) is treated with AcOH (80 ml) and [(1-ethoxycyclopropyl)oxy]trimethyl-silane (57 ml, 0.28 mol), stirred at 75° C. for 3 h, and evaporated. After co-evaporation with PhMe for several times until the smell of AcOH disappeared, the residue is dissolved in EtOAc (2000 ml), and the solution is washed with 10% aqueous solution of K$_2$CO$_3$ (600 ml). After the aqueous layer is extracted with EtOAc (3×600 ml), the combined org. layer is washed with brine (300 ml), dried (Na$_2$SO$_4$), and evaporated to obtain Intermediate 101.6 (55.8 g, 97%) as dark red crystalline.

Intermediate 102.1

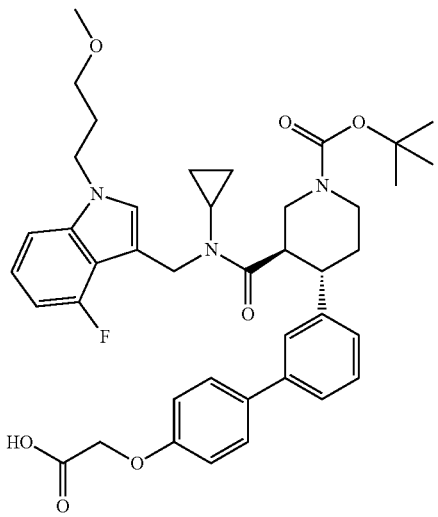

Intermediate 102.1 is synthesized by hydrolysis of intermediate 102.2 (310 mg, 0.42 mmol) analogously to the preparation of intermediate 80.2. White amorphous material; ES-MS: M+H=714; HPLC: $_A t_{Ret}$=4.37 min.

Intermediate 102.2

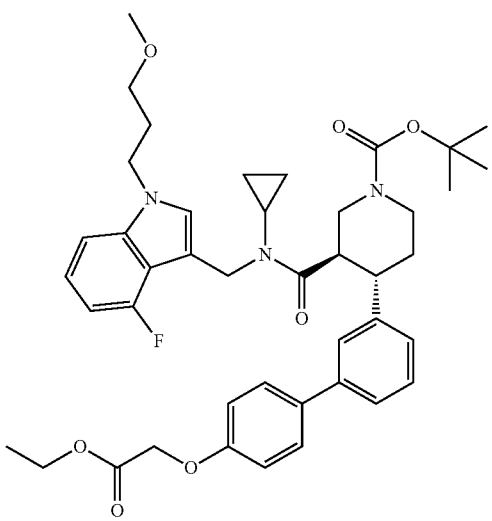

Intermediate 102.2 is synthesized by Alkylation of intermediate 102.3 (300 mg, 0.46 mmol) analogously to the preparation of intermediate 80.3. White amorphous material; ES-MS: M+H=742; HPLC: $_A t_{Ret}$=5.01 min.

Intermediate 102.3

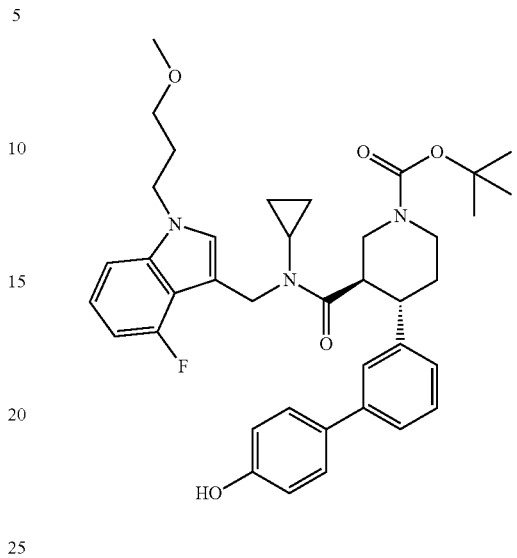

Intermediate 102.3 is synthesized by condensation of Intermediate 46.2 (600 mg, 2.26 mmol) and Intermediate 58.2 (600 mg, 1.51 mmol) analogously to the preparation of Intermediate 4.1. White amorphous material; ES-MS: M+H=656; HPLC: $_A t_{Ret}$=4.55 min.

Intermediate 103.1

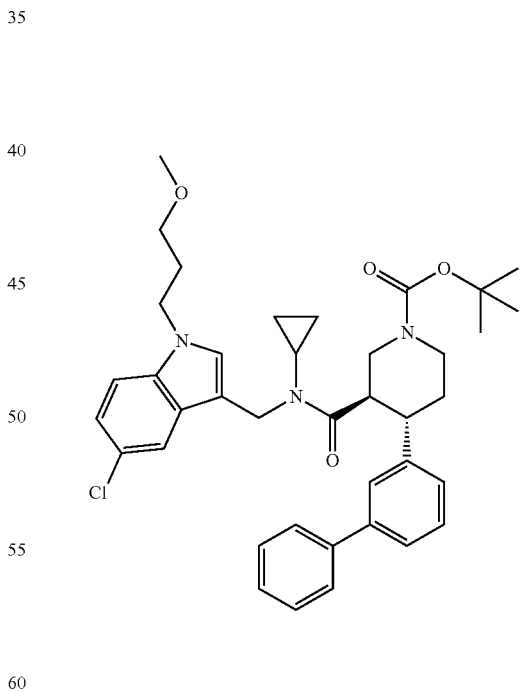

Intermediate 103.1 is synthesized by condensation of Intermediate 1.2 (200 mg, 0.52 mmol) and Intermediate 103.2 (292 mg, 1.04 mmol) analogously to the preparation of Intermediate 4.1. White amorphous material; ES-MS: M+H=656; HPLC: $_A t_{Ret}$=5.77 min.

Intermediate 103.2

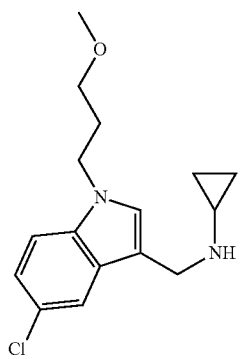

Intermediate 103.2 is synthesized by condensation of Intermediate 103.3 (1.00 g, 4.00 mmol) and cyclopropylamine (342 mg, 6.00 mmol) analogously to the preparation of Intermediate 4.5, which is directly used for the next step without further purification.

Intermediate 103.3

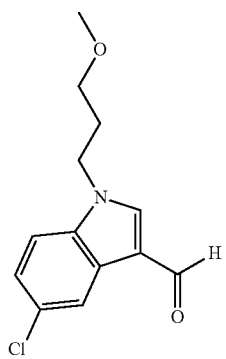

Intermediate 103.3 is synthesized by condensation of 5-chloro-1H-indole-3-carbaldehyde (1.00 g, 5.50 mmol) and toluene-4-sulfonic acid 3-methoxy-propyl ester (1.70 g, 7.20 mmol) analogously to the preparation of Intermediate 4.8. Yellow oil; ES-MS: M+H=252; HPLC: $_At_{Ret}$=3.63 min.

Intermediate 104.1

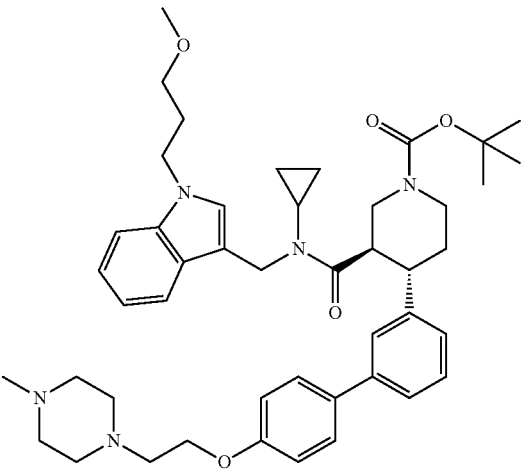

To a solution of Intermediate 42.1 (217 mg, 0.34 mmol), piperazine ethanol (74 mg, 0.51 mmol) and PPh$_3$ (178 mg, 0.68 mmol) in THF is added DEAD (0.27 mL, 0.68 mmol, 40% toluene solution). After stirring at 60° C. for 18 h, the reaction mixture is concentrated and purified by silica gel chromatography to give Intermediate 104.1 as white amorphous; ES-MS: M+=764; HPLC: $_At_{Ret}$=3.52 min.

Intermediate 105.1

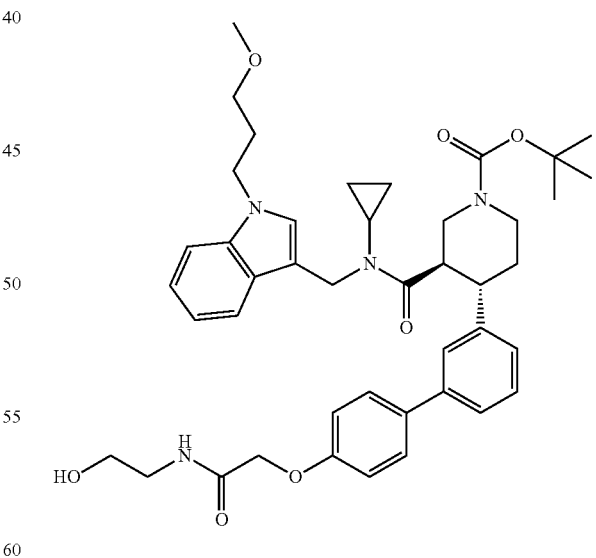

Intermediate 105.1 is synthesized by condensation of Intermediate 80.1 (201 mg, 0.29 mmol) and Aminoethanol (0.035 mL, 0.58 mmol) analogously to the preparation of Intermediate 90.1. White amorphous material; ES-MS: M+H=739; HPLC: $_At_{Ret}$=4.28 min.

Intermediate 106.1

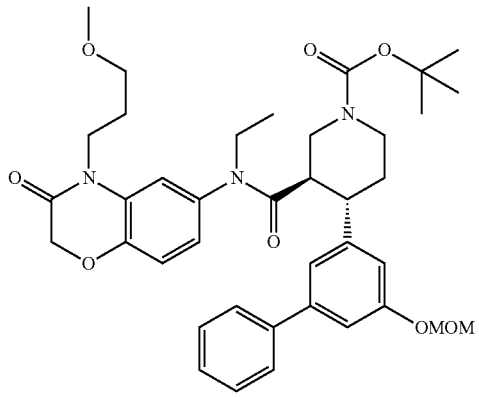

A mixture of Intermediate 106.2 (200 mg, 0.45 mmol) and 1-chloro-N,N-2-trimethyl-1-propenylamine (654, 0.5 mmol) in dichloromethane (5 mL) is stirred at RT. After stirring for 1 h, a mixture of Intermediate 82.2 (130.7 mg, 0.49 mmol) and pyridine (98 μL, 1.2 mmol) is added to the reaction mixture, and stirred for 1.5 at rt. After adding H$_2$O at RT, the reaction mixture is extracted with EtOAc. The combined organic phases are washed with 0.5 N HCl, brine and dried (Na$_2$SO$_4$). Concentration under reduced pressure and silica gel flash chromatography of the residue (hexane/ethyl acetate) affords Intermediate 106.1 as a white solid; ES-MS: M+H=688; HPLC: $_A t_{Ret}$=4.95 min.

Intermediate 106.2

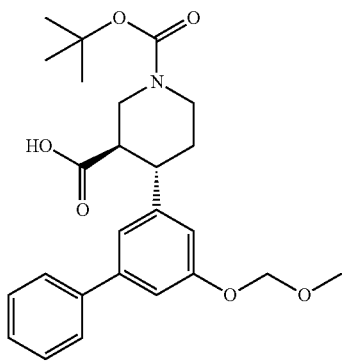

Intermediate 106.2 is synthesized by hydrolysis of Intermediate 48.3 (197 mg, 0.48 mmol) analogously to the preparation of Intermediate 4.2.

Intermediate 107.1

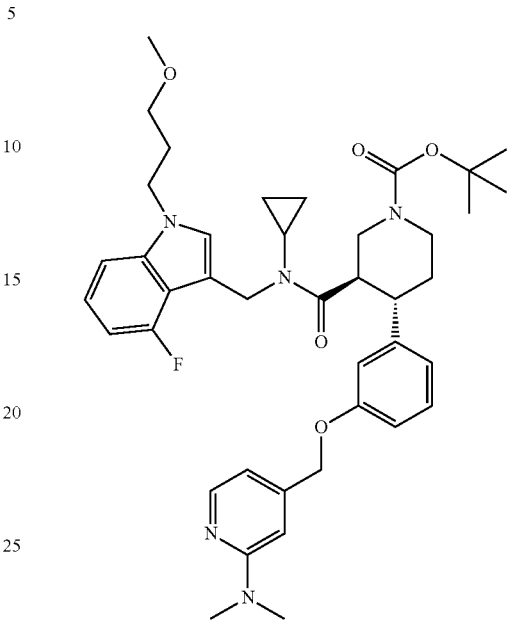

Intermediate 107.1 is synthesized by Mitsunobu reaction of Intermediate 107.2 (300 mg, 0.52 mmol) and 2-(dimethylamino)-4-pyridinemethanol (118 mg, 0.78 mmol) analogously to the preparation of Intermediate 77.1. White amorphous material; ES-MS: M+1=714; HPLC: $_A t_{Ret}$=3.85 min.

Intermediate 107.2

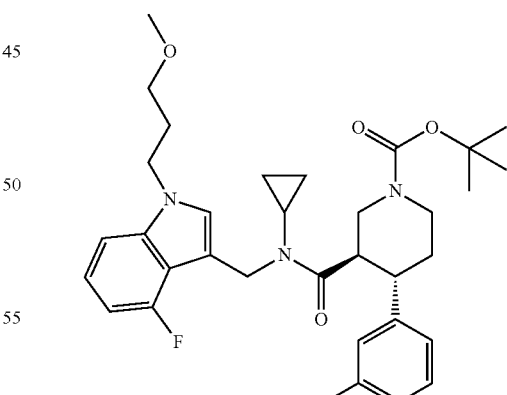

Intermediate 107.2 is synthesized by condensation of Intermediate 26.3 (2.92 g, 9.09 mmol) and Intermediate 46.2 (3.0 g, 10.9 mmol) analogously to the preparation of Intermediate 4.1. White amorphous material; ES-MS: M+H=580; HPLC: $_A t_{Ret}$=4.82 min.

Intermediate 108

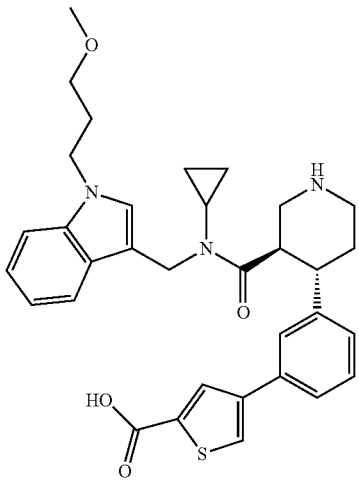

To a solution of Intermediate 108.1 (165 mg, 0.24 mmol) in MeOH (2 mL)-THF (1 mL) is added 2N aq. NaOH (1 mL). After sirred at room temperature for 2.5 h, the reaction mixture is washed with ether. The aqueous layer is acidified with aq. $KHSO_4$, and extracted with EtOAc. The combined organic extracts are dried ($Na_2SO_4$), filtered, and concentrated in vacuo. The residue is treated with TMSOTf (0.070 mL, 0.39 mmol) and 2,6-lutidine (0.090 mL, 0.77 mmol) in $CH_2Cl_2$ (2 mL) at 0° C. for 2 h. The reaction is quenched by the addition of sat. aq. $NaHCO_3$ and MeOH. The mixture is purified by RP-HPLC to give 108 as pale purple solid.

Intermediate 108.1

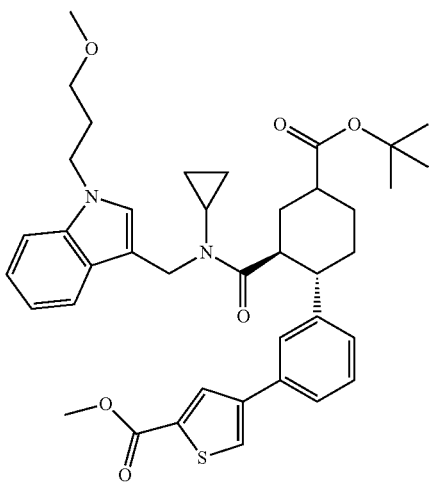

Intermediate 108.1 is synthesized by cross coupling of Intermediate 42.2 (178 mg, 0.26 mmol) and Intermediate 108.2 (83 mg, 0.31 mmol) analogously to the preparation of Intermediate 2.1. Pale yellow oil; ES-MS: M+H=686; HPLC: $_At_{Ret}$=5.34 min.

Intermediate 108.2

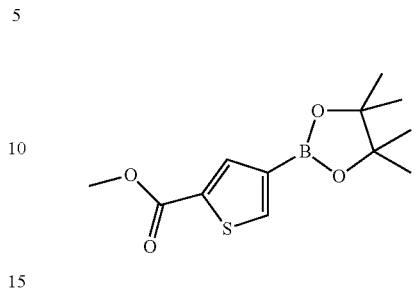

A mixture of methyl 4-bromo-2-thiophenecarboxylate (1.8 g, 8.14 mmol) (see e.g. *Bioorg. Med. Chem. Lett.* 2002, 12, 491.), bis(pinacolate)diboron (2.3 g, 9.06 mmol), KOAc (2.4 g, 24.5 mmol) and Pd(dppf)$Cl_2$ (250 mg, 0.31 mmol) in DMSO (25 mL) is stirred under $N_2$ at 90° C. After stirred for 9 h, the reaction quenched by the addition of $H_2O$, and the resulting mixture is extracted with EtOAc. The combined organic extracts are washed with $H_2O$ and brine, and dried ($Na_2SO_4$). Concentration under reduced pressure and silica gel column chromatography give Intermediate 108.2. White solid; ES-MS: M+H=269; HPLC: $_At_{Ret}$=4.25 min.

Intermediate 109.1

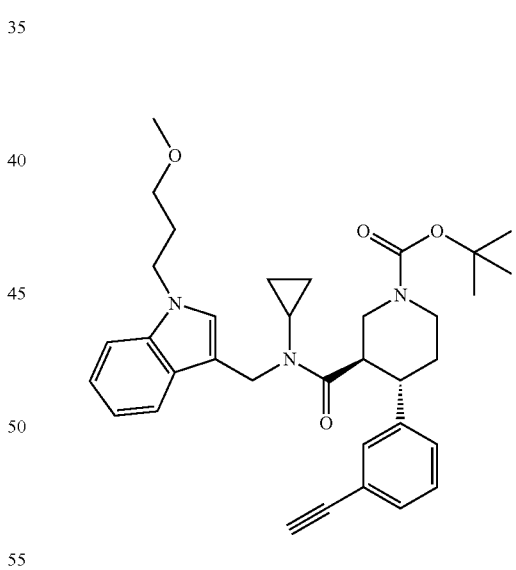

A mixture of Intermediate 109.2 (112.4 mg, 0.17 mmol) and $K_2CO_3$ (72.1 mg, 0.52 mmol) in MeOH (5 mL) is stirred at RT. After stirring for 2 h, adding $H_2O$ at RT, the reaction mixture is extracted with 1,2-dichloroethane. The combined organic phases are dried ($Na_2SO_4$). Concentration under reduced pressure affords Intermediate 109.1 as amorphous; ES-MS: M+H=470; HPLC: $_At_{Ret}$=3.15 min.

Intermediate 109.2

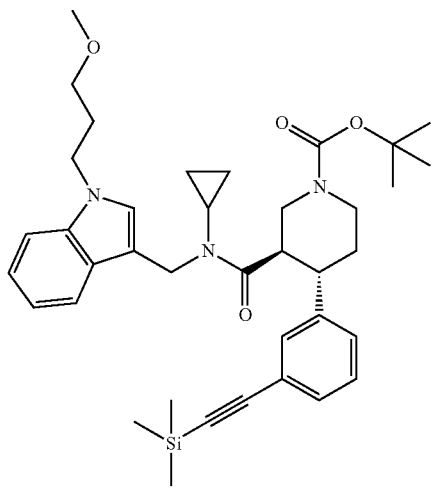

A mixture of Intermediate 42.2 (204.6 mg, 0.30 mmol), (trimethylsliy)acethylene (62 µL, 0.44 mmol), TBAI (326.9 mg, 0.89 mmol), PdCl$_2$(PPh$_3$)$_2$ (20.7 mg, 0.03 mmol) and CuI (16.8 mg, 0.089 mmol) in DMF (5 mL) and Et$_3$N (1 mL) is stirred at 80° C. After stirring for 3.5 h, adding H$_2$O at RT, the reaction mixture is extracted with EtOAc. The combined organic phases are washed with H$_2$O and dried (Na$_2$SO$_4$). Concentration under reduced pressure and silica gel flash chromatography of the residue (hexane/ethyl acetate) affords Intermediate 109.2 as a white solid; ES-MS: M+H=642; HPLC: $_A$t$_{Ret}$=6.02 min.

Intermediate 110.1

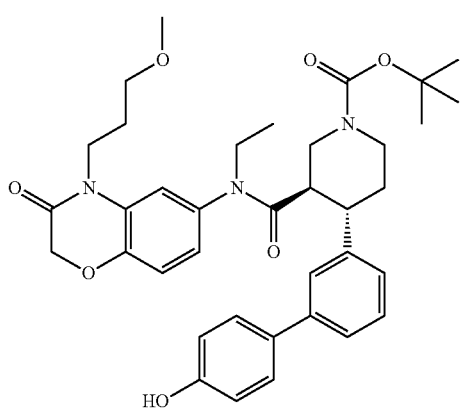

To a solution of intermediate 110.2 (90 mg, 0.13 mmol) in EtOH (2.0 mL) and H$_2$O (2.0 mL) is added 2N NaOH aqueous solution (1.0 mL, 0.5 mmol). After stirring at 60° C. for 1 h, the reaction mixture is cooled to room temperature and acidified with 1N KHSO$_4$ solution. The resulting mixture is extracted with AcOEt and washed with brine. The organic layer is dried over Na$_2$SO$_4$ and concentrated to give intermediate 110.1; ES-MS: M+H=644; HPLC: $_A$t$_{Ret}$=4.20 min.

Intermediate 110.2

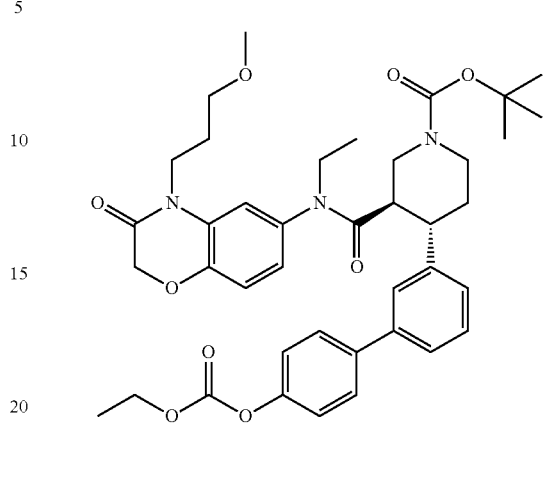

To a solution of intermediate 110.3 (300 mg, 0.76 mmol) in THF (5.0 mL), Et$_3$N (0.40 mL, 2.27 mmol) and Ethyl chloroformate (0.16 mL, 1.65 mmol) are added at 0° C. After stirring for 0.5 h at same temperature, the resulting precipitate is filtered off and the filtrate is concentrated. The residue is dissolved in THF-DMF (1 ml), intermediate 82.2 (502 mg1.9 mmol) and pyridine (0.32 mL, 3.03 mmol) are added at room temperature. After stirring for 1.5 h, the reaction is quenched with H$_2$O. The resulting mixture is extracted with AcOEt, washed with brine, dried (MgSO$_4$), and concentrated. Purification by silica gel column chromatograrphy give intermediate 110.2; M+H=716; HPLC: $_A$t$_{Ret}$=4.99 min.

Intermediate 110.3

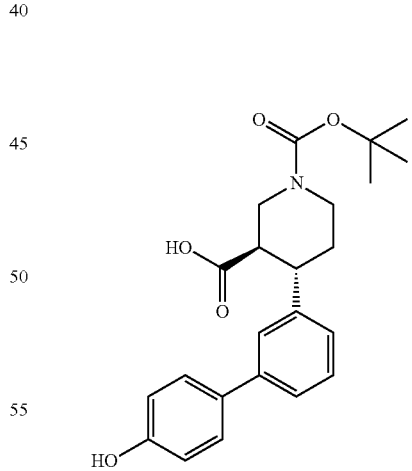

Intermediate 110.3 is synthesized by hydrogenation, epimerization and hydrolysis of Intermediate 110.4 (9.56 g, 23.4 mmol) analogously to the preparation of Intermediate 4.2/4.3. White amorphous material; ES-MS: M-$^t$Bu=342; HPLC: $_A$t$_{Ret}$=3.94 min.

Intermediate 110.4

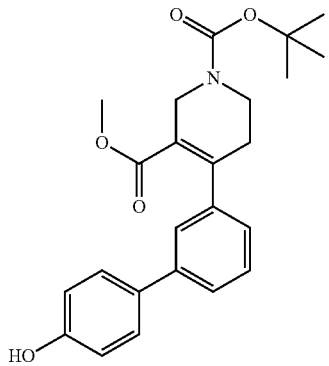

Intermediate 110.4 is synthesized by coupling of Intermediate 2.5 (10.0 g, 25.3 mmol) analogously to the preparation of Intermediate 2.1; ES-MS: M-$^t$Bu=354; HPLC: $_At_{Ret}$=4.38 min.

Intermediate 111.1

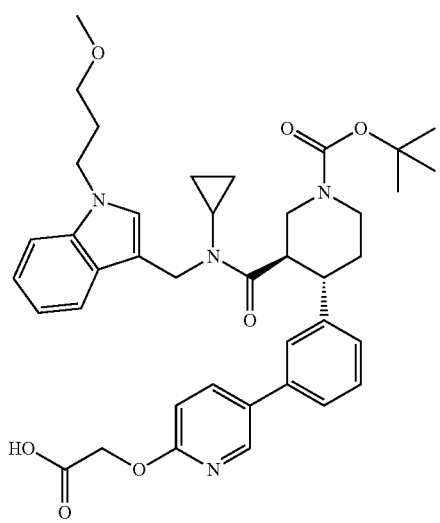

Intermediate 111.1 is synthesized by hydrolysis of intermediate 111.2 (160 mg, 0.42 mmol) analogously to the preparation of intermediate 80.2. White amorphous material; ES-MS: M+H=697; HPLC: $_At_{Ret}$=4.52 min.

Intermediate 111.2

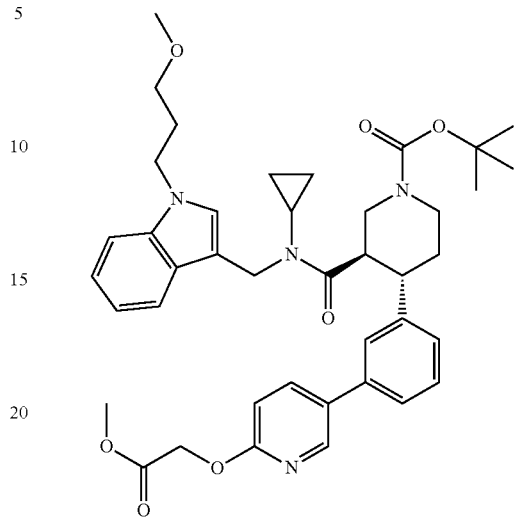

Intermediate 111.2 is synthesized by coupling of Intermediate 42.2 (300 mg, 0.43 mmol) and intermediate 111.3 (190 mg, 0.65 mmol) analogously to the preparation of Intermediate 42.1 White amorphous material; ES-MS: M+H=711; HPLC: $_At_{Ret}$=5.11 min.

Intermediate 111.3

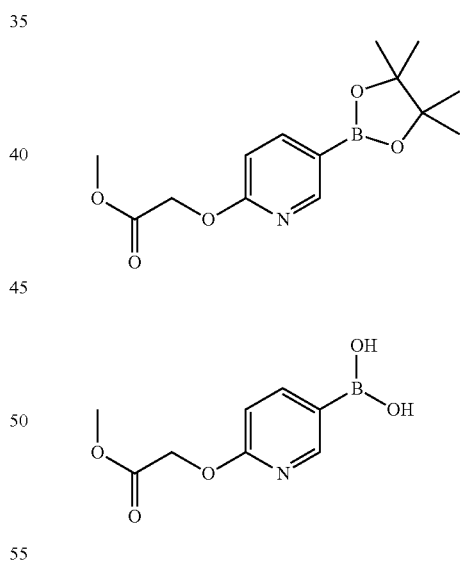

To a solution of (5-Bromo-pyridin-2-yloxy)-acetic acid methyl (1.0 g, 4.08 mmol) ester (see e.g. WO 2005/016870) in DMSO (20.0 mL) is added Bis(pinacolato)diboron (1.55 g, 6.12 mmol), PdCl$_2$(dppf) (0.38 g, 0.41 mmol) and KOAc (1.23 g, 12.54 mmol). After stirring at 80° C. for 2 h under N$_2$, the reaction mixture is diluted with AcOEt and washed with brine. The organic layer is dried (MgSO$_4$), concentrated and purified by silica gel column chromatography to afforded intermediate 111.3 as an oil. ES-MS: M-82=212; HPLC: $_At_{Ret}$=1.93 min as a boronic acid.

Intermediate 112.1

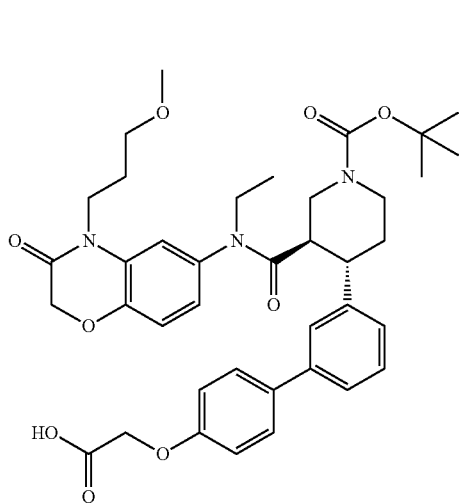

Intermediate 113.1

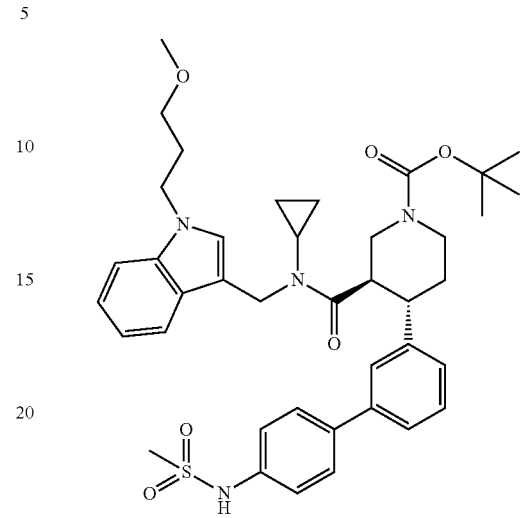

Intermediate 112.1 is synthesized by hydrolysis of intermediate 112.2 (120 mg, 0.17 mmol) analogously to the preparation of intermediate 80.1. White amorphous material; ES-MS: M+H=702; HPLC: $_At_{Ret}$=4.10 min.

Intermediate 112.2

Intermediate 113.1 is synthesized by coupling of Intermediate 42.2 (300 mg, 0.43 mmol) and N-[4-(4,4,5,5-Tetramethyl-[1,3,2]dioxaborolan-2-yl)-phenyl]-methanesulfonamide (170 mg, 0.65 mmol) analogously to the preparation of Intermediate 2.1. White amorphous material; ES-MS: M+H=715; HPLC: $_At_{Ret}$=4.71 min.

Intermediate 114.1

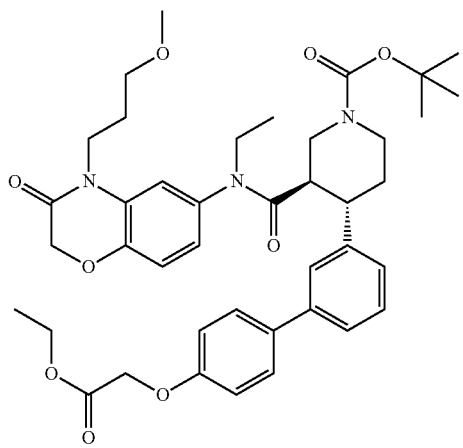

Intermediate 112.2 is synthesized by alkylation of intermediate 110.1 (145 mg, 0.23 mmol) analogously to the preparation of intermediate 80.2. White amorphous material; ES-MS: M+H=742; HPLC: $_At_{Ret}$=5.01 min.

Intermediate 114.1 is synthesized by condensation of Intermediate 13.3 (200 mg, 0.42 mmol) and Intermediate 101.2 (116 mg, 0.42 mmol) analogously to the preparation of Intermediate 106.1. White amorphous material; ES-MS: M+H=730; HPLC: $_At_{Ret}$=4.90 min.

Intermediate 115.1

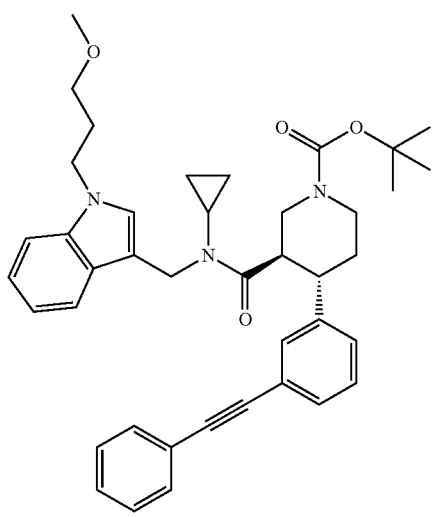

Intermediate 115.1 is synthesized by coupling of Intermediate 42.2 (222 mg, 0.32 mmol) and phenyl acetylene (52.7 μL, 0.48 mmol) analogously to the preparation of Intermediate 109.2. White amorphous material; ES-MS: M+H=646; HPLC: $_At_{Ret}$=5.84 min.

Intermediate 116.1

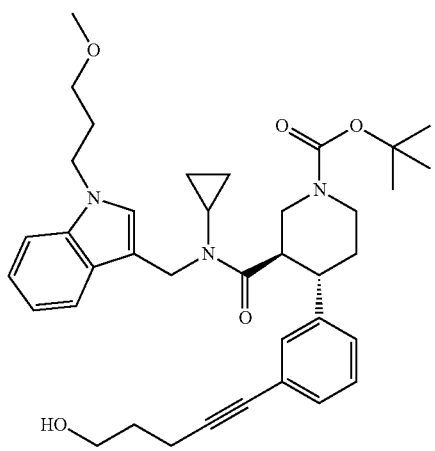

Intermediate 116.1 is synthesized by coupling of Intermediate 42.2 (221.0 mg, 0.31 mmol) and 4-pentyn-1-ol (38 μL, 0.42 mmol) analogously to the preparation of Intermediate 109.2. White amorphous material; ES-MS: M+H=628; HPLC: $_At_{Ret}$=4.67 min.

Intermediate 117.1

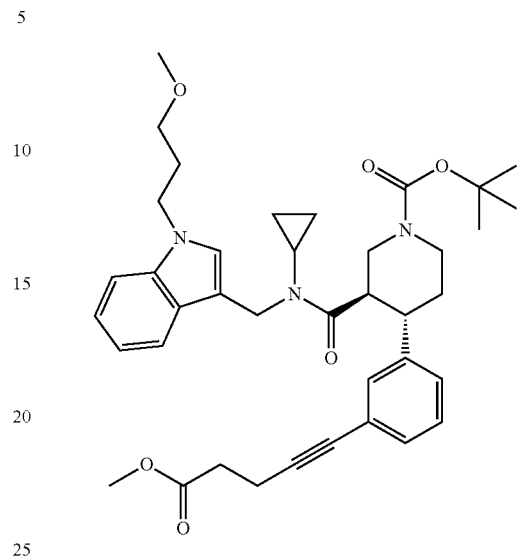

Intermediate 117.1 is synthesized by coupling of Intermediate 42.2 (200.0 mg, 0.28 mmol) and Pent-4-ynoic acid methyl ester (31.3 mg, 0.28 mmol) analogously to the preparation of Intermediate 109.2. White amorphous material; ES-MS: M+H=656; HPLC: $_At_{Ret}$=5.18 min.

Intermediate 118.1

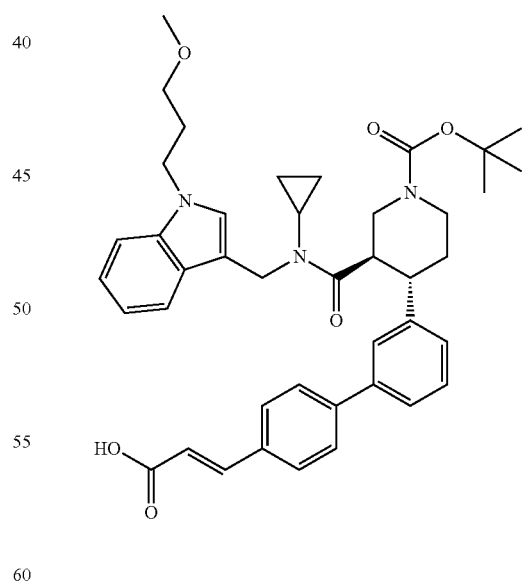

Intermediate 118.1 is synthesized by coupling of Intermediate 42.2 (400 mg, 0.58 mmol) and [4-(E-2-Carboxyvinyl)phenyl]boronic acid (166 mg, 0.87 mmol) analogously to the preparation of Intermediate 42.1 White amorphous material; ES-MS: M+H=692; HPLC: $_At_{Ret}$=4.78 min.

Intermediate 119.1

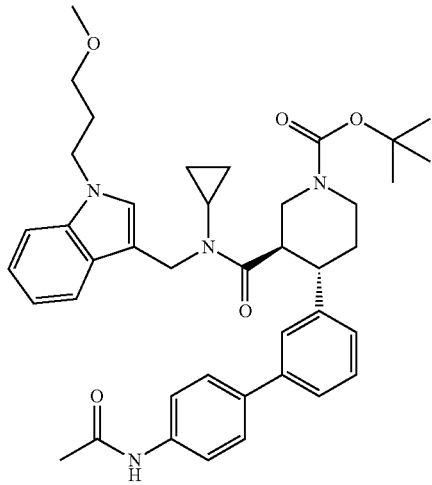

Intermediate 119.1 is synthesized by coupling of Intermediate 42.2 (300 mg, 0.43 mmol) and N-[4-(4,4,5,5-Tetramethyl-[1,3,2]dioxaborolan-2-yl)-phenyl]-acetamide (170 mg, 0.65 mmol) analogously to the preparation of Intermediate 42.1. White amorphous material; ES-MS: M+H=679; HPLC: $_A t_{Ret}$=4.61 min.

Intermediate 120.1

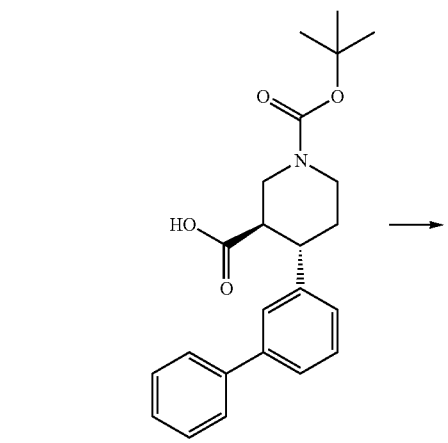

Intermediate 120.1 is synthesized by condensation of Intermediate 1.2 (222 mg, 0.58 mmol) and Intermediate 120.2 (155 mg, 0.53 mmol) analogously to the preparation of Intermediate 82.1. Yellow powder; ES-MS: M+H=656; HPLC: $_A t_{Ret}$=5.17 min.

Intermediate of 120.2

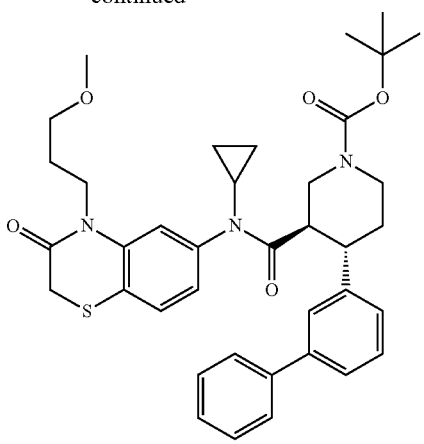

Intermediate 120.2 is synthesized by alkylation of Intermediate 120.3 (228 mg, 1.0 mmol) made analogously to the known method (see e.g. *European Journal of Medicinal Chemistry* 1998, 33, 957-967. or EP 432893). Orange solid; ES-MS: M+H=293; HPLC: $_A t_{Ret}$=3.70 min.

Intermediate 120.3

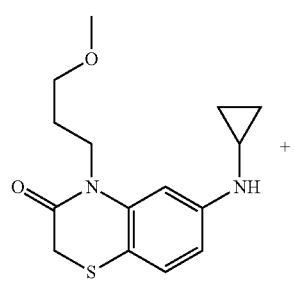

Intermediate 120.3 is synthesized by reduction of Intermediate 120.4 (143 g, 0.5 mmol) analogously to the preparation of Intermediate 76.3. Brown solid; ES-MS: M+H=221; HPLC: $_A t_{Ret}$=2.87 min.

Intermediate 120.4

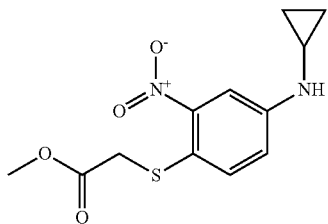

A mixture of Intermediate 120.5 (4.73 g, 2.4 mmol), methylthioglycolate (237 µL, 2.65 mmol), and NaH (115 mg, 2.88 mmol) in DMF (10 mL) is stirred under $N_2$ at 0° C. for 1 h. After adding $H_2O$, the reaction mixture is extracted with EtOAc. The combined organic phases are washed with $H_2O$ and dried ($Na_2SO_4$). Concentration under reduced pressure and silica gel flash chromatography give Intermediate 120.4 as orange oil; ES-MS: M+H=283; HPLC: $_At_{Ret}$=3.84 min.

Intermediate 120.5

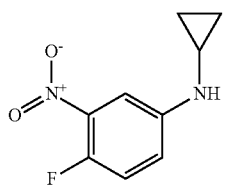

Intermediate 120.5 is synthesized by cyclopropanation of 4-fluoro-3-nitroaniline (3.25 g, 40.0 mmol) analogously to the preparation of Intermediate 101.4. Orange oil; ES-MS: M+H=197; HPLC: $_At_{Ret}$=3.82 min.

Intermediate 122.1

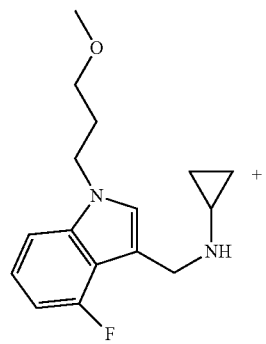

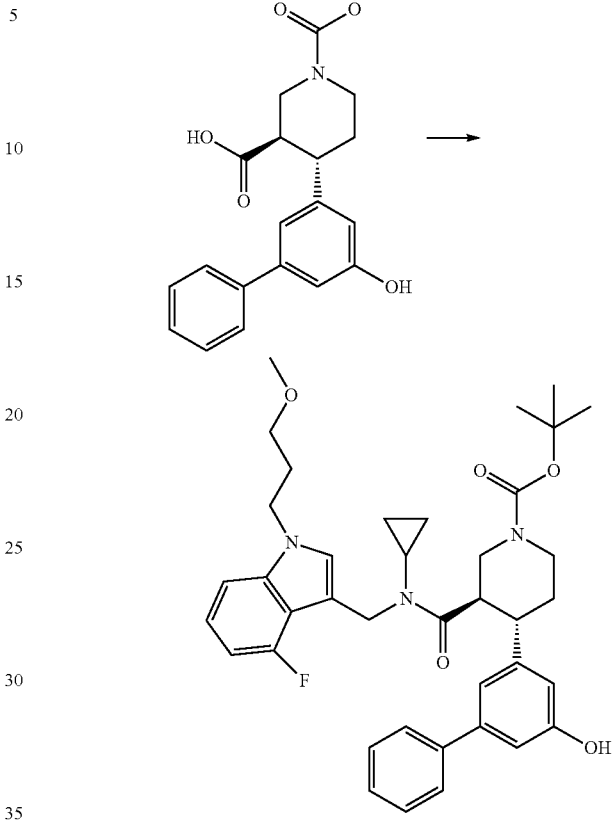

Intermediate 122.1 is synthesized by condensation of Intermediate 46.2 (143 mg, 0.52 mmol) and Intermediate 48.2 (187 mg, 0.47 mmol) analogously to the preparation of Intermediate 76.2. Colorless oil; ES-MS: M+H=656; HPLC: $_At_{Ret}$=5.09 min.

Intermediate 123.1

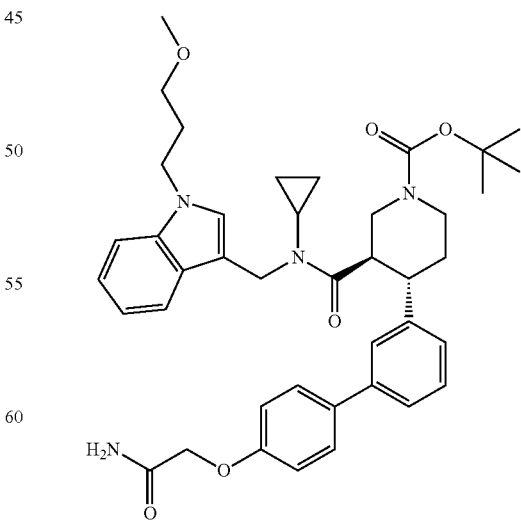

Intermediate 123.1 is synthesized by condensation of Intermediate 80.1 (200 mg, 0.29 mmol) and $NH_4Cl$ (31 mg, 0.58 mmol) analogously to the preparation of Intermediate 90.1. White amorphous material; ES-MS: M+H=695; HPLC: $_A t_{Ret}$=4.45 min.

Intermediate 124.1

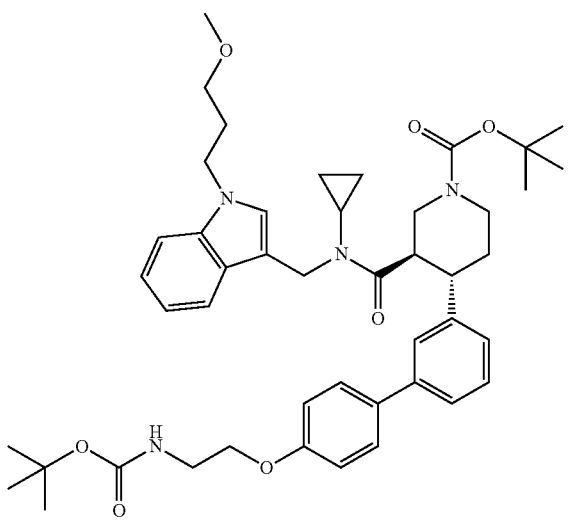

Intermediate 124.1 is synthesized by Mitsunobu reaction of Intermediate 42.1 (220 mg, 0.34 mmol) and N-Boc aminoethanol (0.107 mL, 0.68 mmol) analogously to the preparation of Intermediate 104.1. White amorphous material; ES-MS: M=781; HPLC: $_A t_{Ret}$=5.59 min.

Intermediate 125.1

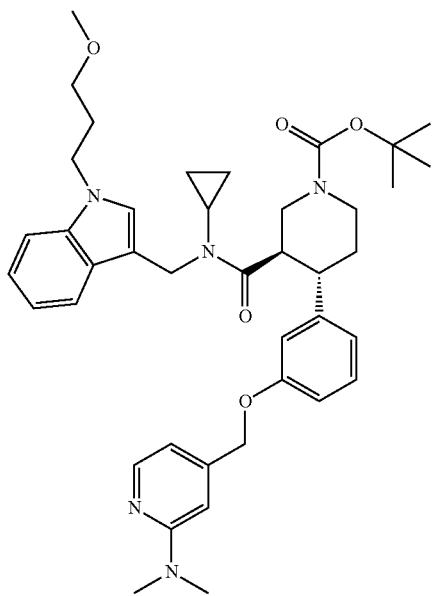

Intermediate 125.1 is synthesized by Mitsunobu reaction of Intermediate 42.3 (208 mg, 0.33 mmol) and 2-(Dimethylamino)-4-pyridinemethanol (99 mg, 0.65 mmol) analogously to the preparation of Intermediate 77.1. White amorphous material; ES-MS: M=772; HPLC: $_A t_{Ret}$=4.12 min.

Intermediate 126.1

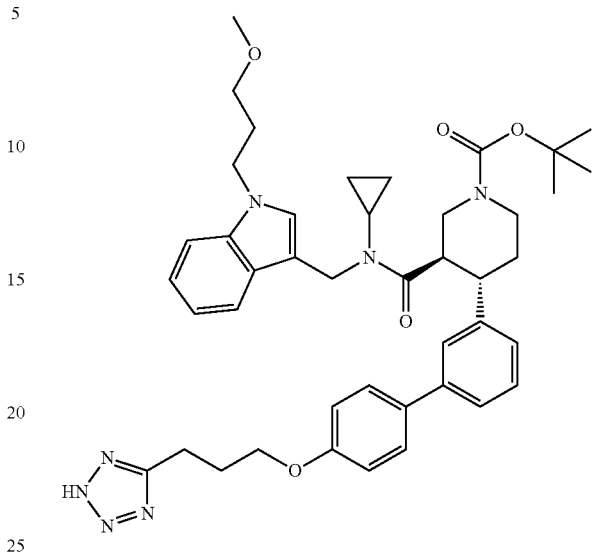

Intermediate 126.1 is synthesized by the reaction of Intermediate 126.2 (200 mg, 0.28 mmol) and NaN$_3$ (55 mg, 0.85 mmol) analogously to the preparation of Intermediate 91.1. White amorphous material; ES-MS: M+1=748; HPLC: $_C t_{Ret}$=2.14 min.

Intermediate 126.2

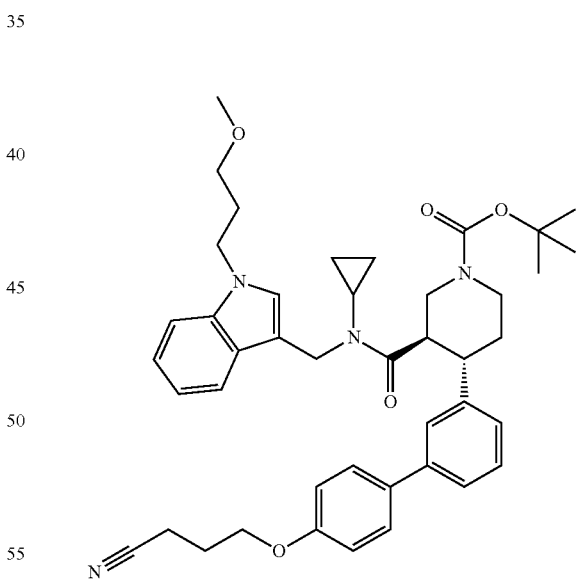

Intermediate 42.1 (250 mg, 0.39 mmol), 4-Bromo-butyronitrile (0.097 mL, 0.98 mmol) and K$_2$CO$_3$ (135 mg, 0.98 mmol) in DMF (3 mL) is stirred at 90° C. for 6 h. After cooling to room temperature, the reaction mixture is diluted with Et$_2$O and washed with H$_2$O and brine. The organic layer is dried (Na$_2$SO$_4$), concentrated and purified by silica gel column chromatography to give Intermediate 126.2 as white amorphous; ES-MS: M+1=705; HPLC: $_A t_{Ret}$=5.27 min.

Intermediate 127.1

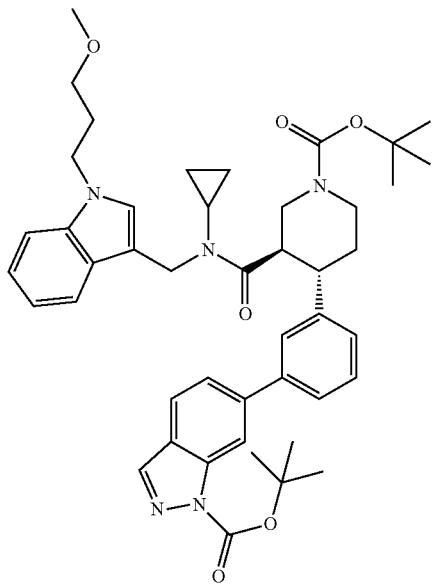

Intermediate 127.1 is synthesized by coupling of Intermediate 127.2 (150 mg, 0.22 mmol) and Intermediate 127.3 (80 mg, 0.27 mmol) analogously to the preparation of Intermediate 2.1. White amorphous material; ES-MS: M-Boc=662; HPLC: $_At_{Ret}$=5.69 min.

Intermediate 12.2

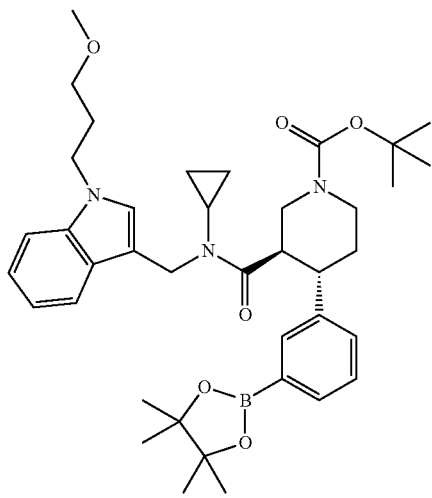

Intermediate 42.2 (500 mg, 0.72 mmol), Bis(pinacolato)diboron (366 mg, 1.44 mmol), PdCl$_2$(dppf) (59 mg, 0.07 mmol) and KOAc (283 mg, 2.88 mmol) in DMSO (3.5 mL) are stirred at 80° C. for 3 h under N$_2$. After cooling to room temperature, the reaction mixture is diluted with AcOEt and washed with brine. The organic layer is dried (Na$_2$SO$_4$), concentrated and purified by silica gel column chromatography to give Intermediate 127.2. White amorphous material; ES-MS: M+H=672; HPLC: $_At_{Ret}$=5.67 min.

Interediate 127.3

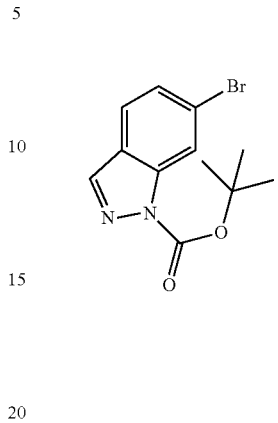

To a solution of 6-Bromo-1H-indazole (700 mg, 3.55 mmol) in DCM (15 mL), Et$_3$N (1.4 mL, 10.7 mmol), BOC$_2$O (0.93 g, 4.26 mmol) and DMAP (615 mg, 5.70 mmol) are added. After stirred at RT for 0.5 h, the reaction mixture is quenched with H$_2$O and extracted with DCM. The combined organic phases are washed with H$_2$O and dried (MgSO$_4$) to give 127.3 as an oil; ES-MS: M-BOC=197: $_At_{Ret}$=4.52 min.

Intermediate 128.

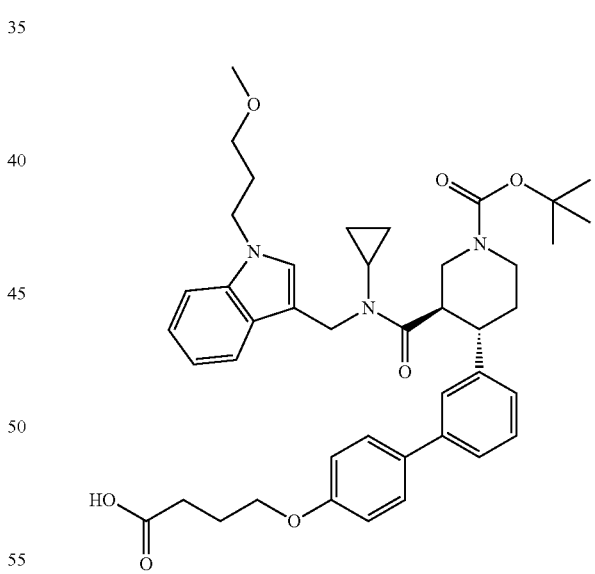

Intermediate 128.1 is synthesized by hydrolysis of Intermediate 128.2 (207 mg, 0.28 mmol) analogously to the preparation of Intermediate 87.1. White amorphous material; ES-MS: M+1=724; HPLC: $_At_{Ret}$=4.89 min.

Intermediate 128.2

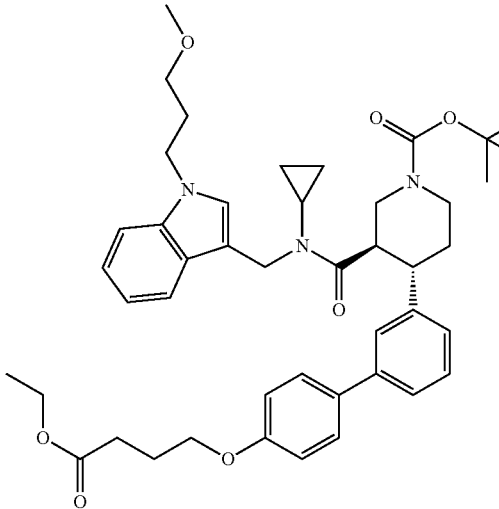

To a solution of Intermediate 42.1 (257 mg, 0.40 mmol) and 4-Bromo-butyric acid ethyl ester (0.146 mL, 1.00 mmol) in DMF is added $K_2CO_3$ (139 mg, 1.00 mmol). After stirring at 60° C. for 3 h, the reaction mixture is cooled to room temperature and $H_2O$ is added. The resulting mixture is diluted with $Et_2O$ and washed with brine. The organic layer is dried ($Na_2SO_4$), concentrated and purified by silica gel column chromatography to give Intermediate 128.2 as white amorphous; ES-MS: M+1=752; HPLC: $_At_{Ret}$=5.70 min.

Intermediate 129.1

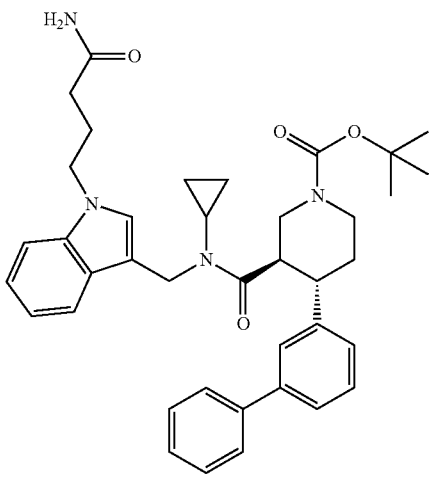

Intermediate 129.1 is synthesized by condensation of Intermediate 1.2 (200 mg, 0.52 mmol) and Intermediate 129.2 (211 mg, 0.78 mmol) analogously to the preparation of Intermediate 4.1. White amorphous material; ES-MS: M+H=635; HPLC: $_At_{Ret}$=4.57 min.

Intermediate 129.2

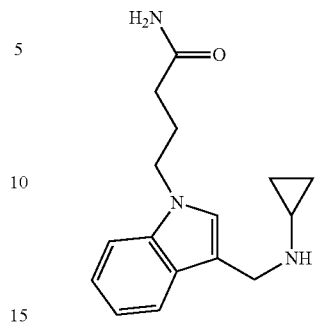

Intermediate 129.2 is synthesized by condensation of Intermediate 129.3 (700 mg, 3.00 mmol) and cyclopropylamine (260 mg, 4.50 mmol) analogously to the preparation of Intermediate 4.5. Yellow oil; ES-MS: M+H=272; HPLC: $_At_{Ret}$=2.02 min.

Intermediate 129.3

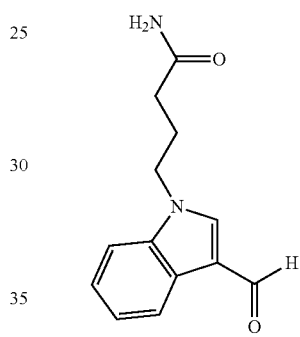

A mixture of Intermediate 129.4 (1.02 g, 5.20 mmol), $Et_3N$ (675 mg, 6.20 mmol), ethyl chloroformate (615 mg, 5.70 mmol) in THF (6 mL) is stirred at RT for 0.5 h. To the reaction mixture, 28% $NH_3$ aqueous solution (1.5 mL, 26 mmol) is added. After adding $H_2O$, the reaction mixture is extracted with EtOAc. The combined organic phases are washed with $H_2O$ and dried ($MgSO_4$) to give Intermediate 129.3 as white amorphous material; ES-MS: M+H=231: $_At_{Ret}$=2.27 min.

Intermediate 129.4

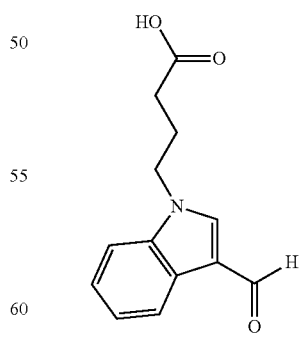

A mixture of Intermediate 129.5 (2.70 g, 11.0 mmol) is hydrolyzed with LiOH in THF/MeOH/$H_2O$ (1:1:1, 48 mL) at RT for 4.0 h. After adding $H_2O$, the reaction mixture is extracted with EtOAc. $H_2O$ layer is acidified by 1M HCl. Thre reaction mixrue is extracted with EtOAc. The organic layer is washed with H$_2$O and dried (MgSO$_4$) to give Intermediate 129.4 as green solids; ES-MS: M+H=232: $_A t_{Ret}$=2.60 min.

Intermediate 129.5

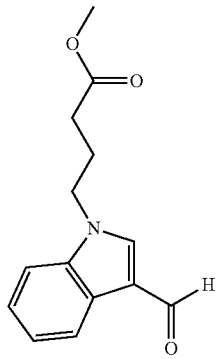

Intermediate 129.5 is synthesized by condensation of indole-3-carbaldehyde (2.00 g, 13.7 mmol) and 4-chlorobutyricacid methylester (2.20 g, 16.6 mmol) analogously to the preparation of Interediate 4.8. Yellow oil; ES-MS: M+H=246; HPLC: $_A t_{Ret}$=3.12 min Intermediate 130.1

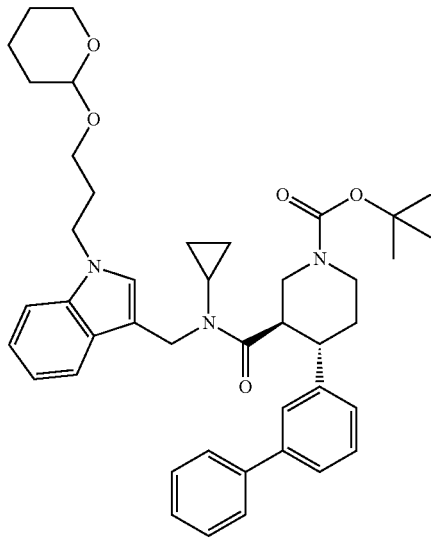

Intermediate 130.1 is synthesized by condensation of Intermediate 1.2 (200 mg, 0.52 mmol) and Intermediate 130.2 (255 mg, 0.78 mmol) analogously to the preparation of Intermediate 4.1. White amorphous material; ES-MS: M+H=692; HPLC: $_A t_{Ret}$=5.92 min.

Intermediate 130.2

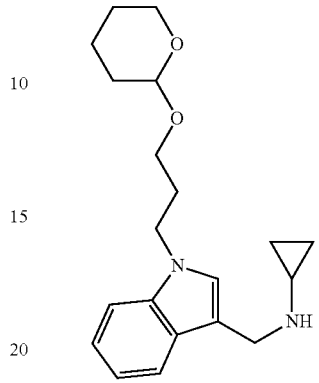

Intermediate 130.2 is synthesized by condensation of Intermediate 130.3 (4.20 g, 14.6 mmol) and cyclopropylamine (1.20 g, 20.6 mmol) analogously to the preparation of Intermediate 4.5. Yellow oil; ES-MS: M+H=329; HPLC: $_A t_{Ret}$=2.79 min.

Intermediate 130.3

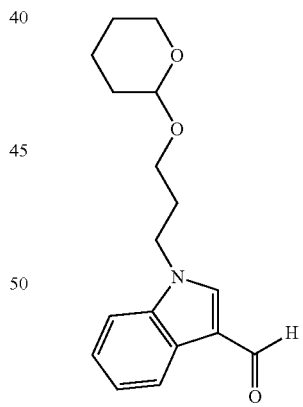

Intermediate 130.3 is synthesized by condensation of indole-3-carbaldehyde (2.00 g, 13.7 mmol) and 2-(3-bromopropoxy)tetrahydro pyran (3.6 g, 16.4 mmol) analogously to the preparation of Intermediate 4.8. Yellow oil; ES-MS: M+H=288; HPLC: $_A t_{Ret}$=3.65 min Intermediate 131.1

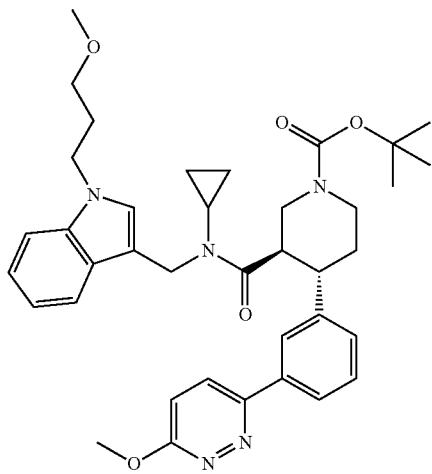

A mixture of Intermediate 127.2 (118.2 mg, 0.18 mmol), 3-Chloro-6-methoxy-pyridazine (96.8 mg, 0.64 mmol), 1N Na$_2$CO$_3$ $_{aq}$ (1.34 mL, 1.34 mmol) and Pd(PPh$_3$)$_4$ (51.4 mg, 0.12 mmol) in touene (10 mL) is stirred at 115° C. After stirring overnight, adding H$_2$O at RT, the reaction mixture is extracted with EtOAc. The combined organic phases are washed with H$_2$O and dried (Na$_2$SO$_4$). Concentration under reduced pressure and silica gel flash chromatography of the residue (hexane/ethyl acetate) affords Intermediate 131.1 as amorphous; ES-MS: M+H=654; LC: $_A$t$_{Ret}$=4.60 min.

Intermediate 132.1

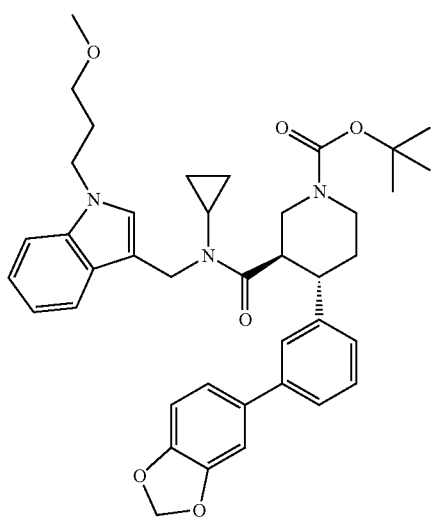

Intermediate 132.1 is synthesized by coupling of Intermediate 42.2 (254 mg, 0.37 mmol) and 3,4-methylenedioxyphenylboronic acid (67 mg, 0.40 mmol) analogously to the preparation of Intermediate 2.1. White amorphous material; ES-MS: M+H=666; HPLC: $_A$t$_{Ret}$=5.40 min.

Intermediate 133.1

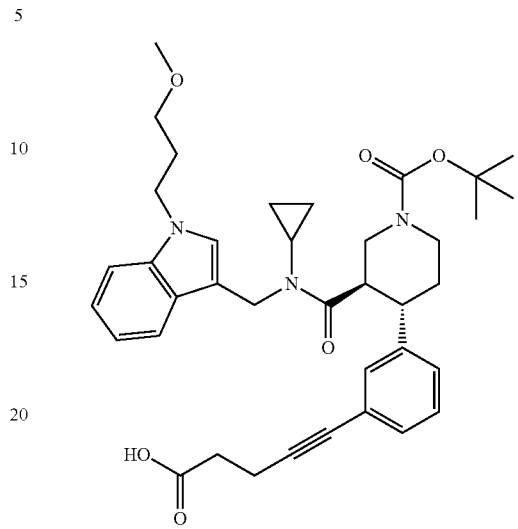

Intermediate 133.1 is synthesized by hydrolysis of Intermediate 117.1 analogously to the preparation of Intermediate 80.2. White amorphous; ES-MS: M+H=642; HPLC: $_A$t$_{Ret}$=4.57 min.

Intermediate 134.1

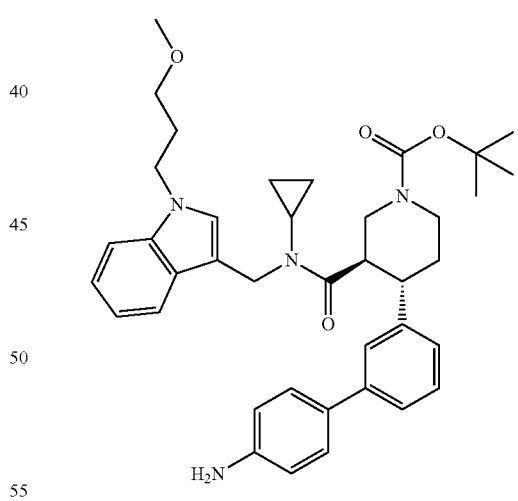

A mixture of intermediate 134.2 (450 mg, 0.68 mmol) and Zn powder (221 mg, 3.38 mmol) in EtOH-sat. NH$_4$Cl(aq.) (7 mL) are stirred at 70° C. for 1 hr. After cooling to room temperature, the reaction mixture is extracted with AcOEt, washed with brine, dried (MgSO$_4$), and concentrated. Purification by silica gel column chromatograrphy give intermediate 134.1 as white amorphous; ES-MS: M+H=637; HPLC: $_A$t$_{Ret}$=3.67 min.

Intermediate 34.2

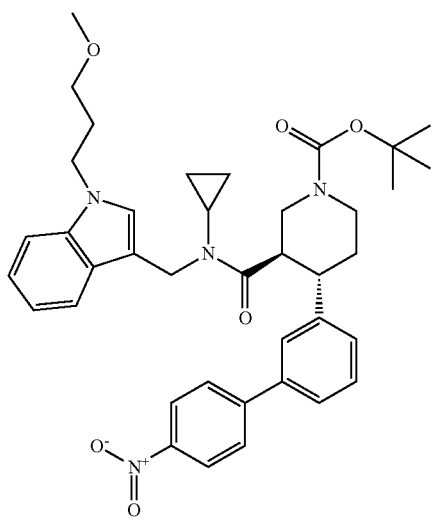

Intermediate 134.2 is synthesized by coupling of Intermediate 42.2 (1.0 g, 1.44 mmol) and 4-Nitrophenylboronic acid, pinacol ester (539 mg, 2.16 mmol) analogously to the preparation of Intermediate 42.1. red amorphous material; ES-MS: M+H=667; HPLC: $_A t_{Ret}$=5.45 min.

Intermediate 135.1

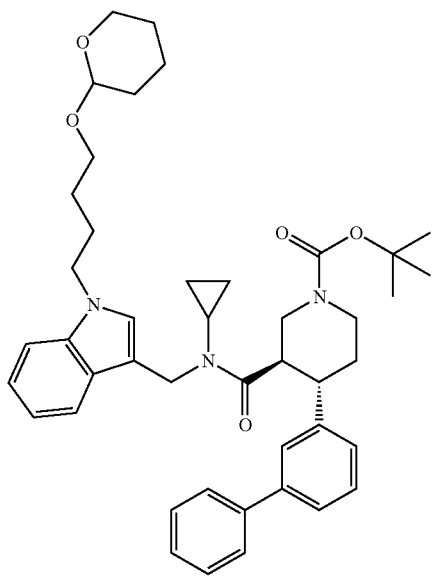

Intermediate 135.1 is synthesized by condensation of Intermediate 1.2 (200 mg, 0.52 mmol) and Intermediate 135.2 (266 mg, 0.78 mmol) analogously to the preparation of Intermediate 4.1. White amorphous material; ES-MS: M+H-THP=622; HPLC: $_A t_{Ret}$=5.92 min.

Intermediate 5.2

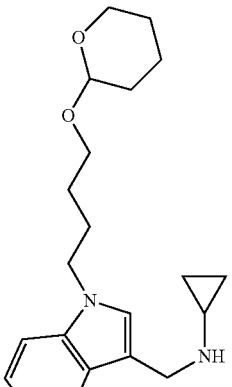

Intermediate 135.2 is synthesized by condensation of Intermediate 135.3 (4.10 g, 13.6 mmol) and cyclopropylamine (1.20 g, 20.6 mmol) analogously to the preparation of Intermediate 4.5. Yellow oil; ES-MS: M+H=343; HPLC: $_A t_{Ret}$=2.87 min.

Intermediat 135.3

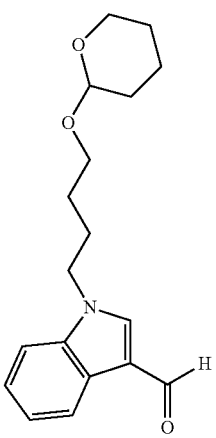

Intermediate 135.3 is synthesized by condensation of indole-3-carbaldehyde (2.00 g, 13.7 mmol) and 2-(4-chlorobutoxy)tetrahydropyran (3.1 g, 16.4 mmol) analogously to the preparation of Intermediate 4.8. Yellow oil; ES-MS: M+H=302; HPLC: $_A t_{Ret}$=3.79 min Intermediate 136.1

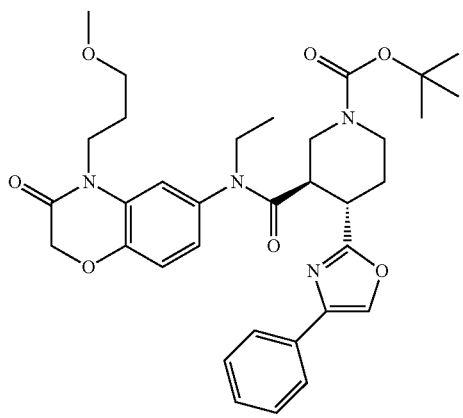

A mixture of Intermediate 99.2 (205 mg, 0.55 mmol) and 1-chloro-N,N-2-trimethyl-1-propenylamine (109 μL, 0.83 mmol) in 1,2-dichloroethane (5 mL) is stirred at RT. After stirring for 1 h, a mixture of Intermediate 82.2 (182 mg, 0.61 mmol) and pyridine (111 μL, 1.38 mmol) is added to the reaction mixture, and stirred for 6 h at 60° C. After adding H$_2$O at RT, the reaction mixture is extracted with EtOAc. The combined organic phases are washed with H$_2$O, brine and dried (Na$_2$SO$_4$). Concentration under reduced pressure and silica gel flash chromatography of the residue (hexane/ethyl acetate) affords Intermediate 136.1 as a pale yellow solid; ES-MS: M+H=619; HPLC: t$_{Ret}$=4.68 min.

Intermediate 137.1

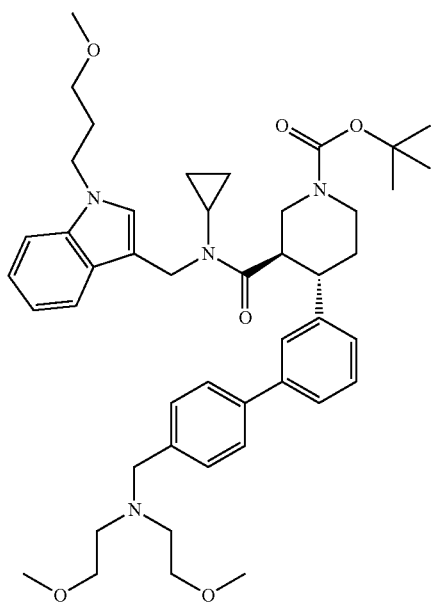

Intermediate 137.1 is synthesized by coupling of Intermediate 42.2 (200 mg, 0.29 mmol) and intermediate 137.2 (116 mg, 0.43 mmol) analogously to the preparation of Intermediate 42.1 as an oil; ES-MS: M+H=767; HPLC: $_A$t$_{Ret}$=4.02 min.

Intermediate 137.2

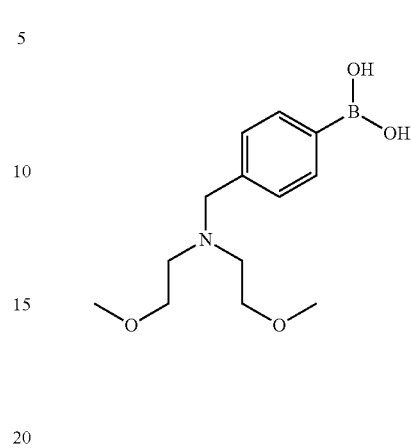

A mixture of 4-formylphenyl-boronic acid (300 mg, 2.0 mmol) and Bis-(2-methoxy-ethyl)-amine (270 mg, 2.0 mmol) and CH$_3$CO$_2$H in MeOH (10 mL) is stirred at RT for 0.5 h. 1.0 M NaBH$_3$CN solution (250 ul, 2.5 mmol) was then added to the reaction mixture and further stirring at RT for 1 hour. The reaction is directly condensed to give Intermediate 137.2 as white solid; ES-MS: M+H=268; HPLC: $_A$t$_{Ret}$=1.74 min.

Intermediate 138.1

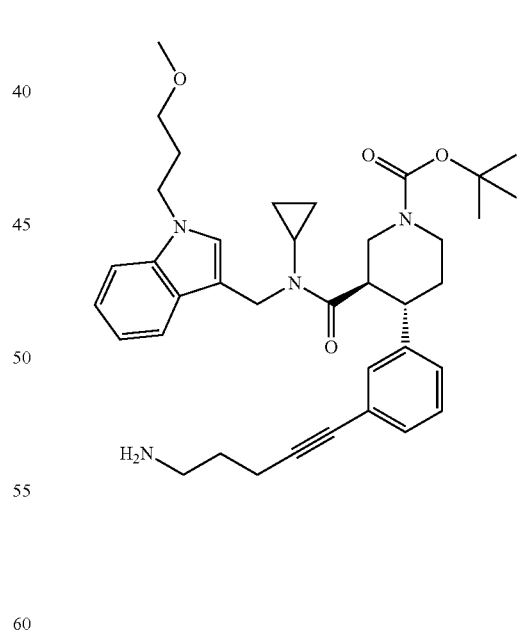

A mixture of Intermediate 138.2 (113.1 mg, 0.15 mmol) and hydrazine monohydrate (36 μL, 074 mmol) in EtOH (5 mL) is stirred at reflux. After stirring for 2 h, Concentration under reduced pressure affords Intermediate 138.1 as amorphous; ES-MS: M+H=627; HPLC: $_A$t$_{Ret}$=3.72 min.

Intermediate 138.2

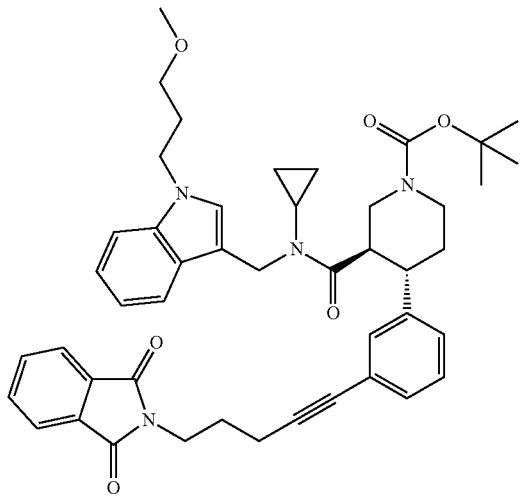

Intermediate 138.2 is synthesized by coupling of Intermediate 42.2 (194 mg, 0.28 mmol) and 2-Pent-4-ynyl-isoindole-1,3-dione (178 mg, 0.83 mmol) analogously to the preparation of Intermediate 109.2. White amorphous material; ES-MS: M+H=757; HPLC: $_At_{Ret}$=5.49 min.

Intermediate 139.1

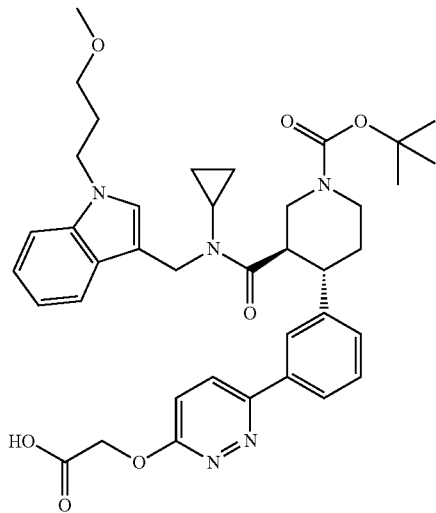

A mixture of Intermediate 127.2 (52.7 mg, 0.078 mmol), (6-Chloro-pyridazine-3-yloxy)-acetic acid methyl ester (94.8 mg, 0.47 mmol), 1N $Na_2CO_3$ $_{aq}$ (0.6 mL, 0.6 mmol) and $Pd(PPh_3)_4$ (18 mg, 0.016 mmol) in dioxane (5 mL) is stirred at 100° C. After stirring overnight, adding $H_2O$ at RT, the reaction mixture is extracted with EtOAc. The combined organic phases are dried ($Na_2SO_4$). Concentration under reduced pressure and silica gel flash chromatography of the residue (hexane/ethyl acetate) affords Intermediate 139.1 as amorphous; ES-MS: M+H=698; HPLC: $_At_{Ret}$=4.22 min.

Intermediate 140.1

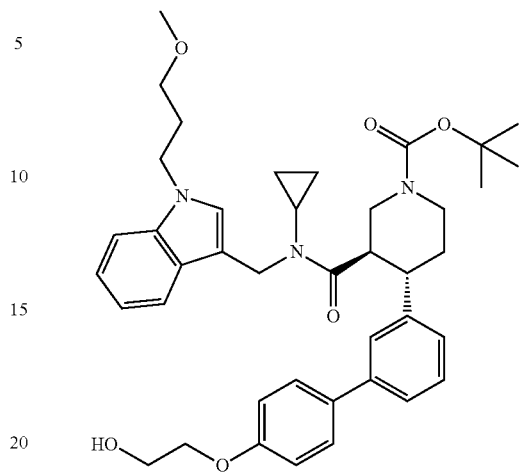

Intermediate 42.1 (293 mg, 0.46 mmol), ethylene carbamate (81 mg, 0.92 mmol) and $K_2CO_3$ (127 mg, 0.92 mmol) in DMF (2 mL) is stirred at 90° C. for 15 h. After cooling to room temperature, the reaction mixture is diluted with AcOEt and washed with $H_2O$ and brine. The organic layer is dried ($Na_2SO_4$), concentrated and purified by silica gel column chromatography to give Intermediate 140.1 as white amorphous; ES-MS: M+1=682; HPLC: $_At_{Ret}$=4.74 min.

Intermediate 141.1 (80.2)

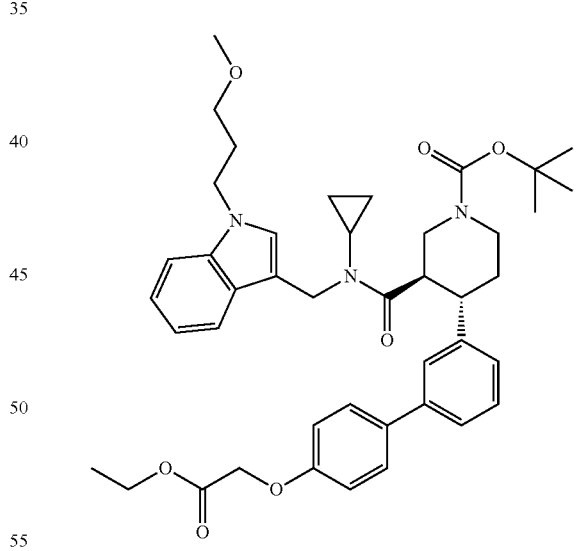

To a solution of Intermediate 42.1 (201 mg, 0.32 mmol) and iodoethyl acetate (0.075 mL, 0.63 mmol) in DMF is added $K_2CO_3$ (87 mg, 0.63 mmol) and stirred at 75° C. for 2 h. After cooling to room temperature, the reaction mixture is diluted with AcOEt and washed with $H_2O$ and brine. The organic layer is dried over $Na_2SO_4$, concentrated and purified by silica gel flash chromatography to give Intermediate 141.1 (80.2) as white amorphous; ES-MS: M+H=724; HPLC: $_At_{Ret}$=4.85 min.

Intermediate 142.1

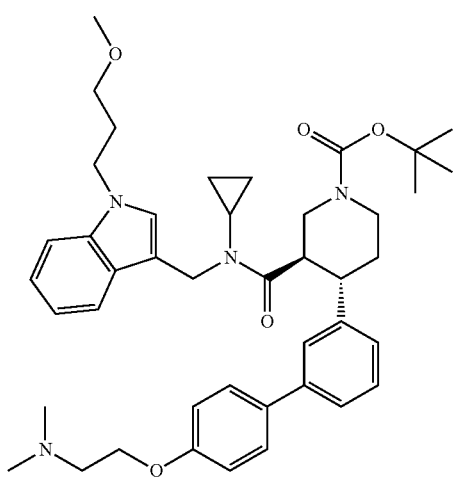

Intermediate 142.1 is synthesized by Mitsunobu reaction of Intermediate 42.1 (344 mg, 0.54 mmol) and dimethylaminoethanol (0.108 mL, 1.08 mmol) analogously to the preparation of Intermediate 104.1. White amorphous material; ES-MS: M=709; HPLC: $_A t_{Ret}$=3.79 min.

143

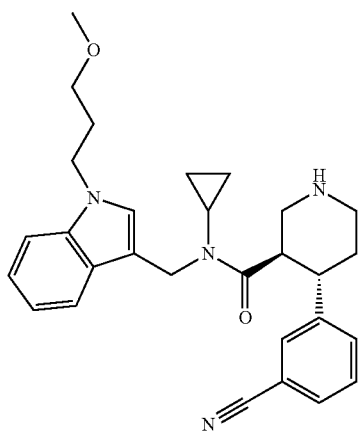

A mixture of Intermediate 42.2 (158.7 mg, 0.23 mmol), ZnCN$_2$ (133.8 mg, 1.14 mmol) and Pd(PPh$_3$)$_4$ (79.3 mg, 0.00.069 mmol) in DMF (5 mL) is stirred at 200° C. under microwave condition. After stirring for 30 min., adding H$_2$O at RT, the reaction mixture is extracted with EtOAc. The combined organic phases are washed with H$_2$O, dried (Na$_2$SO$_4$). Concentration under reduced pressure and reverse phase chromatography of the residue affords 143 as amorphous; ES-MS: M+H=471; HPLC: $_A t_{Ret}$=3.07 min.

Intermediate 144.1

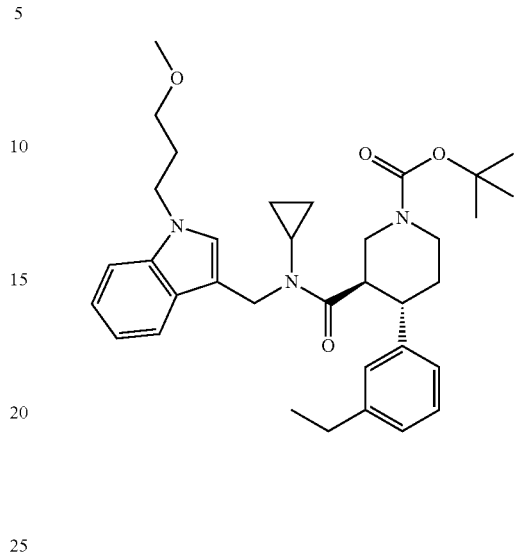

A mixture of Intermediate 42.2 (181.6 mg, 0.26 mmol), 0.97 M EtMgBr (0.85 ml in THF, 0.83 mmol) and PdCl$_2$ (dppf).CH$_2$Cl$_2$ (13.5 mg, 0.017 mmol) in THF (5 mL) is stirred at 80° C. After stirring for 2.5 h, adding H$_2$O at RT, the reaction mixture is extracted with EtOAc. The combined organic phases are washed with brine and dried (Na$_2$SO$_4$). Concentration under reduced pressure and silica gel flash chromatography of the residue (hexane/ethyl acetate) affords Intermediate 144.1 as amorphous; ES-MS: M+H=574; HPLC: $_A t_{Ret}$=5.47 min.

Intermediate 145.1

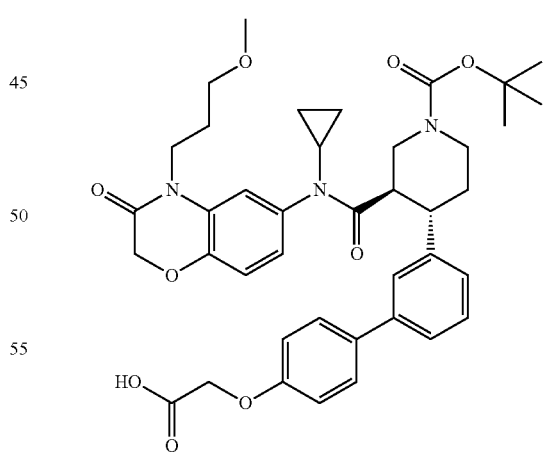

Intermediate 145.1 is synthesized by hydrolysis of intermediate 145.2 (40 mg, 0.05 mmol) analogously to the preparation of intermediate 80.2. White amorphous material; ES-MS: M+H=714; HPLC: $_A t_{Ret}$=4.15 min.

Intermediate 145.2

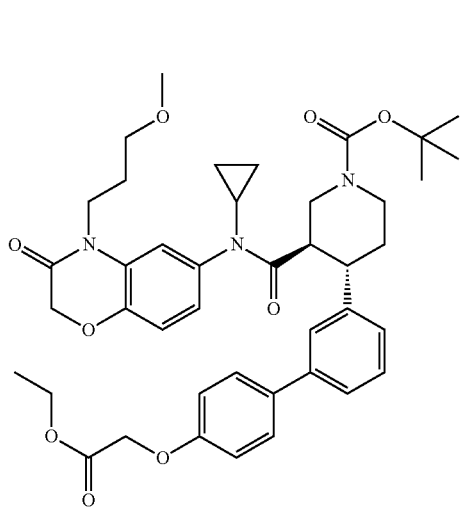

Intermediate 145.2 is synthesized by alkylation of intermediate 145.3 (53.4 mg, 0.082 mmol) analogously to the preparation of intermediate 80.3. White amorphous material; ES-MS: M+H=742; HPLC: $_At_{Ret}$=4.85 min.

Intermediate 145.3

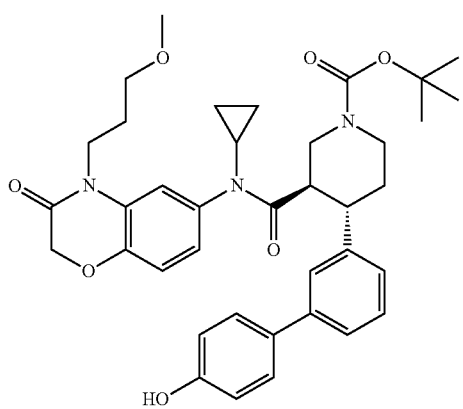

To a solution of intermediate 145.4 (75 mg, 0.10 mmol) in EtOH (2.0 mL) and H$_2$O (1.0 mL) is added 8N KOH aqueous solution (0.03 mL, 0.26 mmol). After stirring at RT for 10 h, the reaction mixture is acidified with 1N HCl solution. The resulting mixture is extracted with AcOEt and washed with brine. The organic layer is dried over MgSO$_4$ and concentrated to give intermediate 145.3 as white solid; ES-MS: M+H=656; HPLC: $_At_{Ret}$=4.24 min.

Intermediate 145.4

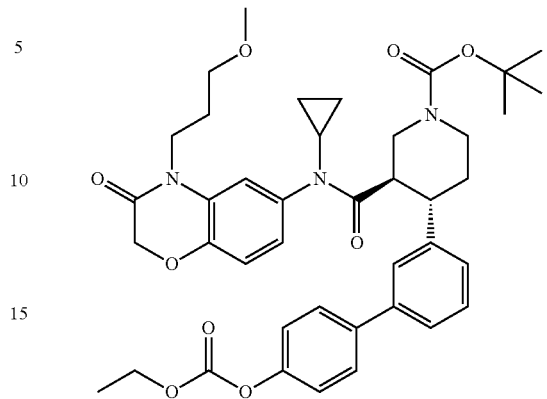

To a solution of intermediate 110.3 (400 mg, 1.01 mmol) in THF (5.0 mL), Et$_3$N (0.40 mL, 3.03 mmol) and Ethyl chloroformate (0.21 mL, 2.11 mmol) are added at 0° C. After stirring for 0.5 h at same temperature, the resulting precipitate is filtered off and the filtrate is concentrated. Part of the residue (95 mg, 0.18 mmol) is dissolved in THF (3 ml), intermediate 101.2 (50 mg, 0.18 mmol) and MgBr$_2$ (51 mg, 0.2 mmol) are added at room temperature. After stirring for 12 h, the reaction is quenched with H$_2$O and resulting mixture is extracted with AcOEt, washed with 1N HCl solution and brine. The organic layer is dried (MgSO$_4$), concentrated and purified by silica gel column chromatography to afforded intermediate 145.4 as an oil; M+H=728; HPLC: $_At_{Ret}$=4.94 min.

Intermediate 146.1

Intermediate 146.1 is synthesized by coupling of Intermediate 42.2 (210 mg, 0.30 mmol) and [4-(4-morpholinylmethyl)phenyl]-boronic acid (100 mg, 0.45 mmol) analogously to the preparation of Intermediate 42.1 as an oil; ES-MS: M+H=721; HPLC: $_At_{Ret}$=3.87 min.

147

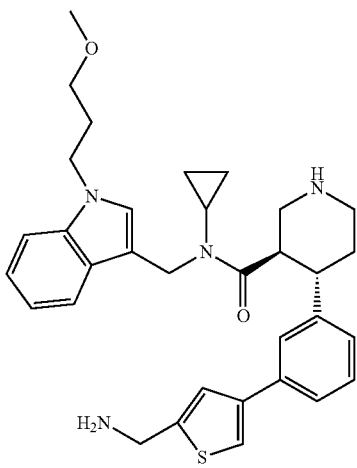

To a solution of Intermediate 147.1 (97 mg, 0.15 mmol) in toluene (0.6 mL) are added DPPA (0.038 mL, 0.18 mmol) and DBU (0.026 mL, 0.17 mmol) at room temperature. After stirred for 6.5 h, the mixture is diluted with EtOAc, and washed with aq. KHSO$_4$, H$_2$O, and brine. The organic layer is dried (Na$_2$SO$_4$), filtered, and concentrated in vacuo. The residue is treated with polymer-supported Ph$_3$P in THF (2 mL)-H$_2$O (0.2 mL) at 40° C. for 12 h. The mixture is filtered through celite, and the filtrate is dried (Na$_2$SO$_4$), filtered, and concentrated in vacuo. The residue is treated with TMSOTf (0.080 mL, 0.44 mmol) and 2,6-lutidine (0.070 mL, 0.60 mmol) in CH$_2$Cl$_2$ (2 mL) at 0° C. for 30 min. The reaction is quenched by the addition of sat. aq. NaHCO$_3$ and MeOH. The mixture is purified by RP-HPLC to give 147 as white amorphous solid.

Intermediate 147.1

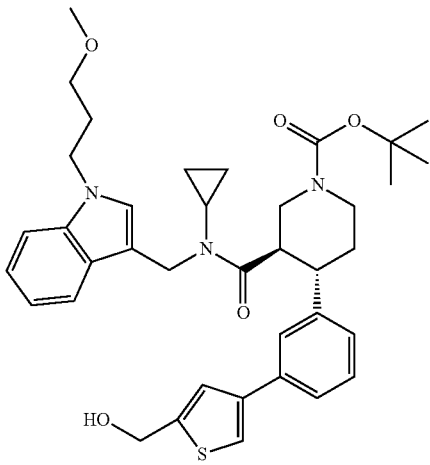

To a solution of Intermediate 108.2 (214 mg, 0.80 mmol) in THF (3 mL) is added LiBH$_4$ (20 mg, 0.92 mmol) at 0° C. After stirred at room temperature for 1 h, an additional LiBH$_4$ (30 mg, 1.38 mmol) is added. After stirrd for 1 h, the reaction mixture is heated to 60° C. for 3 h. The reaction is quenched by the addition of aq. KHSO$_4$, and the mixture is extracted with EtOAc. The organic extracts are washed with water and brine, and dried (Na$_2$SO$_4$), filtered, and concentrated in vacuo.

Intermediate 147.1 is synthesized by condensation of Intermediate 42.1 (259 mg, 0.37 mmol) and the above crude residue analogously to the preparation of Intermediate 2.1. Pale yellow oil; ES-MS: M+H=658; HPLC: $_At_{Ret}$=4.67 min.

Intermediate 148.1

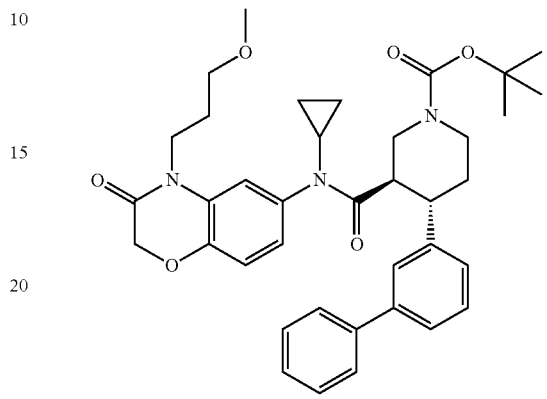

Intermediate 148.1 is synthesized by condensation of Intermediate 75.3 (300 mg, 0.44 mmol) and Intermediate 101.2 (121 mg, 0.44 mmol) analogously to the preparation of Intermediate 145.4. White amorphous material; ES-MS: M+H=640; HPLC: $_At_{Ret}$=5.02 min.

Intermediate 149.1

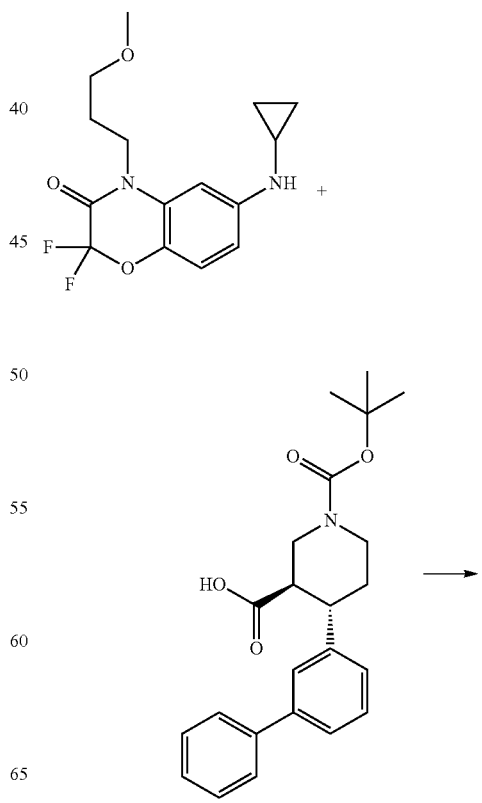

-continued

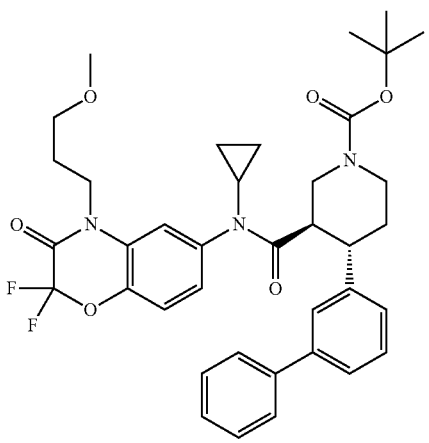

Intermediate 149.1 is synthesized by condensation of Intermediate 1.2 (147 mg, 0.39 mmol) and Intermediate 149.2 (120 mg, 0.39 mmol) analogously to the preparation of Intermediate 145.4. White powder; ES-MS: M+H=676; HPLC: $_At_{Ret}$=5.42 min.

Intermediate 149.2

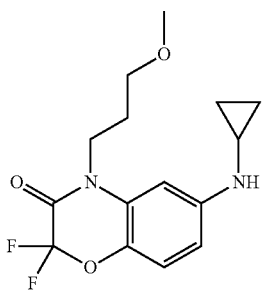

Intermediate 149.2 is synthesized by N-alkylation of intermediate 149.3 (2.38 g, 9.9 mmol) analogously to the preparation of intermediate 101.2. White crystal; ES-MS: M+H=313; HPLC: $_Ct_{Ret}$=1.94 min.

Intermediate 149.3

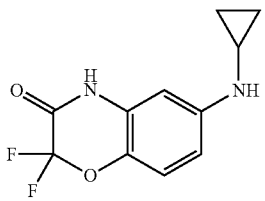

Intermediate 149.4 (140 mg, 0.42 mmol) and potassium carbonate (210 mg, 2.1 mmol) in MeOH (1.4 mL) is stirred at r.t. for 1.5 h. After adding water, the reaction mixture is extracted with EtOAc. The combined organic phases are washed with H$_2$O and dried (MgSO$_4$). Concentration under reduced pressure and recrystallization give Intermediate 149.3. white crystal; ES-MS: M+H=241: $_Ct_{Ret}$=1.73 min.

Intermediate 149.4

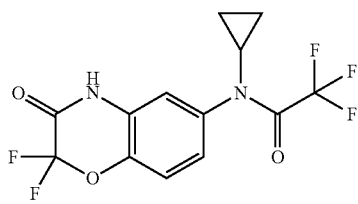

Intermediate 149.5 (1.7 g, 4.08 mmol) and potassium carbonate (843 mg, 6.11 mmol) in DMF (25 mL) is stirred at 70° C. for 5 h. The reaction mixture is concentrated under reduced pressure. The evaporated residue is diluted with EtOAc, washed with H$_2$O and dried (MgSO$_4$). Concentration under reduced pressure and recrytallization give Intermediate 149.4. white powder; ES-MS: M+H=337: $_Ct_{Ret}$=1.81 min.

Intermediate 149.5

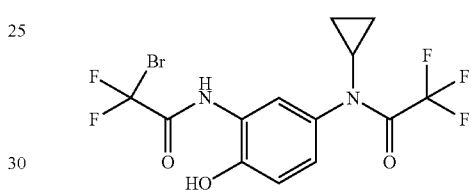

Intermediate 149.6 (1.25 g, 4.8 mmol), potassium carbonate (1.66 g, 12 mmol) and bromo difluoroacetyl chloride (1.02 g, 5.28 mmol) in THF (15 mL) is stirred at 0° C. for 30 min. After adding KHSO$_4$aq., the reaction mixture is extracted with EtOAc. The combined organic phases are washed with sat.NaHCO$_3$aq. and dried (MgSO$_4$). Concentration under reduced pressure and silica gel flash chromatography give Intermediate 149.5. yellow crystal; ES-MS: M+H=417: $_Ct_{Ret}$=1.82 min.

Intermediate 149.6

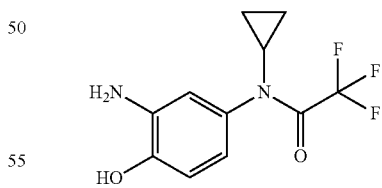

To a solution of Intermediate 149.7 (13 g, 44.8 mmol) in EtOH (60 mL) is added NH$_4$Cl (4.8 g, 89.6 mmol), water (60 mL) and Zn (14.6 g, 224 mmol). The resulting mixture is stirred at 80° C. for 1 h. The reaction mixture is filtered via celite pad and the celite cake is washed with EtOH and EtOAc. Concentration under reduced pressure and silica gel flash chromatography gives Intermediate 149.6. red crystal; ES-MS: M+H=261: $_Ct_{Ret}$=1.31 min.

Intermediate 149.7

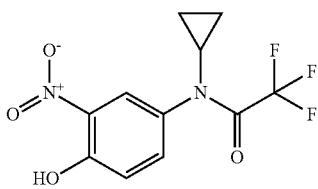

To a solution of Intermediate 149.8 (19 g, 82.4 mmol) and pyridine (32.6 g, 412 mmol) in dichloromethane (200 mL) is added trifluoroacetic anhydride (25 g, 247 mmol) at 0° C. and stirred for 30 min. After adding 2M HClaq (83 mL), the reaction mixture is extracted with dichloromethane. The combined organic phases are washed with water, sat.NaHCO$_3$aq. and dried (MgSO$_4$). Concentration under reduced pressure and recrystallization gives Intermediate 149.7. yellow crystal; ES-MS: M+H=291: $_Ct_{Ret}$=1.82 min.

Intermediate 149.8

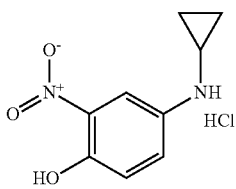

Intermediate 149.9 (23 g, 92 mmol) in EtOAc (50 mL) is added to 4M HCl in EtOAc with small amount of water at r.t. The resulting mixture is stirred for 15 min. The resulting yellow precipitate is collected by filtration and the solid is washed with EtOAc to give Intermediate 149.8. yellow powder; ES-MS: M+H—HCl=195: $_Ct_{Ret}$=1.78 min.

Intermediate 149.9

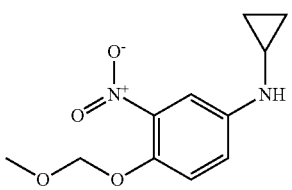

Intermediate 149.9 is synthesized by reduction of intermediate 149.10 (29 g, 130 mmol) analogously to the preparation of 101.4. Red oil; ES-MS: M+H=239; HPLC: $_Ct_{Ret}$=1.83 min.

Intermediate 149.10

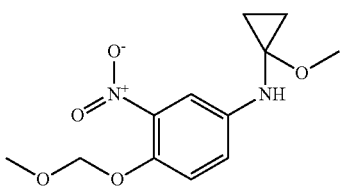

To a solution of Intermediate 101.6 (29.1 g, 130 mmol) in dichloromethane (300 mL) is added N,N-ethyldiisopropylamine (67 g, 520 mmol) and MOMCl (10.5 g, 130 mmol) at 0° C. The reaction mixture is stirred for overnight. After being neutralized by 1M HClaq., the reaction mixture is extracted with dichlomethane. The combined organic phases are washed with sat.NaHCO$_3$aq. and dried (MgSO$_4$). Concentration under reduced pressure gives Intermediate 149.10: red oil; ES-MS: M+H=: $_Ct_{Ret}$=1.82 min.

Intermediate 150.1

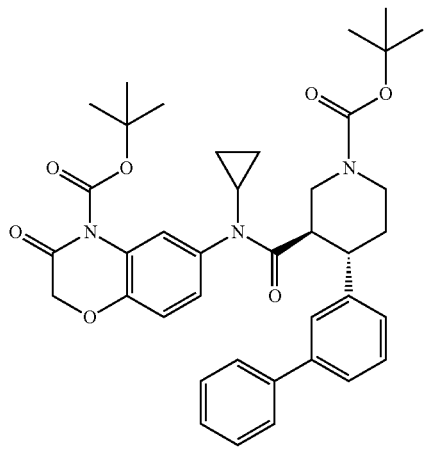

Intermediate 150.1 is synthesized by condensation of Intermediate 1.2 (147 mg, 0.39 mmol) and Intermediate 150.2 (130 mg, 0.43 mmol) analogously to the preparation of Intermediate 82.1. White powder; ES-MS: M+H=668; HPLC: $_At_{Ret}$=5.35 min.

Intermediate 150.2

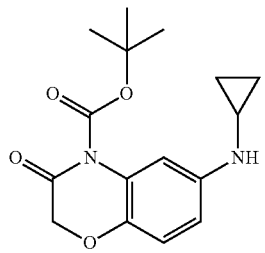

To a solution of Intermediate 101.3 (200 mg, 1.0 mmol) and in THF (5 mL), Boc$_2$O (240 mg, 1.10 mmol) and DMAP (134 mg, 1.10 mmol) are added under N$_2$ at 0° C. After stirring RT for 16 h, H$_2$O is added and the reaction mixture is extracted with EtOAc. The combined organic phases are washed with H$_2$O, and dried (Na$_2$SO$_4$). Concentration under reduced pressure and silica gel flash chromatography give Intermediate 150.2 as colorless amorphous; ES-MS: M+H=305; HPLC: $_At_{Ret}$=3.77 min.

Intermediate 151.1

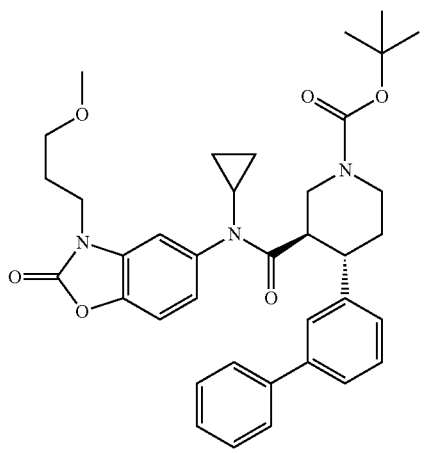

Intermediate of 151.1 is synthesized by condensation of Intermediate 1.2 (71 mg, 0.19 mmol) and Intermediate 151.2 (44 mg, 0.17 mmol) analogously to the preparation of Intermediate 145.4. White powder; ES-MS: M+H=626; HPLC: $_At_{Ret}$=4.97 min.

Intermediate 151.2

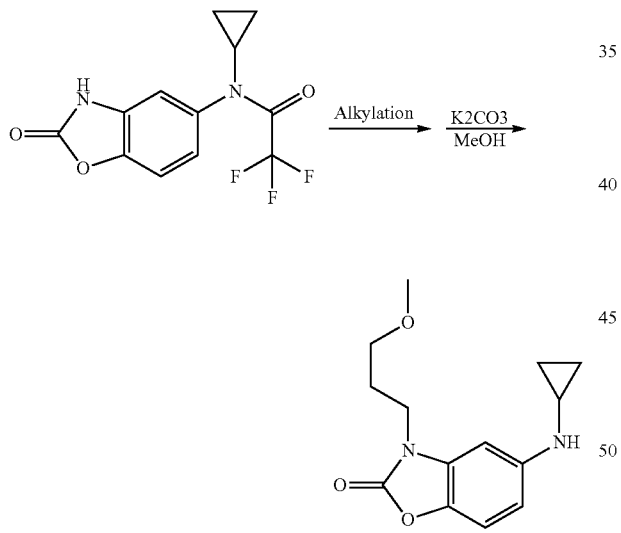

Intermediate 151.3 (252 mg, 0.88 mmol) is treated by toluene-4-sulfonic acid 3-methoxypropyl ester (210 μL, 0.97 mmol) analogously to the known method (see e.g. *European Journal of Medicinal Chemistry* 1998, 33, 957-967. or EP 432893). A crude mixture of the alkylated compound, $K_2CO_3$ (365 mg, 2.64 mmol) in MeOH (5 mL) is stirred under $N_2$ at RT for 7 h. After adding $H_2O$, the reaction mixture is extracted with EtOAc. The combined organic phases are washed with $H_2O$ and dried ($Na_2SO_4$). Concentration under reduced pressure and silica gel flash chromatography give Intermediate 151.2 as colorless oil; ES-MS: M+H=263; HPLC: $_At_{Ret}$=2.79 min.

Intermediate 151.3

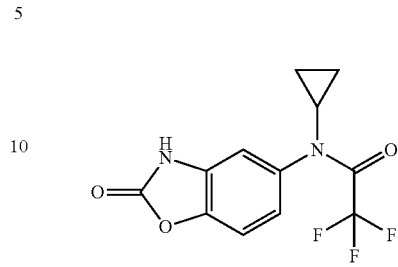

A mixture of Intermediate 149.6 (182 mg, 0.7 mmol) and 1,1'-carbonyldiimidazole (136 mg, 0.84 mmol) in DMF (2 mL) is stirred under $N_2$ at 70° C. for 7 h. After adding $H_2O$, the reaction mixture is extracted with EtOAc. The combined organic phases are washed with $H_2O$ and dried ($Na_2SO_4$). Concentration under reduced pressure and silica gel flash chromatography give Intermediate 151.3; ES-MS: M+H=287; HPLC: $_At_{Ret}$=3.13 min.

Intermediate 152.1

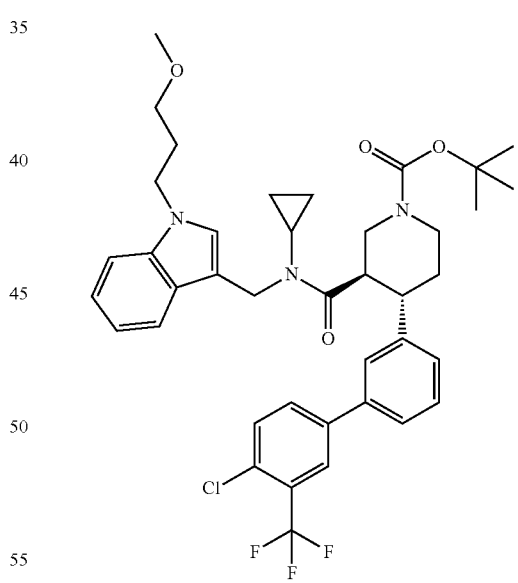

Intermediate 152.1 is synthesized by coupling of Intermediate 42.2 (205 mg, 0.30 mmol) and 4-chloro-3-(trifluoromethyl)benzeneboronic acid (73 mg, 0.33 mmol) analogously to the preparation of Intermediate 2.1. White amorphous material; ES-MS: M+H=724; HPLC: $_At_{Ret}$=5.90 min.

Intermediate 153.1

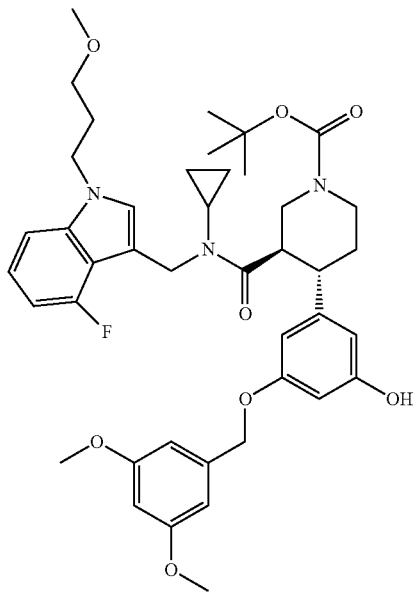

A mixture of Intermediate 153.2 (295 mg, 0.34 mmol) and TBAF (890 mg, 3.40 mmol) in THF (2 mL) are stirred under $N_2$ at 50° C. for 10 h. After adding $H_2O$, the reaction mixture is extracted with EtOAc. The combined organic phases are washed with $H_2O$, dried ($Na_2SO_4$), concentrated under reduced pressure, and silica gel flash chromatography to give Intermediate 153.1; ES-MS: M+H=746; HPLC: $_At_{Ret}$=5.10 min.

Intermediate 153.2

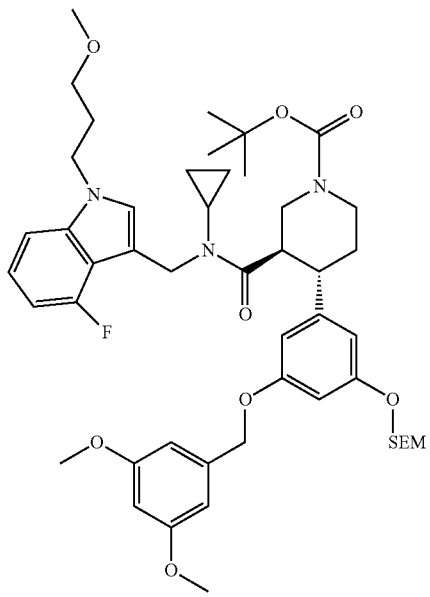

Intermediate 153.2 is synthesized by condensation of Intermediate 153.3 (309 mg, 0.5 mmol) and Intermediate 46.2 (152 mg, 0.55 mmol) analogously to the preparation of Intermediate 76.2. Colorless oil; ES-MS: M+H=618; HPLC: $_At_{Ret}$=6.18 min.

Intermediate 153.3

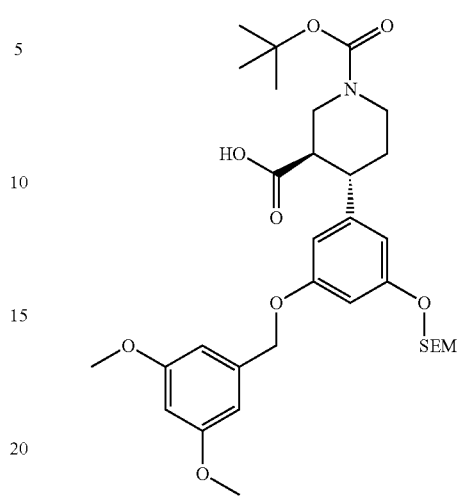

A solution of Intermediate 153.4 (1.23 g, 2.0 mmol) and 25% NaOMe in MeH (1.65 mL, 3.60 mmol) in MeOH (10 mL) is refluxed for 14 h. $H_2O$ (0.50 mL) is added at RT and refluxing is continued for 3 h. After cooling down to RT, the reaction mixture is diluted with EtOAc and aqueous $NH_4Cl$. The organic layer is dried over $Na_2SO_4$ and the solvent is removed in vacuo to give Intermediate 153.3 as amorphous; ES-MS: M+H=618; HPLC: $_Bt_{Ret}$=5.43 min.

Intermediate 153.4

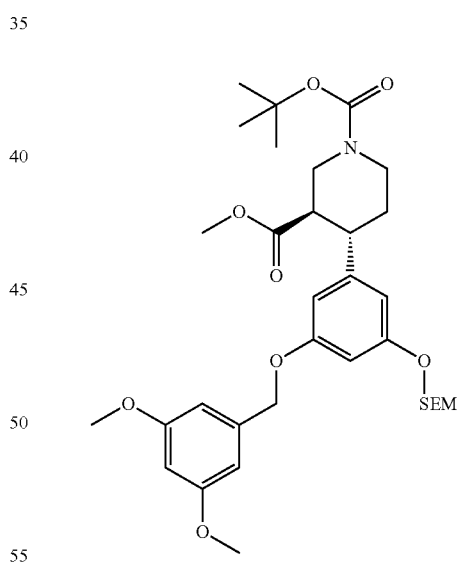

A mixture of Intermediate 153.5 (1.0 g, 2.10 mmol), 1-bromomethyl-3,5-dimethoxybenzene (580 mg, 2.5 mmol) and $K_2CO_3$ (440 mg, 3.20 mmol) in DMF (10 mL) is stirred under $N_2$ at 50° C. for 6 h. After adding $H_2O$, the reaction mixture is extracted with EtOAc. The combined organic phases are washed with $H_2O$ and dried ($Na_2SO_4$). Concentration under reduced pressure and silica gel flash chromatography give Intermediate 153.4 as colorless amorphous; ES-MS: M+H=632; HPLC: $_At_{Ret}$=5.85 min.

Intermediate 153.5

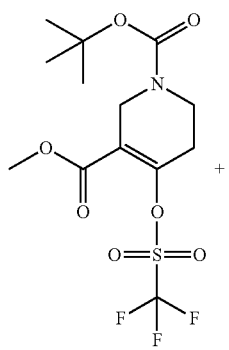

+

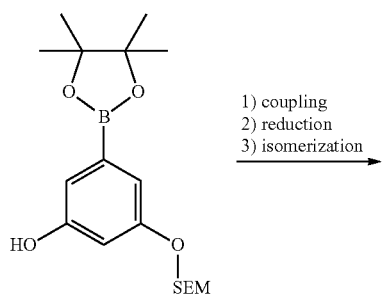 1) coupling
2) reduction
3) isomerization →

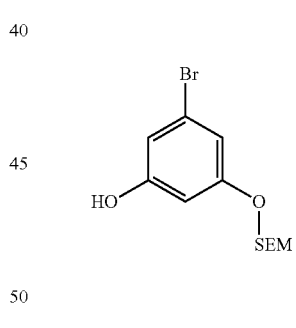

Intermediate 153.6 is synthesized by condensation of 4-trifluoromethanesulfonyloxy-5,6-dihydro-2H-pyridine-1,3-dicarboxylic acid 1-tert-butyl ester 3-methyl ester (1.90 g, 4.9 mmol) (see e.g. WO 2004/002957 or US 2003/216441) and Intermediate 153.7 (1.49 g, 4.07 mmol) analogously to the preparation of Intermediate 2.1. Yellow amorphous; Rf=0.28 (EtOAc:n-Hex=1:2); HPLC: $_At_{Ret}$=4.93 min.

Intermediate 153.5 is synthesized by 1,4-reduction and epimerization of Intermediate 153.6 (1.57 g, 3.3 mmol) analogously to the preparation of Intermediate 4.3. White powder; ES-MS: M+H=482; HPLC: $_At_{Ret}$=4.90 min.

Intermediate 153.7

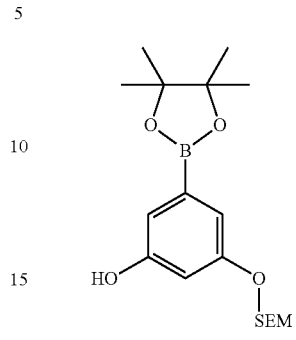

A mixture of Intermediate 153.8 (4.0 g, 12.5 mmol), bis(pinacolato)diboron (4.77 g, 18.8 mmol), KOAc (4.9 g, 50 mmol) and Pd(PPh$_3$)$_4$ (1.44 g, 1.25 mmol) in DMF (50 mL) is stirred under N$_2$ at 80° C. After stirring for 20 h, the reaction mixture is quenched by H$_2$O, and the mixture is extracted with Et$_2$O. The combined organic phases are washed with H$_2$O and dried (Na$_2$SO$_4$). Concentration under reduced pressure and silica gel flash chromatography give Intermediate 153.7 as yellow oil; ES-MS: M+H=367; HPLC: $_At_{Ret}$=4.99 min.

Intermediate 153.8

To a mixture of 5-bromoresorcinol (740 mg, 3.90 mmol) (see e.g. European Journal of Organic Chemistry (1998), (2), 359-364) and DIEA (820 µL, 4/mmol) in DCM (20 mL) THF (2 mL) is added SEMCl (760 µL, 4.3 mmol) at RT. After stirring for 3 h, the reaction mixture is quenched with H$_2$O, and the mixture is extracted with EtOAc. The combined organic phases are washed with H$_2$O and dried (Na$_2$SO$_4$). Concentration under reduced pressure and silica gel flash chromatography give Intermediate 153.8 as colorless oil; Rf=0.34 (EtOAc:n-Hex=1:4); $^1$H NMR (CDCl$_3$), δ: 0.01 (9H, s), 0.94-0.98 (2H, m), 3.71-3.76 (2H, m), 4.99 (3H, s), 5.17 (2H, s), 6.47-6.48 (1H, m), 6.65-6.66 (1H, m), 6.79-6.80 (1H, m).

Intermediate 154.1

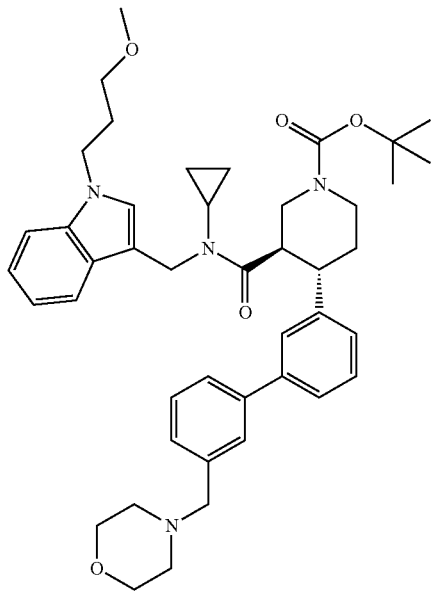

Intermediate 154.1 is synthesized by coupling of Intermediate 42.2 (210 mg, 0.30 mmol) and [4-(4-morpholinylmethyl)phenyl]-boronic acid (200 mg, 0.9 mmol) analogously to the preparation of Intermediate 42.1 as an oil; ES-MS: M+H=721; HPLC: $_A t_{Ret}$=3.85 min.

Intermediate 155.1

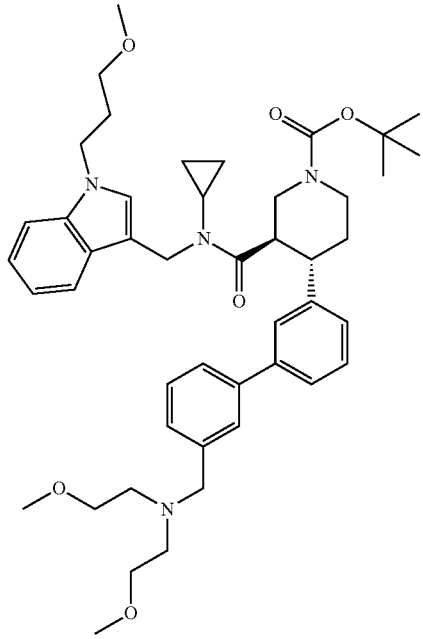

Intermediate 155.1 is synthesized by coupling of Intermediate 42.2 (130, 0.19 mmol) and Intermediate 155.2 (150 mg, 0.56 mmol) analogously to the preparation of Intermediate 2.1 as an oil; ES-MS: M+H=767; HPLC: $_A t_{Ret}$=4.05 min.

Intermediate 155.2

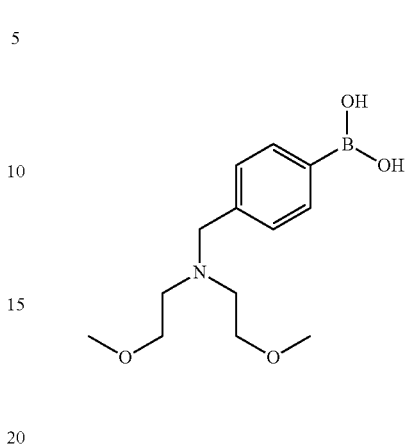

Intermediate 155.2 is synthesized by condensation of 3-formylphenyl-boronic acid (300 mg, 2.0 mmol) and Bis-(2-methoxy-ethyl)-amine (270 mg, 2.0 mmol) analogously to the preparation of Intermediate 137.2 white solid; ES-MS: M+H=268; HPLC: $_A t_{Ret}$=1.75 min.

Intermediate 156.1

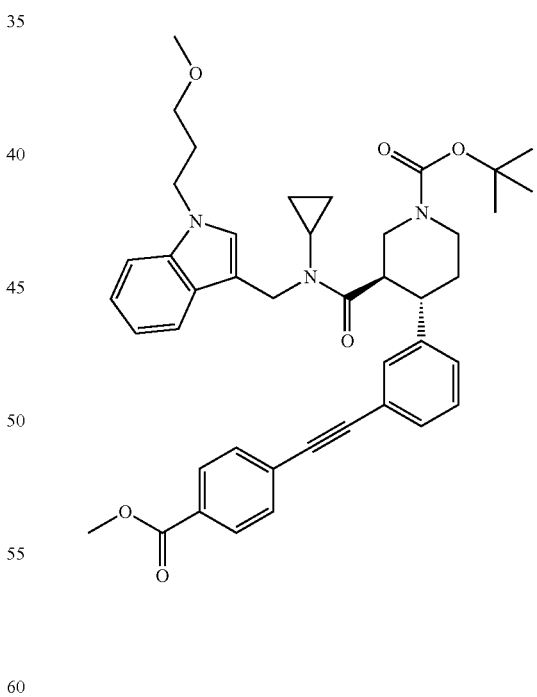

Intermediate 156.1 is synthesized by coupling of Intermediate 42.2 (201.6 mg, 0.29 mmol) and 4-Ethynyl-benzoic acid methyl ester (286.2 mg, 1.78 mmol) analogously to the preparation of Intermediate 109.2. White amorphous material; ES-MS: M+H=704; HPLC: $_A t_{Ret}$=5.70 min.

Intermediate 157.1

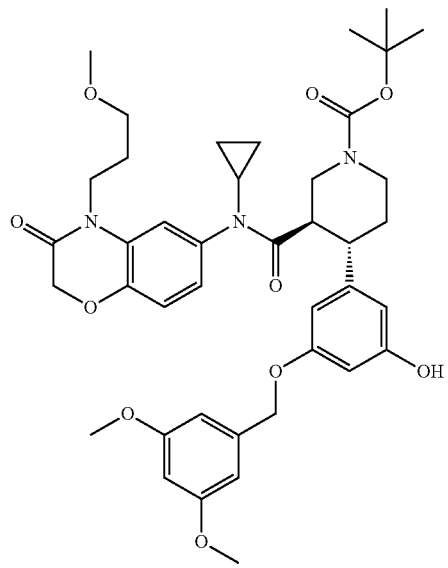

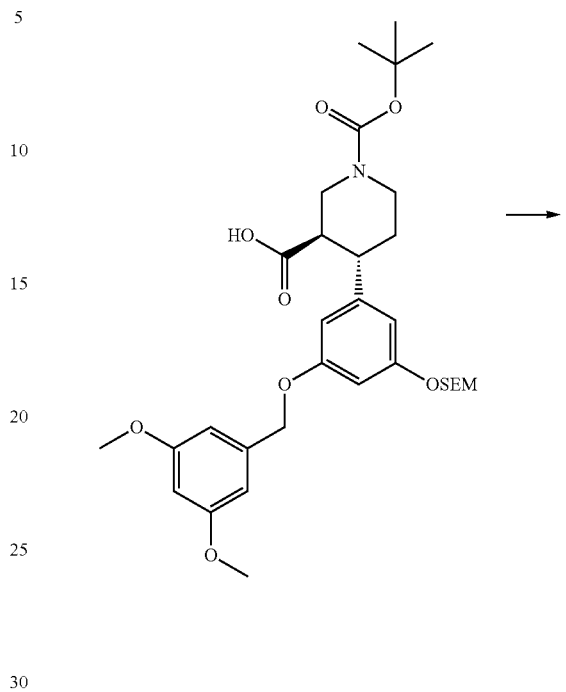

A mixture of Intermediate 157.2 (104 mg, 0.12 mmol) and 1M solution of TBAF in THF (5 mL) are stirred under $N_2$ at 50° C. for 5 h. After adding $H_2O$, the reaction mixture is extracted with EtOAc. The combined organic phases are washed with $H_2O$, dried ($Na_2SO_4$), concentrated under reduced pressure, and silica gel flash chromatography to give Intermediate 157.1; ES-MS: M+H=746; HPLC: $_A t_{Ret}$=4.30 min.

Intermediate 157.2

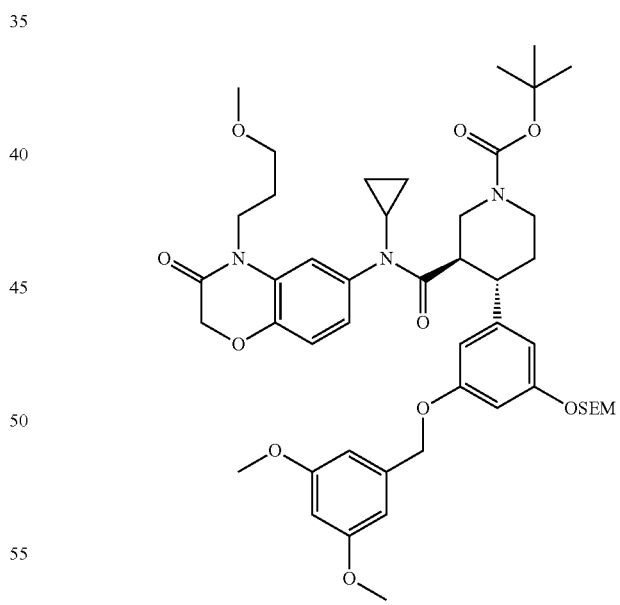

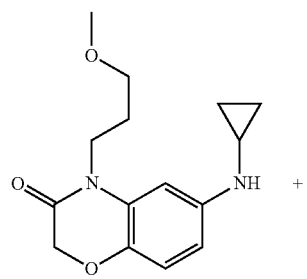 +

Intermediate 157.2 is synthesized by condensation of Intermediate 153.3 (463 mg, 0.75 mmol) and Intermediate 101.2 (217 mg, 0.79 mmol) analogously to the preparation of Intermediate 145.4. Colorless oil; ES-MS: M+H=876; HPLC: $_A t_{Ret}$=5.78 min.

Intermediate 158.1

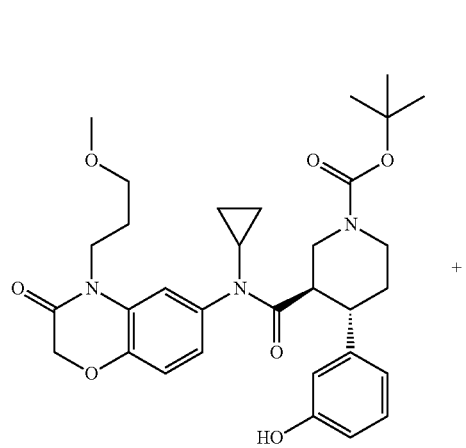

Intermediate 158.2

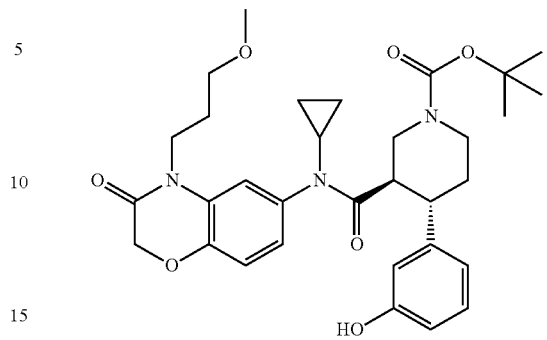

Intermediate 158.2 is synthesized by hydrolysis of Intermediate 158.3 (610 mg, 0.94 mmol) analogously to the preparation of Intermediate 145.3. White amorphous material; ES-MS: M+H=580; HPLC: $_A t_{Ret}$=3.74 min.

Intermediate 158.3

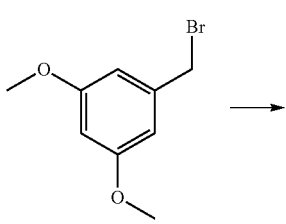

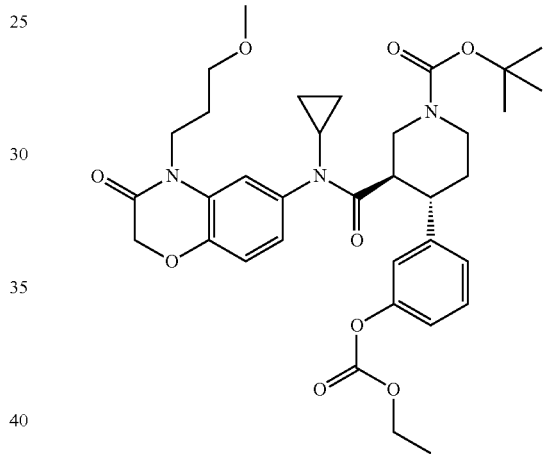

Intermediate 158.3 is synthesized by condensation of Intermediate 158.4 (642 mg, 2.0 mmol) and Intermediate 101.2 (580 mg, 2.10 mmol) analogously to the preparation of Intermediate 145.4. amorphous material; ES-MS: M+H=652; HPLC: $_A t_{Ret}$=4.38 min. Intermediate 158.4 (chiral, salt free)

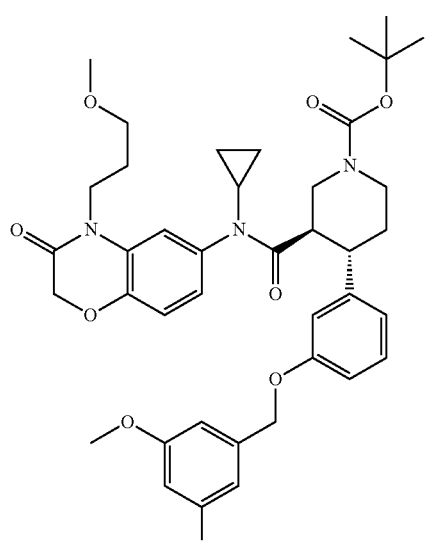

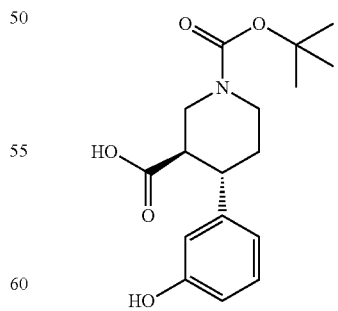

Intermediate 158.1 is synthesized by condensation of Intermediate 158.2 (460 mg, 0.8 mmol) and 1-bromomethyl-3,5-dimethoxybenzene (222 mg, 0.96 mmol) analogously to the preparation of Intermediate 153.4. White powder; ES-MS: M+=630; HPLC: $_A t_{Ret}$=3.20 min.

To a suspension of intermediate 158.5 (2.18 g, 3.38 mmol) in Et$_2$O (80 mL), 1 N HCl aqueous solution (74 mL, 7.44 mmol) are added at 0° C. The organic phases are washed with H$_2$O and dried (MgSO$_4$) to give Intermediate 158.4 as white solid; ES-MS: M-56($^t$Bu)=266: $_A t_{Ret}$=3.17 min.

Intermediate 158.5

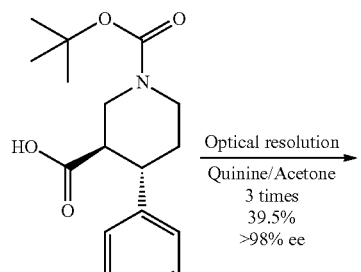

Optical resolution
Quinine/Acetone
3 times
39.5%
>98% ee

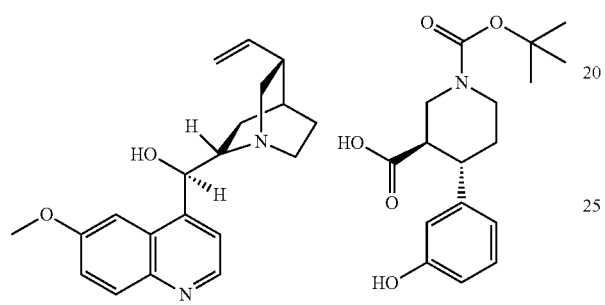

A mixture of intermediate 26.3 (47.92 g) in acetone (600 mL) and quinine (48.37 g) in acetone (600 mL) was stirred at room temperature overnight. The resulting crystals were filtered, and their re-crystallization from acetone was repeated two times to give intermediate 158.5 (38.06 g, 39.5%, >98% ee).

Intermediate 159.1

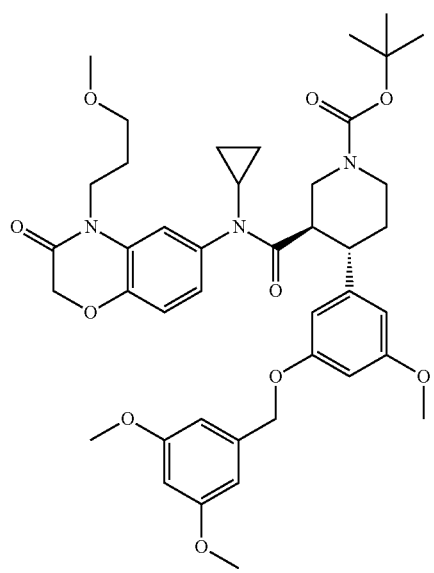

Intermediate 159.1 is synthesized by alkylation of Intermediate 157.1 (100 mg, 0.13 mmol) and MeI (10 μL, 0.16 mmol) analogously to the preparation of Intermediate 153.4. White powder; ES-MS: M+=760; HPLC: $_A t_{Ret}$=4.82 min.

Intermediate 160.1

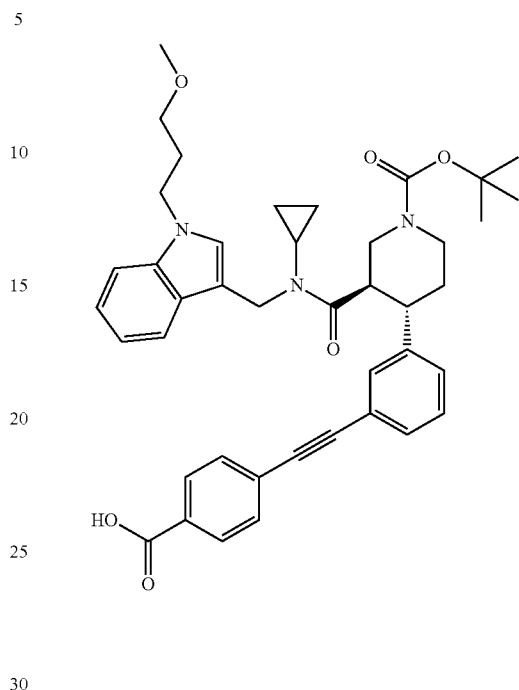

Intermediate 160.1 is synthesized by hydrolysis of Intermediate 156.1 analogously to the preparation of Intermediate 80.2. White amorphous material; ES-MS: M+H=690; HPLC: $_A t_{Ret}$=4.95 min.

Intermediate 161.1

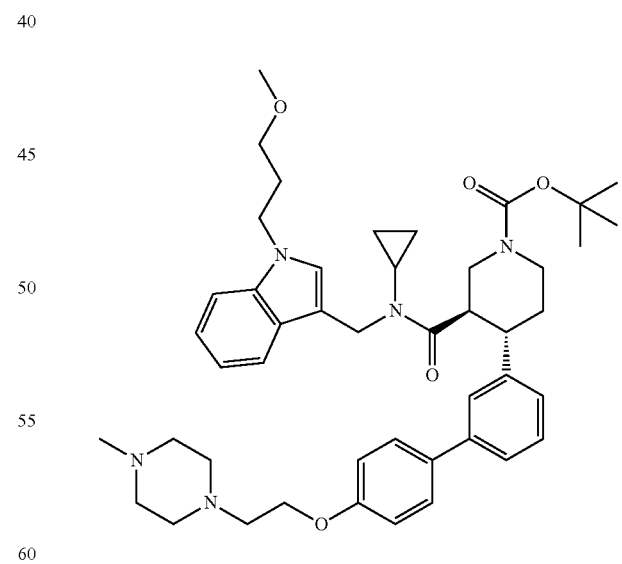

Intermediate 161.1 (chiral) is synthesized by Mitsunobu reaction analogously of intermediate 161.2 to the preparation of intermediate 104.1 (racemic) white amorphous; ES-MS: M+=764; HPLC: $_A t_{Ret}$=3.52 min.

Intermediate 61.2

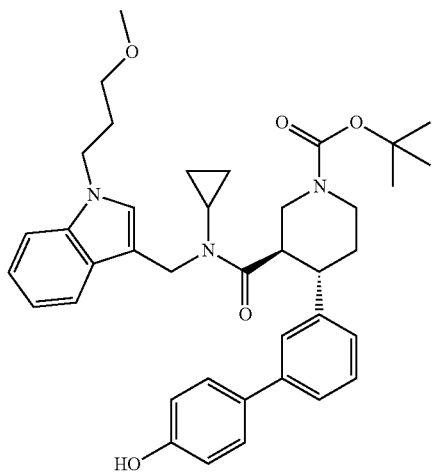

Intermediate 161.2 (chiral) is synthesized from Intermediate 161.3 analogously to the preparation of Intermediate 42.1 (racemic). White amorphous material; ES-MS: M+H=638; HPLC: $_A t_{Ret}$=4.67 min.

Intermediate 161.3

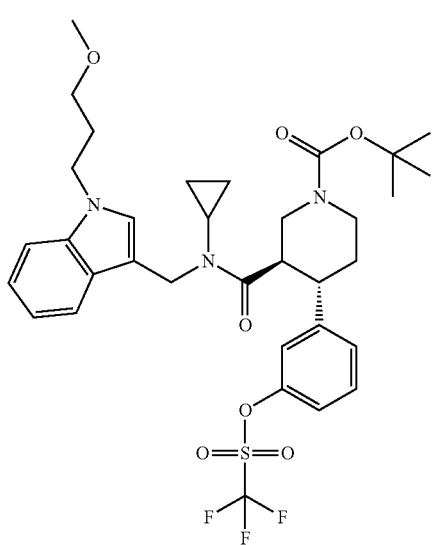

Intermediate 161.3 (chiral) is synthesized from Intermediate 161.4 analogously to the preparation of Intermediate 42.2 (racemic). White amorphous material; ES-MS: M+H=694; HPLC: $_A t_{Ret}$=5.34 min.

Intermediate 161.4

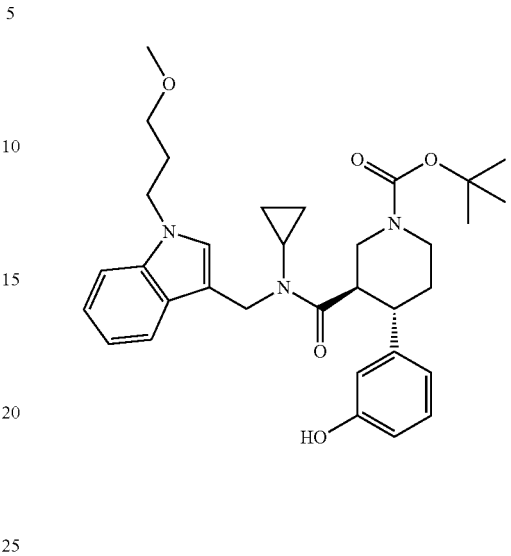

Intermediate 161.4 is synthesized by condensation of Intermediate 158.4 (508 mg, 1.58 mmol) and Intermediate 22.2 (490 mg, 1.90 mmol) analogously to the preparation of Intermediate 4.1. White amorphous material; ES-MS: M+H=562; HPLC: $_A t_{Ret}$=4.35 min.

Intermediate 162.1

Intermediate 42.2 (380 mg, 0.55 mmol), piperidine (0.081 mL, 0.82 mmol), Pd$_2$(dba)$_3$ (50 mg, 0.055 mmol), Di-t-butylphosphinobiphenyl (16 mg, 0.055 mmol) and Cs$_2$CO$_3$ (268 mg, 0.82 mmol) is stirred at 80° C. for 12 h. After cooling to room temperature, the reaction mixture is diluted with AcOEt and washed with brine. The organic layer is dried (Na$_2$SO$_4$), concentrated and purified by silica gel column chromatography to give Intermediate 162.1 as white amorphous; ES-MS: M=629; HPLC: $_A t_{Ret}$=3.57 min.

Intermediate 163.1

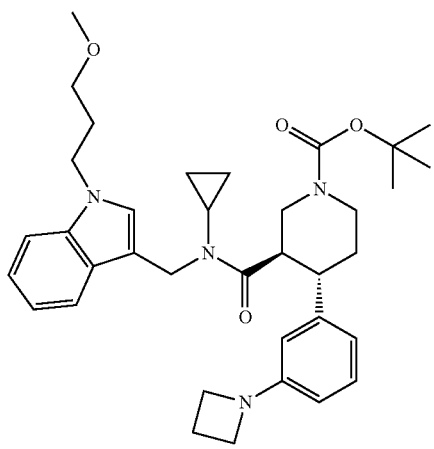

Intermediate 163.1 is synthesized by coupling of Intermediate 42.2 (353 mg, 0.51 mmol) and azetidine hydrochloride (71 mg, 0.76 mmol) analogously to the preparation of Intermediate 162.1. White amorphous material; ES-MS: M+H=601; HPLC: $_A t_{Ret}$=3.80 min.

Intermediate 164.1

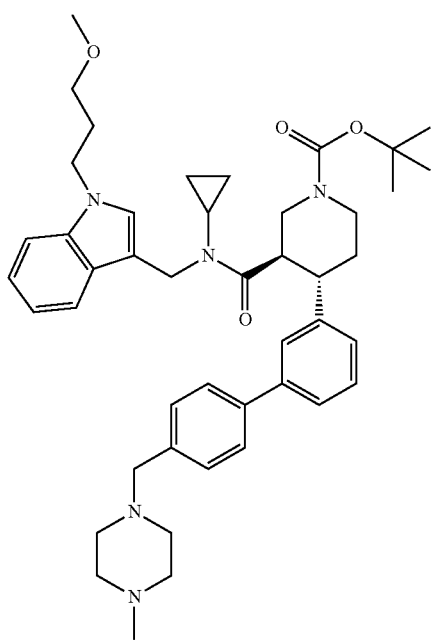

A mixture of intermediate 164.2 (250 mg, 0.39 mmol), 1-Methyl-piperazine (0.10 mL, 0.92 mmol), AcOH (0.4 mL) and NaBH$_3$CN (30 mg, 0.45 mmol) in DCM (1.2 mL) and MeOH (0.4 mL) is stirred under N$_2$ at 0° C. After stirring at RT for 1 hour, the reaction mixture is quenched with saturated aqueous NaHCO$_3$ and extracted with DCM. The combined organic phases are washed with H$_2$O, brine and dried (MgSO$_4$). Concentration under reduced pressure and silica gel flash chromatography give Intermediate 164.1 as yellow oil; ES-MS: M+H=734; HPLC: $_A t_{Ret}$=3.42 min Intermediate 164.2

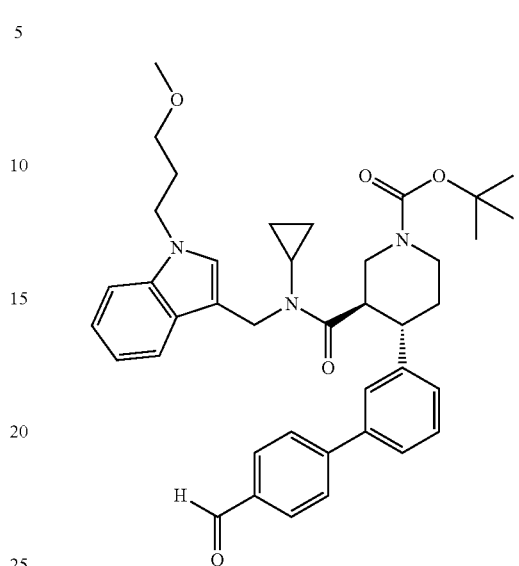

Intermediate 164.2 is synthesized by coupling of Intermediate 42.2 (1.0 g, 1.44 mmol) and 4-formylphenylboronic acid (431 mg, 2.88 mmol) analogously to the preparation of Intermediate 42.1. red amorphous material; ES-MS: M+H=650; HPLC: $_A t_{Ret}$=5.15 min.

Intermediate 165.1

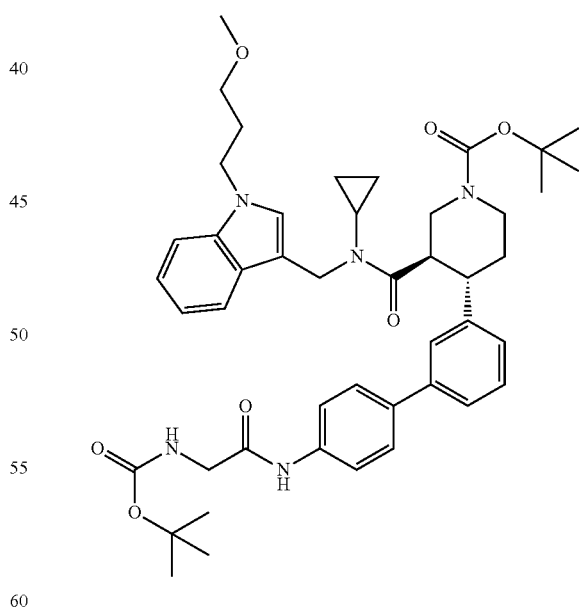

Intermediate 165.1 is synthesized by condensation of intermediate 134.1 (100 mg, 0.16 mmol) and tert-Butoxycarbonylamino-acetic acid (56 mg, 0.32 mmol) analogously to the preparation of Intermediate 83.2. Colorless oil; ES-MS: M+H=794; HPLC: $_A t_{Ret}$=4.97 min.

Intermediate 166.1

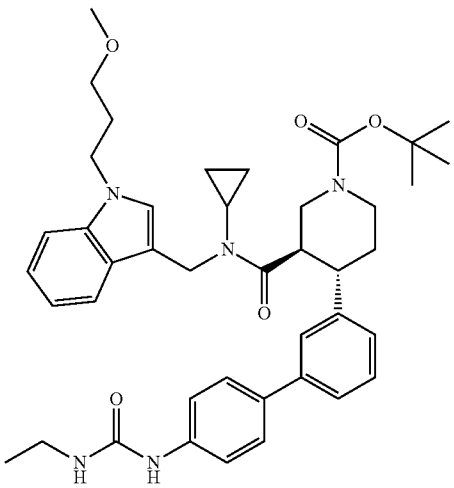

A mixture of intermediate 134.1 (100 mg, 0.16 mmol), ethyl isocyanato (0.02 mL, 0.17 mmol), and Et$_3$N (0.05 mL, 0.35 mmol) in THF (3 mL) is stirred under N$_2$ at RT for 12 h. After adding H$_2$O, the reaction mixture is extracted with EtOAc. The combined organic phases are washed with H$_2$O and dried (MgSO$_4$). Concentration under reduced pressure and silica gel flash chromatography give intermediate 166.1 as colorless amorphous; ES-MS: M+H=708; HPLC: $_A t_{Ret}$=4.64 min.

Intermediate 167.1

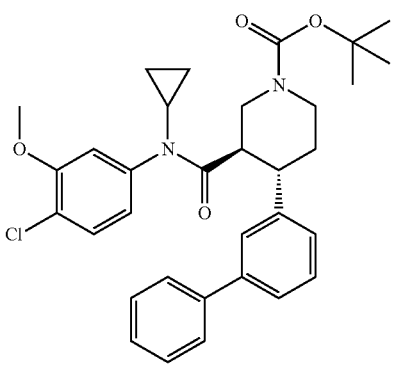

Intermediate 167.1 is synthesized by condensation of Intermediate 1.2 (150 mg, 0.40 mmol) and Intermediate 167.2 (87 mg, 0.44 mmol) analogously to the preparation of Intermediate 145.4 White amorphous material; ES-MS: M+H=561; HPLC: $_A t_{Ret}$=5.50 min.

Intermediate 167.2

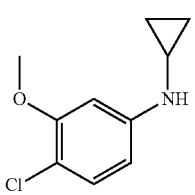

A mixture of 4-bromo-1-chloro-2-methoxybenzene (500 mg, 2.30 mmol), cyclopropylamine (387 mg, 6.80 mmol), Pd$_2$(dba)$_3$ (183 mg, 0.20 mmol), NaOtBu (331 mg, 3.50 mmol) and racemic BINAP (373 mg, 0.60 mmol) in toluene (3 mL) is heated under N$_2$ at 90° C. for 6 h. After adding H$_2$O at RT, the reaction mixture is extracted with EtOAc. The combined organic phases are washed with H$_2$O and dried (MgSO$_4$). Concentration under reduced pressure and silica gel flash chromatography give Intermediate 167.2: Yellow oil; ES-MS: M+H=198: $_A t_{Ret}$=3.82 min.

Intermediate 168.1

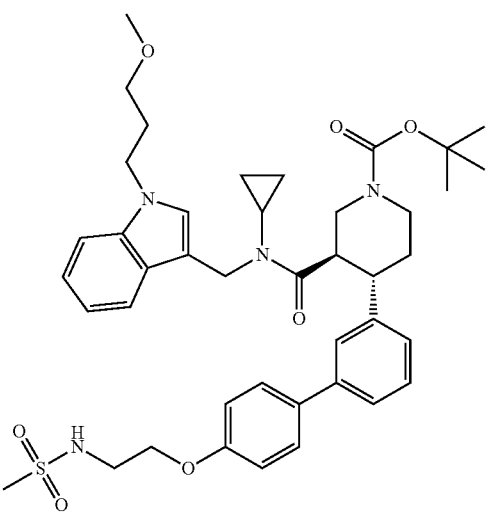

To a solution of Intermediate 168.2 (132 mg, 0.19 mmol) and Et$_3$N (0.04 mL, 0.29 mmol) in CH$_2$Cl$_2$ (3 mL) is added MsCl (0.018 mL, 0.23 mmol). After stirring at room temperature for 0.5 h, the reaction is quenched with saturated aqoueous NaHCO$_3$. The organic layer is separated and concentrated. The residue is purified by silica gel column chromatography to give Intermediate 168.1 as white amorphous; ES-MS: M+1=759; HPLC: $_A t_{Ret}$=4.77 min.

Intermediate 168.2

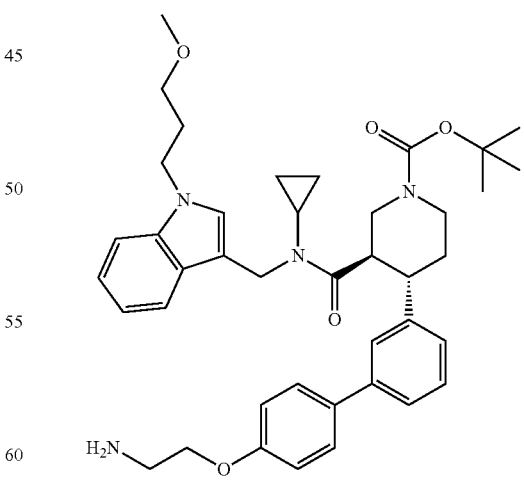

A crude material of Intermediate 168.3 and H$_2$NNH$_2$.H$_2$O (55 mg, 1.10 mmol) are dissolved in EtOH (3 mL) and stirred at 50° C. for 2 h. After adding H$_2$O, the resulting mixture is extracted with AcOEt. The organic layer is washed with brine, dried (Na$_2$SO$_4$) and concentrated. Silica gel column chromatography give Intermediate 168.2 as white amorphous; ES-MS: M+1=681; HPLC: $_At_{Ret}$=3.73 min.

Intermediate 168.3

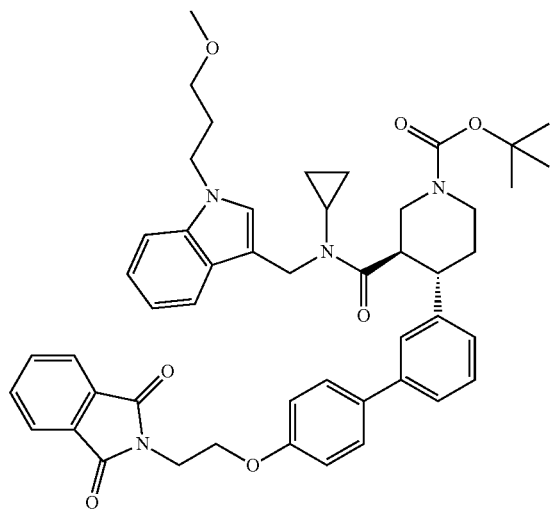

Intermediate 168.3 is synthesized by Mitsunobu reaction of Intermediate 42.1 (351 mg, 0.55 mmol) and N-(2-hydroxyethyl)phtalimide (210 mg, 1.10 mmol) analogously to the preparation of Intermediate 104.1 (including triphenylphosphine oxide as byproduct)I; ES-MS: M=811; HPLC: $_At_{Ret}$=5.52 min.

Intermediate 169.1

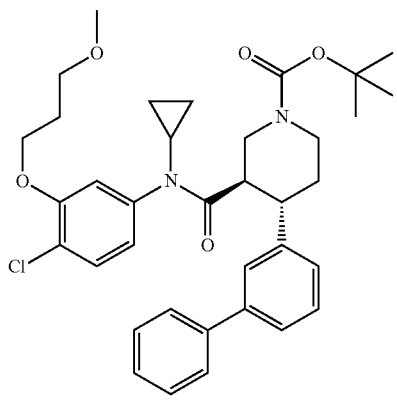

Intermediate 169.1 is synthesized by condensation of Intermediate 1.2 (150 mg, 0.40 mmol) and Intermediate 169.2 (100 mg, 0.39 mmol) analogously to the preparation of Intermediate 145.4 White amorphous material; ES-MS: M+H=619; HPLC: $_At_{Ret}$=5.70 min.

Intermediate 169.2

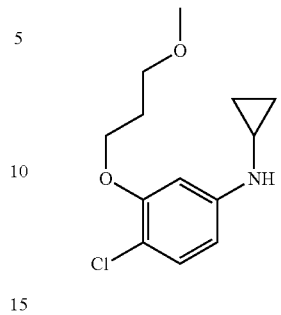

Intermediate 169.2 is synthesized by condensation of Intermediate 169.3 (500 mg, 1.79 mmol) and cyclopropylamine (305 mg, 5.30 mmol) analogously to the preparation of Intermediate 167.2. White amorphous material; ES-MS: M+H=256; HPLC: $_At_{Ret}$=4.07 min.

Intermediate 169.3

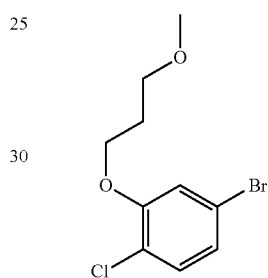

Intermediate 169.3 is synthesized by condensation of 5-bromo-2-chlorophenol (1.50 g, 7.20 mmol) and toluene-4-sulfonicacid 3-methoxypropyl ester (1.95 g, 8.00 mmol) analogously to the preparation of Intermediate 4.8. Colorless oil; ES-MS: M+H=280; HPLC: $_At_{Ret}$=4.59 min.

Intermediate 170.1

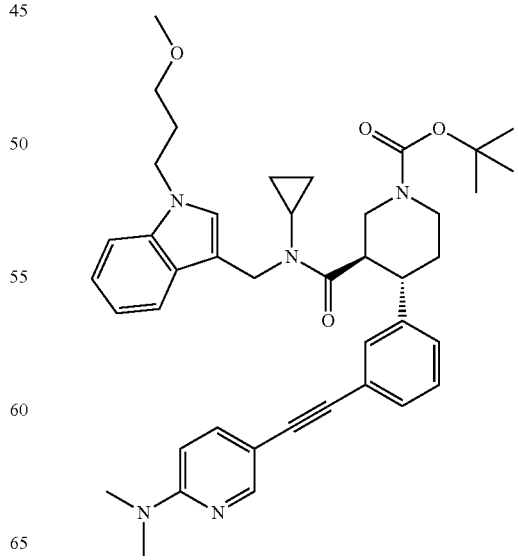

Intermediate 170.1 is synthesized by coupling of Intermediate 42.2 (157.3 mg, 0.23 mmol) and (5-Ethynyl-pyridin-2-yl)-dimethyl-amine (78 mg, 0.53 mmol) analogously to the preparation of Intermediate 109.2. White amorphous material; ES-MS: M+H=690; HPLC: $_At_{Ret}$=3.90 min.

Intermediate 171.1

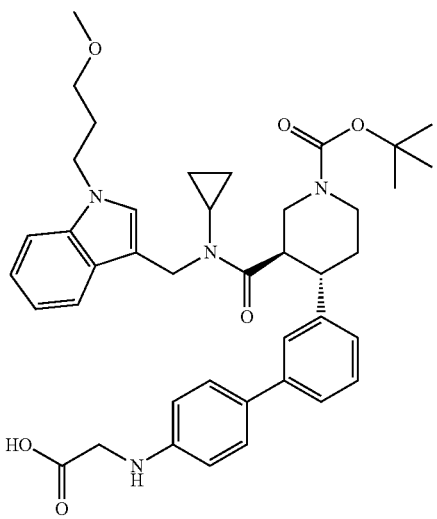

Intermediate 171.1 is synthesized by hydrolysis of intermediate 171.2 (81.2 mg, 0.11 mmol) analogously to the preparation of Intermediate 80.2. White amorphous material; ES-MS: M+H=695; HPLC: $_At_{Ret}$=4.46 min.

Intermediate 171.2

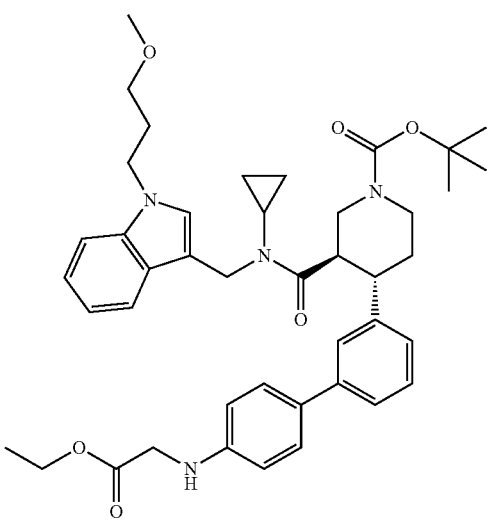

Intermediate 171.2 is synthesized by alkylation of intermediate 134.1 (100 mg, 0.16 mmol) analogously to the preparation of intermediate 80.2. White amorphous material; ES-MS: M+H=723; HPLC: $_At_{Ret}$=5.19 min.

Intermediate 172.1

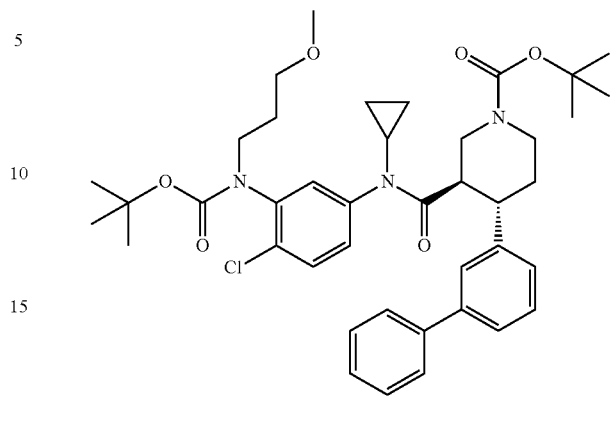

Intermediate 172.1 is synthesized by condensation of Intermediate 1.2 (97 mg, 0.25 mmol) and Intermediate 172.2 (110 mg, 0.28 mmol) analogously to the preparation of Intermediate 145.4. White amorphous material; ES-MS: M+H=718; HPLC: $_At_{Ret}$=5.83 min.

Intermediate 172.2

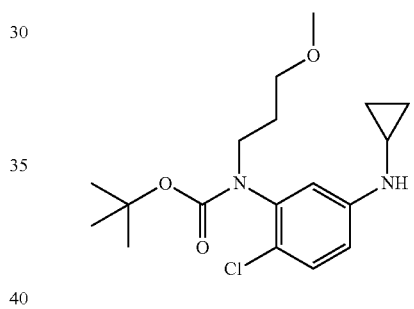

Intermediate 172.2 is synthesized by condensation of Intermediate 172.3 (300 mg, 1.06 mmol) and toluene-4-sulfonic acid 3-methoxy-propyl ester (336 mg, 1.30 mmol) analogously to the preparation of Intermediate 4.8. Yellow oil; ES-MS: M+H—BOC=255; HPLC: $_At_{Ret}$=4.57 min.

Intermediate 172.3

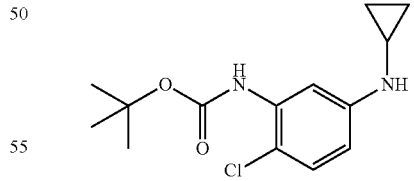

A mixture of Intermediate 172.4 (900 mg, 4.94 mmol), (BOC)$_2$O (1.30 g, 6.10 mmol), Et$_3$N (763 mg, 7.0 mmol) and DMAP (catalytic amount) in THF (10 mL) is stirred at RT for 8 h. After adding H$_2$O, the reaction mixture is extracted with EtOAc. The combined organic phases are washed twice with H$_2$O, and dried (MgSO$_4$). Concentration under reduced pressure and silica gel flash chromatography give Intermediate 172.3. Yellow solids; ES-MS: M+H-tBuO$_2$=196; HPLC: $_At_{Ret}$=5.59 min.

Intermediate 12.4

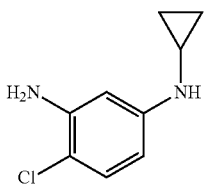

Intermediate 172.4 is synthesized by reduction of Intermediate 172.5 (1.00 g, 4.70 mmol) analogously to the preparation of Intermediate 149.6. Yellow oil; ES-MS: M+H=183; HPLC: $_At_{Ret}$=2.40 min.

Intermediate 172.5

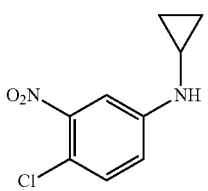

Intermediate 172.5 is synthesized by cyclopropanation of 4-chloro-3-nitrophenylamine (5.00 g, 29 mmol) analogously to the preparation of Intermediate 101.4. Yellow oil; ES-MS: M+H=213; HPLC: $_At_{Ret}$=4.07 min.

Intermediate 173.1

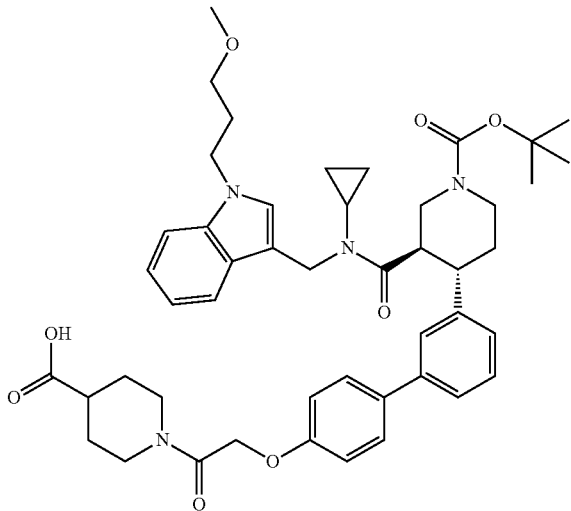

To a solution of Intermediate 80.1 (141 mg, 0.20 mmol), EDCl (58 mg, 0.30 mmol) and HOAt (28 mg, 0.20 mmol) in DMF (2 mL) is added isonipecotic acid (39 mg, 0.30 mmol). After stirring at room temperature for 2 h, H₂O is added. The resulting mixture is extracted with AcOEt and washed with brine. The organic layer is dried (Na₂SO₄) and concentrated. Purification by silica gel column chromatography give Intermediate 173.1 as white Intermediate 174.1

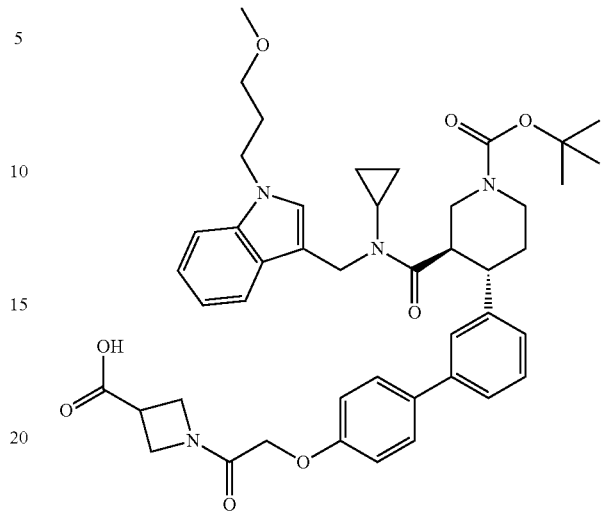

Intermediate 174.1 is synthesized by condensation of Intermediate 80.1 (141 mg, 0.20 mmol) and 3-Azetidinecarboxylic acid (31 mg, 0.30 mmol) analogously to the preparation of Intermediate 173.1; ES-MS: M+1=779; HPLC: $_At_{Ret}$=4.28 min.

Intermediate 175.1

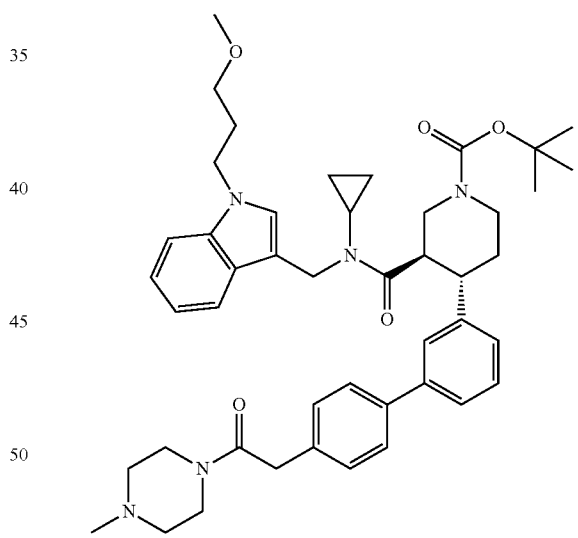

A mixture of Intermediate 127.2 (50 mg, 0.07 mmol), 1-[(4-bromophenyl)acetyl]-4-methylpiperazine (24 mg, 2.88 mmol), Pd(OAc)₂ (1.7 mg, 0.007 mmol), 2-(Dicyclohexylphosphino)-2',6'-dimethoxy-1,1-biphenyl (6.0 mg, 0.015 mmol) and K₃PO₄ (31.4 mg, 0.15 mmol) in toluene (2 mL) and H₂O (0.2 mL) is stirred at 100° C. After stirring for 12 h, adding H₂O at RT, the reaction mixture is extracted with EtOAc. The combined organic phases are washed with brine, dried (Na₂SO₄). Concentration under reduced pressure and silica gel flash chromatography of the residue (hexane/ethyl acetate) affords Intermediate 175.1 as amorphous; ES-MS: M+H=762; HPLC: $_At_{Ret}$=3.72 min.

Intermediate 176.1

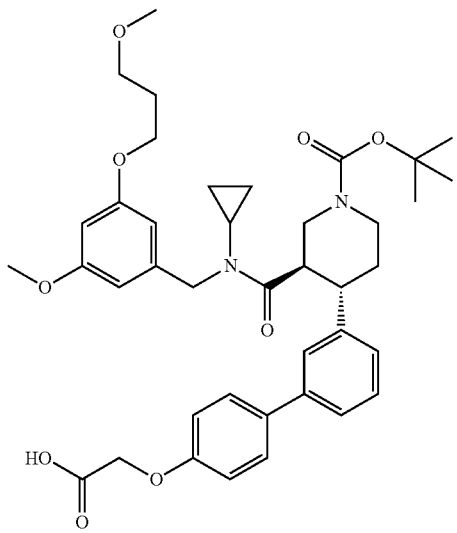

Intermediate 176.1 is synthesized by hydrolysis of Intermediate 176.2 (140 mg, 0.19 mmol) analogously to the preparation of Intermediate 80.1. White amorphous material; ES-MS: M+H=703; HPLC: $_A t_{Ret}$=4.47 min.

Intermediate 176.2

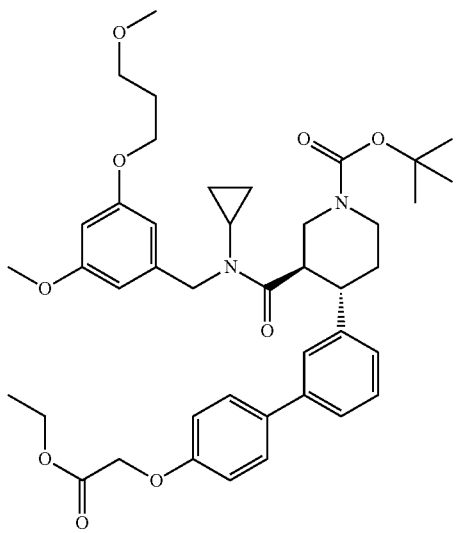

Intermediate 176.2 is synthesized by reaction of Intermediate 58.1 (164 mg, 0.25 mmol) and iodoethyl acetate (0.06 mL, 0.51 mmol) analogously to the preparation of Intermediate 80.2. White amorphous material; ES-MS: M+H=732; HPLC: $_A t_{Ret}$=5.17 min.

Intermediate 177.1

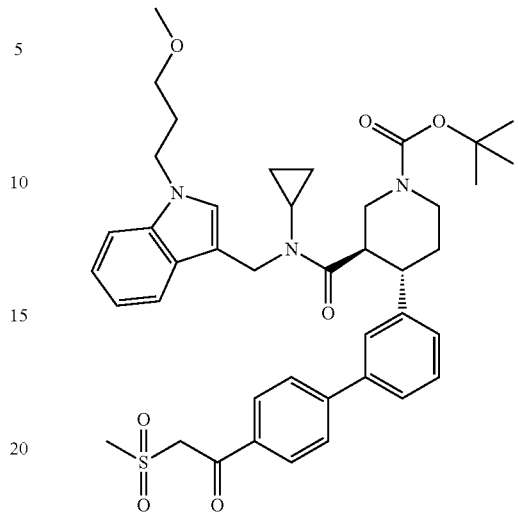

Intermediate 177.1 is synthesized by coupling of Intermediate 42.2 (340, 0.49 mmol) and Intermediate 177.2 (130 mg, 0.54 mmol) analogously to the preparation of Intermediate 2.1 as an White amorphous material; ES-MS: M+H=742; HPLC: $_A t_{Ret}$=4.67 min.

Intermediate 177.2

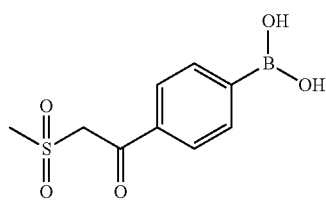

To a solution of 4-Ethoxycarbonylphenylboronic acid, pinacol ester (276 mg, 1.00 mmol) in DMSO (5 mL), 1-Methanesulfonyl-propan-2-one (990 mg, 10.0 mmol) and NaH are added. After stirred at RT for 2 h, the reaction mixture is quenched with $H_2O$ and extracted with AcOEt. The combined organic phases are washed with $H_2O$ and dried ($MgSO_4$) to give Intermediate 177.2 as white solid; ES-MS: M-48= 195: $_A t_{Ret}$=2.68 min.

Intermediate 178.1

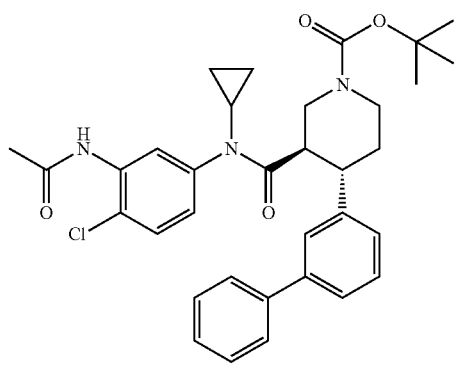

Intermediate 178.1 is synthesized by condensation of Intermediate 1.2 (150 mg, 0.40 mmol) and Intermediate 178.2

(98.0 mg, 0.44 mmol) analogously to the preparation of intermediate 145.4. White amorphous material; ES-MS: M+H=588; HPLC: $_At_{Ret}$=4.68 min.

Intermediate 178.2

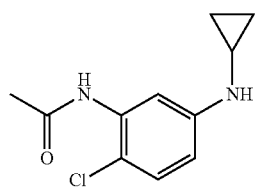

Intermediate 178.2 is synthesized by cyclopropanation of N-(5-amino-2-chlorophenyl)acetamide (2.40 g, 13.0 mmol) analogously to the preparation of Intermediate 101.4. Yellow oil; ES-MS: M+H=225; HPLC: $_At_{Ret}$=2.88 min.

Intermediate 179.1

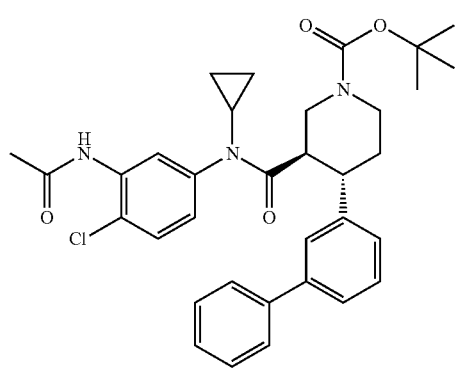

Intermediate 179.1 is synthesized by condensation of Intermediate 1.2 (150 mg, 0.40 mmol) and Intermediate 179.2 (130 mg, 0.48 mmol) analogously to the preparation of Intermediate 145.4. White amorphous material; ES-MS: M+H=660; HPLC: $_At_{Ret}$=5.02 min.

Intermediate 179.2

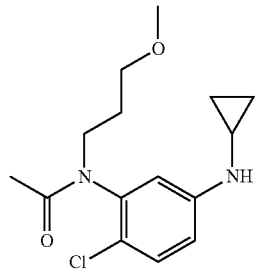

Intermediate 179.2 is synthesized by condensation of Intermediate 178.2 (250 mg, 1.11 mmol) and toluene-4-sulfonic acid 3-methoxypropyl ester (350 mg, 1.45 mmol) analogously to the preparation of Intermediate 4.8. Yellow oil; ES-MS: M+H=297; HPLC: $_At_{Ret}$=3.50 min.

180

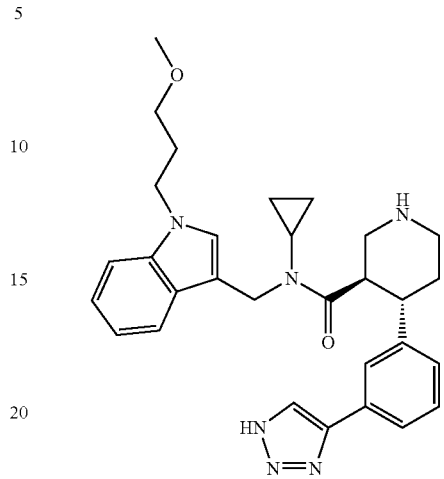

A mixture of Intermediate 109.1 (136.7 mg, 0.11 mmol) and NaN$_3$ (301 mg, 2.2 mmol) in DMF (5 mL) is stirred at 150° C. under microwave condition. After stirring for 1.5 hr, adding H$_2$O at RT, the reaction mixture is extracted with EtOAc. The combined organic phases are washed with H$_2$O, dried (Na$_2$SO$_4$). Concentration under reduced pressure and reverse phase chromatography of the residue affords 180 as amorphous; ES-MS: M+H=513; HPLC: $_At_{Ret}$=2.72 min.

Intermediate 181.1

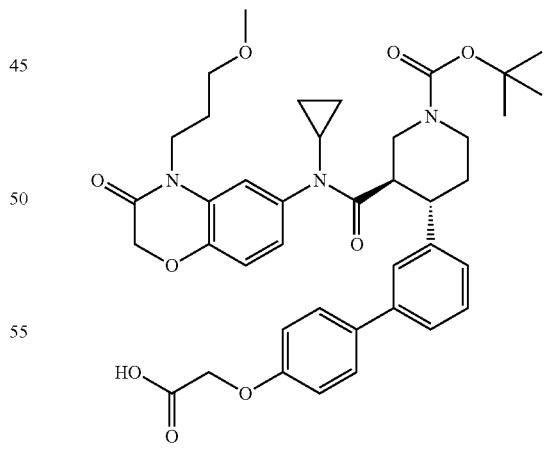

Intermediate 181.1 is synthesized by hydrolysis of Intermediate 181.2 (281 mg, 0.38 mmol) analogously to the preparation of Intermediate 80.2. White amorphous material; ES-MS: M+H=714; HPLC: $_At_{Ret}$=4.06 min.

Intermediate 181.2

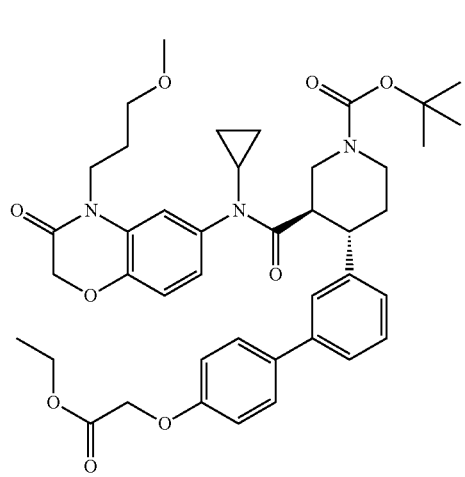

Intermediate 182.1

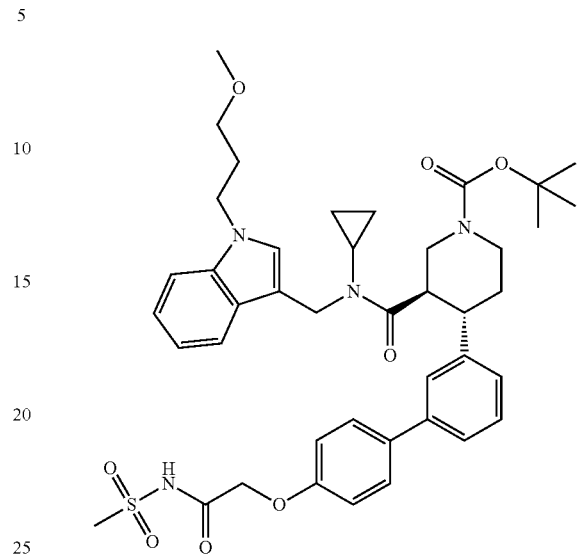

Intermediate 181.2 is synthesized by coupling of Intermediate 181.3 (100 mg, 0.14 mmol) and Ethylphenoxyacetate-4-boronic acid pinacol ester (56 mg, 0.18 mmol) analogously to the preparation of Intermediate 175.1. Amorphous material; ES-MS: M+H=743; HPLC: $_A t_{Ret}$=4.76 min.

Intermediate 181.3

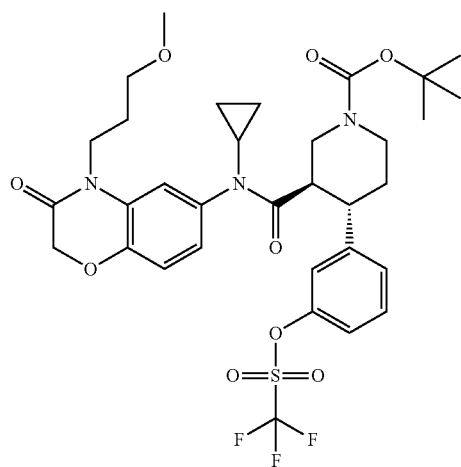

Intermediate 80.1 (169 mg, 0.24 mmol), methanesulfonamide (35 mg, 0.36 mmol), EDCl (70 mg, 0.36 mmol) and 4-DMAP (9 mg, 0.07 mmol) in $CH_2Cl_2$ (3 mL) are stirred at room temperature for 12 h. After adding $H_2O$, the organic layer is separated and concentrated. Purification by silica gel chromatography give Intermediate 182.1 as white amorphous; ES-MS: M+1=773; HPLC: $_A t_{Ret}$=4.65 min.

Intermediate 183.1

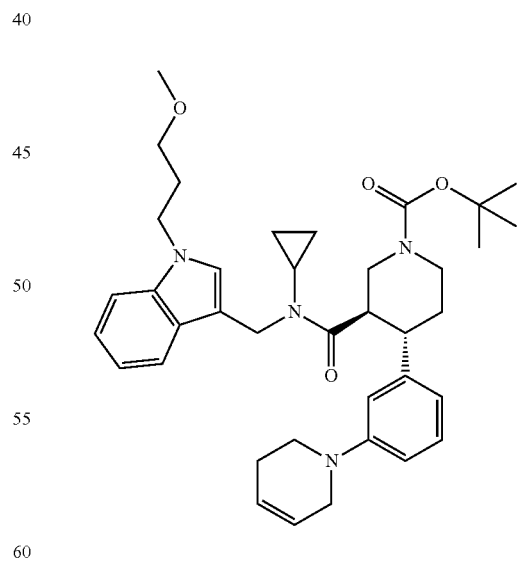

Intermediate 181.3 is synthesized by condensation of Intermediate 158.2 (455 mg, 0.79 mmol) analogously to the preparation of Intermediate 29.4. White amorphous material; ES-MS: M+H=712; HPLC: $_A t_{Ret}$=4.77 min.

Intermediate 183.1 is synthesized by coupling of Intermediate 42.2 (241 mg, 0.35 mmol) and 1,2,3,6-tetrahydropyridine (0.048 mL, 0.52 mmol) analogously to the preparation of Intermediate 162.1. White amorphous material; ES-MS: M+H=627; HPLC: $_A t_{Ret}$=3.70 min.

Intermediate 184.1

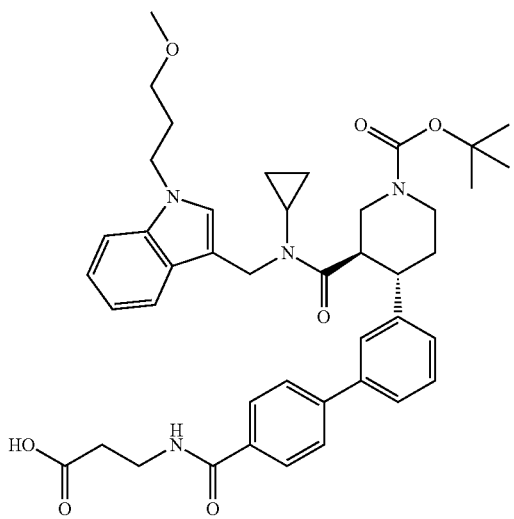

Intermediate 185.1

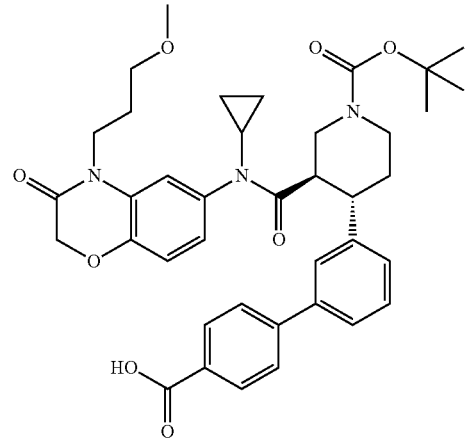

Intermediate 184.1 is synthesized by hydrolysis of Intermediate 184.2 analogously to the preparation of Intermediate 80.2 White amorphous material; ES-MS: ES-MS: M+H=737; HPLC: $_At_{Ret}$=4.28 min.

Intermediate 184.2

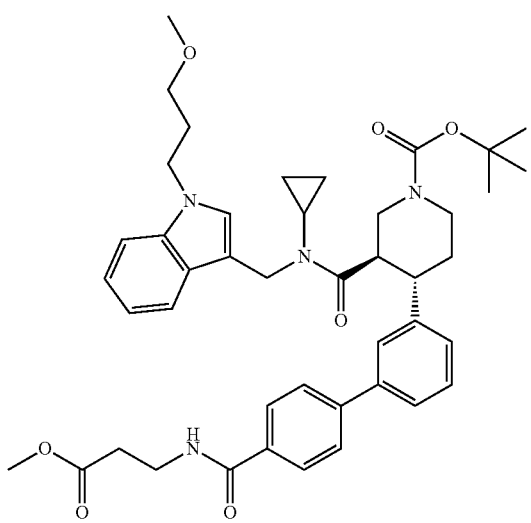

A mixture of Intermediate 86.1 (87.9 mg, 0.13 mmol), WSCD.HCl (36 mg, 0.16 mmol), HOAt (21.5 mg, 0.16 mmol), triethylamine (55 µL, 0.40 mmol) in DMF (5 mL) is stirred at 80° C. After stirring for 3 h, adding H₂O at RT, the reaction mixture is extracted with 1,2-dichloroethane. The combined organic phases are dried (Na₂SO₄). Concentration under reduced pressure affords Intermediate 184.2 as amorphous; ES-MS: M+H=751; HPLC: $_At_{Ret}$=4.68 min.

Intermediate 185.1 is synthesized by hydrolysis of Intermediate 185.2 analogously to the preparation of Intermediate 80.2 White amorphous material; ES-MS: M+H=684; HPLC: $_At_{Ret}$=4.25 min.

Intermediate 185.2

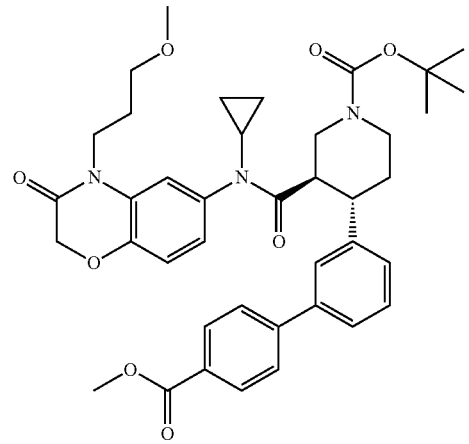

Intermediate 185.2 is synthesized by coupling of Intermediate 181.3 (60.3 mg, 0.084 mmol) and 4-methoxycarbonylphenyl boronic acid (22.6 mg, 0.13 mmol) analogously to the preparation of Intermediate 2.1. White amorphous material; ES-MS: M+H=698; HPLC: $_At_{Ret}$=4.93 min.

Intermediate 186.1

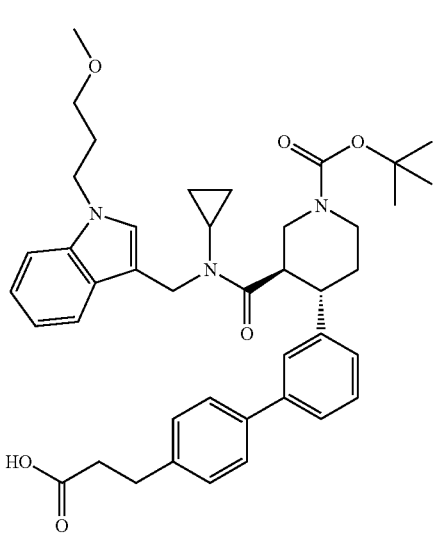

Intermediate 186.1 is synthesized by coupling of Intermediate 42.2 (200 mg, 0.3 mmol) and 3-(4-bromophenyl)-propionic acid (82 mg, 0.36 mmol) analogously to the preparation of intermediate 42.1. Amorphous material; ES-MS: M+H=694; HPLC: $_At_{Ret}$=4.89 min.

Intermediate 187.1

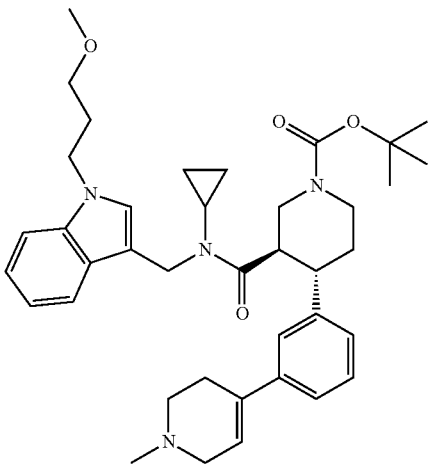

Intermediate 187.2 (138 mg, 0.21 mmol), 1,2,3,6-tetrahydro-1-methyl-4-pyridinyl ester (76 mg, 0.31 mmol) (see e.g. Tetrahedron 2003, 59, 5507-5514.), Pd(PPh$_3$)$_4$ (24 mg, 0.021 mmol) and TBAF (0.62 mL, 0.62 mmol, 1.0 M in THF) in THF (2 mL) are stirred under N$_2$ at 75° C. for 12 h. After cooling to room temperature, the reaction mixture is diluted with AcOEt and washed with H$_2$O and brine. The organic layer is dried (Na$_2$SO$_4$), concentrated and purified by silica gel column chromatography to give Intermediate 187.1 as white amorphous; ES-MS: M+H=641; HPLC: $_At_{Ret}$=3.72 min.

Intermediate 187.2

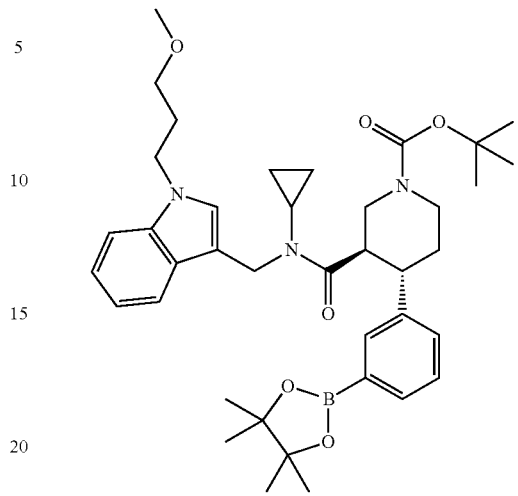

Intermediate 42.2 (1.58 g, 2.28 mmol), Bis(pinacolato)diboron (1.16 g, 4.56 mmol), PdCl$_2$(dppf)$_2$ (0.19 g, 0.228 mmol) and KOAc (0.89 g, 9.12 mmol) in DMSO (8 mL) are stirred at 80° C. for 3 h under N$_2$. After cooling to room temperature, the reaction mixture is diluted with AcOEt and washed with brine. The organic layer is dried (Na$_2$SO$_4$), concentrated and purified by silica gel column chromatography to give Intermediate 187.2. White amorphous material; ES-MS: M+H=672; HPLC: $_At_{Ret}$=5.64 min.

Intermediate 188.1

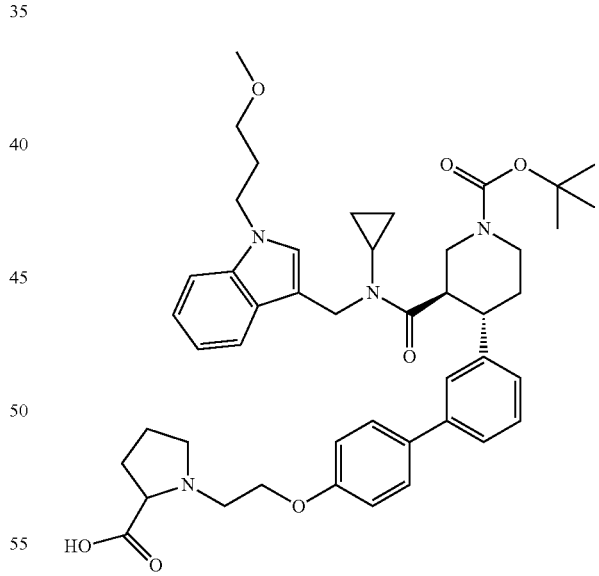

To a solution of Intermediate 188.2 (90 mg, 0.115 mmol) in MeOH (1 mL) is added 1N aqueous NaOH (1 mL) and stirred for 1.5 h at 60° C. After cooling to room temperature, the resulting mixture is acidified with 5% KHSO$_4$ solution and extracted with CH$_2$Cl$_2$. The organic layer is washed with brine, dried over Na$_2$SO$_4$, and concentrated. Silica gel flash chromatography gives Intermediate 188.1 as white amorphous; ES-MS: M+H=779; HPLC: $_At_{Ret}$=3.87 min.

Intermediate 188.2

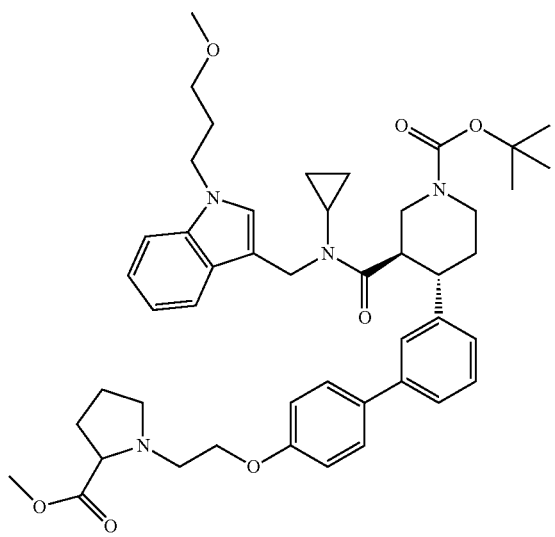

A mixture of Intermediate 42.1 (200 mg, 0.31 mmol), Intermediate 188.3 (229.11 mg, 0.63 mmol) and Cs$_2$CO$_3$ (205 mg, 0.63 mmol) in DMF (1 mL) is stirred at room temperature. After stirring for 11 h, the reaction mixture is diluted with CH$_2$Cl$_2$ and washed with H$_2$O and brine. The organic layer is dried (Na$_2$SO$_4$), concentrated and purified by RP-HPLC to give Intermediate 188.2 as white amorphous; ES-MS: M=793; HPLC: $_A$t$_{Ret}$=3.97 min.

Intermediate 188.3

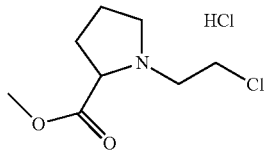

A mixture of Methyl proline hydrochloride (720 mg, 4.3 mmol), 2-Bromochloroethane (0.72 mL, 8.6 mmol) and Cs$_2$CO$_3$ (1.68 g, 5.16 mmol) in DMF (10 mL) is stirred at 60° C. After stirring for 3 h, the reaction mixture is diluted with Et$_2$O at room temperature and washed with H$_2$O and brine and dried over Na$_2$SO$_4$. The Na$_2$SO$_4$ is filtered off, then the filtrate is added HCl in MeOH, then concentrated to give Intermediate 188.3 as white amorphous; ES-MS: M=192; HPLC: $_A$t$_{Ret}$=1.03 min.

Intermediate 189.1

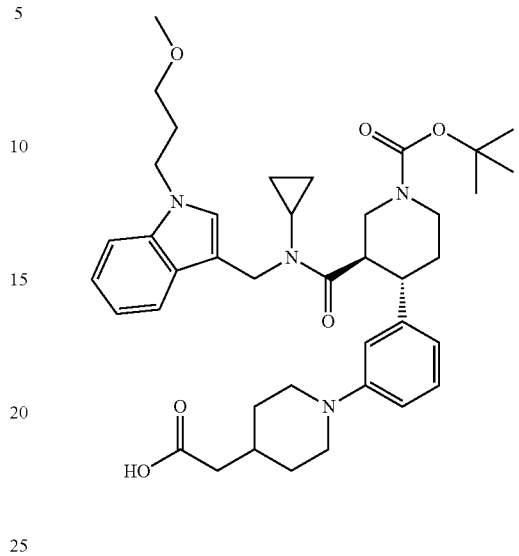

To a solution of Intermediate 189.2 (230 mg, 0.32 mmol) in MeOH (2 mL) is added 2N aqueous NaOH (1 mL) and stirred for 1.5 h at 50° C. After cooling to room temperature, the resulting mixture is acidified with 5% KHSO$_4$ solution and extracted with AcOEt. The organic layer is washed with brine, dried over Na$_2$SO$_4$, and concentrated. Silica gel flash chromatography gives Intermediate 189.1 as white amorphous; ES-MS: M+H=687; HPLC: $_A$t$_{Ret}$=3.38 min.

Intermediate 189.2

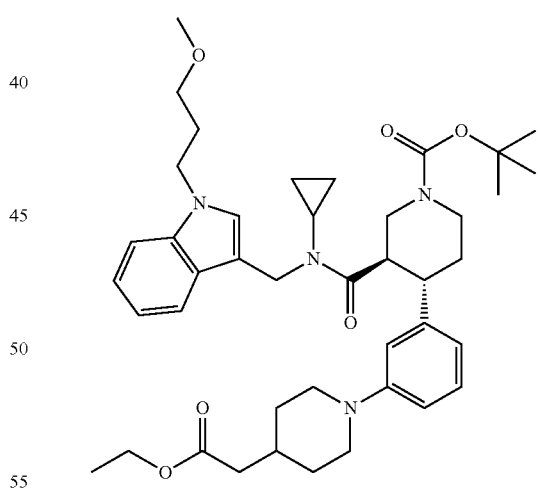

A mixture of Intermediate 42.2 (280 mg, 0.40 mmol), piperidine (103 mg, 0.60 mmol), Pd$_2$(dba)$_3$ (36.7 mg, 0.04 mmol), Di-t-butylphosphinobiphenyl (24 mg, 0.08 mmol) and Cs$_2$CO$_3$ (260 mg, 0.8 mmol) is stirred at 80° C. for 11 h. After cooling to room temperature, the reaction mixture is diluted with AcOEt and washed with brine. The organic layer is dried (Na$_2$SO$_4$), concentrated and purified by silica gel column chromatography to give Intermediate 189.2 as white amorphous; ES-MS: M=715; HPLC: $_A$t$_{Ret}$=3.79 min.

Intermediate 190.1

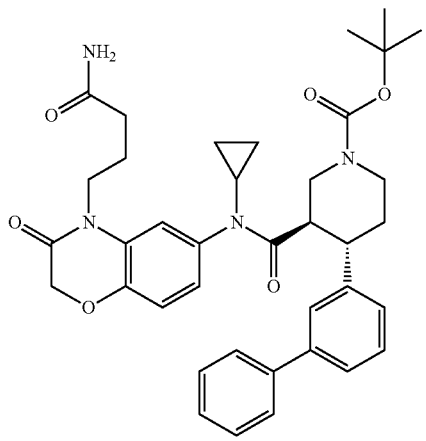

To a solution of Intermediate 190.2 (110 mg, 0.15 mmol) and Et₃N (26 µL, 0.18 mmol) in THF (2 mL), chloroformic acid ethylester (16 µL, 0.17 mmol) is added at 0° C. After stirring for 0.5 h, the reaction mixture is filtered for removing inorganic salt, and the filtrate is concentrated under reduced pressure. A solution of this crude product in EtOAc (2 mL) was treated with NH₄OH (1 mL) at 0° C. for 2 h. After adding H₂O, the reaction mixture is extracted with EtOAc. The combined organic phases are washed with H₂O and dried (Na₂SO₄). Concentration under reduced pressure and silica gel flash chromatography give Intermediate 190.1 as white powder; ES-MS: M+H=653; HPLC: $_A t_{Ret}$=4.28 min.

Intermediate 190.2

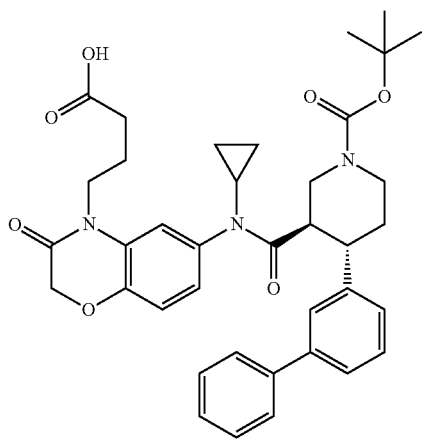

A mixture of Intermediate 190.3 (330 mg, 0.48 mmol) and 5N NaOH (1.5 mL) in THF (1 mL) and MeOH (1 mL) is stirred under N₂ for 2.5 h. The reaction mixture is adjusted to weakly acidic pH by slowly adding 1N HCl, and the mixture is extracted with EtOAc. The combined organic phases are washed with H₂O and dried (Na₂SO₄). Concentration under reduced pressure and silica gel flash chromatography give Intermediate 190.2 as white powder; ES-MS: M+H=654; HPLC: $_A t_{Ret}$=4.50 min.

Intermediate 190.3

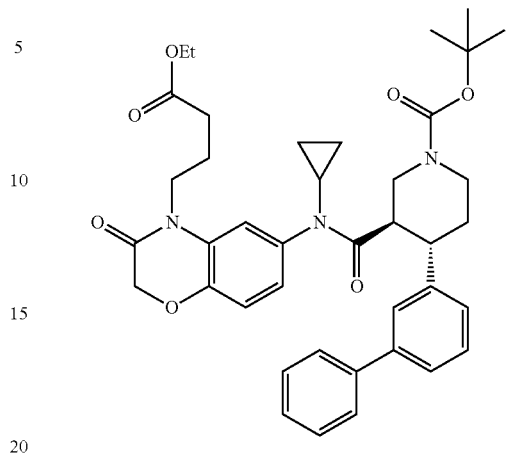

Intermediate 190.3 is synthesized by condensation of Intermediate 2.1 (300 mg, 0.79 mmol) and Intermediate 190.4 (250 mg, 0.79 mmol) analogously to the preparation of Intermediate 145.4. White powder; ES-MS: M+H=682; HPLC: $_A t_{Ret}$=5.18 min.

Intermediate 190.4

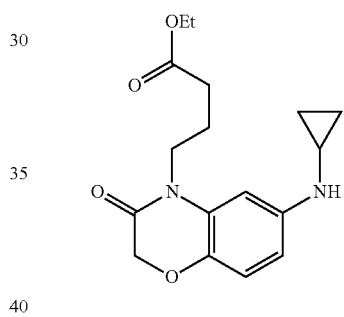

Intermediate 190.4 is synthesized by alkylation of Intermediate 101.3 (300 mg, 1.47 mmol) and ethyl 4-bromobutyrate (232 µL, 1.62 mmol) analogously to a known method (see e.g. *European Journal of Medicinal Chemistry* 1998, 33, 957-967. or EP 432893). Orange solid; ES-MS: M+H=319; HPLC: $_A t_{Ret}$=3.07 min.

Intermediate 191.1

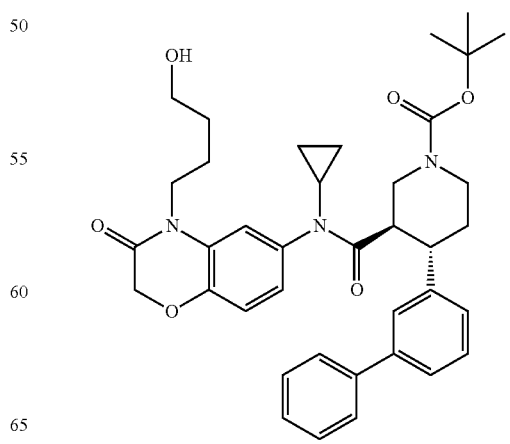

To a solution of Intermediate 190.2 (110 mg, 0.15 mmol) and Et$_3$N (26 μL, 0.18 mmol) in THF (2 mL), chloroformic acid ethylester (16 μL, 0.17 mmol) is added at 0° C. After stirring for 30 min, the reaction mixture is filtered for removing inorganic salt, and the filtrate is concentrated under reduced pressure. A solution of this crude product in MeOH (2 mL) was treated with NaBH$_4$ (11.0 mg, 0.3 mmol) at 0° C. for 2 h. After adding H$_2$O, the reaction mixture is extracted with EtOAc. The combined organic phases are washed with H$_2$O and dried (Na$_2$SO$_4$). Concentration under reduced pressure and silica gel flash chromatography give Intermediate 191.1 as white powder; ES-MS: M+H=640; HPLC: $_A$t$_{Ret}$=4.53 min.

Intermediate 192.1

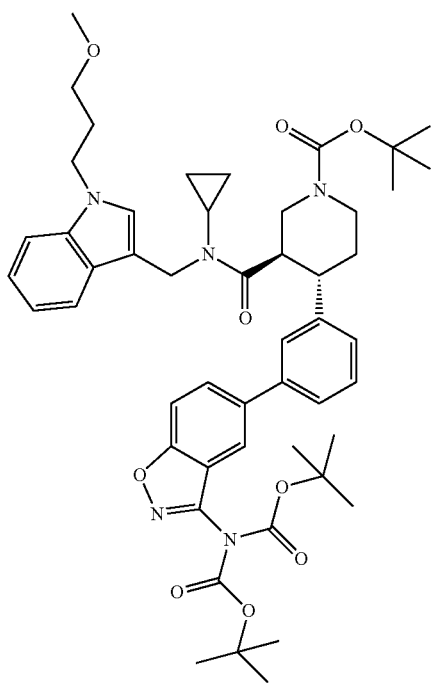

Intermediate 192.1 is synthesized by coupling of Intermediate 127.2 (100 mg, 0.15 mmol) and Intermediate 192.2 (80 mg, 0.19 mmol) analogously to the preparation of Intermediate 175.1. Amorphous material; ES-MS: M+H=878; HPLC: $_A$t$_{Ret}$=5.78 min.

Intermediate 192.2

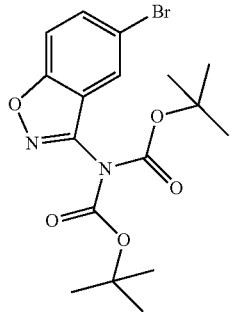

Intermediate 192.2 is synthesized by protection of 5-bromo-1,2-Benzisoxazol-3-amine (500 mg, 2.35 mmol) (see e.g. WO 2002/067939) analogously to the preparation of Intermediate 127.3. Amorphous material; ES-MS: M-(Boc)= 313; HPLC: $_A$t$_{Ret}$=5.03 min.

Intermediate 193.1

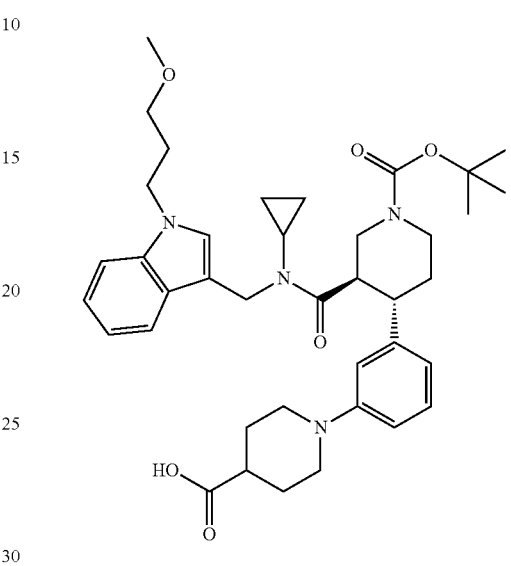

Intermediate 193.1 is synthesized by hydrolysis of Intermediate 193.2 (230 mg, 0.33 mmol) analogously to the preparation of Intermediate 87.1. White amorphous material; ES-MS: M+1=673; HPLC: $_A$t$_{Ret}$=3.40 min.

Intermediate 193.2

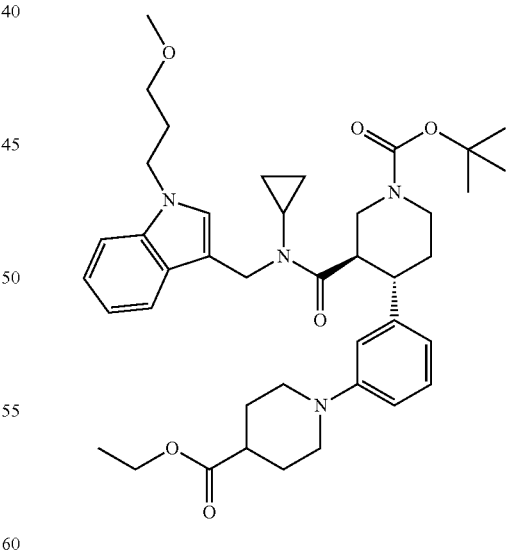

Intermediate 193.2 is synthesized by coupling of Intermediate 42.2 (292 mg, 0.43 mmol) and Ethyl isonipecotate (99 mg, 0.63 mmol) analogously to the preparation of Intermediate 162.1. White amorphous material; ES-MS: M+H=701; HPLC: $_A$t$_{Ret}$=3.75 min.

Intermediate 194.1

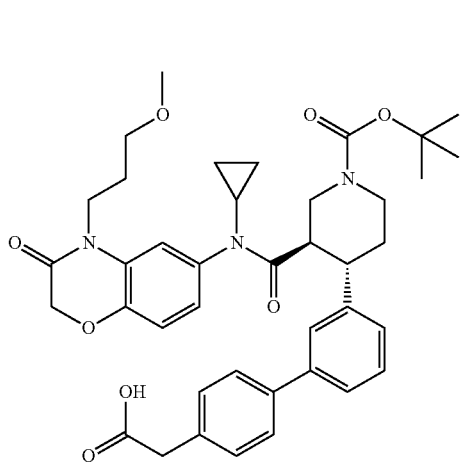

Intermediate 194.1 is synthesized by coupling of Intermediate 181.3 (150 mg, 0.22 mmol) and 4-bromophenylacetic acid (94 mg, 0.44 mmol) analogously to the preparation of intermediate 175.1. Amorphous material; ES-MS: M+H=698; HPLC: $_At_{Ret}$=4.07 min.

Intermediate 195.1

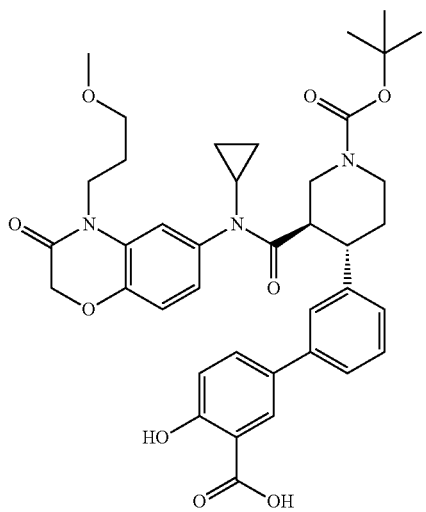

A mixture of Intermediate 195.2 (110 mg, 0.14 mmol) and LiOH (34 mg, 1.4 mmol) in THF (1 mL) and MeOH (1 mL) is stirred under $N_2$ for 2 h. The reaction mixture is adjusted to weakly acidic pH by adding saturated $NH_4Cl$ solution, and the mixture is extracted with EtOAc. The combined organic phases are washed with $H_2O$ and dried ($Na_2SO_4$). Concentration under reduced pressure and silica gel flash chromatography give Intermediate 195.1 as white powder; ES-MS: M+H=744; HPLC: $_At_{Ret}$=4.09 min.

Intermediate 195.2

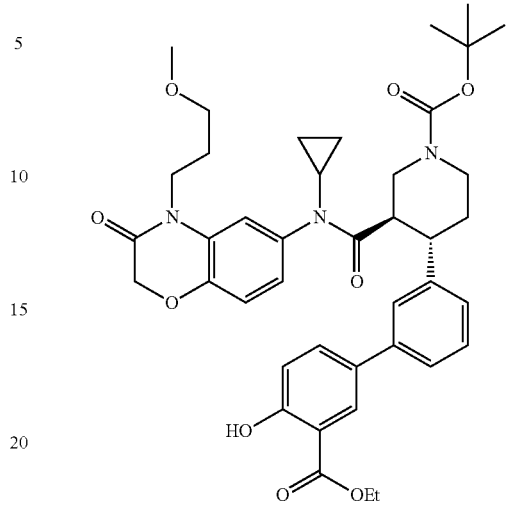

Intermediate 195.2 is synthesized by condensation of Intermediate 181.3 (142 mg, 0.2 mmol) and Intermediate 195.3 (100 mg, 0.3 mmol) analogously to the preparation of Intermediate 2.1. White powder; ES-MS: M+H=758; HPLC: $_At_{Ret}$=4.57 min.

Intermediate 195.3

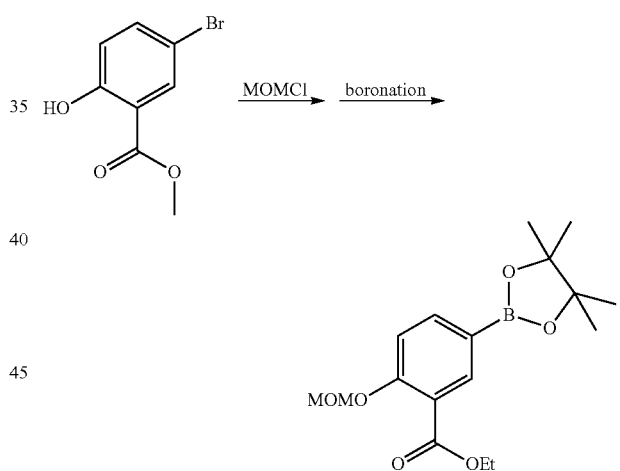

A mixture of Intermediate 195.4 (690 mg, 4.2 mmol), MOMCl (273 µL, 3.6 mmol), and DIEA (770 µL, 4.5 mmol) in DMF (10 mL) is stirred at 0° C. for 12 h. After adding saturated $NaHCO_3$ solution, the reaction mixture is extracted with $Et_2O$. The combined organic phases are washed with $H_2O$ and dried ($Na_2SO_4$). Concentration under reduced pressure give crude mono-MOM ether. This crude product is used without purification. A mixture of this crude, bis(pinacolato) diboron (1.14 mg, 4.5 mmol), KOAc (1.18 g, 12 mmol) and $PdCl_2$(dppf) (250 mg, 0.3 mmol) in 1,4-dioxane (15 mL) is stirred under $N_2$ at 80° C. After stirring for 5 h, the reaction mixture is quenched with $H_2O$, and the mixture is extracted with EtOAc. The combined organic phases are washed with $H_2O$ and dried ($Na_2SO_4$). Concentration under reduced pressure and silica gel flash chromatography give Intermediate 195.3 as yellow oil; Rf=0.43 (EtOAc:n-Hex=1:2); $^1$H NMR ($CDCl_3$), δ: 1.34 (12H, s), 3.51 (3H, s), 3.89 (3H, s), 5.29 (3H, s), 7.18 (1H, d), 7.86-7.88 (1H, m), 8.21 (1H, d).

Intermediate 195.4

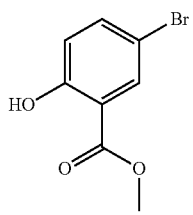

A mixture of 5-bromosalicylic acid (3.04 g, 14 mmol) and conc. H₂SO₄ (0.7 mL) in MeOH (30 mL) is refluxed under N₂ for 20 h. The mixture is extracted with Et₂O. The combined organic phases are washed with H₂O and dried (Na₂SO₄). Concentration under reduced pressure and silica gel flash chromatography give Intermediate 195.4 as white solid; ES-MS: M=231; HPLC: $_A t_{Ret}$=4.25 min.

Intermediate 196.1

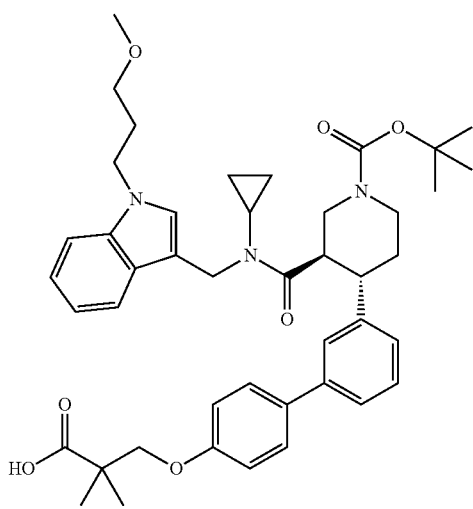

To a solution of Intermediate 196.2 (170 mg, 0.22 mmol) in MeOH (2 mL) and THF (2 mL) is added 5N aqueous NaOH (1.5 mL). After stirring at 75° C. for 3 h, the reaction mixture is cooled to room temperature, and acidified with 1N aqueous KHSO₄. The resulting mixture is extracted with AcOEt, washed with brine, dried (Na₂SO₄) and concentrated. Purification by silica gel column chromatography give Intermediate 196.1 as white amorphous; ES-MS: M+H=756; HPLC: $_A t_{Ret}$=4.57 min.

Intermediate 196.2

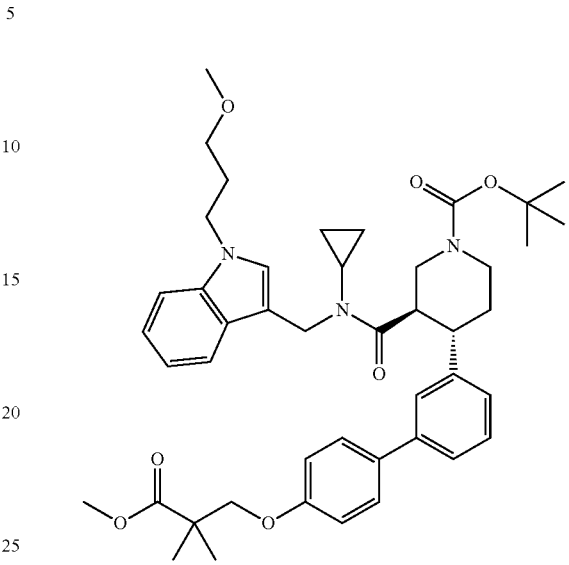

Intermediate 187.2 (250 mg, 0.36 mmol), Intermediate 196.3 (135 mg, 0.47 mmol), Pd(OAc)₂ (8.1 mg, 0.036 mmol), 2-(Dicyclohexylphosphino)-2',6'-dimethoxy-1,1'-biphenyl (29 mg, 0.072 mmol) and K₃PO₄ (192 mg, 0.90 mmol) in toluene (3 mL) and H₂O (0.3 mL) are stirred under N₂ at 100° C. for 15 h. After cooling to room temperature, the reaction mixture is diluted with AcOEt. The resulting mixture is washed with H₂O and brine. The organic layer is dried (Na₂SO₄), concentrated and purified by silica gel column chromatography to give Intermediate 196.2 as white amorphous; ES-MS: M+H=770; HPLC: $_A t_{Ret}$=5.17 min.

Intermediate 196.3

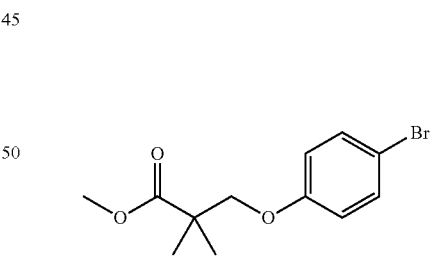

To a solution of Methyl 2,2-dimethyl-3-hydroxypropionate (1.31 g, 9.91 mmol), 4-bromophenol (1.72 g, 9.91 mmol) and PPh₃ (3.12 g, 11.9 mmol) in THF (20 mL) is added DEAD (4.70 mL, 11.9 mmol, 40% in toluene solution). After stirring at 65° C. for 3 h, the reaction mixture is concentrated and purified by silica gel column chromatography to give Intermediate 196.3 as colorless oil; ES-MS: M+H=288; HPLC: $_A t_{Ret}$=4.53 min.

Intermediate 197.1

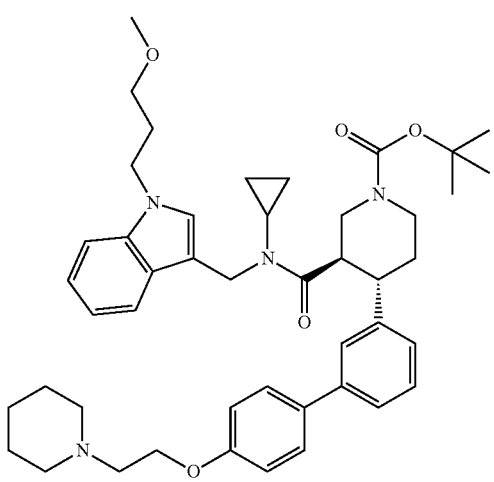

To a solution of Intermediate 42.1 (200 mg, 0.31 mmol) and 1-piperidineethanol (80 mg, 0.62 mmol) in THF are added DEAD and PPh$_3$ at room temperature. After stirring for 15 h, the resulting mixture is concentrated and purified by silicagel column chromatography to give Intermediate 197.1 as white amorphous; ES-MS: M+H=749; HPLC: $_A$t$_{Ret}$=4.02 min.

Intermediate 198.1

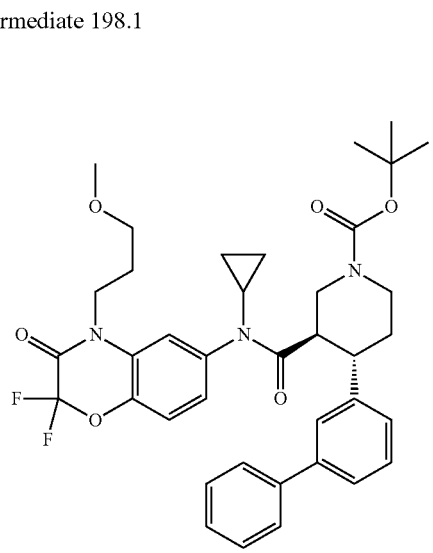

Intermediate 198.1 is synthesized by condensation of Intermediate 75.3 (84 mg, 0.26 mmol) and Intermediate 149.2 (78 mg, 0.25 mmol) analogously to the preparation of Intermediate 145.4. White powder; ES-MS: M+H=676; HPLC: $_A$t$_{Ret}$=5.32 min.

Intermediate 199.1

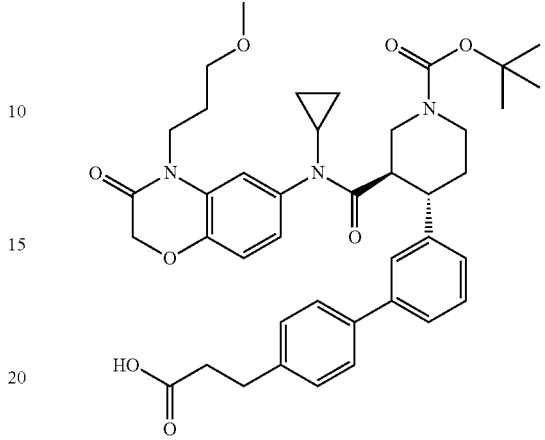

Intermediate 199.1 is synthesized by coupling of Intermediate 181.3 (90 mg, 0.13 mmol) and 3-(4-bromophenyl)-propionic acid (42 mg, 0.2 mmol) analogously to the preparation of intermediate 175.1. Amorphous material; ES-MS: M+H=712; HPLC: $_A$t$_{Ret}$=4.22 min.

Intermediate 200.1

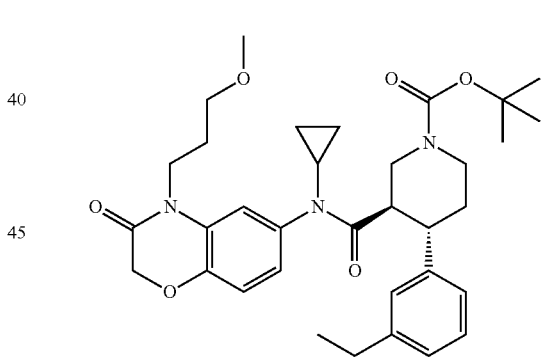

A mixture of Intermediate 181.3 (154.7 mg, 0.21 mmol), ethylboronic acid (77.8 mg, 1.05 mmol), Pd(OAc)$_2$ (4.7 mg, 0.021 mmol), 2-(Dicyclohexylphosphino)-2',6'-dimethoxy-1,1'-biphenyl (17.2 mg, 0.042 mmol) and K$_3$PO$_4$ (445.7 mg, 2.1 mmol) in dioxane (10 mL) and H$_2$O (1 mL) is stirred at 100° C. After stirring for ca. 8 hr, adding H$_2$O at RT, the reaction mixture is extracted with EtOAc. The combined organic phases are washed with brine, dried (Na$_2$SO$_4$). Concentration under reduced pressure and silica gel flash chromatography of the residue (hexane/ethyl acetate) affords intermediate 200.1 as amorphous; ES-MS: M+H=592; HPLC: $_A$t$_{Ret}$=4.72 min.

Intermediate 201.1

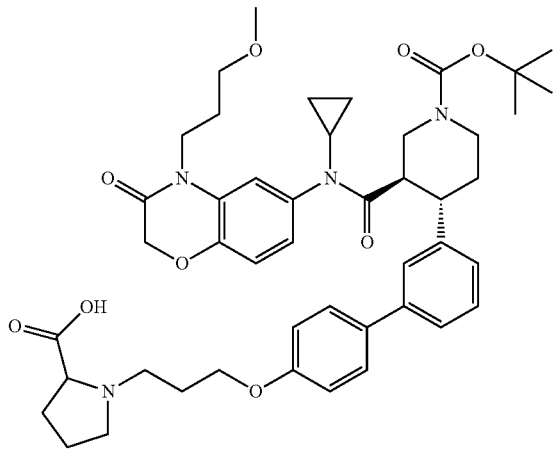

To a solution of Intermediate 201.2 (260 mg, 0.32 mmol) in MeOH (4 mL) is added 2N aqueous NaOH (2 mL) and stirred for 17 h at room temperature. The resulting mixture is acidified with 1N $KHSO_4$ solution and extracted with $CH_2Cl_2$. The organic layer is washed with brine, dried over $Na_2SO_4$, and concentrated. RP-HPLC purification give Intermediate 201.1 as white amorphous; ES-MS: M+H=811; HPLC: $_At_{Ret}$=3.50 min.

Intermediate 201.2

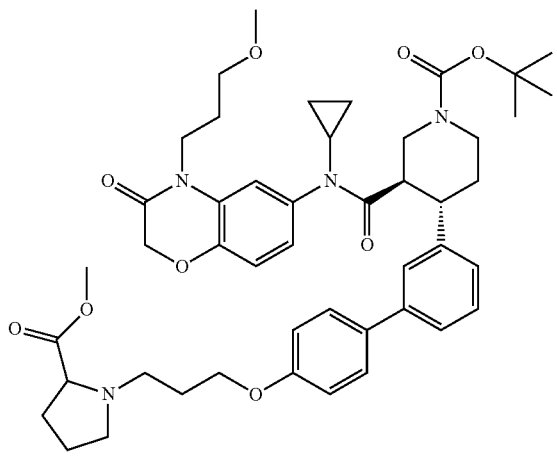

A mixture of Intermediate 181.3 (250 mg, 0.36 mmol), Intermediate 201.3 (185 mg, 0.54 mmol), $PdCl(dppf)_2$ dichloromethane complex (1:1) (15 mg, 0.018 mmol) and 2M $Na_2CO_3$ (0.55 mL, 1.1 mmol) in DMF (6 mL) is stirred under $N_2$ at 80° C. for 10 h. After cooling to room temperature, the reaction mixture is diluted with EtOAc and washed with brine. The organic layer is dried ($Na_2SO_4$), concentrated and purified by silica gel column chromatography to give Intermediate 201.2; ES-MS: M+1=825; HPLC: $_At_{Ret}$=3.65 min.

Intermediate 201.3

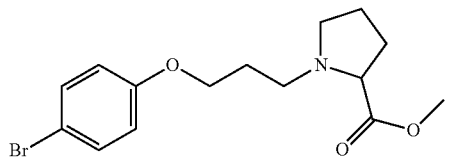

To a solution of 1-bromo-4-(3-chloro-propoxy)-benzene (674 mg, 2.7 mmol) and methyl prolinate (500 mg, 3 mmol) in DMF (10 mL) are added $K_2CO_3$ (830 mg, 6 mmol) and NaI (81 mg, 0.54 mmol), then the mixture is stirred for 14 h at 80° C. After cooling to room temperature, the reaction mixture is diluted with EtOAc and washed with brine. The organic layer is dried ($Na_2SO_4$), concentrated and purified by silica gel column chromatography to give Intermediate 201.3; ES-MS: M+1=343; HPLC: $_At_{Ret}$=2.77 min.

Intermediate 202.1

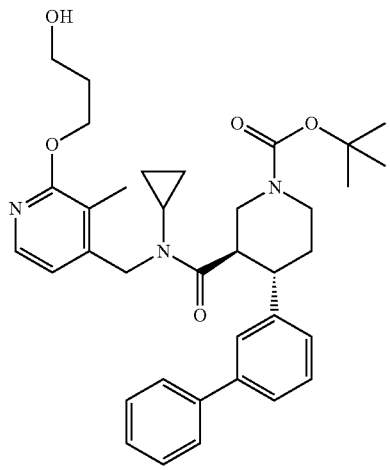

To a solution of Intermediate 202.2 (262 mg, 0.37 mmol) in THF (2 mL) is added TBAF (0.8 mL, 1 M solution in THF) at room temperature. After stirred for 40 min, the mixture is diluted by EtOAc, washed with $H_2O$ and brine, dried ($Na_2SO_4$), filtered, and concentrated in vacuo. The residue is purified by silica gel column chromatography to give Intermediate 202.1. Colorless oil; ES-MS: M+H=600; HPLC: $_At_{Ret}$=4.20 min.

Intermediate 202.2

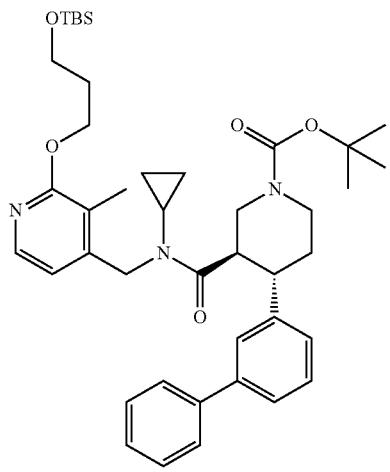

Intermediate 202.2 is synthesized by condensation of Intermediate 4.2 (156 mg, 0.41 mmol) and {2-[3-tert-Butyldimethylsilanyloxy]propoxy}-3-methylpyridin-4-ylmethyl}-cyclopropylamine (143 mg, 0.41 mmol) (see e.g. WO 2005/054244) analogously to the preparation of Intermediate 4.1. Colorless oil; ES-MS: M+H=714; HPLC: $_A t_{Ret}$=5.92 min.

Intermediate 203.1

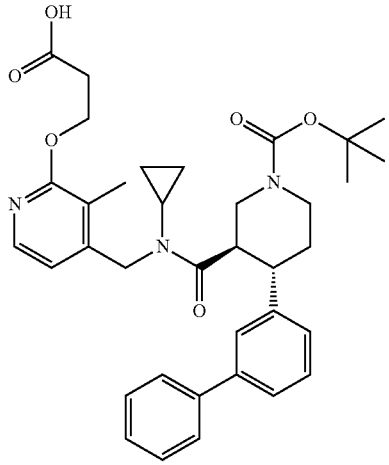

To a solution of Intermediate 202.1 (50 mg, 0.083 mmol) in CH$_2$Cl$_2$ (1 mL) is added Dess-Martin periodinate (50 mg, 0.12 mmol) at room temperature. After stirred for 40 min, the mixture is diluted with EtOAc, washed with aq. Na$_2$SO$_3$, H$_2$O and brine. The organic layer is dried (Na$_2$SO$_4$), filtered, and concentrated in vacuo. The residue is dissolved in t-BuOH (0.8 mL)-H$_2$O (0.3 mL). To this solution are added 2-methyl-2-butene (0.05 mL, 0.47 mmol), NaH$_2$PO$_4$ (10 mg, 0.083 mmol), and NaClO$_2$ (26 mg, 0.29 mmol) at room temperature. After stirred for 30 min, the mixture is diluted with EtOAc, washed with aq. KHSO$_4$, H$_2$O, and brine. The organic layer is dried (Na$_2$SO$_4$), filtered, and concentrated in vacuo. The residue is purified by silica gel column chromatography to give Intermediate 203.1. Colorless oil; ES-MS: M+H=614; HPLC: $_A t_{Ret}$=4.34 min.

Intermediate 204.1

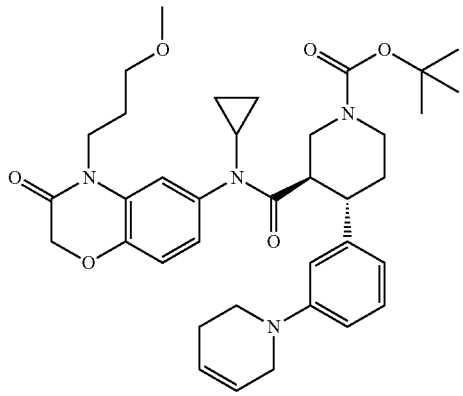

Intermediate 204.1 is synthesized by coupling of Intermediate 181.3 (170 mg, 0.24 mmol) and 1,2,3,6-tetrahydropyridine (0.033 mL, 0.36 mmol) analogously to the preparation of Intermediate 162.1. White amorphous material; ES-MS: M+H=645; HPLC: $_A t_{Ret}$=3.20 min.

Intermediate 205.1

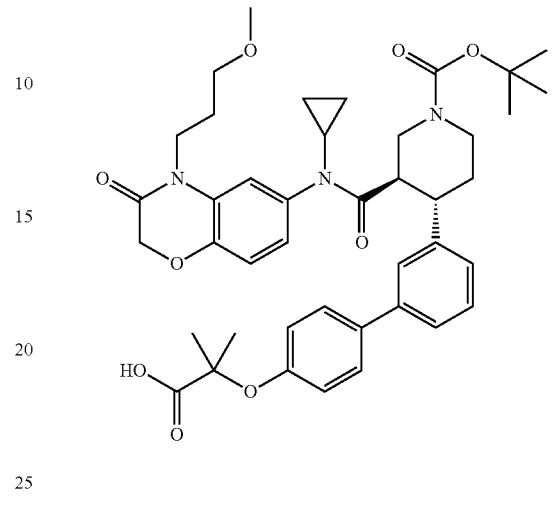

Intermediate 205.1 is synthesized by hydrolysis of Intermediate 205.2 (84 mg, 0.11 mmol) analogously to the preparation of Intermediate 80.2. White amorphous material; ES-MS: M+H=742; HPLC: $_A t_{Ret}$=4.39 min.

Intermediate 205.2

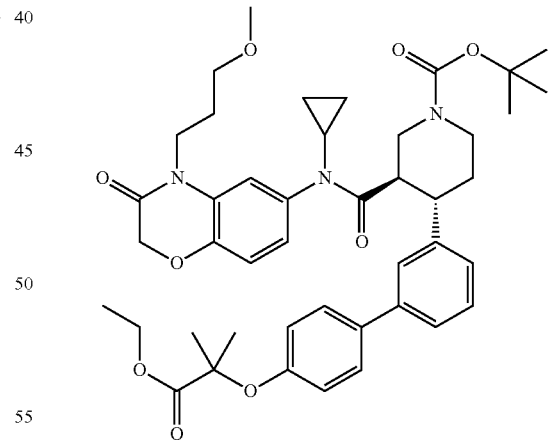

Intermediate 205.2 is synthesized by coupling of Intermediate 181.3 (100 mg, 0.15 mmol) and 2-(4-bromophenoxy)-2-methyl-Propanoic acid (54 mg, 0.19 mmol) analogously to the preparation of intermediate 175.1. Amorphous material; ES-MS: M+H=770; HPLC: $_A t_{Ret}$=5.13 min.

Intermediate 205.3 (eut.)

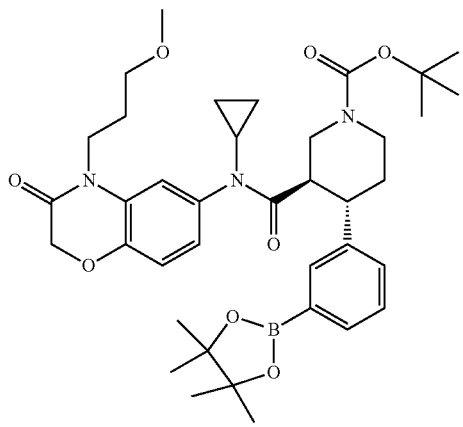

Intermediate 181.3 (340 mg, 0.48 mmol), Bis(pinacolato)diboron (242 mg, 0.95 mmol), PdCl$_2$(dppf) (39 mg, 0.07 mmol) and KOAc (187 mg, 2.80 mmol) in DMSO (3.5 mL) are stirred at 80° C. for 3 h under N$_2$. After cooling to room temperature, the reaction mixture is diluted with AcOEt and washed with brine. The organic layer is dried (Na$_2$SO$_4$), concentrated and purified by silica gel column chromatography to give. Intermediate 205.3. White amorpus material; ES-MS: M+H=690; HPLC: $_At_{Ret}$=4.99 min.

Intermediate 206.1

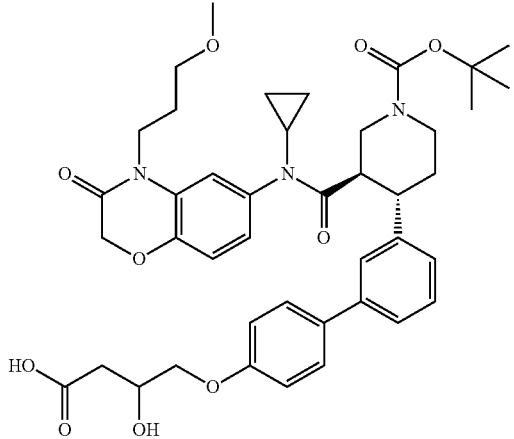

Intermediate 206.1 is synthesized by hydrolysis of Intermediate 206.2 (130 mg, 0.16 mmol) analogously to the preparation of Intermediate 87.1. White amorphous material; ES-MS: M+1=758; HPLC: $_At_{Ret}$=3.87 min.

Intermediate 206.2

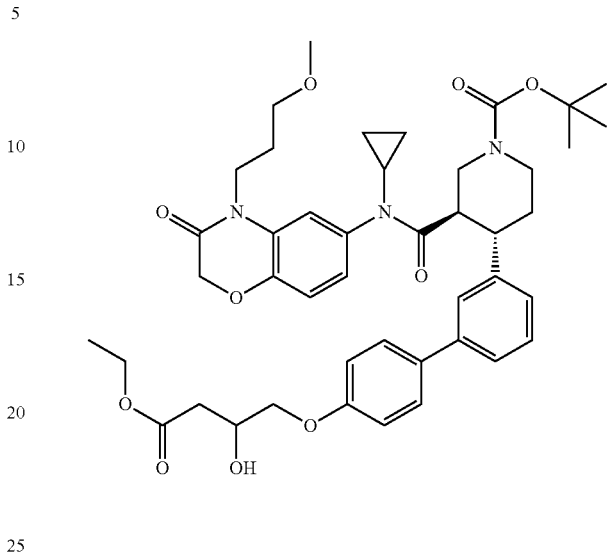

Intermediate 181.3 (203 mg, 0.29 mmol), Ethyl 4-(4-bromophenoxy)-3-hydroxybutanoate (see e.g. U.S. Pat. Appl. Publ. 2002, 2002019539), PdCl$_2$(dppf)$_2$ (24 mg, 0.029 mmol) and Na$_2$CO$_3$ (94 mg, 0.89 mmol) in DMF (3 mL) and H$_2$O (0.3 mL) are stirred under N$_2$ at 80° C. for 15 h. After cooling to room temperature, the reaction mixture is diluted with AcOEt and washed with brine. The organic layer is dried (Na$_2$SO$_4$), concentrated and purified by silica gel column chromatography to give Intermediate 206.2; ES-MS: M+1=786; HPLC: $_At_{Ret}$=4.45 min.

Intermediate 207.1

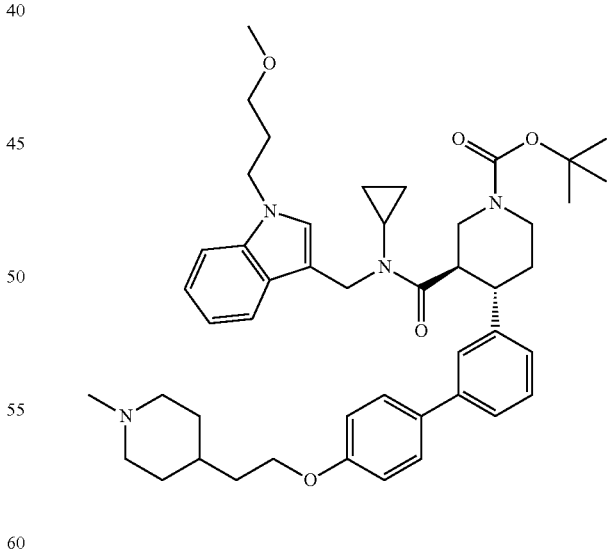

Intermediate 207.1 is synthesized by Mitsunobu reaction of Intermediate 42.1 (211 mg, 0.33 mmol) and 2-(1-Methylpiperidin-4-yl)-ethanol (95 mg, 0.66 mmol) analogously to the preparation of Intermediate 104.1; ES-MS: M=763; HPLC: $_At_{Ret}$=4.05 min.

Intermediate 208.1

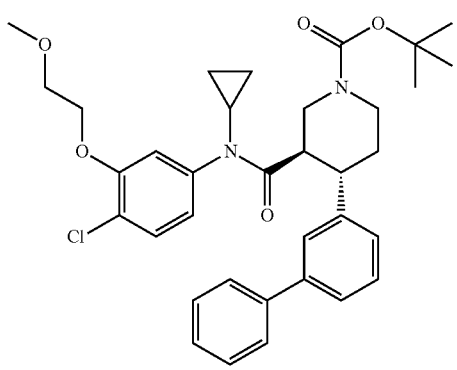

Intermediate 208.1 is synthesized by condensation of Intermediate 1.2 (150 mg, 0.39 mmol) and Intermediate 208.2 (90.5 mg, 0.374 mmol) analogously to the preparation of Intermediate 145.4. White amorphous material; ES-MS: M+H=605; HPLC: $_A t_{Ret}$=5.35 min.

Intermediate 208.2

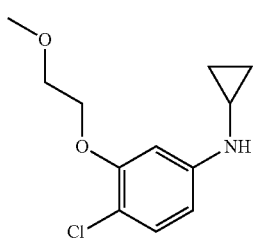

Intermediate 208.2 is synthesized by amination of intermediate 208.3 (500 mg, 1.88 mmol) and cyclopropylamine (322 mg, 5.64 mmol) analogously to the preparation of Intermediate 167.2: Yellow oil; ES-MS: M+H=242: $_A t_{Ret}$=3.77 min.

Intermediate 208.3

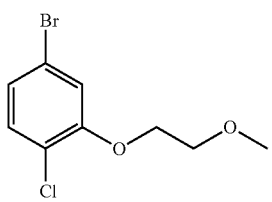

Intermediate 208.3 is synthesized by condensation of 5-bromo-2-chlorophenol (2.0 g, 9.6 mmol) and 1-Bromo-2-methoxyethane (1.6 g, 11.6 mmol) analogously to the preparation of Intermediate 4.8. Colorless oil; ES-MS: M+H=266; HPLC: $_A t_{Ret}$=4.14 min.

Intermediate 209.1

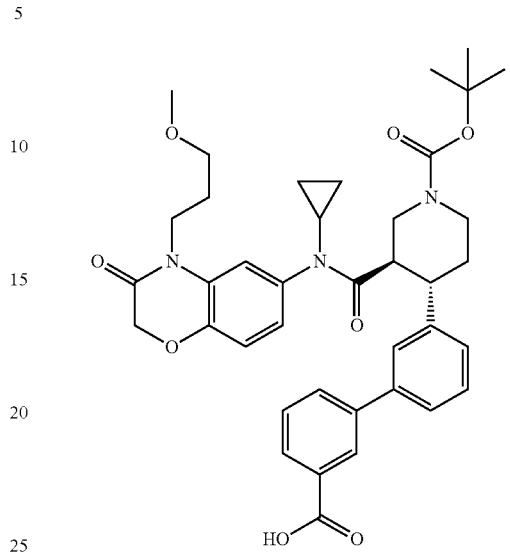

Intermediate 209.1 is synthesized by hydrolysis of Intermediate 209.2 (111 mg, 0.16 mmol) analogously to the preparation of Intermediate 195.1. White powder; ES-MS: M+H=684; HPLC: $_A t_{Ret}$=4.12 min.

Intermediate 209.2

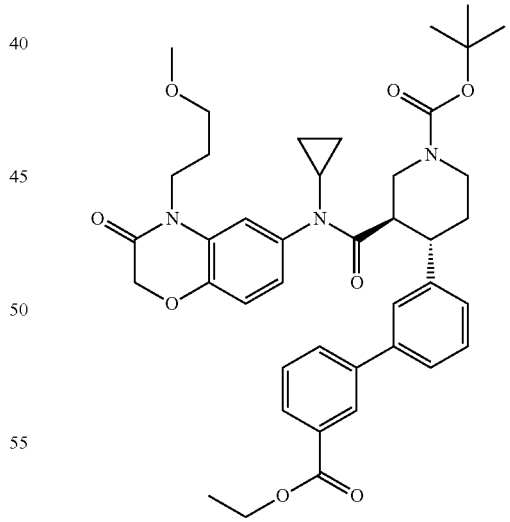

Intermediate 209.2 is synthesized by condensation of Intermediate 181.3 (142 mg, 0.2 mmol) and 3-ethoxycarbonylphenylboronic acid (58 mg, 0.3 mmol) analogously to the preparation of Intermediate 2.1; ES-MS: M+H=712; HPLC: $_A t_{Ret}$=5.03 min.

Intermediate 210.1

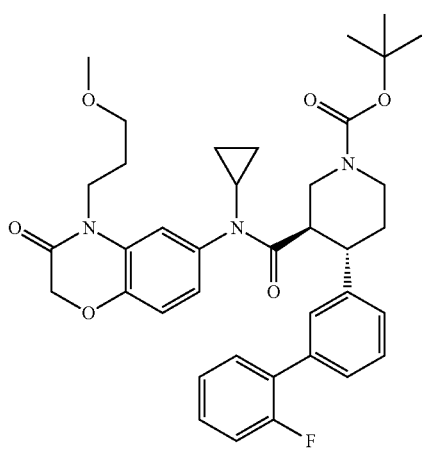

Intermediate 210.1 is synthesized by condensation of Intermediate 181.3 (142 mg, 0.2 mmol) and 2-fluorophenylboronic acid (42 mg, 0.3 mmol) analogously to the preparation of Intermediate 2.1; ES-MS: M+H=658; HPLC: $_A t_{Ret}$=4.87 min.

Intermediate 211.1

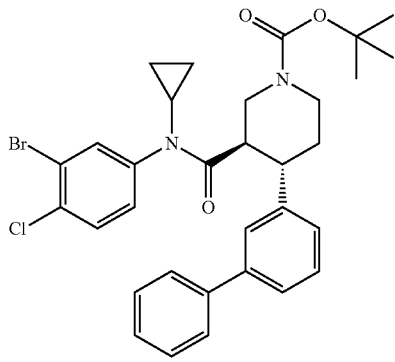

Intermediate 211.1 is synthesized by condensation of Intermediate 1.2 (100 mg, 0.26 mmol) and Intermediate 211.2 (64 mg, 0.26 mmol) analogously to the preparation of Intermediate 145.4. White amorphous material; ES-MS: M+H=610; HPLC: $_A t_{Ret}$=5.74 min.

Intermediate 211.2

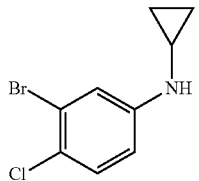

Intermediate 211.2 is synthesized by cyclopropanation of 3-bromo-4-chlorophenylamine (3.60 g, 17.5 mmol) analogously to the preparation of Intermediate 101.4. Yellow oil; ES-MS: M+H=247; HPLC: $_A t_{Ret}$=4.62 min.

Intermediate 212.1

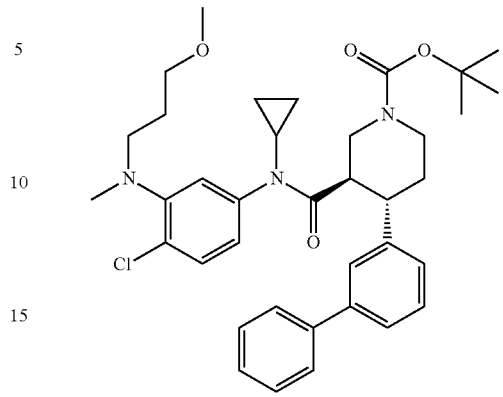

Intermediate 212.1 is synthesized by condensation of Intermediate 1.2 (133 mg, 0.35 mmol) and Intermediate 212.2 (100 mg, 0.37 mmol) analogously to the preparation of Intermediate 145.4. White amorphous material; ES-MS: M+H=632; HPLC: $_A t_{Ret}$=5.20 min.

Intermediate 212.2

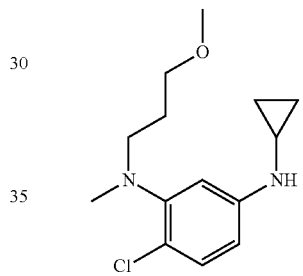

Intermediate 212.2 is synthesized by condensation of Intermediate 211.2 (1.00 g, 4.10 mmol) and (3-methoxypropyl)methylamine hydrochloride (667 mg, 4.8 mmol) analogously to the preparation of Intermediate 167.2. White amorphous material; ES-MS: M+H=269; HPLC: $_A t_{Ret}$=2.80 min.

Intermediate 213.1

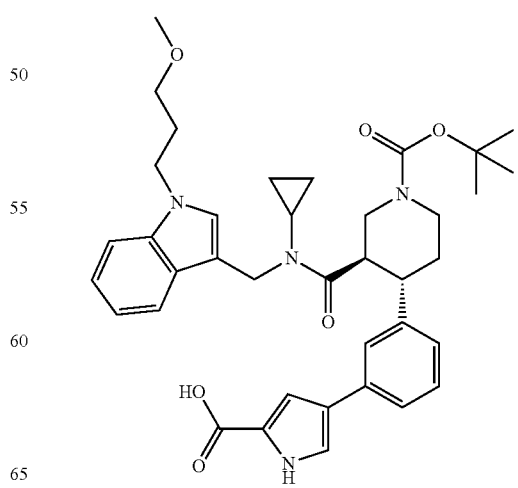

Intermediate 213.1 is synthesized by hydrolysis of Intermediate 213.2 analogously to the preparation of Intermediate 80.2 White amorphous; ES-MS: M+H=655; HPLC: $_At_{Ret}$=4.22 min.

Intermediate 213.2

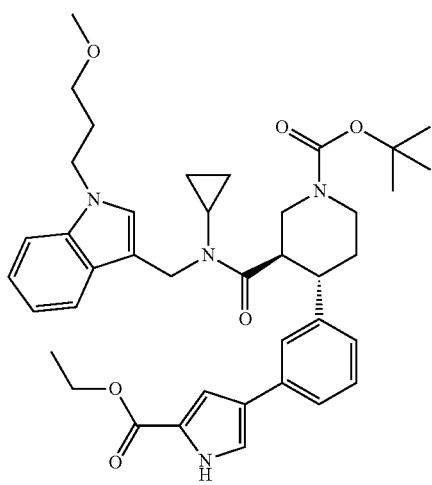

Intermediate 213.2 is synthesized under coupling condition of Intermediate 127.2 (100 mg, 0.15 mmol) and 4-Bromo-1H-pyrrole-2-carboxylic acid ethyl ester (84 mg, 0.38 mmol) analogously to the preparation of Intermediate 175.1 White amorphous material; ES-MS: M+H=683; HPLC: $_At_{Ret}$=4.89 min.

Intermediate 214.1

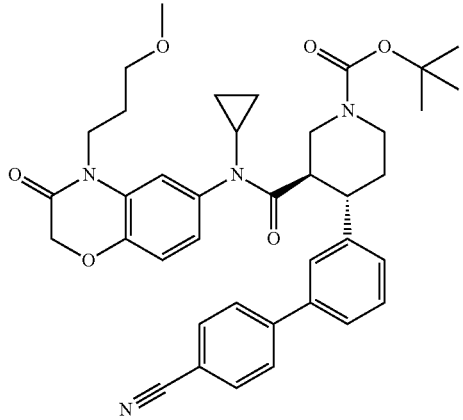

Intermediate 181.3 (170 mg, 0.24 mmol), 4-cyanobenzeneboronic acid (41 mg, 0.28 mmol), Pd(PPh$_3$)$_4$ (22 mg, 0.024 mmol) and K$_3$PO$_4$ (99 mg, 0.47 mmol) are stirred under N$_2$ at 90° C. for 3 h. After cooling to room temperature, the reaction mixture is diluted with AcOEt and washed with brine. The organic layer is dried (Na$_2$SO$_4$), concentrated and purified by silica gel column chromatography to give Intermediate 214.1 as white amorphous; ES-MS: M+H=665; HPLC: $_At_{Ret}$=4.59 min.

Intermediate 215.1

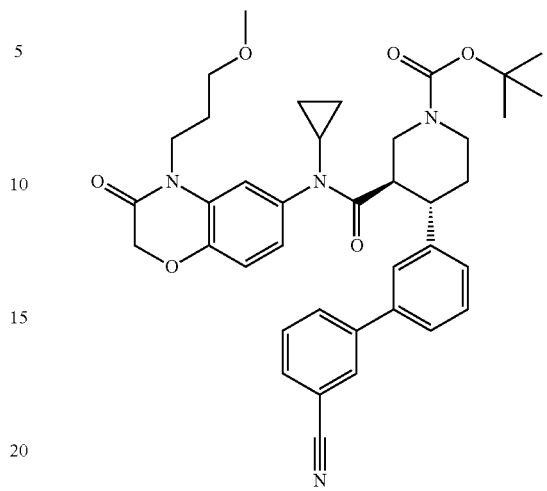

Intermediate 215.1 is synthesized by coupling of Intermediate 181.3 (129 mg, 0.18 mmol) and 3-cyanobenzeneboronic acid (40 mg, 0.27 mmol) analogously to the preparation of Intermediate 214.1. White amorphous material; ES-MS: M+H=665; HPLC: $_At_{Ret}$=4.59 min.

Intermediate 216.1

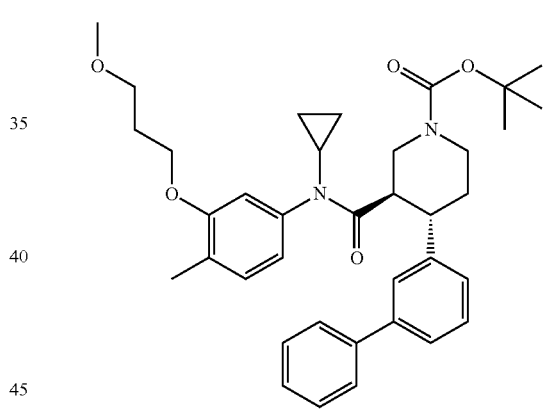

Intermediate 216.1 is synthesized by condensation of Intermediate 1.2 (159 mg, 0.42 mmol) and Intermediate 216.2 (90 mg, 0.42 mmol) analogously to the preparation of Intermediate 145.4. White amorphous material; ES-MS: M+H=599; HPLC: $_At_{Ret}$=5.65 min.

Intermediate 216.2

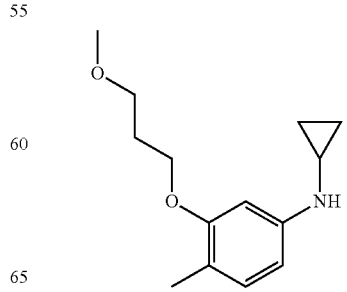

Intermediate 216.2 is synthesized by cyclopropanation of intermediate 216.3 (800 mg, 4.1 mmol) analogously to the preparation of Intermediate 101.4. Yellow oil; ES-MS: M+H=236; HPLC: $_At_{Ret}$=2.98 min.

Intermediate 216.3

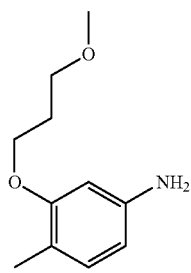

Intermediate 216.3 is synthesized by reduction of Intermediate 216.4 (266 mg, 1.00 mmol) analogously to the preparation of Intermediate 37.2. Brown solid; ES-MS: M+H=197; HPLC: $_At_{Ret}$=2.19 min.

Intermediate 216.4

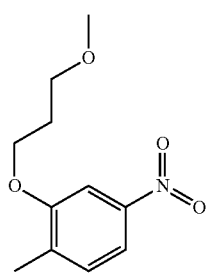

Intermediate 216.4 is synthesized by alkylation of 5-methyl-2-nitro-phenol (5.0 g, 32.6 mmol) analogously to the preparation of Intermediate 14.4. red solid; ES-MS: M+H=226; HPLC: $_At_{Ret}$=4.06 min.

Intermediate 217.1

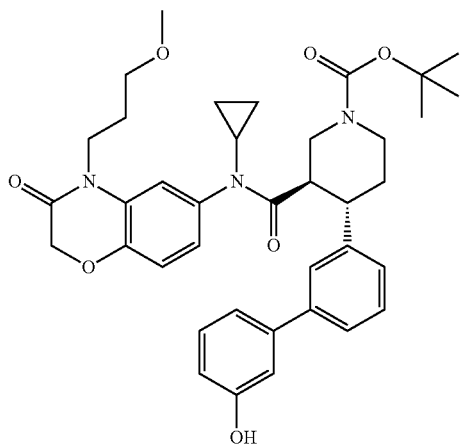

Intermediate 217.1 is synthesized by coupling of Intermediate 181.3 (130 mg, 0.18 mmol) and 3-hydroxybenzeneboronic acid (38 mg, 0.27 mmol) analogously to the preparation of Intermediate 214.1. White amorphous material; ES-MS: M+H=656; HPLC: $_At_{Ret}$=4.27 min.

Intermediate 218.1

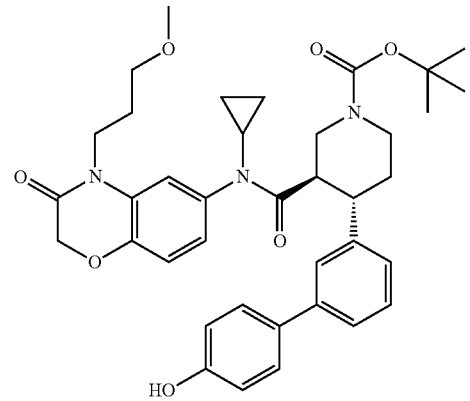

Intermediate 218.1 is synthesized by coupling of Intermediate 181.3 (167 mg, 0.23 mmol) and 4-hydroxybenzeneboronic acid (49 mg, 0.36 mmol) analogously to the preparation of Intermediate 214.1. White amorphous material; ES-MS: M+H=656; HPLC: $_At_{Ret}$=4.20 min.

Intermediate 219.1 (eut.)

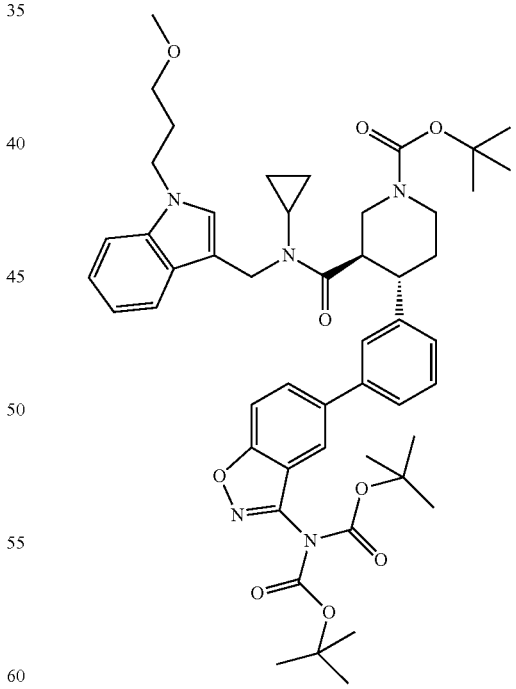

Intermediate 219.1 is synthesized by coupling of Intermediate 181.3 (300 mg, 0.54 mmol) and Intermediate 192.2 (290 mg, 0.70 mmol) analogously to the preparation of Intermediate 175.1. Amorphous material; ES-MS: M+H=878; HPLC: $_At_{Ret}$=5.81 min.

Intermediate 220.1

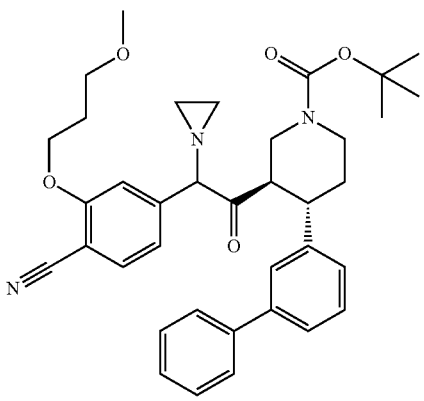

Intermediate 220.1 is synthesized by condensation of Intermediate 1.2 (150 mg, 0.39 mmol) and Intermediate 220.2 (96 mg, 0.39 mmol) analogously to the preparation of Intermediate 145.4. White amorphous material; ES-MS: M+H=610; HPLC: $_At_{Ret}$=5.09 min.

Intermediate 220.2

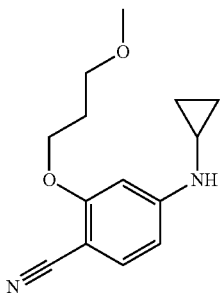

Intermediate 220.2 is synthesized by condensation of Intermediate 220.3 (4.20 g, 15.5 mmol) and cyclopropylamine (639 mg, 11.1 mmol) analogously to the preparation of Intermediate 167.2. White amorphous material; ES-MS: M+H=247; HPLC: $_At_{Ret}$=3.57 min.

Intermediate 220.3

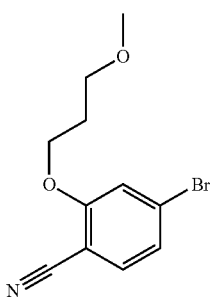

A mixture of 4-bromo-2-fluorobenzonitrile (5.00 g, 25.0 mmol), 3-methoxypropan-1-ol (3.30 g, 38.0 mmol) and K$_2$CO$_3$ (3.50 g, 38 mmol) in DMF (30 mL) is heated at 80° C. for 24 h. After adding H$_2$O at RT, the reaction mixture is extracted with EtOAc. The combined organic phases are washed twice with H$_2$O, and dried (MgSO$_4$). Concentration under reduced pressure and silica gel flash chromatography give Intermediate 220.3. White solids; ES-MS: M+H=270; HPLC: $_At_{Ret}$=2.40 min.

Intermediate 221.1

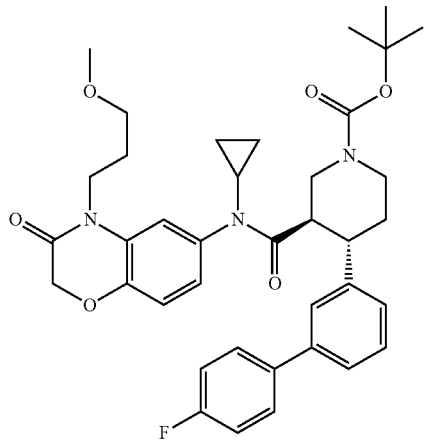

Intermediate 221.1 is synthesized by condensation of Intermediate 181.3 (142 mg, 0.2 mmol) and 4-fluorophenylboronic acid (34 mg, 0.24 mmol) analogously to the preparation of Intermediate 2.1; ES-MS: M+H=658; HPLC: $_At_{Ret}$=4.82 min.

Intermediate 222.1

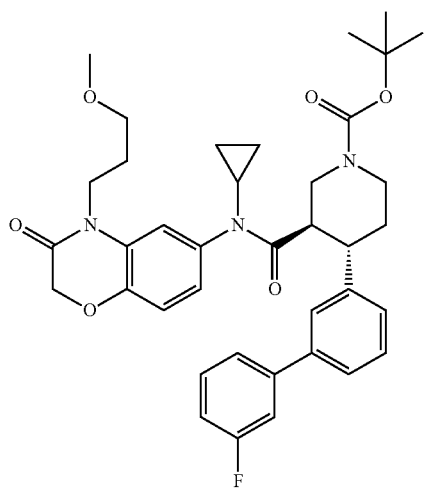

Intermediate 222.1 is synthesized by condensation of Intermediate 181.3 (142 mg, 0.2 mmol) and 3-fluorophenylboronic add (34 mg, 0.24 mmol) analogously to the preparation of Intermediate 2.1; ES-MS: M+H=658; HPLC: $_At_{Ret}$=4.84 min.

Intermediate 223.1

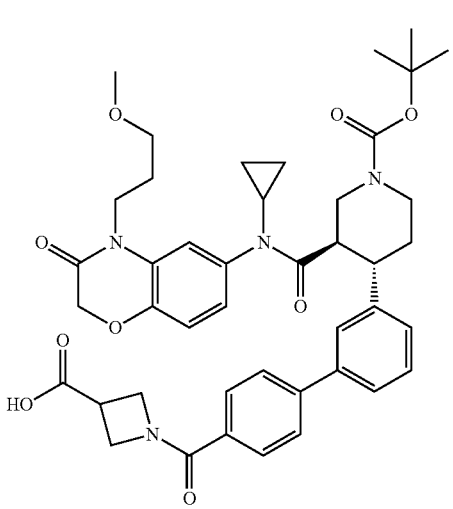

Intermediate 223.1 is synthesized by condensation of intermediate 185.1 (68 mg, 0.1 mmol) and 3-azetidinecarboxylic acid (11 mg, 0.11 mmol) analogously to the preparation of Intermediate 82.1. Amorphous; ES-MS: M+H=767; HPLC: $_At_{Ret}$=3.67 min.

Intermediate 224.1

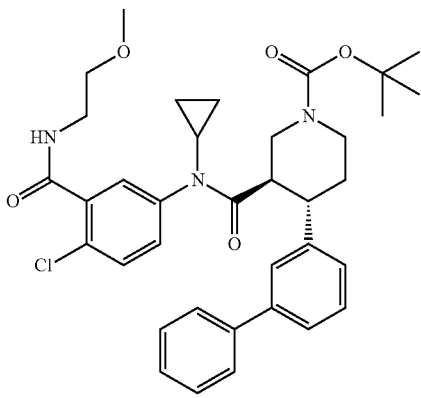

To a solution of Intermediate 4.2 (100 mg, 0.0.26 mmol) in CH$_2$Cl$_2$ (1 mL), 1-chloro-N,N-2-trimethylpropaneamine (133 µL, 1 mmol) is added at 0° C. After stirring at 0° C. for 1 h, to the solution are added Intermediate 224.2 (70 mg, 0.26 mmol) and pyridine (0.2 mL), then stirred for 3 h at room temperature. The resulting mixture is diluted with H$_2$O and extracted with EtOAc. The organic layer is washed with brine, dried over Na$_2$SO$_4$, and concentrated. RP-HPLC purification give Intermediate 224.1 as white amorphous; ES-MS: Mi-H=632; HPLC: $_At_{Ret}$=4.60 min.

Intermediate 224.2

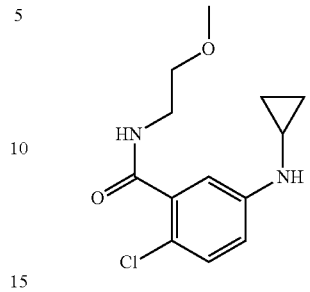

Intermediate 224.2 is synthesized by condensation of Intermediate 224.3 (550 mg, 2.6 mmol) and 2-methoxyethylamine (233 mg, 3.1 mmol) analogously to the preparation of Intermediate 2.3. white solid; ES-MS: M+H=282; HPLC: $_At_{Ret}$=2.95 min.

Intermediate 224.3

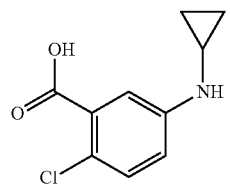

Intermediate 224.3 is synthesized by hydrolysis of Intermediate 224.4 (1.5 g, 6.6 mmol) analogously to the preparation of Intermediate 201.2. White solid; ES-MS: M+H=211; HPLC: $_At_{Ret}$=3.05 min.

Intermediate 224.4

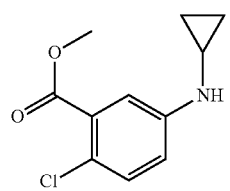

Intermediate 224.4 is synthesized by cyclopropanation of 5-amino-2-chlorobenzoic acid methyl ester (2 g, 10.8 mmol) analogously to the preparation of Intermediate 101.4. White solid; ES-MS: M+H=225; HPLC: $_At_{Ret}$=3.84 min. Intermediate 225.1

Intermediate 226.1

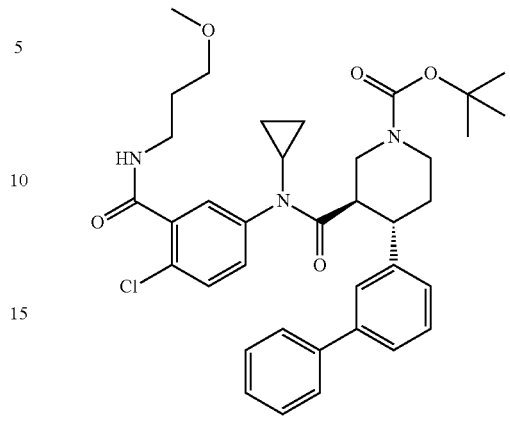

Intermediate 226.1 is synthesized by condensation of Intermediate 4.2 (100 mg, 0.26 mmol) and Intermediate 226.2 (75 mg, 2.6 mmol) analogously to the preparation of Intermediate 2.3. white solid; ES-MS: M+H=646; HPLC: $_A t_{Ret}$=4.55 min.

Intermediate 226.2

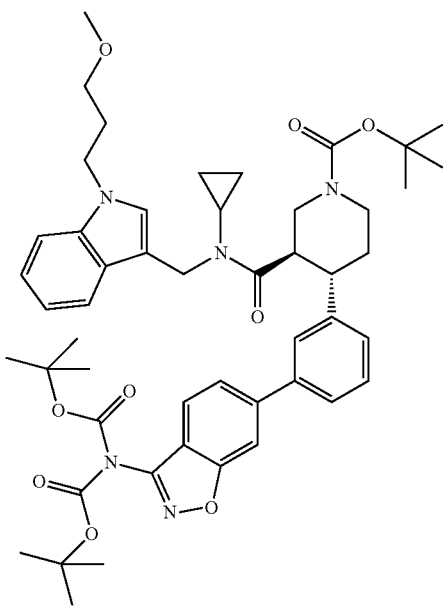

Intermediate 225.1 is synthesized by coupling of Intermediate 127.2 (150 mg, 0.22 mmol) and Intermediate 225.2 (118 mg, 0.29 mmol) analogously to the preparation of Intermediate 175.1. Amorphous material; ES-MS: M+H=878; HPLC: $_A t_{Ret}$=5.70 min.

Intermediate 225.2

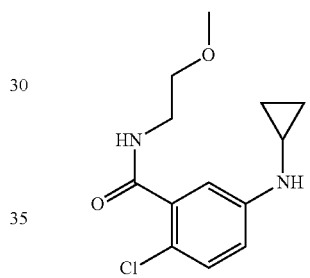

Intermediate 226.2 is synthesized by condensation of Intermediate 224.3 (550 mg, 2.6 mmol) and 3-methoxypropylamine (278 mg, 3.1 mmol) analogously to the preparation of Intermediate 2.3. white solid; ES-MS: M+H=282; HPLC: $_A t_{Ret}$=2.72 min.

Intermediate 227.1

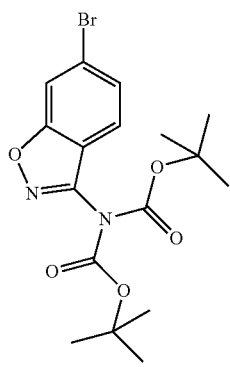

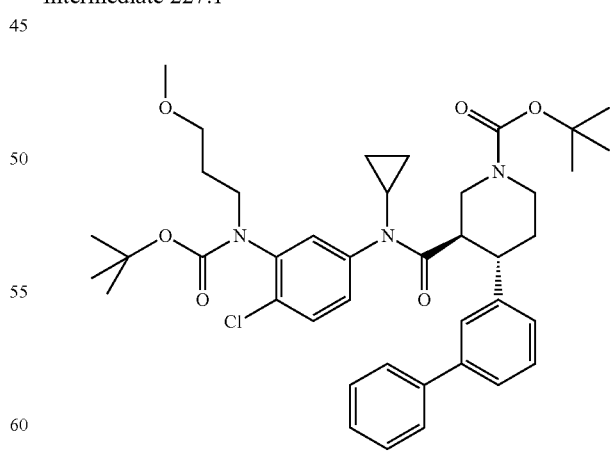

Intermediate 225.2 is synthesized by protection of 3-Amino-6-bromo-1,2-benzisoxazole (1.0 g, 4.69 mmol) (see e.g. WO 2000/027199) analogously to the preparation of Intermediate 127.3. Amorphous material; ES-MS: M-(Boc)= 314; HPLC: $_A t_{Ret}$=4.93 min.

Intermediate 227.1 is synthesized by condensation of Intermediate 1.2 (420 mg, 1.1 mmol) and Intermediate 172.2 (355 mg, 1.0 mmol) analogously to the preparation of Intermediate 145.4. White amorphous material; ES-MS: M+H=718; HPLC: $_A t_{Ret}$=5.49 min.

Intermediate 228.1

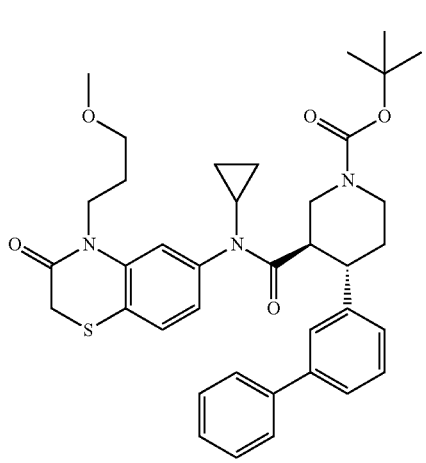

Intermediate 228.1 is synthesized by condensation of Intermediate 75.3 (95 mg, 0.30 mmol) and Intermediate of 120.2 (80 mg, 0.27 mmol) analogously to the preparation of Intermediate 145.4. White powder; ES-MS: M+H=656; HPLC: $_A t_{Ret}$=4.89 min.

Intermediate 229.1 (eut.)

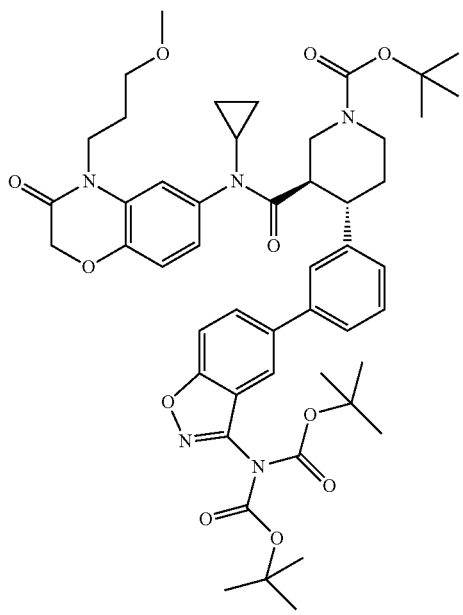

Intermediate 229.1 is synthesized by coupling of Intermediate 205.3 (244 mg, 0.35 mmol) and Intermediate 192.2 (190 mg, 0.46 mmol) analogously to the preparation of Intermediate 175.1. Amorphous material; ES-MS: M-(Boc)=796; HPLC: $_A t_{Ret}$=5.14 min.

Intermediate 230.1

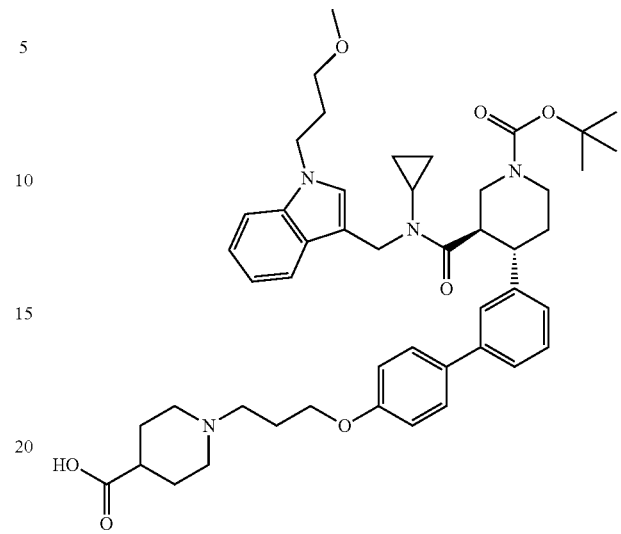

Intermediate 230.1 is synthesized by hydrolysis of Intermediate 230.2 (80 mg, 0.096 mmol) analogously to the preparation of Intermediate 87.1. White amorphous material; ES-MS: M+1=758; HPLC: $_A t_{Ret}$=3.87 min.

Intermediate 230.2

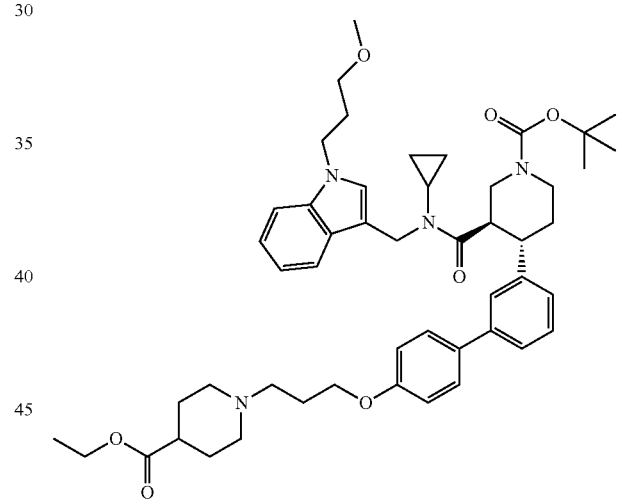

Intermediate 230.2 is synthesized by coupling of Intermediate 187.2 (220 mg, 0.33 mmol) and Intermediate 230.3 (182 mg, 0.49 mmol) analogously to the preparation of Intermediate 187.2. White amorphous material; ES-MS: M+H=835; HPLC: $_A t_{Ret}$=4.00 min.

Intermediate 230.3

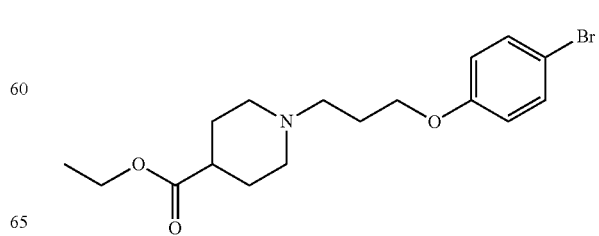

To a solution of 1-Bromo-4-(3-chloropropoxy)benzene (373 mg, 1.49 mmol) (see e.g. Bioorganic & Medicinal Chemistry Letters 2002, 12(21), 3077-3079) and Ethyl isonipecotate (352 mg, 2.24 mmol) in DMF (8 mL) is added $K_2CO_3$ (516 mg, 3.73 mmol). After stirring at 100° C. for 3 h, the reaction mixture is cooled to room temperature and diluted with AcOEt. The resulting mixture is washed with $H_2O$ and brine, dried ($Na_2SO_4$) and concentrated. Purification by silica gel column chromatography to give Intermediate 230.3 as colorless oil; ES-MS: M=369; HPLC: $_At_{Ret}$=2.88 min.

Intermediate 231.1

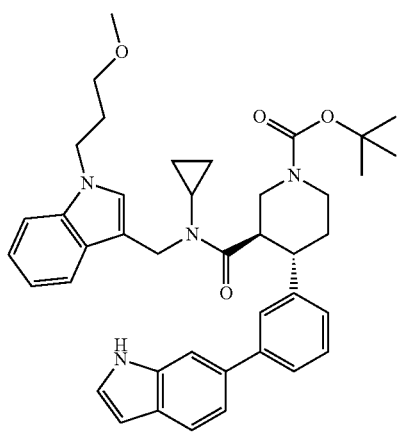

Intermediate 231.1 is synthesized by coupling of Intermediate 187.2 (106 mg, 0.18 mmol) and 6-Bromoindole (46 mg, 0.24 mmol) analogously to the preparation of Intermediate 187.2. White amorphous material; ES-MS: M+H=661; HPLC: $_At_{Ret}$=4.92 min.

Intermediate 232.1

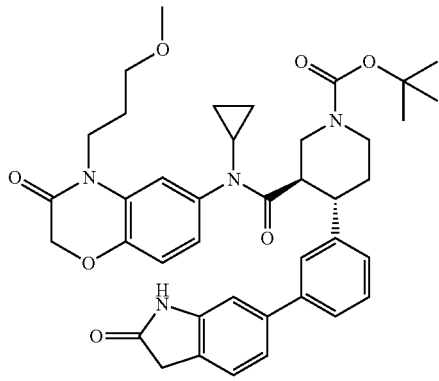

Intermediate 232.1 is synthesized by coupling of Intermediate 205.3 (129 mg, 0.19 mmol) and 6-Bromooxindole (59 mg, 0.28 mmol) analogously to the preparation of Intermediate 187.2; ES-MS: M+H=695; HPLC: $_At_{Ret}$=3.73 min.

Intermediate 233.1

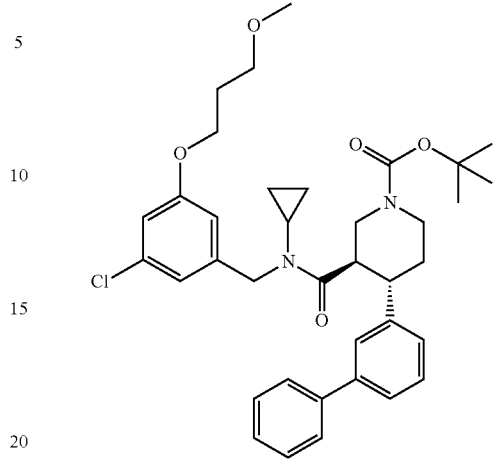

Intermediate 233.1 is synthesized by condensation of Intermediate 233.2 (40 mg, 0.15 mmol) and Intermediate 4.2 (62 mg, 0.16 mmol) analogously to the preparation of Intermediate 2.3. white amorphous; ES-MS: M+H=633; HPLC: $_At_{Ret}$=5.35 min.

Intermediate 233.2

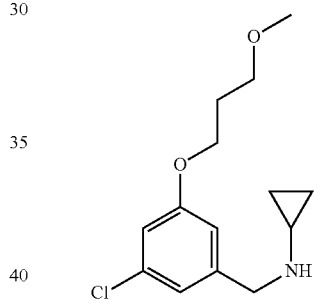

Intermediate 233.2 is synthesized by condensation of Intermediate 233.3 (70 mg, 0.31 mmol) and cyclopropylamine (35 mg, 0.6 mmol) analogously to the preparation of Intermediate 4.5. Yellow oil; ES-MS: M+H=270; HPLC: $_At_{Ret}$=2.29 min.

Intermediate 233.3

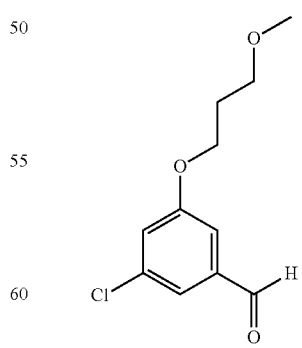

Intermediate 233.3 is synthesized by alkylation of 3-chloro-5-hydroxybenzaldehyde (120 mg, 0.77 mmol) analogously to the preparation of Intermediate 14.4. White solid; ES-MS: M+H=228; HPLC: $_At_{Ret}$=3.63 min.

Intermediate 234.1

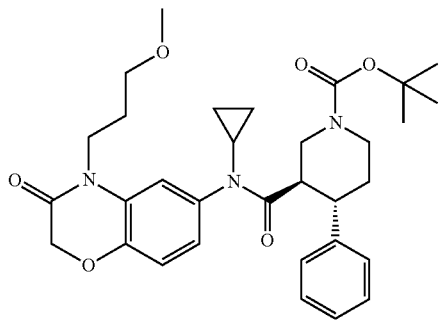

Intermediate 234.1 is synthesized under coupling condition of Intermediate 181.3 (192.6 mg, 0.27 mmol) analogously to the preparation of Intermediate 175.1 White amorphous material; ES-MS: M+H=564; HPLC: $_At_{Ret}$=4.07 min.

Intermediate 235.1

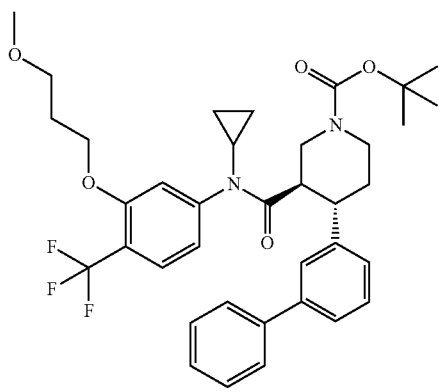

Intermediate 235.1 is synthesized by condensation of Intermediate 1.2 (210 mg, 0.55 mmol) and Intermediate 235.2 (145 mg, 0.5 mmol) analogously to the preparation of Intermediate 145.4. White amorphous material; ES-MS: M+H=653; HPLC: $_At_{Ret}$=5.35 min.

Intermediate 235.2

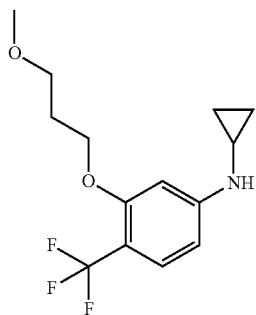

Intermediate 235.2 is synthesized by condensation of Intermediate 235.3 (626 mg, 2.00 mmol) and cyclopropylamine (343 mg, 6.00 mmol) analogously to the preparation of Intermediate 208.2. Yellow oil; ES-MS: M+H=290; HPLC: $_At_{Ret}$=4.12 min.

Intermediate 235.3

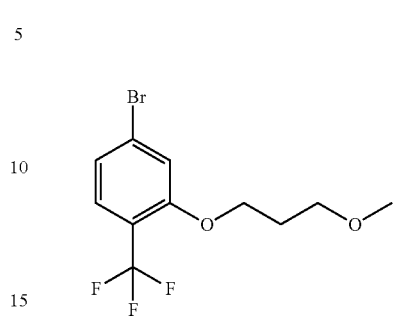

A mixture of 3-fluoro-4-(trifluoromethyl)bromobenzene (3.00 g, 12.35 mmol), 60% NaH (1.48 g, 37.05 mmol) and 3-methoxy-1-propanol (1.67 g, 18.5 mmol) in DMF (80 mL) is stirred at 0° C. for 30 min. The reaction mixture is stirred at 60° C. for 30 min. After adding H$_2$O, the reaction mixture is extracted with EtOAc. The combined organic phases are washed with brine and dried (MgSO$_4$). Concentration under reduced pressure and silica gel flash chromatography gives Intermediate 235.3: Yellow oil; ES-MS: M+H= 292: $_At_{Ret}$=4.39 min.

Intermediate 236.1

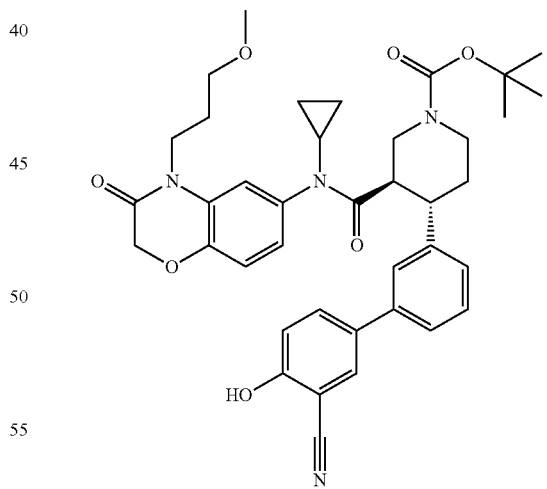

Intermediate 236.1 is synthesized by coupling of Intermediate 205.3 (158 mg, 0.23 mmol) and 2-Hydroxy-5-bromobenzonitrile (68 mg, 0.34 mmol) analogously to the preparation of Intermediate 187.2. White amorphous material; ES-MS: M+H=681; HPLC: $_At_{Ret}$=3.87 min.

Intermediate 237.1

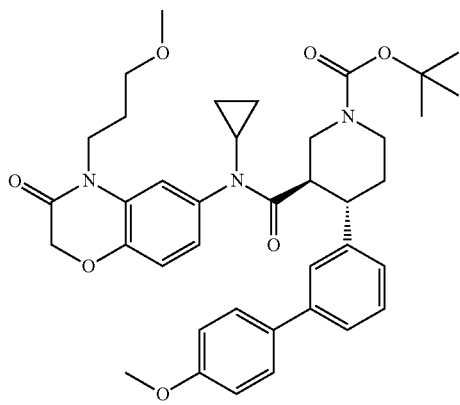

Intermediate 237.1 is synthesized by coupling of Intermediate 181.3 (146 mg, 0.21 mmol) and 4-Methoxybenzeneboronic acid (47 mg, 0.31 mmol) analogously to the preparation of Intermediate 214.1. White amorphous material; ES-MS: M+H=670; HPLC: $_A t_{Ret}$=4.55 min.

Intermediate 238.1

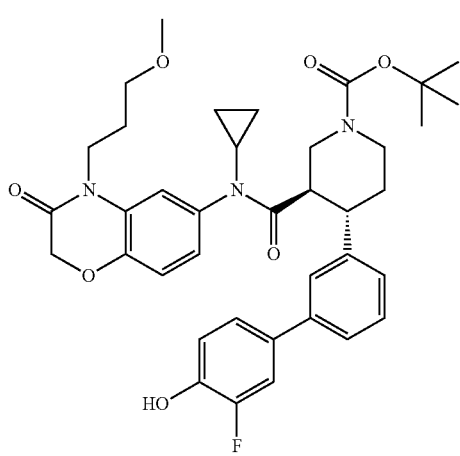

Intermediate 238.1 is synthesized by coupling of Intermediate 205.3 (161 mg, 0.23 mmol) and 2-Fluoro-4-bromophenol (67 mg, 0.35 mmol) analogously to the preparation of Intermediate 187.2. White amorphous material; ES-MS: M+H=674; HPLC: $_A t_{Ret}$=3.98 min.

Intermediate 239.1

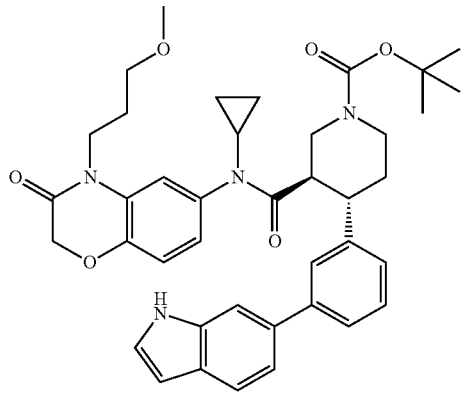

Intermediate 239.1 is synthesized by coupling of Intermediate 205.3 (166 mg, 0.24 mmol) and 6-bromoindole (71 mg, 0.36 mmol) analogously to the preparation of Intermediate 187.2. White amorphous material; ES-MS: M+H=679; HPLC: $_A t_{Ret}$=4.39 min.

Intermediate 240.1

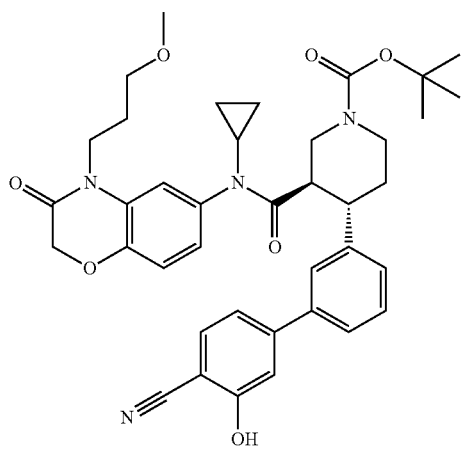

Intermediate 240.1 is synthesized by coupling of Intermediate 205.3 (164 mg, 0.24 mmol) and 2-Hydroxy-4-bromobenzonitrile (71 mg, 0.36 mmol) (see e.g. Synthetic Communications 2004, 34(5), 751-758) analogously to the preparation of Intermediate 187.2. White amorphous material; ES-MS: M+H=681; HPLC: $_A t_{Ret}$=4.00 min.

Intermediate 242.1

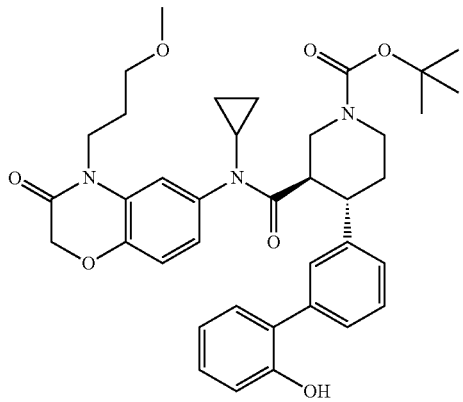

Intermediate 242.1 is synthesized by coupling of Intermediate 205.3 (165 mg, 0.24 mmol) and 2-bromophenol (42 mg, 0.24 mmol) analogously to the preparation of Intermediate 187.2. White amorphous material; ES-MS: M+H=656; HPLC: $_A t_{Ret}$=4.07 min.

Intermediate 241.1

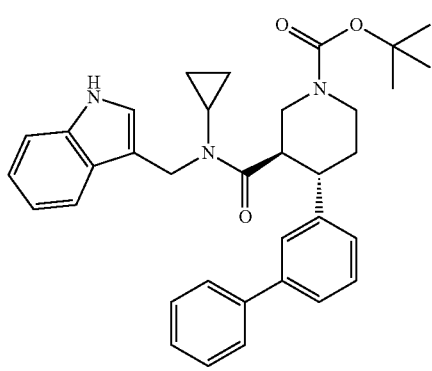

Intermediate 241.1 is synthesized by condensation of Intermediate 241.2 (100 mg, 0.54 mmol) and Intermediate 4.2 (204 mg, 0.54 mmol) analogously to the preparation of Intermediate 2.3. white amorphous; ES-MS: M+H=550; HPLC: $_A t_{Ret}$=4.70 min.

Intermediate 241.2

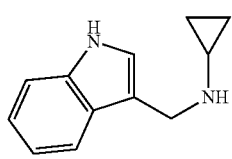

Intermediate 241.2 is synthesized by condensation of indole-3-carbaldehyde (1 g, 6.9 mmol) and cyclopropylamine (1.2 mg, 20 mmol) analogously to the preparation of Intermediate 4.5. brown solid; ES-MS: M+H=185; HPLC: $_A t_{Ret}$=1.78 min.

Intermediate 243.1

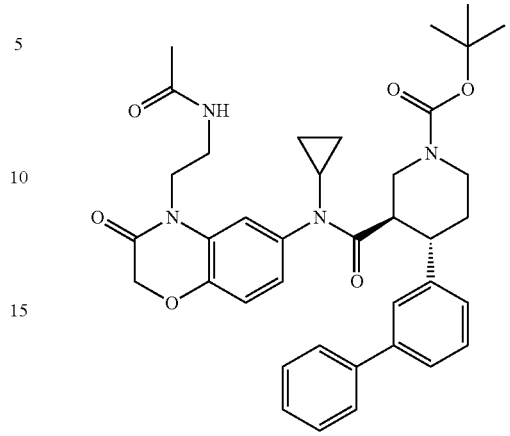

Intermediate 243.1 is synthesized by condensation of Intermediate 75.3 (110 mg, 0.35 mmol) and Intermediate 243.2 (100 mg, 0.35 mmol) analogously to the preparation of Intermediate 145.4; ES-MS: M+H=653; HPLC: $_A t_{Ret}$=4.02 min.

Intermediate 243.2

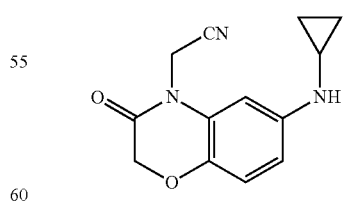

A mixture of Intermediate 243.3 (600 mg, 2.5 mmol), Ac$_2$O (470 μL, 5.0 mmol), and NiCl$_2$-6H$_2$O (650 mg, 2.75 mmol) in MeOH (20 mL) is cooled to 0° C., and NaBH$_4$ (660 mg, 17.5 mmol) is added portionwise. After stirred at 0° C. for 1 h, then ice is added. The reaction mixture is filtered through Celite pad and extracted with EtOAc. The combined organic phases are washed with brine and dried over Na$_2$SO$_4$. Concentration under reduced pressure and silica gel flash chromatography give Intermediate 243.2 as brown powder; ES-MS: M+H=290; HPLC: $_A t_{Ret}$=1.77 min.

Intermediate 243.3

Intermediate 243.3 is synthesized by alkylation of Intermediate 101.3 (610 mg, 3.00 mmol) and chloroacetonitril (210 μL, 3.3 mmol) made analogously to the known method (see e.g. *European Journal of Medicinal Chemistry* 1998, 33, 957-967. or EP 432893). White solid; ES-MS: M+H=244; HPLC: $_A t_{Ret}$=2.45 min.

Intermediate 244.1

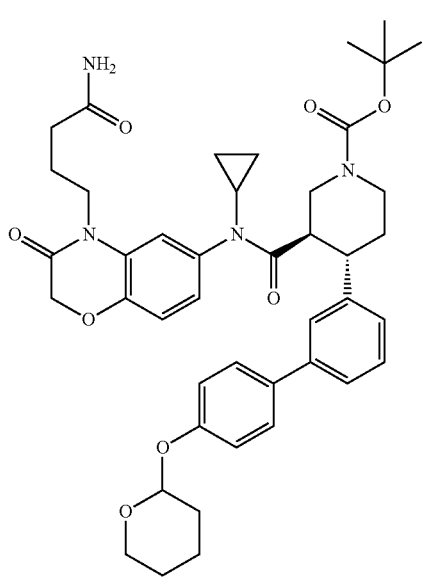

Intermediate 244.1 is synthesized by amidation of Intermediate 244.2 (160 mg, 0.21 mmol) analogously to the preparation of Intermediate 190.1. White powder; ES-MS: M+H=753; HPLC: $_At_{Ret}$=4.32 min.

Intermediate 244.2

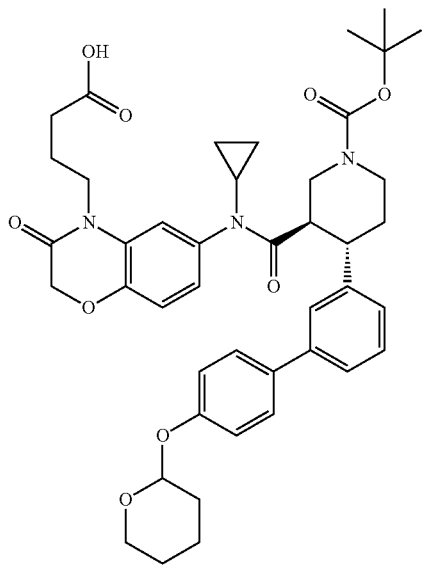

Intermediate 244.2 is synthesized by hydrolysis of Intermediate 244.3 (560 mg, 0.72 mmol) analogously to the preparation of Intermediate 195.1. White powder; ES-MS: M=753; HPLC: $_At_{Ret}$=4.34 min.

Intermediate 244.3

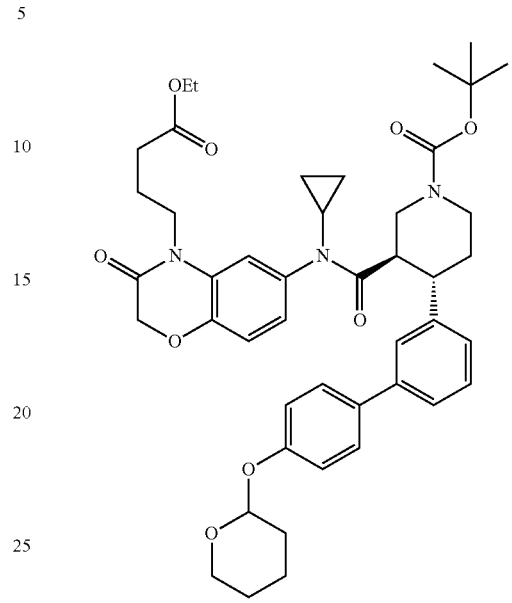

Intermediate 244.3 is synthesized by condensation of Intermediate 244.4 (300 mg, 1.00 mmol) and Intermediate 244.5 (500 mg, 0.66 mmol) analogously to the preparation of Intermediate 175.1; ES-MS: M+H=782; HPLC: $_At_{Ret}$=5.14 min.

Intermediate 244.4

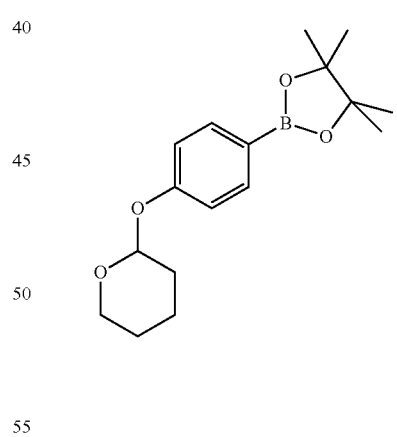

To a mixture of 4-(4,4,5,5-Tetramethyl-1,3,2-dioxaborolan-2-yl)phenol (660 mg, 3.00 mmol) and PPTS (75 mg, 0.3 mmol) in DCM (15 mL) is added 3,4-dihydropyran (820 μL, 9.0 mmol). After refluxed for 2.5 h, the reaction is quenched by the addition of H$_2$O. The resulting mixture is extracted with DCM and EtOAc, and the organic extracts are washed with H$_2$O. The organic layer is dried (Na$_2$SO$_4$) and filtered through Celite pad. After concentration, the residue is purified by silica gel flash chromatography to give Intermediate 244.4 as brown oil; ES-MS: M+H=305; HPLC: $_At_{Ret}$=4.64 min.

Intermediate 244.5

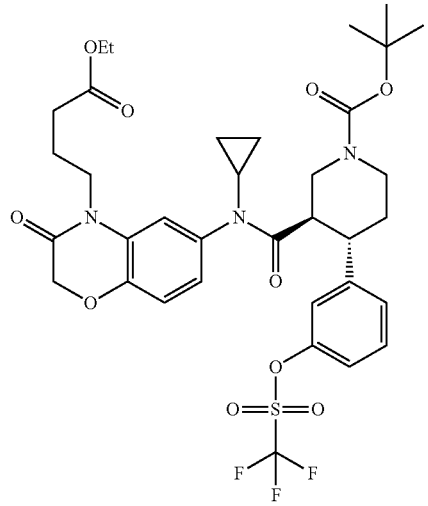

A mixture of Intermediate 244.6 (440 mg, 0.70 mmol), Tf$_2$O (170 µL, 1.10 mmol) and DIEA (300 µL, 1.80 mmol) in DCM (5 mL) is stirred at −78° C. for 0.5 h. After adding H$_2$O, the reaction mixture is extracted with DCM and EtOAc, and the combined organic phases are washed with H$_2$O. The organic layer is dried over Na$_2$SO$_4$ and filtered through Celite and silica pad. Concentration under reduced pressure gives Intermediate 244.5 as colorless amorphous ; ES-MS: M+H=754; HPLC: $_A t_{Ret}$=4.65 min.

Intermediate 244.6

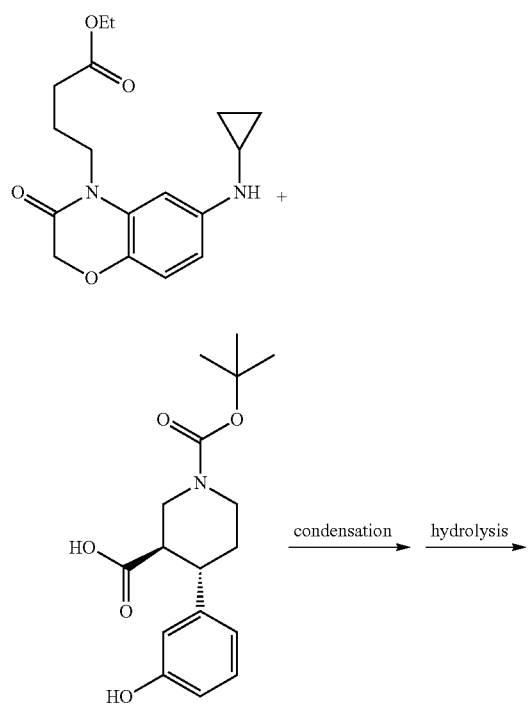

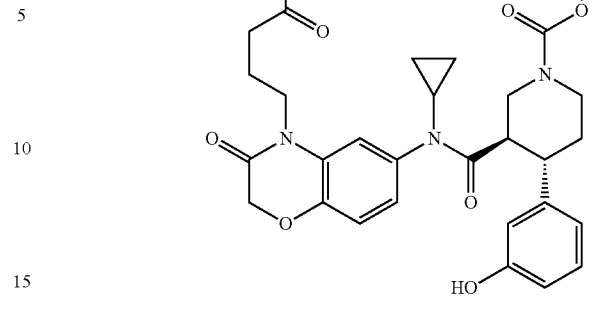

Intermediate 244.6 is synthesized by condensation of intermediate 158.4 (600 mg, 1.90 mmol) and Intermediate 190.4 (600 mg, 1.90 mmol), followed by hydrolysis analogously to the preparation of Intermediate 145.3 & 4. White powder; ES-MS: M+H=622; HPLC: $_A t_{Ret}$=3.72 min.

Intermediate 245.1

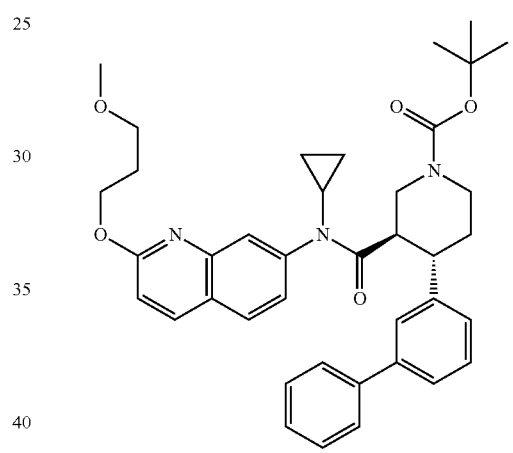

Intermediate of 245.1 is synthesized by condensation of Intermediate 75.3 (130 mg, 0.40 mmol) and Intermediate 245.2 (110 mg, 0.40 mmol) analogously to the preparation of Intermediate 145.4. White powder; ES-MS: M+H=636; HPLC: $_A t_{Ret}$=5.14 min.

Intermediate 245.2

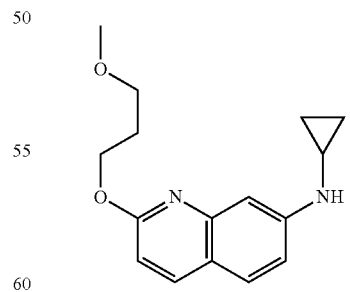

Intermediate 245.2 is synthesized by alkylation of Intermediate 245.3 (750 mg, 3.40 mmol) and toluene-4-sulfonic acid 3-methoxy-propyl ester (810 µL, 3.74 mmol) analogously to the known method (see e.g. *European Journal of Medicinal Chemistry* 1998, 33, 957-967. or EP 432893). Yellow oil; ES-MS: M+H=273; HPLC: $_A t_{Ret}$=2.88 min.

Intermediate 245.3

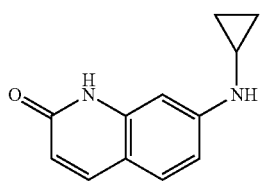

To a solution of Intermediate 245.4 in EtOH (15 mL) and aqueous NH₄Cl (5 mL), zinc powder (1.12 g, 17.2 mmol) is added at RT under $N_2$. After stirring at 80° C. for 6 h, the reaction mixture is filtered through Celite pad. The mixture is extracted with EtOAc. The combined organic phases are washed with $H_2O$ and dried over $Na_2SO_4$. Concentration under reduced pressure gives Intermediate 245.3 as orange powder; ES-MS: M+H=201; HPLC: $_At_{Ret}$=2.27 min.

Intermediate 245.4

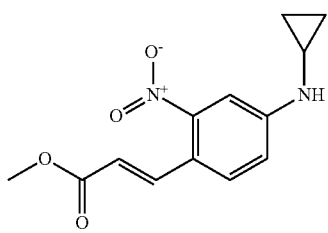

A mixture of Intermediate 245.5 (880 mg, 3.44 mmol), methyl acrylate (470 mL, 5.20 mmol), Pd(OAc)₂ (46 mg, 0.20 mmol), (o-Tol)₃P (104 mg, 0.34 mmol), and Et₃N (1.44 mL, 10.3 mmol) in toluene (15 mL) is stirred at 70° C. under $N_2$ for 3 h. After adding $H_2O$, the reaction mixture is extracted with Et₂O. The combined organic phases are washed with $H_2O$ and dried over $Na_2SO_4$. The organic layer is filtered through Celite and silica pad to give Intermediate 245.4 as orange oil; ES-MS: M+H=263; HPLC: $_At_{Ret}$=3.63 min.

Intermediate 245.5

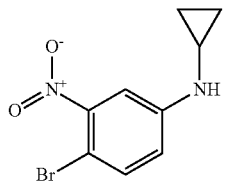

Intermediate 245.5 is synthesized by cyclopropanation of 4-bromo-3-nitroaniline (3.04 g, 14.0 mmol) analogously to the preparation of intermediate 101.4. Orange oil; ES-MS: M+H=258; HPLC: $_At_{Ret}$=3.82 min.

Intermediate 246.1

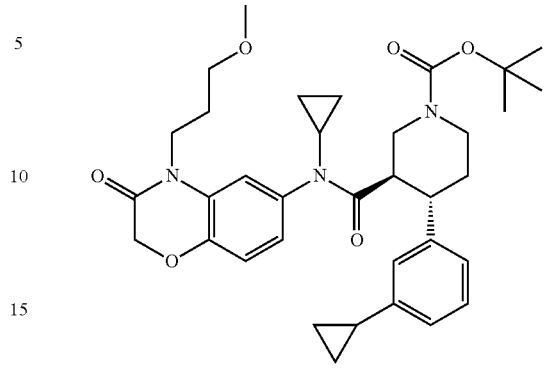

Intermediate 246.1 is synthesized under coupling condition of Intermediate 181.3 (100 mg, 0.14 mmol) and cyclopropylboronic acid (60.3 mg, 0.7 mmol) analogously to the preparation of Intermediate 175.1 White amorphous material; ES-MS: M+H=604; HPLC: $_At_{Ret}$=4.45 min.

Intermediate 247.1

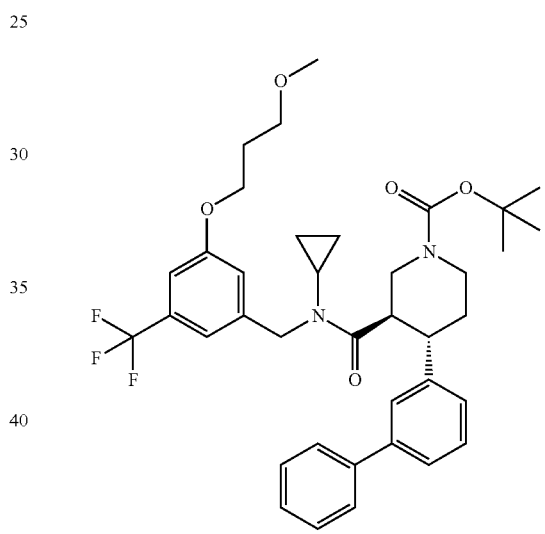

Intermediate 247.1 is synthesized by condensation of Intermediate 1.2 (20 mg, 0.05 mmol) and Intermediate 247.2 (16 mg, 0.05 mmol) analogously to the preparation of Intermediate 2.3. White amorphous material; ES-MS: M+H=667; HPLC: $_At_{Ret}$=5.39 min.

Intermediate 247.2

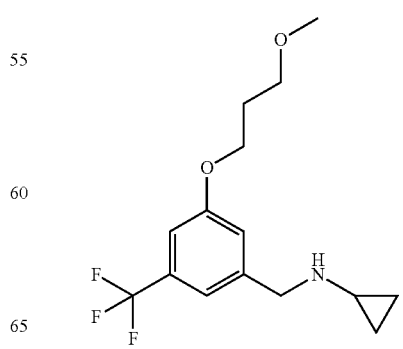

A mixture of 3-fluoro-5-(trifluoromethyl)benzylbromide (1.00 g, 3.9 mmol), potassium carbonate (1.62 g, 11.7 mmol), cyclopropylamine (223 mg, 39 mmol) in DMF (15 mL) is stirred at 60° C. for 1 h. The mixture is filtered, and the filtrate is added to a suspension of 60% NaH (312 mg, 7.8 mmol) and 3-methoxy-1-propanol (417 mg, 4.68 mmol) in DMF (30 ml) at 0° C. over 10 min. The reaction mixture is stirred for 5 h at 60° C. After adding $H_2O$, the reaction mixture is extracted with EtOAc. The combined organic phases are washed with water and brine and dried ($MgSO_4$). Concentration under reduced pressure and silica gel flash chromatography give Intermediate 247.2: Yellow oil; ES-MS: M+H= 304: $_At_{Ret}$=2.47 min.

Intermediate 248.1

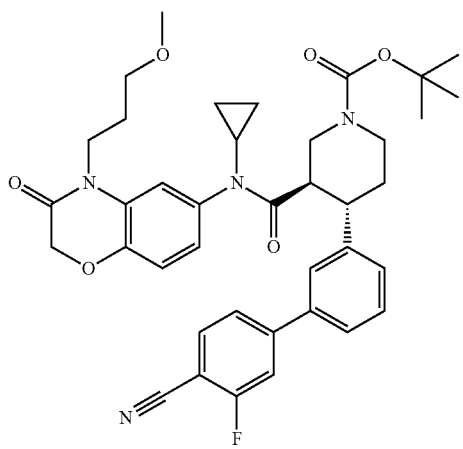

Intermediate 248.1 is synthesized by coupling of Intermediate 205.3 (205 mg, 0.30 mmol) and 2-Fluoro-4-bromobenzonitrile (89 mg, 0.45 mmol) analogously to the preparation of Intermediate 187.2. White amorphous material; ES-MS: M+H=683; HPLC: $_At_{Ret}$=4.42 min.

Intermediate 249.1

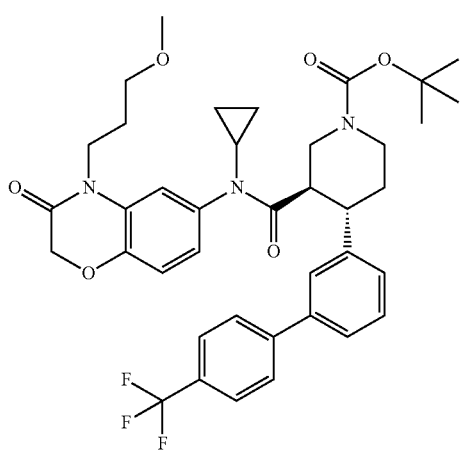

Intermediate 249.1 is synthesized by coupling of Intermediate 181.3 (214 mg, 0.30 mmol) and 4-Trifluoromthylbenzeneboronic acid (87 mg, 0.45 mmol) analogously to the preparation of Intermediate 214.1. White amorphous material; ES-MS: M+H=708; HPLC: $_At_{Ret}$=4.92 min.

Intermediate 250.1

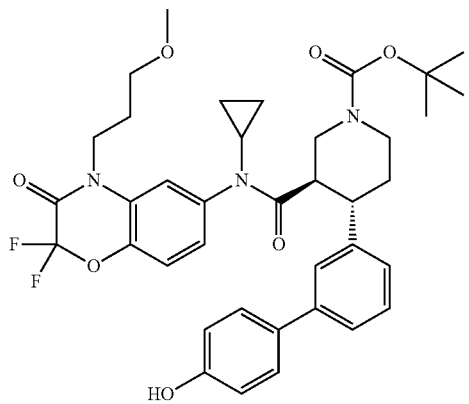

Intermediate 250.1 is synthesized by coupling of Intermediate 250.2 (197 mg, 0.26 mmol) and 4-hydroxybenzeneboronic acid (55 mg, 0.40 mmol) analogously to the preparation of Intermediate 214.1. White amorphous material; ES-MS: M+H=692; HPLC: $_At_{Ret}$=4.32 min.

Intermediate 250.2

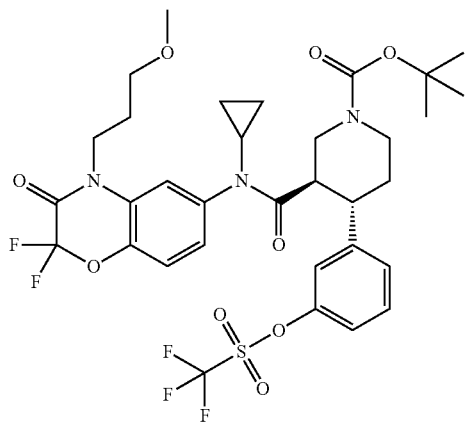

Intermediate 250.2 is synthesized by Intermediate 250.3 (1.5 g, 2.44 mmol) and trifluoromethanesulfonic anhydride (824 mg, 2.92 mmol) analogously to the preparation of 181.3. White amorphous material; ES-MS: M+H=748; HPLC: $_At_{Ret}$=4.85 min.

Intermediate 250.3

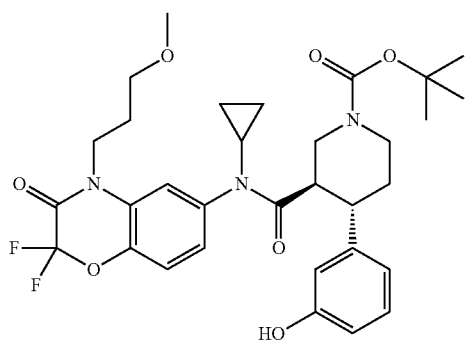

Intermediate 250.3 is synthesized by condensation of Intermediate 149.2 (1.6 g, 5.12 mmol) and intermediate 158.4 (1.8 g, 5.63 mmol) analogously to the preparation of Intermediate 145.4. White amorphous material; ES-MS: M+H=616; HPLC: $_C t_{Ret}$=2.04 min.

Intermediate 251.1

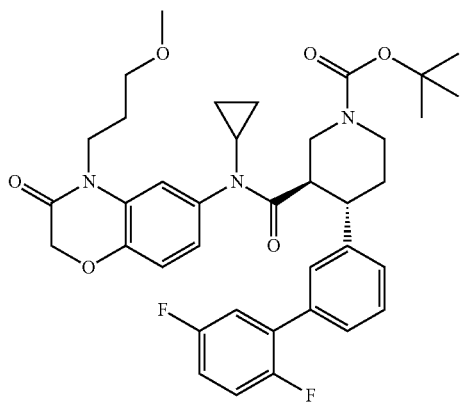

Intermediate 251.1 is synthesized by coupling of Intermediate 181.3 (171 mg, 0.24 mmol) and 2,5-Difluorobenzeneboronic acid (57 mg, 0.36 mmol) analogously to the preparation of Intermediate 214.1. White amorphous material; ES-MS: M+H=676; HPLC: $_A t_{Ret}$=4.64 min.

Intermediate 252.1

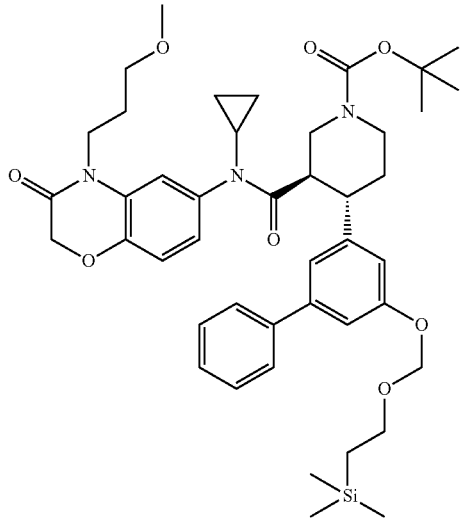

Intermediate 252.1 is synthesized by coupling of Intermediate 252.2 (265 mg, 0.31 mmol) and Phenylboronic acid (56 mg, 0.50 mmol) analogously to the preparation of Intermediate 214.1. White amorphous material; ES-MS: M+H=786; HPLC: $_A t_{Ret}$=5.57 min.

Intermediate 252.2

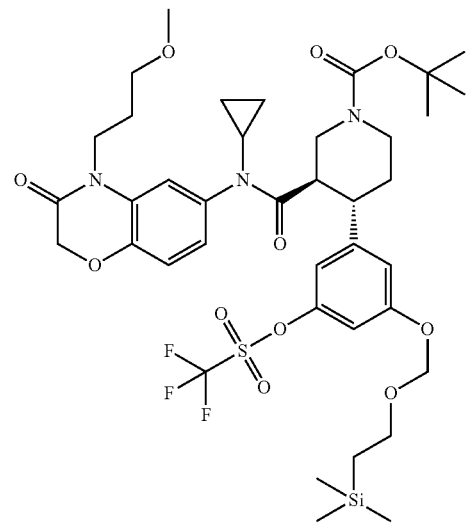

Intermediate 252.2 is synthesized by reaction of Intermediate 252.3 (360 mg, 0.50 mmol) analogously to the preparation of Intermediate 181.3; ES-MS: M+H=859; HPLC: $_A t_{Ret}$=5.50 min.

Intermediate 252.3

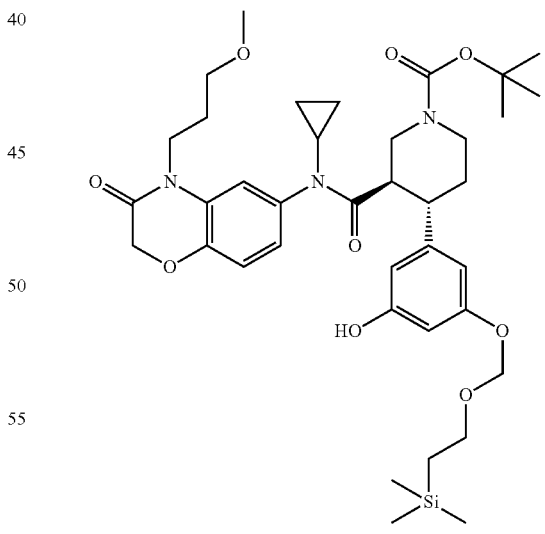

Intermediate 252.3 is synthesized by reaction of Intermediate 252.4 (459 mg, 0.98 mmol) and Intermediate 101.2 (285 mg, 1.03 mmol) analogously to the preparation of Intermediate 145.4; ES-MS: M+H=726; HPLC: $_A t_{Ret}$=4.57 min.

Intermediate 252.4

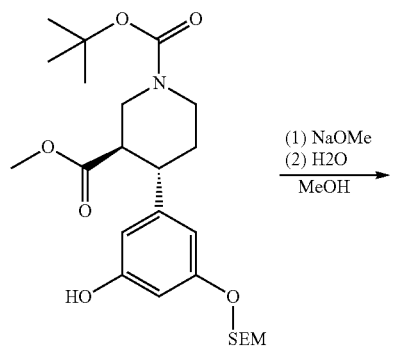

Intermediate 253.2

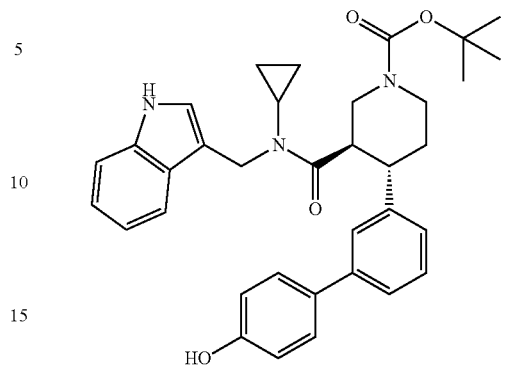

Intermediate 253.2 is synthesized by condensation of Intermediate 145.5 (250 mg, 1.35 mmol) and Intermediate 1.2 (535 mg, 1.35 mmol) analogously to the preparation of Intermediate 2.3. white amorphous; ES-MS: M+H=566; HPLC: $_A t_{Ret}$=4.05 min.

Intermediate 254.1

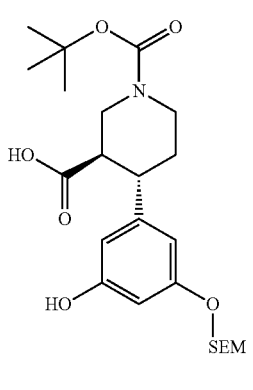

Intermediate 252.4 is synthesized by epimerization and hydrolysis of Intermediate 153.5 (340 mg, 0.71 mmol) analogously to the preparation of Intermediate 4.2. White powder; ES-MS: M+H=468; HPLC: AtRet=4.39 min.

Intermediate 253.1

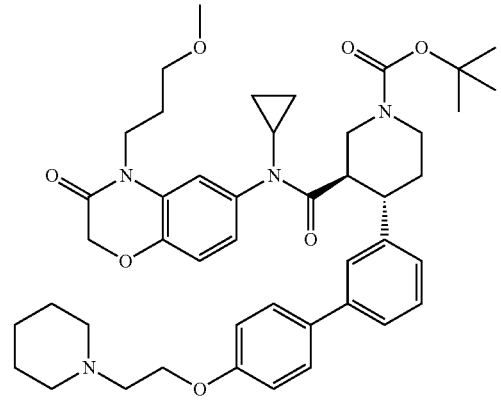

Intermediate 254.1 is synthesized by Mitsunobu reaction of Intermediate 145.3 (231 mg, 0.353 mmol) and 1-piperidineethanol (0.59 mg, 0.46 mmol) analogously to the preparation of Intermediate 77.1. White amorphous; ES-MS: M=767; HPLC: $_A t_{Ret}$=3.38 min.

Intermediate 255.1

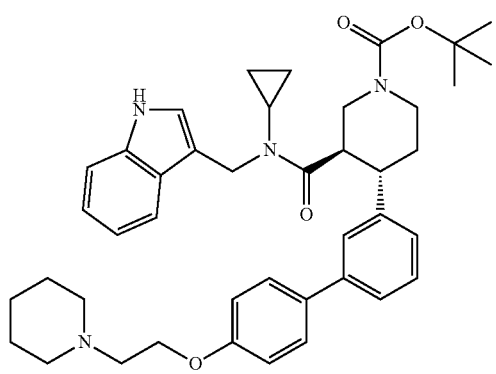

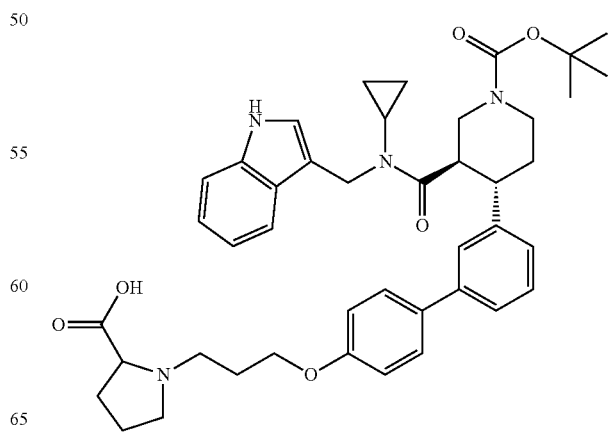

Intermediate 253.1 is synthesized by Mitsunobu reaction of Intermediate 253.2 (200 mg, 0.353 mmol) and 1-piperidineethanol (0.59 mg, 0.46 mmol) analogously to the preparation of Intermediate 77.1 White amorphous; ES-MS: M=677; HPLC: $_A t_{Ret}$=3.52 min.

Intermediate 255.1 is synthesized by hydrolysis of Intermediate 255.2 (100 mg, 0.136 mmol) analogously to the preparation of Intermediate 201.1. White amorphous; ES-MS: M=721; HPLC: $_A t_{Ret}$=3.43 min.

Intermediate 255.2

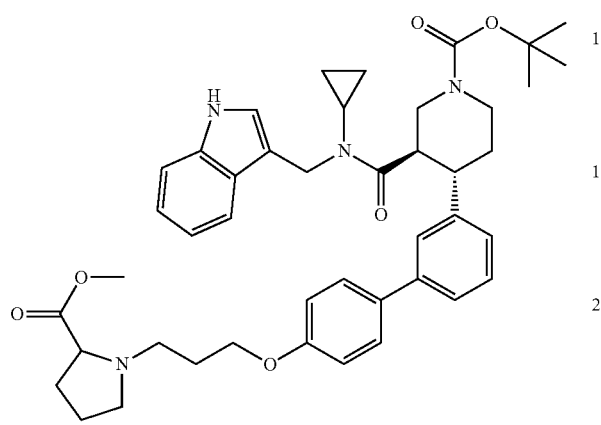

To a solution of Intermediate 255.3 (170 mg, 0.26 mmol) and methyl prolinate (90 mg, 0.54 mmol) in DMF (1 mL) are added K$_2$CO$_3$ (150 mg, 1.08 mmol) and KI (20 mg, 0.12 mmol), then the mixture is stirred for 21 h at 80° C. After cooling to room temperature, the reaction mixture is diluted with EtOAc and washed with brine. The organic layer is dried (Na$_2$SO$_4$), concentrated and purified by RP-HPLC to give Intermediate TA169.2; ES-MS: M+1=735; HPLC: $_A t_{Ret}$=3.57 min.

Intermediate 255.3

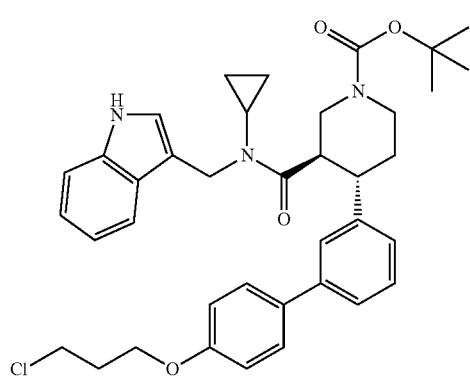

To a solution of Intermediate 253.2 (150 mg, 0.27 mmol) and 3-iodo-1-chloropropane (83.6 mg, 0.41 mmol) in DMF (1 mL) are added K$_2$CO$_3$ (44 mg, 0.32 mmol), then the mixture is stirred for 13 h at room temperature. The reaction mixture is diluted with EtOAc and washed with brine. The organic layer is dried (Na$_2$SO$_4$), concentrated and purified by silica gel column chromatography to give Intermediate 255.3; ES-MS: M+1=642; HPLC: $_A t_{Ret}$=4.97 min.

Intermediate 256.1

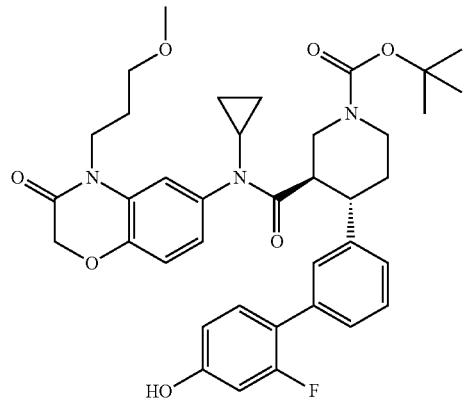

Intermediate 256.1 is synthesized by coupling of Intermediate 205.3 (210 mg, 0.30 mmol) and 4-Bromo-3-fluorophenol (87 mg, 0.46 mmol) analogously to the preparation of Intermediate 187.2. White amorphous material; ES-MS: M+H=674; HPLC: $_A t_{Ret}$=3.98 min.

Intermediate 257.1

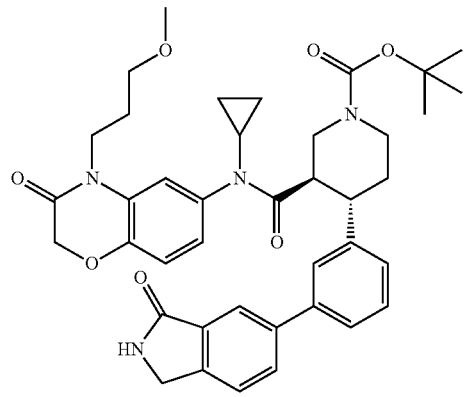

Intermediate 257.1 is synthesized by coupling of Intermediate 205.3 (147 mg, 0.21 mmol) and 6-Bromo-2,3-dihydroisoindol-1-one (83 mg, 0.32 mmol) (see e.g. WO2005073205) analogously to the preparation of Intermediate 187.2; ES-MS: M+H=695; HPLC: $_A t_{Ret}$=3.57 min.

Intermediate 258.1

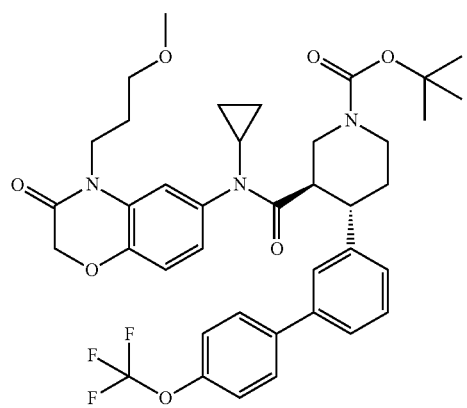

Intermediate 258.1 is synthesized by coupling of Intermediate 181.3 (219 mg, 0.31 mmol) and 4-Trifluoromethoxy-benzeneboronic acid (95 mg, 0.46 mmol) analogously to the preparation of Intermediate 214.1. White amorphous material; ES-MS: M+H=724; HPLC: $_At_{Ret}$=5.00 min.

Intermediate 259.1

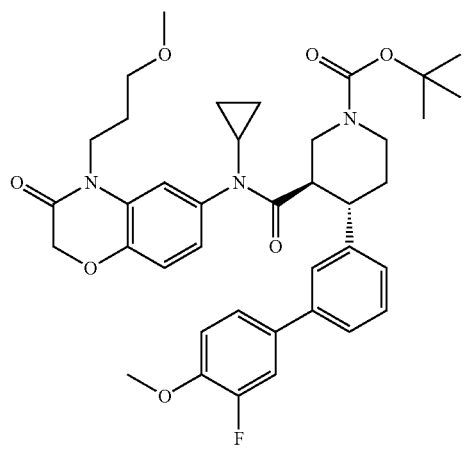

Intermediate 259.1 is synthesized by coupling of Intermediate 181.3 (197 mg, 0.28 mmol) and 3-Fluoro-4-methoxy-benzeneboronic acid (71 mg, 0.42 mmol) analogously to the preparation of Intermediate 214.1. White amorphous material; ES-MS: M+H=688; HPLC: $_At_{Ret}$=4.50 min.

Intermediate 260.1 (=intermediate 158.2)

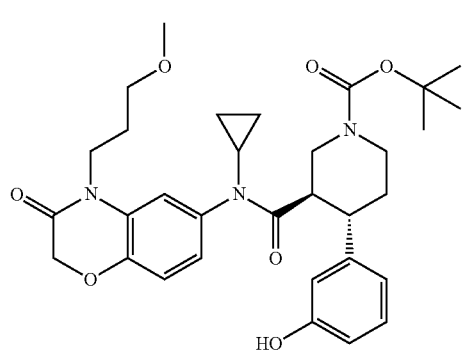

Intermediate 261.1

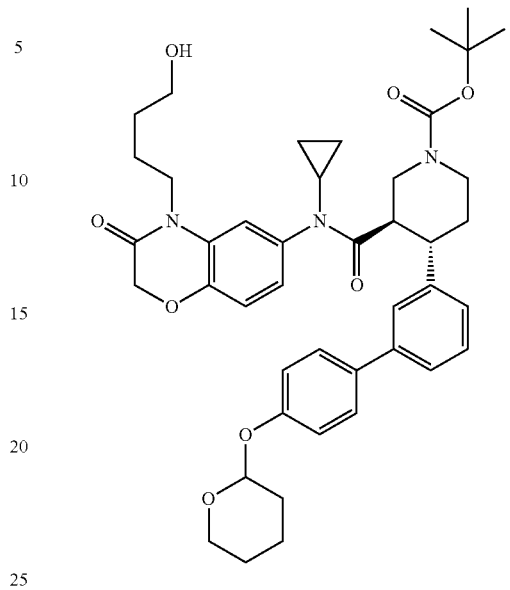

Intermediate 261.1 is synthesized by reduction of Intermediate 244.2 (160 mg, 0.21 mmol) analogously to the preparation of Intermediate 191.1. White powder; ES-MS: M+H=740; HPLC: $_At_{Ret}$=4.53 min.

Intermediate 262.1

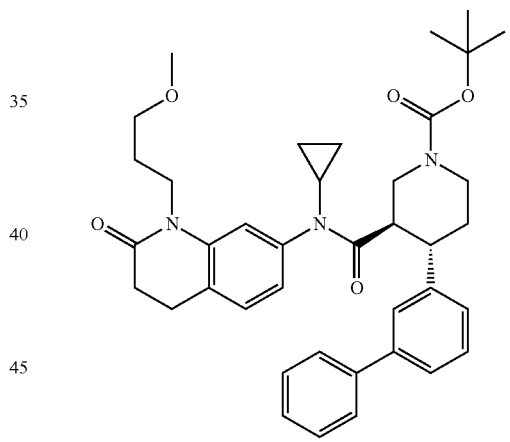

Intermediate 262.1 is synthesized by condensation of Intermediate 75.3 (47 mg, 0.15 mmol) and Intermediate 262.2 (40 mg, 0.15 mmol) analogously to the preparation of Intermediate 145.4; ES-MS: M+H=638; HPLC: $_At_{Ret}$=4.53 min.

Intermediate 262.2

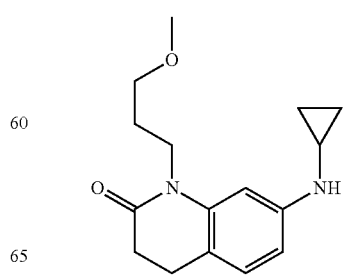

Intermediate 262.2 is synthesized by alkylation of Intermediate 262.3 (85 mg, 0.42 mmol) and toluene-4-sulfonic acid 3-methoxy-propyl ester (100 µL, 0.46 mmol) analogously to the known method (see e.g. *European Journal of Medicinal Chemistry* 1998, 33, 957-967. or EP 432893). Yellow oil; ES-MS: M+H=275; HPLC: $_A t_{Ret}$=2.52 min.

Intermediate 262.3

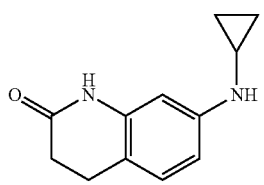

A mixture of Intermediate 245.4 (130 mg, 0.50 mmol) and NiCl$_2$-6H$_2$O (120 mg, 0.50 mmol) in MeOH (5 mL) is cooled to 0° C. and NaBH$_4$ (113 mg, 3.0 mmol) is added portionwise. The resulting solution is stirred at 0° C. for 2 h, then at 60° C. for 21 h. The reaction mixture is diluted with H$_2$O and extracted with EtOAc. The combined organic phases are washed with H$_2$O and dried over Na$_2$SO$_4$. Concentration under reduced pressure and silica gel flash chromatography give Intermediate 262.3 as brown powder; Rf=0.2 (EtOAc:n-Hex=1:1); $^1$H NMR (CDCl$_3$), δ: 0.48-0.52 (2H, m), 0.71-0.75 (2H, m), 2.37-2.42 (1H, m), 2.60 (1H, t), 2.86 (2H, t), 4.15 (1H, s), 6.18 (1H, d), 6.38-6.41 (1H, m), 6.95 (1H, d), 7.31 (1H, s).

Intermediate 263.1

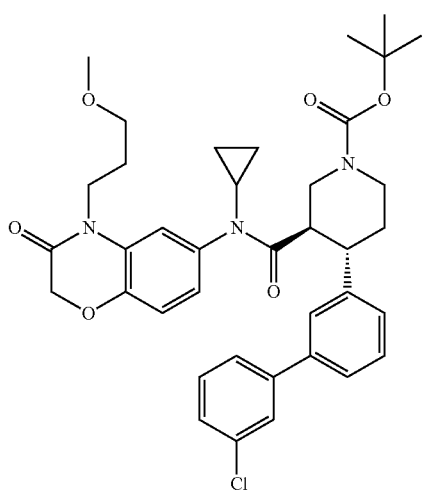

Intermediate 263.1 is synthesized by condensation of Intermediate 181.3 (151 mg, 0.2 mmol) and 3-chlorophenylboronic acid (47 mg, 0.30 mmol) analogously to the preparation of Intermediate 2.1; ES-MS: M+H=674; HPLC: $_A t_{Ret}$=4.89 min.

Intermediate 264.1

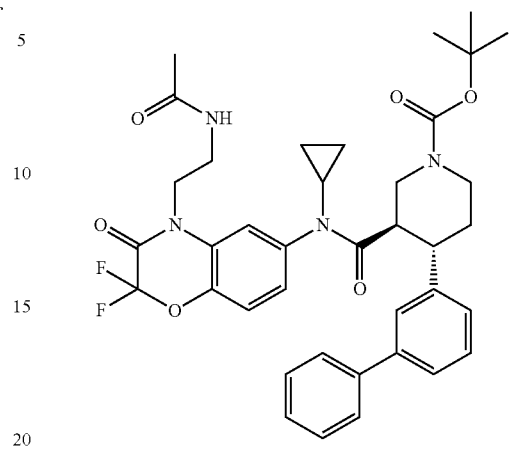

Intermediate 264.1 is synthesized by condensation of Intermediate 75.3 (66 mg, 0.17 mmol) and Intermediate 264.2 (51 mg, 0.16 mmol) analogously to the preparation of Intermediate 145.4; ES-MS: M+H=689; HPLC: $_A t_{Ret}$=5.68 min.

Intermediate 264.2

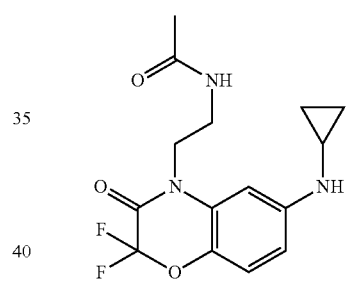

Intermediate 264.2 is prepared by the same methodology described for Intermediate 243.2. Colorless amorphous; ES-MS: M+H=326; HPLC: $_A t_{Ret}$=2.87 min.

Intermediate 264.3

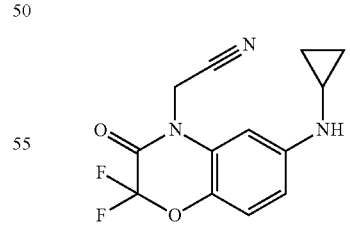

Intermediate 264.3 is synthesized by alkylation of Intermediate 149.3 (610 mg, 3.00 mmol) and chloroacetonitril (210 µL, 3.3 mmol) analogously to the known method (see e.g. *European Journal of Medicinal Chemistry* 1998, 33, 957-967. or EP 432893). White solid; ES-MS: M+H=244; HPLC: $_A t_{Ret}$=2.45 min.

ES-MS: M+H=280; HPLC: $_A t_{Ret}$=3.52 min.

Intermediate 265.1

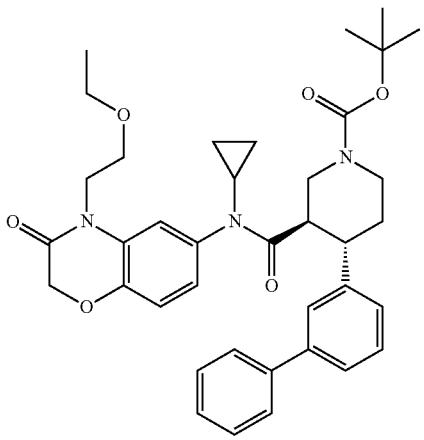

Intermediate 265.1 is synthesized by condensation of Intermediate 75.3 (153 mg, 0.40 mmol) and Intermediate 265.2 (110 mg, 0.40 mmol) analogously to the preparation of Intermediate 145.4; ES-MS: M+H=640; HPLC: $_A t_{Ret}$=4.70 min.

Intermediate 265.2

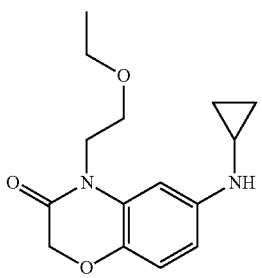

Intermediate 265.2 is synthesized by alkylation of Intermediate 101.3 (204 mg, 1.00 mmol) and bromoethyl ethyl ether (124 µL, 1.1 mmol) analogously to a known method (see e.g. *European Journal of Medicinal Chemistry* 1998, 33, 957-967. or EP 432893). White solid; ES-MS: M+H=277; HPLC: $_A t_{Ret}$=2.45 min.

Intermediate 266.1

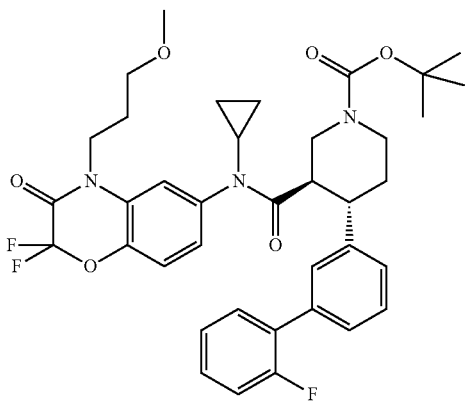

Intermediate 266.1 is synthesized by the Suzuki coupling of 250.2 (175 mg, 0.27 mmol) and 2-fluorophenylboronic acid (57.6 mg, 0.41 mmol) analogously to the preparation of Intermediate 2.1: White amorphous material; ES-MS: M+H=694; HPLC: $_A t_{Ret}$=5.03 min.

Intermediate 267.1

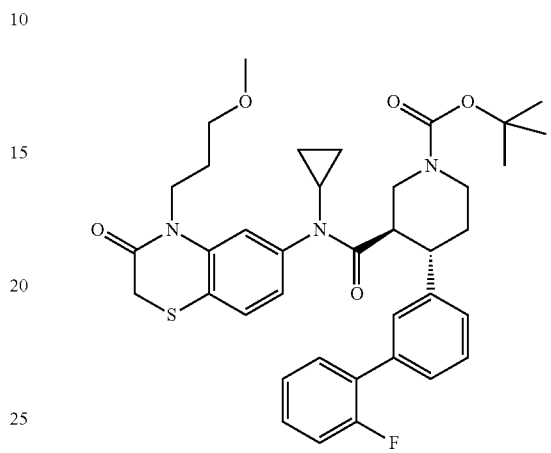

Intermediate 267.1 is synthesized by the Suzuki coupling of 267.2 (200 mg, 0.27 mmol) and 2-fluorophenylboronic acid (57.6 mg, 0.41 mmol) analogously to the preparation of Intermediate 2.1. White amorphous material; ES-MS: M+H=674; HPLC: $_A t_{Ret}$=4.75 min.

Intermediate 267.2

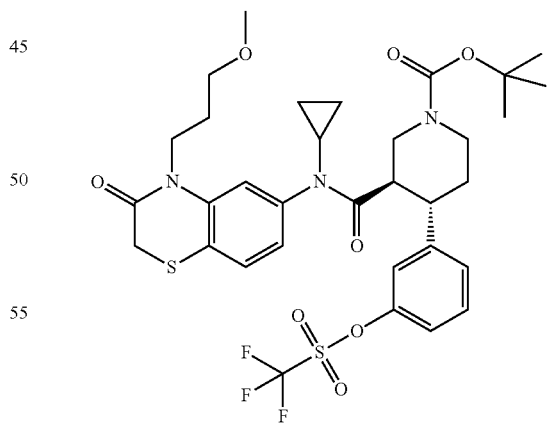

Intermediate 267.2 is synthesized by condensation of Intermediate 267.3 (2.0 g, 3.34 mmol) analogously to the preparation of Intermediate 29.4. White amorphous material; ES-MS: M+H=728; HPLC: $_A t_{Ret}$=4.56 min.

Intermediate 267.3

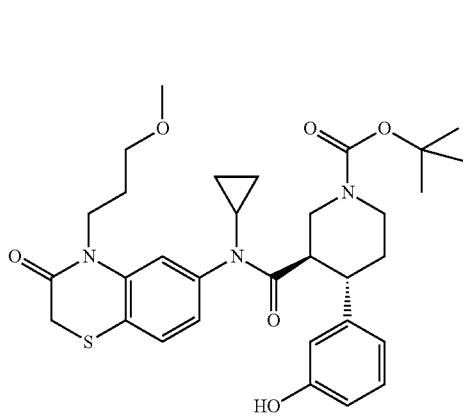

Intermediate 267.3 is synthesized by condensation of Intermediate 158.4 (1.76 g, 5.48 mmol) and Intermediate 120.2 (1.68 g, 5.75 mmol) analogously to the preparation of Intermediate 145.4. Amorphous material; ES-MS: M+H=596; HPLC: $_A t_{Ret}$=3.59 min.

Intermediate 268.1

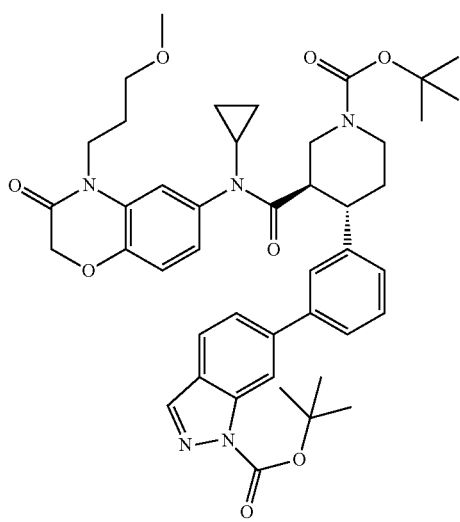

Intermediate 268.1 is synthesized by coupling of Intermediate 205.3 (200 mg, 0.35 mmol) and Intermediate 127.2 (112 mg, 0.38 mmol) analogously to the preparation of Intermediate 175.1. Amorphous material; ES-MS: M-(Boc)=780; HPLC: $_A t_{Ret}$=4.67 min.

Intermediate 269.1

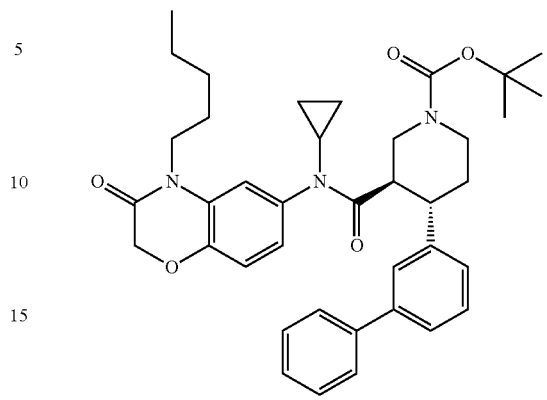

Intermediate 269.1 is synthesized by condensation of Intermediate 75.3 (252 mg, 0.660 mmol) and intermediate 269.2 (181 mg, 0.660 mmol) analogously to the preparation of Intermediate 2-1. White amorphous material; (LC/MS): [M+H]$^+$=638; HPLC: $_C t_{Ret}$=2.42 min Intermediate 269.2

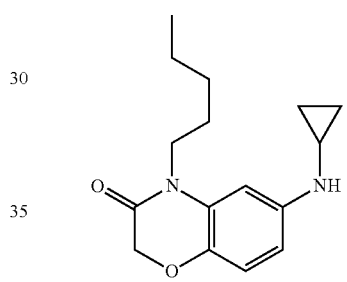

Intermediate 269.2 is synthesized by alkylation of intermediate 101.3 (300 mg, 1.47 mmol) and 1-bromo-pentane (333 mg, 2.21 mmol) analogously to the known method (see e.g. European Journal of Medicinal Chemistry 1998, 33, 957-967. or EP 432893). White amorphous material; ES-MS: M+H=275; HPLC: $_A t_{Ret}$=3.38 min.

Intermediate 270.1

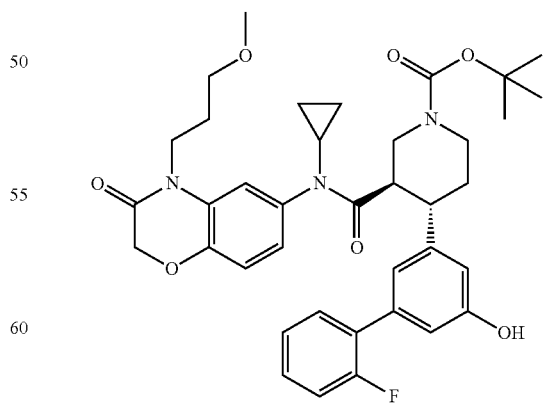

A mixture of Intermediate 270.2 (113.9 mg, 0.14 mmol) and 1N TBAF (0.21 mL in THF, 2.1 mmol) in THF (1 mL) is stirred at 80° C. After stirring overnight, adding MeOH, Concentration under reduced pressure and silica gel flash chromatography of the residue (hexane/ethyl acetate) affords intermediate 270.1 as amorphous; ES-MS: M+H=674; HPLC: $_At_{Ret}$=4.00 min.

Intermediate 270.2

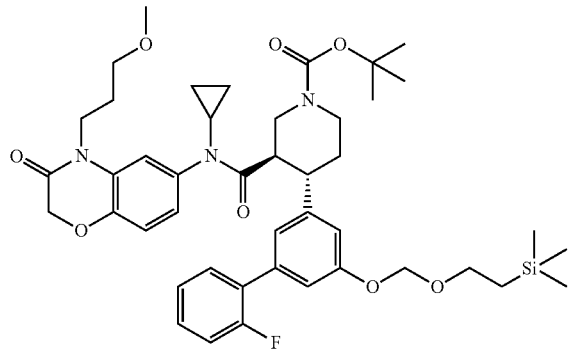

Intermediate 270.2 is synthesized by coupling of Intermediate 270.3 (284.6 mg, 0.33 mmol) and 2-Fluorophenylboronic acid (22.6 mg, 0.13 mmol) analogously to the preparation of Intermediate 2.1 White amorphous material; ES-MS: M+H=804; HPLC: $_At_{Ret}$=5.53 min.

Intermediate 270.3

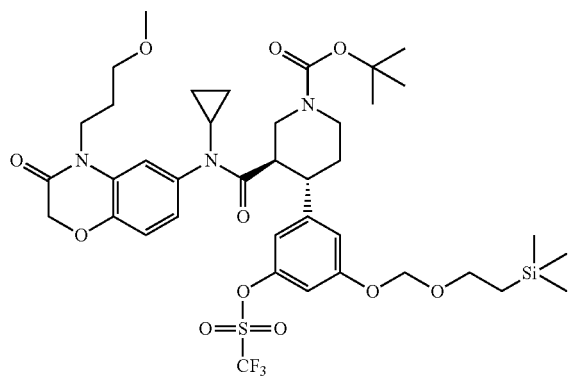

Intermediate 270.3 is synthesized by sulfonylation of Intermediate 270.4 (341 mg, 0.46 mmol) analogously to the preparation of Intermediate 29.4 White amorphous material; ES-MS: M+H=858; HPLC: $_At_{Ret}$=5.49 min.

Intermediate 270.4

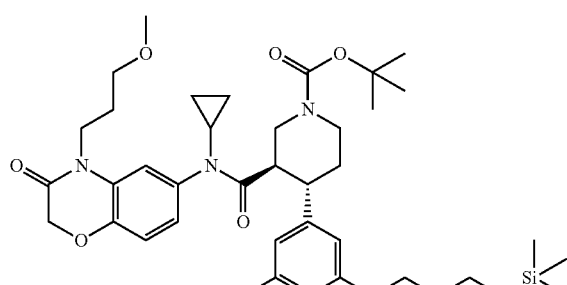

Intermediate 270.4 is synthesized by hydrolysis of Intermediate 270.5 analogously to the preparation of Intermediate 80.2 White amorphous material; ES-MS: M+H=726; HPLC: $_At_{Ret}$=4.57 min.

Intermediae 270.5

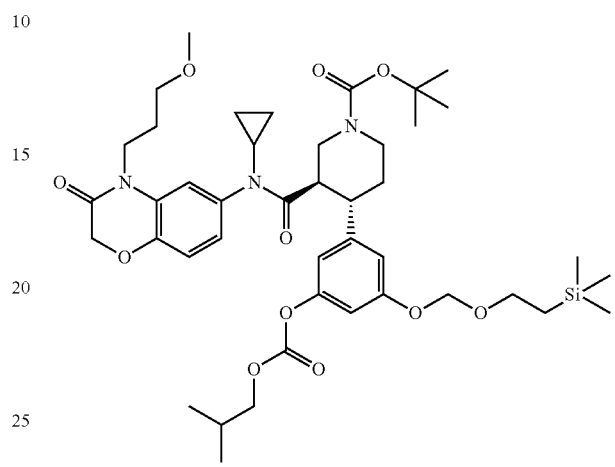

Intermediate 270.5 is synthesized by condensation of Intermediate 252.4 (506.5 mg, 1.08 mmol) analogously to the preparation of 145.4 as amorphous; ES-MS: M+H=826; HPLC: $_At_{Ret}$=5.50 min.

Intermediate 271.1

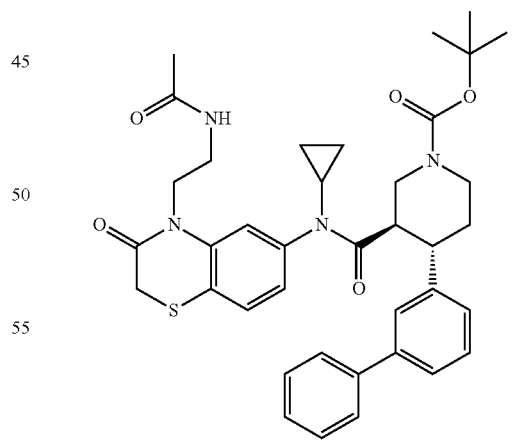

Intermediate 271.1 is synthesized by condensation of Intermediate 75.3 (95 mg, 0.25 mmol) and Intermediate 271.2 (75 mg, 0.25 mmol) analogously to the preparation of Intermediate 145.4; ES-MS: M+H=669; HPLC: $_At_{Ret}$=4.17 min.

Intermediate 271.2

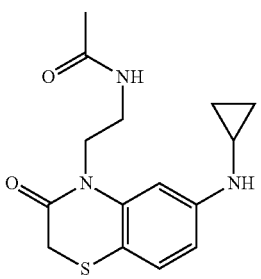

Intermediate 271.2 is prepared by the same methodology described for Intermediate 243.2 ES-MS: M+H=306; HPLC: $_At_{Ret}$=2.45 min.

Intermediate 271.3

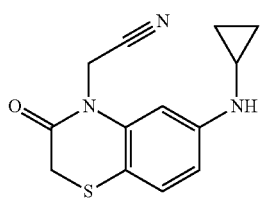

Intermediate 271.3 is synthesized by alkylation of Intermediate 120.3 (330 mg, 1.50 mmol) and chloroacetonitril (114 μL, 1.8 mmol) analogously to the known method (see e.g. *European Journal of Medicinal Chemistry* 1998, 33, 957-967. or EP 432893). The crude product is used without purification; ES-MS: M+H=260; HPLC: $_At_{Ret}$=3.18 min.

Intermediate 272.1

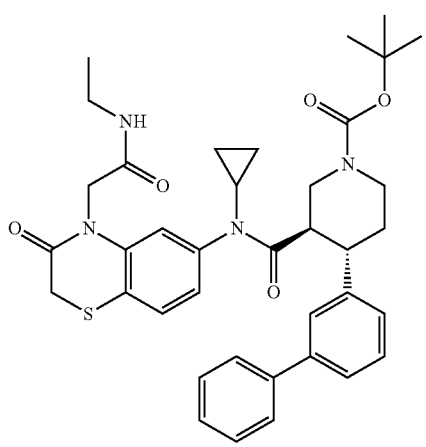

Intermediate 272.1 is synthesized by condensation of Intermediate 272.2 (72 mg, 0.11 mmol) and 2M solution of ethylamine in THF (112 μL, 0.22 mmol) analogously to the preparation of Intermediate 82.1. Amorphous; ES-MS: M+H=669; HPLC: $_At_{Ret}$=4.39 min.

Intermediate 272.2

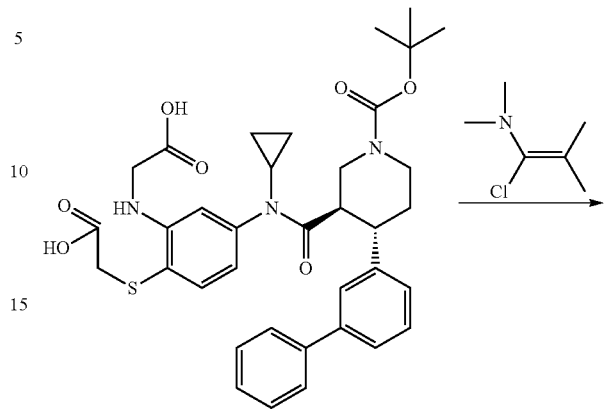

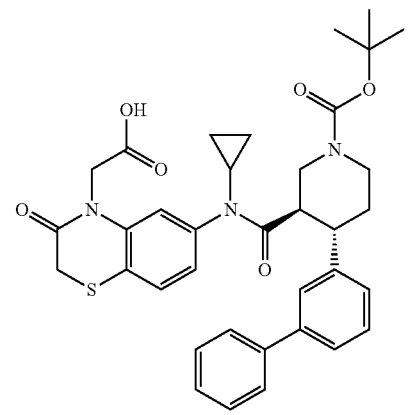

Intermediate 272.2 is synthesized by intramolecular condensation analogously to the preparation of Intermediate 82.1. Amorphous; ES-MS: M+H=642; HPLC: $_At_{Ret}$=4.22 min.

Intermediate 272.3

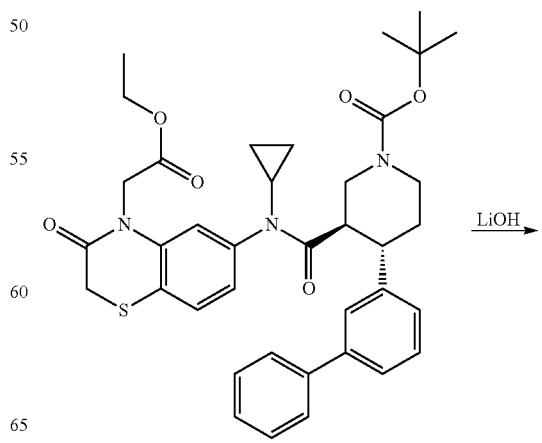

-continued

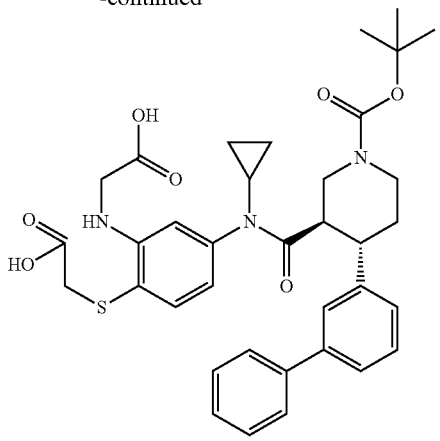

Intermediate 272.3 is synthesized by hydrolysis of Intermediate 272.4 (350 mg, 0.52 mmol) analogously to the preparation of Intermediate 195.1. Yellow powder; ES-MS: M=660; HPLC: $_At_{Ret}$=3.84 min.

Intermediate 272.4

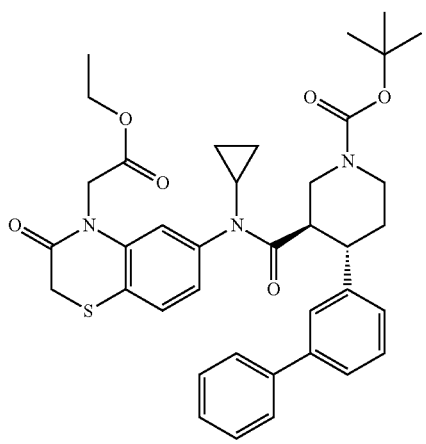

Intermediate 272.4 is synthesized by condensation of Intermediate 75.3 (350 mg, 0.91 mmol) and Intermediate 272.5 (320 mg, 1.00 mmol) analogously to the preparation of Intermediate 145.4; ES-MS: M+H=670; HPLC: $_At_{Ret}$=4.75 min.

Intermediate 272.4

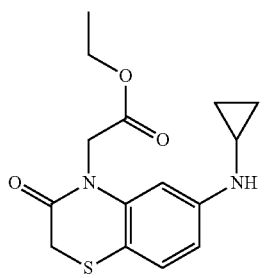

Intermediate 272.4 is synthesized by alkylation of Intermediate 120.3 (330 mg, 1.50 mmol) and ethyl chloroacetate (193 μL, 1.8 mmol) analogously to the known method (see e.g. *European Journal of Medicinal Chemistry* 1998, 33, 957-967. or EP 432893). The crude product is directly used without further purification.

Intermediae 273.1

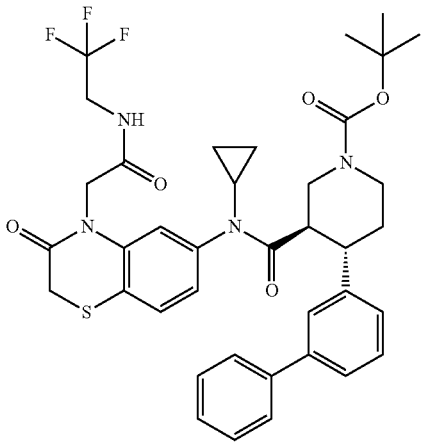

Intermediate 273.1 is synthesized by condensation of Intermediate 272.2 (80 mg, 0.13 mmol) and 2,2,2-trifluoromethylamine (20 μL, 0.25 mmol) analogously to the preparation of Intermediate 82.1. Amorphous; ES-MS: M+H=667; HPLC: $_At_{Ret}$=4.64 min.

Intermediate 274.1

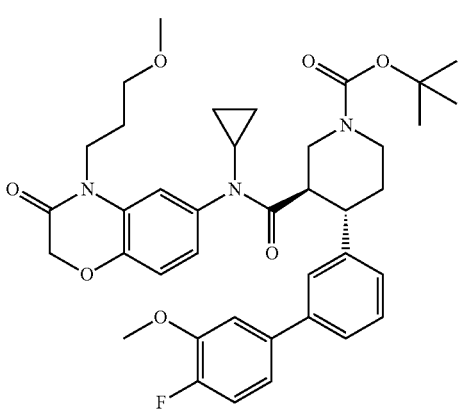

To a solution of Intermediate 274.2 (40 mg, 0.059 mmol) and iodomethane (17 mg, 0.118 mmol) in DMF (1 mL) are added $K_2CO_3$ (16 mg, 0.118 mmol), then the mixture is stirred for 19 h at 50° C. The reaction mixture is diluted with EtOAc and washed with brine. The organic layer is dried ($Na_2SO_4$), concentrated and purified by silica gel column chromatography to give Intermediate 274.1; ES-MS: M+1=688; HPLC: $_At_{Ret}$=4.53 min.

Intermediate 274.2

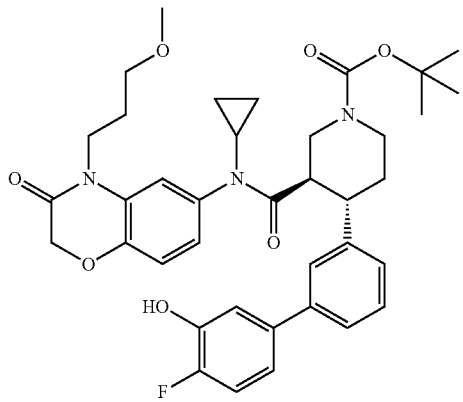

Intermediate 274.2 is synthesized by coupling of Intermediate 181.3 (150 mg, 0.22 mmol) and 5-bromo-2-fluorophenol (81 mg, 0.0.42 mmol) analogously to the preparation of Intermediate 201.2. Amorphous material; ES-MS: M+1=674; HPLC: $_At_{Ret}$=4.03 min.

Intermediate 275.1 (=274.2)

Intermediate 276.1

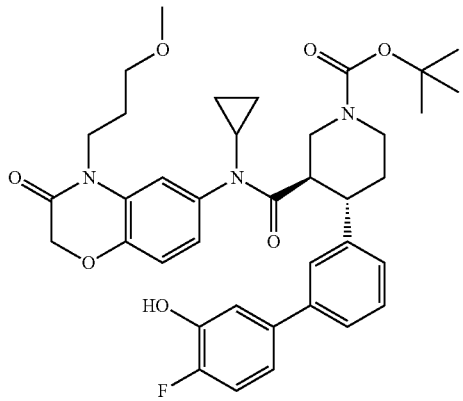

Intermediate 276.1 is synthesized by coupling of Intermediate 181.3 (150 mg, 0.22 mmol) and intermediate 276.2 (72 mg, 0.3 mmol) analogously to the preparation of intermediate 201.2. White amorphous; ES-MS: M=674; HPLC: $_At_{Ret}$=3.98 min.

Intermediate 276.2

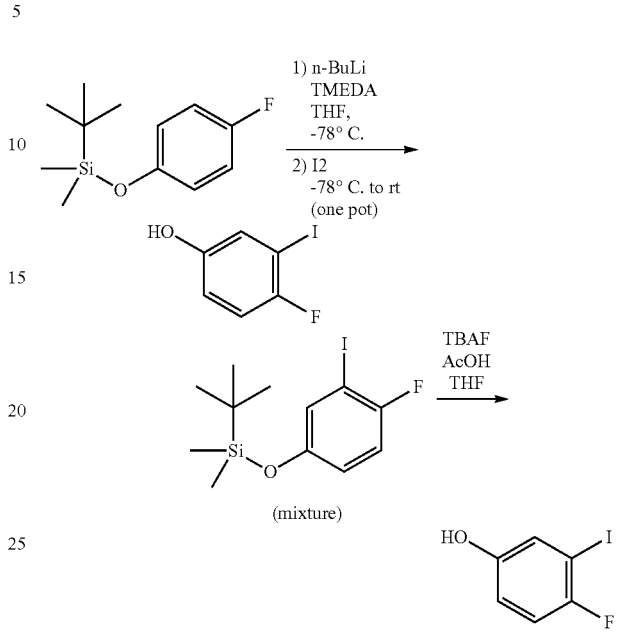

To a solution of tert-Butyl-(4-fluorophenoxy)dimethylsilane (700 mg, 3.09 mmol) and TMEDA (534 mg, 4.6 mmol) are added n-butyllithium (1.6M in THF, 4.6 mmol) at −78° C. After stirring for 2 h at −78° C., I$_2$ (3.8 g, 15 mmol) in THF (7.5 mL) is added dropwise, then the mixture is warm up to room temperature. After stirring for 1 h, the resulting mixture is added aqueous KHSO$_4$, then diluted with Et$_2$O and washed with H$_2$O and brine. The organic layer is dried (Na$_2$SO$_4$), concentrated under reduced pressure. The residue is treated with TBAF (1.0M in THF, 5 mmol) and stirred for 2 h at room temperature. Concentration under reduced pressure and RP-HPLC purification give Intermediate 276.2 as a colorless oil; $^1$H NMR (CDCl$_3$), δ: 6.74-6.78 (1H, m), 7.05 (1H, dd), 7.16 (1H, dd), 9.65 (1H, s); HPLC: $_At_{Ret}$=3.02 min.

Intermediate 277.1

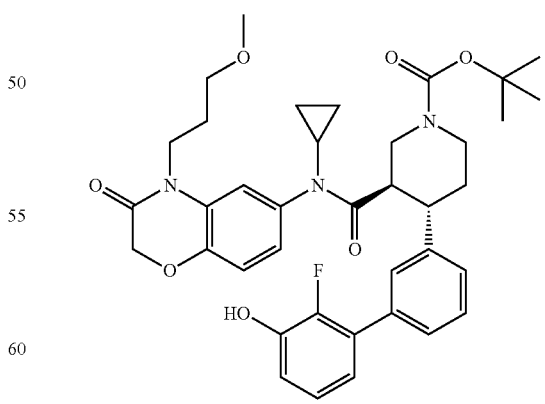

Intermediate 277.1 is synthesized by coupling of Intermediate 181.3 (150 mg, 0.22 mmol) and 277.2 (72 mg, 0.3 mmol) analogously to the preparation of Intermediate 201.2. White amorphous; ES-MS: M=674; HPLC: $_At_{Ret}$=3.95 min.

Intermediate 27.2

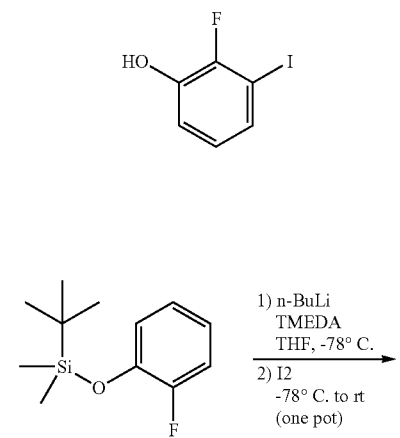

Intermediate 277.2 is synthesized by iodation of tert-Butyl-(2-fluorophenoxy)dimethylsilane (1.9 g, 8.4 mmol) analogously to the preparation of Intermediate 276.2. colorless oil; $^1$H NMR (CDCl$_3$), δ: 6.83 (1H, dt), 6.98 (1H, dt), 7.22-7.25 (1H, m), 10.18 (1H, s); HPLC: $_A$t$_{Ret}$=3.00 min.

Intermediate 278.1

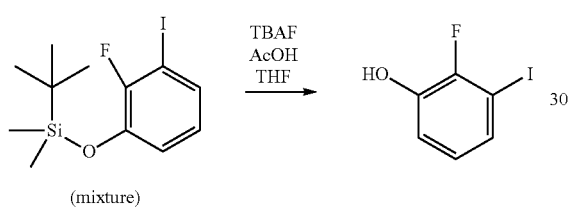

Intermediate 278.1 is synthesized by coupling reaction of Intermediate 181.3 (100 mg, 0.14 mmol) and 3-methoxybenzeneboronic acid (42 mg, 0.28 mmol) analogously to the preparation of Intermediate 2.1. White amorphous; ES-MS: M+H=670; HPLC: $_A$t$_{Ret}$=4.53 min.

Intermediate 279.1

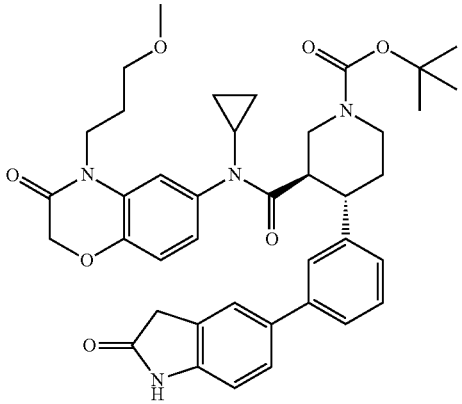

Intermediate 279.1 is synthesized by coupling of Intermediate 205.3 (115 mg, 0.17 mmol) and 5-Bromo-oxindole (53 mg, 0.25 mmol) analogously to the preparation of Intermediate 187.2; ES-MS: M+H=695; HPLC: $_A$t$_{Ret}$=3.63 min.

Intermediate 280.1

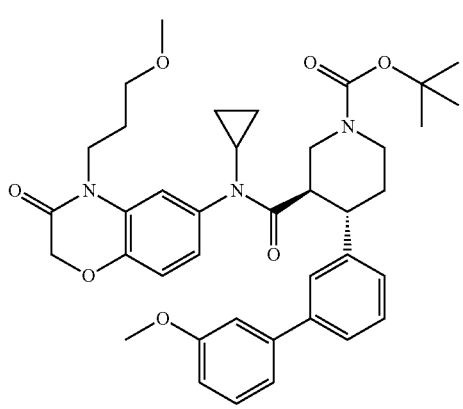

A mixture of Intermediate 280.2 (71.6 mg, 0.11 mmol), K$_2$CO$_3$ (110 mg, 0.80 mmol) and MeI (15.8 μL, 0.25 mmol) in DMF (3 mL) is stirred at RT. After stirring for a few minutes, adding H$_2$O at RT, the reaction mixture is extracted with EtOAc. The combined organic phases are washed with H$_2$O, dried (Na$_2$SO$_4$). Concentration under reduced pressure and silica gel flash chromatography of the residue (hexane/ethyl acetate) affords intermediate 279.1 as amorphous; ES-MS: M+H=688; HPLC: $_A$t$_{Ret}$=4.55 min.

Intermediate 280.2

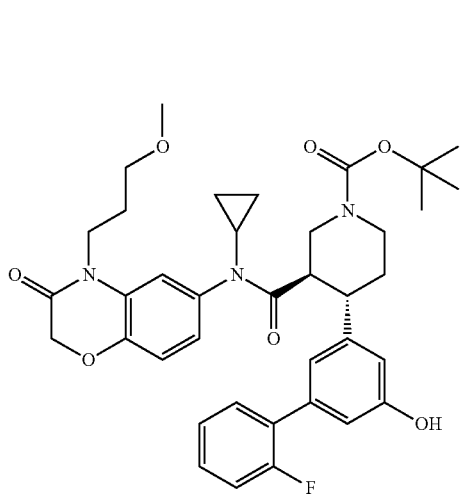

A mixture of Intermediate 280.3 (113.9 mg, 0.14 mmol) and 1N TBAF (0.21 mL in THF, 2.1 mmol) in THF (1 mL) is stirred at 80° C. After stirring overnight, MeOH is added. Concentration under reduced pressure and silica gel flash chromatography of the residue (hexane/ethyl acetate) affords intermediate 280.2 as amorphous; ES-MS: M+H=674; HPLC: $_A t_{Ret}$=4.00 min.

Intermediate 280.3

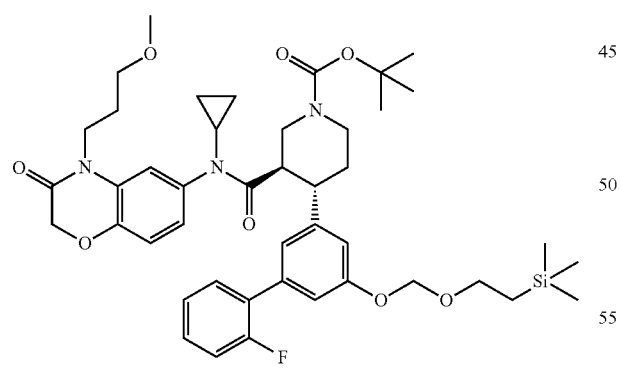

Intermediate 280.3 is synthesized by coupling of Intermediate 252.2 (284.6 mg, 0.33 mmol) and 2-Fluorophenylboronic acid (22.6 mg, 0.13 mmol) analogously to the preparation of Intermediate 2.1 White amorphous material; ES-MS: M+H=804; HPLC: $_A t_{Ret}$=5.53 min.

Intermediate 281.1

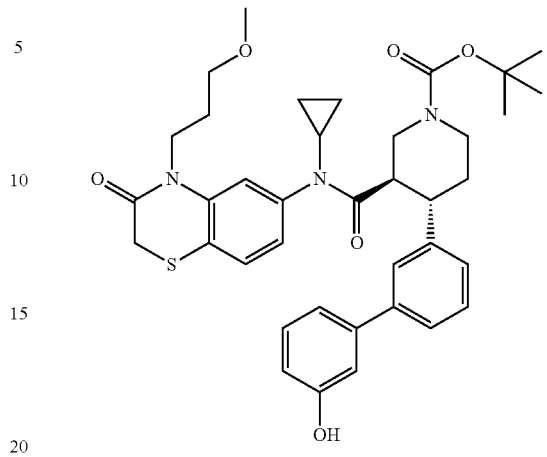

Intermediate 281.1 is synthesized by the Suzuki coupling of intermediate 267.2 (200 mg, 0.27 mmol) and 3-hydroxyphenylboronic acid (56.0 mg, 0.41 mmol) analogously to the preparation of Intermediate 2.1. White amorphous material; ES-MS: M+H=672; HPLC: $_A t_{Ret}$=4.09 min.

Intermediate 282.1

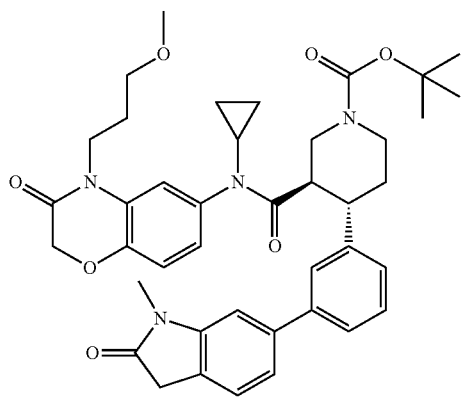

Intermediate 282.1 is synthesized by coupling of Intermediate 205.3 (140 mg, 0.20 mmol) and Intermediate 282.2 (69 mg, 0.31 mmol) analogously to the preparation of Intermediate 187.2; ES-MS: M+H=709; HPLC: $_A t_{Ret}$=3.93 min.

Intermediate 282.2

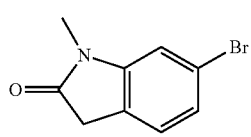

To a solution of 6-Bromooxindole (202 mg, 0.95 mmol) and K$_2$CO$_3$ (395 mg, 2.86 mmol) in acetone (3 mL) is added Iodomethane (0.12 mL, 1.90 mmol). After stirring at room temperature for 13 h, the reaction mixture is diluted with CH$_2$Cl$_2$ and washed with H$_2$O. The organic layer is concentrated and purified by silica gel column chromatography to give Intermediate 282.2; ES-MS: M+H=227; HPLC: $_A t_{Ret}$=2.88 min.

Intermediate 283.1

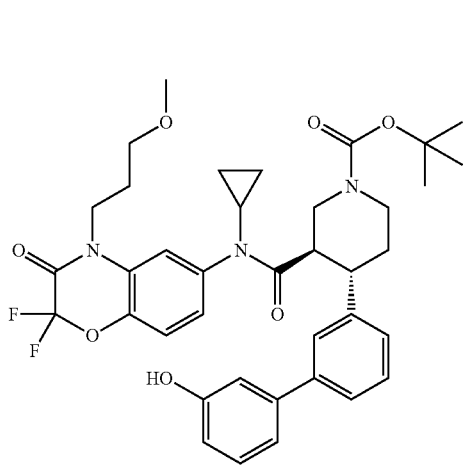

Intermediate 283.1 is synthesized by Suzuki coupling of intermediate 250.2 (175 mg, 0.27 mmol) and 3-hydroxyphenylboronic acid (56.0 mg, 0.41 mmol) analogously to the preparation of Intermediate 2.1. White amorphous material; ES-MS: M+H=692; HPLC: $_A t_{Ret}$=4.37 min.

Intermediate 284.1

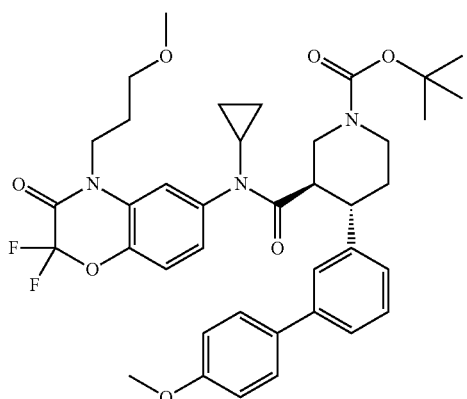

Intermediate 284.1 is synthesized by coupling of Intermediate 2502 (159 mg, 0.21 mmol) and 4-Methoxybenzeneboronic acid (48 mg, 0.32 mmol) analogously to the preparation of Intermediate 214.1. White amorphous material; ES-MS: M+H=706; HPLC: $_A t_{Ret}$=4.93 min.

Intermediat 285.1

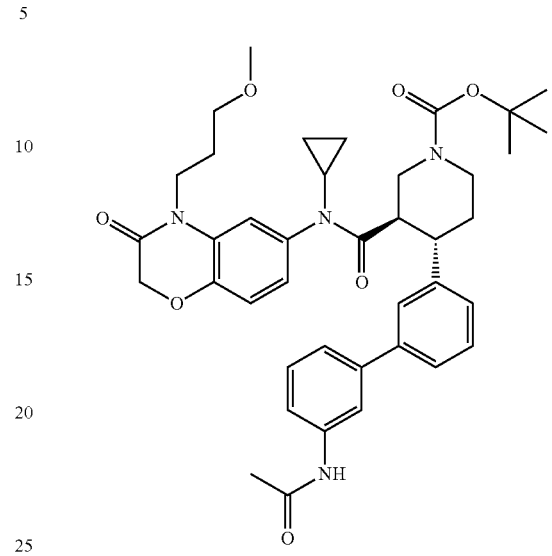

Intermediate 285.1 is synthesized by coupling of Intermediate 181.3 (198 mg, 0.28 mmol) and 3-Acetamidobenzeneboronic acid (75 mg, 0.42 mmol) analogously to the preparation of Intermediate 214.1. White amorphous material; ES-MS: M+H=697; HPLC: $_A t_{Ret}$=3.85 min.

Intermediate 286.1

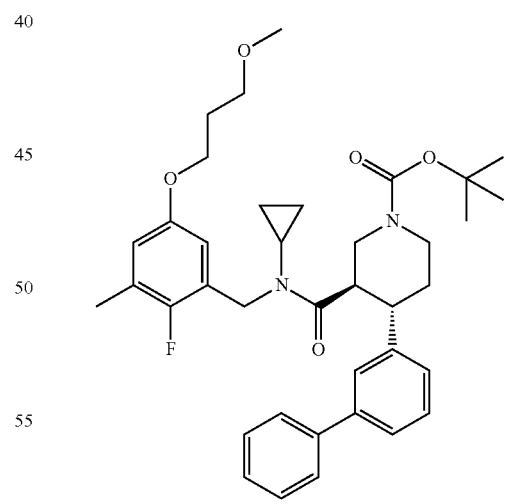

Intermediate 286.1 is synthesized by condensation of Intermediate 1.2 (57 mg, 0.15 mmol) and Intermediate 286.2 (40 mg, 0.15 mmol) analogously to the preparation of Intermediate 2.3. White amorphous material; ES-MS: M+H=631; HPLC: $_A t_{Ret}$=5.30 min.

Intermediate 286.2

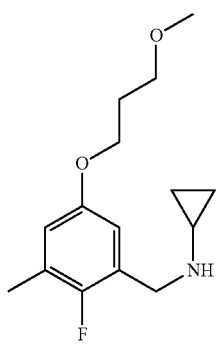

A mixture of Intermediate 286.3 (100 mg), 3-(p-toluenesulfonyloxy)propylmethyl ether (150 mg, 0.61 mmol), 60% NaH (22.4 mg, 0.56 mmol) and KI (5 mg, 0.05 mmol) in DMF is stirred at 0° C. for 20 min. The resulting mixture is warmed up to r.t. and is stirred for 2 h. After adding water, the reaction mixture is extracted with EtOAc. The combined organic phases are washed with water and dried (MgSO$_4$). Concentration under reduced pressure and preparative TLC purification gives Intermediate 286.2 yellow oil; ES-MS: M+H=268; HPLC: $_At_{Ret}$=2.22 min.

Intermediate 286.3

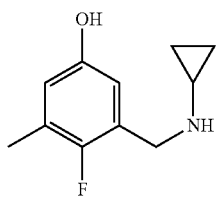

To a solution of Intermediate 286.4 (500 mg, 2.08 mmol) in THF (10 ml) is added sec-BuLi (1.0M in cyclohexane, 4.16 mmol) at −78° C. The reaction mixture is stirred for 2 h. After adding DMF (0.79 ml, 8.32 mmol), the resulting mixture is warmed up to r.t. and is stirred for 30 min. The reaction mixture is poured into sat. NH$_4$Claq and is extracted with EtOAc. washed with water and brine and dried (MgSO$_4$). Concentration under reduced pressure and the evaporated residue is dissolved in dichloromethane (8 ml), MeOH (2 ml) and AcOH (2 ml) then stirred at r.t. for 2.5 h. After neutralized with 1M KOHaq, the reaction mixture is extracted with EtOAc. The combined organic phases are washed with sat. NaHCO$_3$ aq., brine and dried (MgSO$_4$). The evaporated residue is treated with TBAF (1.0M in THF, 4 mmol). Concentration under reduced pressure and silica gel flash chromatography gives Intermediate 286.3 colorless crystals; ES-MS: M+H=310; HPLC: $_At_{Ret}$=3.29 min.

Intermediate 286.4

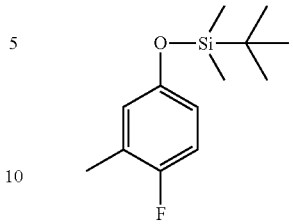

A mixture of 4-fluoro-3-methylphenol (2.0 g, 15.9 mmol), TBDMSCl (2.27 g, 15.1 mmol) and imidazole (1.1 g, 15.9 mmol) in DMF (8 mL) is stirred at RT for 30 min. The reaction mixture is extracted with ether. The combined organic phases are washed three times with H$_2$O, brine and dried (MgSO$_4$). Concentration under reduced pressure and silica gel flash chromatography gives Intermediate 286.4. Colorless oil; HPLC: $_At_{Ret}$=5.45 min, TLC: Rf=0.6 (hexane).

Intermediate 288.1

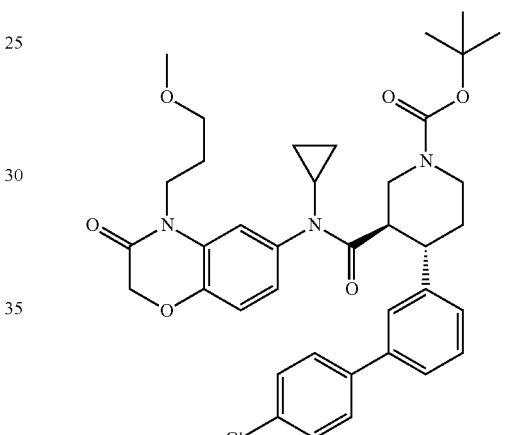

Intermediate 288.1 is synthesized by condensation of Intermediate 181.3 (178 mg, 0.25 mmol) and 4-chlorophenylboronic acid (59 mg, 0.38 mmol) analogously to the preparation of Intermediate 2.1; ES-MS: M+H=674; HPLC: $_At_{Ret}$=4.90 min.

Intermediate 287.1

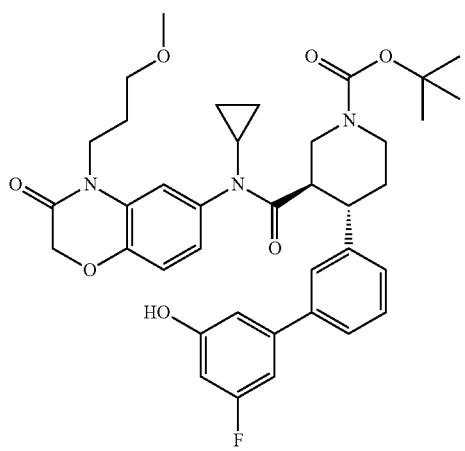

Intermediate 287.1 is synthesized by condensation of Intermediate 205.3 (150 mg, 0.22 mmol) and 3-bromo-5-fluorophenol (62 mg, 0.32 mmol) analogously to the preparation of Intermediate 145.4. White amorphous material; ES-MS: M+H=674; HPLC: $_C t_{Ret}$=2.03 min.

Intermediate 289.1

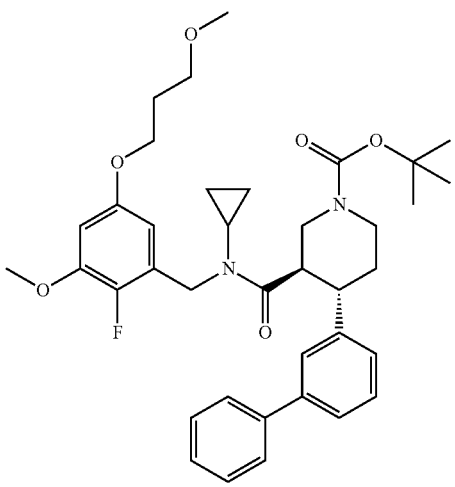

Intermediate 289.1 is synthesized by condensation of Intermediate 289.2 (58 mg, 0.21 mmol) and Intermediate 4.2 (80 mg, 0.21 mmol) analogously to the preparation of Intermediate 2.3. white amorphous; ES-MS: M+H=647; HPLC: $_A t_{Ret}$=5.00 min.

Intermediate 289.2

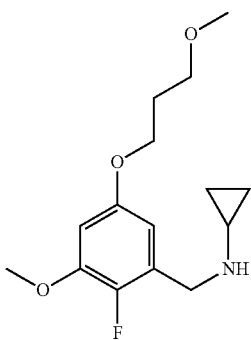

To a mixture of Intermediate 289.3 (500 mg, 2.9 mmol), toluene-4-sulfonic acid 3-methoxy-propyl ester (1.4 g, 6 mmol) and KI (166 mg, 1 mmol) in DMF (10 mL) are added $K_2CO_3$ (830 mg, 6 mmol). After stirring at 80° C. for 4 h, the reaction mixture is cool down at room temperature, then supplemented with $H_2O$ and extracted with $Et_2O$. The combined organic phases are washed with $H_2O$ and brine, dried ($Na_2SO_4$), and concentrated under reduced pressure.

To a solution of the resulting residue in $CH_2Cl_2$/MeOH (4/1, 10 mL) are added cyclopropylamine (660 mg, 11.6 mmol) and acetic acid (1.2 mL, 20.3 mmol). After stirring for 1 h at room temperature, sodium borohydride (380 mg, 10 mmol) are added. After stirring for 19 h, the resulting mixture is added $H_2O$, extracted with $CH_2Cl_2$ and washed with $H_2O$ and brine. The organic layer is dried ($Na_2SO_4$) and silica gel flash chromatography give Intermediate 289.2 as a yellow oil; ES-MS: M+H=284; HPLC: $_A t_{Ret}$=2.05 min.

Intermediate 289.3

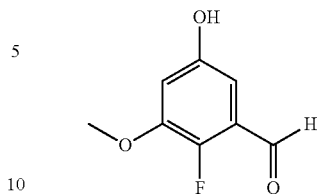

To a solution of Intermediate 289.4 (900 mg, 3.5 mmol) and TMEDA (1.2 mL, 8 mmol) in THF (210 mL) are added n-butyllithium (1.6M in THF, 8 mmol) at −78° C. After stirring for 2 h at −78° C., DMF (5 mL) is added dropwise, then the mixture is warm up to room temperature. After stirring for 2.5 h, the resulting mixture is added aqueous $KHSO_4$, then diluted with $Et_2O$ and washed with $H_2O$ and brine. The organic layer is dried ($Na_2SO_4$), concentrated under reduced pressure. The residue is treated with TBAF (1.0M in THF, 8 mmol) and stirred for 2 h at room temperature. Concentration under reduced pressure and silica gel flash chromatography give Intermediate 289.3 as a colorless oil; ES-MS: M+H=171; HPLC: $_A t_{Ret}$=2.27 min.

Intermediate 289.4

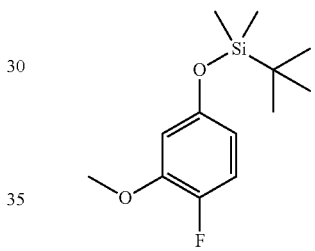

Intermediate 289.4 is synthesized by alkylation of tert-butyl-(4-fluoro-3-methoxyphenoxy)dimethylsilane (1 mg, 4.1 mmol) analogously to the preparation of Intermediate 274.1. colorless oil; ES-MS: M+H=257; HPLC: $_A t_{Ret}$=5.03 min.

Intermediate 290.1

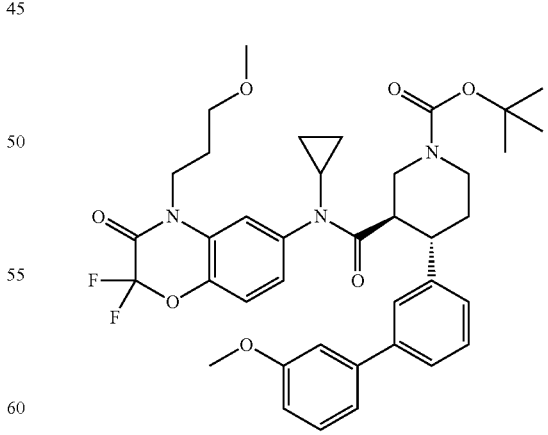

Intermediate 283.1 (44 mg, 0.064 mmol), $K_2CO_3$ (18 mg, 0.128 mmol) and MeI (18 mg, 0.128 mmol) in DMF (1 mL) is stirred at r.t. for 3.5 h. RP-HPLC purification give Intermediate 290.1. White amorphous material; ES-MS: M+H=706, TLC: Rf=0.4 (hexane:EtOAc=1:1).

Intermediate 291.1

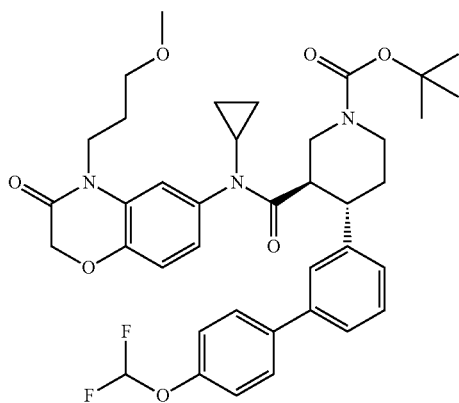

Intermediate 291.1 is synthesized by coupling of Intermediate 205.3 (205 mg, 0.30 mmol) and 4-Difluoromethoxybromobenzene (0.061 mL, 0.45 mmol) analogously to the preparation of Intermediate 187.2; ES-MS: M+H=706; HPLC: $_At_{Ret}$=4.59 min.

Intermediate 292.1

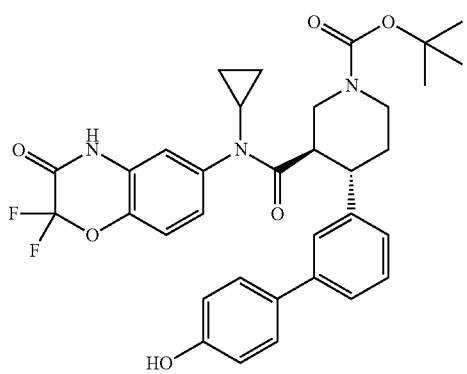

To a solution of Intermediate 292.2 (140 mg, 2.0 mmol) in CH$_3$CN (2 mL) is added 0.2% TFA in H$_2$O (1 mL). After stirring for 3 h, aqueous NaHCO$_3$ is added and extracted with CH$_2$Cl$_2$. The organic layer is washed with brine, dried (Na$_2$SO$_4$), then concentrated. Purification by silica gel column chromatography give intermediate 292.1 as a brown solid; ES-MS: M+H=620; HPLC: $_At_{Ret}$=3.92 min.

Intermediate 292.2

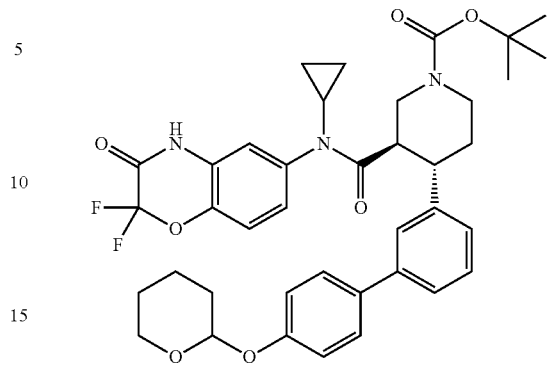

Intermediate 292.2 is synthesized by coupling of Intermediate 292.3 (140 mg, 0.21 mmol) and 4-tetrahydropiranyloxybenzeneboronic acid (69 mg, 0.31 mmol) analogously to the preparation of Intermediate 2.1; ES-MS: M+H=704; HPLC: $_At_{Ret}$=4.97 min.

Intermediate 292.3

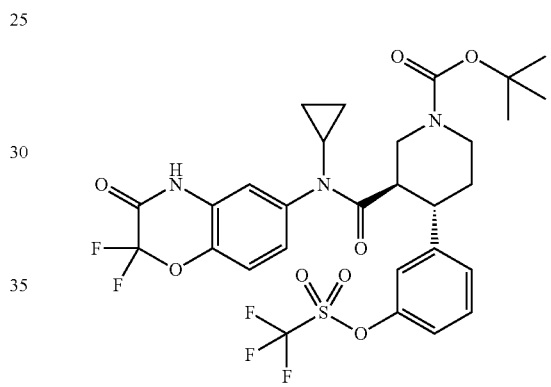

To a solution of Intermediate 292.4 and pyridine (0.2 mL) is added trifluoro methanesulfonyl anhydride (75.5 mg, 0.26 mmol) at −40° C., then the mixture is warmed up to room temperature. After stirring for 1 h, H$_2$O is added and extracted with EtOAc. The organic layer is washed with brine, dried (Na$_2$SO$_4$), then concentrated. Purification by silica gel column chromatography give Intermediate 292.3 as a brown amorphous: M+H=676; HPLC: $_At_{Ret}$=4.45 min.

Intermediate 292.4

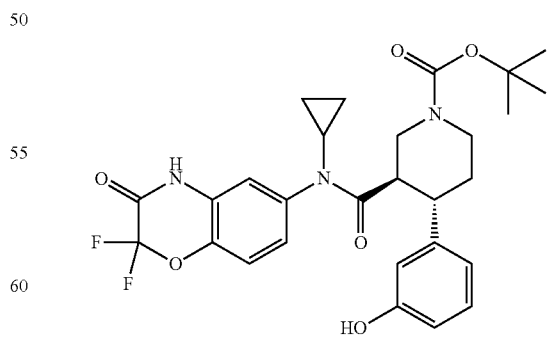

Intermediate 292.4 is synthesized by hydrolysis of the crude material of Intermediate 292.5 analogously to the preparation of Intermediate 145.3. White amorphous material; ES-MS: M+H=544; HPLC: $_At_{Ret}$=3.57 min.

Intermediate 292.5

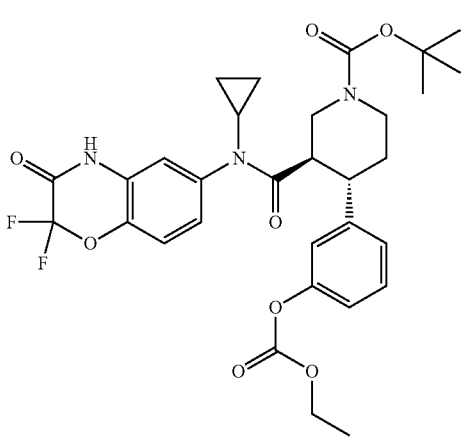

Intermediate 292.5 is synthesized by condensation of Intermediate 158.4 (170 mg, 0.55 mmol) and Intermediate 149.3 (180 mg, 0.55 mmol) analogously to the preparation of Intermediate 145.4. amorphous material; ES-MS: M+H=644; HPLC: $_At_{Ret}$=4.60 min.

Intermediate 293.1

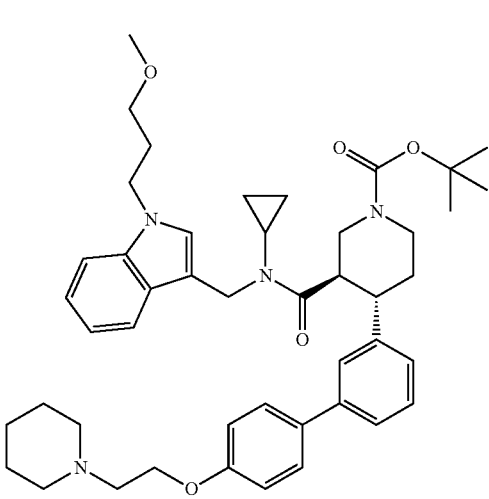

Intermediate 293.1 is synthesized by Mitsunobu reaction of Intermediate 161.2 (200 mg, 0.353 mmol) and 1-piperidineethanol (0.59 mg, 0.46 mmol) analogously to the preparation of Intermediate 77.1 white amorphous; ES-MS: M+H=749; HPLC: $_At_{Ret}$=4.02 min.

Intermediate 294.1

A solution of Intermediate 294.2 (180 mg, 0.25 mmol), 5-bromo-2-fluorophenol (97 mg, 0.51 mmol), Pd(dppf)$_2$Cl$_2$—CH$_2$Cl$_2$ (10.4 mg, 0.013 mmol) and 2M Na$_2$CO$_3$ aq (0.51 mL, 1.02 mmol) in DMF (1 mL) is stirred at 85° C. for 1 h. After cool to r.t., the reaction mixture is extracted with EtOAc and the combined organic phases are washed with brine, dried (MgSO$_4$). Concentration under reduced pressure and RP-HPLC purification gives Intermediate 294.1. White amorphous material; ES-MS: M+H=690; HPLC: $_At_{Ret}$=4.15 min.

Intermediate 294.2

A solution of intermediate 267.2 (600 mg, 0.824 mmol), Bis(pinacolato)diboron (418 mg, 1.65 mmol), Pd(dppf)$_2$Cl$_2$—CH$_2$Cl$_2$ (67 mg, 0.082 mmol) and AcOK (243 mg, 2.47 mmol) in DMSO (3 mL) is stirred at 80° C. for 5 h. After cool to r.t., the reaction mixture is extracted with EtOAc and the combined organic phases are washed with water, brine and dried (MgSO$_4$). Concentration under reduced pressure and Silicagel column chromatography gives Intermediate 294.2. White amorphous material; ES-MS: M+H=706; HPLC: $_At_{Ret}$=4.89 min.

Intermediate 295.1

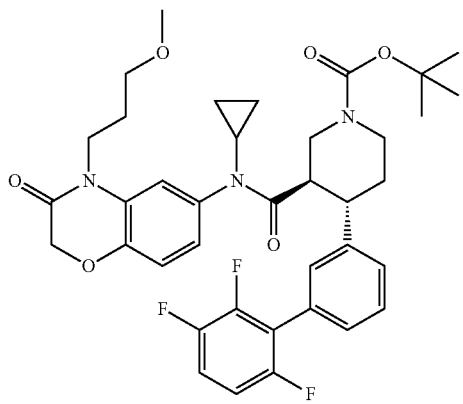

Intermediate 295.1 is synthesized by condensation of intermediate 205.3 (160 mg, 0.232 mmol) and Intermediate 295.2 (130 mg, 0.46 mmol) analogously to the preparation of Intermediate 294.1. White amorphous material; ES-MS: M+H=694; HPLC: $_At_{Ret}$=4.57 min.

Intermediate 295.2

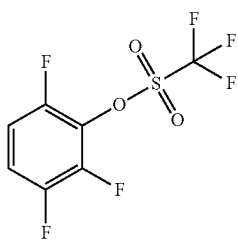

A solution of 2,3,6-trifluorophenol (300 mg, 2.03 mmol), trifluoromethanesulfonyl anhydride (1.14 g, 4.05 mmol) and Pyridine (807 mg, 10.2 mmol) in CH$_2$Cl$_2$ (3 mL) is stirred at −10° C. for 1 h. The reaction mixture is extracted with CH$_2$Cl$_2$ and the combined organic phases are washed with 1M HCl aq, brine and dried (MgSO$_4$). Concentration under reduced pressure and Silica gel column chromatography gives Intermediate 295.2 Colorless oil; HPLC: $_At_{Ret}$=4.07 min, TLC: Rf=0.7 (hexane:EtOAc=2:1).

Intermediate 296.1

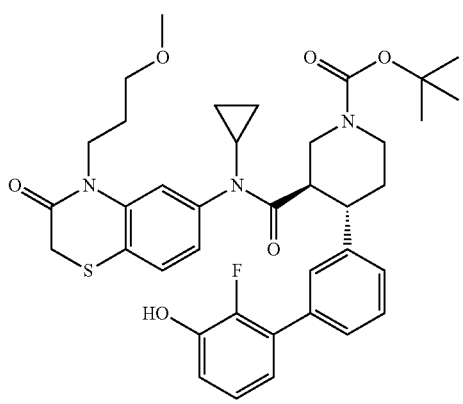

Intermediate 296.1 is synthesized by condensation of intermediate 294.2 (200 mg, 0.28 mmol) and intermediate 277.2 (135 mg, 0.57 mmol) analogously to the preparation of Intermediate 294.1. White amorphous material; ES-MS: M+H=690; HPLC: $_At_{Ret}$=4.07 min.

Intermediate 297.1

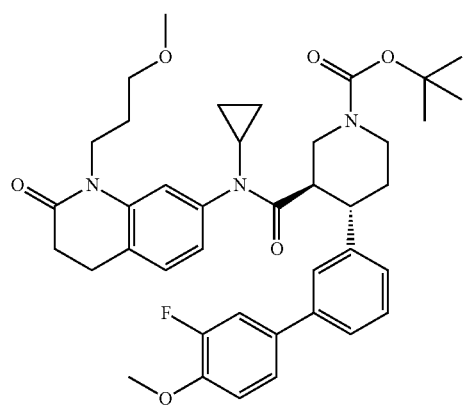

Intermediate 297.1 is synthesized by the Suzuki coupling of Intermediate 297.2 (200 mg, 0.28 mmol) and 3-fluoro-4-methoxyphenylboronic acid (72 mg, 0.42 mmol) analogously to the preparation of Intermediate 266.1. White amorphous material; ES-MS: M+H=686; HPLC: $_At_{Ret}$=4.40 min.

Intermediate 297.2

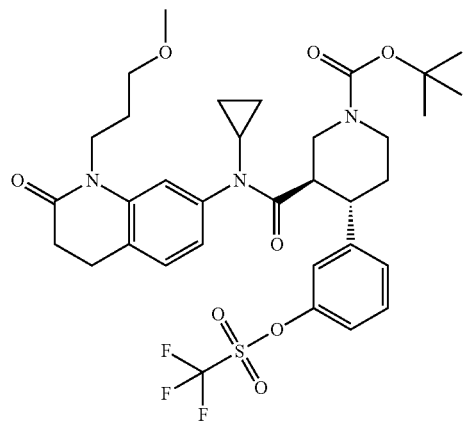

To a solution of Intermediate 297.3 (450 mg, 0.78 mmol) in dichloromethane (4 ml) is added N,N-diisopropylethylamine (252 mg, 1.95 mmol) and trifluoromethanesulfonyl anhydride (262 mg, 0.93 mmol) at −78° C. then stirred for 1 h. After adding water, the reaction mixture is extracted with dichloromethane. The combined organic phases are washed with brine and dried (MgSO$_4$). Concentration under reduced pressure and silica gel flash chromatography gives Intermediate 297.2: White amorphous material; ES-MS: M+H= 710: $_At_{Ret}$=4.37 min.

Intermediate 297.3

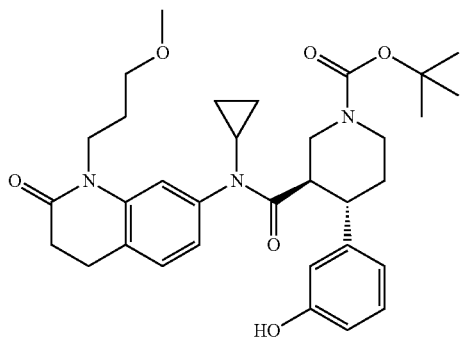

Intermediate 297.3 is synthesized by condensation of intermediate 158.4 (446 mg, 1.39 mmol) and Intermediate 262.2 (400 mg, 1.46 mmol) analogously to the preparation of Intermediate 145.4. White amorphous material; ES-MS: M+H=578; HPLC: $_At_{Ret}$=3.40 min.

Intermediate 298.1

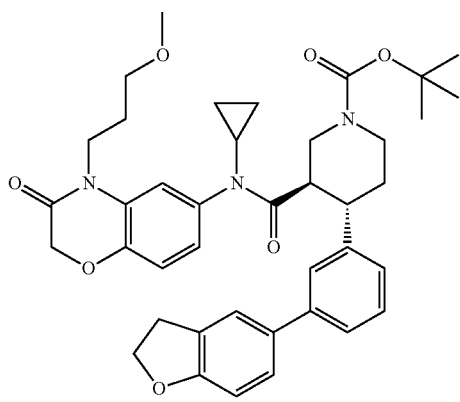

Intermediate 298.1 is synthesized by coupling of Intermediate 181.3 (197 mg, 0.28 mmol) and 2,3-Dihydro-1-benzofuran-5-ylboronic acid (68 mg, 0.41 mmol) analogously to the preparation of Intermediate 214.1. White amorphous material; ES-MS: M+H=682; HPLC: $_At_{Ret}$=4.52 min.

Intermediate 299.1

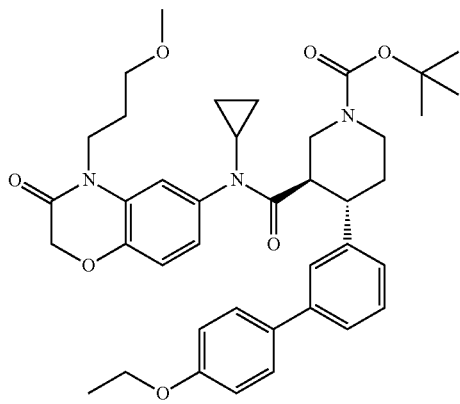

Intermediate 299.1 is synthesized by coupling of Intermediate 181.3 (206 mg, 0.29 mmol) and 4-Ethoxybenzeneboronic acid (72 mg, 0.43 mmol) analogously to the preparation of Intermediate 214.1. White amorphous material; ES-MS: M+H=684; HPLC: $_At_{Ret}$=4.77 min.

Intermediate 300.1

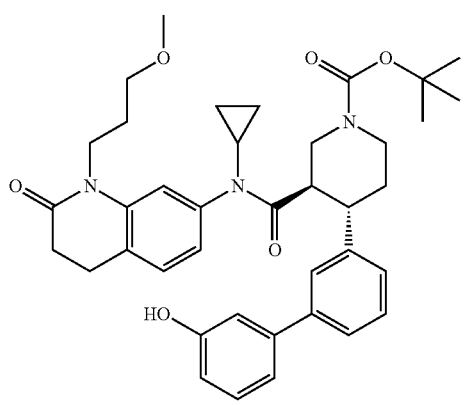

Intermediate 300.1 is synthesized by Suzuki coupling of Intermediate 297.2 (220 mg, 0.31 mmol) and 3-hydroxyphenylboronic acid (64 mg, 0.46 mmol) analogously to the preparation of Intermediate 2.1. White amorphous material; ES-MS: M+H=654; HPLC: $_At_{Ret}$=3.87 min.

Intermediate 301.1

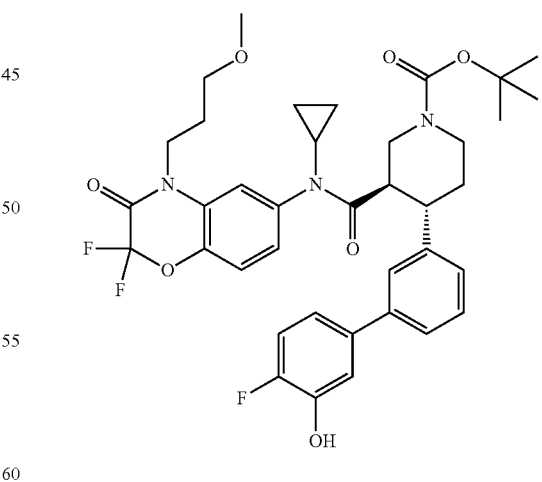

Intermediate 301.1 is synthesized by coupling of Intermediate 301.2 (95 mg, 0.13 mmol) and 5-bromo-2-fluorophenol (38 mg, 0.20 mmol) analogously to the preparation of Intermediate 187.2; ES-MS: M+H=710; HPLC: $_At_{Ret}$=4.42 min.

Intermediate 301.2

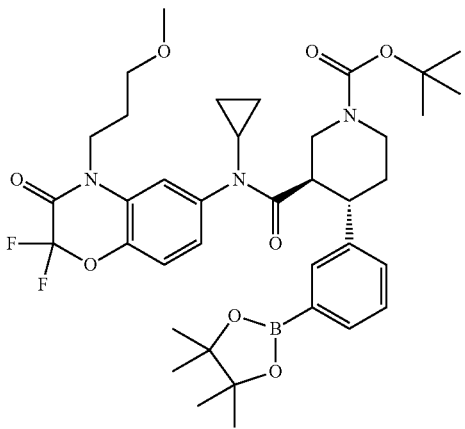

Intermediate 301.2 is synthesized by coupling of Intermediate 250.2 (141 mg, 0.19 mmol) and Bis(pinacolato)diboron (96 mg, 0.38 mmol) analogously to the preparation of Intermediate 187.2; ES-MS: M+H=726; HPLC: $_A t_{Ret}$=5.14 min.

Intermediate 302.1

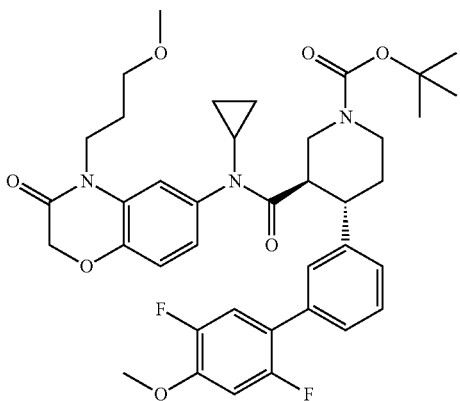

Intermediate 302.1 is synthesized by coupling of Intermediate 205.3 (206 mg, 0.30 mmol) and 2,5-Difluoro-4-methoxybenzeneboronic acid (100 mg, 0.45 mmol) analogously to the preparation of Intermediate 187.2; ES-MS: M+H=706; HPLC: $_A t_{Ret}$=4.57 min.

Intermediate 303.1 (=250.3)

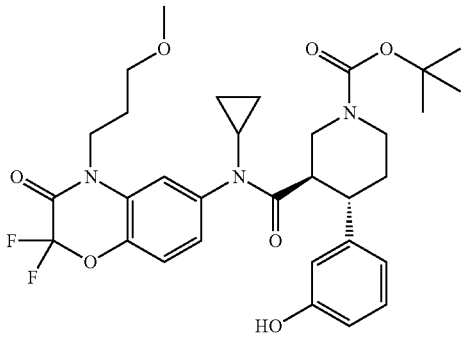

Intermediate 250.3 is synthesized by condensation of Intermediate 149.2 (1.6 g, 5.12 mmol) and intermediate 158.4 (1.8 g, 5.63 mmol) analogously to the preparation of Intermediate 145.4. White amorphous material; ES-MS: M+H=616; HPLC: $_C t_{Ret}$=2.04 min.

Intermediate 304.1

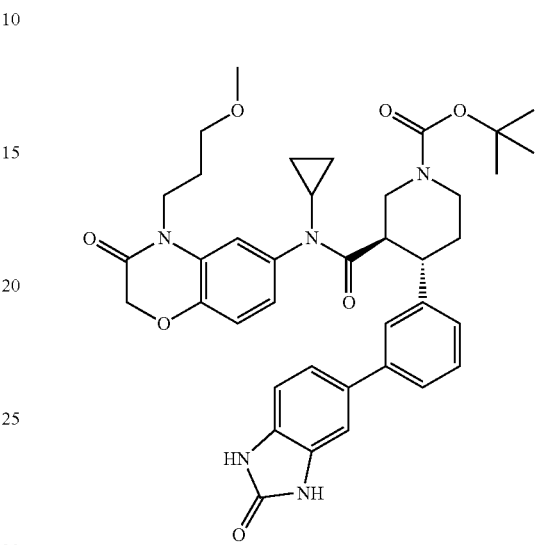

A solution of Intermediate 304.2 in AcOH (2 mL) are stirred at 155° C. for 5 h. then, the reaction is quenched with saturated aqueous NaHCO₃ and extracted with AcOEt. The combined organic phases are washed with H₂O and dried (MgSO₄) to give Intermediate 304.1 as a solid; ES-MS: M⁺=696: $_A t_{Ret}$=3.38 min.

Intermediate 304.2

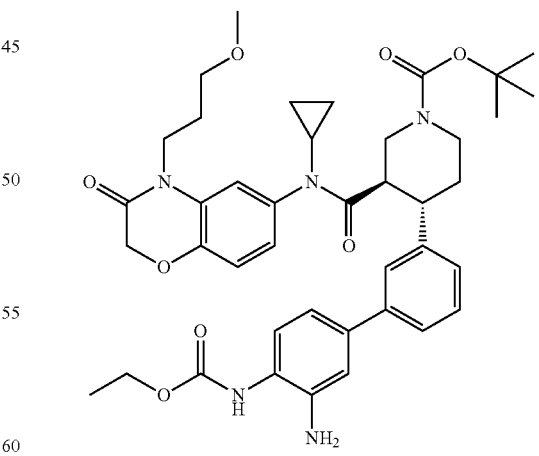

Intermediate 304.2 is synthesized by reduction of Intermediate 304.3 (80 mg, 0.10 mmol) analogously to the preparation of Intermediate 134.1. Led amorphous material; ES-MS: M+=742; HPLC: $_A t_{Ret}$=3.45 min.

Intermediate 304.3

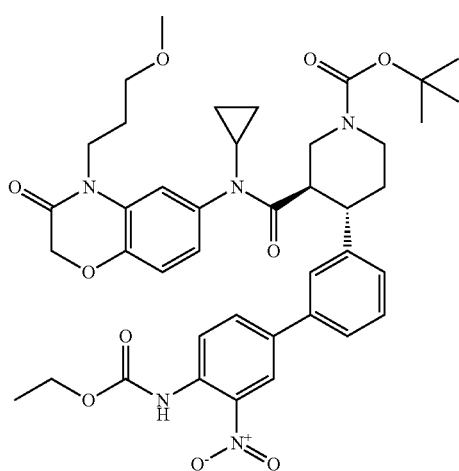

Intermediate 304.3 is synthesized by coupling of Intermediate 205.3 (80 mg, 0.12 mmol) and (4-bromo-2-nitrophenyl)-arbamic acid ethyl ester (50 mg, 0.174 mmol) (see e.g. Zhurnal Analiticheskoi Khimii 1987, 42, 2043-2047.) analogously to the preparation of Intermediate 175.1. amorphous material; ES-MS: M+H=772; HPLC: $_A t_{Ret}$=4.74 min.

Intermediate 305.1

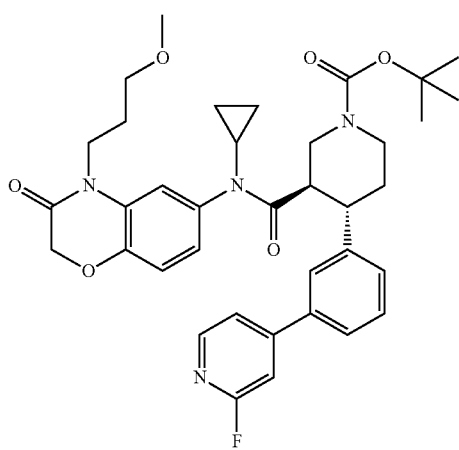

Intermediate 305.1 is synthesized by cross coupling of Intermediate 181.3 (57 mg, 0.08 mmol) and 2-fluoropyridine-4-boronic acid (23 mg, 0.16 mmol) analogously to the preparation of Intermediate 2.1. Pale yellow oil; ES-MS: M+H=659; HPLC: $_A t_{Ret}$=2.23 min.

Intermediate 306.1

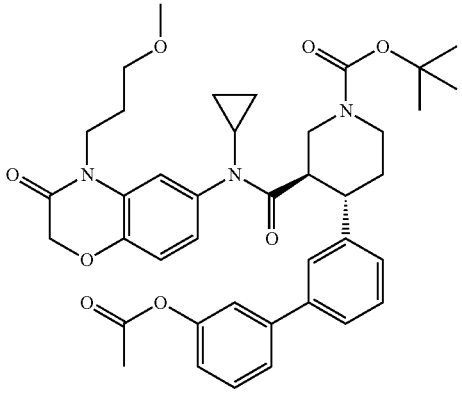

To a solution of Intermediate 217.1 (100 mg, 0.15 mmol) are added pyridine (500 mg), and acetic anhydride (100 mg) at 0° C. After stirring for 16 h at room temperature, H₂O is added and the mixture is extracted with EtOAc. The organic layer is washed with H₂O and brine, dried (Na₂SO₄), then concentrated. Purification by silica gel column chromatography gives Intermediate 306.1 as a white amorphous; ES-MS: M+H=698; HPLC: $_A t_{Ret}$=4.32 min.

Intermediate 307.1

Intermediate 307.1 is synthesized by hydrolysis of Intermediate 307.2 (140 mg, 0.18 mmol) analogously to the preparation of Intermediate 292.1; ES-MS: M+H=700; HPLC: $_A t_{Ret}$=3.87 min.

Intermediate 307.2

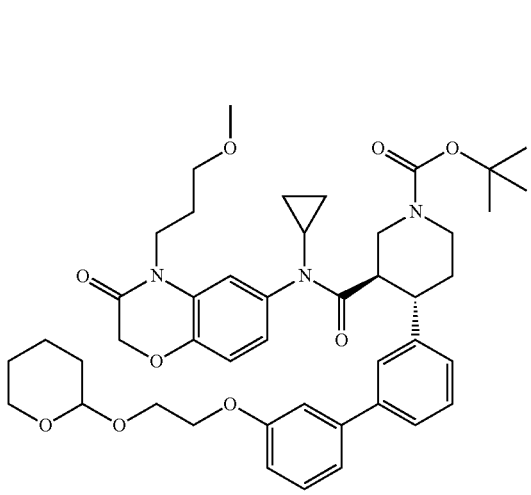

To a solution of Intermediate 217.1 (120 mg, 0.18 mmol) in DMF (2 mL) are added 2-(2-bromoethoxy) tetrahydropyran (76 mg, 0.36 mmol) and $K_2CO_3$ (50 mg, 0.36 mmol). After stirring for 16 h at 50° C., $H_2O$ is added and extracted with EtOAc. The organic layer is washed with $H_2O$ and brine, dried ($Na_2SO_4$), then concentrated. Purification by silica gel column chromatography give Intermediate 307.2 as a white amorphous; ES-MS: M+H=784; HPLC: $_At_{Ret}$=4.87 min.

Intermediate 308.1

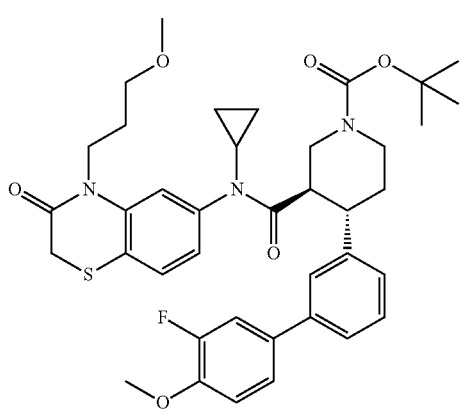

Intermediate 308.1 is synthesized by coupling of intermediate 267.2 (150 mg, 0.21 mmol) and 3-fluoro-4-methoxybenzeneboronic acid (53 mg, 0.32 mmol) analogously to the preparation of Intermediate 2.1; ES-MS: M+H=704; HPLC: $_At_{Ret}$=4.62 min.

Intermediate 309.1

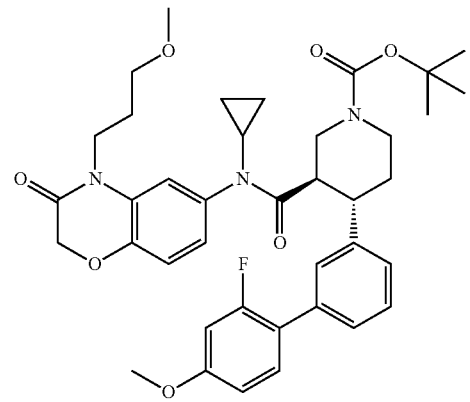

Intermediate 309.1 is synthesized by coupling reaction of Intermediate 205.3 (120 mg, 0.17 mmol) and 3-fluoro-4-bromoanisole (54 mg, 0.26 mmol) analogously to the preparation of Intermediate 2.1. White amorphous; ES-MS: M+H=688; HPLC: $_At_{Ret}$=4.60 min.

Intermediate 310.1

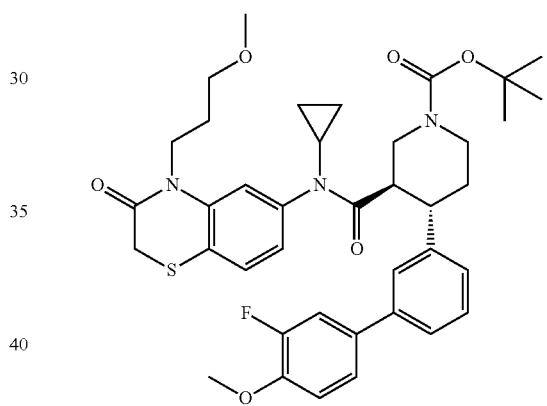

Intermediate 310.1 is synthesized by coupling reaction of Intermediate 267.2 (150 mg, 0.21 mmol) and 4-propoxybenzeneboronic acid (57 mg, 0.32 mmol) analogously to the preparation of Intermediate 2.1. White amorphous; ES-MS: M+H=698; HPLC: $_At_{Ret}$=5.07 min Intermediate 311.1

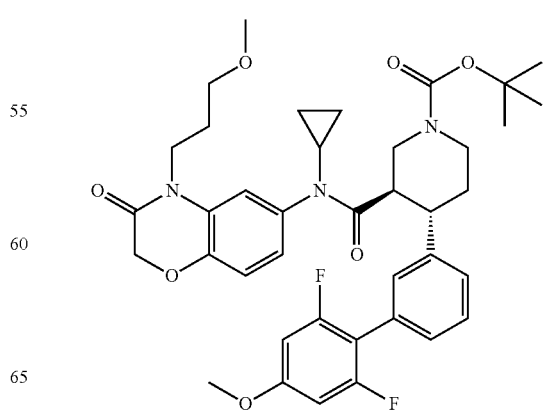

Intermediate 311.1 is synthesized by coupling of Intermediate 205.3 (196 mg, 0.28 mmol) and 2,6-Difluoro-4-methoxybenzeneboronic acid (95 mg, 0.43 mmol) analogously to the preparation of Intermediate 187.2; ES-MS: M+H=706; HPLC: $_C t_{Ret}$=2.27 min.

Intermediate 312.1

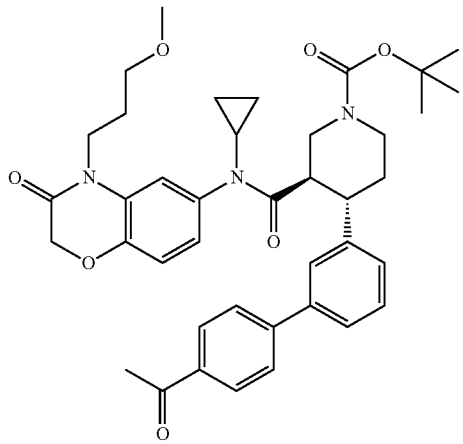

Intermediate 312.1 is synthesized by coupling of Intermediate 181.3 (158 mg, 0.22 mmol) and 4-Acetylbenzeneboronic acid (55 mg, 0.34 mmol) analogously to the preparation of Intermediate 214.1. White amorphous material; ES-MS: M+H=682; HPLC: $_A t_{Ret}$=4.24 min.

Intermediate 313.1

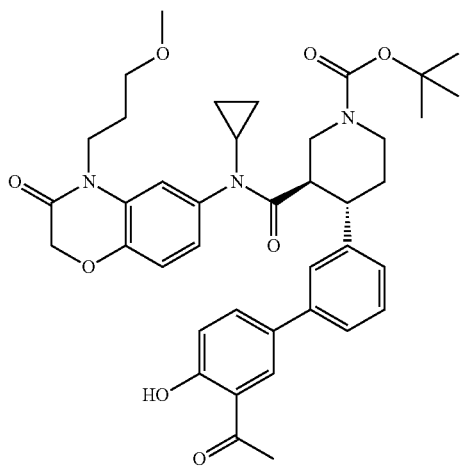

Intermediate 313.1 is synthesized by coupling of Intermediate 205.3 (210 mg, 0.30 mmol) and 5-Bromo-2-hydroxyacetophenone (98 mg, 0.46 mmol) analogously to the preparation of Intermediate 187.2; ES-MS: M+H=698; HPLC: $_C t_{Ret}$=2.18 min.

Intermediate 314.1

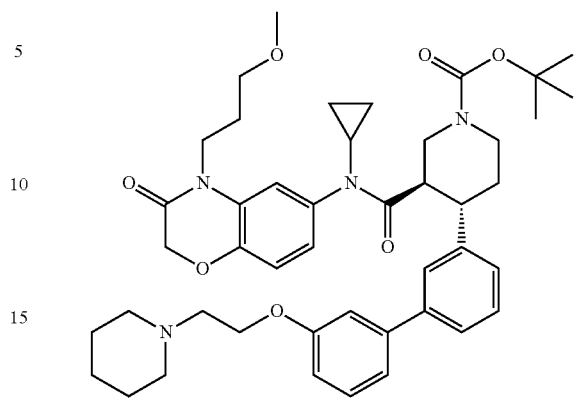

Intermediate 314.1 is synthesized by Mitsunobu reaction of Intermediate 217.1 (60 mg, 0.09 mmol) and 1-piperidineethanol (18 mg, 0.14 mmol) analogously to the preparation of Intermediate 77.1 white amorphous; ES-MS: M+H=767; HPLC: $_A t_{Ret}$=3.40 min.

Intermediate 315.1

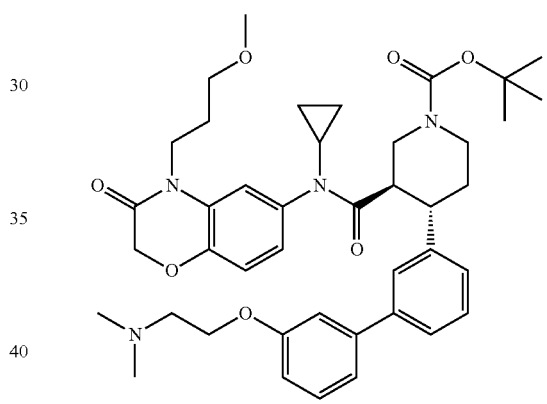

Intermediate 315.1 is synthesized by Mitsunobu reaction of Intermediate 217.1 (60 mg, 0.09 mmol) and 2-dimethylaminoethanol (13 mg, 0.14 mmol) analogously to the preparation of Intermediate 77.1 white amorphous; ES-MS: M+H=727; HPLC: $_A t_{Ret}$=3.23 min.

Intermediate 316.1

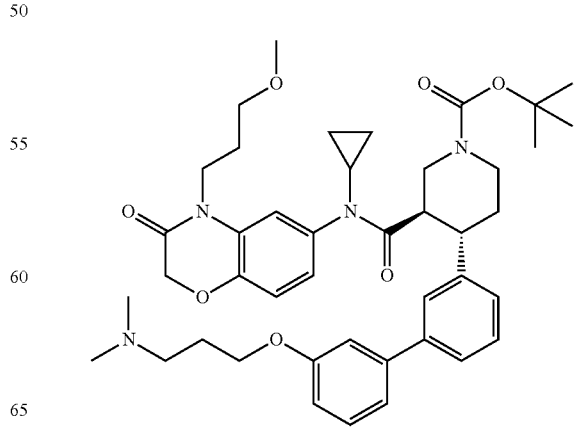

Intermediate 316.1 is synthesized by Mitsunobu reaction of Intermediate 217.1 (60 mg, 0.09 mmol) and 3-dimethylaminopropanol (14 mg, 0.14 mmol) analogously to the preparation of Intermediate 77.1 white amorphous; ES-MS: M+H=741; HPLC: $_A t_{Ret}$=3.29 min.

Intermediate 317.1

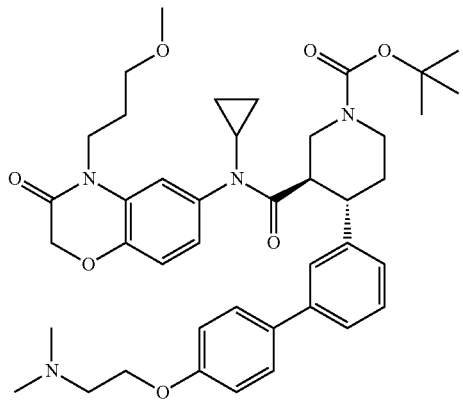

Intermediate 317.1 is synthesized by Mitsunobu reaction of Intermediate 218.1 (60 mg, 0.09 mmol) and 2-dimethylaminoethanol (13 mg, 0.14 mmol) analogously to the preparation of Intermediate 77.1 white amorphous; ES-MS: M+H=727; HPLC: $_A t_{Ret}$=3.20 min.

Intermediate 318.1

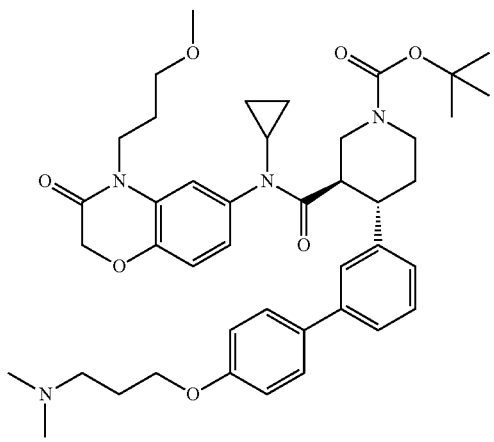

Intermediate 318.1 is synthesized by Mitsunobu reaction of Intermediate 218.1 (60 mg, 0.09 mmol) and 3-dimethylaminopropanol (14 mg, 0.14 mmol) analogously to the preparation of Intermediate 77.1 white amorphous; ES-MS: M+H=741; HPLC: $_A t_{Ret}$=3.30 min.

Intermediate 319.1

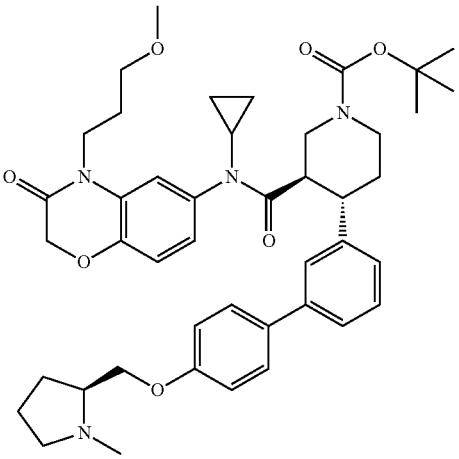

Intermediate 319.1 is synthesized by Mitsunobu reaction of Intermediate 218.1 (30 mg, 0.045 mmol) and N-methylprolinol (9 mg, 0.068 mmol) analogously to the preparation of Intermediate 77.1 white amorphous; ES-MS: M+H=753; HPLC: $_A t_{Ret}$=3.32 min.

Intermediate 320.1

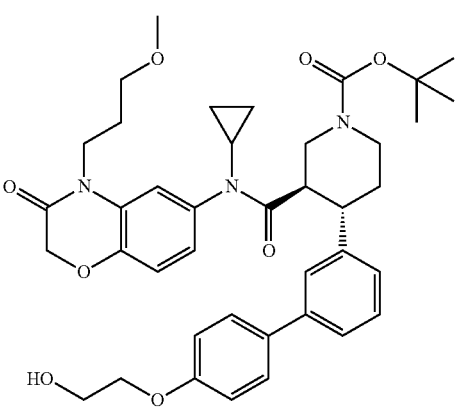

Intermediate 320.1 is synthesized by hydrolysis of Intermediate 320.2 (80 mg, 0.11 mmol) analogously to the preparation of Intermediate 292.1; ES-MS: M+H=700; HPLC: $_A t_{Ret}$=3.82 min.

Intermediate 320.2

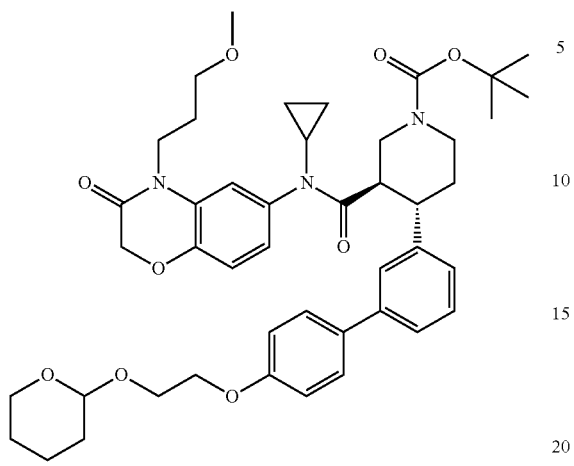

To a solution of Intermediate 218.1 (120 mg, 0.18 mmol) in DMF (2 mL) are added 2-(2-bromoethoxy) tetrahydropyran (76 mg, 0.36 mmol) and K$_2$CO$_3$ (50 mg, 0.36 mmol). After stirring for 16 h at 50° C., H$_2$O is added and the mixture is extracted with EtOAc. The organic layer is washed with H$_2$O and brine, dried (Na$_2$SO$_4$), then concentrated. Purification by silica gel column chromatography gives Intermediate 320.2 as a white amorphous; ES-MS: M+H=784; HPLC: $_A$t$_{Ret}$=4.84 min.

Intermediate 321.1

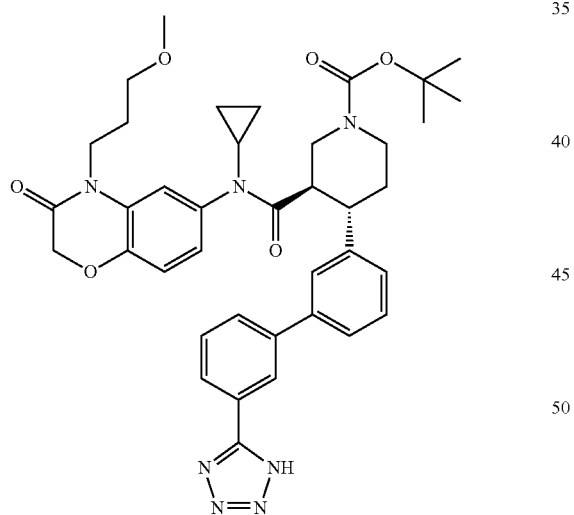

To a solution of Intermediate 215.1 (51 mg, 0.077 mmol) in toluene (1 mL) are added NaN$_3$ (30 mg, 0.46 mmol) and triethylamine hydrochloride (64 mg, 0.47 mmol). After stirred at 120° C. for 63 h, additional NaN$_3$ (40 mg, 0.62 mmol) and triethylamine hydrochloride (70 mg, 0.51 mmol) are added. The reaction mixture is stirred at the same temperature for 12 h, and diluted with EtOAc. The mixture is washed with aq. KHSO$_4$ and brine, dried (Na$_2$SO$_4$), filtered, and concentrated in vacuo. The residue is purified by silica gel column chromatography to give Intermediate 321.1. Colorless oil; ES-MS: M+H=708; HPLC: $_A$t$_{Ret}$=3.88 min.

Intermediate 322.1

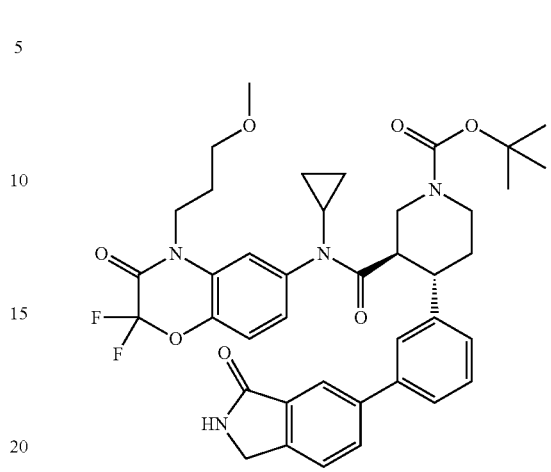

Intermediate 322.1 is synthesized by coupling of Intermediate 250.2 (250 mg, 0.34 mmol) and 5-Iodo-2,3-dihydro-isoindol-1-one (134 mg, 0.52 mmol) (see e.g. US 2004/058970) analogously to the preparation of Intermediate 187.3. White solid; ES-MS: M+1=731; HPLC: $_A$t$_{Ret}$=3.96 min.

Intermediate 323.1

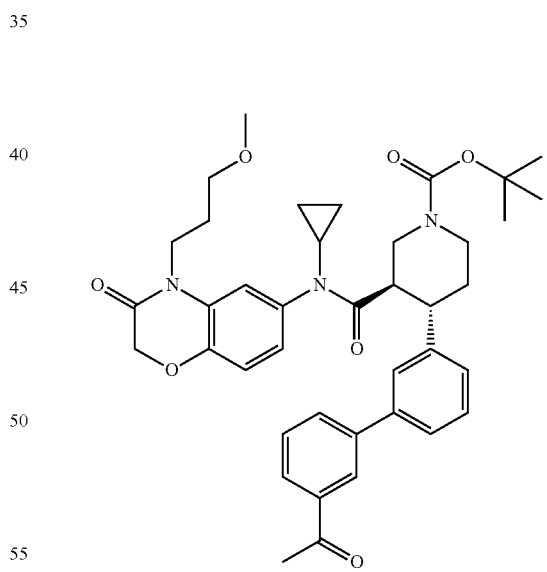

Intermediate 323.1 is synthesized by coupling of Intermediate 181.3 (173 mg, 0.24 mmol) and 3-Acetylbenzeneboronic acid (60 mg, 0.37 mmol) analogously to the preparation of Intermediate 214.1. White amorphous material; ES-MS: M+H=682; HPLC: $_C$t$_{Ret}$=2.16 min.

Intermediate 24.1

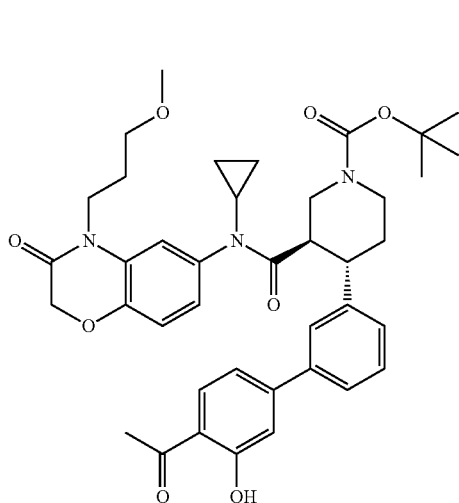

Intermediate 324.1 is synthesized by coupling of Intermediate 205.3 (100 mg, 0.14 mmol) and 4-Bromo-2-hydroxyacetophenone (78 mg, 0.36 mmol) analogously to the preparation of Intermediate 187.2; ES-MS: M+H=698; HPLC: $_Ct_{Ret}$=2.18 min.

Intermediate 325.1

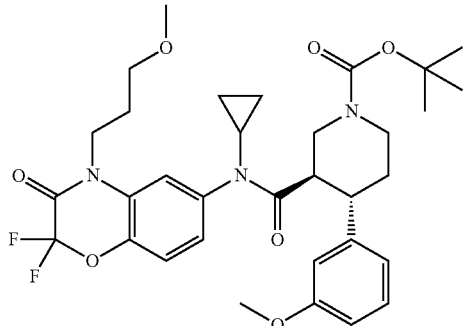

Intermediate 325.1 is synthesized by alkylation of Intermediate 250.3 (120 mg, 0.20 mmol) and MeI (55 mg, 0.39 mmol) analogously to the preparation of Intermediate 126.2. White amorphous material; ES-MS: M+H=630; HPLC: $_At_{Ret}$=4.45 min.

Intermediate 326.1

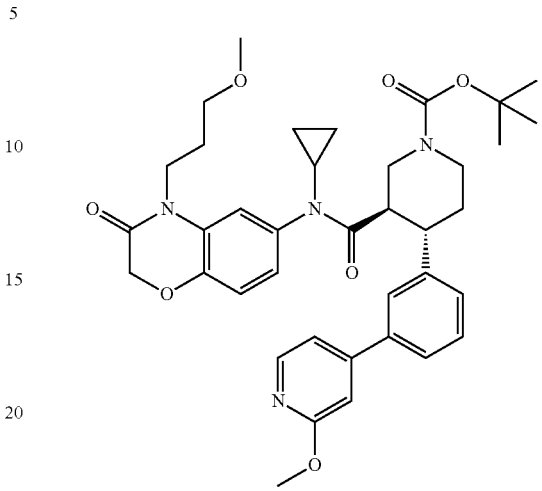

Intermediate 326.2 (74 mg, 0.11 mmol) and NaOMe (0.05 mL, 25 wt % in MeOH) in DMF (2 ML) are stirred at 100° C. for 4 h. After cooling to room temperature, H₂O is added and the resulting solution is extracted with AcOEt. The organic layer is washed with brine, dried (Na₂SO₄) and concentrated. Purification by silica gel column chromatography give Intermediate 326.1 as white amorphous; ES-MS: M+H=671; HPLC: $_At_{Ret}$=3.84 min.

Intermediate 326.2

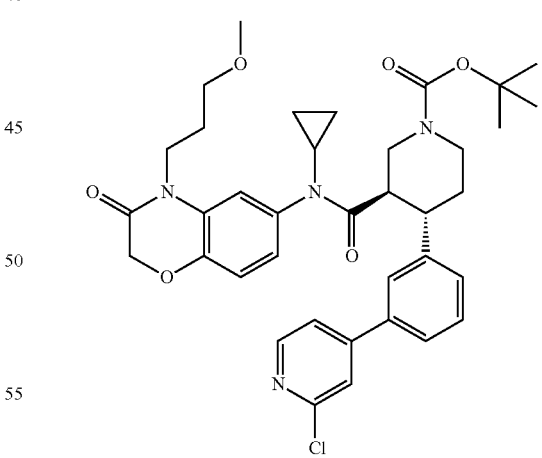

Intermediate 326.2 is synthesized by coupling or Intermediate 205.3 (100 mg, 0.36 mmol) and 2-Chloro-4-iodopyridine (52 mg, 0.22 mmol) analogously to the preparation of Intermediate 187.2; ES-MS: M+H=675; HPLC: $_Ct_{Ret}$=2.11 min.

Intermediate 327.1

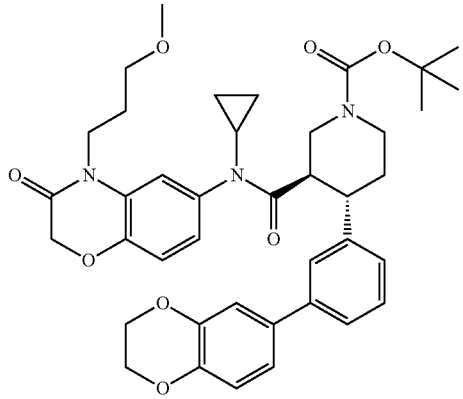

Intermediate 327.1 is synthesized by coupling of Intermediate 205.3 (60 mg, 0.087 mmol) and 6-bromo-1,4-benzodioxane (28 mg, 0.13 mmol) analogously to the preparation of Intermediate 187.2; ES-MS: M+H=698; HPLC: $c_{t_{Ret}}$=2.18 min.

Intermediate 328.1

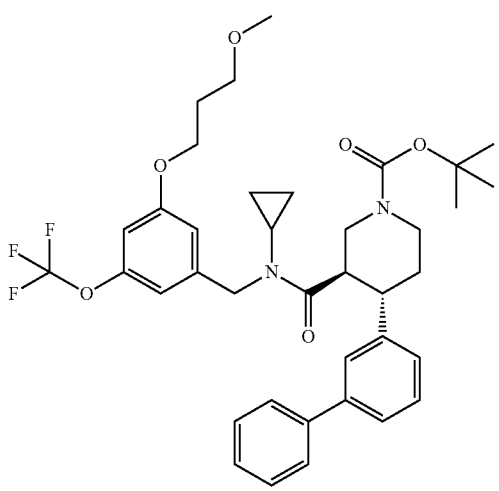

Intermediate 328.1 is synthesized by condensation of Intermediate 75.3 (72 mg, 0.19 mmol) and Intermediate 328.2 (60 mg, 0.19 mmol) analogously to the preparation of Intermediate 4.1. White amorphous material; ES-MS: M+H=683; HPLC: $c_{t_{Ret}}$=2.47 min.

Intermediate 328.2

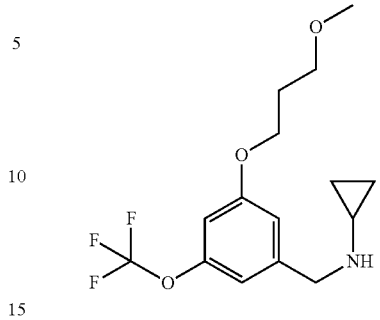

Intermediate 328.2 is synthesized by condensation of Intermediate 328.3 (340 g, 1.22 mmol) and cyclopropylamine (140 mg, 2.4 mmol) analogously to the preparation of Intermediate 4.5. Colorless oil; ES-MS: M+H=320; HPLC: $c_{t_{Ret}}$=1.56 min.

Intermediate 328.3

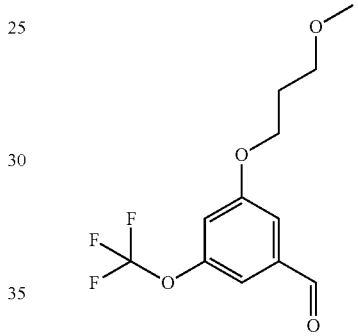

To a solution of Intermediate 328.4 (550 mg, 1.7 mmol) in Et$_2$O (3 mL) are added n-BuLi (1.3 mL, 1.6 M hexane solution) and DMF (190 mg, 2.6 mmol) at −78° C. under N$_2$ atmosphere. After stirring at −78° C. for 1 h, the reaction is quenched with sat. aqueous NH$_4$Cl. The resulting mixture is allowed to warm to room temperature and extracted with AcOEt. The organic layer is washed with H$_2$O and brine, dried (Na$_2$SO$_4$) and concentrated. The residue is purified by silica gel column chromatography to give Intermediate 328.3 as colorless oil; ES-MS: M+H=279; HPLC: $c_{t_{Ret}}$=1.97 min.

Intermediate 328.4

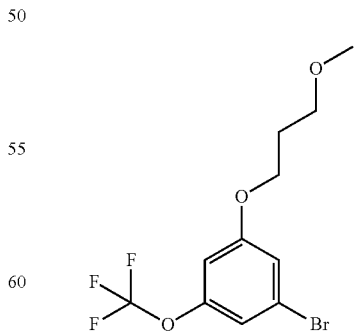

To a solution of 1,3-Dibromo-5-trifluoromethoxybenzene (200 mg, 0.63 mmol) in Et$_2$O (3 mL) is added n-BuLi (0.75 mL, 1.6M hexane solution) at −78° C. under N$_2$ atmosphere. After stirring for 10 min., (MeO)$_3$B (98 mg, 0.95 mmol) is added at −78° C. The reaction mixture is allowed to warm to room temperature and stirred for 4 h. The reaction was quenched with 1N HCl, and the resulting mixture is extracted with AcOEt. The organic layer is washed with H₂O, dried (Na₂SO₄) and concentrated. The residue is dissolved in EtOH (3 mL) and H₂O₂ solution (3 mL). After stirring at room temperature for 14 h, Na₂S₂O₃ is added, and the resulting mixture is extracted with AcOEt. The organic layer is washed with H₂O, dried (Na₂SO₄) and concentrated. To a solution of the resulting residue (600 mg, 2.3 mmol) in DMF (5 mL) are added Toluene-4-sulfonic acid 3-methoxypropyl ester (852 mg, 3.5 mmol), K₂CO₃ (480 mg, 3.5 mmol) and a small portion of KI. After stirring at 60° C. for 7 h, the reaction mixture is cooled to room temperature and diluted with H₂O and AcOEt. The organic layer is separated, dried (Na₂SO₄) and concentrated. The residue is purified by silica gel column chromatography to give Intermediate 328.4 as colorless oil; ES-MS: M+=329; HPLC: $_c t_{Ret}$=2.34 min.

Intermediate 329.1

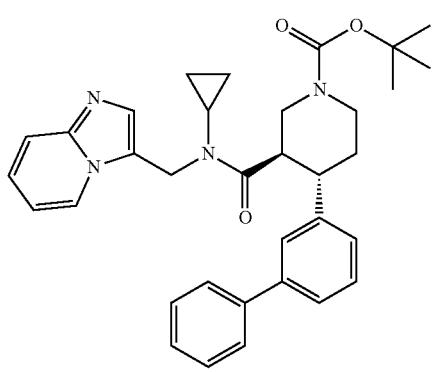

Intermediate 329.1 is synthesized by condensation of Intermediate 75.3 (60 mg, 0.16 mmol) and Intermediate 329.2 (30 mg, 0.16 mmol) analogously to the preparation of Intermediate 2.3. White amorphous; ES-MS: M+H=551; HPLC: $_A t_{Ret}$=3.27 min.

Intermediate 329.2

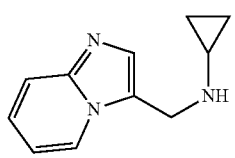

Intermediate 329.2 is synthesized by condensation of imidazo[1,2-a]pyridine-3-carbaldehyde (1 g, 6.9 mmol) and cyclopropylamine (1.2 mg, 20 mmol) analogously to the preparation of Intermediate 4.5. brown solid; ES-MS: M+H=188; HPLC: $_A t_{Ret}$=0.48 min.

Intermediate 330.1

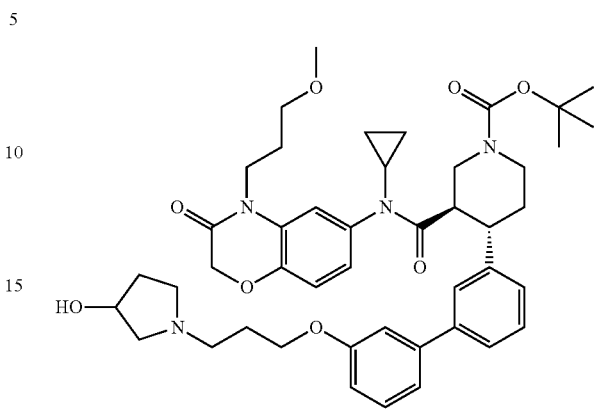

To a solution of Intermediate 330.2 (80 mg, 0.11 mmol) in DMF (1 mL) are added 3-hydroxypyrrolidine (27 mg, 0.22 mmol), K₂CO₃ (61 mg, 0.44 mmol) and KI (20 mg, 0.12 mmol), then the mixture is stirred for 3 h at 80° C. After cooling to room temperature, the reaction mixture is diluted with EtOAc and washed with brine. The organic layer is dried (Na₂SO₄), concentrated and purified by RP-HPLC to give Intermediate 330.1. White amorphous; ES-MS: M+1=783; HPLC: $_A t_{Ret}$=3.29 min.

Intermediate 330.2

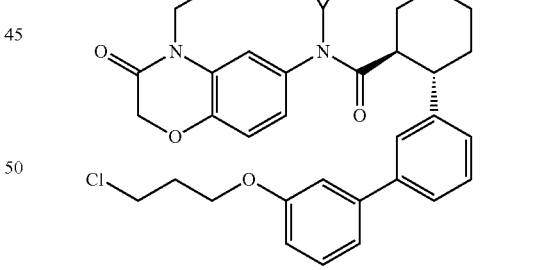

To a solution of Intermediate 217.1 (200 mg, 0.28 mmol) in DMF (1 mL) are added 3-iodo-1-chloropropane (112 mg, 0.55 mmol) and K₂CO₃ (76 mg, 0.55 mmol), then the mixture is stirred at room temperature. After stirring for 15 h, the reaction mixture is diluted with EtOAc and washed with brine. The organic layer is dried (Na₂SO₄), concentrated and purified by silica gel column chromatography to give Intermediate 330.2. White amorphous; ES-MS: M+1=732; HPLC: $_A t_{Ret}$=4.95 min.

Intermediate 331.1

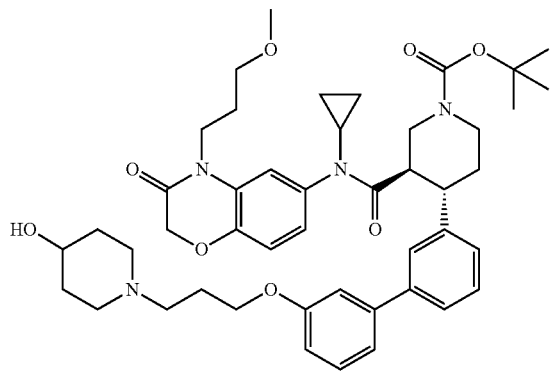

Intermediate 331.1 is synthesized by alkylation of Intermediate 330.2 (80 mg, 0.11 mmol) analogously to the preparation of Intermediate 330.1. White amorphous; ES-MS: M+H=797; HPLC: $_A t_{Ret}$=3.25 min.

Intermediate 332.1

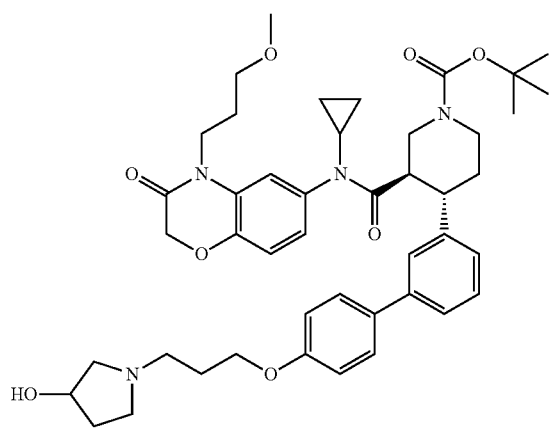

Intermediate 332.1 is synthesized by alkylation of Intermediate 332.2 (80 mg, 0.11 mmol) analogously to the preparation of Intermediate 330.1. White amorphous; ES-MS: M+H=783; HPLC: $_A t_{Ret}$=3.25 min.

Intermediate 332.2

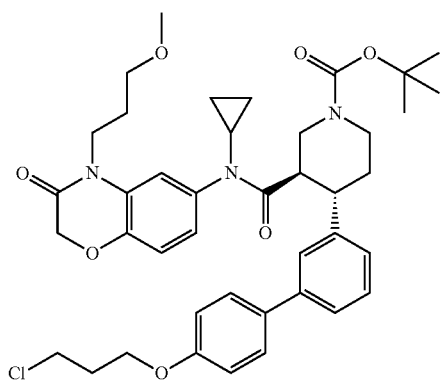

Intermediate 332.2 is synthesized by alkylation of Intermediate 218.1 (200 mg, 0.28 mmol) analogously to the preparation of Intermediate 330.2. White amorphous; ES-MS: M+H=732; HPLC: $_A t_{Ret}$=4.93 min.

Intermediate 333.1

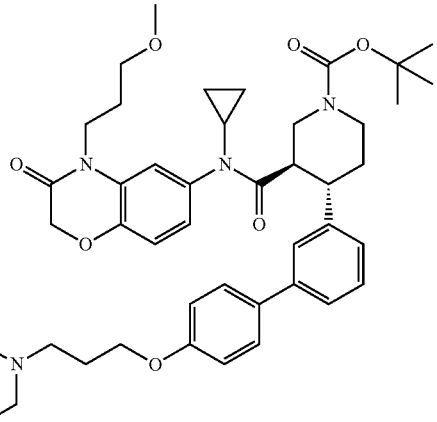

Intermediate 333.1 is synthesized by alkylation of Intermediate 332.2 (80 mg, 0.11 mmol) analogously to the preparation of Intermediate 330.1. White amorphous; ES-MS: M+H=797; HPLC: $_A t_{Ret}$=3.23 min.

Intermediate 334.1

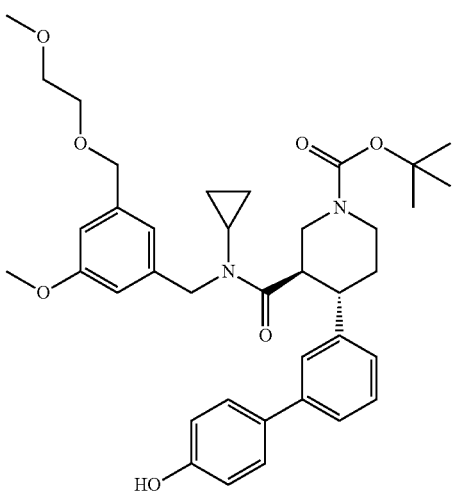

Intermediate 334.1 is synthesized by coupling of Intermediate 334.2 (600 mg, 0.86 mmol) and 4-hydroxyphenylboronic acid (236 mg, 1.71 mmol) analogously to the preparation of Intermediate 2.1. White amorphous; ES-MS: M+H=645; HPLC: $_A t_{Ret}$=4.05 min.

Intermediate 334.2

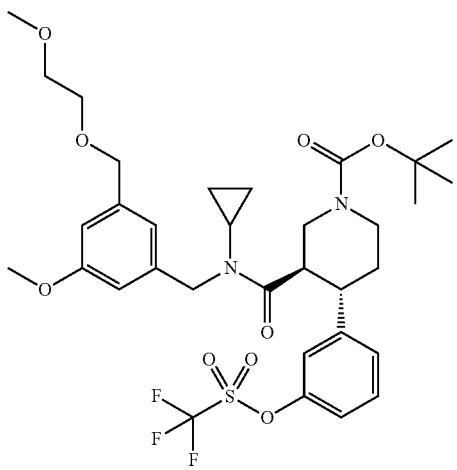

Intermediate 334.2 is synthesized by sulfonylation of Intermediate 334.3 (1.3 g, 2.3 mmol) analogously to the preparation of Intermediate 292.3. White amorphous; ES-MS: M+H=701; HPLC: $_A t_{Ret}$=4.65 min.

Intermediate 334.3

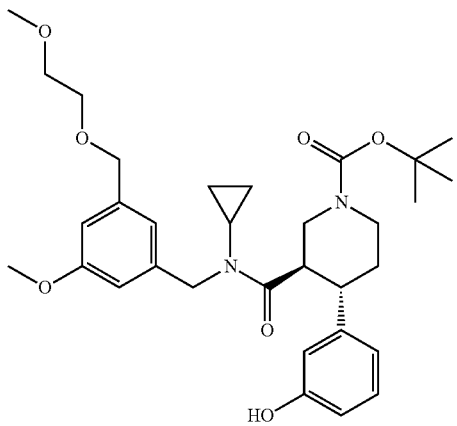

Intermediate 334.3 is synthesized by condensation of Intermediate 158.4 (2 g, 3.1 mmol) and Intermediate 334.4 (822 mg, 3.1 mmol) analogously to the preparation of Intermediate 4.1; ES-MS: M+H=569; HPLC: $_A t_{Ret}$=3.72 min.

Intermediate 334.4

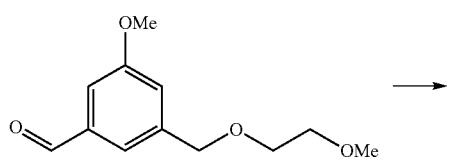

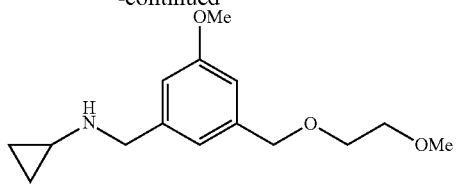

At 0° C., a solution of intermediate 334.5 (10.3 g, 45.9 mmol) and cyclopropylamine (6.4 ml, 91.8 mmol) in CH$_2$Cl$_2$ (150 ml) is treated with NaBH(OAc)$_3$ (14.8 g, 69.8 mmol) over 10 min, treated with AcOH (10 ml) over 5 min, stirred for 30 min, warmed to room temperature, stirred for 13 h, and treated CH$_2$Cl$_2$ (200 ml) and 5N NaOH (100 ml). After the layers are separated, the aqueous layer is extracted with CH$_2$Cl$_2$ (3×60 ml), and the combined organic layer is washed with brine (100 ml), dried (Na$_2$SO$_4$), and evaporated to obtain intermediate 334.4 (12.7 g, 98%) as yellow oil.

Intermediate 334.5

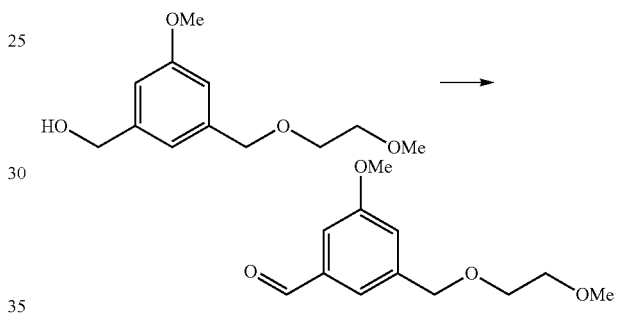

At room temperature, a solution of intermediate 334.6 (12.9 g, 57.0 mmol) in EtOAc (200 ml) is treated with 85% activated MnO$_2$ (18.1 g, 0.18 mol), heated to 60° C., stirred for 4 h under reflux, filtered via celite pad, and the cake is washed with EtOAc for several times. The combined filtrate is evaporated, and the residue is applied to a SiO$_2$ flash chromatography (400 g, hexane/EtOAc 4:5) to give intermediate 334.5 (10.3 g, 80%) as light yellow oil.

Intermediate 334.6

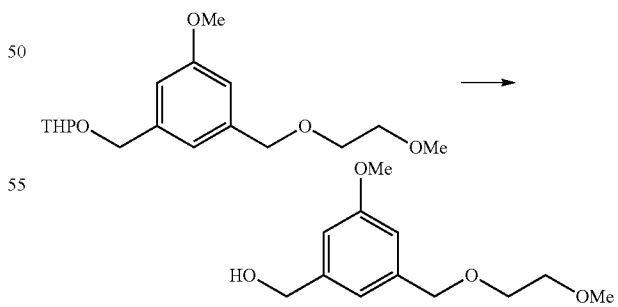

At room temperature, a methanolic solution (420 ml) of intermediate 334.7 (30.6 g, 98.7 mmol) is treated with DL-10-camphorsulfonic acid (2.1 g, 9.4 mmol) stirred for 14 h, treated with Et$_3$N (1.5 ml), and evaporated. A SiO$_2$ flash chromatography (700 g, hexane/EtOAc 2:5) gives intermediate 334.6 (22.0 g, 99%) as light yellow oil.

Intermediate 334.7

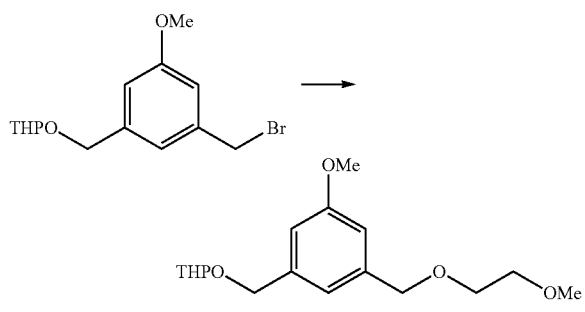

At 0° C., a solution of intermediate 334.8 (31.1 g, 98.7 mmol) and 2-methoxyethanol (12 ml, 0.15 mol) in DMF (460 ml) is treated with 60% NaH (5.89 g, 0.15 mol) over 5 min, stirred for 45 min, warmed to room temperature, stirred for 3 h, and treated with H$_2$O (1200 ml). After the extraction of the mixture with EtOAc (2×250 ml) and Et$_2$O (2×250 ml), the combined org. layer is washed with H$_2$O (2×200 ml), dried (Na$_2$SO$_4$), and evaporated to obtain intermediate 334.7 (33.8 g, 100%) as yellow oil.

Intermediate 334.8

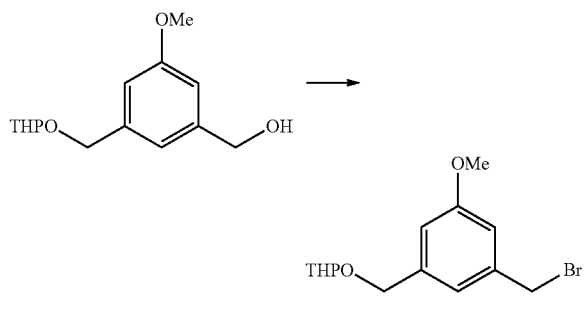

At 0° C., a solution of intermediate 334.9 (74.5 g, 0.30 mol) and Ph$_3$P (124.7 g, 0.48 mol) in CH$_2$Cl$_2$ (750 ml) is treated with NBS (79.0 g, 0.44 mol) over 20 min, stirred for 2 h at the same temperature, and warmed to room temperature. After stirring for 16 h, the reaction mixture is diluted with CH$_2$Cl$_2$ (1200 ml), washed with 0.5N NaOH (300 ml) and brine (300 ml), dried (Na$_2$SO$_4$), and evaporated. A SiO$_2$ flash chromatography (2700 g, hexane/EtOAc 6:1) gives intermediate 334.8 (31.1 g, 33%) as colorless oil.

Intermediate 334.9

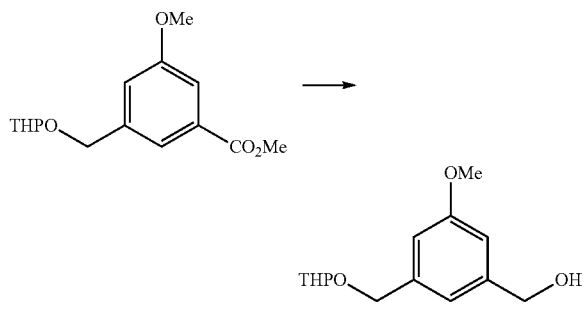

At 0° C., a solution of intermediate 334.10 (82.3 g, 0.29 mol) in THF (820 ml) is treated portionwise with LiAlH$_4$ (8.90 g, 0.23 mol) over 15 min, stirred at the same temperature for 40 min, and warmed to room temperature. After stirring for 6 h, the reaction mixture is treated with Na$_2$SO$_4$.10 H$_2$O, filtered, and evaporated to obtain intermediate 334.9 (74.5 g, 100%) as light yellow oil.

Intermediate 334.10

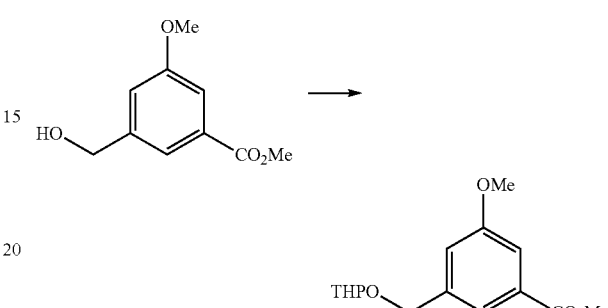

At room temperature, a solution of methyl 3-hydroxymethyl-5-methoxybenzoate (56.4 g, 0.29 mol, Synth. Commn. 2001, 31, 1921.) in CH$_2$Cl$_2$ (680 ml) is treated with DL-10-camphorsulfonic acid (6.6 g, 28.4 mmol) and 3,4-dihydro-2H-pyran (40 ml, 0.43 mol), stirred for 5.5 h, treated with Et$_3$N (40 ml), and evaporated. A SiO$_2$ flash chromatography (2000 g, hexane/EtOAc 2:1) gives intermediate 334.10 (82.3 g, 100%) as light yellow oil.

Intermediate 335.1

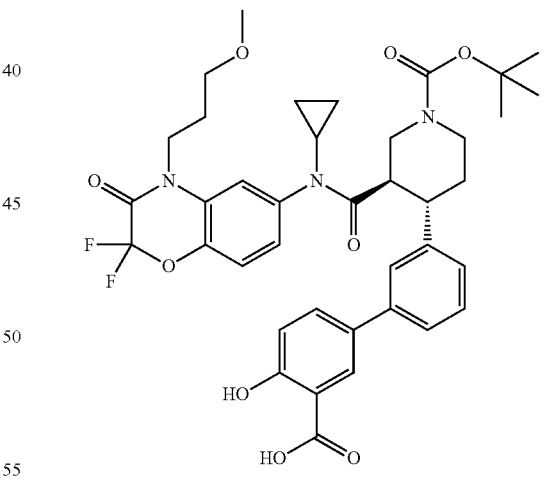

To a solution of Intermediate 335.2 (190 mg, 0.24 mmol) in EtOH (3 mL) is added 8N aqueous KOH (2 mL). After stirring at 70° C., the reaction mixture is cooled to room temperature, and acidified with 1N aqueous KHSO$_4$. The resulting mixture is extracted with AcOEt. The organic layer is washed with brine, dried (Na$_2$SO$_4$), and purified by silica gel column chromatography to give Intermediate 335.1 as white amorphous; ES-MS: M+H=736; HPLC: $ct_{Ret}$=2.13 min.

Intermediate 335.2

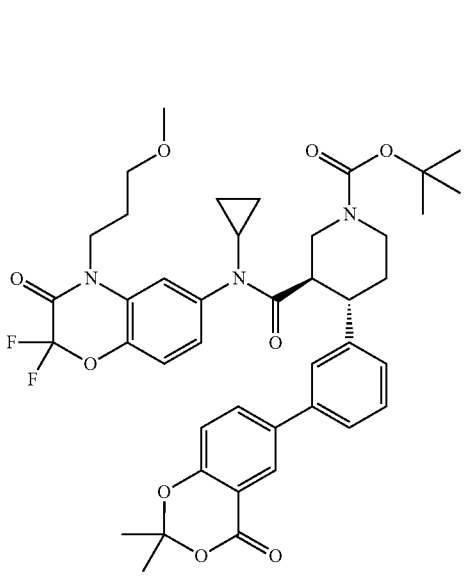

Intermediate 335.2 is synthesized by coupling of Intermediate 301.2 (202 mg, 0.27 mmol) and 6-Bromo-2,2-dimethyl-3-benzodioxin-4-one (CAS 82944-17-0) (164 mg, 0.54 mmol) analogously to the preparation of Intermediate 187.2; ES-MS: M+H=776; HPLC: $_C t_{Ret}$=2.29 min.

Intermediate 336.1

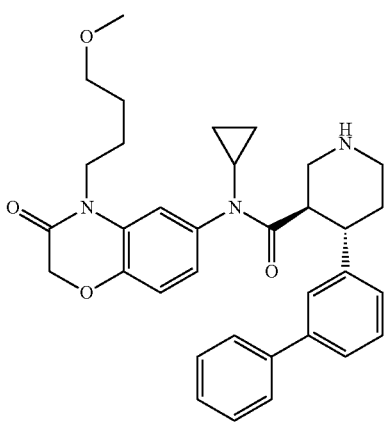

Intermediate 336.1 is synthesized by condensation of Intermediate 2.1 (160 mg, 0.42 mmol) and Intermediate 336.2 (110 mg, 0.38 mmol) analogously to the preparation of Intermediate 145.4. White powder; ES-MS: M+H=654; HPLC: $_A t_{Ret}$=5.02 min.

Intermediate 336.2

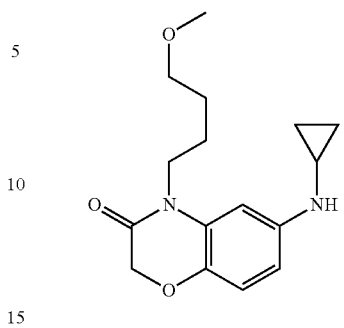

Intermediate 336.2 is synthesized by alkylation of Intermediate 101.3 (400 mg, 1.96 mmol) and toluene-4-sulfonic acid 4-methoxy-propyl ester (560 mg, 2.15 mmol) analogously to a known method (see e.g. *European Journal of Medicinal Chemistry* 1998, 33, 957-967. or EP 432893). Orange solid; ES-MS: M+H=291; HPLC: $_A t_{Ret}$=2.79 min.

EXAMPLE 337

Soft Capsules 5000 soft gelatin capsules, each comprising as active ingredient 0.05 g of any one of the compounds of formula I mentioned in any one of the preceding Examples, are prepared as follows:

1. Composition

| | |
|---|---|
| Active ingredient | 250 g |
| Lauroglycol | 2 liters |

Preparation process: The pulverized active ingredient is suspended in Lauroglykol® (propylene glycol laurate, Gattefossé S. A., Saint Priest, France) and ground in a wet pulverizer to produce a particle size of about 1 to 3 μm. 0.419 g portions of the mixture are then introduced into soft gelatin capsules using a capsule-filling machine.

EXAMPLE 338

Tablets Comprising Compounds of the Formula I

Tablets, comprising, as active ingredient, 100 mg of any one of the compounds of formula I in any one of the preceding Examples are prepared with the following composition, following standard procedures:

Composition

| | |
|---|---|
| Active Ingredient | 100 mg |
| crystalline lactose | 240 mg |
| Avicel | 80 mg |
| PVPPXL | 20 mg |
| Aerosil | 2 mg |
| magnesium stearate | 5 mg |
| | 447 mg |

Manufacture: The active ingredient is mixed with the carrier materials and compressed by means of a tabletting machine (Korsch EKO, stamp diameter 10 mm). Avicel® is microcrystalline cellulose (FMC, Philadelphia, USA). PVP- PXL is polyvinyl-polypyrrolidone, cross-linked (BASF, Germany). Aerosil® is silicon dioxide (Degussa, Germany).

The invention claimed is:

1. A compound of the formula I:

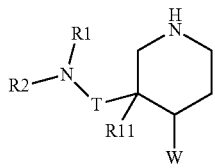
(I)

wherein

R1 is hydrogen or $C_1$-$C_7$-alkyl;

R2 is phenyl-$C_1$-$C_7$-alkyl, di-(phenyl)-$C_1$-$C_7$-alkyl, naphthyl-$C_1$-$C_7$-alkyl, phenyl, naphthyl, pyridyl-$C_1$-$C_7$-alkyl, indolyl-$C_1$-$C_7$-alkyl, 1H-indazolyl-$C_1$-$C_7$-alkyl, quinolyl-$C_1$-$C_7$-alkyl, isoquinolyl-$C_1$-$C_7$-alkyl, 1,2,3,4-tetrahydro-1,4-benzoxazinyl-$C_1$-$C_7$-alkyl, 2H-1,4-benzoxazin-3(4H)-onyl-$C_1$-$C_7$alkyl, 9-xanthenyl-$C_1$-$C_7$-alkyl, 1-benzothiophenyl-$C_1$-$C_7$-alkyl, pyridyl, indolyl, 1H-indazolyl, quinolyl, isoquinolyl, 1,2,3,4-tetrahydro-1,4-benzoxazinyl, 2H-1,4-benzoxazin-3(4H)-onyl, 9-xanthenyl or 1-benzothiophenyl, where each phenyl, naphthyl, pyridyl, indolyl, 1H-indazolyl, quinolyl, isoquinolyl, 1,2,3,4-tetrahydro-1,4-benzoxazinyl, 2H-1,4-benzoxazin-3(4H)-only or 1-benzothiophenyl is unsubstituted or substituted by one or more substituents independently selected from the group consisting of $C_1$-$C_7$-alkyl, hydroxy-$C_1$-$C_7$-alkyl, $C_1$-$C_7$-alkoxy-$C_1$-$C_7$alkyl, $C_1$-$C_7$-alkoxy-$C_1$-$C_7$-alkoxy-$C_1$-$C_7$alkyl, $C_1$-$C_7$-alkanoyloxy-$C_1$-$C_7$-alkyl, amino-$C_1$-$C_7$-alkyl, $C_1$-$C_7$-alkoxy-$C_1$-$C_7$-alkylamino-$C_1$-$C_7$-alkyl, $C_1$-$C_7$-alkanoylamino-$C_1$-$C_7$alkyl, $C_1$-$C_7$-alkylsulfonylamino-$C_1$-$C_7$-alkyl, carboxy-$C_1$-$C_7$-alkyl, $C_1$-$C_7$-alkoxycarbonyl-$C_1$-$C_7$alkyl, halo, hydroxy, $C_1$-$C_7$-alkoxy, $C_1$-$C_7$-alkoxy-$C_1$-$C_7$-alkoxy, amino-$C_1$-$C_7$-alkoxy, N—$C_1$-$C_7$-alkanoylamino-$C_1$-$C_7$-alkoxy, carbamoyl-$C_1$-$C_7$-alkoxy, N—$C_1$-$C_7$alkylcarbamoyl-$C_1$-$C_7$-alkoxy, $C_1$-$C_7$-alkanoyl, $C_1$-$C_7$alkyloxy-$C_1$-$C_7$-alkanoyl, $C_1$-$C_7$-alkoxy-$C_1$-$C_7$-alkanoyl, carboxyl, carbamoyl and N—$C_1$-$C_7$-alkoxy-$C_1$-$C_7$-alkylcarbamoyl;

W is either a moiety of the formula IA,

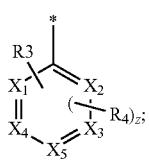
(IA)

wherein the asterisk (*) denotes the position where the moiety W is bound to the 4-carbon in the piperidine ring in formula I, and wherein one of $X_1$ and $X_2$ is nitrogen or CH, while the other and $X_3$, $X_4$ and $X_5$ are CH; or a moiety of the formula IB,

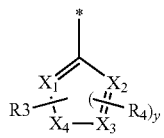
(IB)

wherein the asterisk (*) denotes the position where the moiety W is bound to the 4-carbon in the piperidine ring in formula I, and wherein $X_4$ is $CH_2$, NH, S or O and one of $X_1$, $X_2$ and $X_3$, is N, while the others are each CH, with the proviso that at least one ring nitrogen is present and that R3 is bound to $X_3$;

or a moiety of the formula IC,

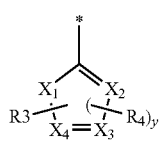
(IC)

wherein the asterisk (*) denotes the position where the moiety W is bound to the 4-carbon in the piperidine ring in formula I, and wherein $X_1$ is $CH_2$, NH, S or O and one of $X_2$, $X_3$ and $X_4$ is N, while the others are CH, with the proviso that at least one ring nitrogen is present;

where in each case where R3 is bond to a moiety of the formula IA, IB or IC, instead of a hydrogen atom at a ring member NH, $CH_2$ or CH mentioned so far where R3 is bound a moiety R3 is present;

y is 0 or 1 and z is 0, 1 or 2;

R3 is hydrogen or $C_1$-$C_7$-alkyloxy-$C_1$-$C_7$-alkyloxy, phenyloxy-$C_1$-$C_7$-alkyl, phenyl, pyridyl, phenyl-$C_1$-$C_7$-alkoxy, phenyloxy, phenyloxy-$C_1$-$C_7$-alkoxy, pyridyl-$C_1$-$C_7$-alkoxy, tetrahydropyranyloxy, 2H,3H-1,4-benzodioxinyl-$C_1$-$C_7$-alkoxy, phenylaminocarbonyl or phenylcarbonylamino, wherein each phenyl or pyridyl is unsubstituted or substituted by one or more substituents independently selected from $C_1$-$C_7$-alkyl, hydroxy, $C_1$-$C_7$-alkoxy, phenyl-$C_1$-$C_7$-alkoxy wherein phenyl is unsubstituted or substituted by $C_1$-$C_7$-alkoxy and/or halo, carboxy-$C_1$-$C_7$-alkyloxy, N-mono- or N,N-di-($C_1$-$C_7$-alkyl)-aminocarbonyl-$C_1$-$C_7$-alkyloxy, halo, amino, N-mono- or N,N-di-($C_1$-$C_7$-alkyl)amino, $C_1$-$C_7$-alkanoylamino, morpholino-$C_1$-$C_7$-alkoxy, thiomorpholino-$C_1$-$C_7$-alkoxy, pyridyl-$C_1$-$C_7$-alkoxy, pyrazolyl, 4-$C_1$-$C_7$-alkylpiperidin-1-yl, tetrazolyl, carboxyl, N-mono- or N,N-di-($C_1$-$C_7$-alkylamino)-carbonyl and cyano; or is 2-oxo-3-phenyl-tetrahydropyrazolidin-1-yl, oxetidin-3-yl-$C_1$-$C_7$-alkyloxy, 3-$C_1$-$C_7$-alkyl-oxetidin-3-yl-$C_1$-$C_7$-alkyloxy or 2-oxo-tetrahydrofuran-4-yl-$C_1$-$C_7$-alkyloxy; with the proviso that if R3 is hydrogen y and z are 0;

R4 if present is hydroxy, halo or $C_1$-$C_7$-alkoxy;

T is methylene or carbonyl, and

R11 is hydrogen, or a pharmaceutically acceptable salt thereof.

2. The compound of the formula I according to claim 1, wherein

R1 is hydrogen or $C_1$-$C_4$-alkyl;

R2 is phenyl-$C_1$-$C_7$-alkyl, di-(phenyl)-$C_1$-$C_7$-alkyl, phenyl, indolyl-$C_1$-$C_7$-alkyl, 1H-indazolyl-$C_1$-$C_7$-alkyl, 9-xanthenyl-$C_1$-$C_7$-alkyl, 1,2,3,4-tetrahydro-1,4-benzoxazinyl or 2H-1,4-benzoxazin-3(4H)-onyl, where each phenyl, indolyl, 1H-indazolyl, 1,2,3,4-tetrahydro-1,4-benzoxazinyl or 2H-1,4-benzoxazin-3(4H)-only is unsubstituted or substituted by up to three substituents independently selected from the group consisting of $C_1$-$C_7$-alkyl, $C_1$-$C_7$-alkoxy-$C_1$-$C_7$-alkyl, $C_1$-$C_7$-alkoxy-$C_1$-$C_7$-alkoxy-$C_1$-$C_7$-alkyl, $C_1$-$C_7$-alkanoylamino-$C_1$-$C_7$-alkyl, $C_1$-$C_7$-alkylsulfonylamino-$C_1$-$C_7$alkyl, carboxy-$C_1$-$C_7$-alkyl, $C_1$-$C_7$-alkoxycarbonyl-$C_1$-$C_7$-alkyl, halo, $C_1$-$C_7$-alkoxy, $C_1$-$C_7$-alkoxy-$C_1$-$C_7$-alkoxy and $C_1$-$C_7$-alkyloxy-$C_1$-$C_7$-alkanoyl;

W is either a moiety of the formula IA,

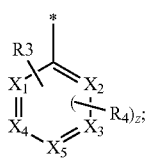

(IA)

wherein the asterisk (*) denotes the position where the moiety W is bound to the 4-carbon in the piperidine ring in formula I, and wherein one of $X_1$ and $X_2$ is nitrogen or CH, while the other and $X_3$, $X_4$ and $X_5$ are CH; with the proviso that R3 is bound to $X_1$ or $X_2$ or to $X_3$ or $X_4$; or a moiety of the formula IC,

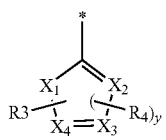

(IC)

wherein the asterisk (*) denotes the position where the moiety W is bound to the 4-carbon in the piperidine ring in formula I, and wherein $X_1$ is O, $X_2$ is CH or N, $X_3$ is CH and $X_4$ is CH or N, with the proviso that not more than one of $X_2$ and $X_4$ is N; and with the proviso that R3 is bound to $X_2$ or to $X_3$ or $X_4$;

where in each case where R3 is bond to a moiety of the formula IA or IC, instead of a hydrogen atom at a ring member NH or CH mentioned so far where R3 is bound a moiety R3 is present;

y is 0 or 1 and z is 0, 1 or 2;

R3 is hydrogen or $C_1$-$C_7$-alkyloxy-$C_1$-$C_7$-alkyloxy, phenyl, pyridyl, phenyl-$C_1$-$C_7$-alkoxy, phenyloxy, phenyloxy-$C_1$-$C_7$-alkoxy, pyridyl-$C_1$-$C_7$-alkoxy, tetrahydropyranyloxy, 2H,3H-1,4-benzodioxinyl-$C_1$-$C_7$-alkoxy, phenylaminocarbonyl or phenylcarbonylamino, wherein each phenyl or pyridyl is unsubstituted or substituted by up to three substituents independently selected from hydroxy, $C_1$-$C_7$-alkoxy, halo, amino and N-mono- or N,N-di-($C_1$-$C_7$-alkyl)amino, with the proviso that if R3 is hydrogen then y and z are 0;

R4 if present (z=1) is hydroxy, halo or $C_1$-$C_7$-alkoxy;

T is carbonyl or methylene, and

R11 is hydrogen, or a pharmaceutically acceptable salt thereof.

3. The compound of the formula I according to claim 1 with the following configuration

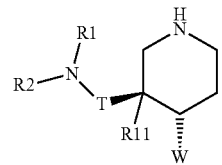

(A)

wherein R1, R2, R11, T and W are as defined for a compound of the formula I in claim 3, or a pharmaceutically acceptable salt thereof.

4. The compound of the formula I according to claim 1 of the following formula:

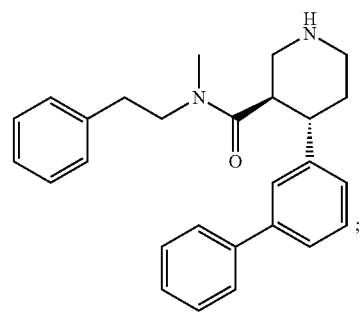

or a pharmaceutically acceptable salt thereof.

5. A pharmaceutical formulation, comprising a compound of the formula I, or a pharmaceutically acceptable salt thereof, according to claim 1 and at least one pharmaceutically acceptable carrier material.

6. A method of treating hypertension, comprising administering to a human, in need of such treatment a pharmaceutically effective amount of a compound of the formula I, or a pharmaceutically acceptable salt thereof, according to claim 1.

7. A process for the manufacture of a compound of the formula I, or a pharmaceutically acceptable salt thereof, according to claim 1, comprising (a) for the synthesis of a compound of the formula I wherein T is carbonyl and the other moieties are as defined for a compound of the formula I, reacting a carbonic acid compound of the formula II

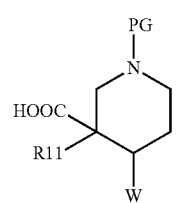

(II)

wherein W and R11 are as defined for a compound of the formula I and PG is a protecting group, or an active derivative thereof, with an amine of the formula III,

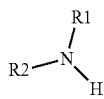
(III)

wherein R1 and R2 are as defined for a compound of the formula I, and removing protecting groups to give the corresponding compound of the formula I, or (b) for the preparation of a compound of the formula I wherein $R_3$ is unsubstituted or substituted aryl, unsubstituted or substituted heterocyclyl, etherified or esterified hydroxy, unsubstituted or substituted mercapto or unsubstituted or substituted amino, and W is a moiety of the formula IA given above, by reacting a compound of the formula IV,

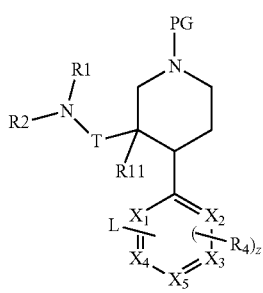
(IV)

wherein R1, R2, T, R11, $X_1$, $X_2$, $X_3$, $X_4$, z and $R_4$ are as defined for a compound of the formula I, PG is a protecting group and L is a leaving group or hydroxy, with a compound of the formula V,

R3-Q  (V)

wherein R3 is as just defined and Q is —B(OH)$_2$ or a leaving group, and removing protecting groups to give the corresponding compound of the formula I, or (c) for the preparation of a compound of the formula I wherein T is —CH$_2$—, reacting an aldehyde compound of the formula VI,

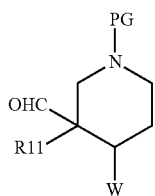
(VI)

wherein R11 and W are as defined for a compound of the formula I and PG is a protecting group, under the conditions of reductive amination with an amine of the formula III as given above wherein R1 is as defined for a compound of the formula I and R2 is hydrogen, to give the corresponding protected compound of the formula I, if desired introducing R2 as defined above for a compound of the formula I other than hydrogen by reacting with a compound of the formula VII,

R2*-D  (VII)

wherein R2* is defined as R2 in a compound of the formula I other than hydrogen and D is a leaving group, and removing protecting groups to give the corresponding compound of the formula I, and, if desired, subsequent to any one or more of the processes mentioned above converting an obtainable compound of the formula I or a protected form thereof into a different compound of the formula I, converting a salt of an obtainable compound of formula I into the free compound or a different salt, converting an obtainable free compound of formula I into a salt thereof, and/or separating an obtainable mixture of isomers of a compound of formula I into individual isomers;

where in any of the starting materials, in addition to specific protecting groups mentioned, further protecting groups may be present, and any protecting groups are removed at an appropriate stage in order to obtain the corresponding compound of the formula I, or a salt thereof.

8. The compound according to claim 1 wherein W is either a moiety of the formula IA,

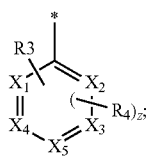
(IA)

wherein the asterisk (*) denotes the position where the moiety W is bound to the 4-carbon in the piperidine ring in formula I, and wherein one of $X_1$ and $X_2$ is nitrogen or CH, while the other and $X_3$, $X_4$ and $X_5$ are CH; and R3 is bound to $X_3$ or $X_4$; or W is a moiety of the formula IB,

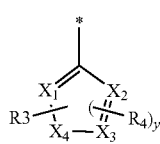
(IB)

wherein the asterisk (*) denotes the position where the moiety W is bound to the 4-carbon in the piperidine ring in formula I, and wherein $X_1$ is CH or N, $X_2$ is CH or N, $X_3$ is CH or N and $X_4$ is NH, O or S, with the proviso that not more than one of $X_1$, $X_2$ and $X_3$ is N; and R3 is bound to $X_3$ or $X_4$;

or W is a moiety of the formula IC,

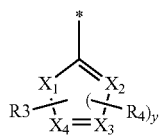
(IC)

wherein the asterisk (*) denotes the position where the moiety W is bound to the 4-carbon in the piperidine ring in formula I, and wherein $X_1$ is S or O, $X_2$ is CH or N, $X_3$ is CH or N, and $X_4$ is CH or N, with the proviso that not more than one of $X_2$, $X_3$ and $X_4$ is N; and R3 is bound to $X_3$ or $X_4$; or pharmaceutically acceptable salt thereof.
9. A compound of the formula I according to claim 1, selected from the compounds of the formula
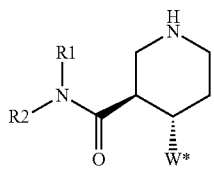
as represented in the following table:

| 561 -continued | | |
|---|---|---|
| R1 | R2 | W* |
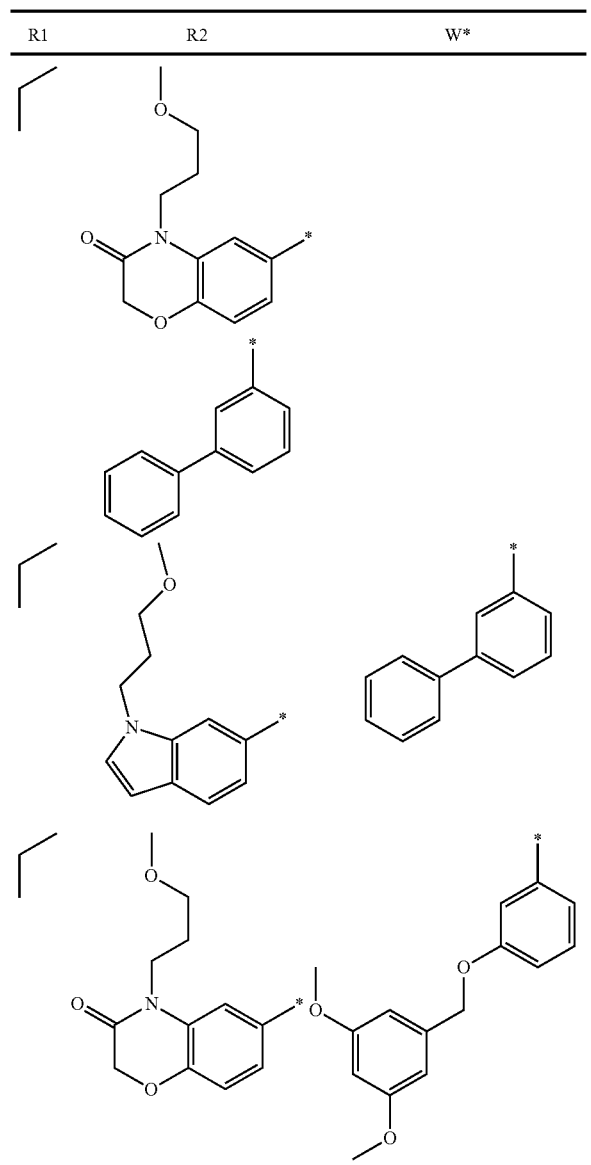
| 562 -continued | | |
|---|---|---|
| R1 | R2 | W* |
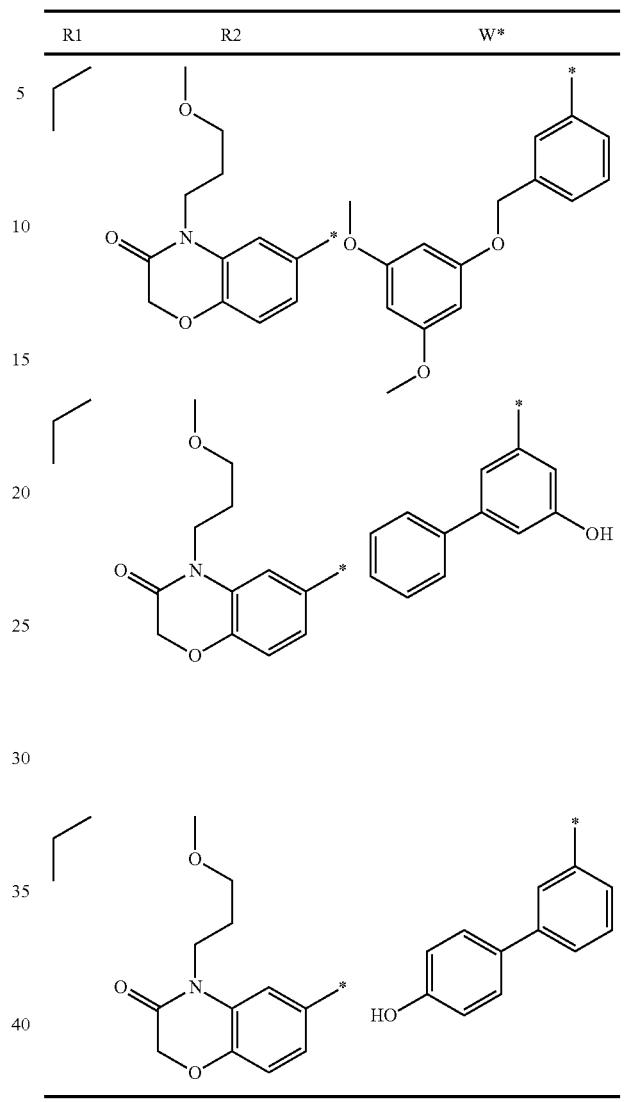
or in each case a pharmaceutically acceptable salt thereof.
* * * * *